United States Patent
Kadoma et al.

(10) Patent No.: US 9,034,486 B2
(45) Date of Patent: May 19, 2015

(54) TRIAZOLE DERIVATIVE, HETEROCYCLIC COMPOUND, LIGHT-EMITTING ELEMENT, LIGHT-EMITTING DEVICE, ELECTRONIC DEVICE AND LIGHTING DEVICE

(75) Inventors: Hiroshi Kadoma, Kanagawa (JP); Yuko Kawata, Kanagawa (JP); Nobuharu Ohsawa, Kanagawa (JP); Satoshi Seo, Kanagawa (JP)

(73) Assignee: SEMICONDUCTOR ENERGY LABORATORY CO., LTD (JP)

( * ) Notice: Subject to any disclaimer, the term of this patent is extended or adjusted under 35 U.S.C. 154(b) by 737 days.

(21) Appl. No.: 13/194,196

(22) Filed: Jul. 29, 2011

(65) Prior Publication Data
US 2012/0025697 A1    Feb. 2, 2012

(30) Foreign Application Priority Data

Aug. 2, 2010    (JP) ................ 2010-173707

(51) Int. Cl.
| | |
|---|---|
| *H01J 1/63* | (2006.01) |
| *C07D 471/04* | (2006.01) |
| *C07D 471/00* | (2006.01) |
| *H01L 51/00* | (2006.01) |
| *H01L 51/50* | (2006.01) |

(52) U.S. Cl.
CPC ............ *C07D 471/04* (2013.01); *C07D 471/00* (2013.01); *H01L 51/0072* (2013.01); *H01L 51/0074* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 7,351,481 B2 | 4/2008 | Lee et al. | |
| 7,915,415 B2 | 3/2011 | Knowles et al. | |
| 2005/0074632 A1 | 4/2005 | Lee et al. | |
| 2007/0059554 A1 | 3/2007 | Takeda | |
| 2008/0286607 A1 | 11/2008 | Nomura et al. | |
| 2008/0297033 A1 | 12/2008 | Knowles et al. | |
| 2010/0244674 A1 | 9/2010 | Nomura et al. | |
| 2010/0264405 A1 | 10/2010 | Molt et al. | |
| 2011/0073849 A1 | 3/2011 | Knowles et al. | |
| 2011/0127513 A1 | 6/2011 | Lee et al. | |
| 2011/0284799 A1* | 11/2011 | Stoessel et al. | .......... 252/301.16 |

FOREIGN PATENT DOCUMENTS

| | | |
|---|---|---|
| EP | 2 311 826 A2 | 4/2011 |
| JP | 11-246559 | 9/1999 |
| JP | 2001-81452 | 3/2001 |
| JP | 2002-352957 | 12/2002 |

(Continued)

OTHER PUBLICATIONS

Partial International Search Report, "Invitation to Pay Additional Fees," re application No. PCT/JP2011/066770, dated Aug. 23, 2011.

*Primary Examiner* — J. L. Yang
(74) *Attorney, Agent, or Firm* — Husch Blackwell LLP

(57) ABSTRACT

A triazole derivative represented by General Formula (G0) is provided. In the General formula (G0), A represents a substituted or unsubstituted carbazolyl group, a substituted or unsubstituted dibenzothiophenyl group, or a substituted or unsubstituted dibenzofuranyl group, E represents substituted or unsubstituted triazolo [4,3 f]phenanthridine or substituted or unsubstituted triazolo [3,4-α]isoquinoline, and Ar represents a substituted or unsubstituted arylene group having 6 to 13 carbon atoms.

E-Ar-A                  (G0)

39 Claims, 65 Drawing Sheets

(56) References Cited

FOREIGN PATENT DOCUMENTS

| | | |
|---|---|---|
| JP | 2005-112856 | 4/2005 |
| JP | 2007-81050 | 3/2007 |
| JP | 2010-215759 | 9/2010 |
| JP | 2010-267847 | 11/2010 |
| JP | 2011-500644 | 1/2011 |
| WO | WO 02/081474 A1 | 10/2002 |
| WO | WO 2008/156879 A1 | 12/2008 |
| WO | WO 2009/050281 A1 | 4/2009 |
| WO | WO 2010/032663 A1 | 3/2010 |
| WO | WO 2010/062065 A2 | 6/2010 |
| WO | WO 2010/086089 A1 * | 8/2010 ............... C07F 1/00 |
| WO | WO 2011/024737 A1 | 3/2011 |

* cited by examiner

TRIAZOLE DERIVATIVE, HETEROCYCLIC COMPOUND, LIGHT-EMITTING ELEMENT, LIGHT-EMITTING DEVICE, ELECTRONIC DEVICE AND LIGHTING DEVICE

TECHNICAL FIELD

The present invention relates to a triazole derivative, a heterocyclic compound, a light-emitting element, a light-emitting device, an electronic device, and a lighting device.

BACKGROUND ART

In recent years, research and development have been extensively conducted on light-emitting elements utilizing electroluminescence (EL). In the basic structure of such a light-emitting element, a layer containing a light-emitting substance is interposed between a pair of electrodes. By voltage application to this element, light emission from the light-emitting substance can be obtained.

Such light-emitting elements are self-luminous elements and hence have advantages over liquid crystal displays in having high pixel visibility and eliminating the need for backlights, for example; thus, light-emitting elements are thought to be suitable for flat panel display elements. Light-emitting elements are also highly advantageous in that they can be thin and lightweight. Furthermore, very high speed response is also one of the features of such elements.

Furthermore, since such light-emitting elements can be formed in a film form, they make it possible to provide planar light emission; thus, large-area elements can be easily formed. This is a difficult feature to obtain with point light sources typified by incandescent lamps and LEDs or linear light sources typified by fluorescent lamps. Thus, light-emitting elements also have great potential as planar light sources applicable to lighting devices and the like.

Such light-emitting elements utilizing EL can be broadly classified according to whether the light-emitting substance is an organic compound or an inorganic compound. In the case of an organic EL element in which a layer containing an organic compound used as the light-emitting substance is provided between a pair of electrodes, application of a voltage to the light-emitting element causes injection of electrons from the cathode and holes from the anode into the layer containing the organic compound having a light-emitting property and thus a current flows. The injected electrons and holes then lead the organic compound having a light-emitting property to its excited state, so that light emission is obtained from the excited organic compound having a light-emitting property.

An excited state formed by an organic compound can be a singlet excited state or a triplet excited state. Luminescence from a singlet excited state (S*) is called fluorescence, and luminescence from a triplet excited state (T*) is called phosphorescence. In addition, the ratio of S* to T* formed in a light-emitting element is statistically considered to be 1:3.

At room temperature, observations of a compound that can convert energy of a singlet excited state into luminescence (hereinafter, referred to as a fluorescent compound) usually show only luminescence from the singlet excited state (fluorescence) without luminescence from the triplet excited state (phosphorescence). Thus, the internal quantum efficiency (the ratio of generated photons to injected carriers) of a light-emitting element using a fluorescent compound is assumed to have a theoretical limit of 25% based on a S*-to-T* ratio of 1:3.

In contrast, with a compound that can convert energy of a triplet excited state into luminescence (hereinafter, called a phosphorescent compound), luminescence from the triplet excited state (phosphorescence) is observed. Further, with a phosphorescent compound, since intersystem crossing (i.e., transition from a singlet excited state to a triplet excited state) easily occurs, the internal quantum efficiency can be increased to 75% to 100% in theory. In other words, an element using a phosphorescent compound can have three to four times as high emission efficiency as that of an element using a fluorescent compound. For these reasons, a light-emitting element using a phosphorescent compound has been actively developed in recent years in order to achieve a highly-efficient light-emitting element.

When formed using the above-described phosphorescent compound, a light-emitting layer of a light-emitting element is often formed such that a phosphorescent compound is dispersed in a matrix of another compound in order to suppress concentration quenching or quenching due to triplet-triplet annihilation in the phosphorescent compound. Here, the compound serving as a matrix is called a host material, and the compound dispersed in a matrix, such as a phosphorescent compound, is called a guest material.

A host material needs to have higher triplet excitation energy (an energy difference between a ground state and a triplet excited state) than a phosphorescent compound in the case where the phosphorescent compound is a guest material.

Furthermore, since singlet excitation energy (an energy difference between a ground state and a singlet excited state) is higher than triplet excitation energy, a substance that has high triplet excitation energy also has high singlet excitation energy. Therefore the above substance that has high triplet excitation energy is also effective in a light-emitting element using a fluorescent compound as a light-emitting substance.

In Patent Document 1, 3-(4-biphenylyl)-5-(4-tert-butylphenyl)-4-phenyl-1,2,4-triazole (abbreviation: TAZ) is used as a host material for a phosphorescent compound that emits green light.

REFERENCE

Patent Document

Patent Document 1: Japanese Published Patent Application No. 2002-352957

DISCLOSURE OF INVENTION

A compound having high triplet excitation energy like TAZ is useful as a host material for a phosphorescent compound. However, TAZ has high singlet excitation energy and it is also used as a hole-blocking material; that is, a feature of TAZ is that it has great difficulty with hole injection. Thus, use of TAZ as a host material of a light-emitting layer hampers hole injection into the light-emitting layer, and accordingly a light-emitting region has a strong tendency to be concentrated in and around an interface between the light-emitting layer and a hole-transport layer. If the light-emitting region is concentrated in the interface, there occurs concentration quenching or quenching due to triplet-triplet annihilation of a light-emitting substance in an excited state, which could result in a decrease of emission efficiency.

Therefore, an object of one embodiment of the present invention is to provide a substance that facilitates hole injection and has high triplet excitation energy.

An object of one embodiment of the present invention is to provide a light-emitting element having high emission efficiency. Another object of one embodiment of the present invention is to provide a light-emitting element driven with a low voltage. Yet another object of one embodiment of the present invention is to provide a light-emitting element having a long lifetime. Still another object of one embodiment of the present invention is to provide a light-emitting device, an electronic device, and a lighting device each having low power consumption.

The present inventors have focused on the use of a triazolo[4,3-f]phenanthridine derivative or a triazolo[3,4-a]isoquinoline derivative for a light-emitting element.

Thus, one embodiment of the present invention is a light-emitting element including a triazolo[4,3-f]phenanthridine derivative or a triazolo[3,4-a]isoquinoline derivative.

It is particularly preferable that a light-emitting layer of a light-emitting element include a triazolo[4,3-f]phenanthridine derivative or a triazolo[3,4-a]isoquinoline derivative as a material in which a phosphorescent material is to be dispersed (as a host material).

Thus, one embodiment of the present invention is a light-emitting element which has a light-emitting layer between a pair of electrodes and in which the light-emitting layer includes a phosphorescent material and a triazolo[4,3-f]phenanthridine derivative or a triazolo[3,4-a]isoquinoline derivative.

Further, one embodiment of the present invention also includes a triazole derivative which is a triazolo[4,3-f]phenanthridine derivative or a triazolo[3,4-a]isoquinoline derivative described below.

One embodiment of the present invention is a triazole derivative represented by a general formula (G0).

        (G0)

In the formula, A represents a substituted or unsubstituted carbazolyl group, a substituted or unsubstituted dibenzothiophenyl group, or a substituted or unsubstituted dibenzofuranyl group, E represents substituted or unsubstituted triazolo[4,3-f]phenanthridine or substituted or unsubstituted triazolo[3,4-a]isoquinoline, and Ar represents a substituted or unsubstituted arylene group having 6 to 13 carbon atoms. Note that substituents of the arylene group may be bonded to form a ring.

One embodiment of the present invention is a triazole derivative represented by a general formula (G1-1).

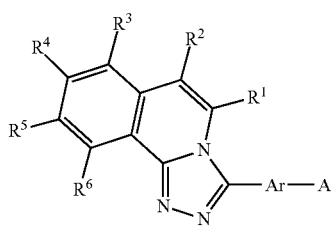

(G1-1)

In the formula, A represents a substituted or unsubstituted carbazolyl group, a substituted or unsubstituted dibenzothiophenyl group, or a substituted or unsubstituted dibenzofuranyl group, $R^1$ to $R^6$ separately represent hydrogen, an alkyl group having 1 to 4 carbon atoms, or a substituted or unsubstituted aryl group having 6 to 13 carbon atoms, and Ar represents a substituted or unsubstituted arylene group having 6 to 13 carbon atoms. Note that substituents of the arylene group may be bonded to form a ring. $R^1$ and $R^2$ may be bonded to form a six-membered ring.

One embodiment of the present invention is a triazole derivative represented by a general formula (G1-2).

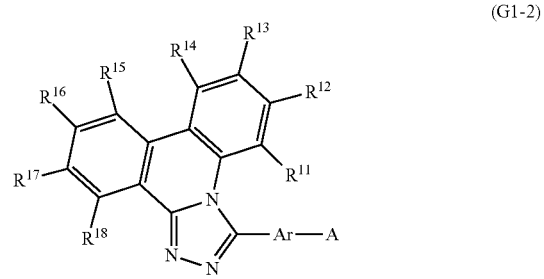

(G1-2)

In the formula, A represents a substituted or unsubstituted carbazolyl group, a substituted or unsubstituted dibenzothiophenyl group, or a substituted or unsubstituted dibenzofuranyl group, $R^{11}$ to $R^{18}$ separately represent hydrogen, an alkyl group having 1 to 4 carbon atoms, or a substituted or unsubstituted aryl group having 6 to 13 carbon atoms, and Ar represents a substituted or unsubstituted arylene group having 6 to 13 carbon atoms. Note that substituents of the arylene group may be bonded to form a ring.

One embodiment of the present invention is a triazole derivative represented by a general formula (G2-1).

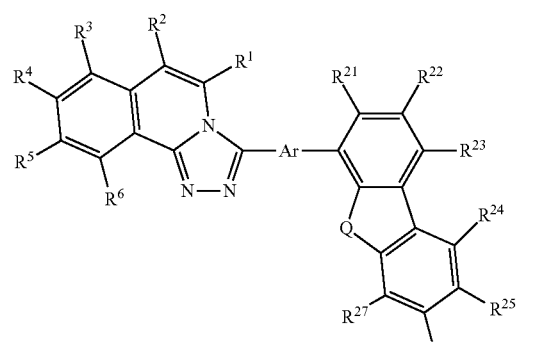

(G2-1)

In the formula, Q represents oxygen or sulfur, $R^1$ to $R^6$ and $R^{21}$ to $R^{27}$ separately represent hydrogen, an alkyl group having 1 to 4 carbon atoms, or a substituted or unsubstituted aryl group having 6 to 13 carbon atoms, and Ar represents a substituted or unsubstituted arylene group having 6 to 13 carbon atoms. Note that substituents of the arylene group may be bonded to form a ring. $R^1$ and $R^2$ may be bonded to form a six-membered ring.

One embodiment of the present invention is a triazole derivative represented by a general formula (G2-2).

(G2-2)

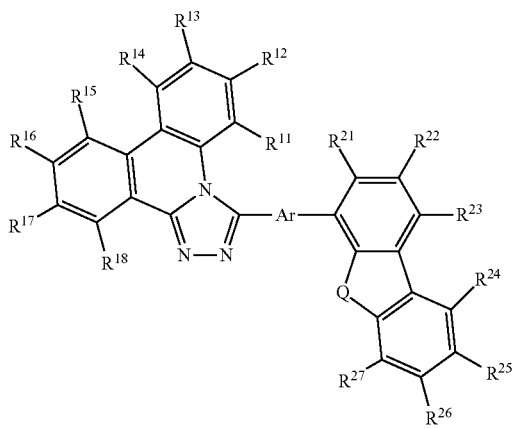

In the formula, Q represents oxygen or sulfur, $R^{11}$ to $R^{18}$ and $R^{21}$ to $R^{27}$ separately represent hydrogen, an alkyl group having 1 to 4 carbon atoms, or a substituted or unsubstituted aryl group having 6 to 13 carbon atoms, and Ar represents a substituted or unsubstituted arylene group having 6 to 13 carbon atoms. Note that substituents of the arylene group may be bonded to form a ring.

One embodiment of the present invention is a triazole derivative represented by a general formula (G3-1).

(G3-1)

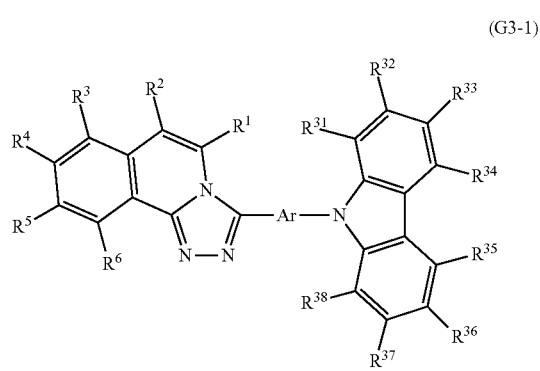

In the formula, $R^1$ to $R^6$ and $R^{31}$ to $R^{38}$ separately represent hydrogen, an alkyl group having 1 to 4 carbon atoms, or a substituted or unsubstituted aryl group having 6 to 13 carbon atoms, and Ar represents a substituted or unsubstituted arylene group having 6 to 13 carbon atoms. Note that substituents of the arylene group may be bonded to form a ring. $R^1$ and $R^2$ may be bonded to form a six-membered ring.

One embodiment of the present invention is a triazole derivative represented by a general formula (G3-2).

(G3-2)

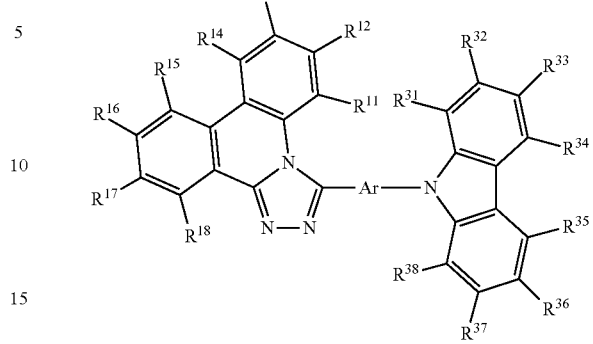

In the formula, $R^{11}$ to $R^{18}$ and $R^{31}$ to $R^{38}$ separately represent hydrogen, an alkyl group having 1 to 4 carbon atoms, or a substituted or unsubstituted aryl group having 6 to 13 carbon atoms, and Ar represents a substituted or unsubstituted arylene group having 6 to 13 carbon atoms. Note that substituents of the arylene group may be bonded to form a ring.

In any triazole derivative illustrated above, Ar is preferably a substituted or unsubstituted phenylene group or a substituted or unsubstituted biphenyldiyl group, and especially preferably a substituted or unsubstituted phenylene group.

Since any triazole derivative described above is a triazolo[4,3-f]phenanthridine derivative or a triazolo[3,4-a]isoquinoline derivative, a light-emitting element including any triazole derivative described above is also included in one embodiment of the present invention.

Furthermore, a light-emitting element of one embodiment of the present invention is driven with a low voltage. A light-emitting element of one embodiment of the present invention has high current efficiency. A light-emitting element of one embodiment of the present invention has a long lifetime. Consequently, a light-emitting device using such a light-emitting element has the same effect as the light-emitting element and can realize low power consumption. Thus, one embodiment of the present invention is a light-emitting device using any light-emitting element described above. In addition, electronic devices and lighting devices using the light-emitting device are also included in embodiments of the present invention.

Note that the light-emitting device in this specification includes an image display device using a light-emitting element. In addition, the light-emitting device includes all the following modules: a module in which a connector, such as an anisotropic conductive film, a TAB (tape automated bonding) tape or a TCP (tape carrier package), is attached to a light-emitting element, a module in which a printed wiring board is provided on the tip of a TAB tape or a TCP, and a module in which an IC (integrated circuit) is directly mounted on a light-emitting element by a COG (chip on glass) method. The light-emitting device also includes the one used in lighting equipment and the like.

Furthermore, a heterocyclic compound used for the synthesis of a triazole derivative according to one embodiment of the present invention is also a novel substance; therefore, this heterocyclic compound is also included in the present invention. Thus, one embodiment of the present invention is a heterocyclic compound represented by the following general formula (G4).

E—Ar—X (G4)

In the formula, E represents substituted or unsubstituted triazolo[4,3-f]phenanthridine or substituted or unsubstituted triazolo[3,4-a]isoquinoline, X represents iodine or bromine, and Ar represents a substituted or unsubstituted arylene group having 6 to 13 carbon atoms. Note that substituents of the arylene group may be bonded to form a ring.

One embodiment of the present invention is a heterocyclic compound represented by the following general formula (G5-1).

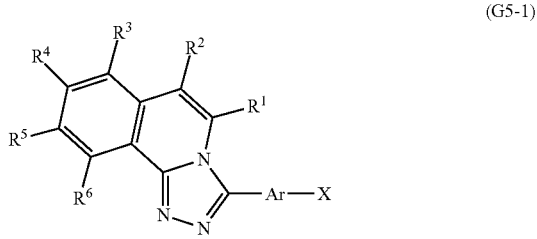

(G5-1)

In the formula, $R^1$ to $R^6$ separately represent hydrogen, an alkyl group having 1 to 4 carbon atoms, or a substituted or unsubstituted aryl group having 6 to 13 carbon atoms, X represents iodine or bromine, and Ar represents a substituted or unsubstituted arylene group having 6 to 13 carbon atoms. Note that substituents of the arylene group may be bonded to form a ring. $R^1$ and $R^2$ may be bonded to form a six-membered ring.

Another embodiment of the present invention is a heterocyclic compound represented by the following general formula (G5-2).

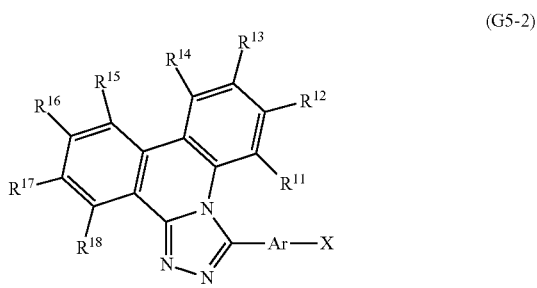

(G5-2)

In the formula, $R^{11}$ to $R^{18}$ separately represent hydrogen, an alkyl group having 1 to 4 carbon atoms, or a substituted or unsubstituted aryl group having 6 to 13 carbon atoms, X represents iodine or bromine, and Ar represents a substituted or unsubstituted arylene group having 6 to 13 carbon atoms. Note that substituents of the arylene group may be bonded to form a ring.

In any heterocyclic compound described above, Ar is preferably a substituted or unsubstituted phenylene group or a substituted or unsubstituted biphenyldiyl group, and especially preferably a substituted or unsubstituted phenylene group.

According to one embodiment of the present invention, a substance that facilitates hole injection and has high triplet excitation energy can be provided. A light-emitting element having high emission efficiency can be provided. A light-emitting element driven with a low voltage can be provided. A light-emitting element having a long lifetime can also be provided. A light-emitting device, an electronic device, and a lighting device having low power consumption can also be provided.

BEST MODE FOR CARRYING OUT THE INVENTION

Figure 1A:
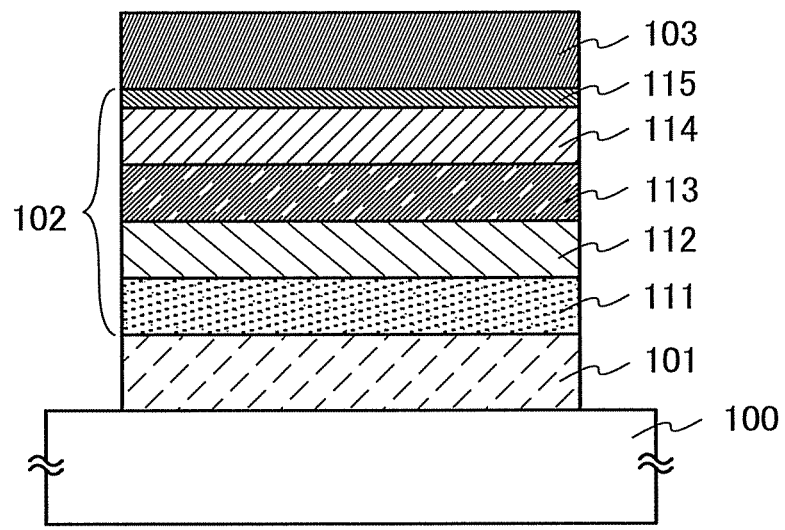
FIGS. 1A and 1B each illustrate a light-emitting element of one embodiment of the present invention.

Embodiments will now be described with reference to the accompanying drawings. Note that the invention is not limited to the description given below, and it will be easily understood by those skilled in the art that various changes and modifications can be made without departing from the spirit and scope of the invention. Therefore, the invention should not be construed as being limited to the description in the following embodiments. Note also that in the structures described below, the same reference numerals in different drawings represent components that are identical or have similar functions, the description of which is not repeated.

(Embodiment 1)

In Embodiment 1, a triazole derivative of one embodiment of the present invention and a heterocyclic compound used in the synthesis of the triazole derivative will be described.

A triazole derivative of one embodiment of the present invention has a triazolo[4,3-j]phenanthridine skeleton or a triazolo[3,4-a]isoquinoline skeleton. A triazole derivative of one embodiment of the present invention is a substance which has a carrier-transport property in addition to high triplet excitation energy, and accordingly the triazole derivative can be suitably used for a light-emitting element.

One embodiment of the present invention is a triazole derivative represented by the general formula (G0).

$$E-Ar-A \qquad (G0)$$

In the general formula (G0), A represents a substituted or unsubstituted carbazolyl group, a substituted or unsubstituted dibenzothiophenyl group, or a substituted or unsubstituted dibenzofuranyl group, E represents substituted or unsubstituted triazolo[4,3-f]phenanthridine or substituted or unsubstituted triazolo[3,4-a]isoquinoline, and Ar represents a substituted or unsubstituted arylene group having 6 to 13 carbon atoms. Note that substituents of the arylene group may be bonded to form a ring.

As the above triazole derivative, a triazole derivative represented by the general formula (G1-1) can be given, for example.

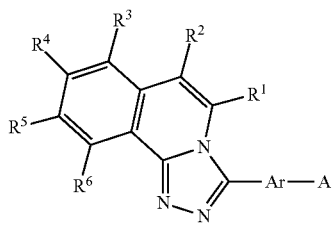

(G1-1)

In the formula, A represents a substituted or unsubstituted carbazolyl group, a substituted or unsubstituted dibenzothiophenyl group, or a substituted or unsubstituted dibenzofuranyl group, $R^1$ to $R^6$ separately represent hydrogen, an alkyl group having 1 to 4 carbon atoms, or a substituted or unsubstituted aryl group having 6 to 13 carbon atoms, and Ar represents a substituted or unsubstituted arylene group having 6 to 13 carbon atoms. Note that substituents of the arylene group may be bonded to form a ring. $R^1$ and $R^2$ may be bonded to form a six-membered ring.

As a triazole derivative represented by the general formula (G1-1), a triazole derivative having a triazolo[4,3-f]phenanthridine skeleton, in particular, is represented by the general formula (G1-2).

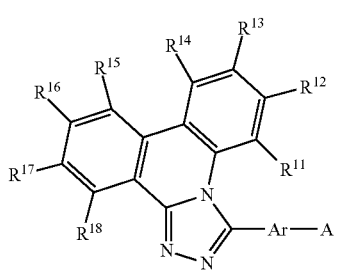

(G1-2)

In the formula, A represents a substituted or unsubstituted carbazolyl group, a substituted or unsubstituted dibenzothiophenyl group, or a substituted or unsubstituted dibenzofuranyl group, $R^{11}$ to $R^{18}$ separately represent hydrogen, an alkyl group having 1 to 4 carbon atoms, or a substituted or unsubstituted aryl group having 6 to 13 carbon atoms, and Ar represents a substituted or unsubstituted arylene group having 6 to 13 carbon atoms. Note that substituents of the arylene group may be bonded to form a ring.

A triazole derivative of one embodiment of the present invention is a triazole derivative represented by the general formula (G2-1).

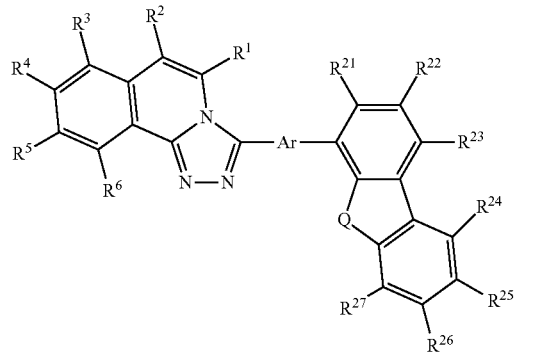

(G2-1)

In the formula, Q represents oxygen or sulfur, $R^1$ to $R^6$ and $R^{21}$ to $R^{27}$ separately represent hydrogen, an alkyl group having 1 to 4 carbon atoms, or a substituted or unsubstituted aryl group having 6 to 13 carbon atoms, and Ar represents a substituted or unsubstituted arylene group having 6 to 13 carbon atoms. Note that substituents of the arylene group may be bonded to form a ring. $R^1$ and $R^2$ may be bonded to form a six-membered ring.

As a triazole derivative represented by the general formula (G2-1), a triazole derivative having a triazolo[4,3-f]phenanthridine skeleton, in particular, is represented by a general formula (G2-2).

(G2-2)

In the formula, Q represents oxygen or sulfur, $R^{11}$ to $R^{18}$ and $R^{21}$ to $R^{27}$ separately represent hydrogen, an alkyl group having 1 to 4 carbon atoms, or a substituted or unsubstituted aryl group having 6 to 13 carbon atoms, and Ar represents a substituted or unsubstituted arylene group having 6 to 13 carbon atoms. Note that substituents of the arylene group may be bonded to form a ring.

One embodiment of the present invention is a triazole derivative represented by the general formula (G3-1).

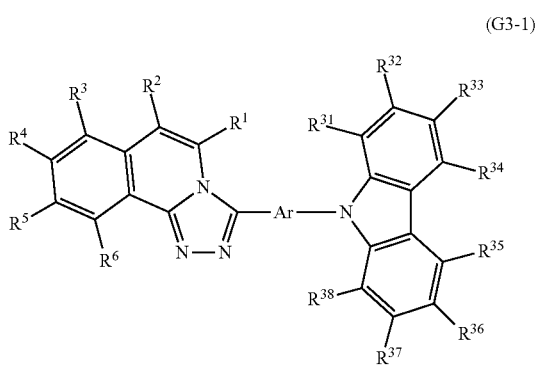

(G3-1)

In the formula, $R^1$ to $R^6$ and $R^{31}$ to $R^{38}$ separately represent hydrogen, an alkyl group having 1 to 4 carbon atoms, or a substituted or unsubstituted aryl group having 6 to 13 carbon atoms, and Ar represents a substituted or unsubstituted arylene group having 6 to 13 carbon atoms. Note that substituents of the arylene group may be bonded to form a ring. $R^1$ and $R^2$ may be bonded to form a six-membered ring.

As a triazole derivative represented by the general formula (G3-1), a triazole derivative having a triazolo[4,3-f]phenanthridine skeleton, in particular, is represented by a general formula (G3-2).

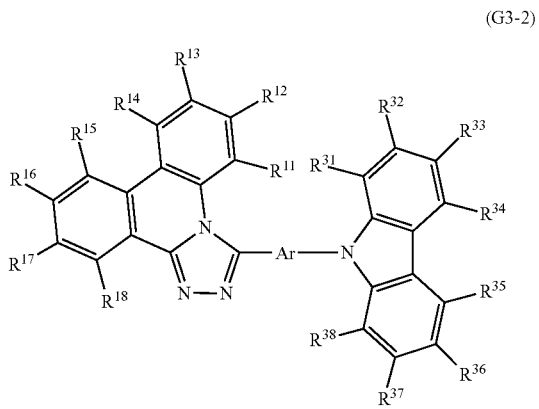

(G3-2)

In the formula, $R^{11}$ to $R^{18}$ and $R^{31}$ to $R^{38}$ separately represent hydrogen, an alkyl group having 1 to 4 carbon atoms, or a substituted or unsubstituted aryl group having 6 to 13 carbon atoms, and Ar represents a substituted or unsubstituted arylene group having 6 to 13 carbon atoms. Note that substituents of the arylene group may be bonded to form a ring.

As another mode of a triazole derivative represented by the general formula (G0), a triazole derivative represented by a general formula (G1-3) can be given, for example.

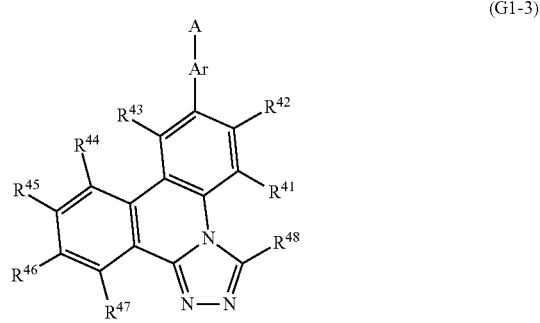

(G1-3)

In the formula, A represents a substituted or unsubstituted carbazolyl group, a substituted or unsubstituted dibenzothiophenyl group, or a substituted or unsubstituted dibenzofuranyl group, $R^{41}$ to $R^{48}$ separately represent hydrogen, an alkyl group having 1 to 4 carbon atoms, or a substituted or unsubstituted aryl group having 6 to 13 carbon atoms, and Ar represents a substituted or unsubstituted arylene group having 6 to 13 carbon atoms. Note that substituents of the arylene group may be bonded to faun a ring.

One embodiment of the present invention is a triazole derivative represented by a general formula (G2-3).

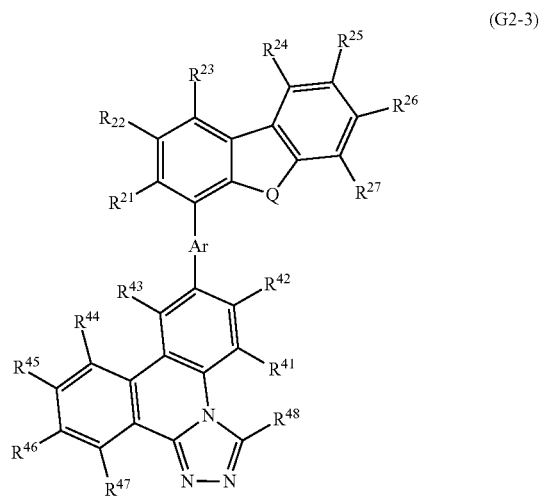

(G2-3)

In the formula, Q represents oxygen or sulfur, $R^{21}$ to $R^{27}$ and $R^{41}$ to $R^{48}$ separately represent hydrogen, an alkyl group having 1 to 4 carbon atoms, or a substituted or unsubstituted aryl group having 6 to 13 carbon atoms, and Ar represents a substituted or unsubstituted arylene group having 6 to 13 carbon atoms. Note that substituents of the arylene group may be bonded to form a ring.

One embodiment of the present invention is a triazole derivative represented by a general formula (G3-3).

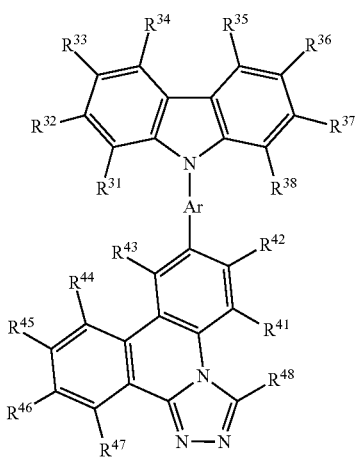
(G3-3)

In the formula, $R^{31}$ to $R^{38}$ and $R^{41}$ to $R^{48}$ separately represent hydrogen, an alkyl group having 1 to 4 carbon atoms, or a substituted or unsubstituted aryl group having 6 to 13 carbon atoms, and Ar represents a substituted or unsubstituted arylene group having 6 to 13 carbon atoms. Note that substituents of the arylene group may be bonded to faun a ring.

In any triazole derivative illustrated above, Ar is preferably a substituted or unsubstituted phenylene group or a substituted or unsubstituted biphenyldiyl group, more preferably a substituted or unsubstituted phenylene group, for ease of synthesis.

As specific structures of $R^1$ to $R^6$, $R^{11}$ to $R^{18}$, $R^{21}$ to $R^{27}$, $R^{31}$ to $R^{38}$ and $R^{41}$ to $R^{48}$ in a triazole derivative of one embodiment of the present invention, substituents represented by any of structural formulae (1-1) to (1-23) can be given, for example.

H— (1-1)

CH₃— (1-2)

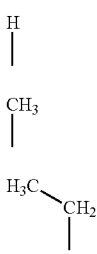
(1-3)

(1-4)

(1-5)

(1-6)

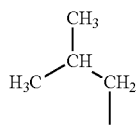
(1-7)

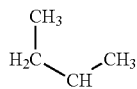
(1-8)

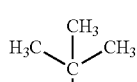
(1-9)

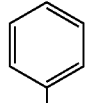
(1-10)

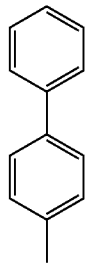
(1-11)

(1-12)

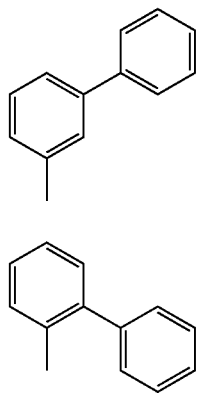
(1-13)

(1-14)

(1-15)

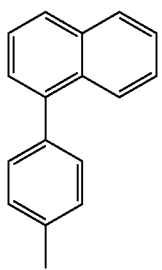
(1-16)
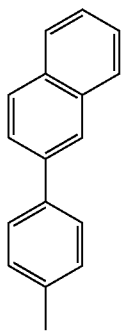
(1-17)
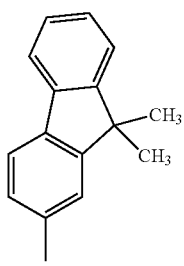
(1-18)
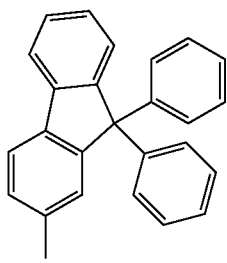
(1-19)
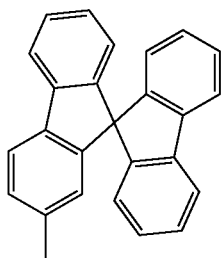
(1-20)
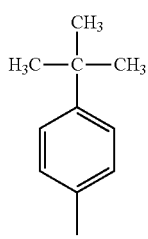
(1-21)
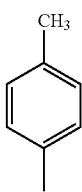
(1-22)
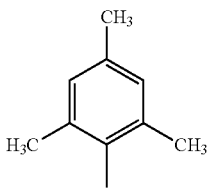
(1-23)
As specific structures of Ar in a triazole derivative of one embodiment of the present invention, substituents represented by any of structural formulae (2-1) to (2-15) can be given, for example.
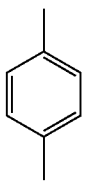
(2-1)
(2-2)
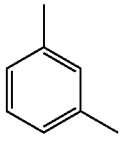
(2-3)
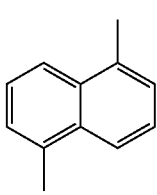
(2-4)
(2-5)
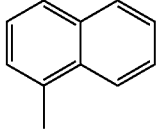
(2-6)

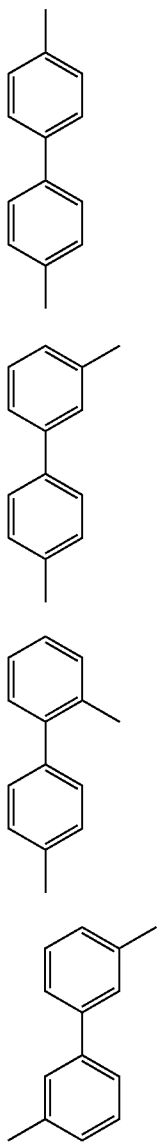
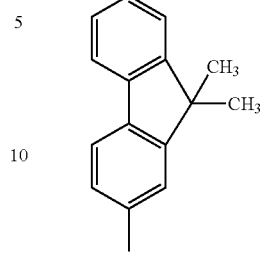
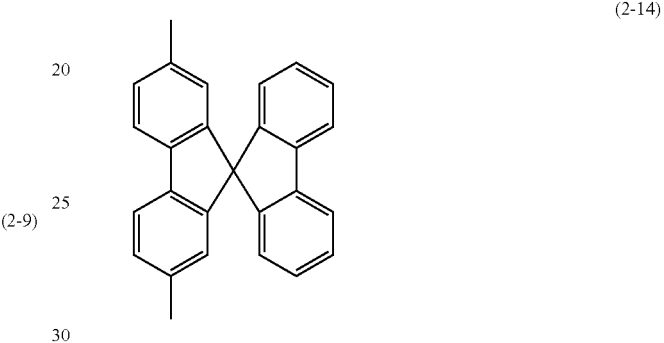
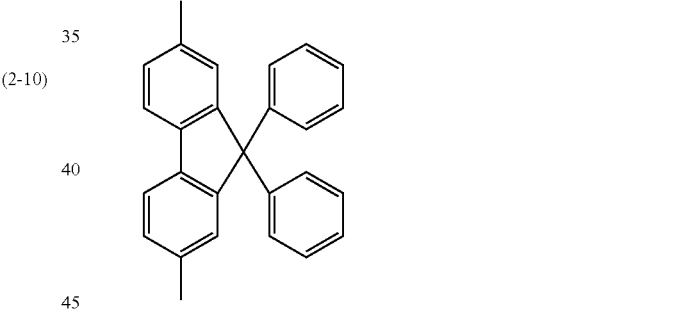
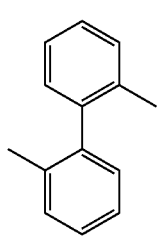
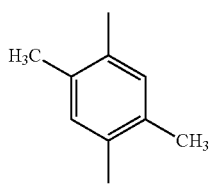
(2-7)
(2-8)
(2-9)
(2-10)
(2-11)
(2-12)
(2-13)
(2-14)
(2-15)
As a triazole derivative of one embodiment of the present invention, a triazole derivative represented by any of structural formulae (100) to (166), (200) to (266), (300) to (366), (400) to (468), (500) to (568), (600) to (668), and (1000) to (1027) can be given, for example. However, the present invention is not limited thereto.
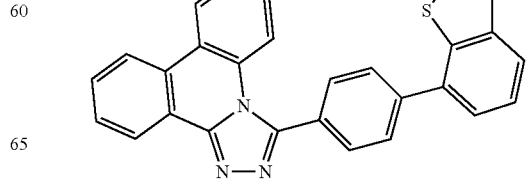
(100)

(101)
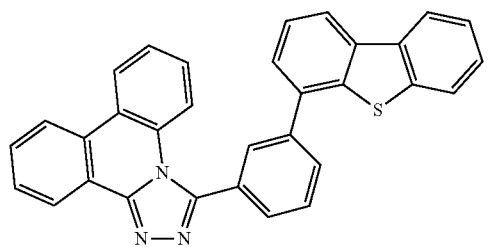
(102)
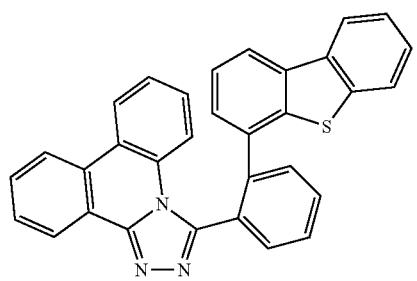
(103)
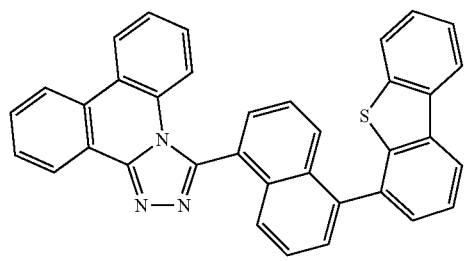
(104)
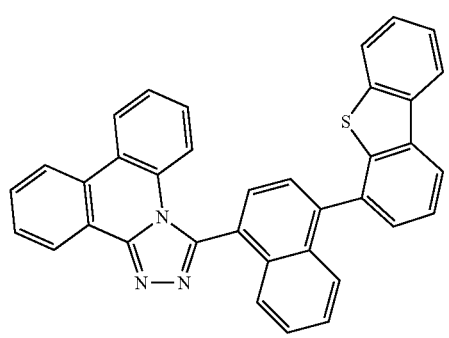
(105)
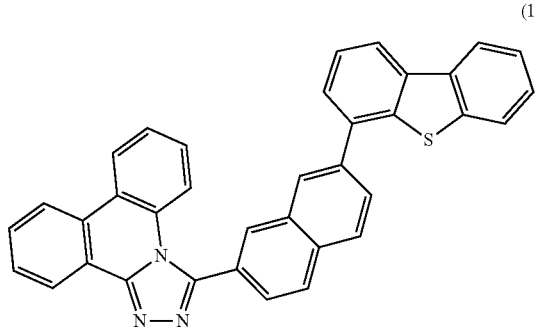
(106)
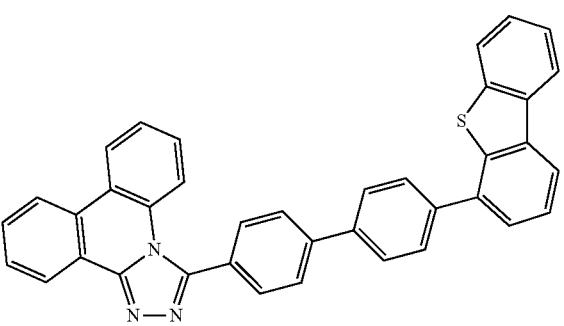
(107)
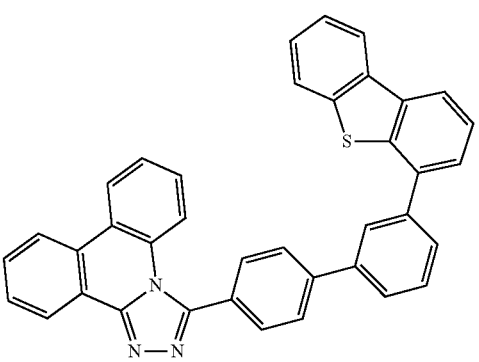
(108)
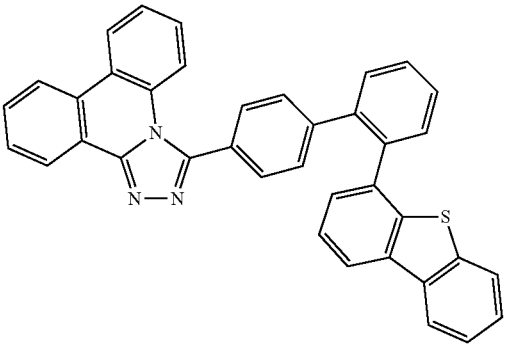
(109)
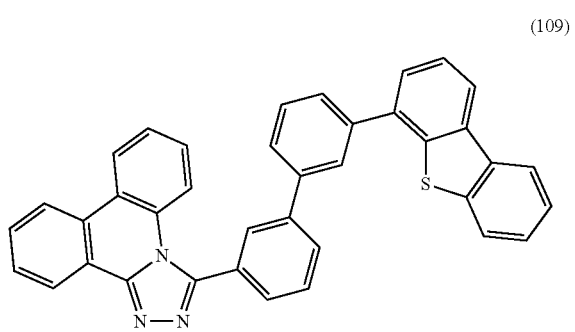

-continued
(110)
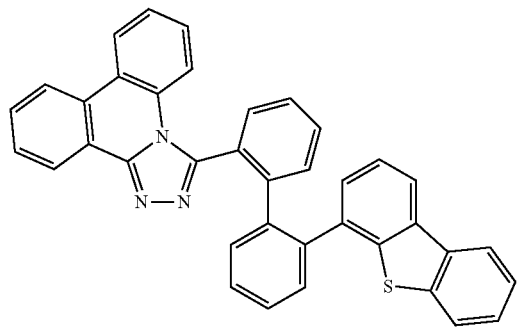
(111)
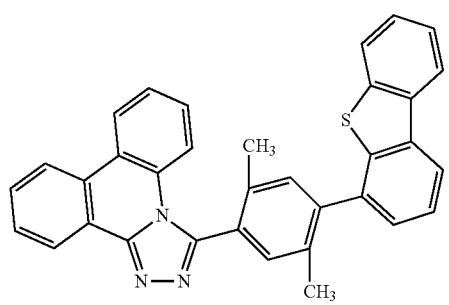
(112)
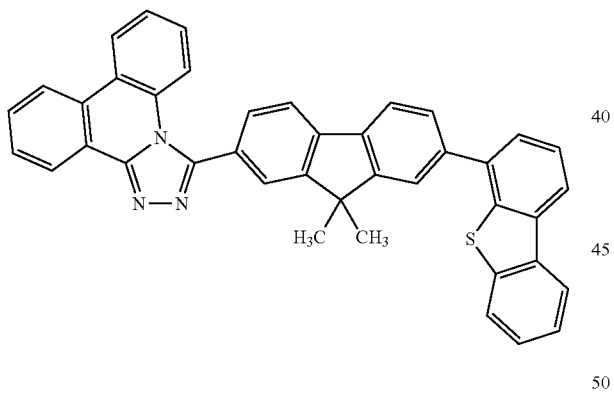
(113)
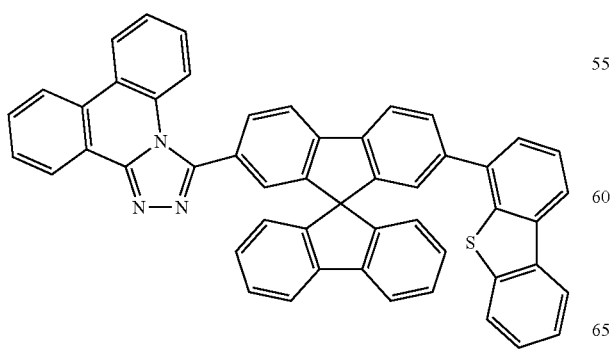
(114)
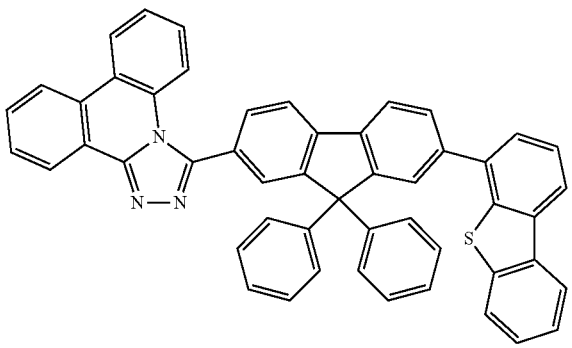
(115)
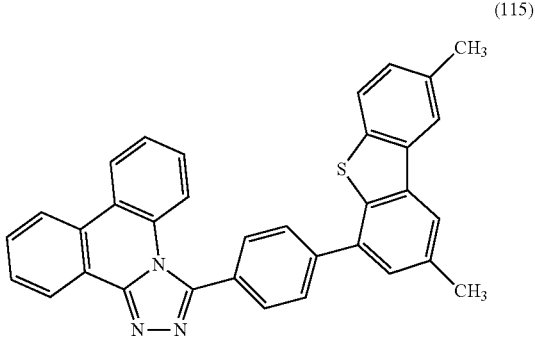
(116)
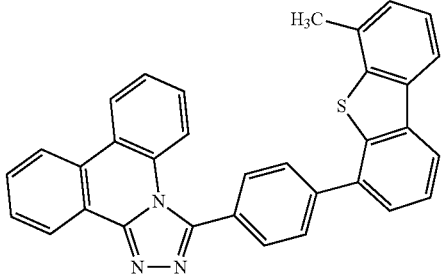
(117)
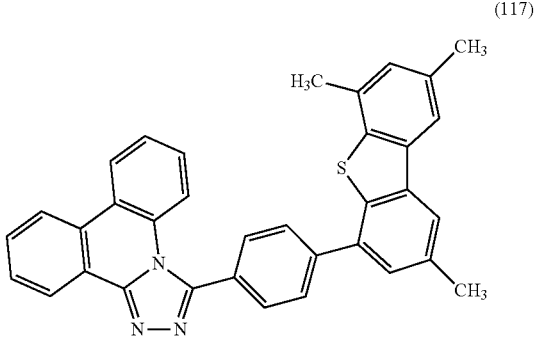

-continued
(118)
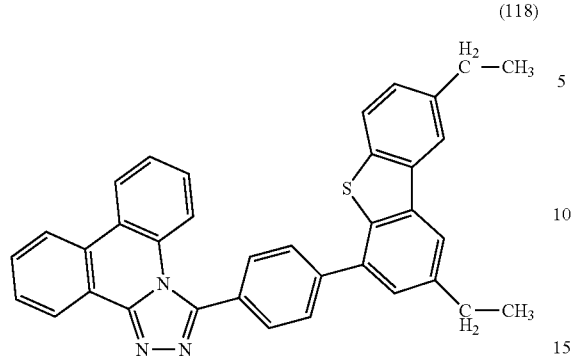
(119)
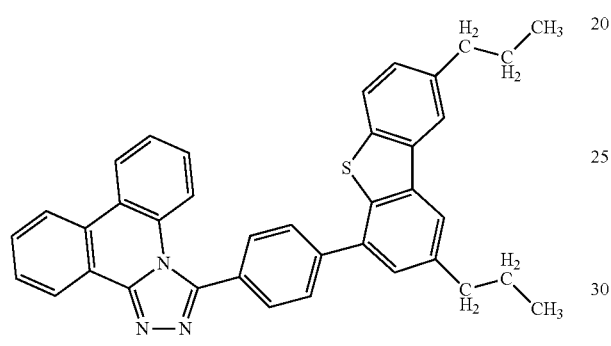
(120)
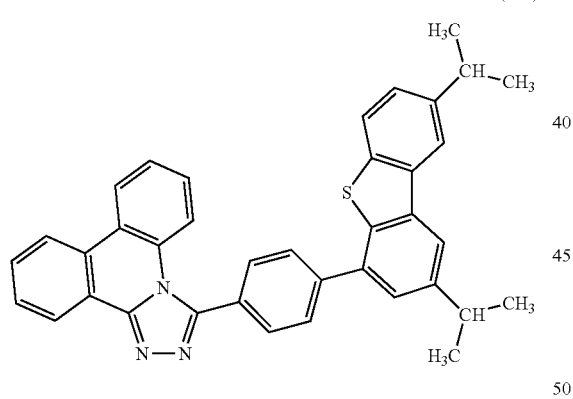
(121)
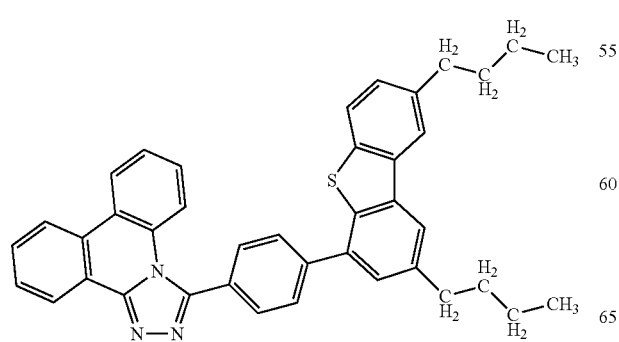
-continued
(122)
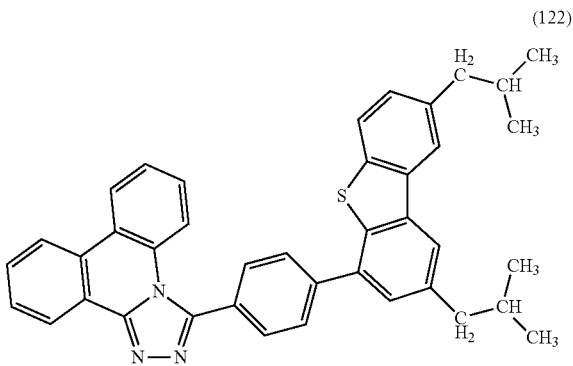
(123)
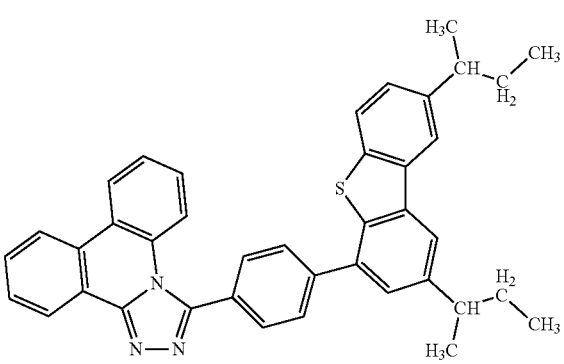
(124)
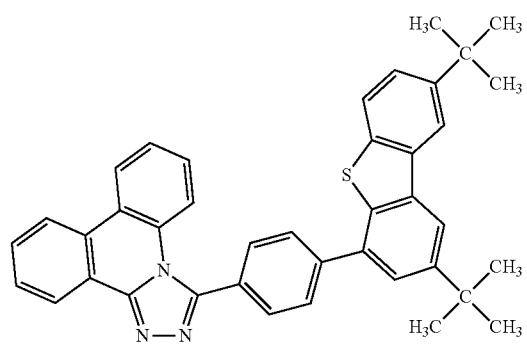
(125)
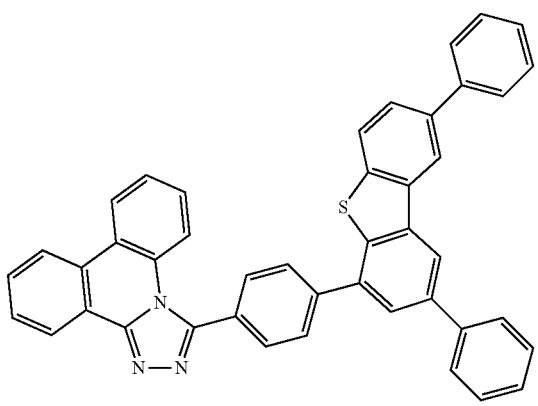

(126)
(127)
(128)
(129)
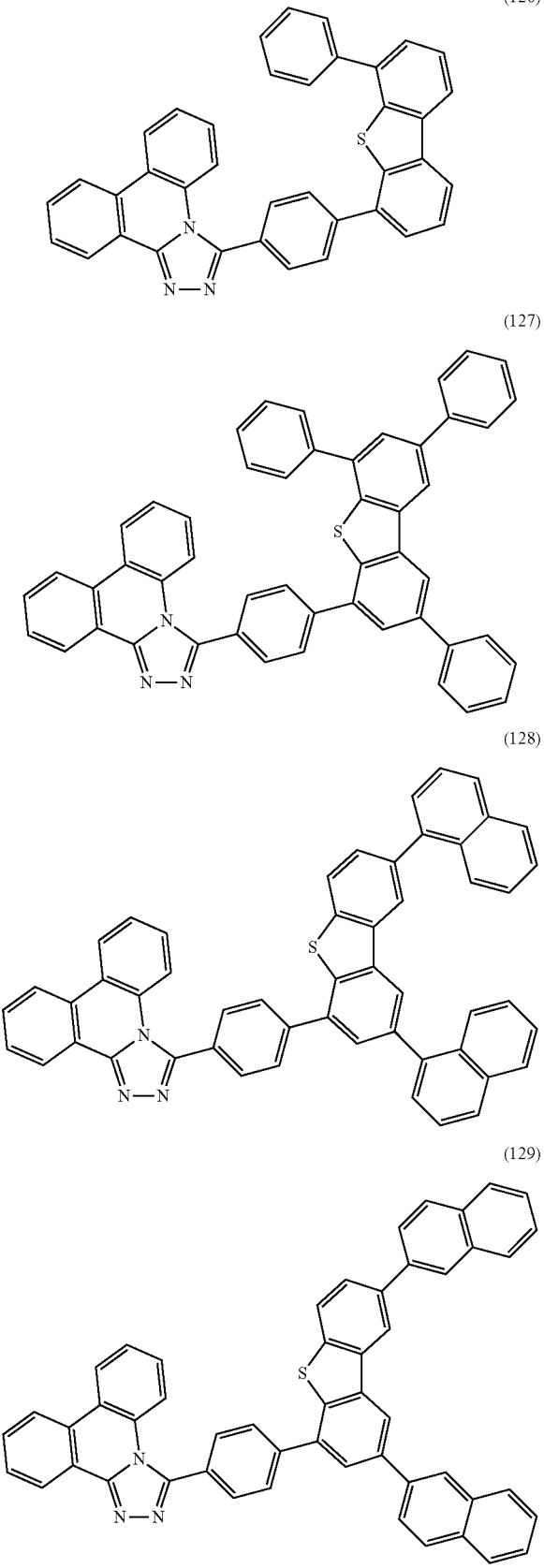
(130)
(131)
(132)
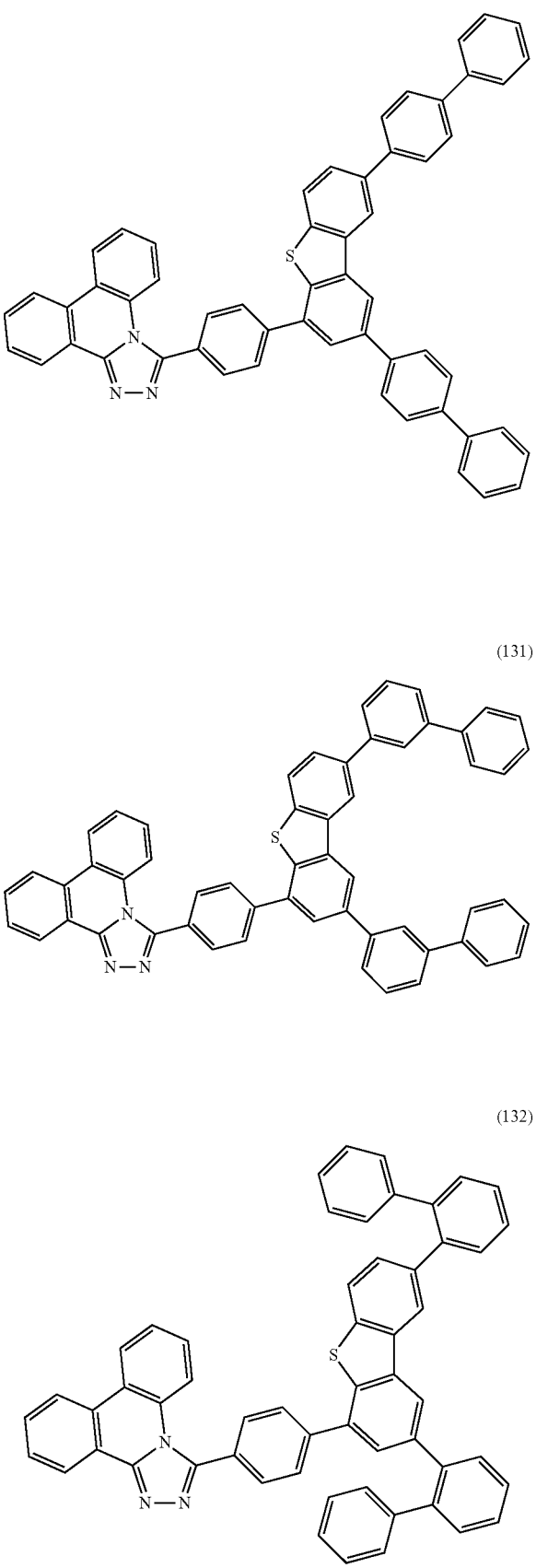

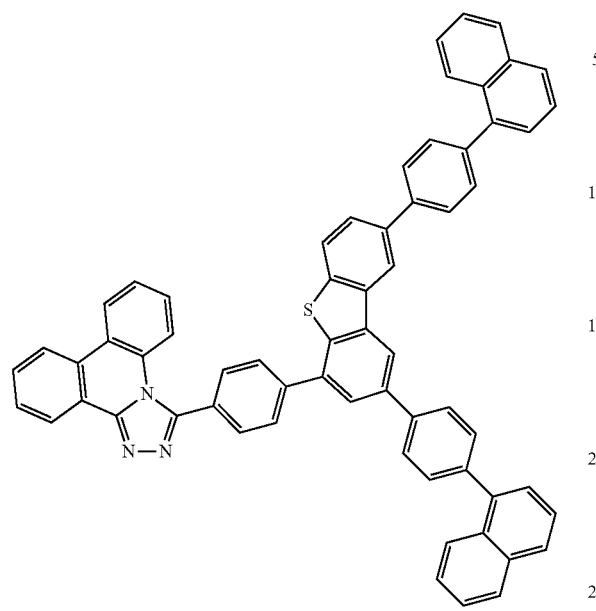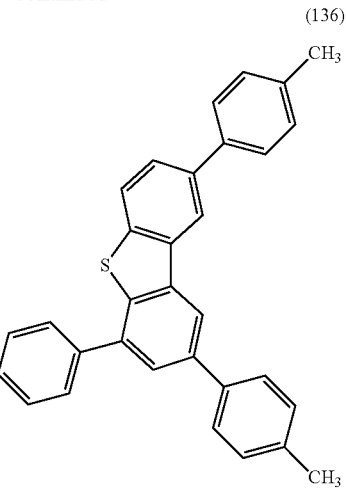

31
-continued
(139)
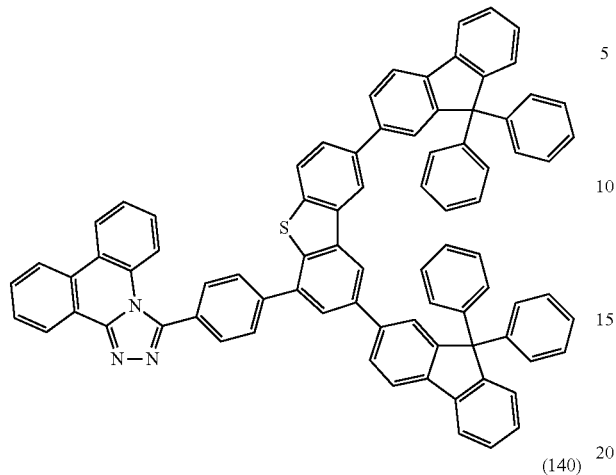
(140)
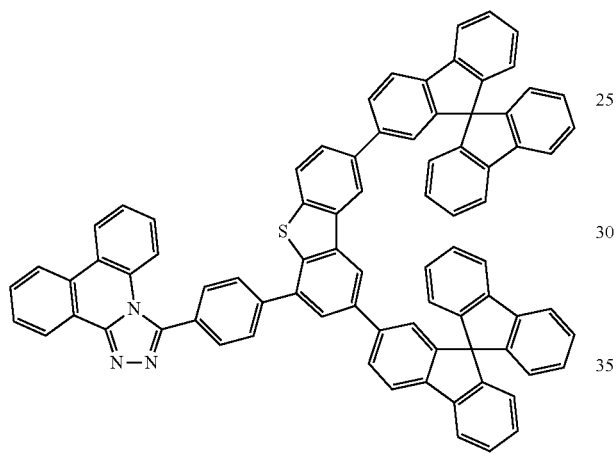
(141)
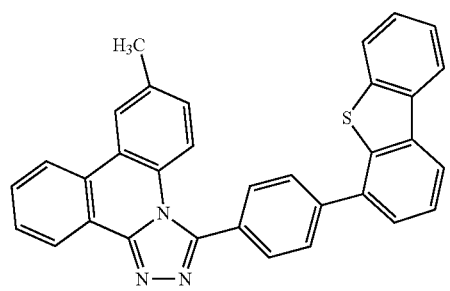
(142)
32
-continued
(143)
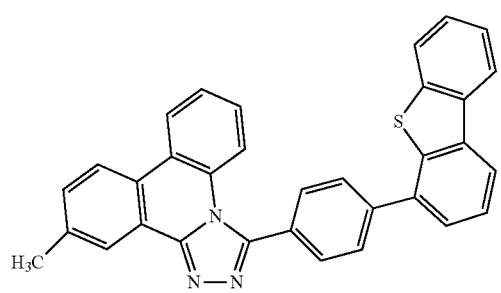
(144)
(145)
(146)
(147)
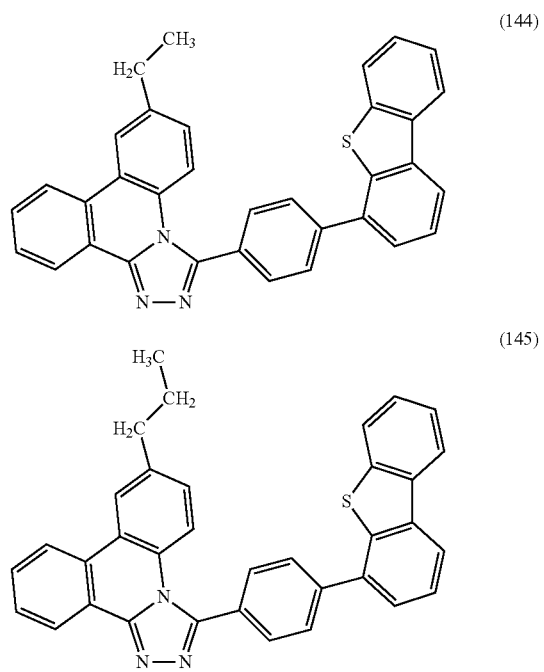

(148)
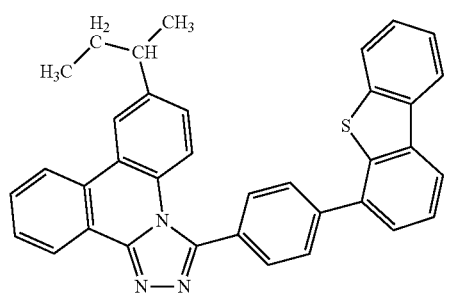
(149)
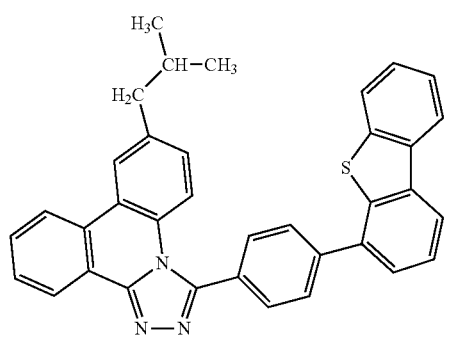
(150)
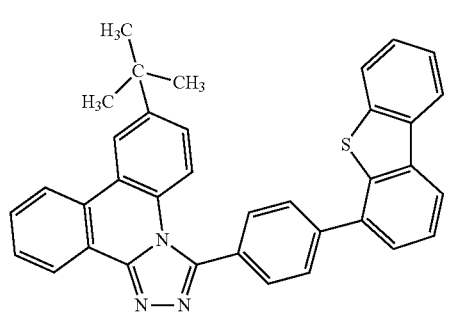
(151)
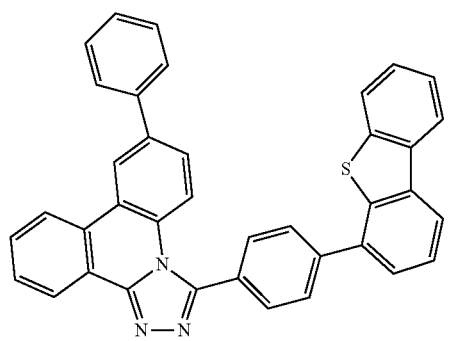
(152)
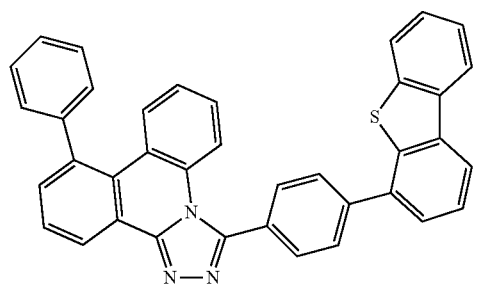
(153)
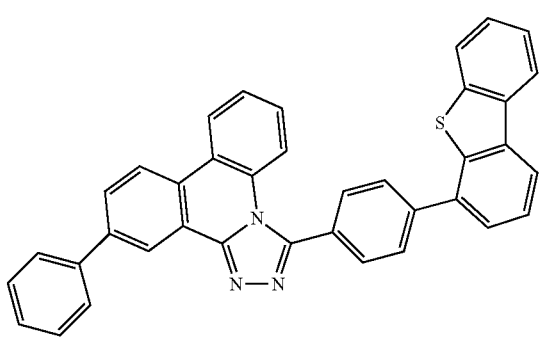
(154)
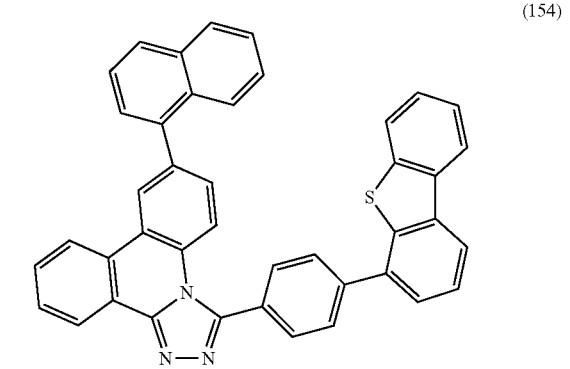
(155)
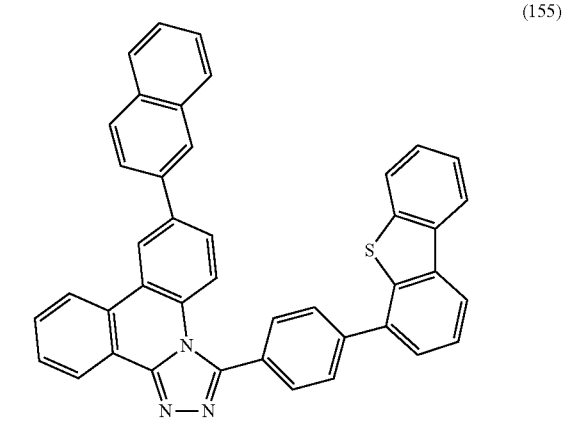
(156)
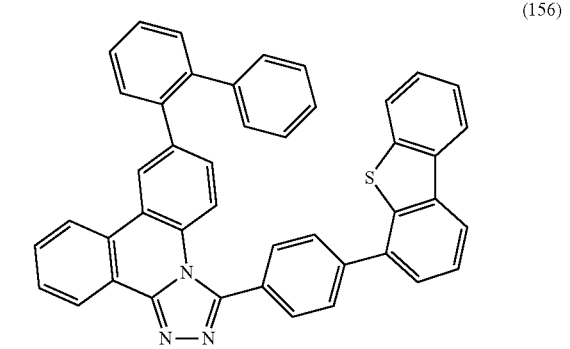

(157)
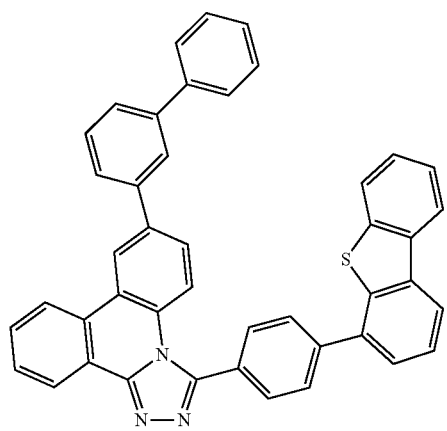
(158)
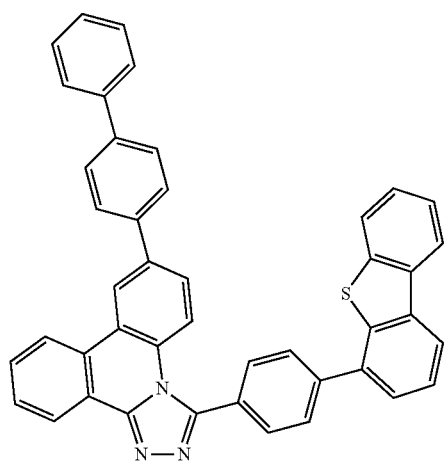
(159)
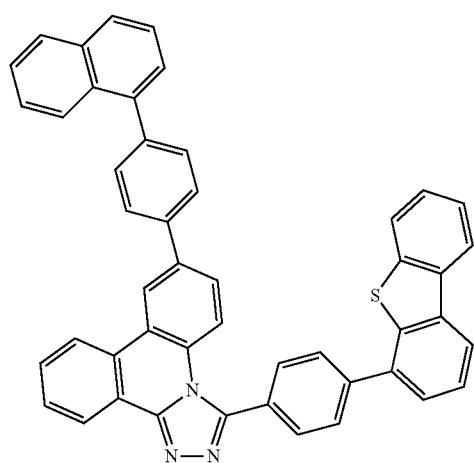
(160)
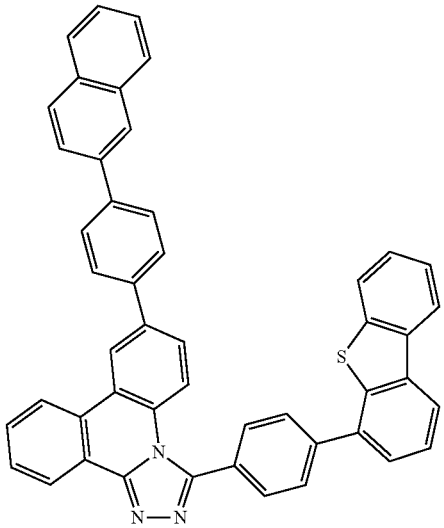
(161)
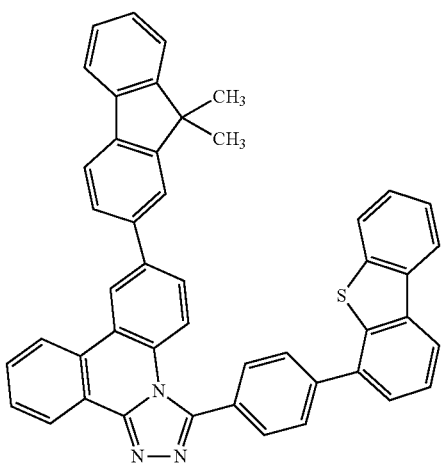
(162)
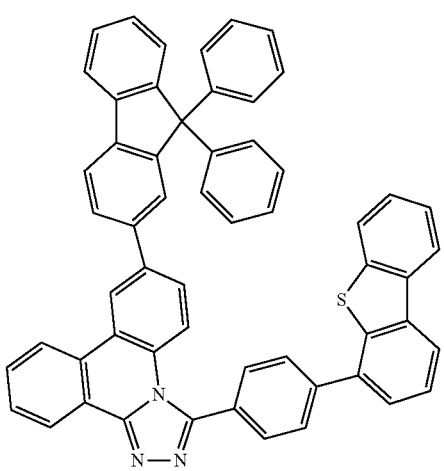

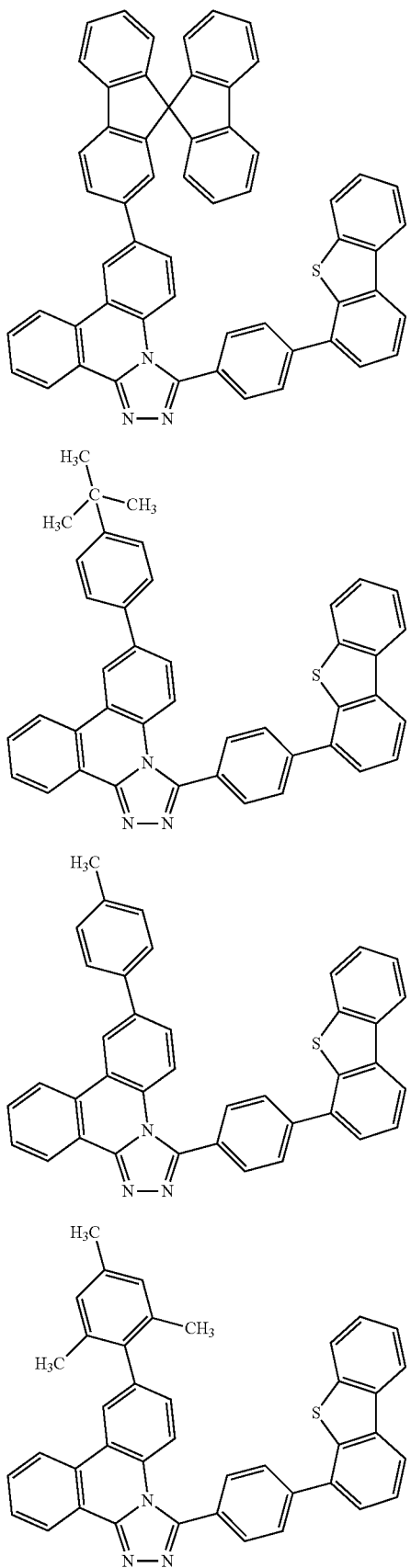
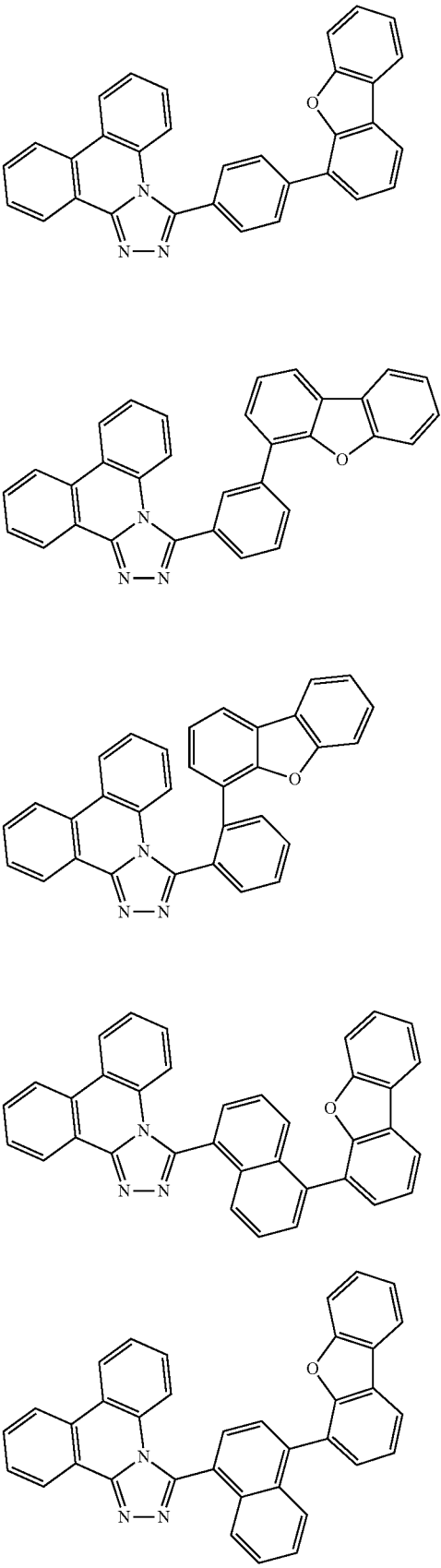

(205)
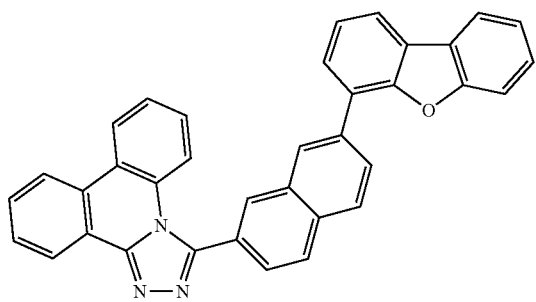
(206)
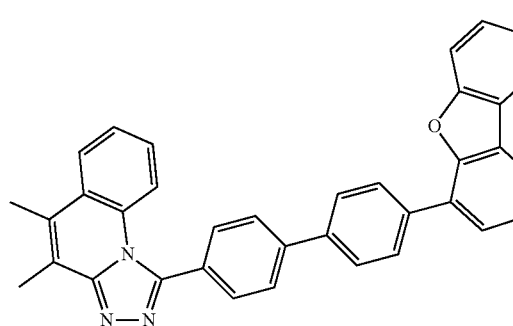
(207)
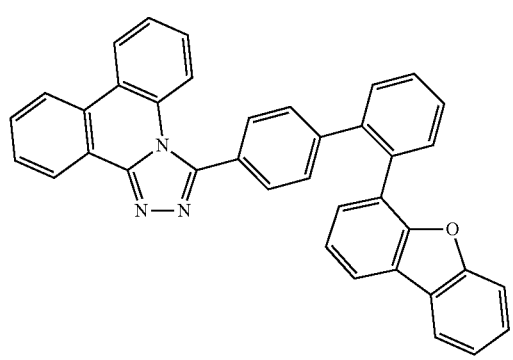
(208)
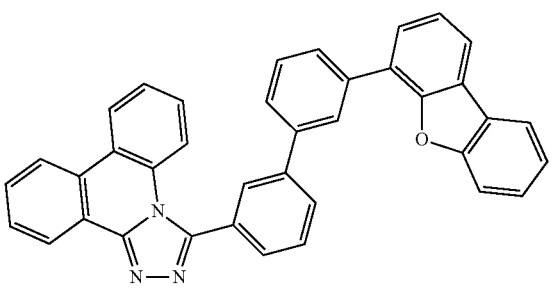
(209)
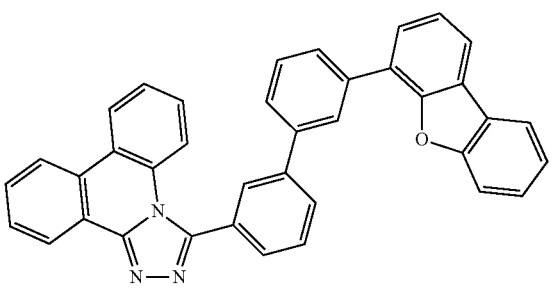
(210)
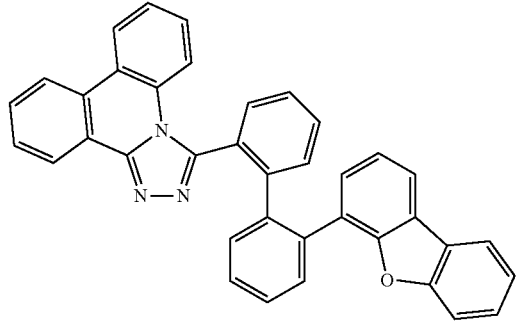
(211)
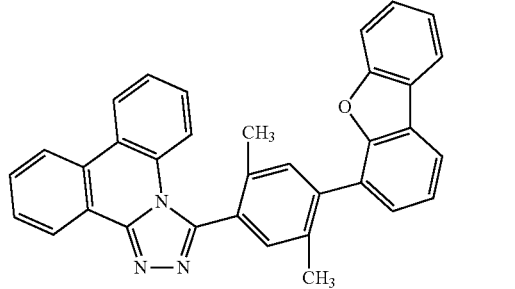
(212)
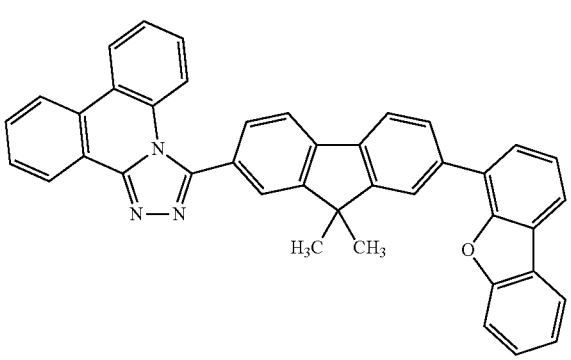

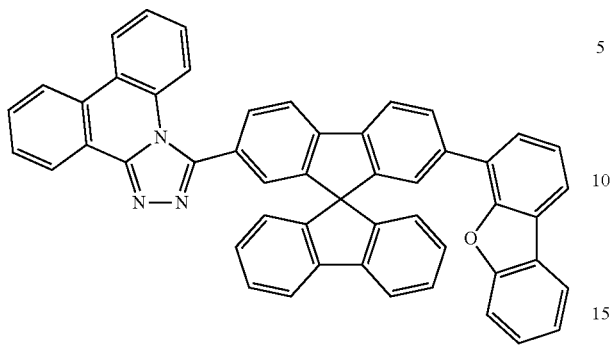
(213)
(214)
(215)
(216)
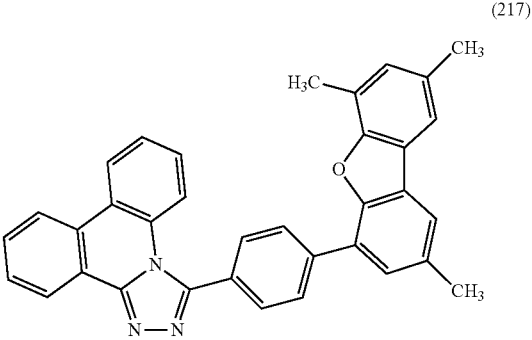
(217)
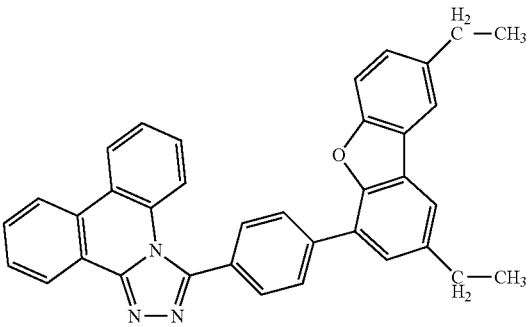
(218)
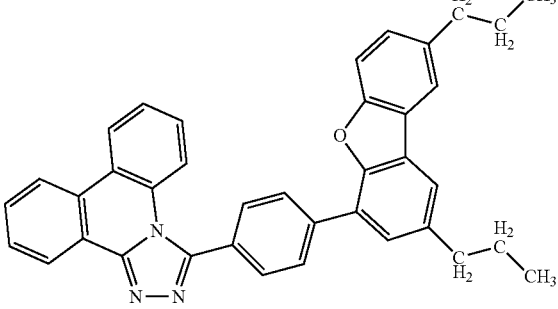
(219)
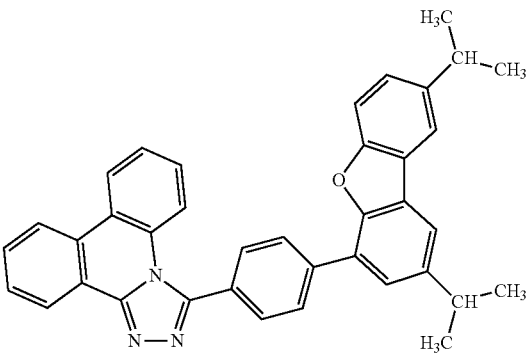
(220)

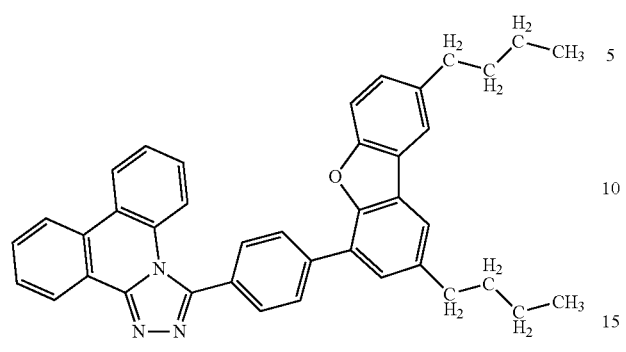
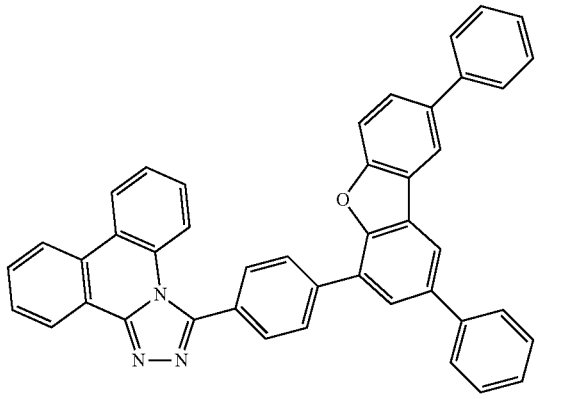

(229)
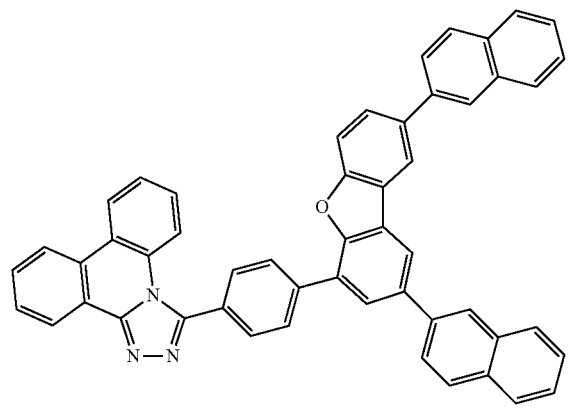
(232)
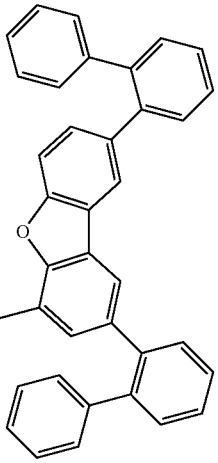
(230)
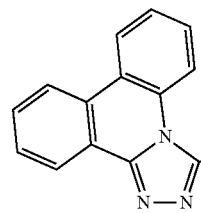
(233)
(231)
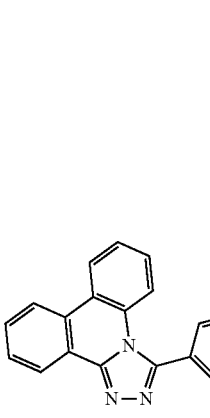
(234)
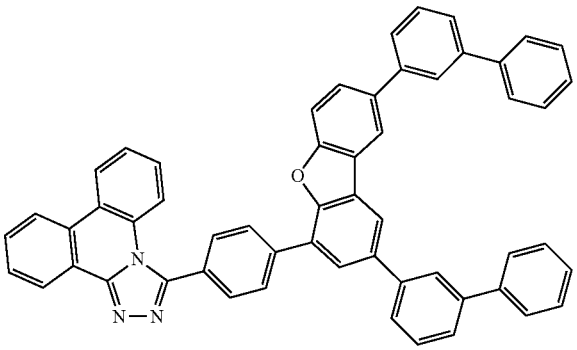

(235)
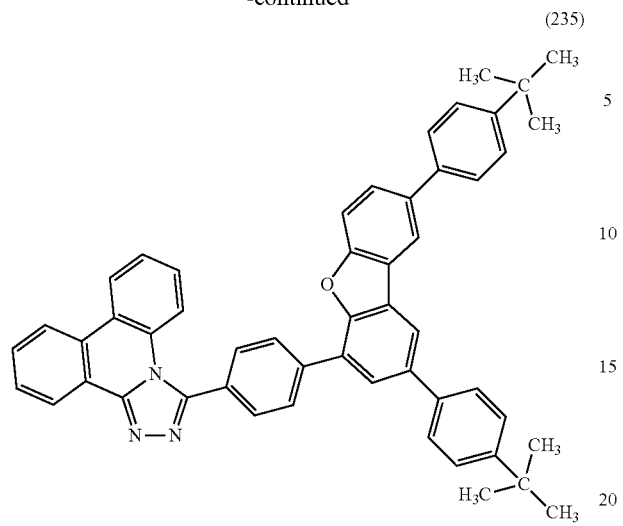
(238)
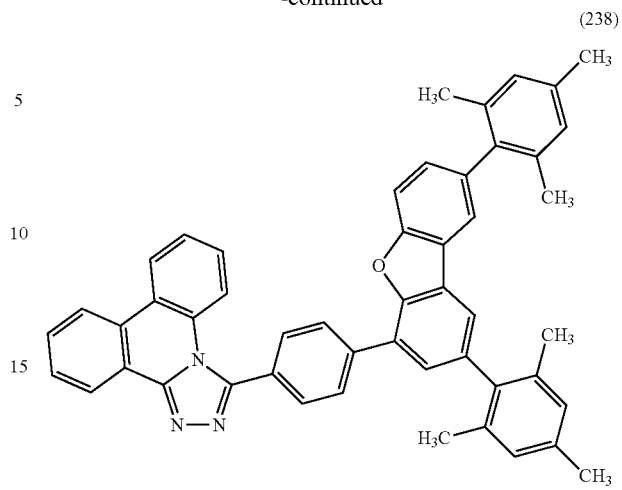
(236)
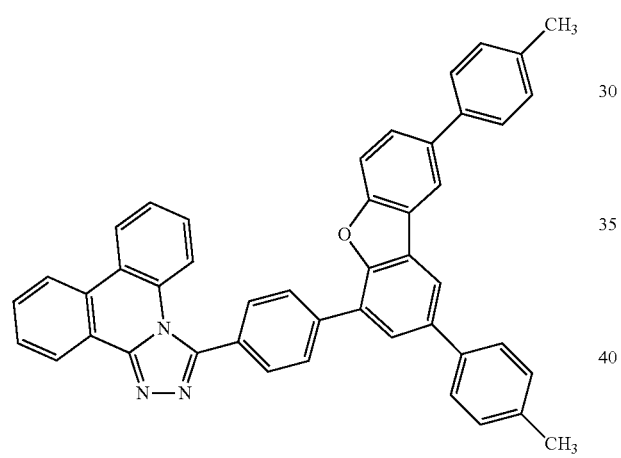
(239)
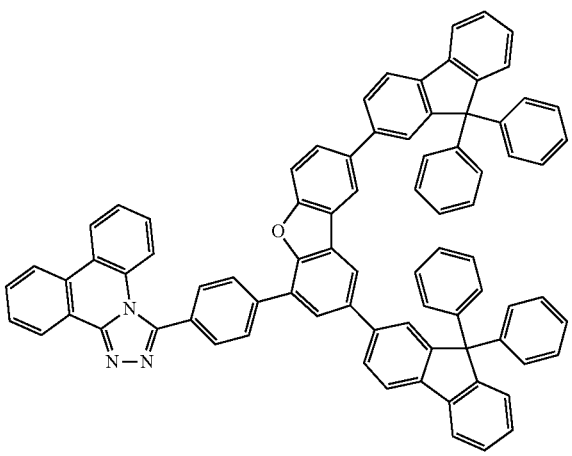
(237)
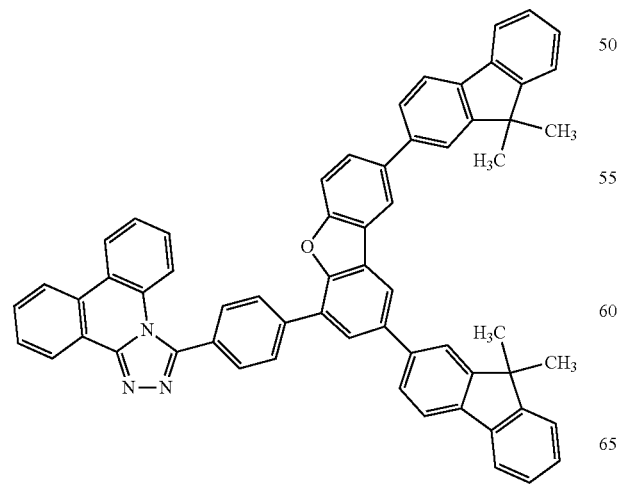
(240)
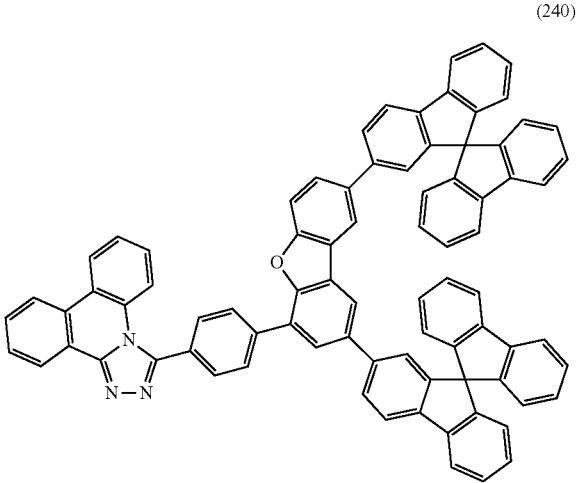

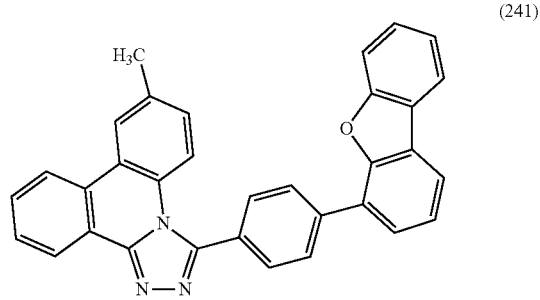
(241)
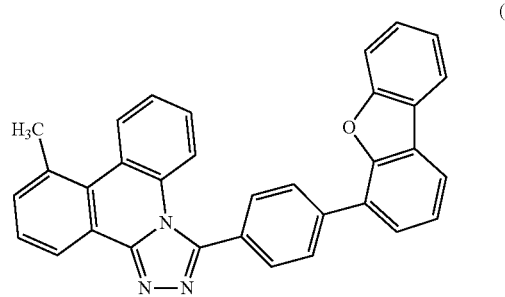
(242)
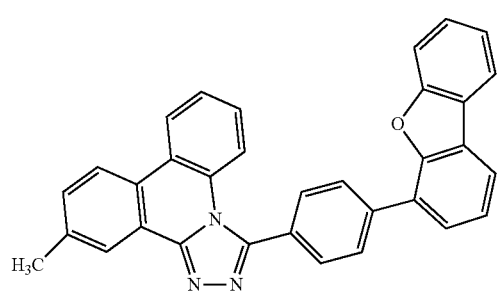
(243)
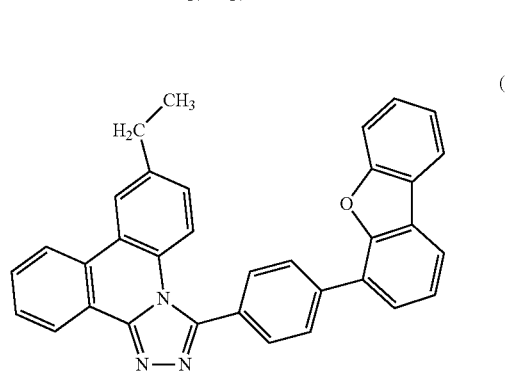
(244)
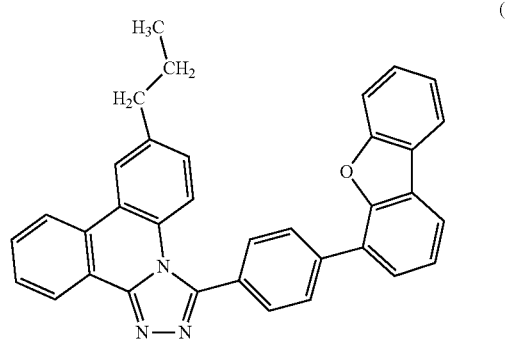
(245)
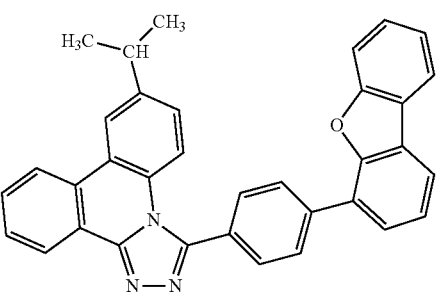
(246)
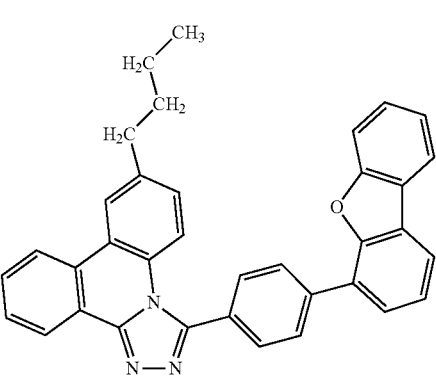
(247)
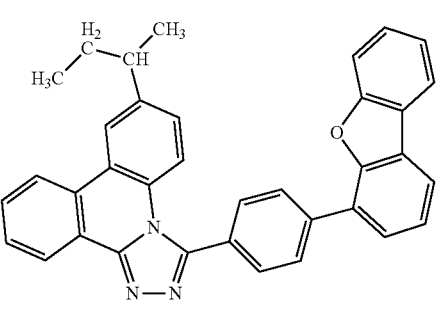
(248)
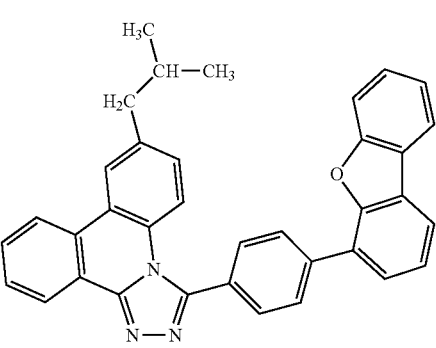
(249)
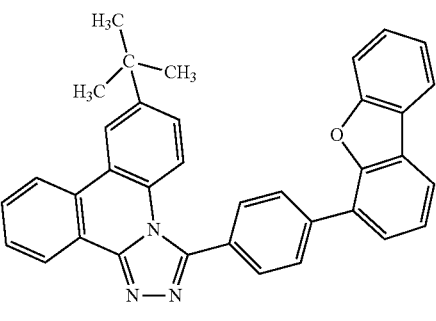
(250)

(251)
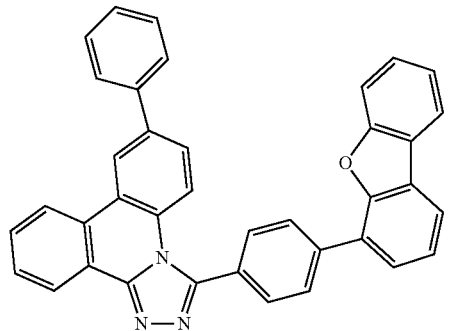
(252)
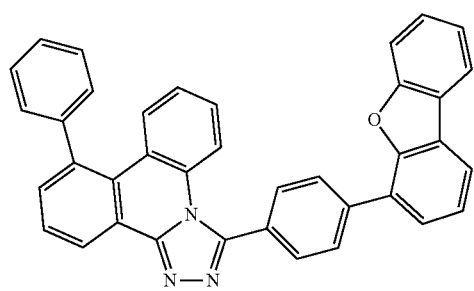
(253)
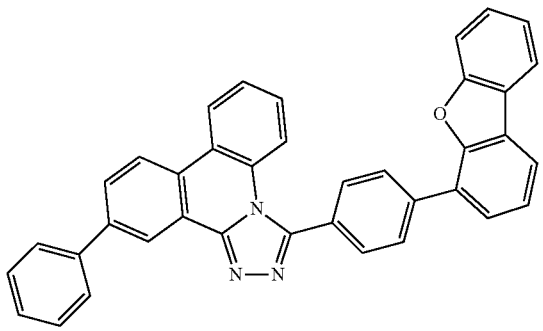
(254)
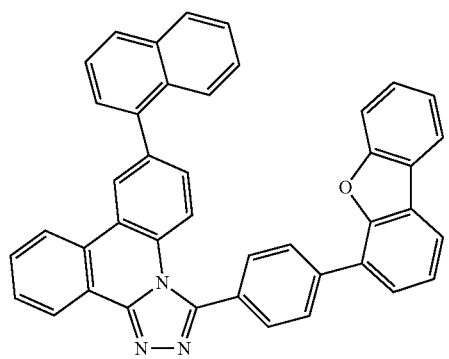
(255)
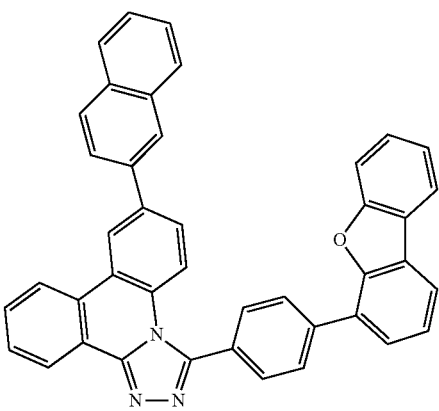
(256)
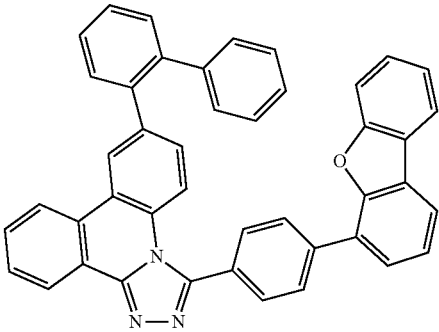
(257)
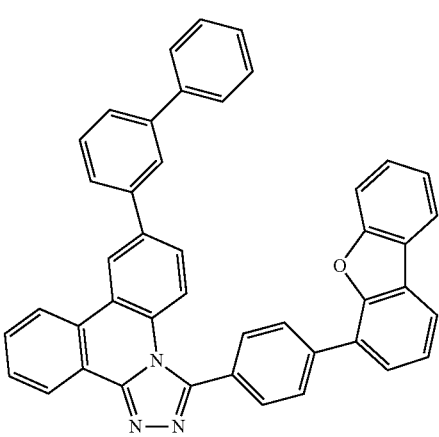
(258)
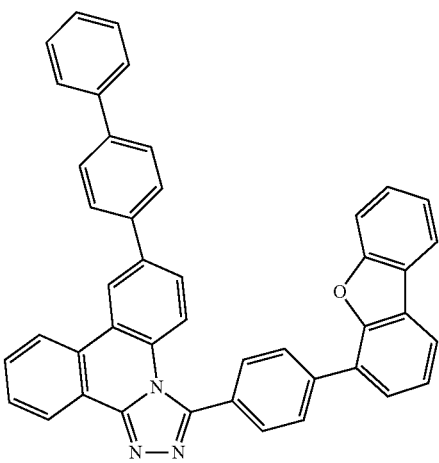

(259)
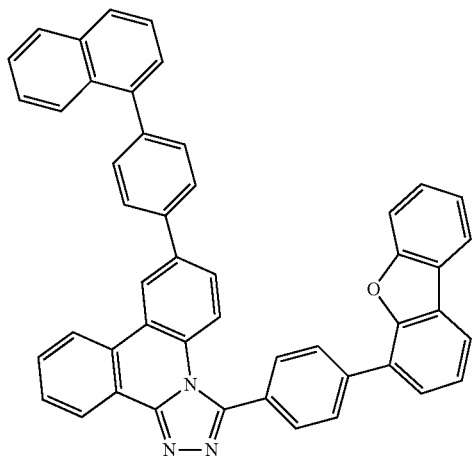
(262)
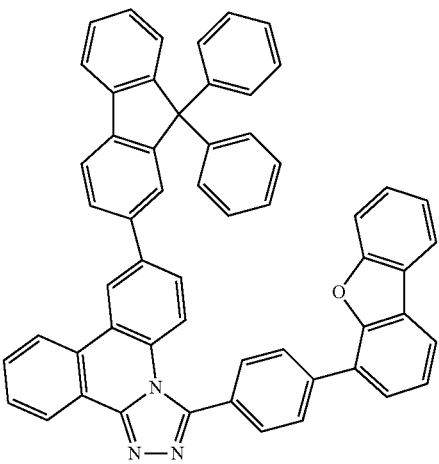
(260)
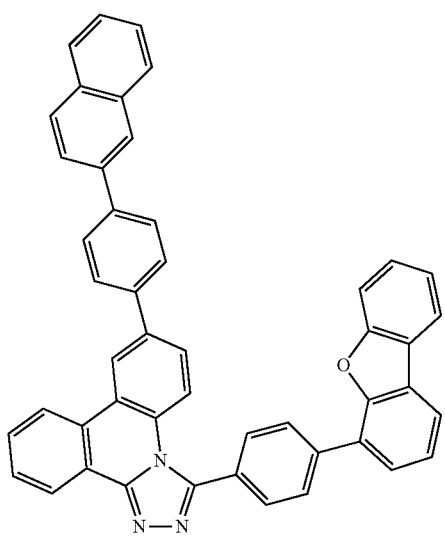
(263)
(261)
(264)
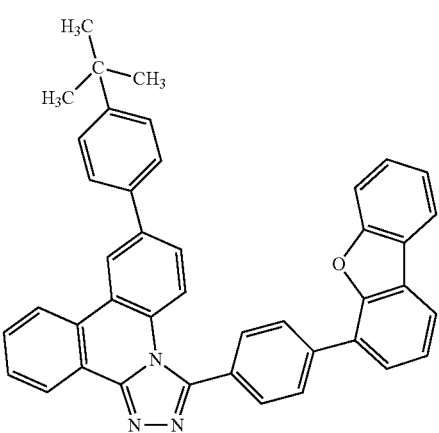

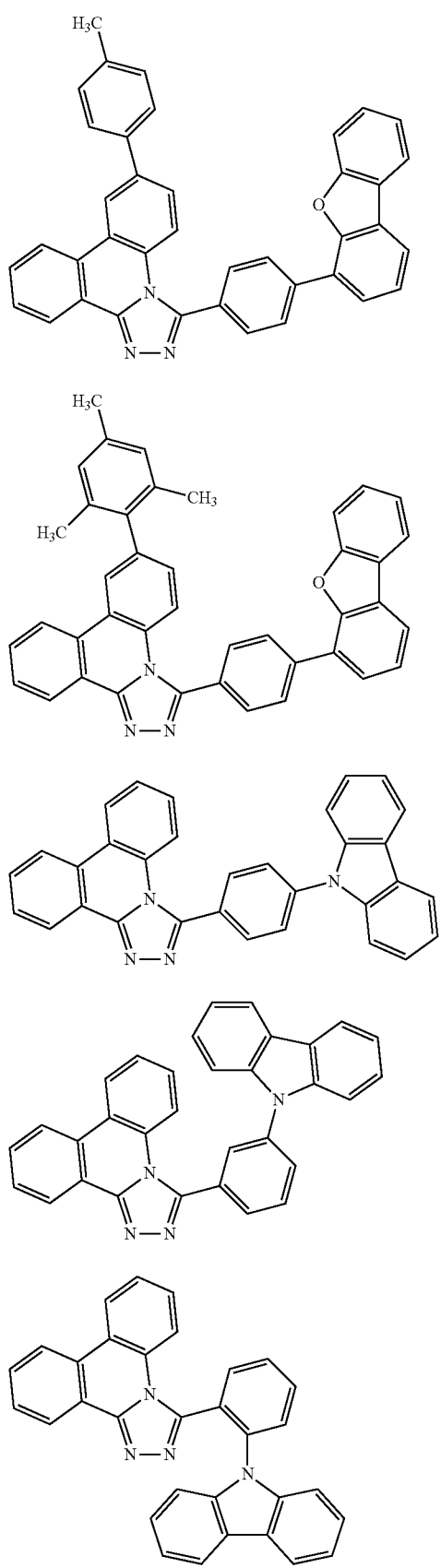
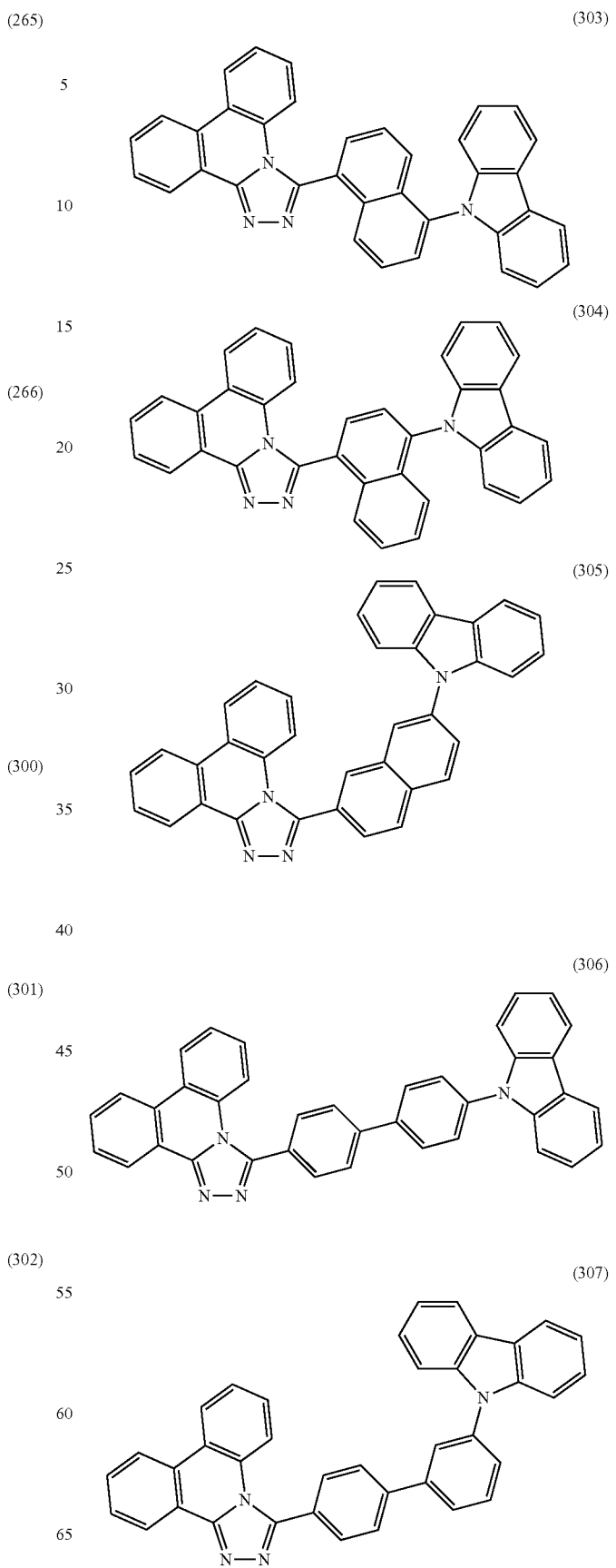

(308) 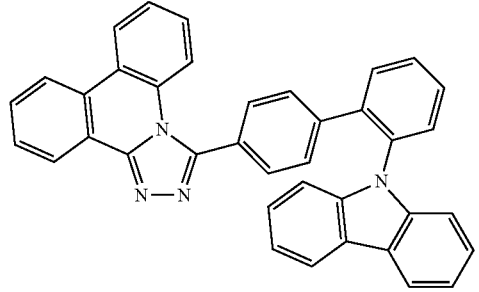
(309) 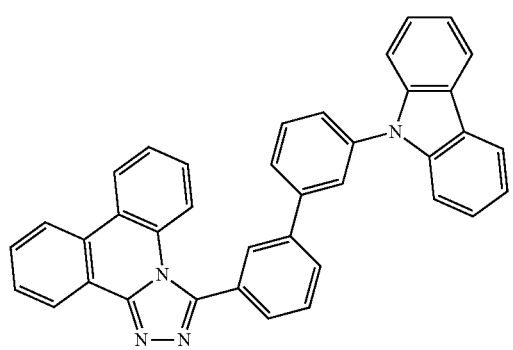
(310) 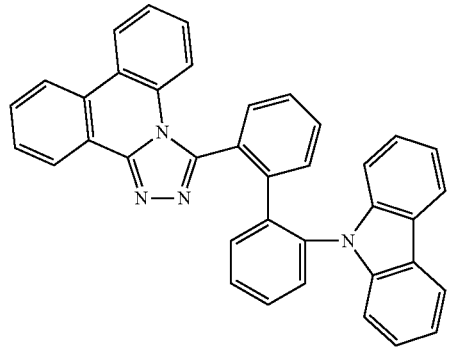
(311) 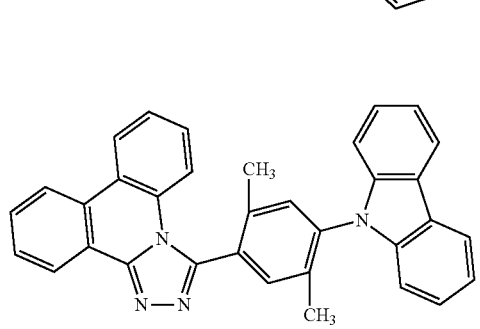
(312) 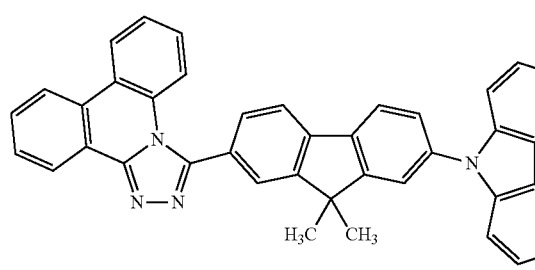
(313) 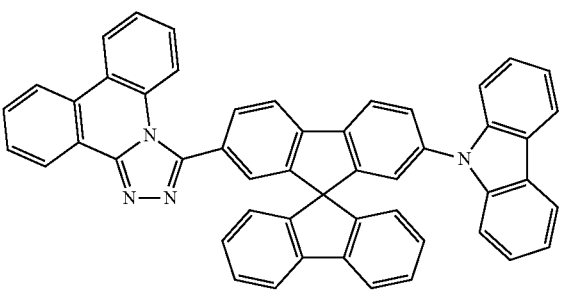
(314) 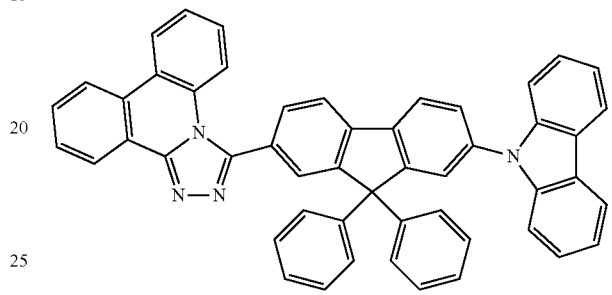
(315) 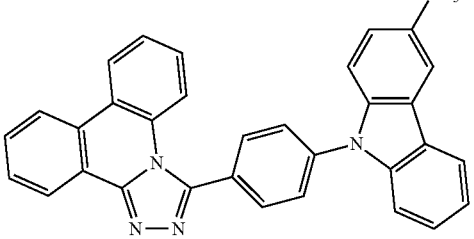
(316) 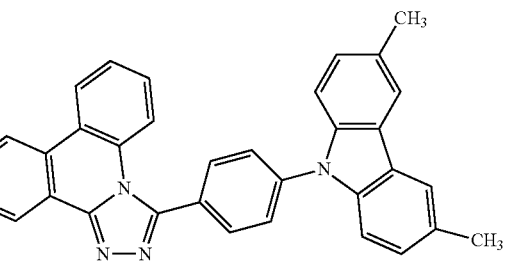
(317) 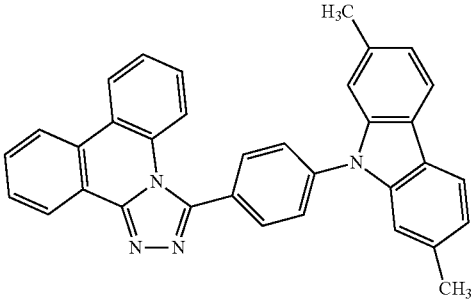

(318)
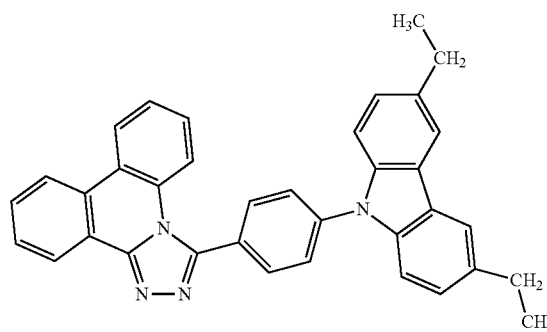
(319)
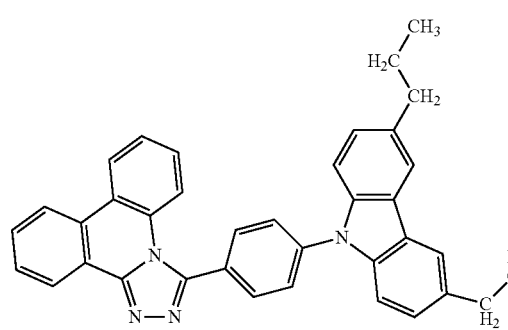
(320)
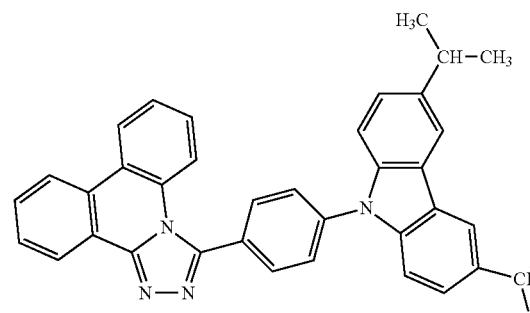
(321)
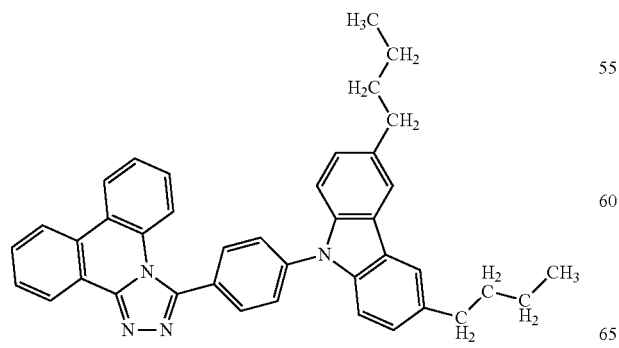
(322)
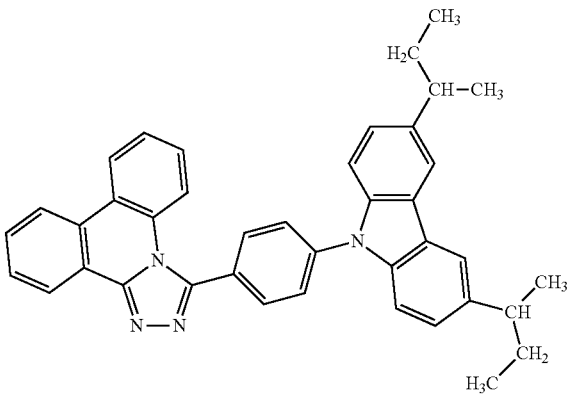
(323)
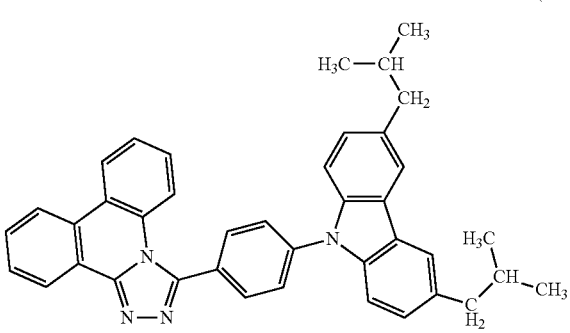
(324)
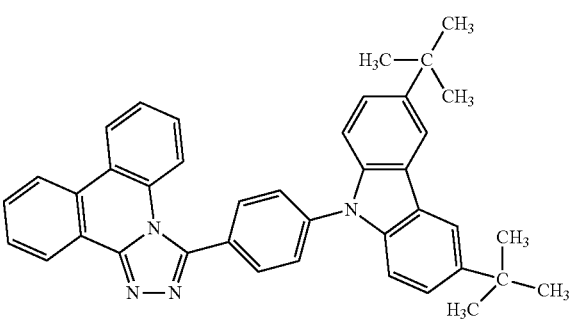
(325)
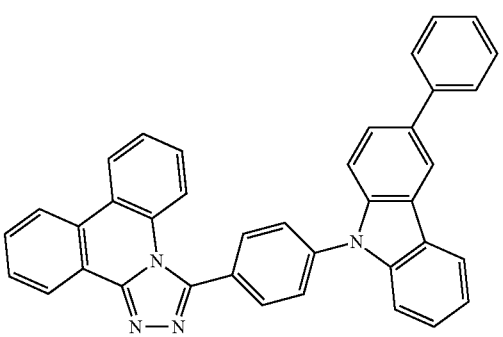

(326)
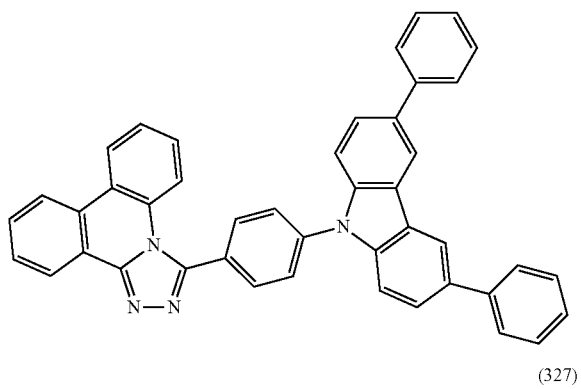
(327)
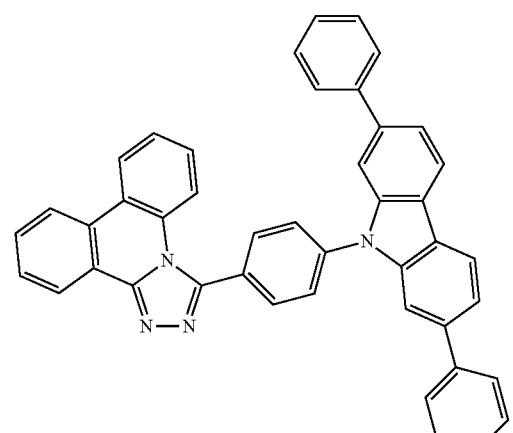
(328)
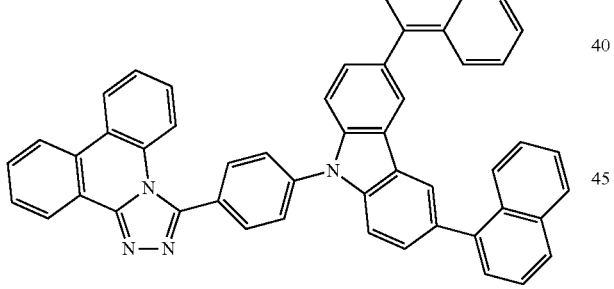
(329)
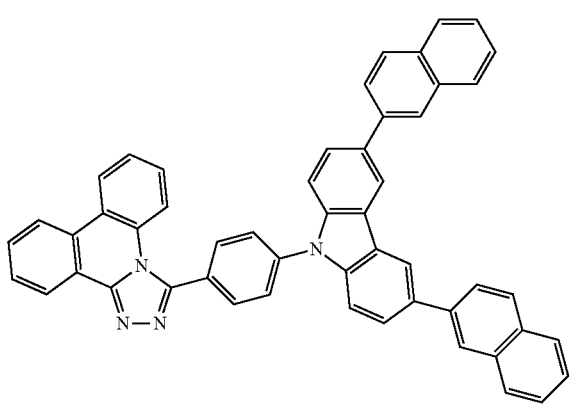
(330)
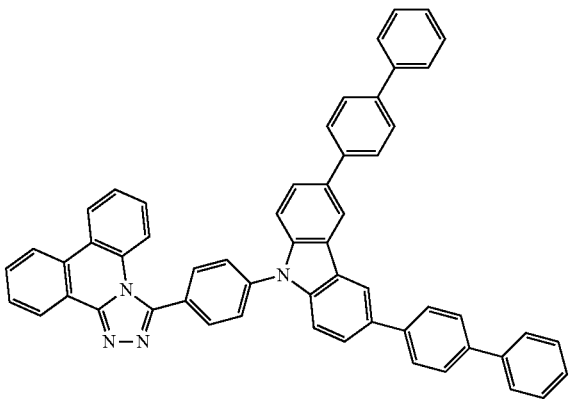
(331)
(332)
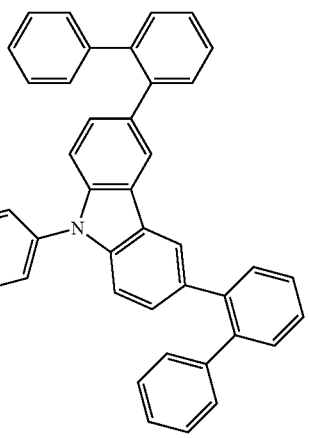

(333)
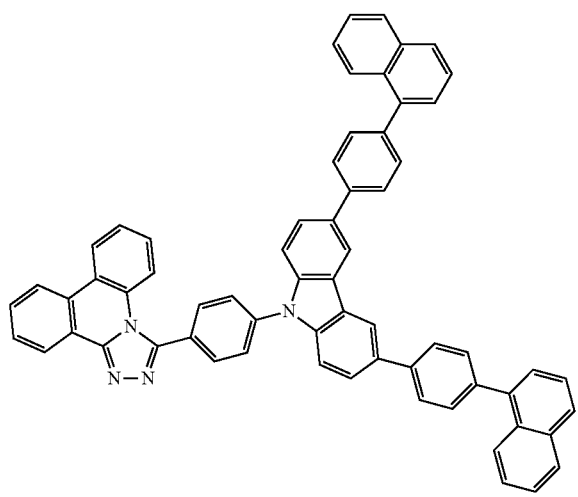
(334)
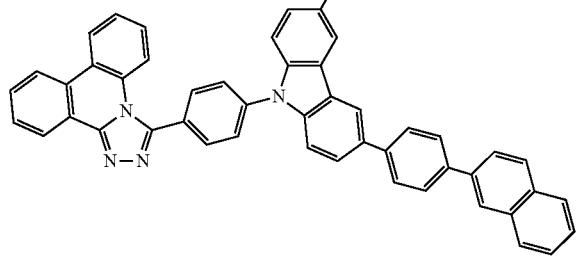
(335)
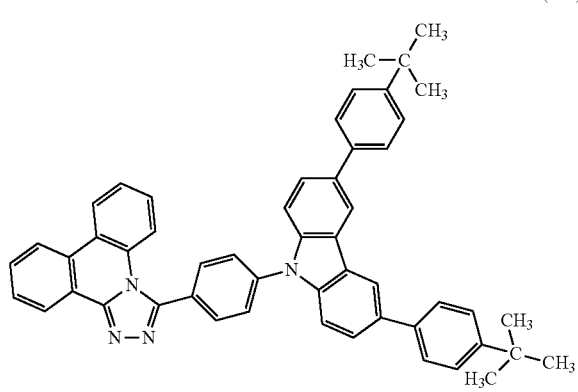
(336)
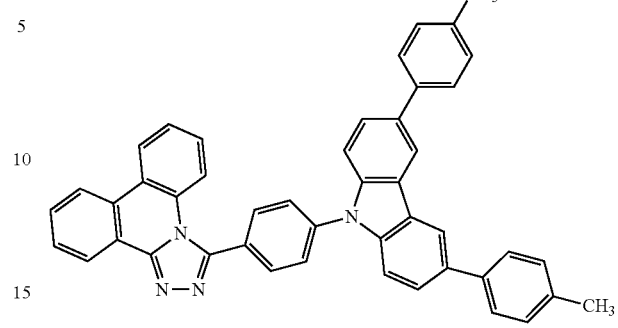
(337)
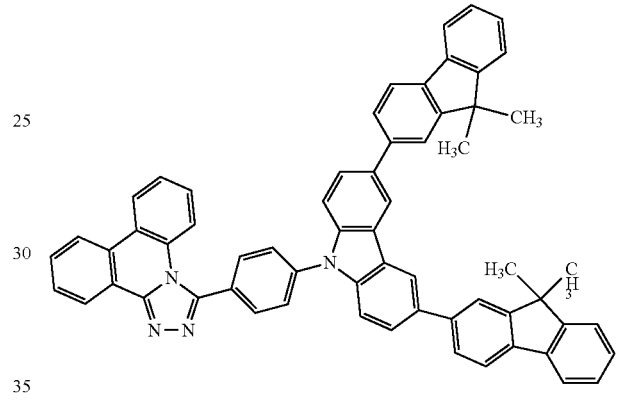
(338)
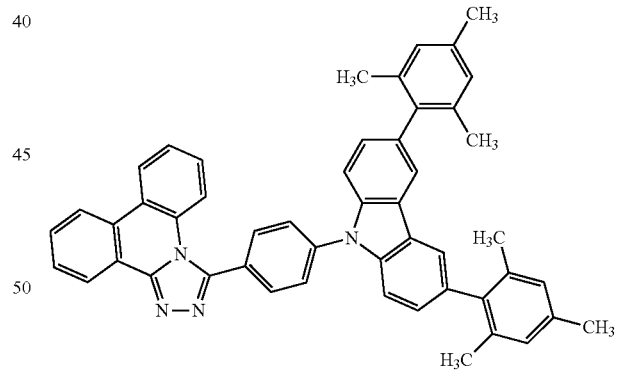
(339)
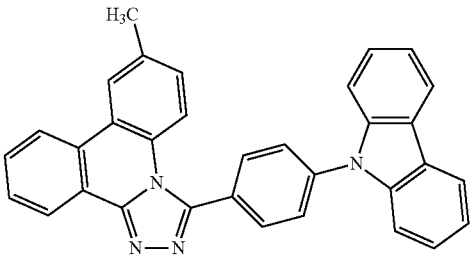

(340)
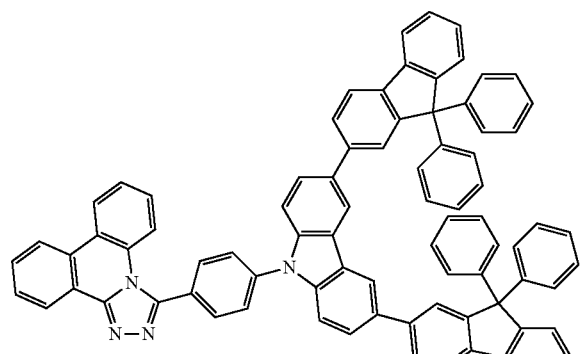
(341)
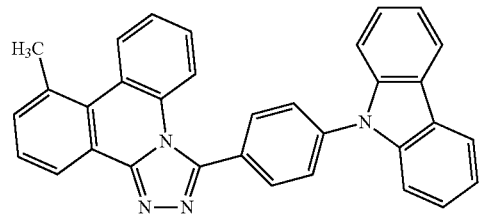
(342)
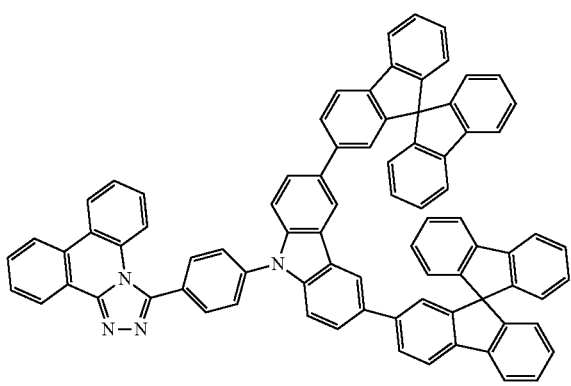
(343)
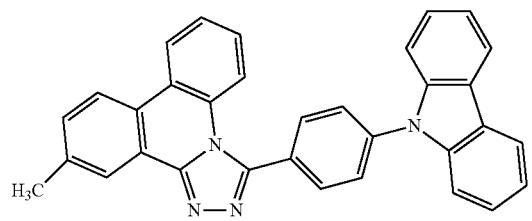
(344)
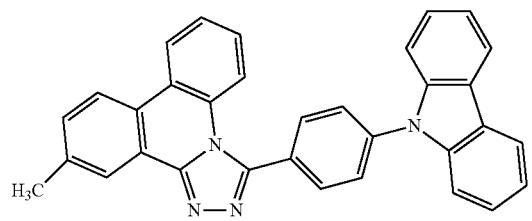
(345)
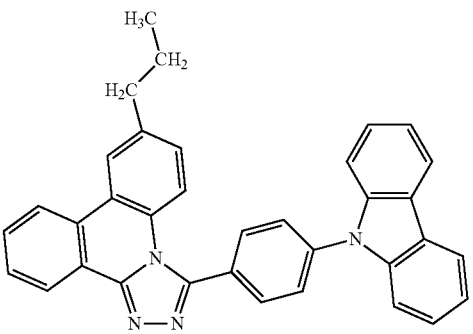
(346)
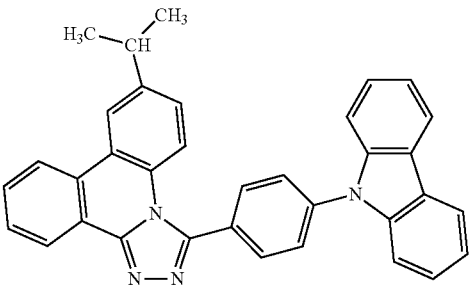
(347)
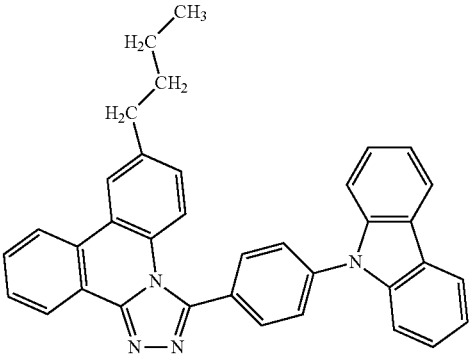
(348)
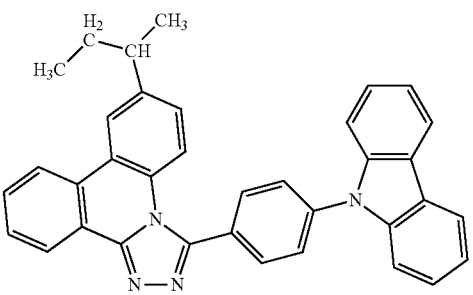
(349)
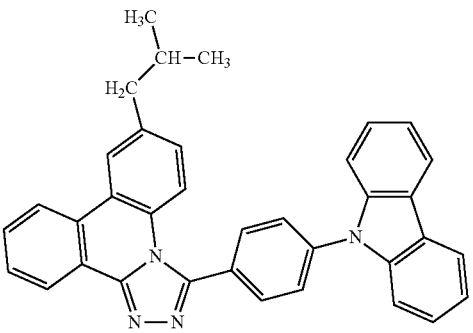

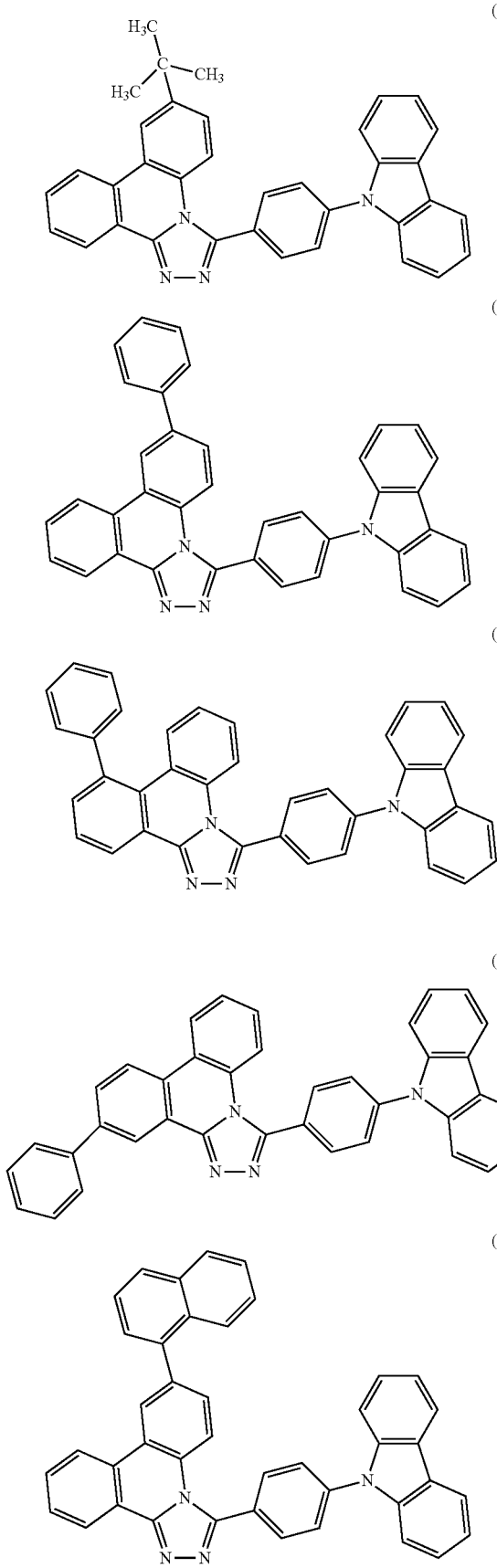
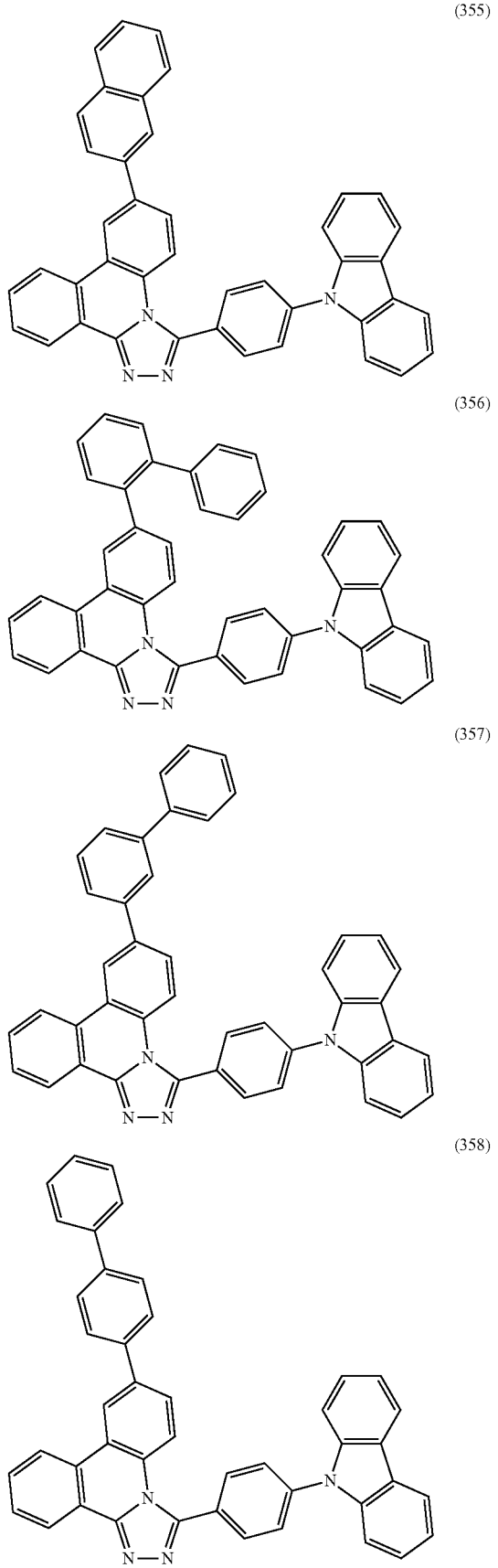

(359)
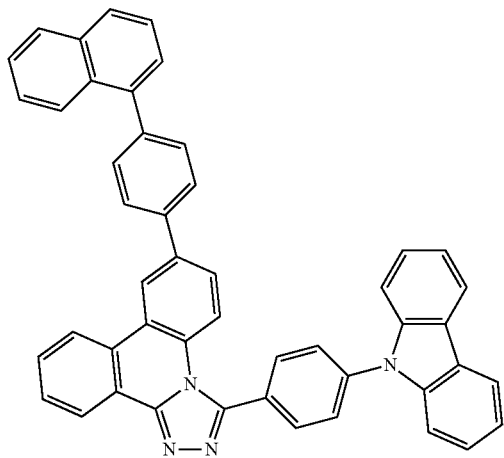
(362)
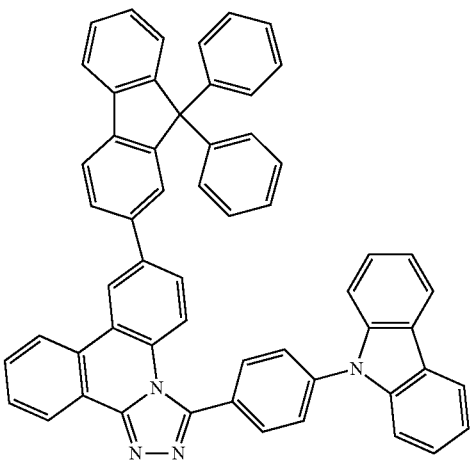
(360)
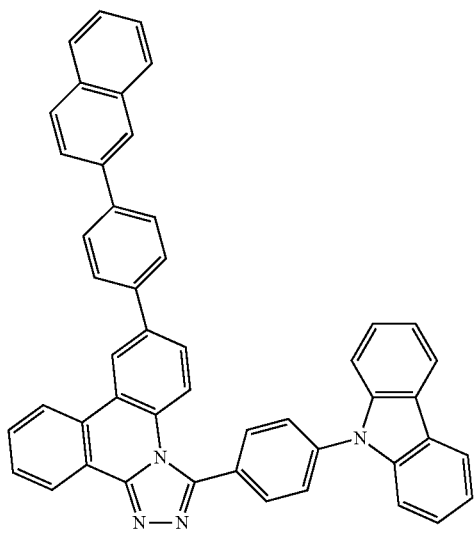
(363)
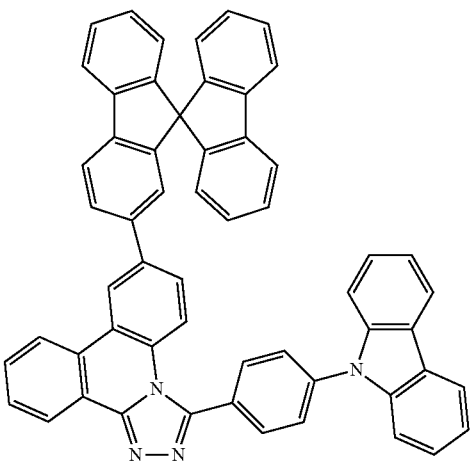
(361)
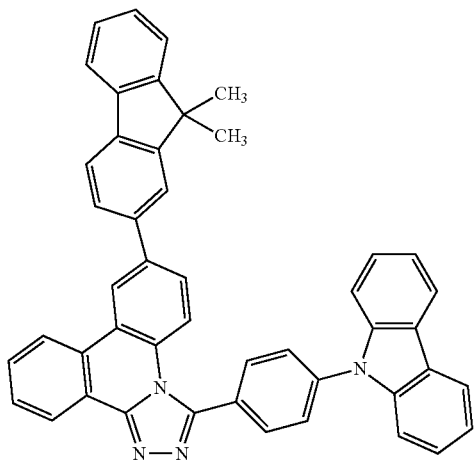
(364)
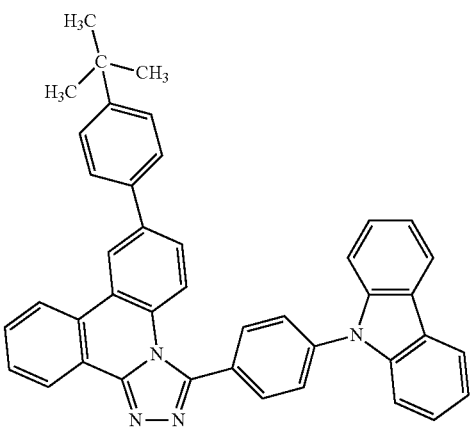

(365)
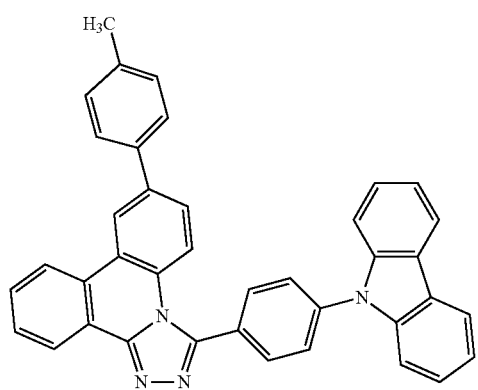
(366)
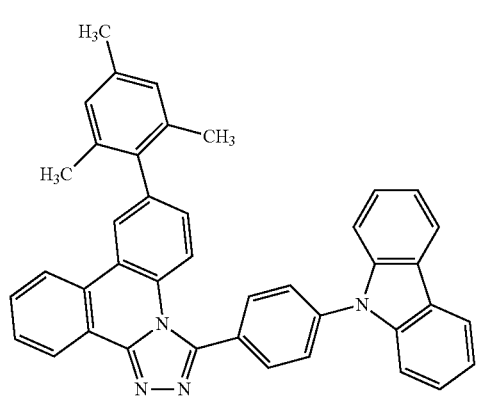
(400)
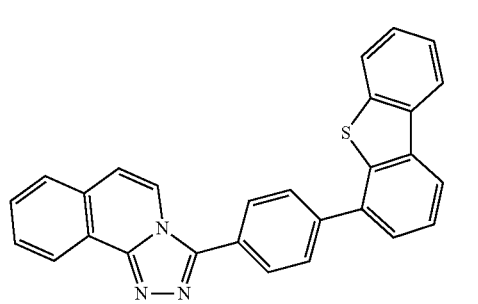
(401)
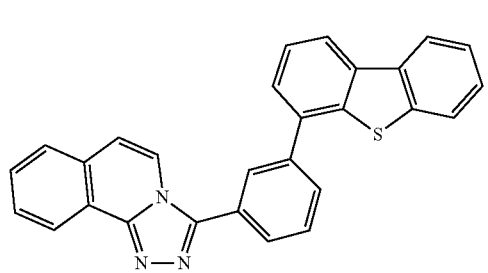
(402)
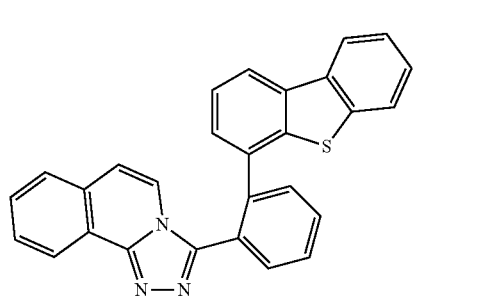
(403)
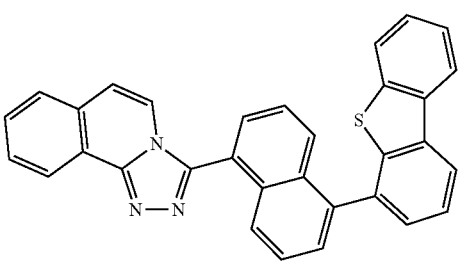
(404)
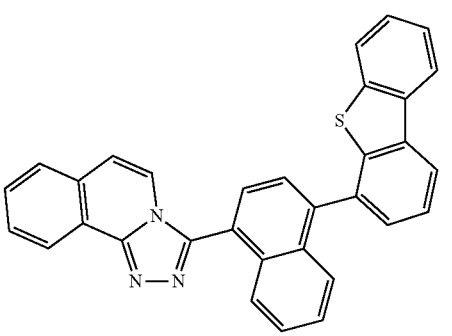
(405)
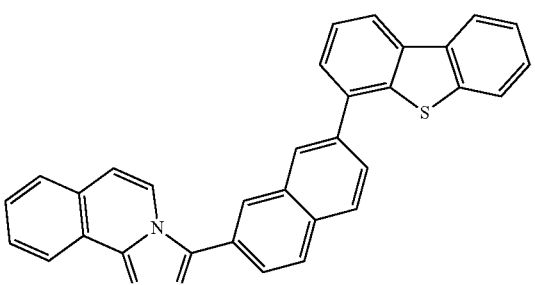
(406)
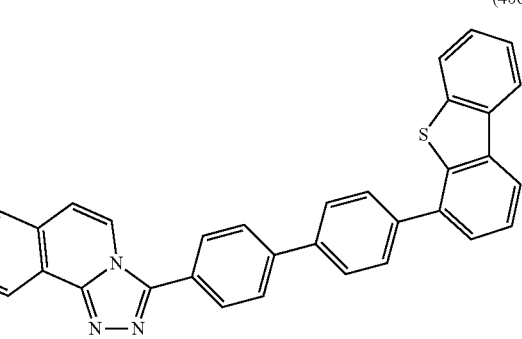
(407)
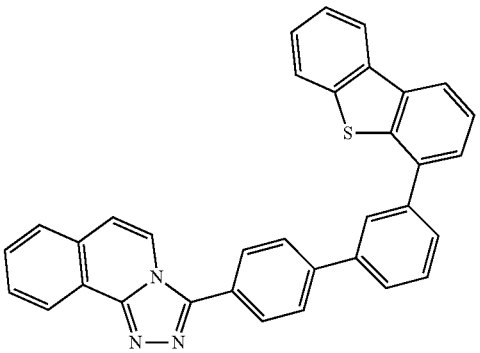

(408)
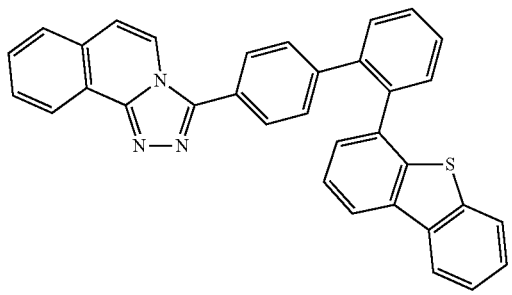
(409)
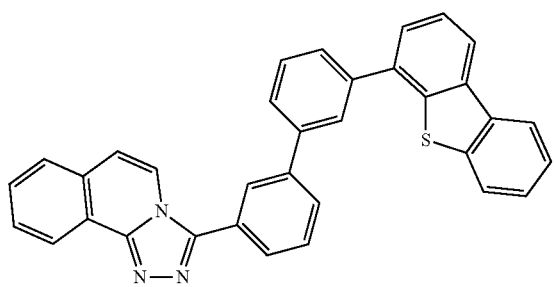
(410)
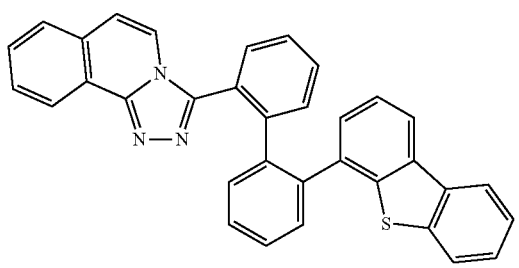
(411)
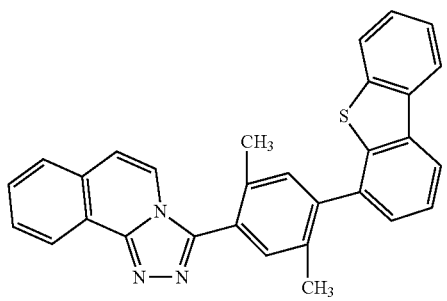
(412)
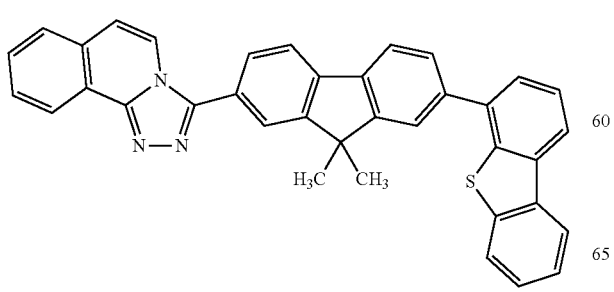
(413)
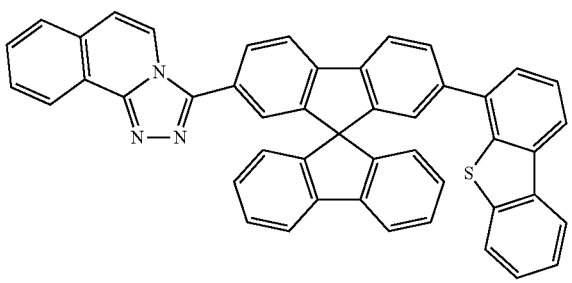
(414)
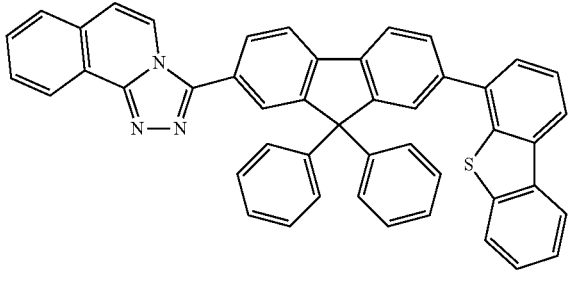
(415)
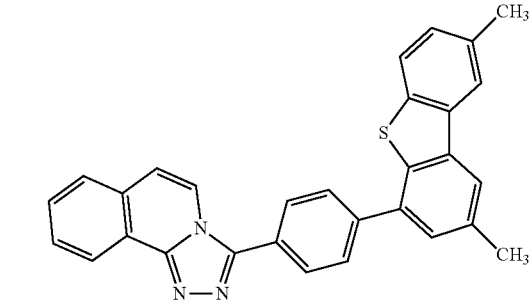
(416)
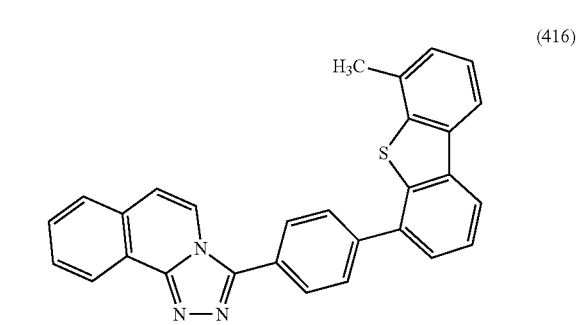
(417)
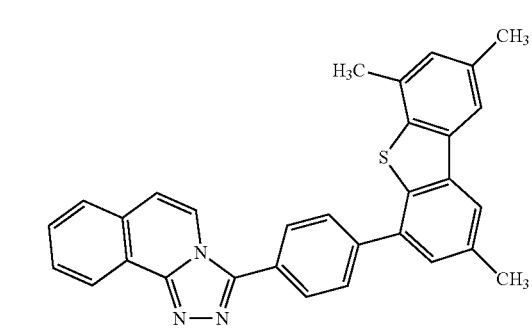

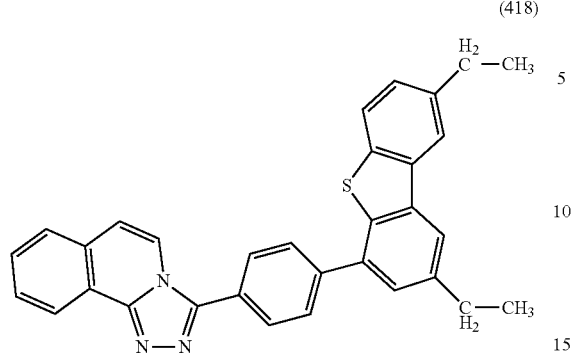
(418)
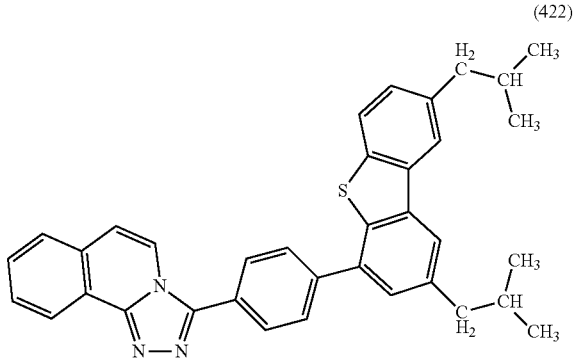
(422)
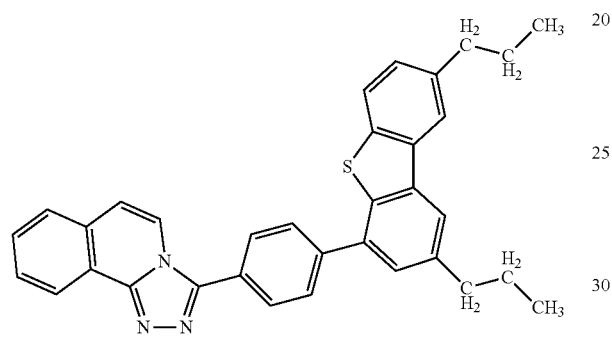
(419)
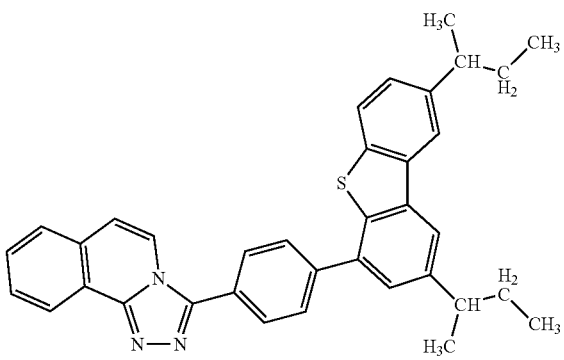
(423)
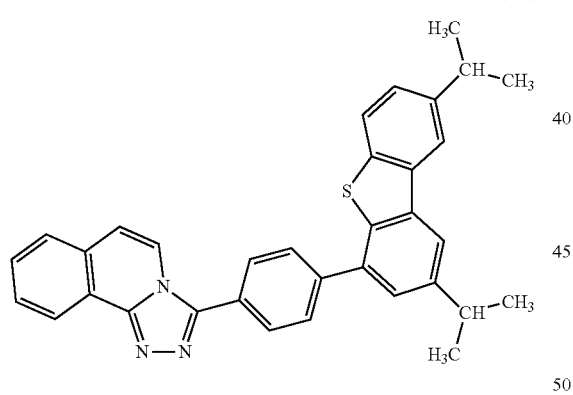
(420)
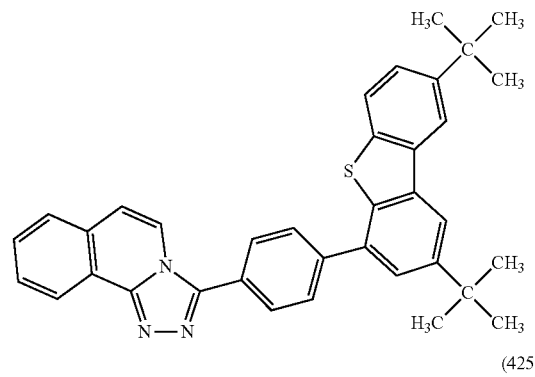
(424)
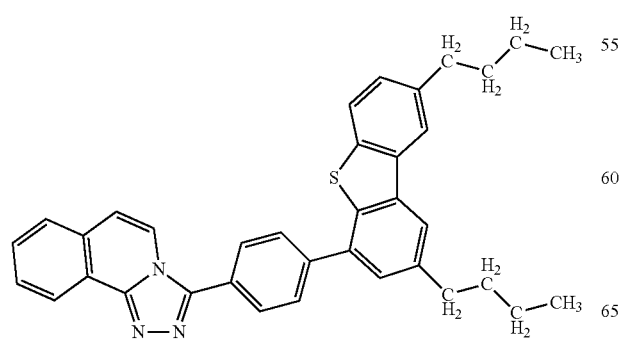
(421)
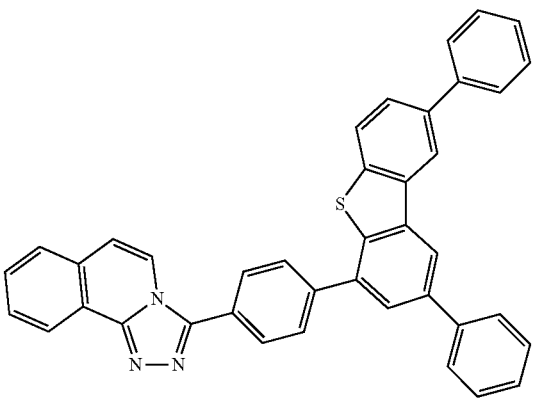
(425)

-continued
(426)
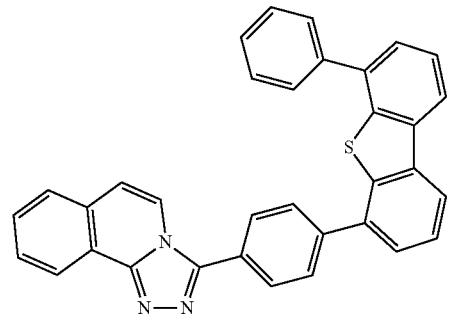
(427)
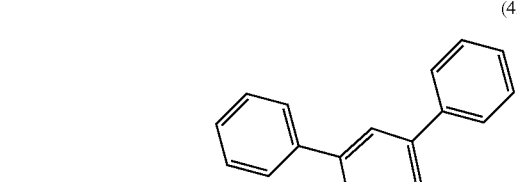
(428)
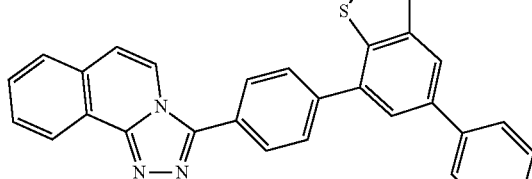
(429)
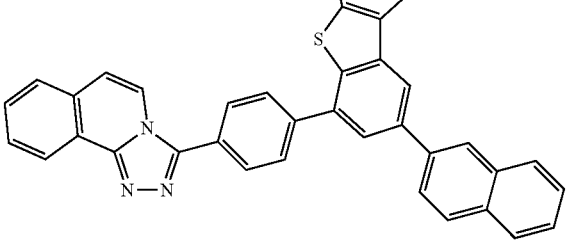
-continued
(430)
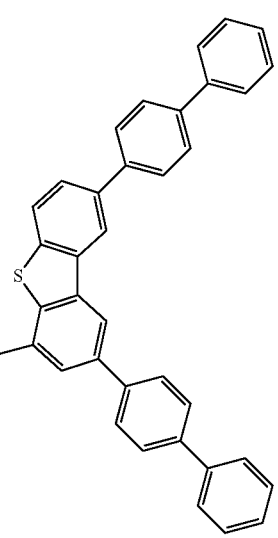
(431)
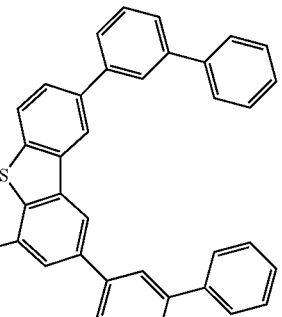
(432)
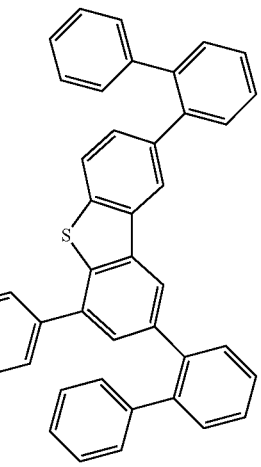

(433)
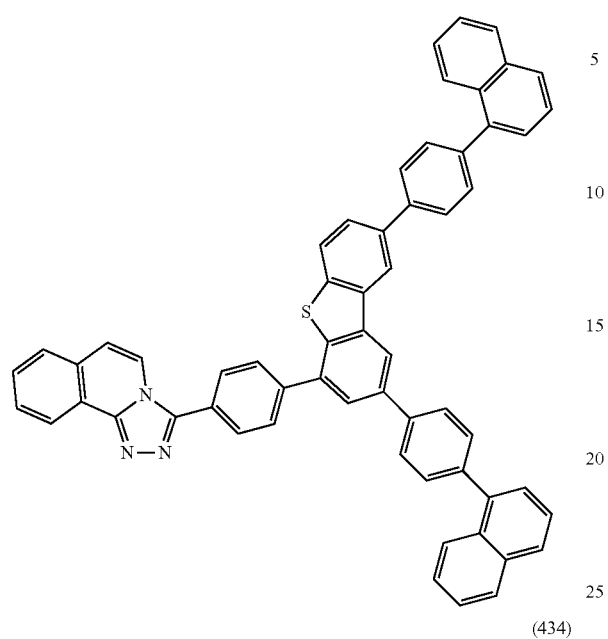
(436)
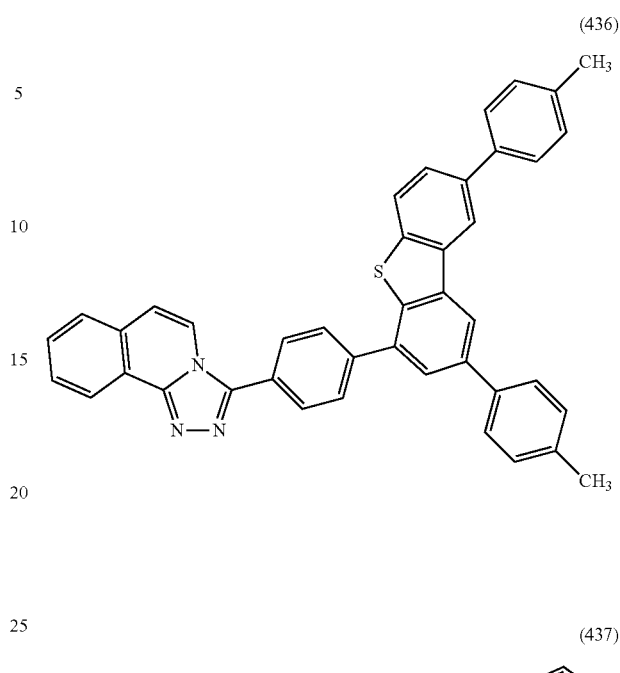
(434)
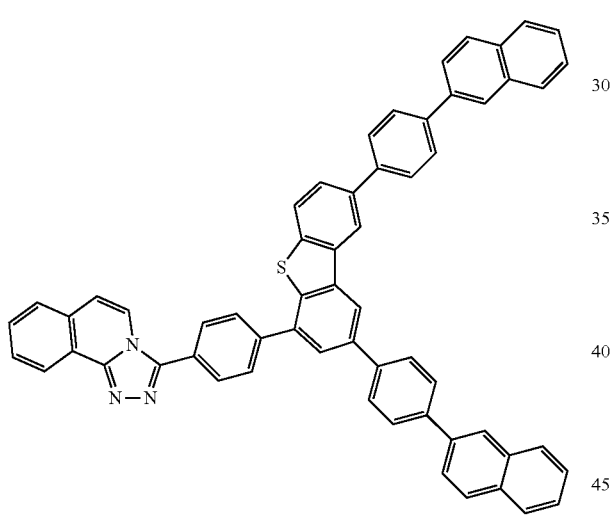
(437)
(435)
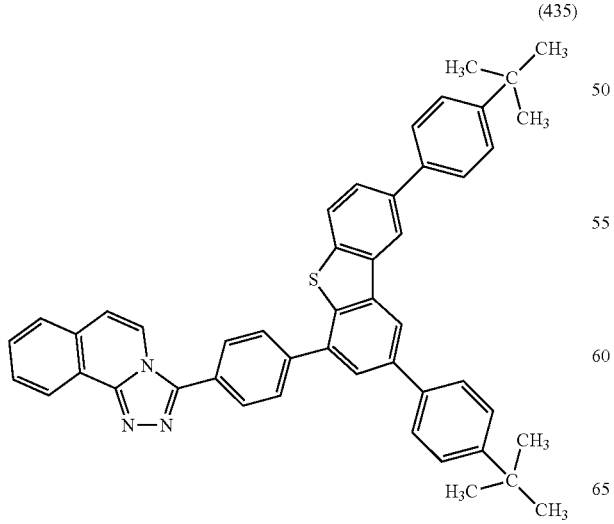
(438)
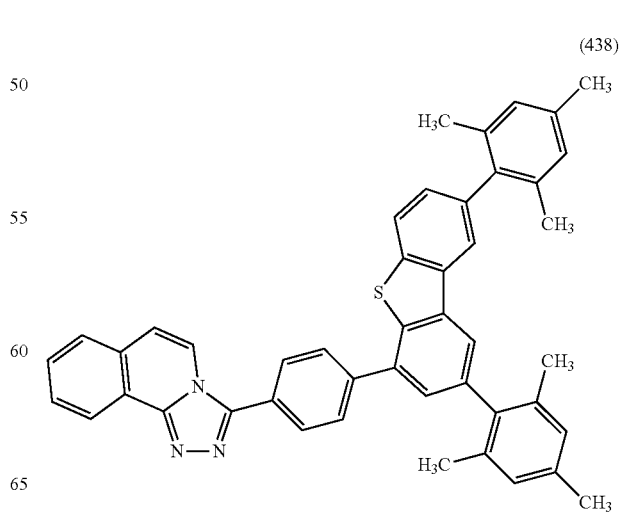

-continued
(439)
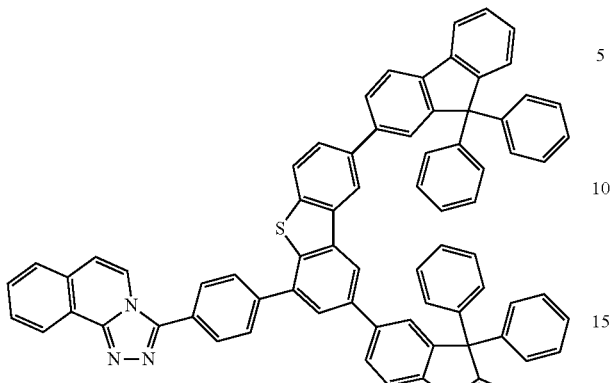
(440)
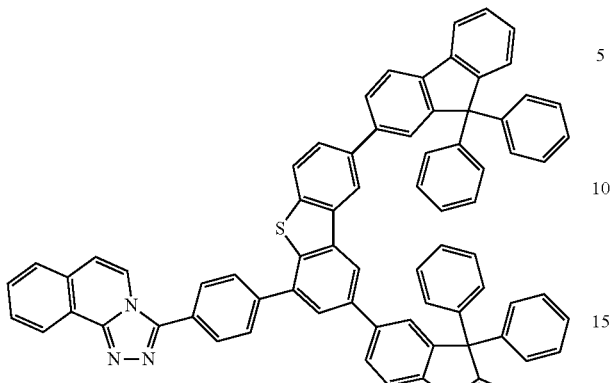
(441)
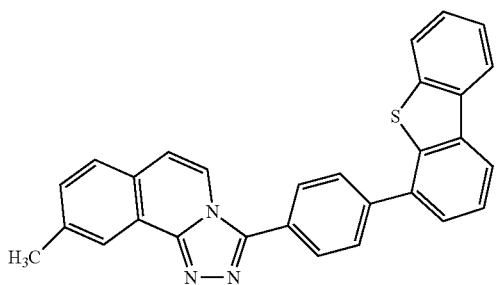
(442)
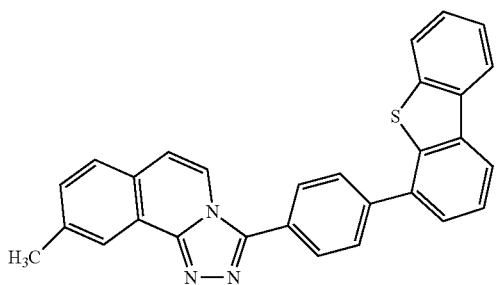
-continued
(443)
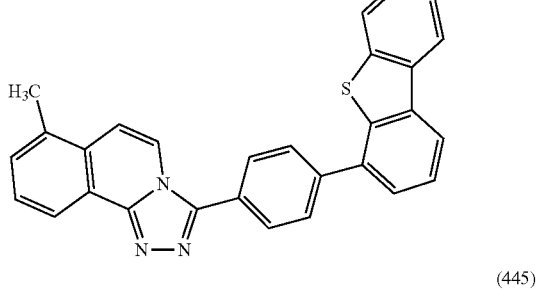
(444)
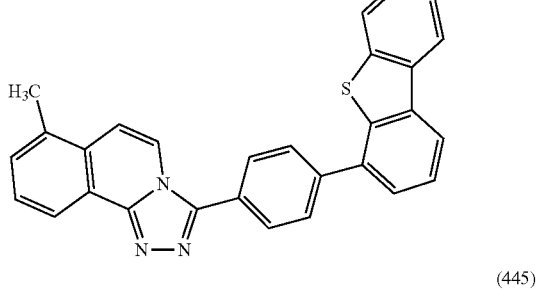
(445)
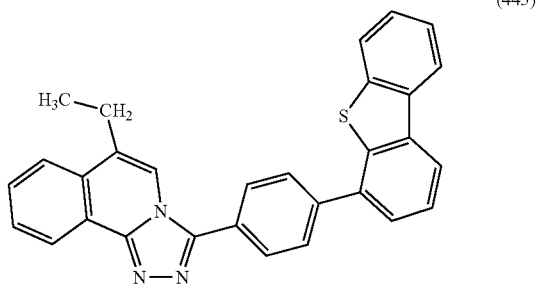
(446)
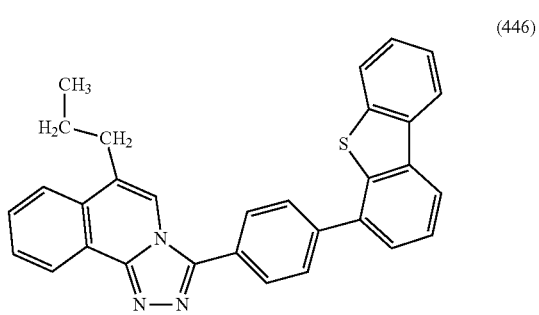
(447)
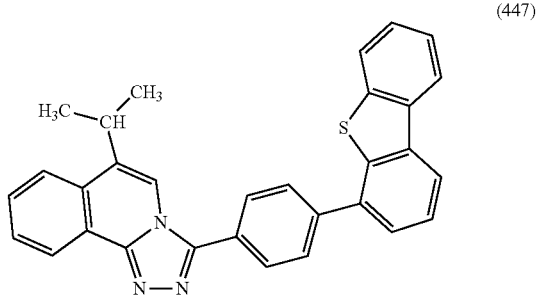

(448)
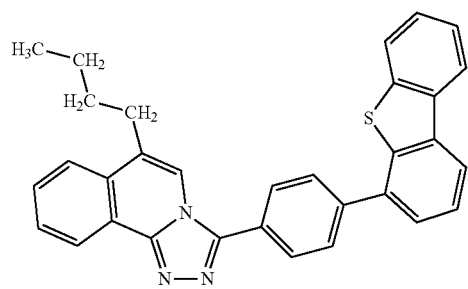
(449)
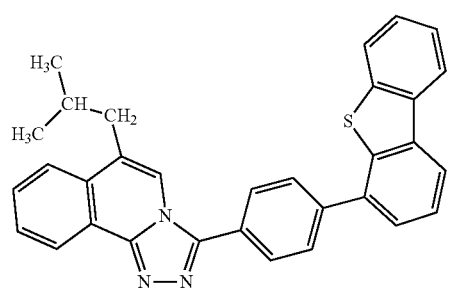
(450)
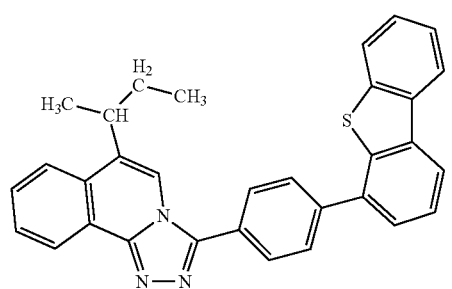
(451)
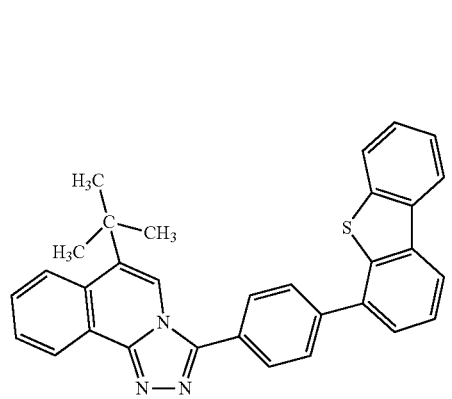
(452)
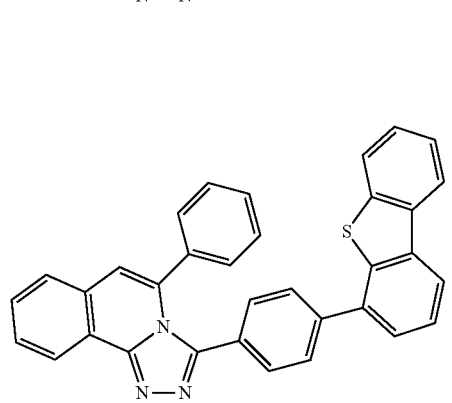
(453)
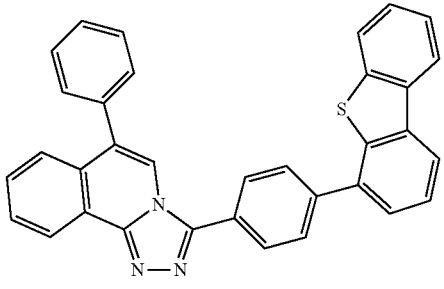
(454)
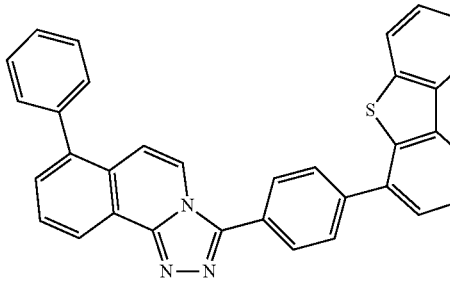
(455)
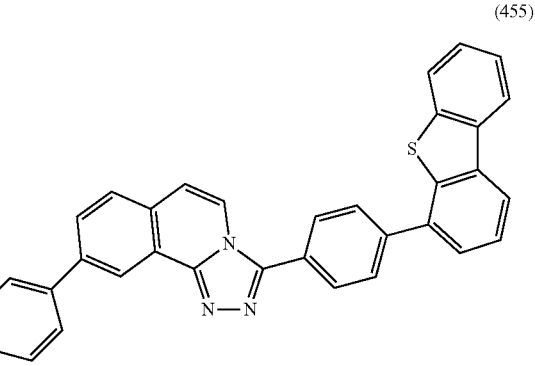
(456)
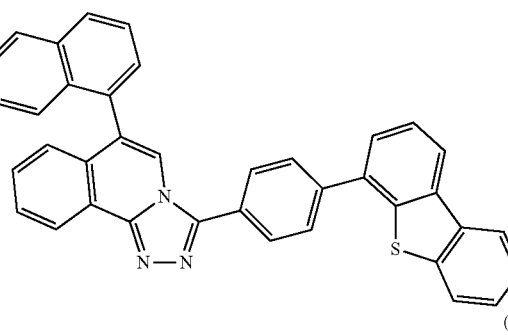
(457)
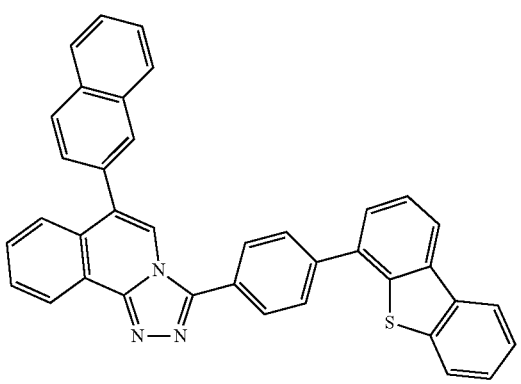

(458)
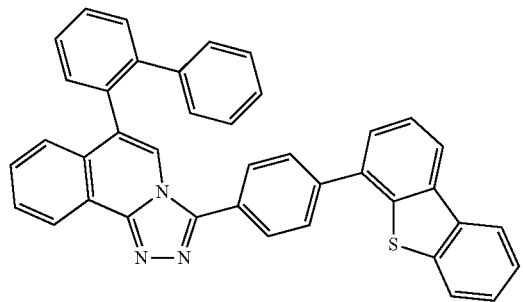
(459)
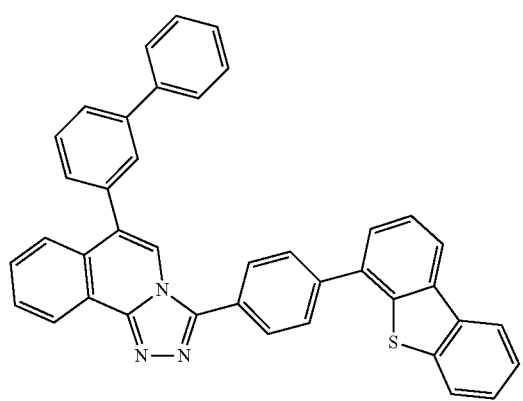
(460)
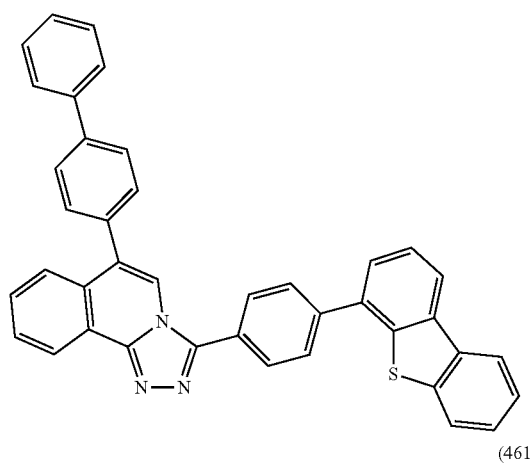
(461)
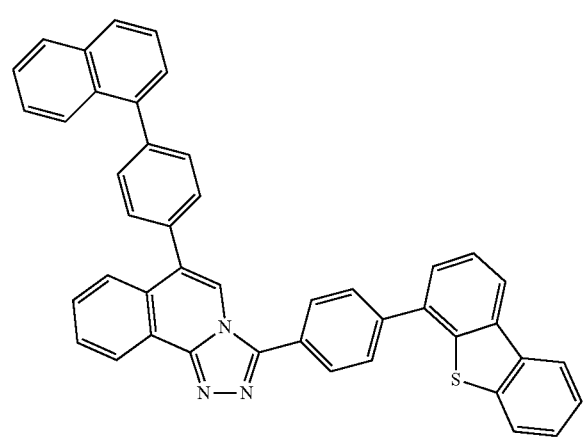
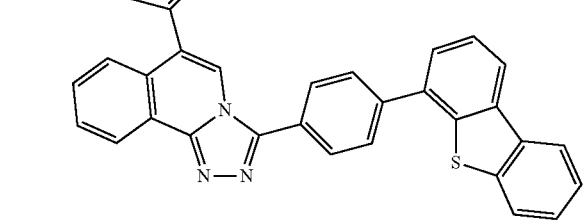
(462)
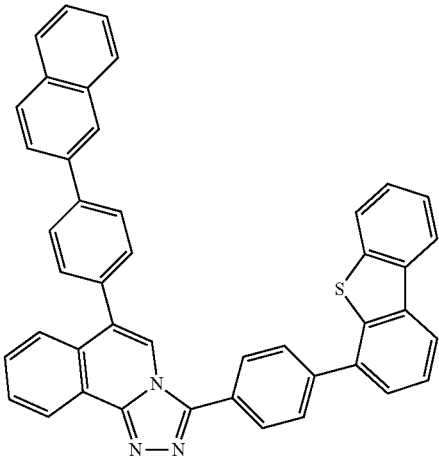
(463)
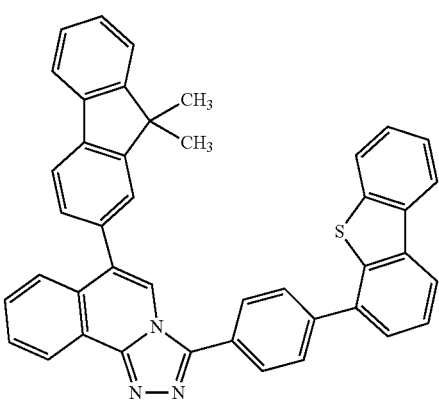
(464)
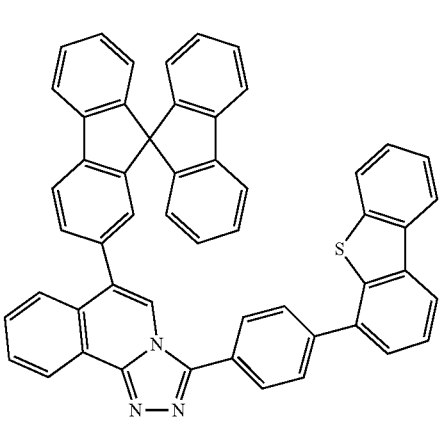
(465)
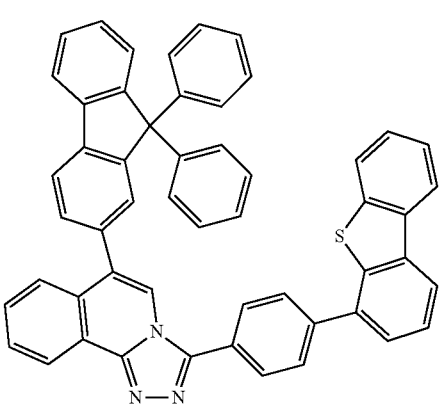

-continued
(466)
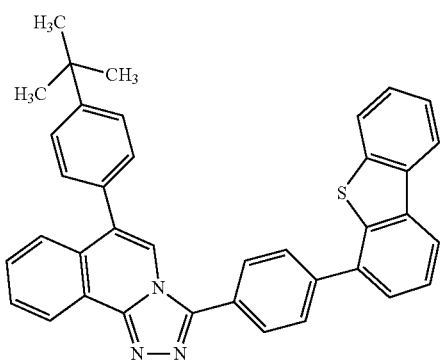
(467)
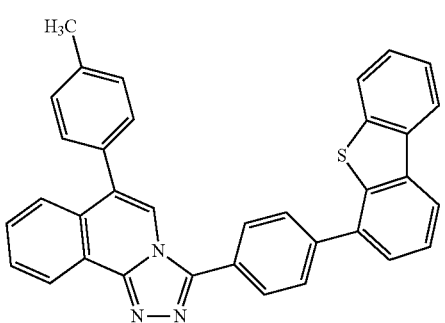
(468)
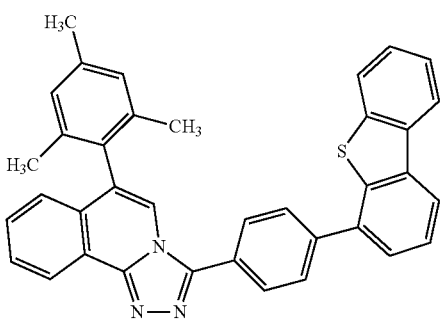
(500)
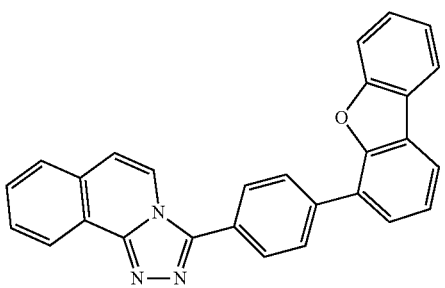
(501)
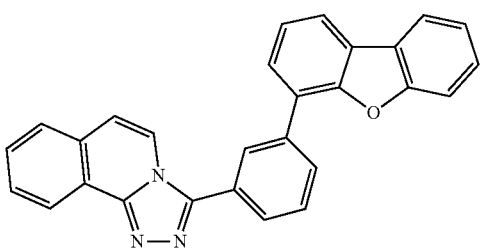
-continued
(502)
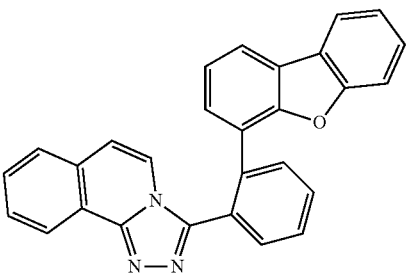
(503)
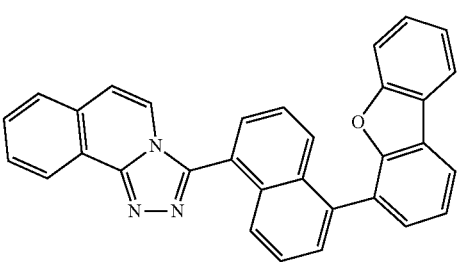
(504)
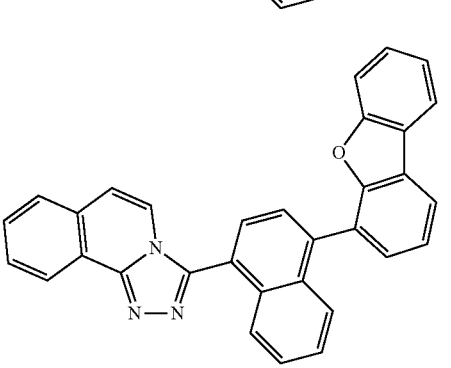
(505)
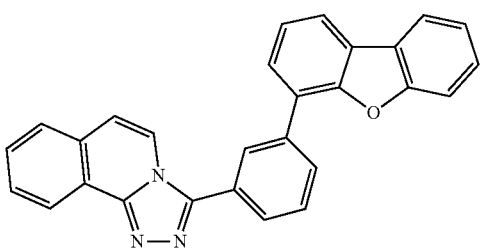
(506)
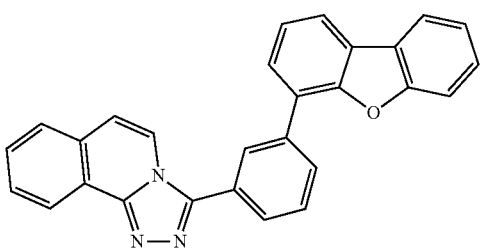

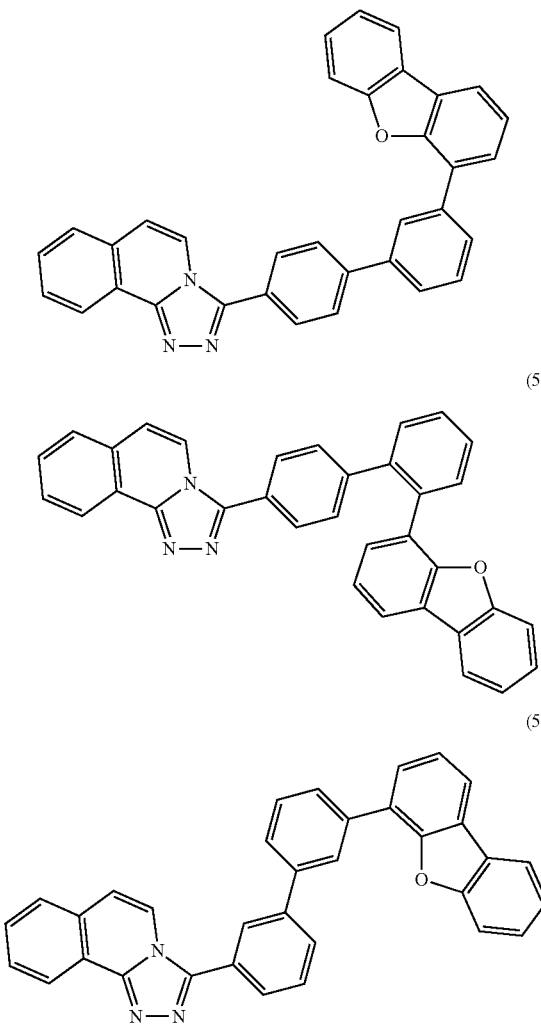
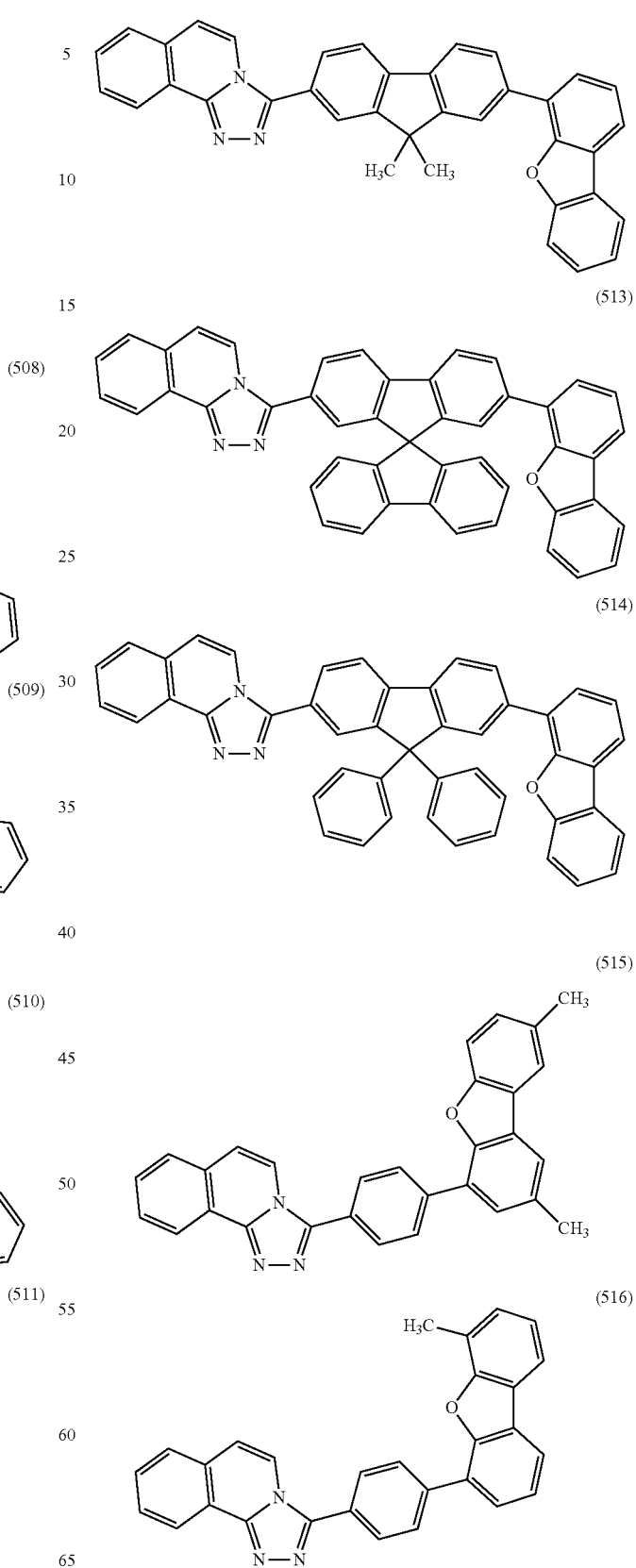

(517) 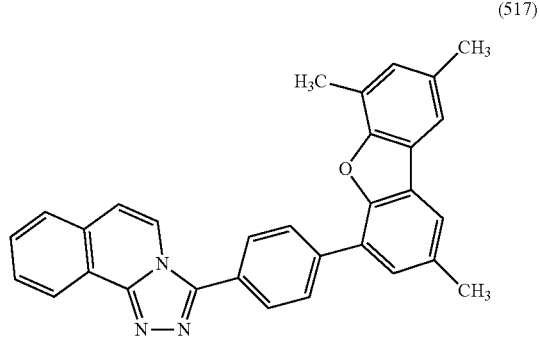
(518) 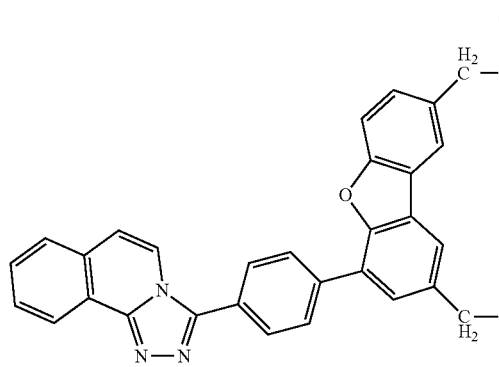
(519) 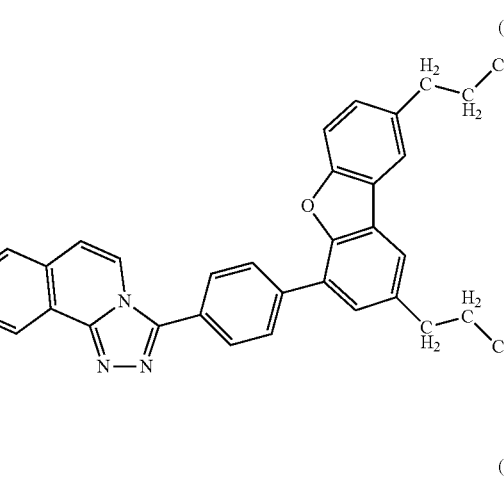
(520) 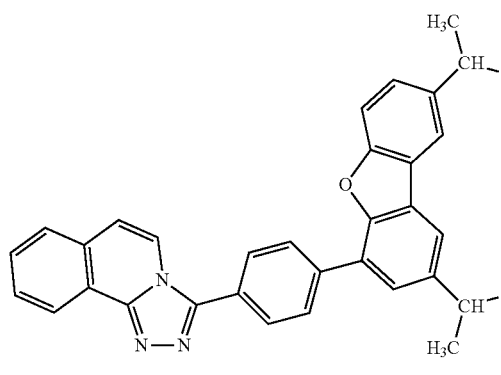
(521) 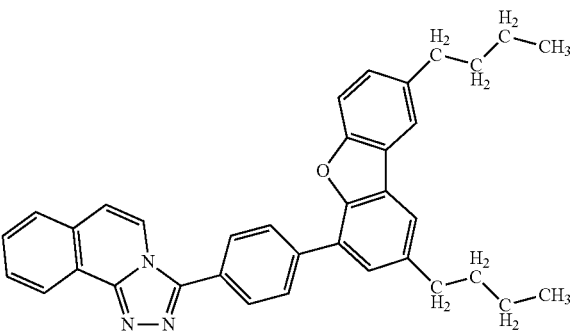
(522) 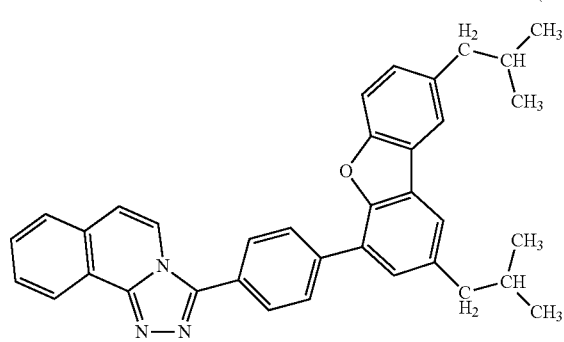
(523) 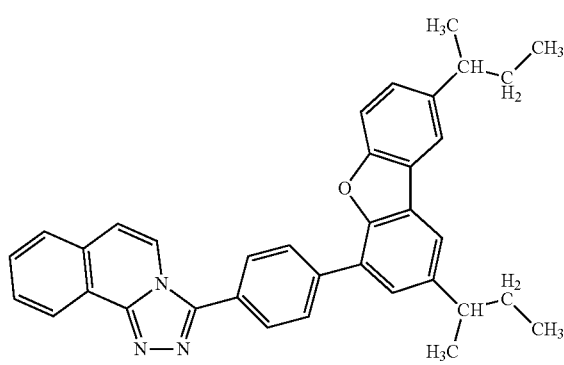
(524) 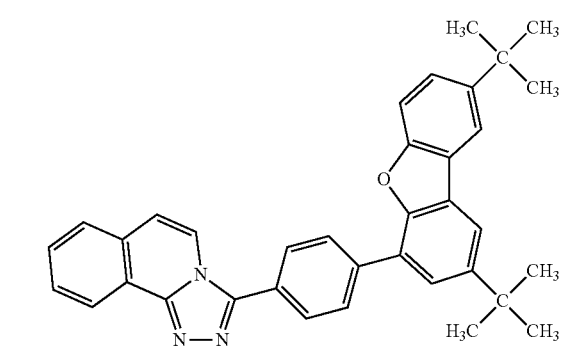

(525)
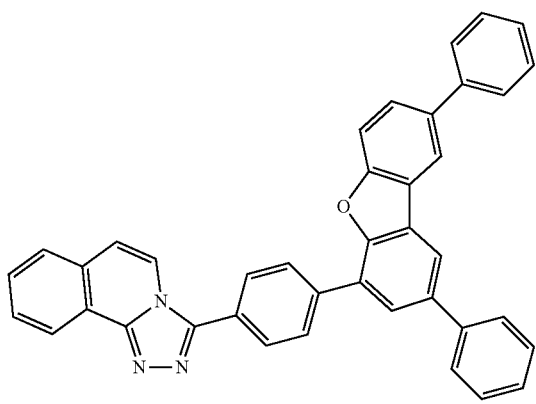
(526)
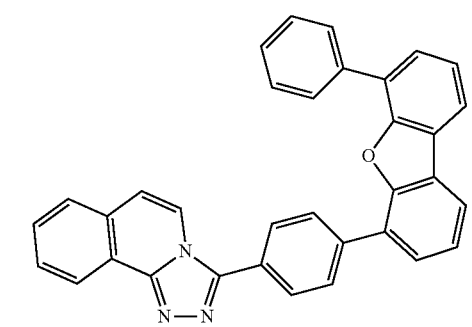
(529)
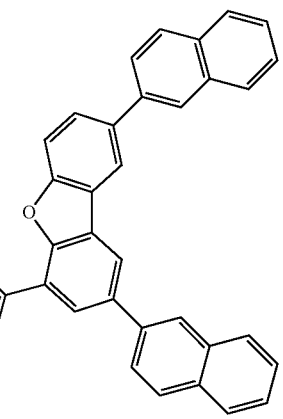
(527)
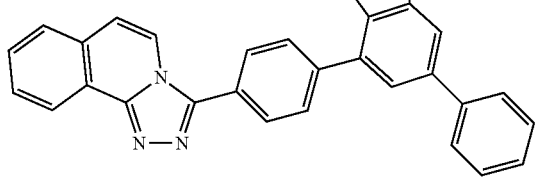
(530)
(528)
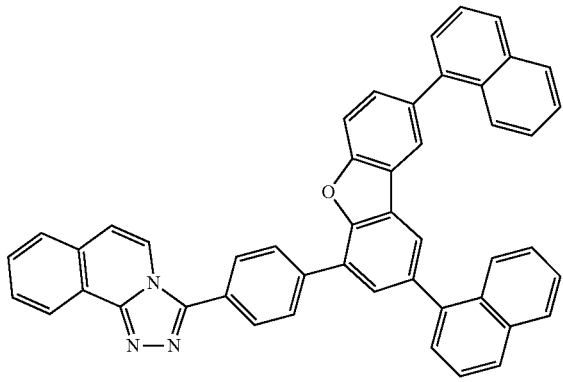
(531)
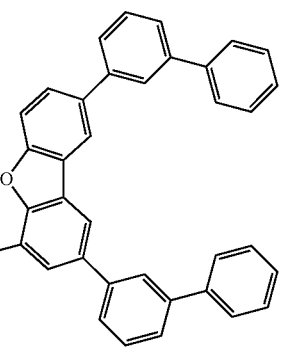

(532)
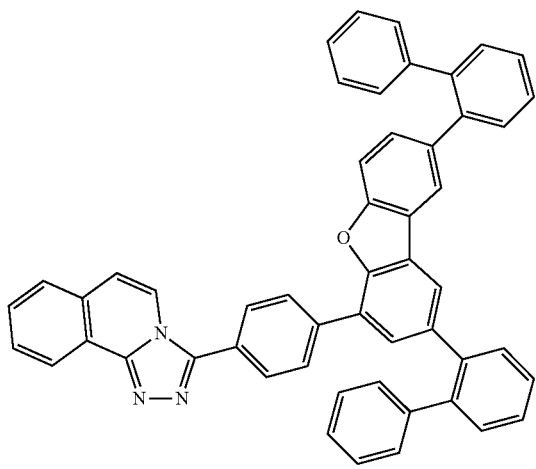
(533)
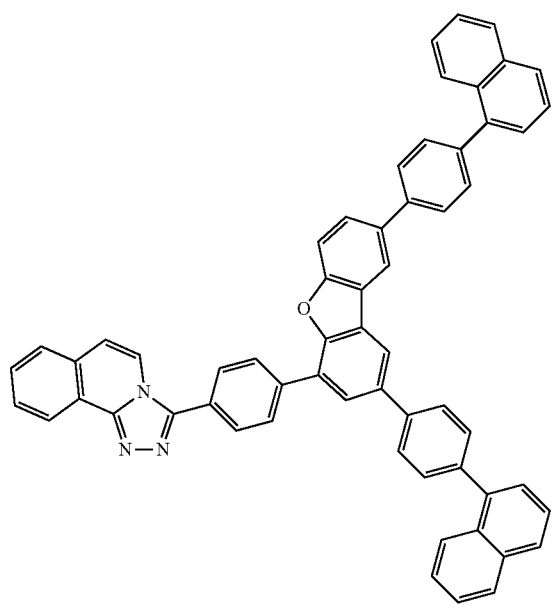
(534)
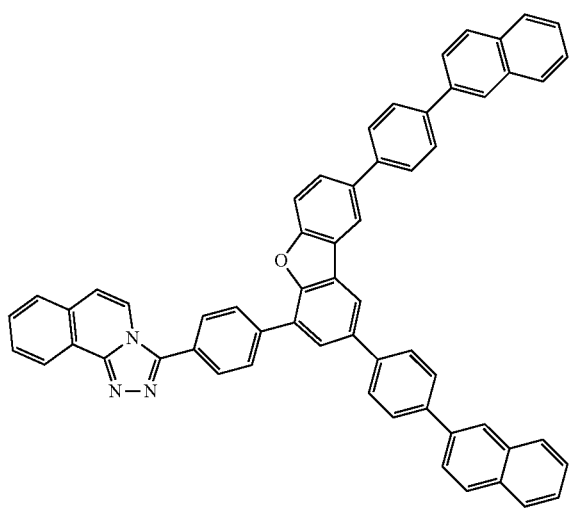
(535)
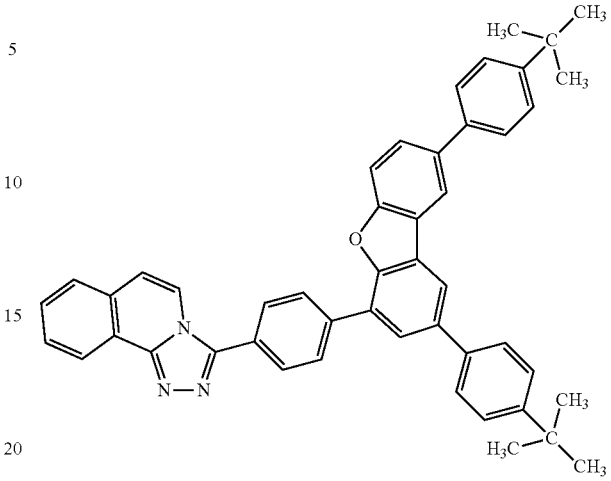
(536)
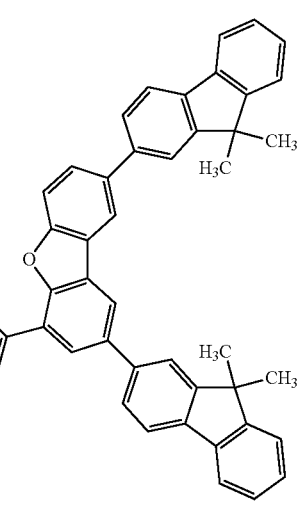
(537)

-continued
(538)
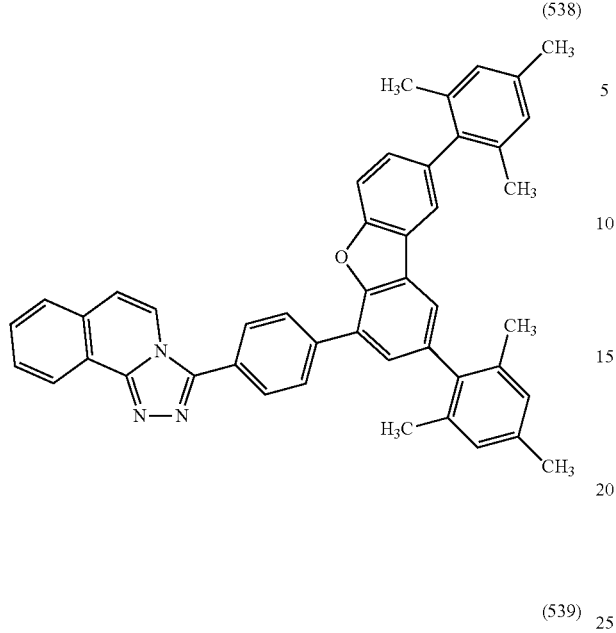
(539)
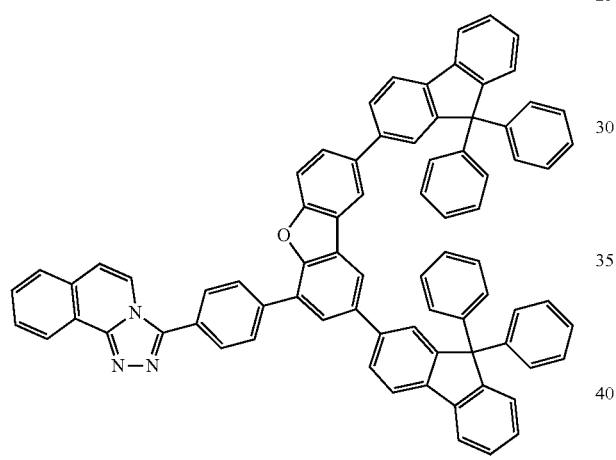
(540)
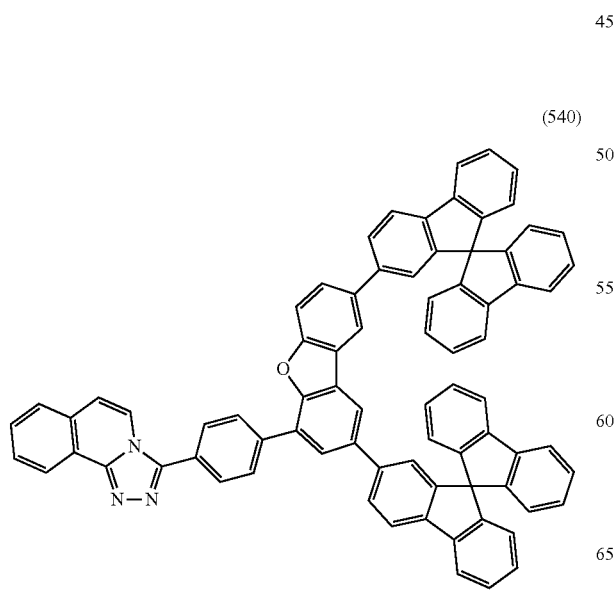
-continued
(541)
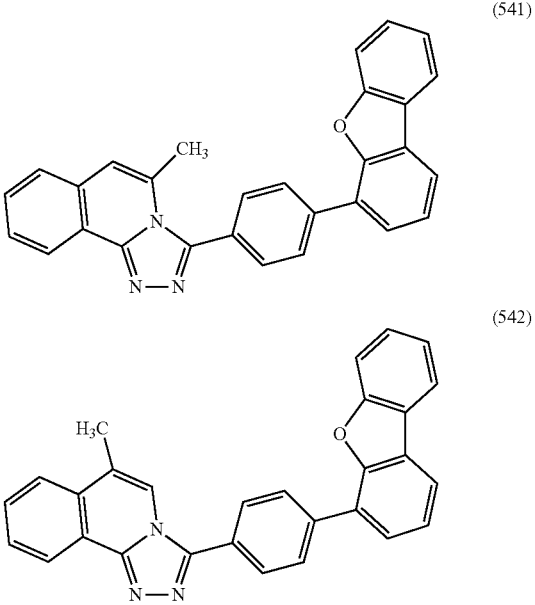
(542)
(543)
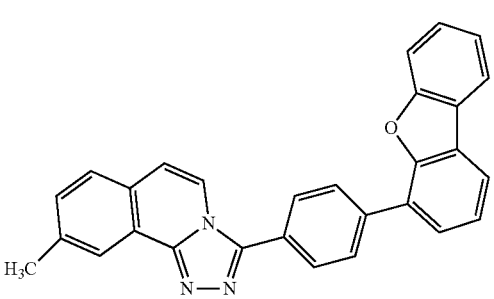
(544)
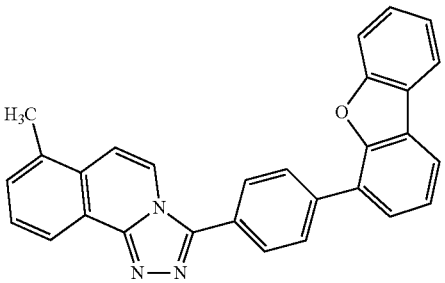
(545)
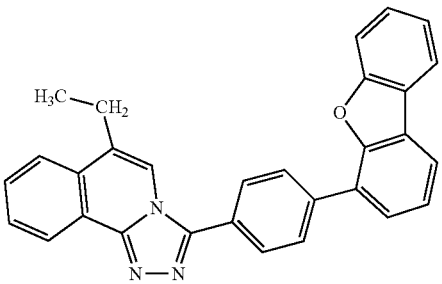

(546) 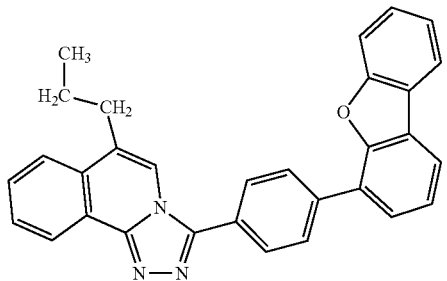
(547) 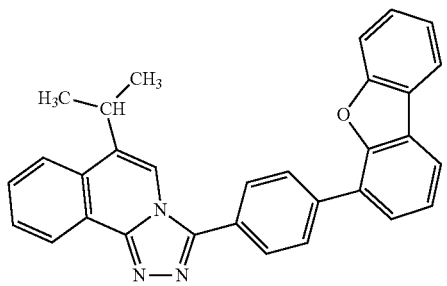
(548) 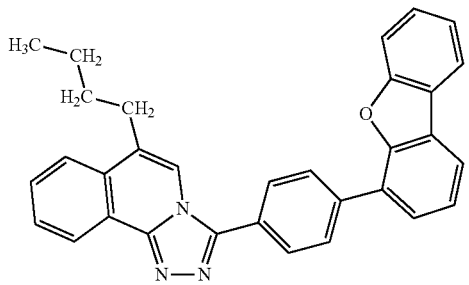
(549) 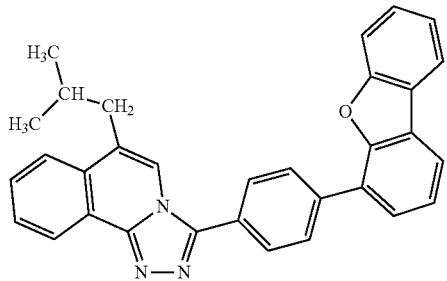
(550) 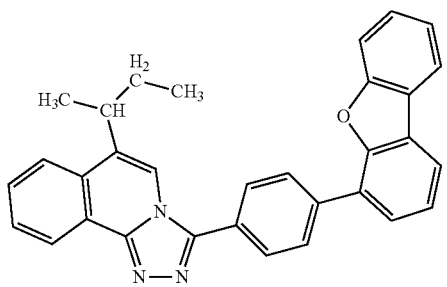
(551) 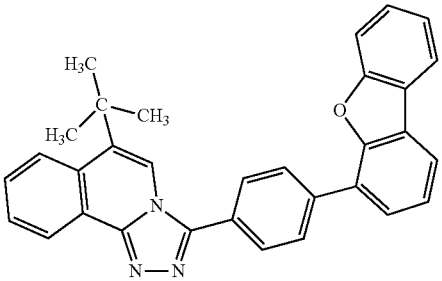
(552) 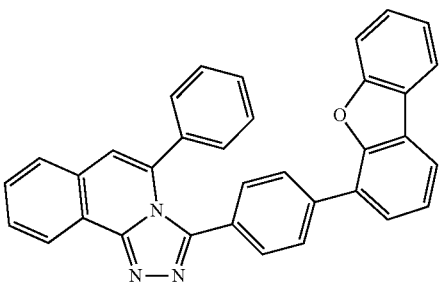
(553) 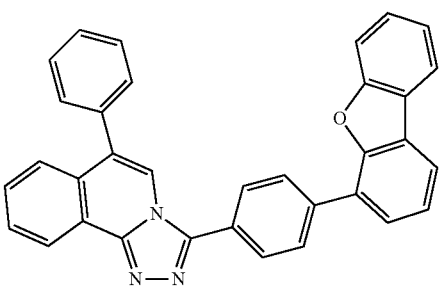
(554) 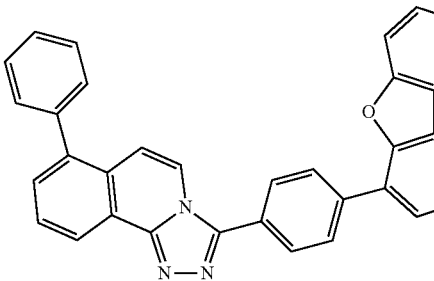
(555) 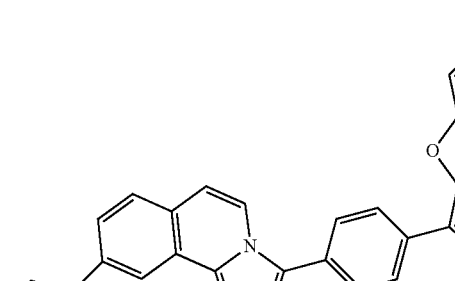

101
-continued
(556)
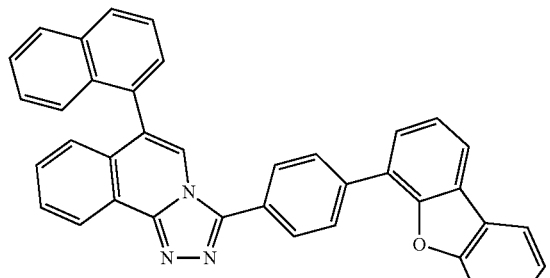
(557)
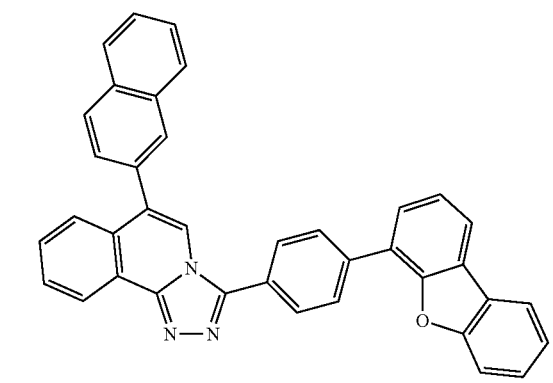
(558)
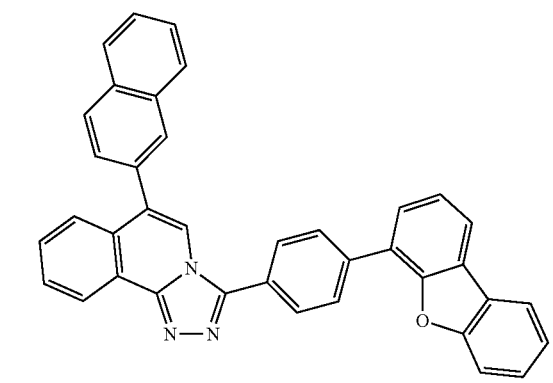
(559)
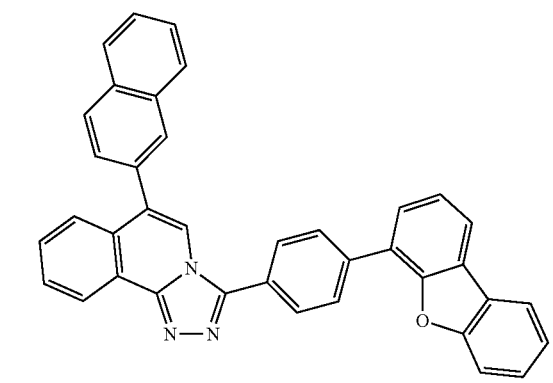
102
-continued
(560)
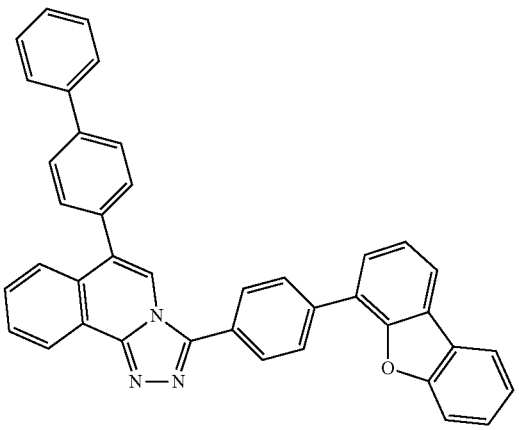
(561)
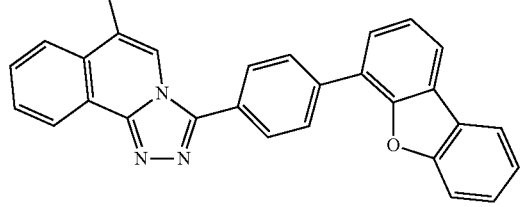
(562)
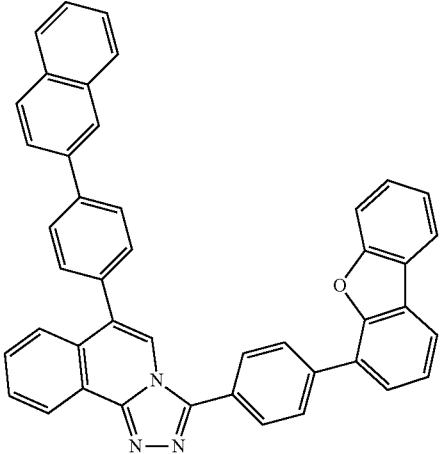

(563)
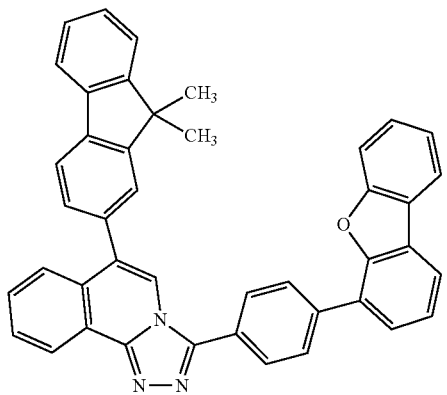
(564)
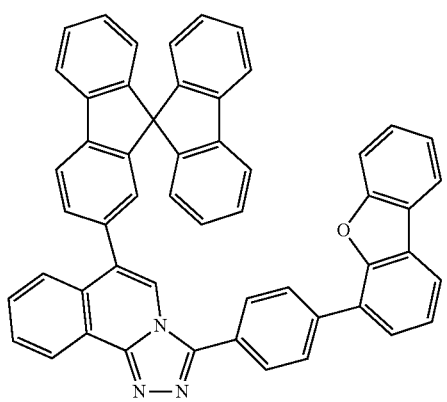
(565)
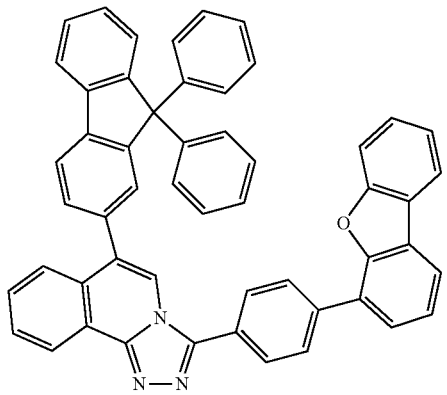
(566)
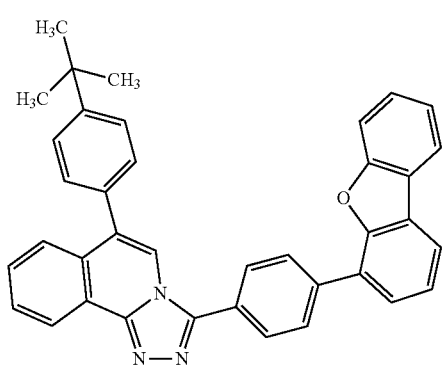
(567)
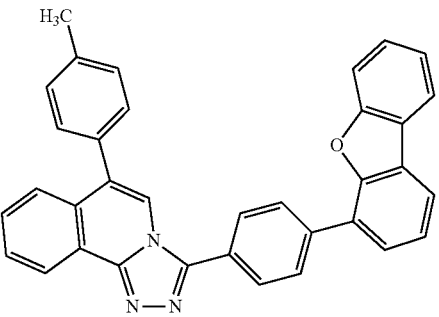
(568)
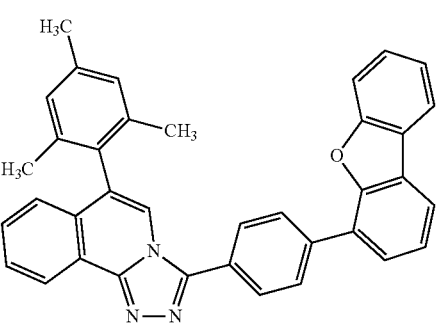
(600)
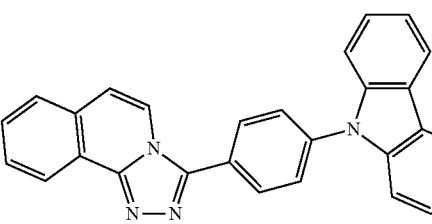
(601)
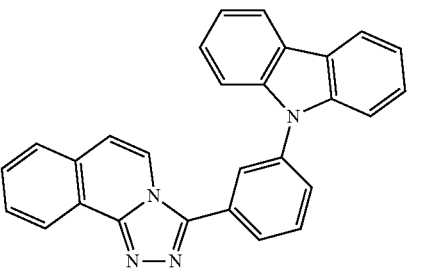
(602)
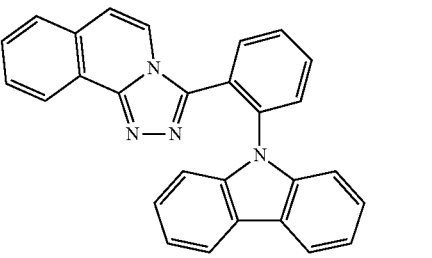
(603)
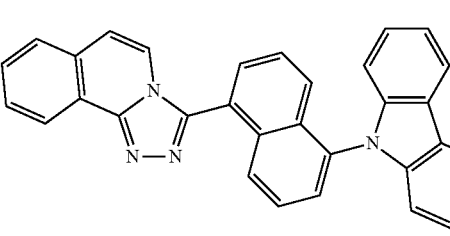

(604) 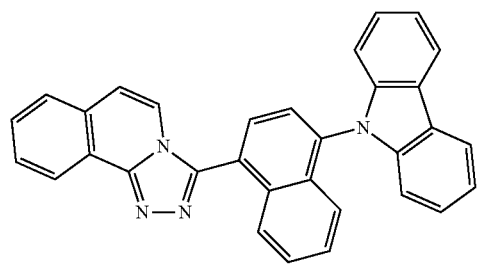
(605) 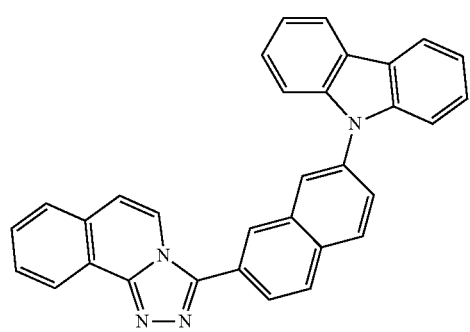
(606) 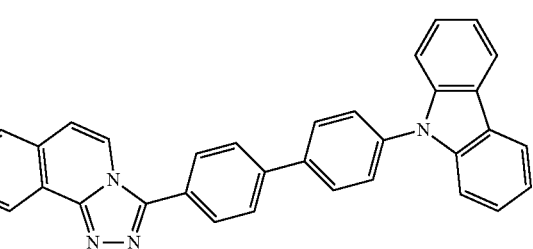
(607) 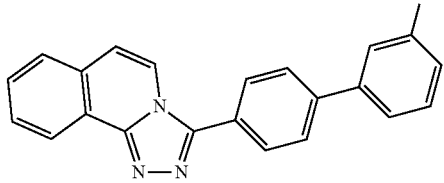
(608) 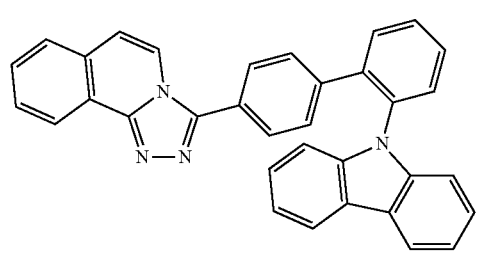
(609) 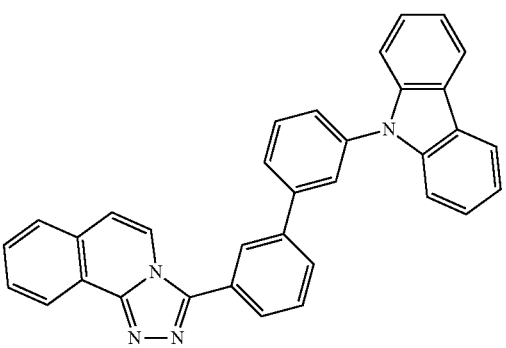
(610) 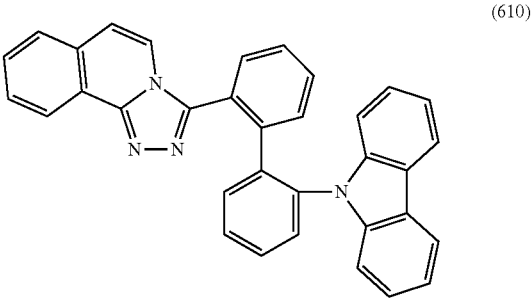
(611) 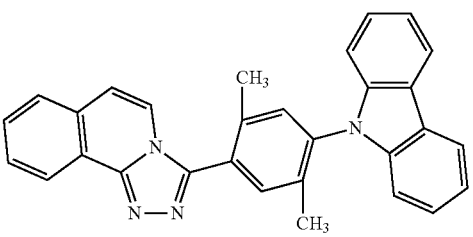
(612) 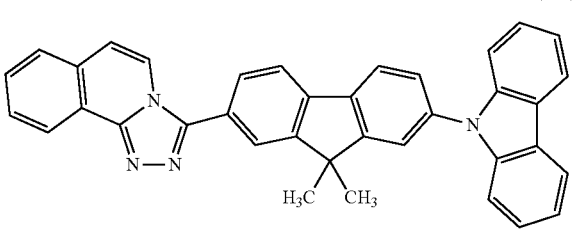
(613) 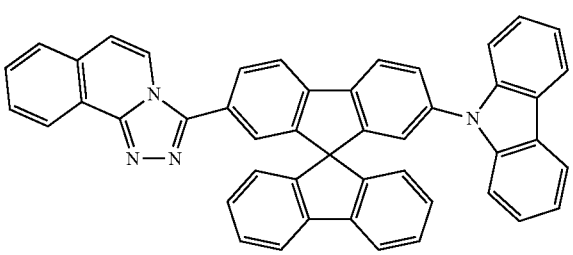

(614)
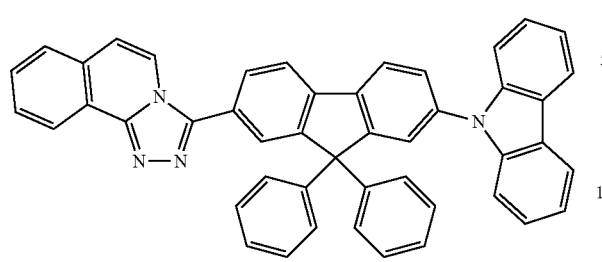
(615)
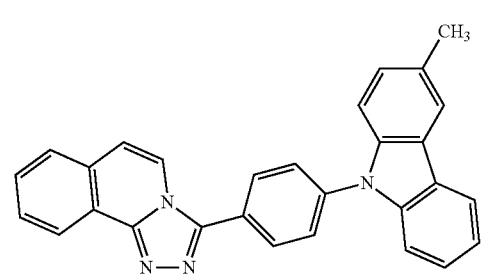
(616)
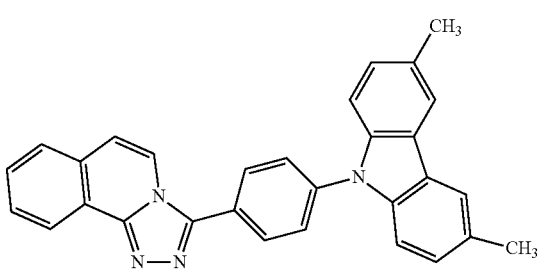
(617)
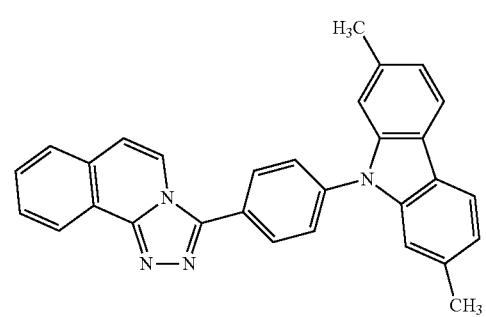
(618)
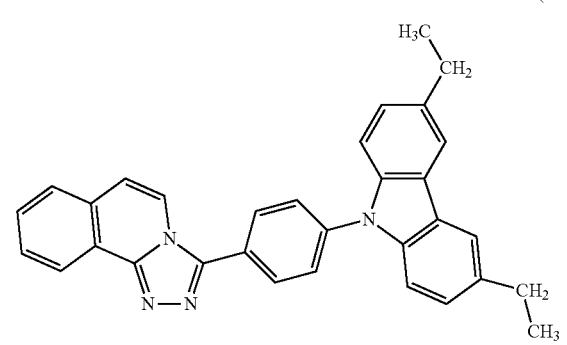
(619)
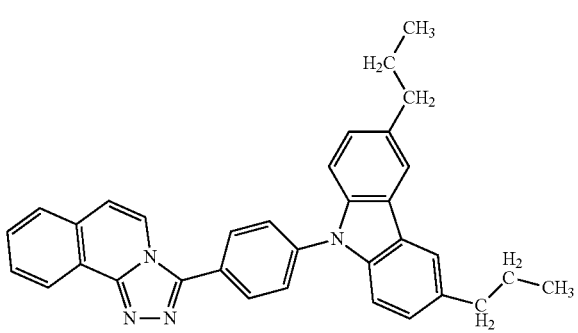
(620)
(621)
(622)

(623)
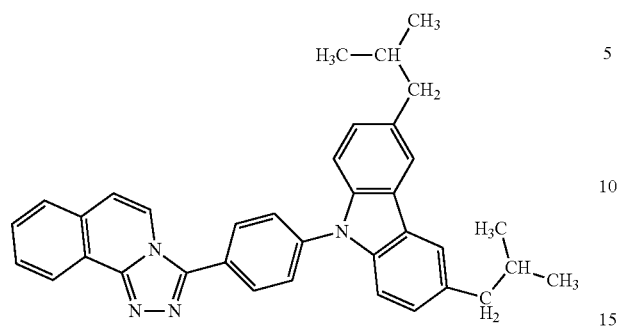
(624)
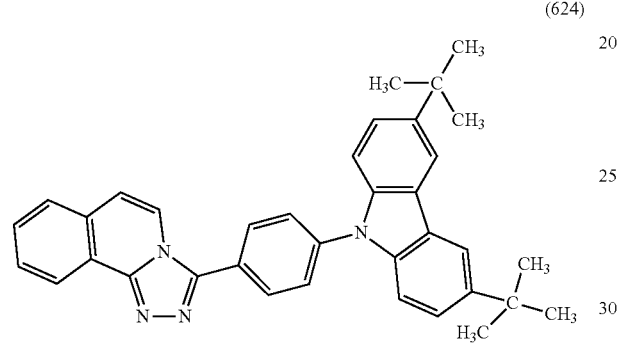
(625)
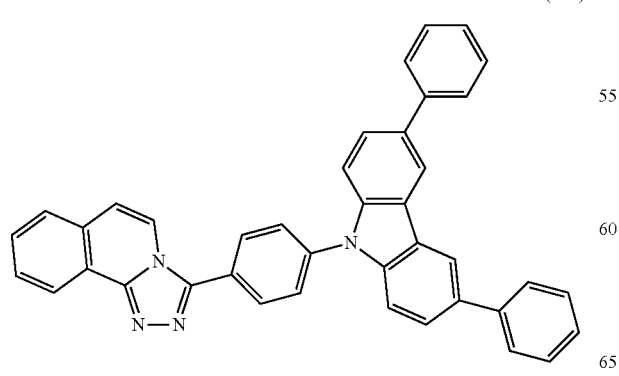
(626)
(627)
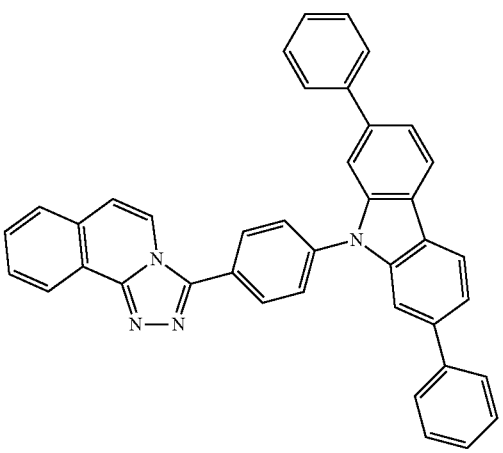
(628)
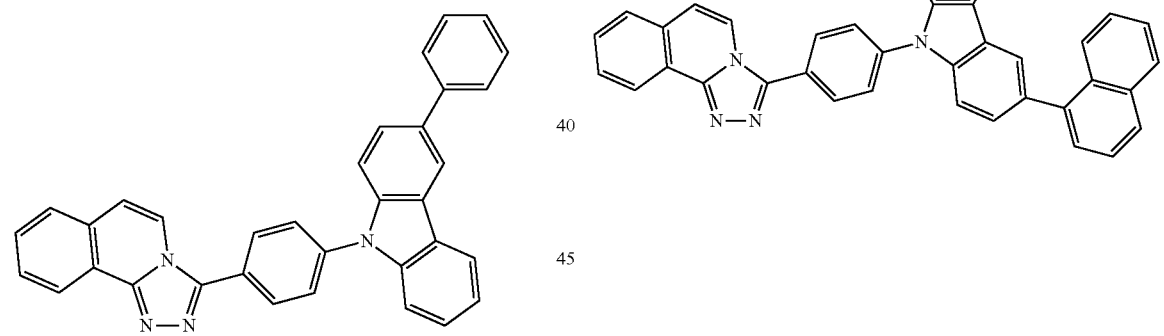
(629)
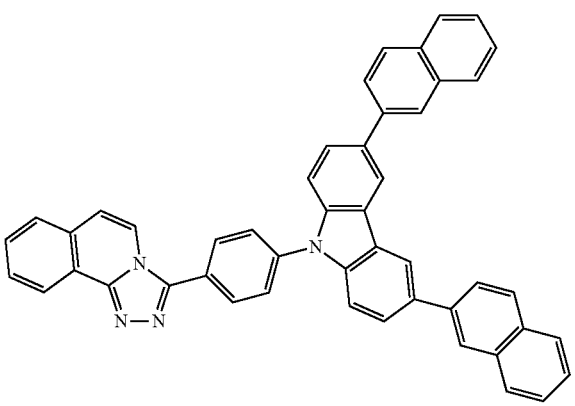

-continued
(630)
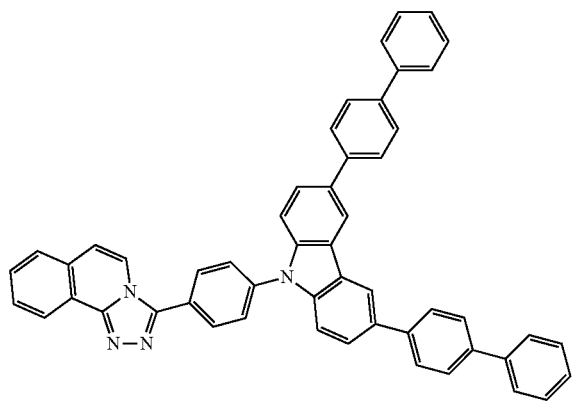
(631)
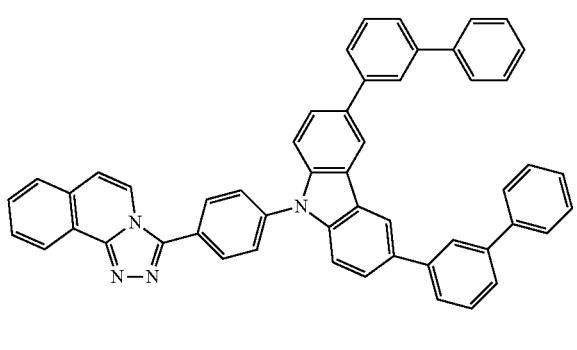
(632)
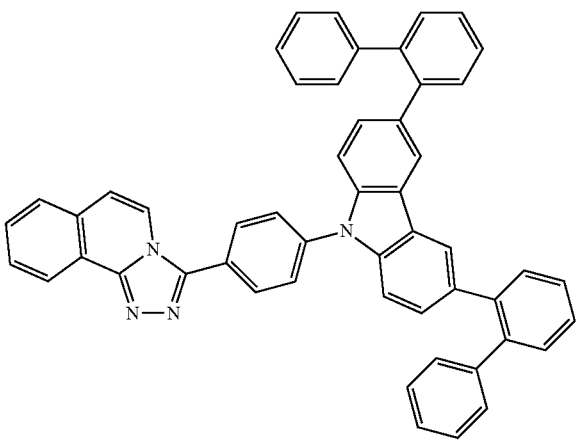
-continued
(633)
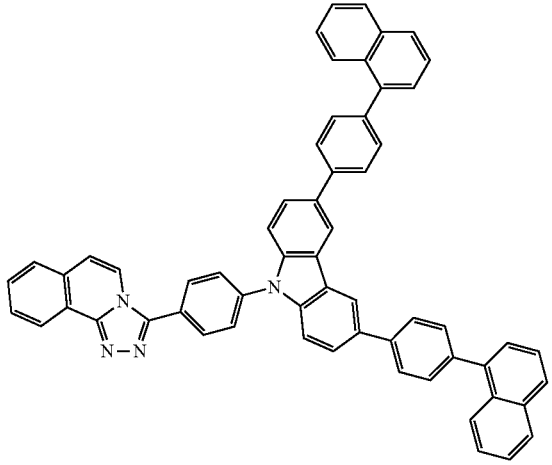
(634)
(635)
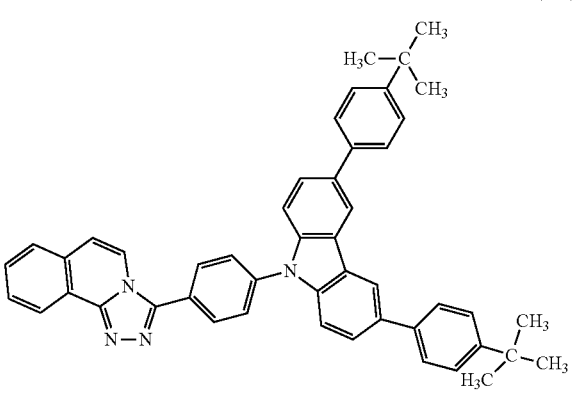

(636)
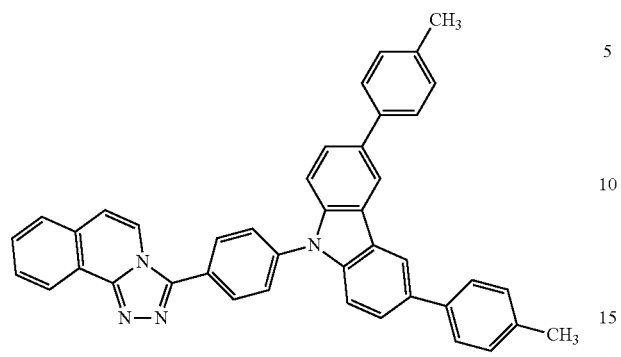
(640)
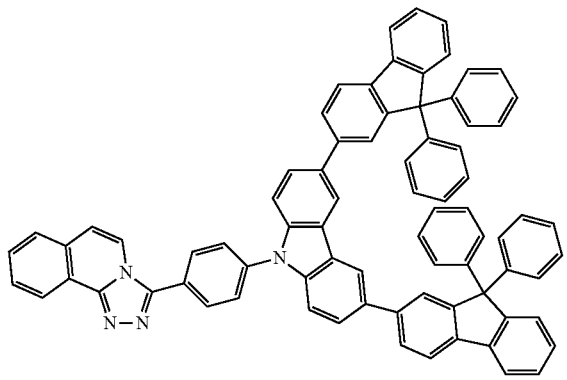
(637)
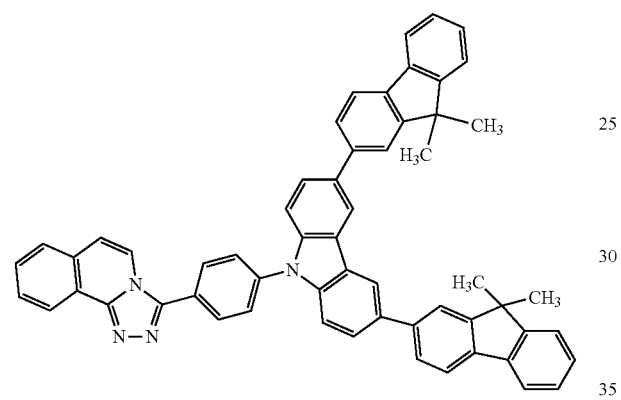
(641)
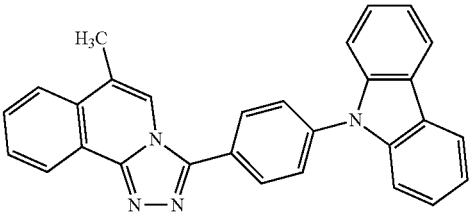
(642)
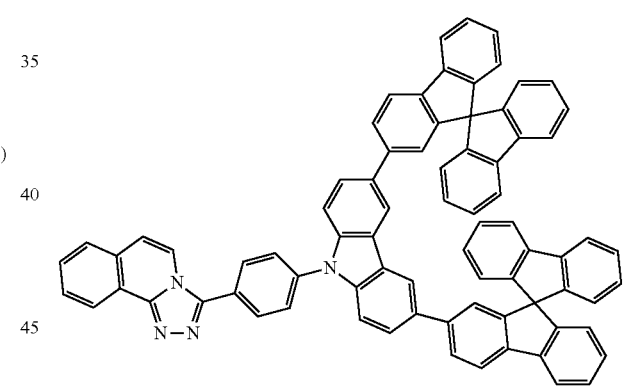
(638)
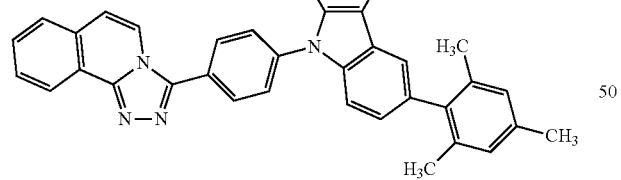
(643)
(639)
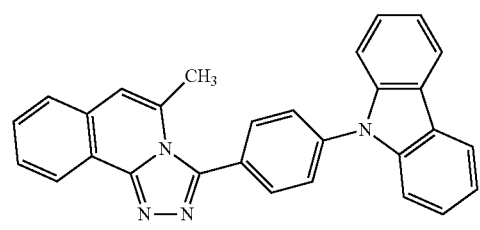
(644)
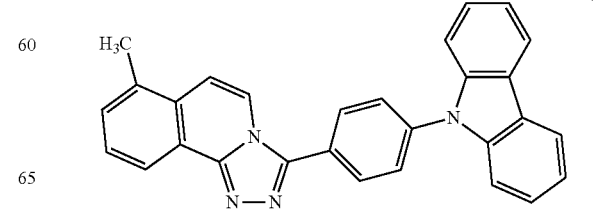

(645) 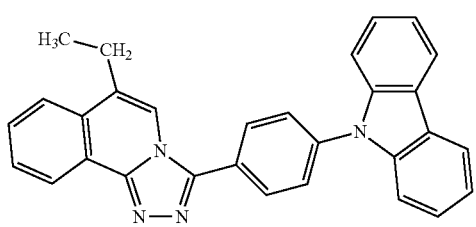
(646) 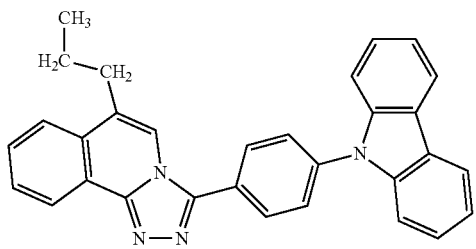
(647) 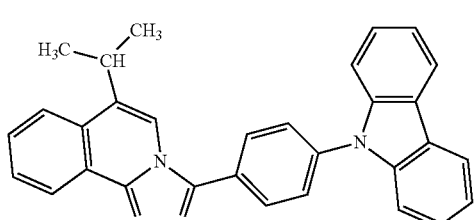
(648) 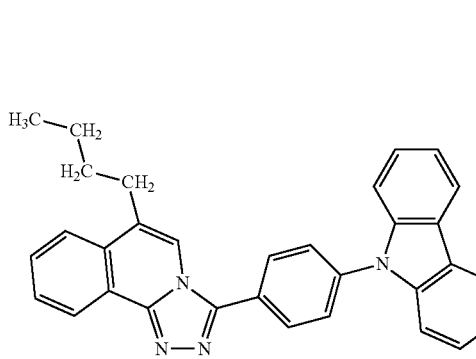
(649) 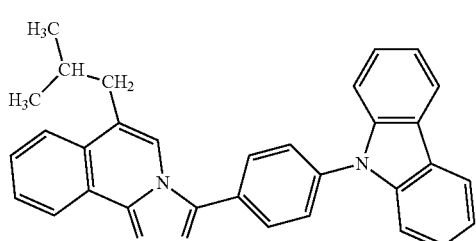
(650) 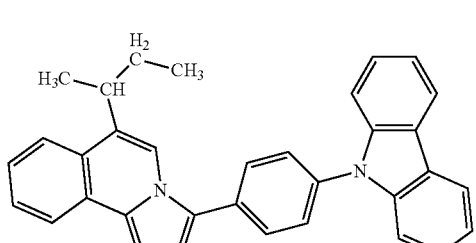
(651) 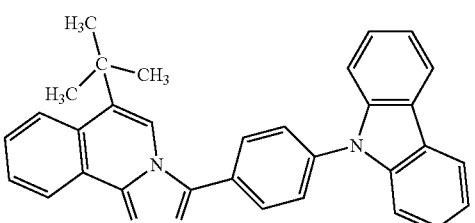
(652) 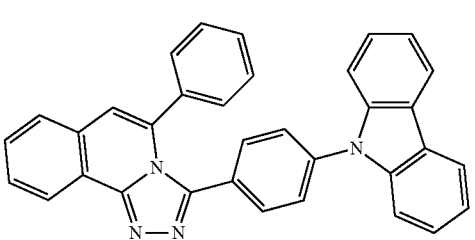
(653) 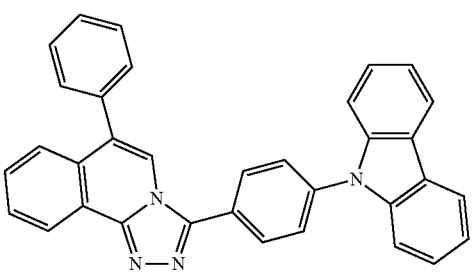
(654) 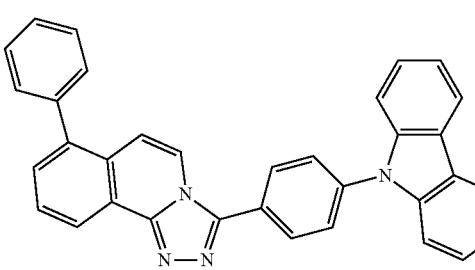
(655) 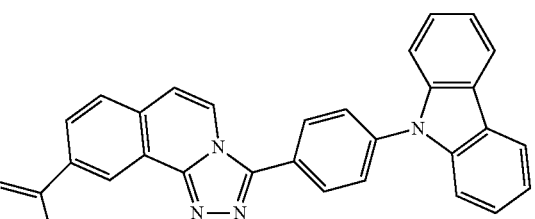
(656) 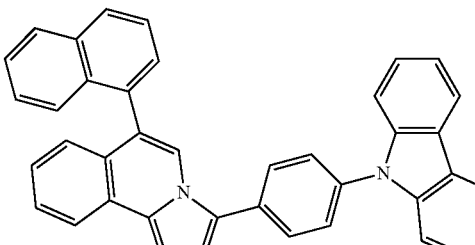

-continued
(657)
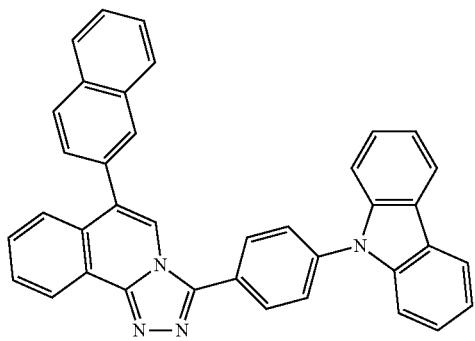
(658)
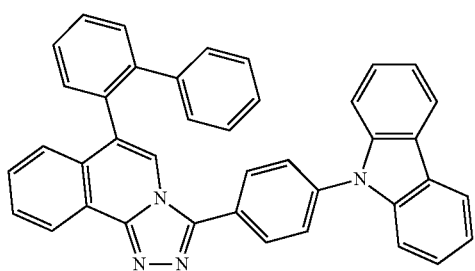
(659)
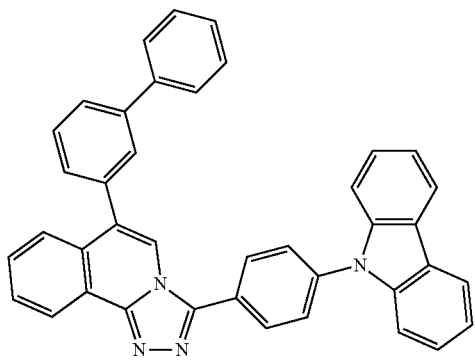
(660)
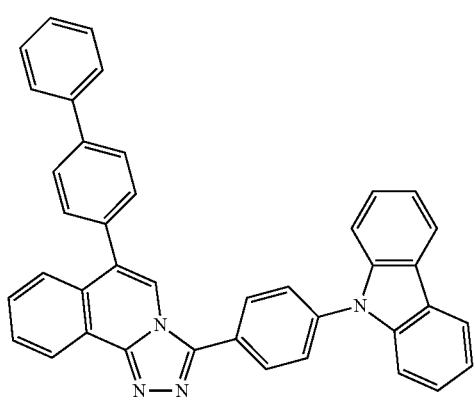
-continued
(661)
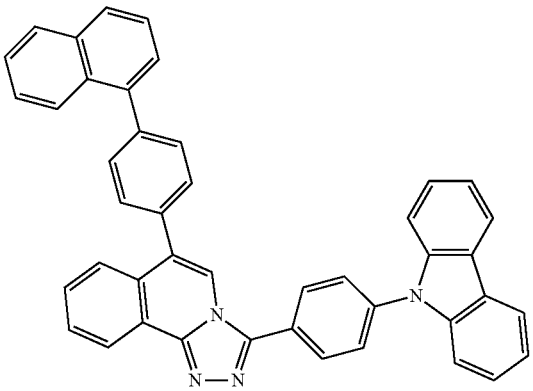
(662)
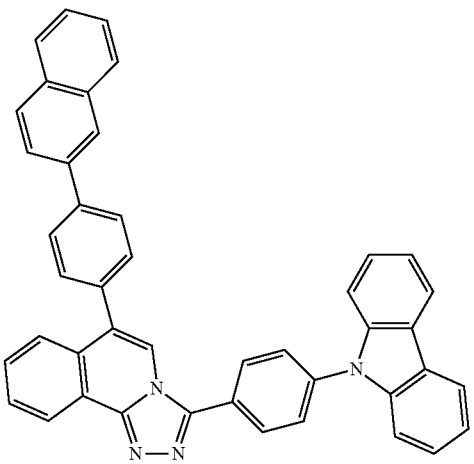
(663)
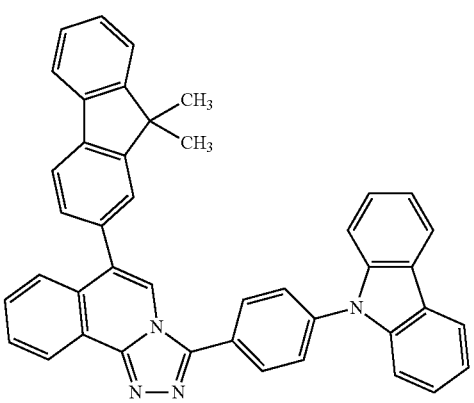

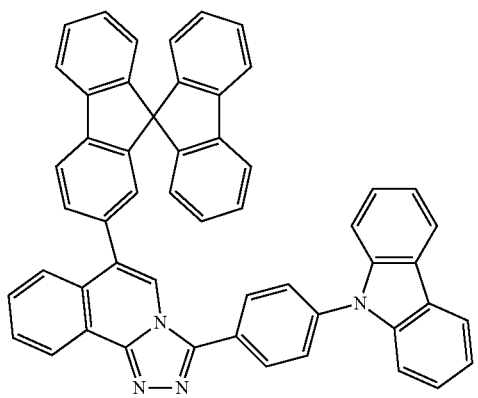
(664)
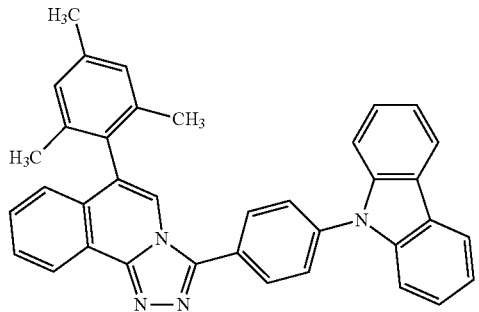
(668)
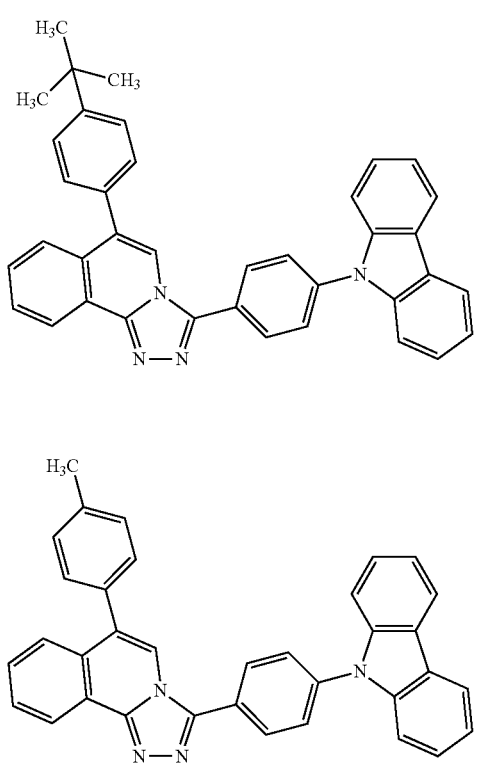
(665)
(666)
(667)
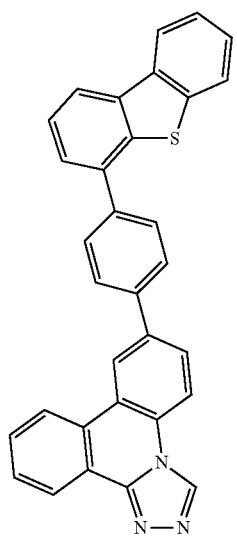
(1001)
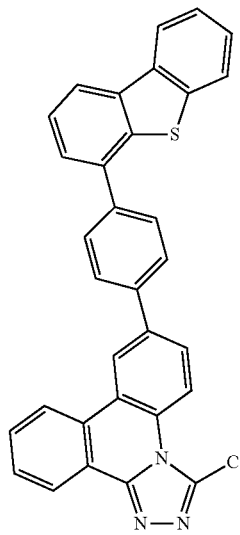
(1002)

(1003) 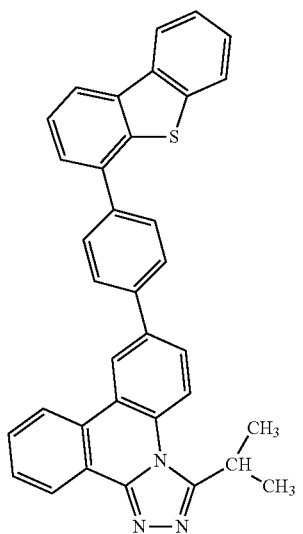
(1004) 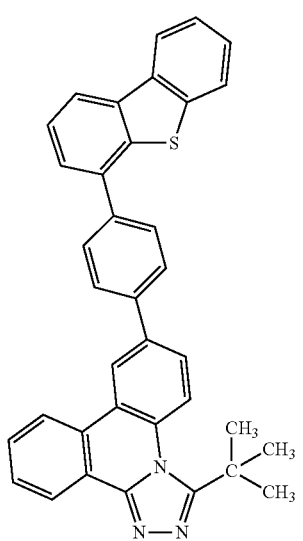
(1005) 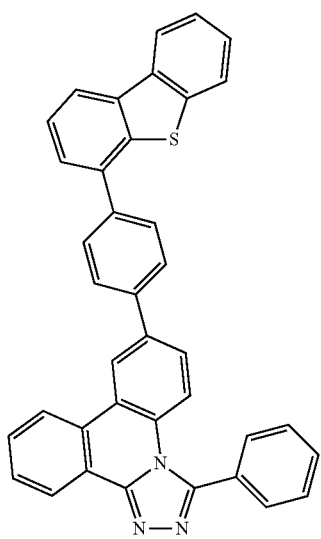
(1006) 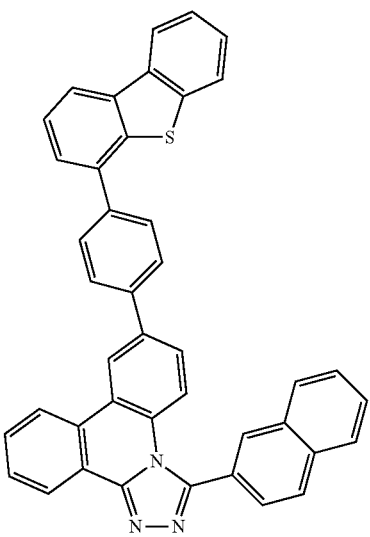
(1007) 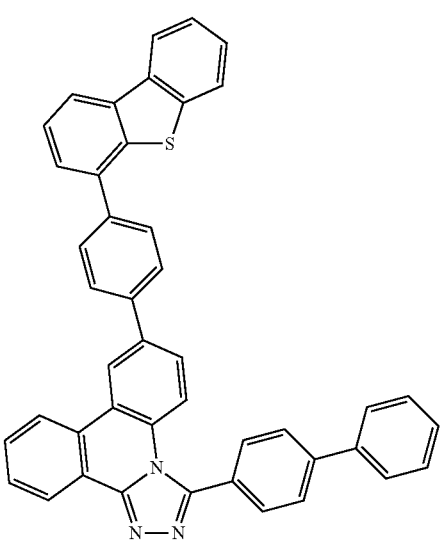
(1008) 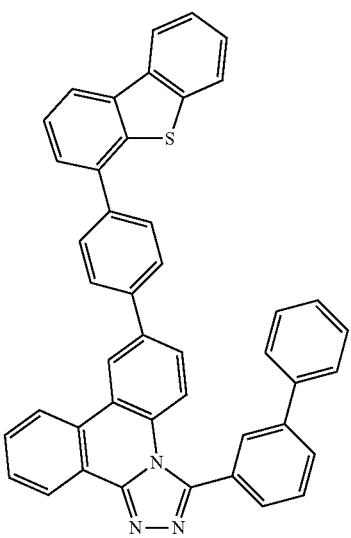

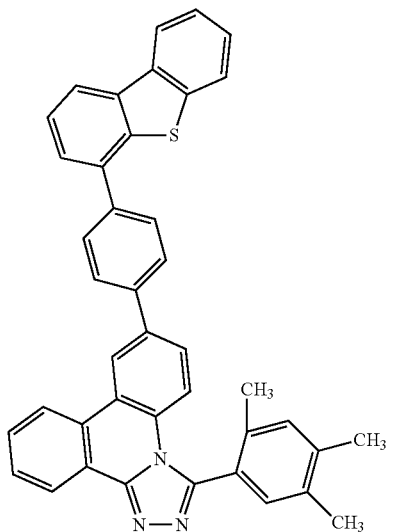
(1009)
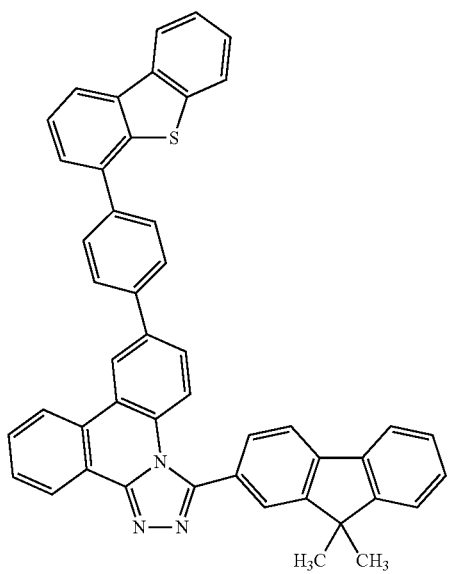
(1010)
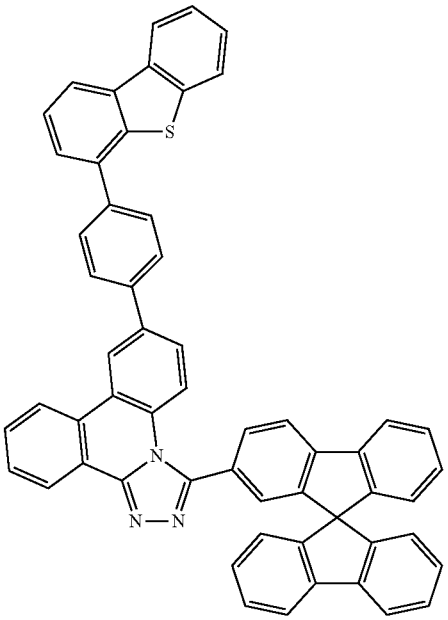
(1011)
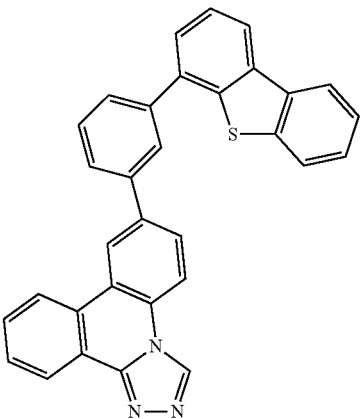
(1012)
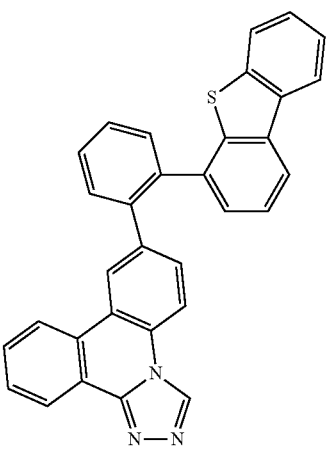
(1013)

-continued
(1014)
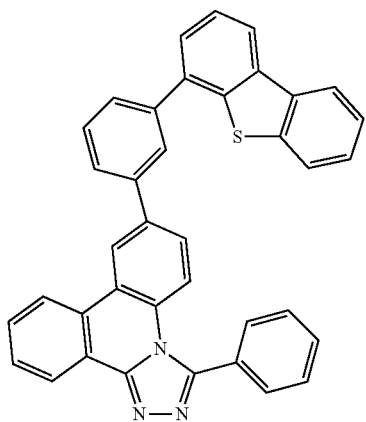
(1015)
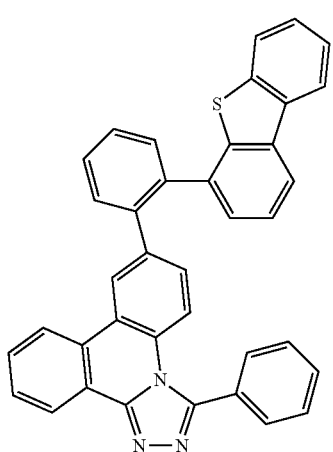
(1016)
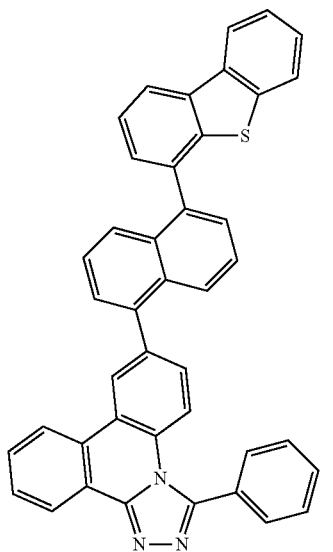
-continued
(1017)
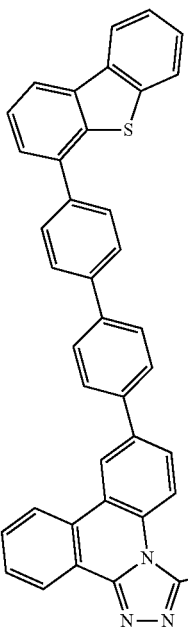
(1018)
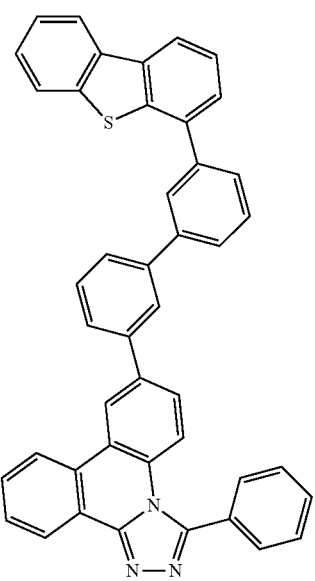

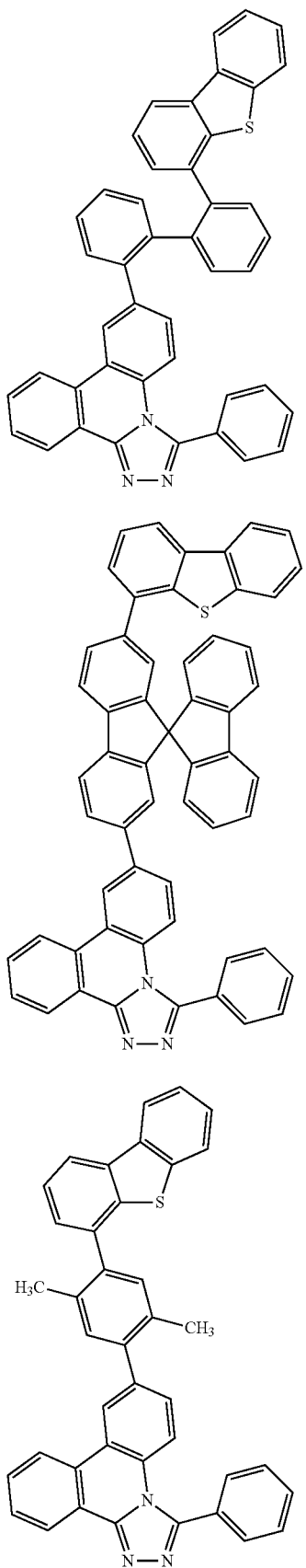
(1019)
(1020)
(1021)
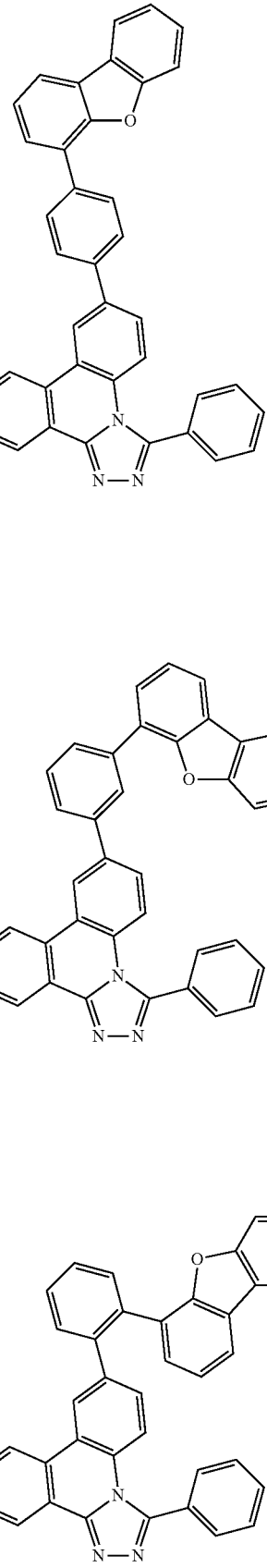
(1022)
(1023)
(1024)

-continued

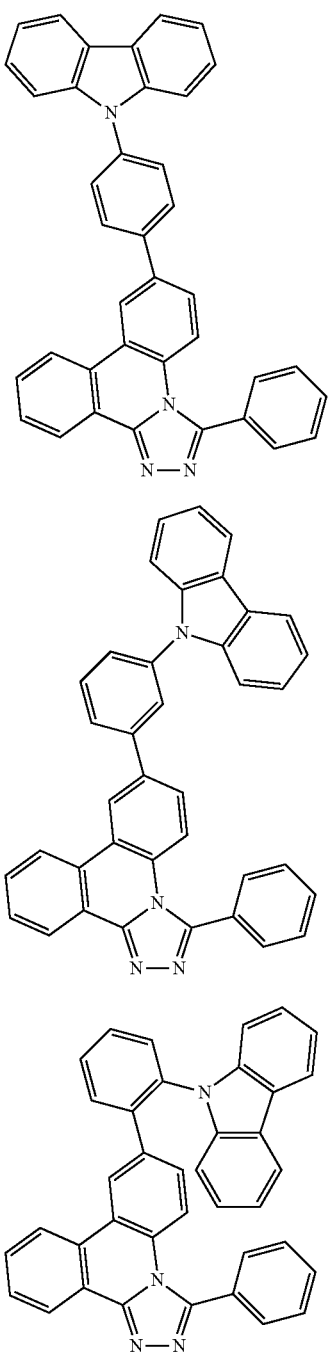

(1025)

(1026)

(1027)

Furthermore, a heterocyclic compound used for the synthesis of a triazole derivative described in Embodiment 1 is also a novel substance; therefore, this heterocyclic compound is also included in the present invention. Thus, one embodiment of the present invention is a heterocyclic compound represented by the general formula (G4).

E—Ar—X           (G4)

In the formula, E represents substituted or unsubstituted triazolo[4,3-f]phenanthridine or substituted or unsubstituted triazolo[3,4-a]isoquinoline, X represents iodine or bromine, and Ar represents a substituted or unsubstituted arylene group having 6 to 13 carbon atoms. Note that substituents of the arylene group may be bonded to form a ring.

One embodiment of the present invention is the heterocyclic compound represented by the following general formula (G5-1).

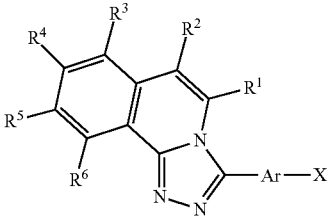

(G5-1)

In the formula, $R^1$ to $R^6$ separately represent hydrogen, an alkyl group having 1 to 4 carbon atoms, or a substituted or unsubstituted aryl group having 6 to 13 carbon atoms, X represents iodine or bromine, and Ar represents a substituted or unsubstituted arylene group having 6 to 13 carbon atoms. Note that substituents of the arylene group may be bonded to form a ring. $R^1$ and $R^2$ may be bonded to form a six-membered ring.

Another embodiment of the present invention is a heterocyclic compound represented by the following general formula (G5-2).

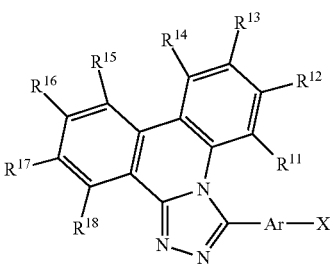

(G5-2)

In the formula, $R^{11}$ to $R^{18}$ separately represent hydrogen, an alkyl group having 1 to 4 carbon atoms, or a substituted or unsubstituted aryl group having 6 to 13 carbon atoms, X represents iodine or bromine, and Ar represents a substituted or unsubstituted arylene group having 6 to 13 carbon atoms. Note that substituents of the arylene group may be bonded to form a ring.

In any heterocyclic compound described above, Ar is preferably a substituted or unsubstituted phenylene group or a substituted or unsubstituted biphenyldiyl group, and especially preferably a substituted or unsubstituted phenylene group.

As specific structures of Ar in a heterocyclic compound of one embodiment of the present invention, the substituents represented by any of the above structural formulae (2-1) to (2-15) can be given, for example.

As specific structures of $R^1$ to $R^6$ and $R^{11}$ to $R^{18}$ in a heterocyclic compound of one embodiment of the present invention, the substituents represented by any of the above structural formulae (1-1) to (1-23) can be given, for example.

Another embodiment of the present invention is a heterocyclic compound represented by a general formula (G6).

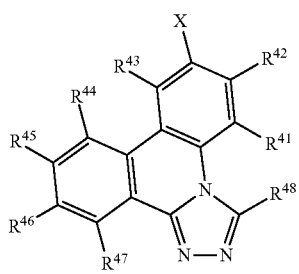

(G6)

In the formula, $R^{41}$ to $R^{48}$ separately represent hydrogen, an alkyl group having 1 to 4 carbon atoms, or a substituted or unsubstituted aryl group having 6 to 13 carbon atoms, and X represents iodine or bromine.

As specific structures of $R^{41}$ to $R^{48}$ in a heterocyclic compound of one embodiment of the present invention, the substituents represented by any of the above structural formulae (1-1) to (1-23) can be given, for example.

As a heterocyclic compound used in the synthesis of a triazole derivatives according to one embodiment of the present invention, a heterocyclic compound represented by any of structural formulae (700) to (783), (800) to (883), and (900) to (936) can be given, for example. However, the present invention is not limited thereto.

(700)

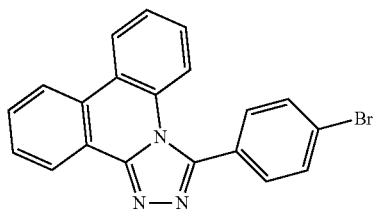

(701)

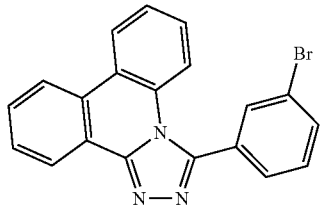

(702)

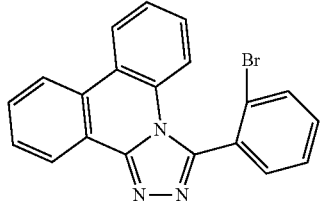

(703)

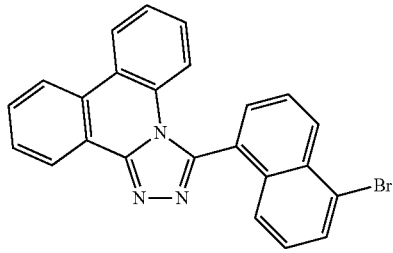

(704)

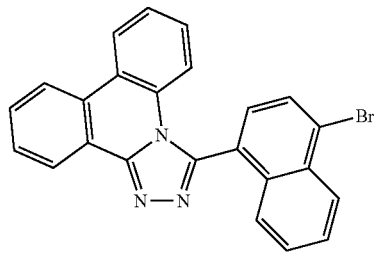

(705)

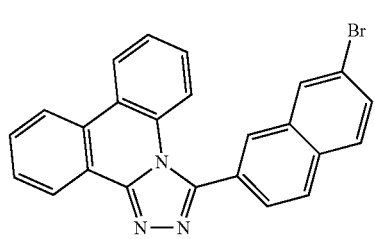

(706)

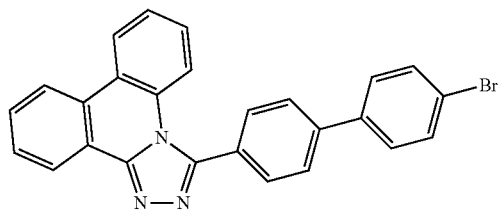

(707)

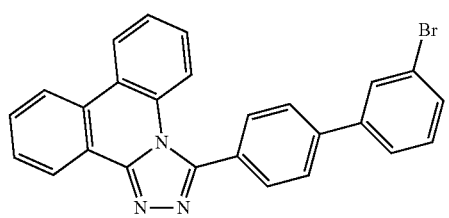

(708)

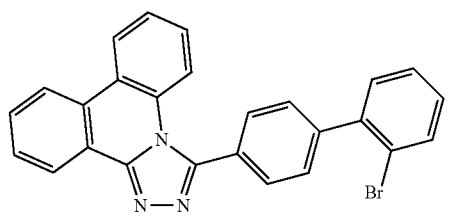

(709)

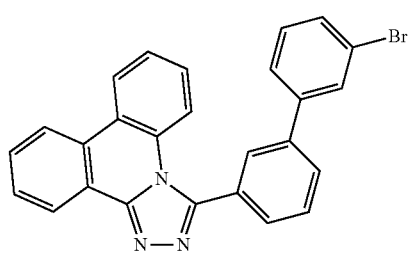

-continued
(710)
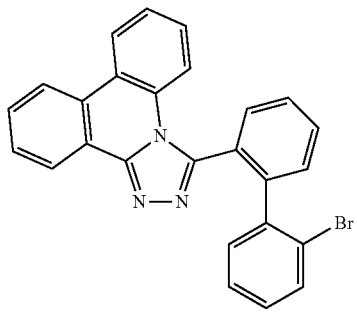
(711)
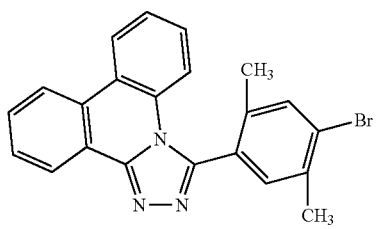
(712)
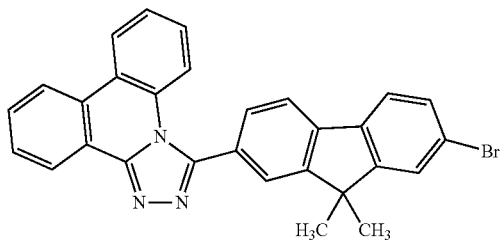
(713)
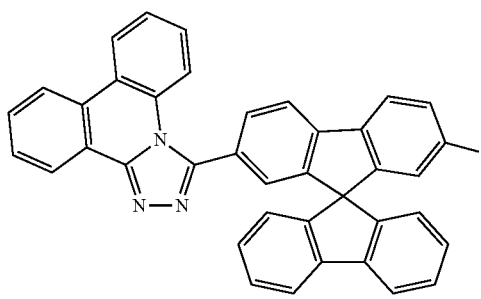
(714)
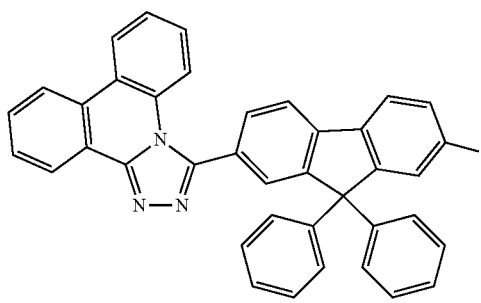
-continued
(715)
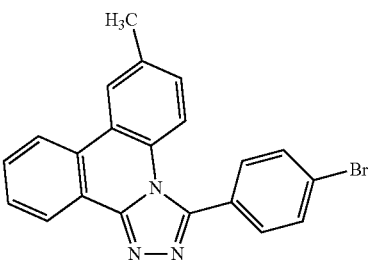
(716)
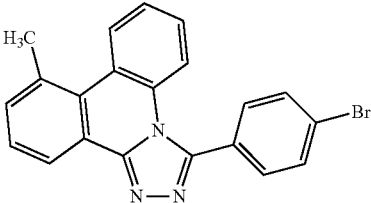
(717)
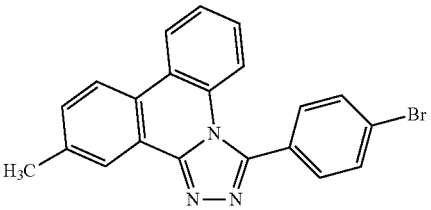
(718)
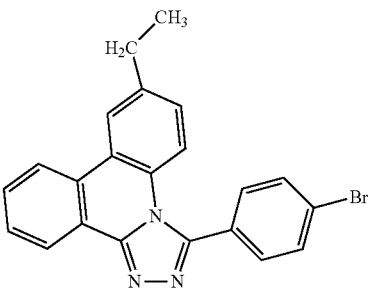
(719)
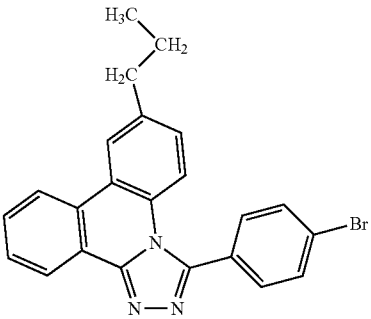
(720)
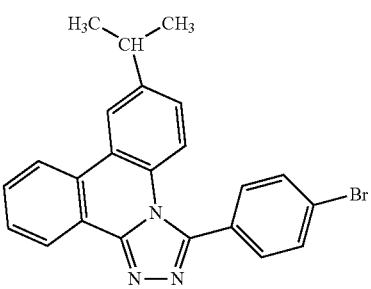

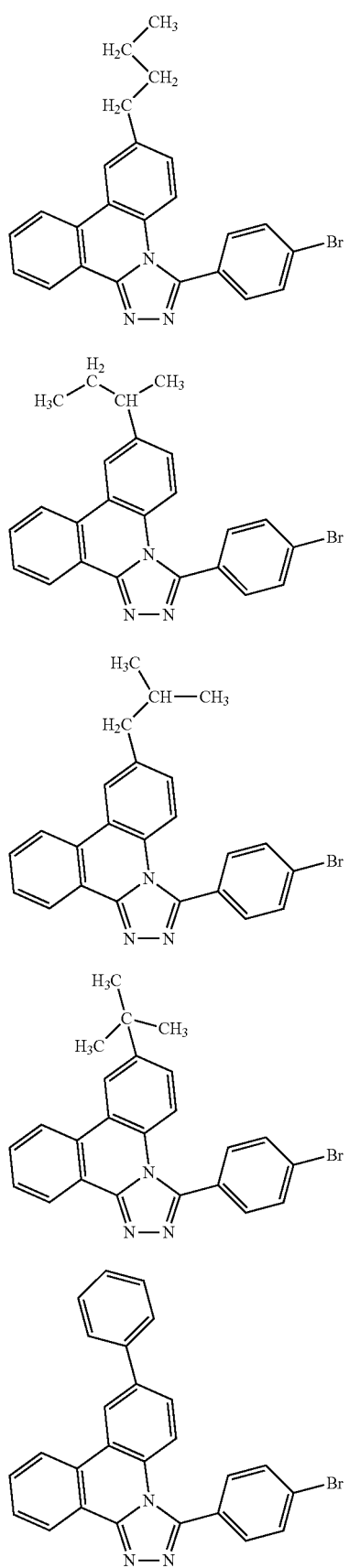
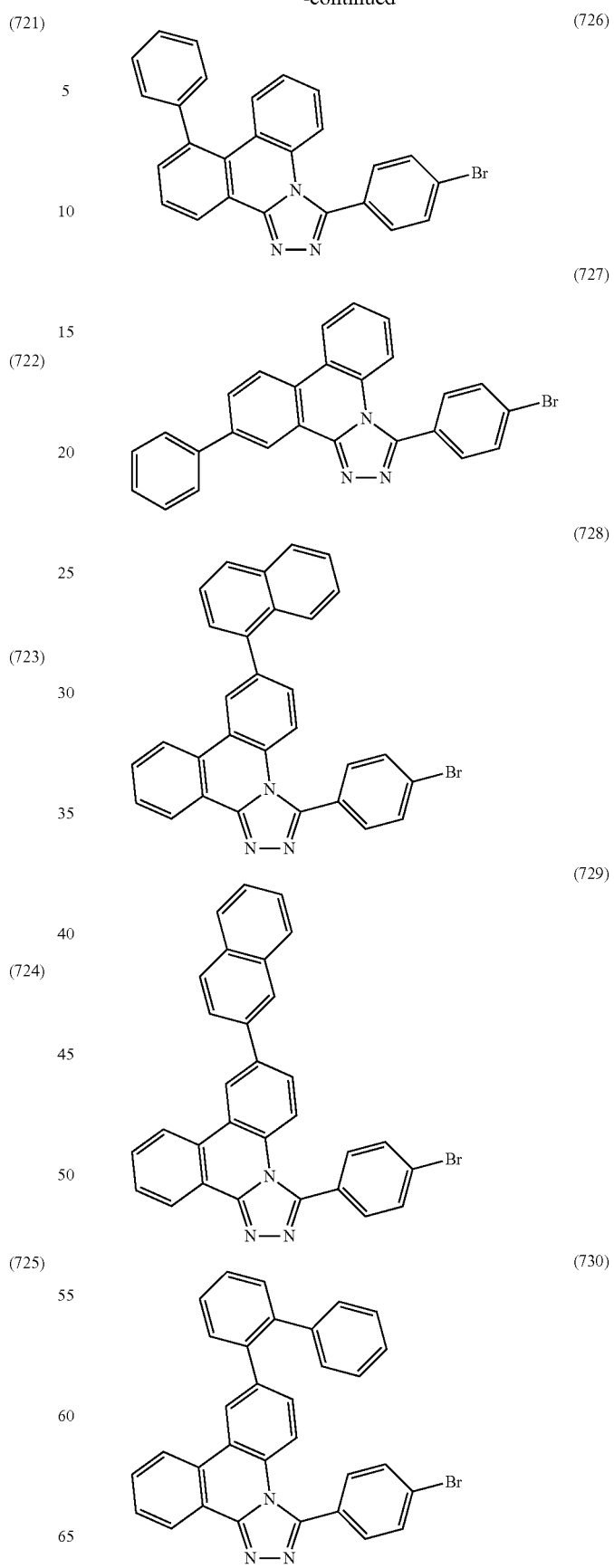

-continued
(731)
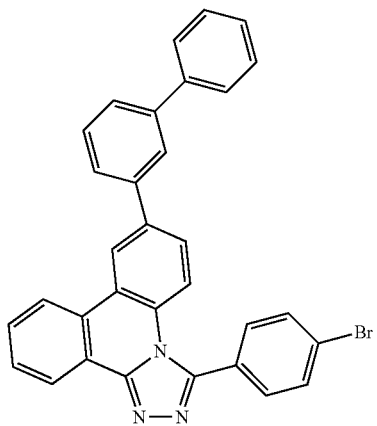
(732)
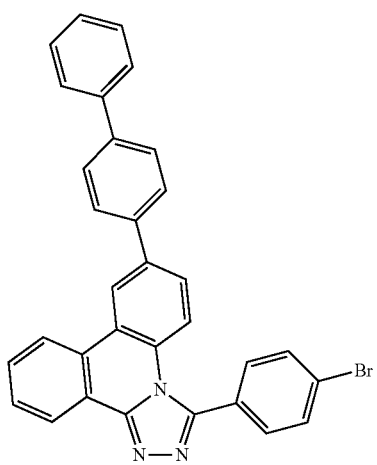
(733)
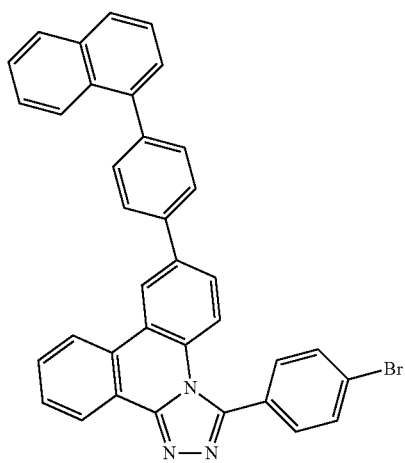
-continued
(734)
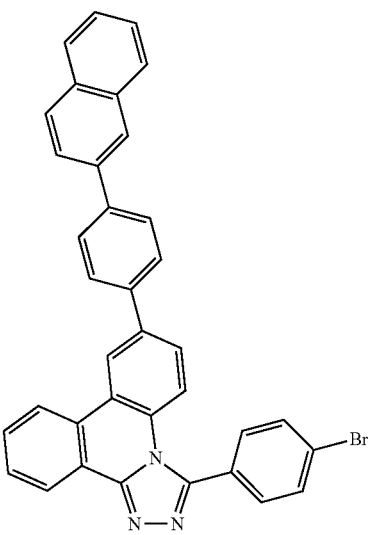
(735)
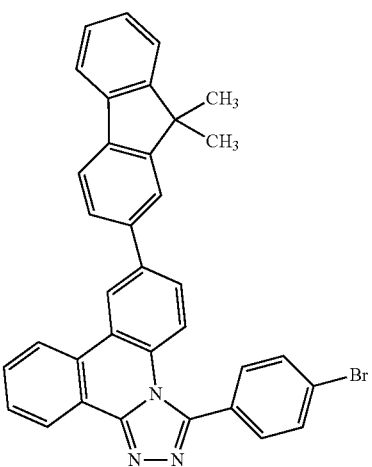
(736)
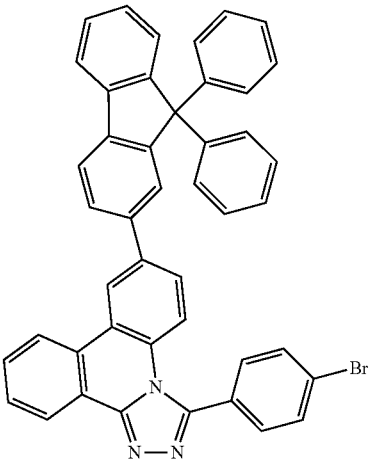

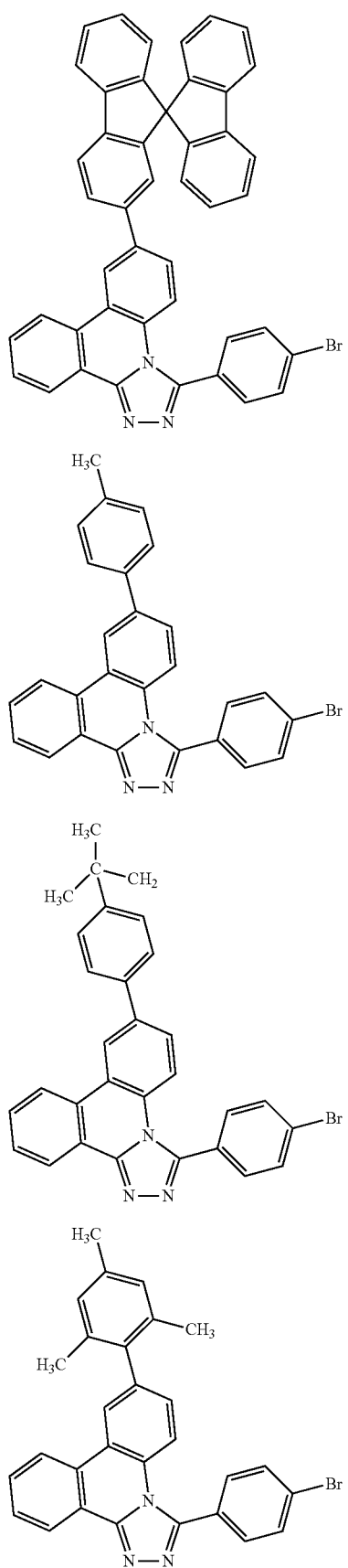
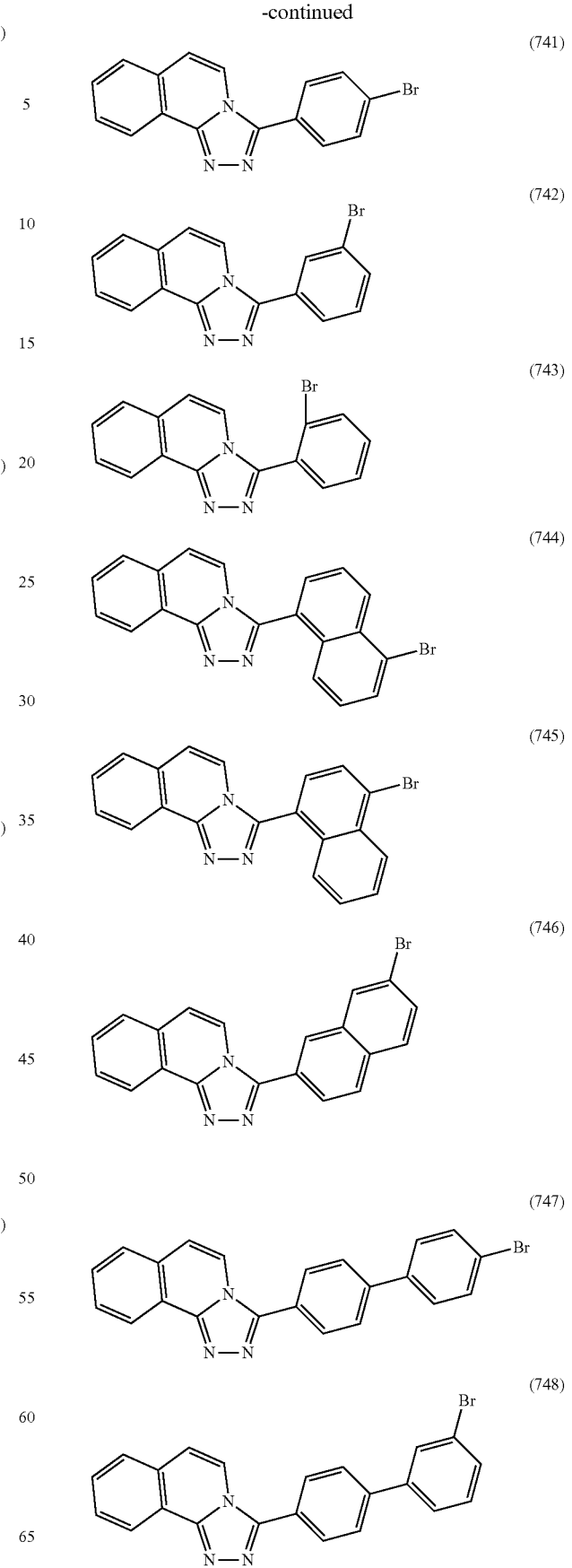

(749) 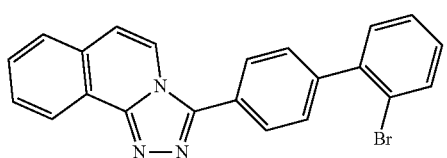
(750) 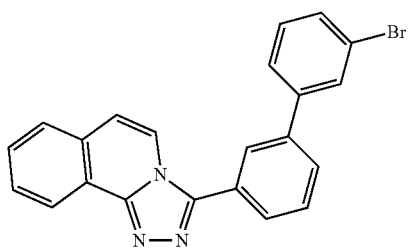
(751) 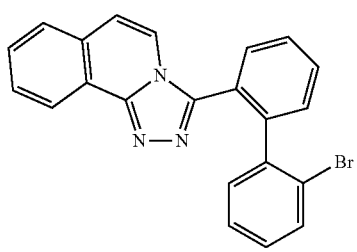
(752) 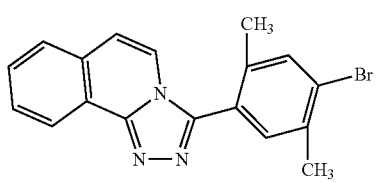
(753) 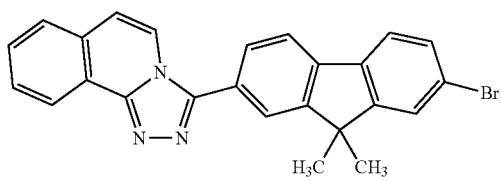
(754) 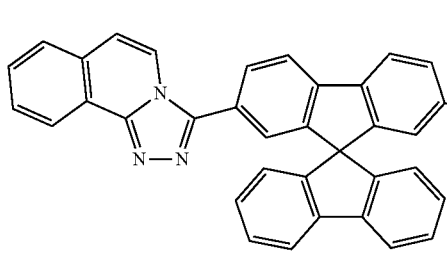
(755) 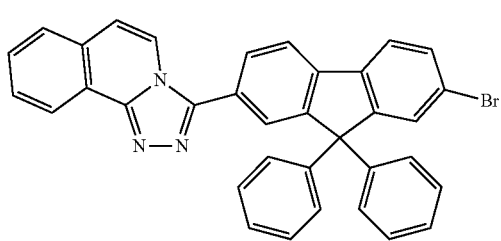
(756) 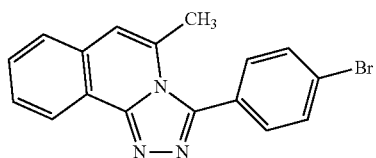
(757) 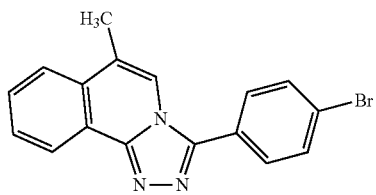
(758) 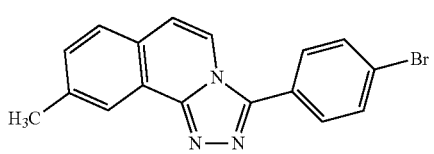
(759) 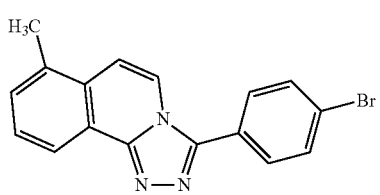
(760) 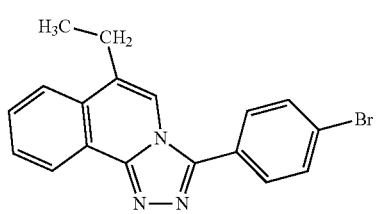
(761) 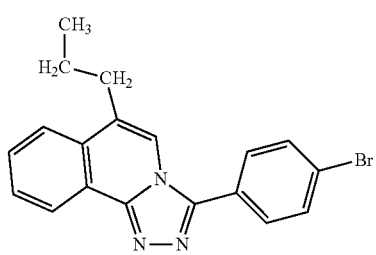
(762) 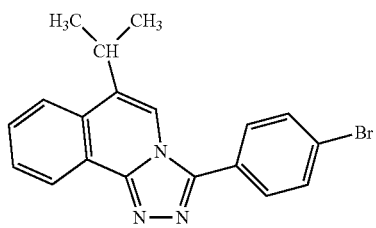

(763) 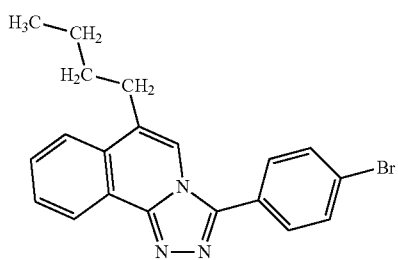
(764) 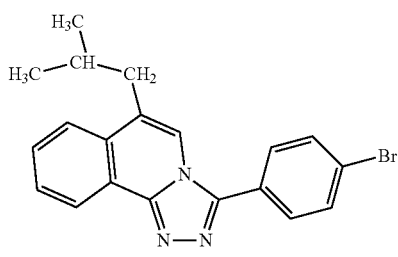
(765) 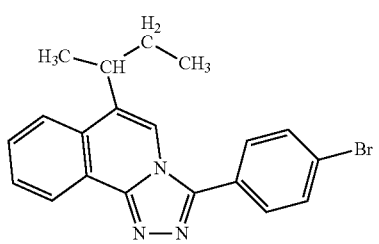
(766) 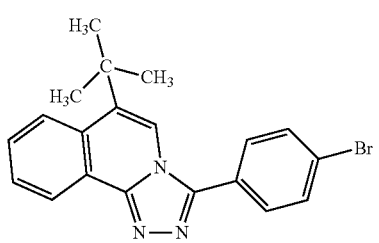
(767) 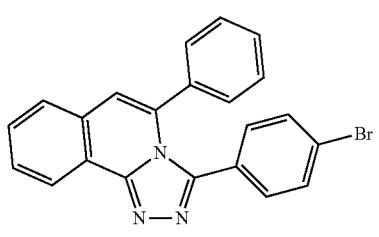
(768) 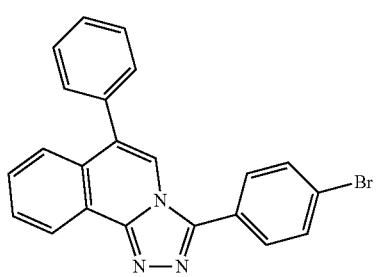
(769) 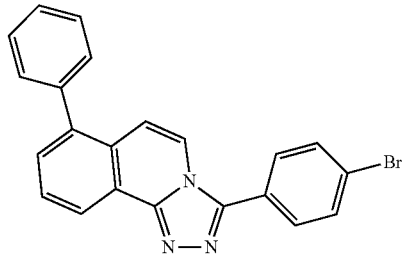
(770) 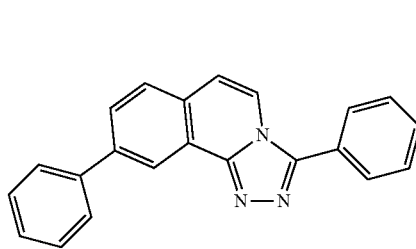
(771) 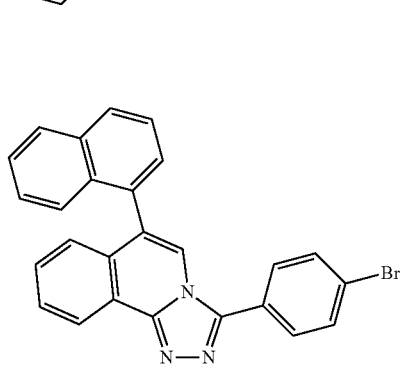
(772) 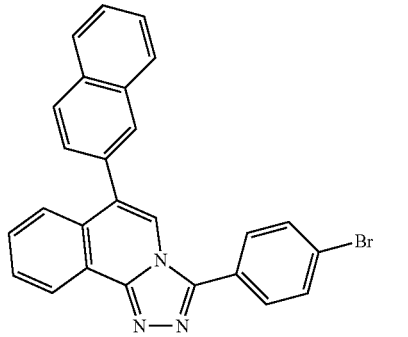
(773) 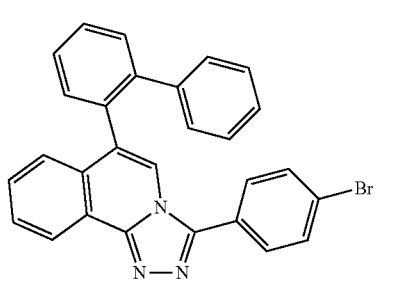

(774) 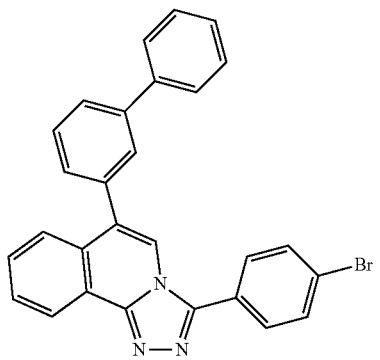
(775) 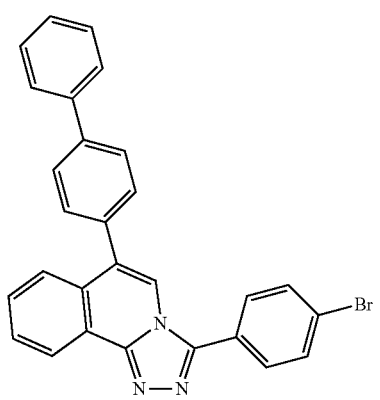
(776) 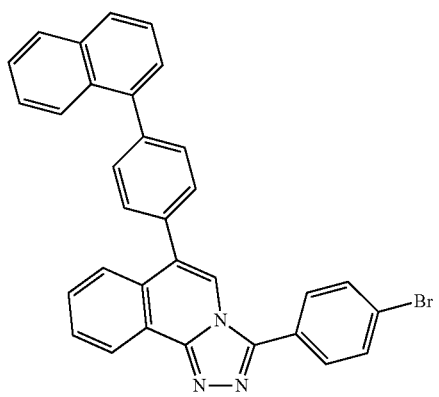
(777) 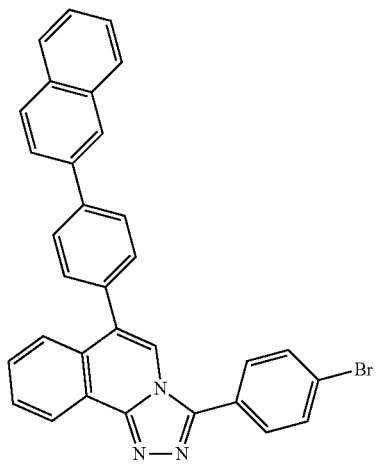
(778) 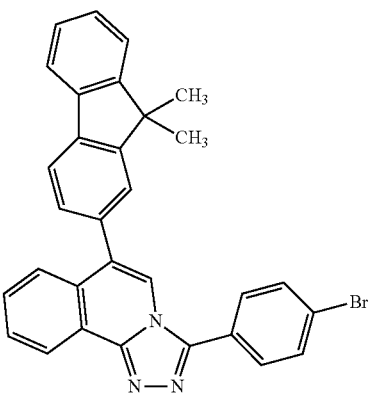
(779) 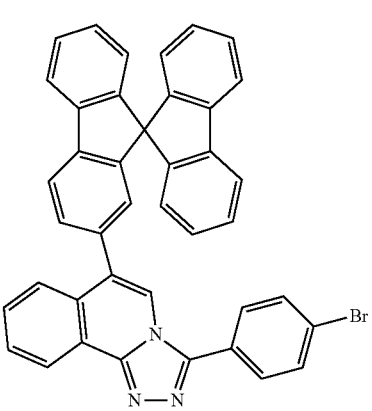
(780) 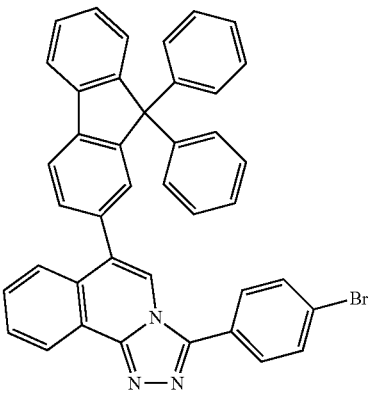
(781) 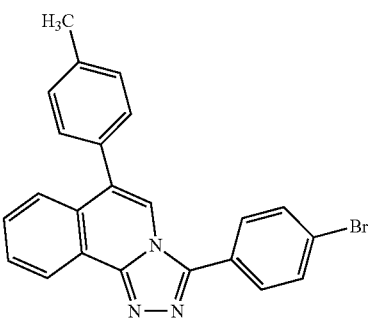

(782) 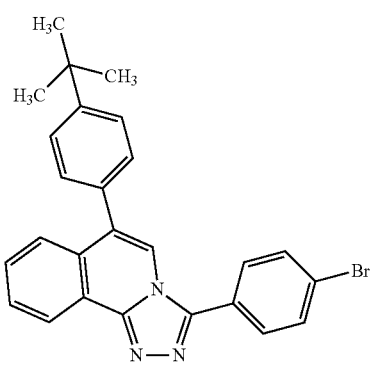
(783) 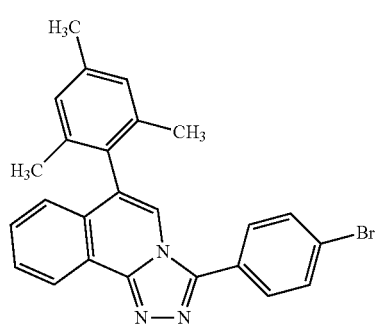
(800) 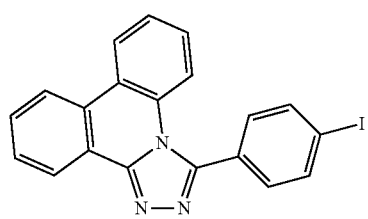
(801) 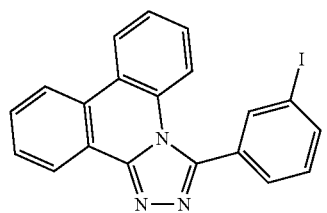
(802) 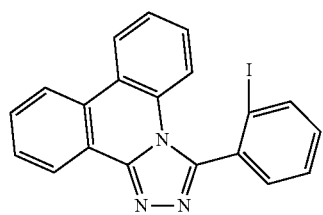
(803) 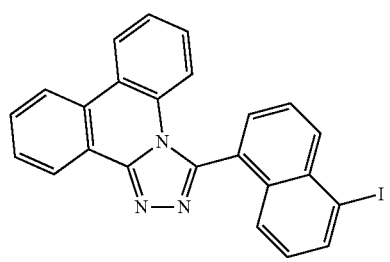
(804) 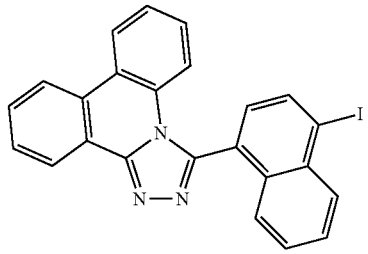
(805) 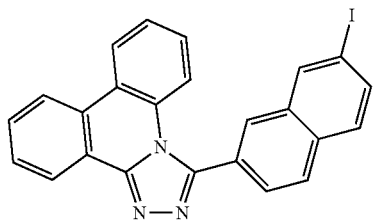
(806) 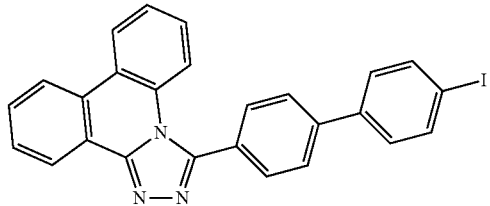
(807) 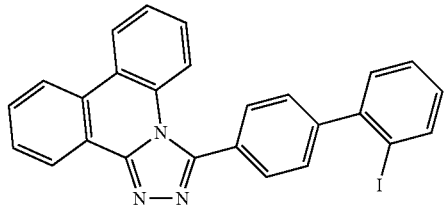
(808) 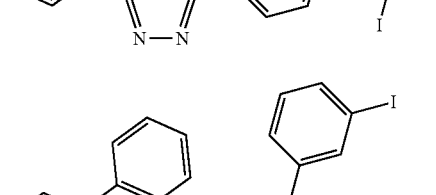
(809) 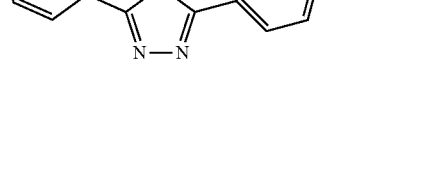

(810) 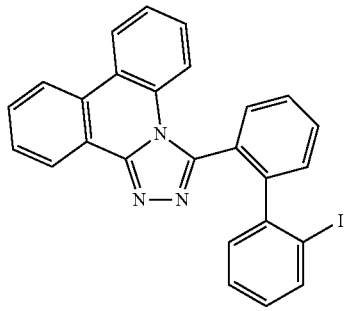
(811) 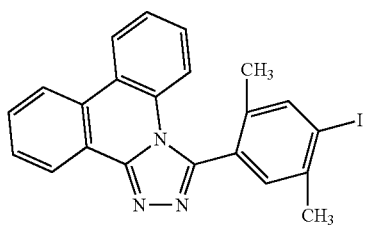
(812) 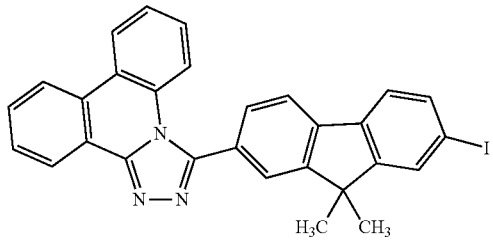
(813) 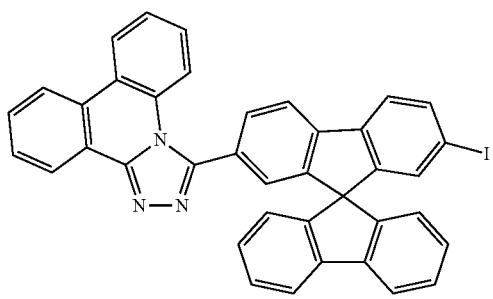
(814) 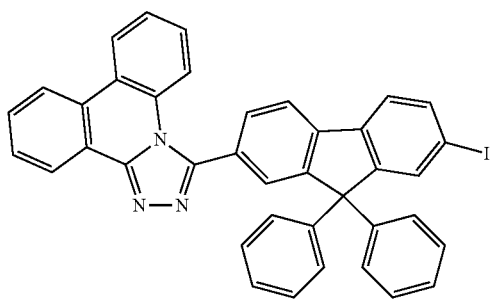
(815) 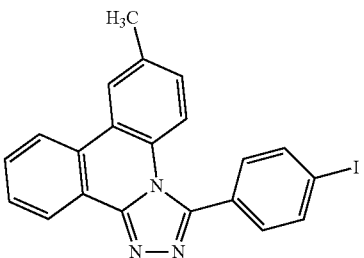
(816) 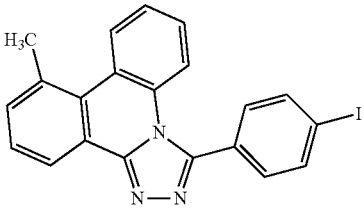
(817) 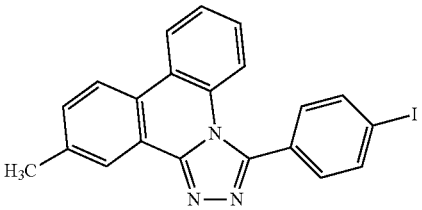
(818) 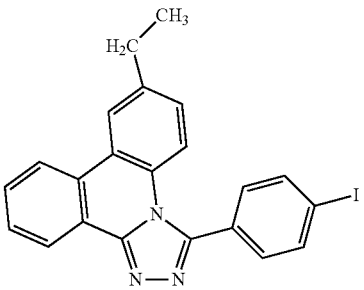
(819) 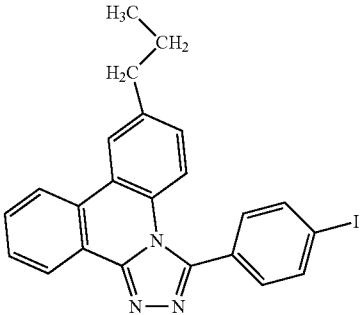
(820) 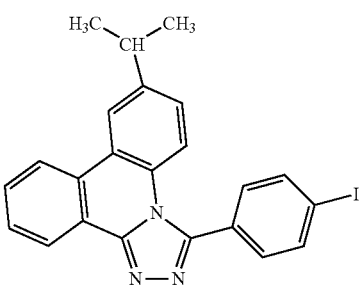

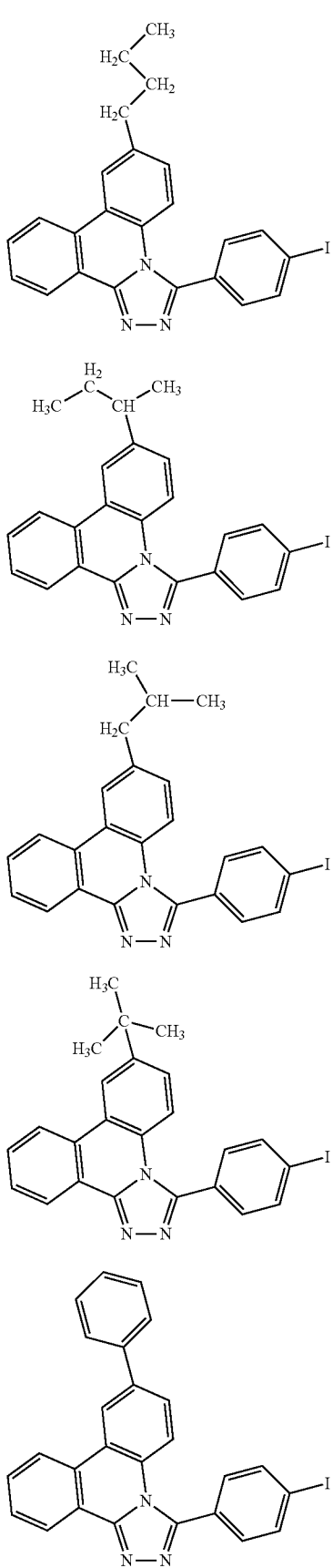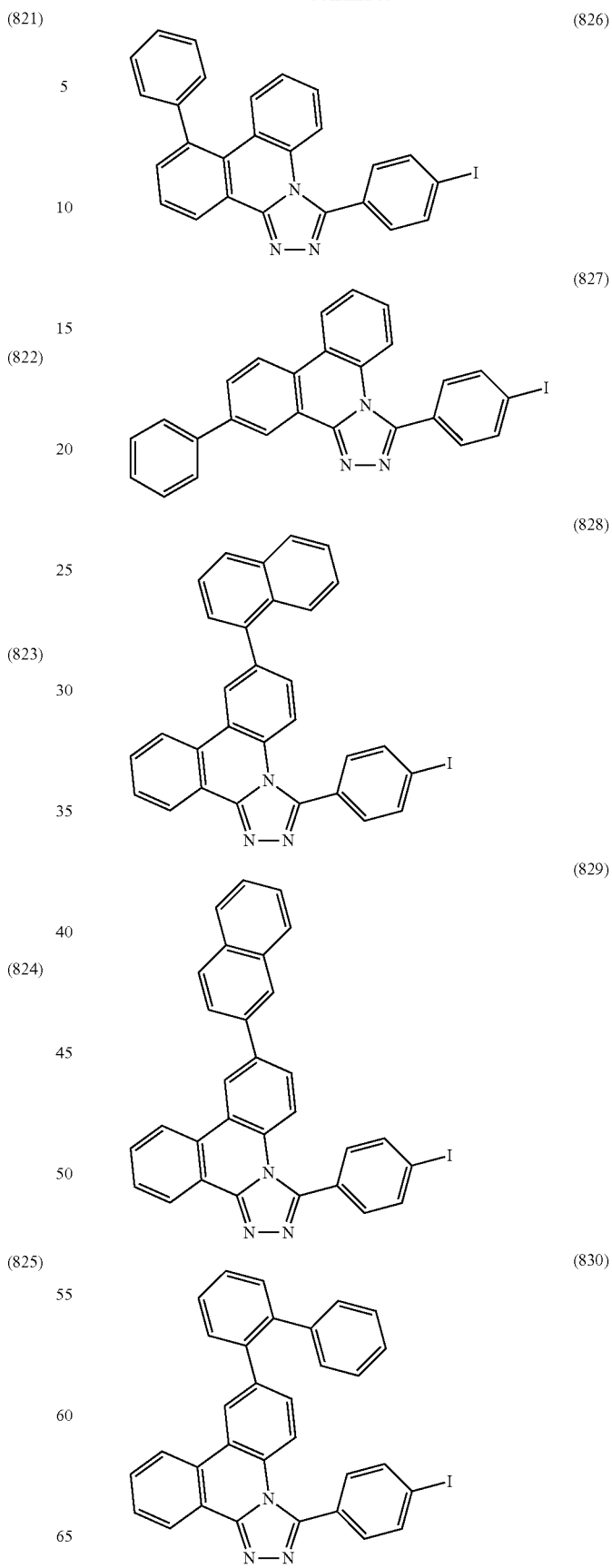

-continued
(831)
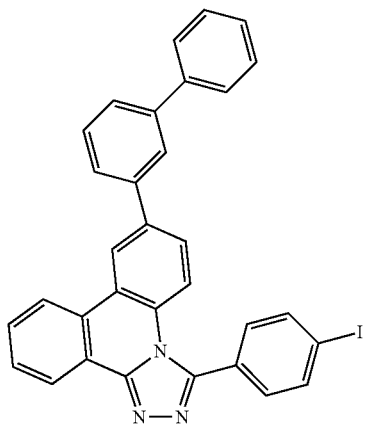
(832)
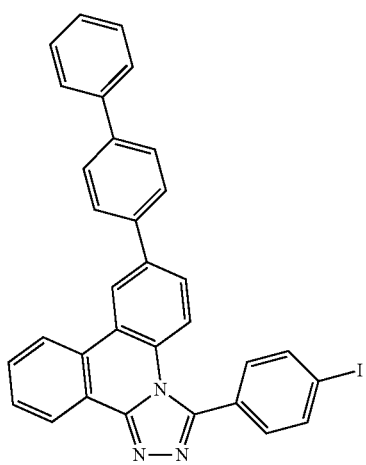
(833)
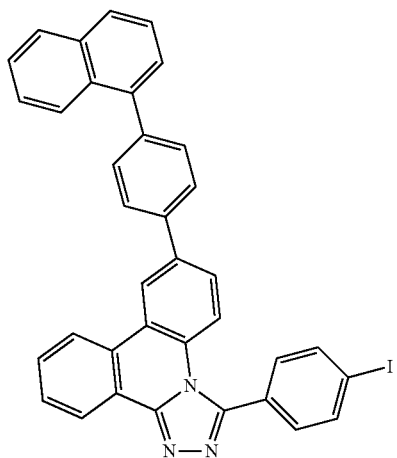
-continued
(834)
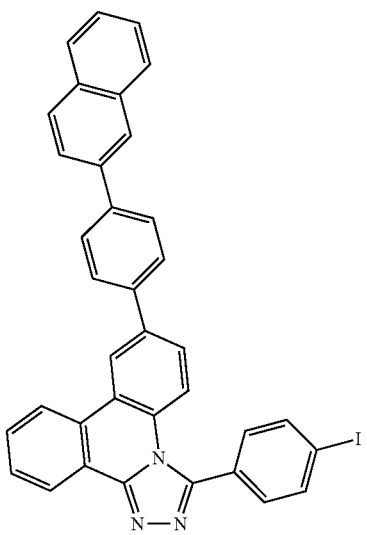
(835)
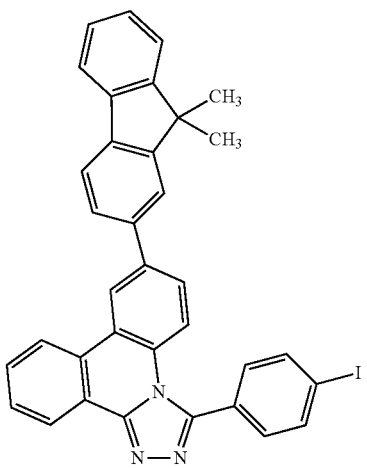
(836)
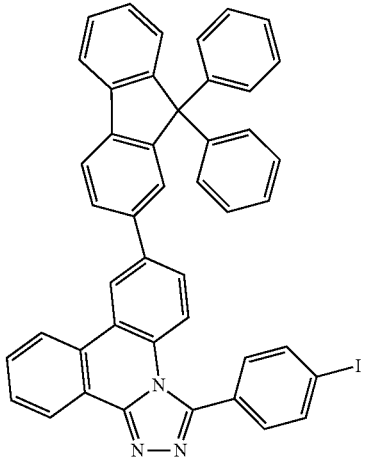

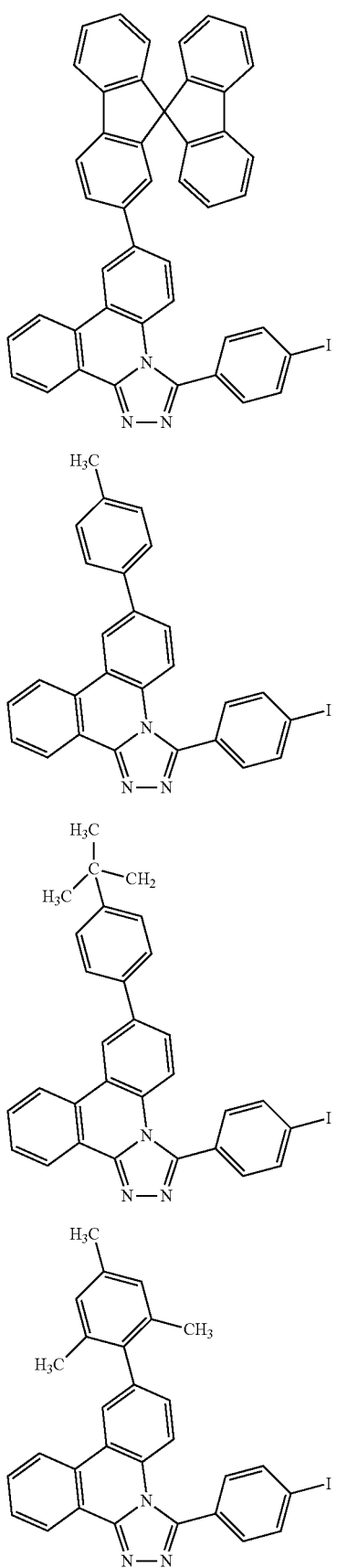
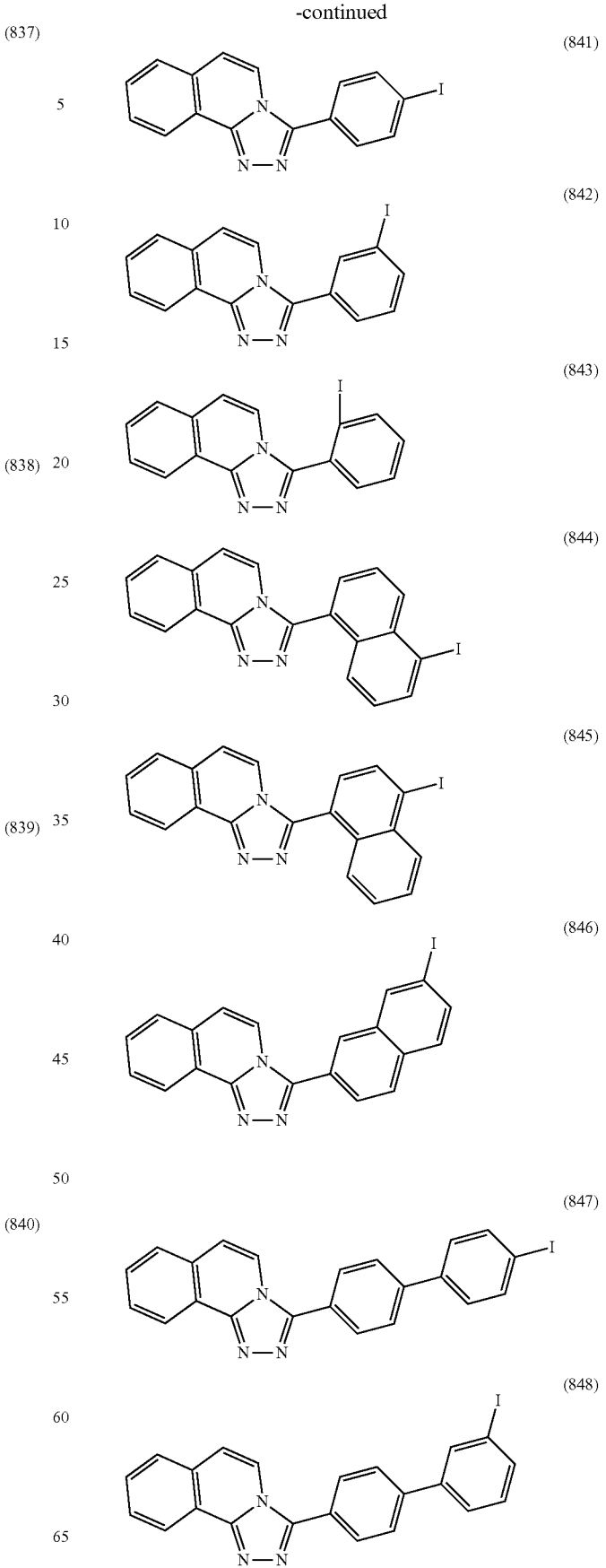

(849) 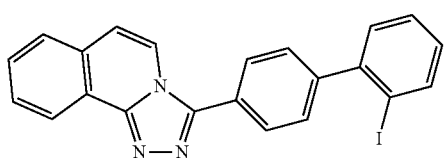
(850) 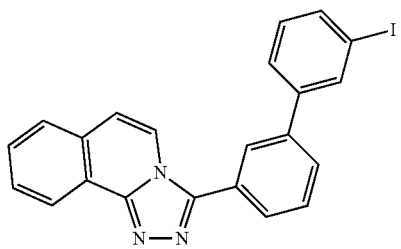
(851) 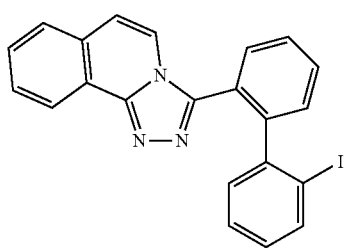
(852) 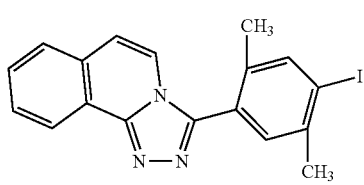
(853) 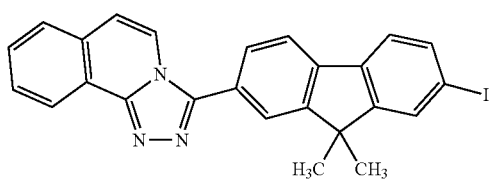
(854) 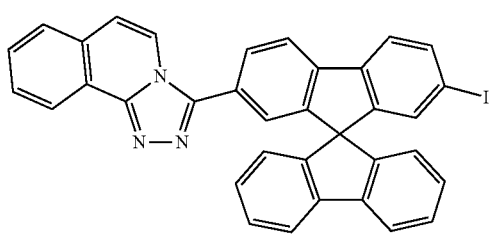
(855) 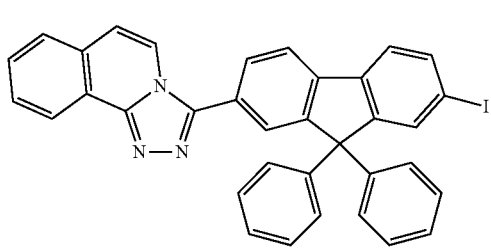
(856) 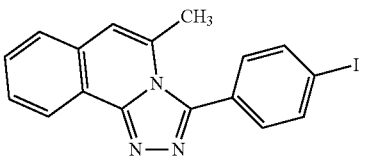
(857) 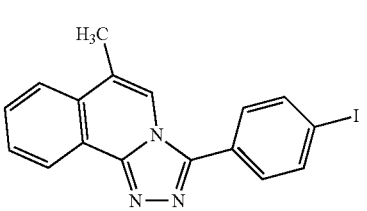
(858) 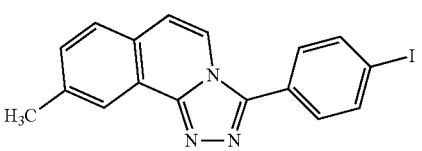
(859) 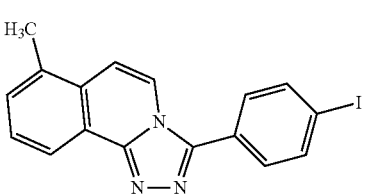
(860) 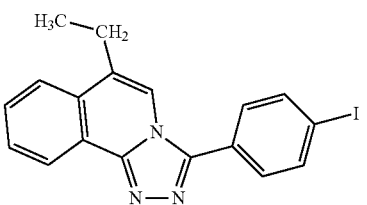
(861) 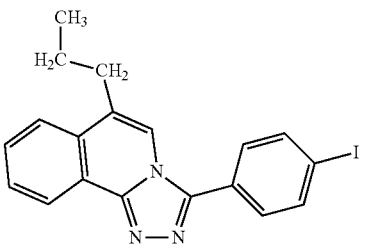
(862) 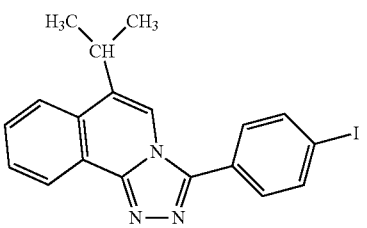

(863)
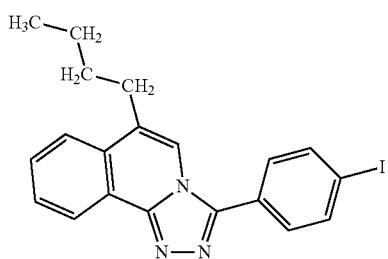
(864)
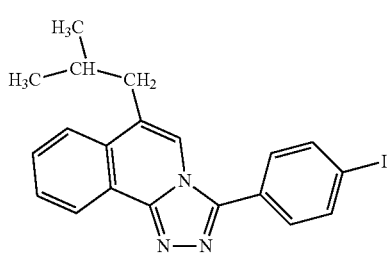
(865)
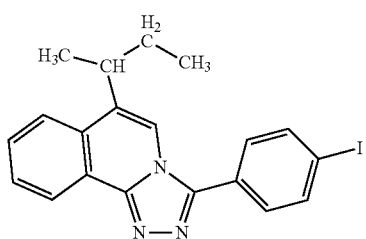
(866)
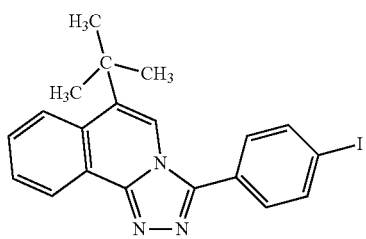
(867)
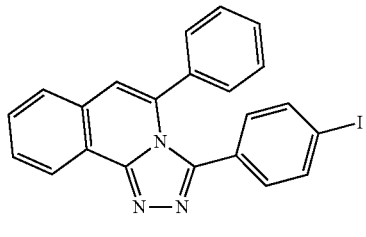
(868)
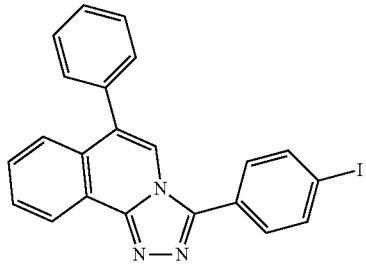
(869)
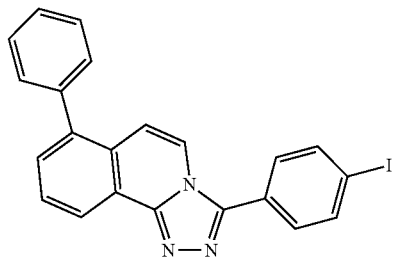
(870)
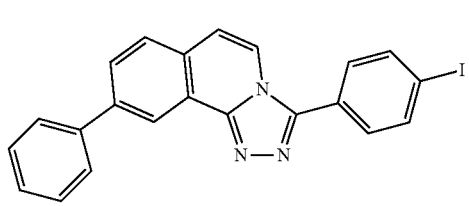
(871)
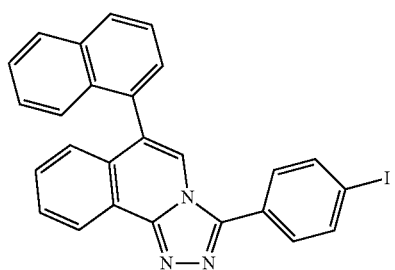
(872)
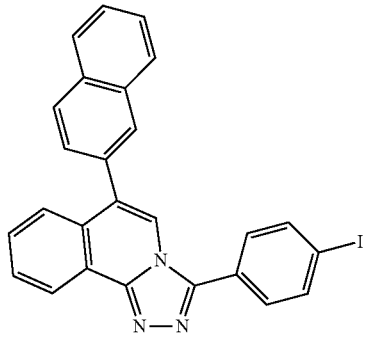
(873)
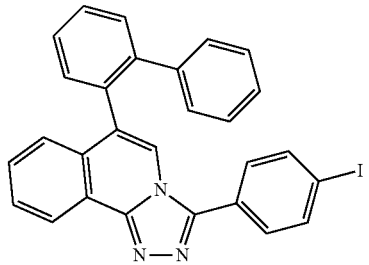

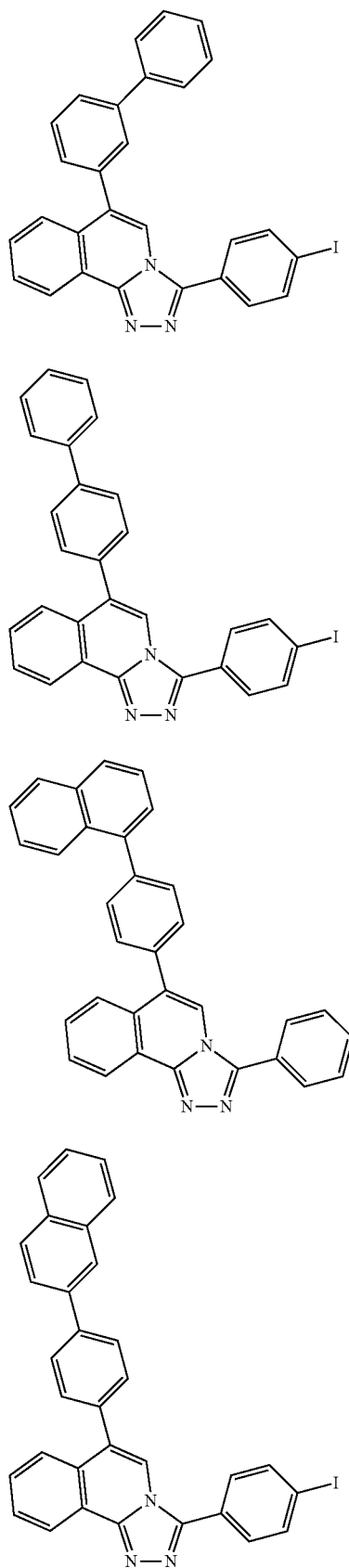
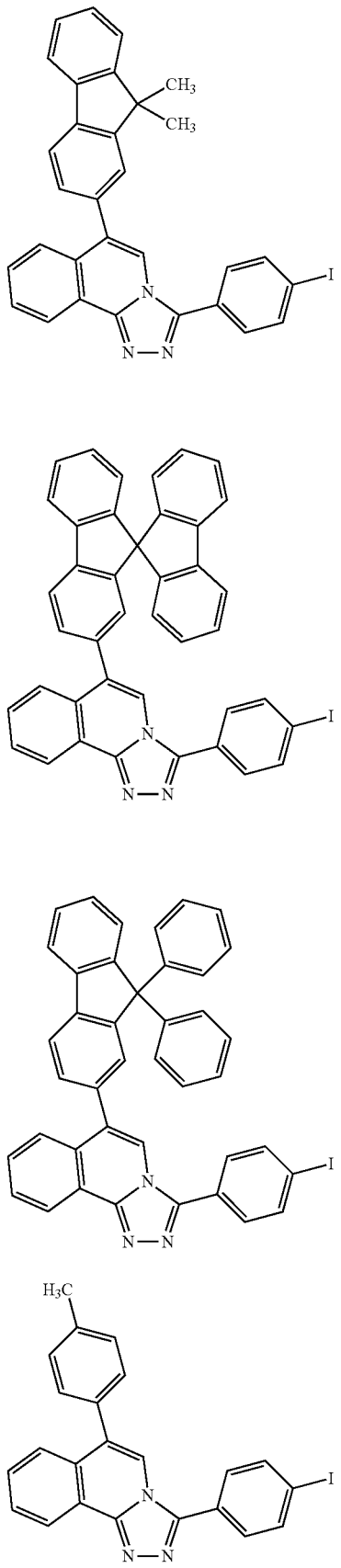

-continued
(882) 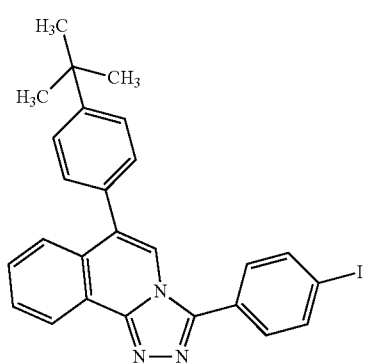
(883) 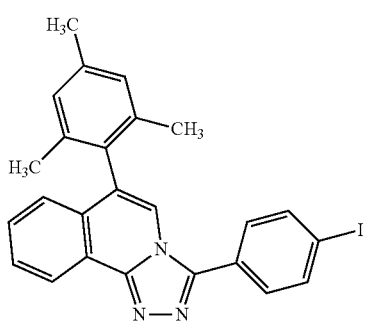
(900) 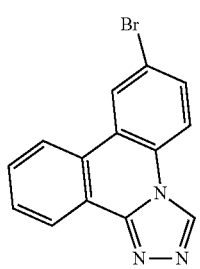
(901) 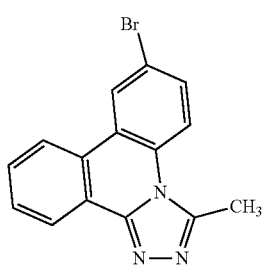
(902) 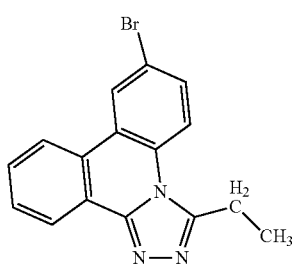
-continued
(903) 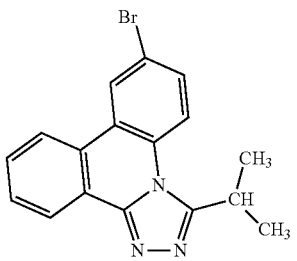
(904) 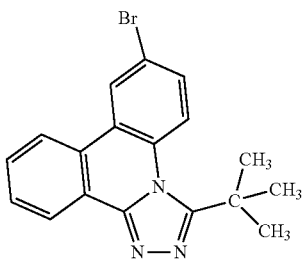
(905) 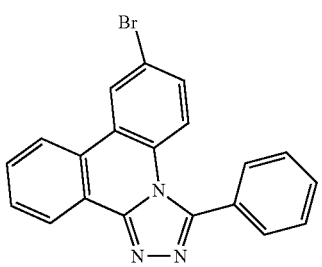
(906) 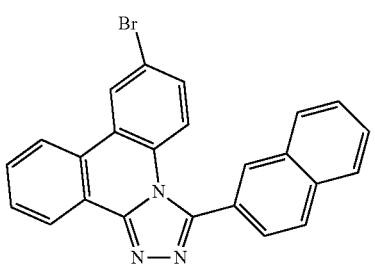
(907) 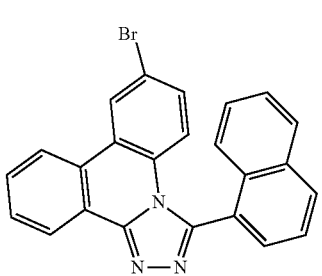
(908)

(909) 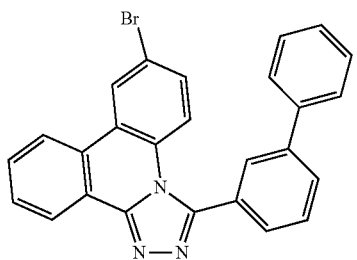
(910) 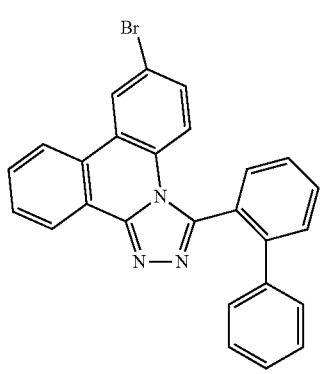
(911) 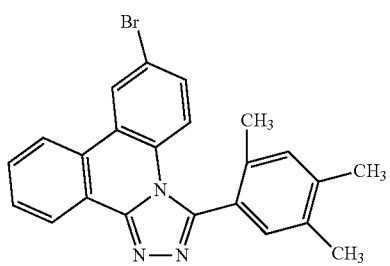
(912) 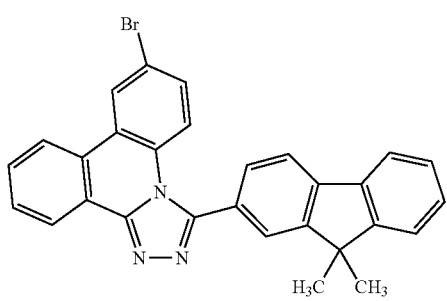
(913) 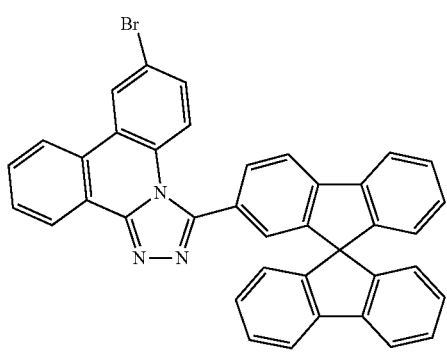
(914) 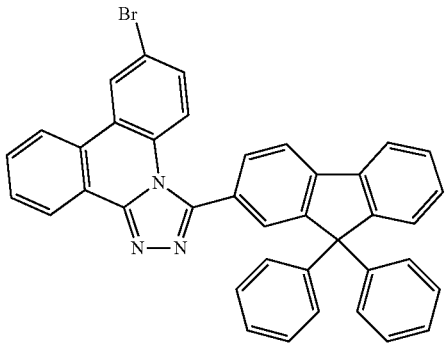
(915) 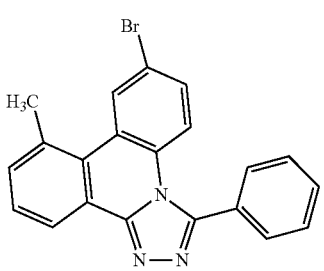
(916) 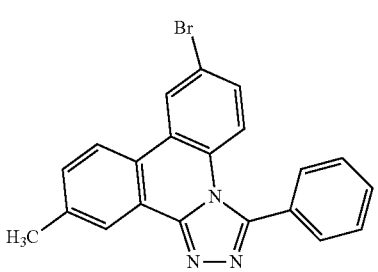
(917) 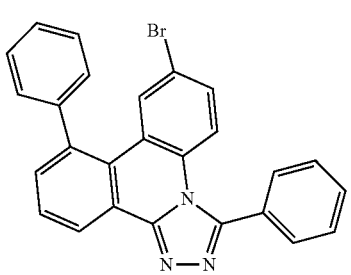
(918) 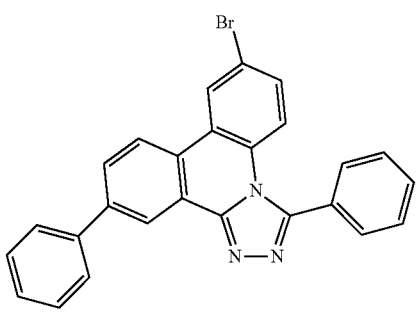

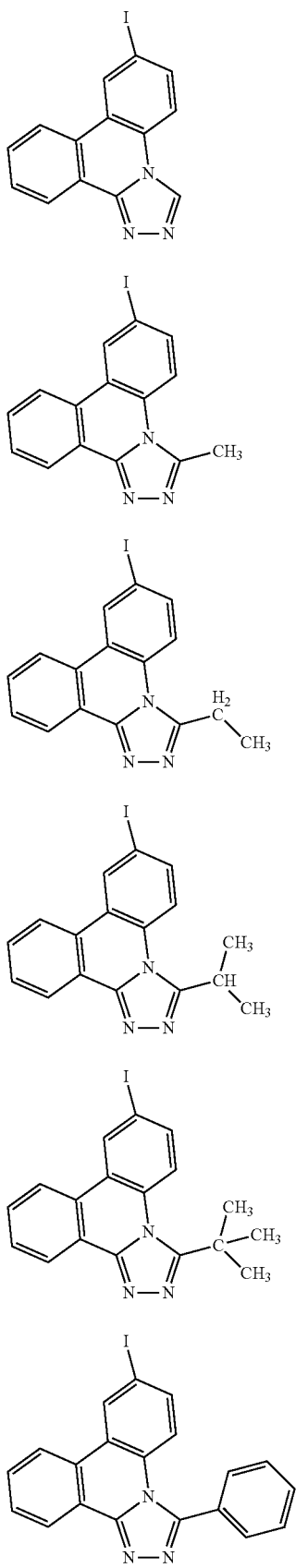
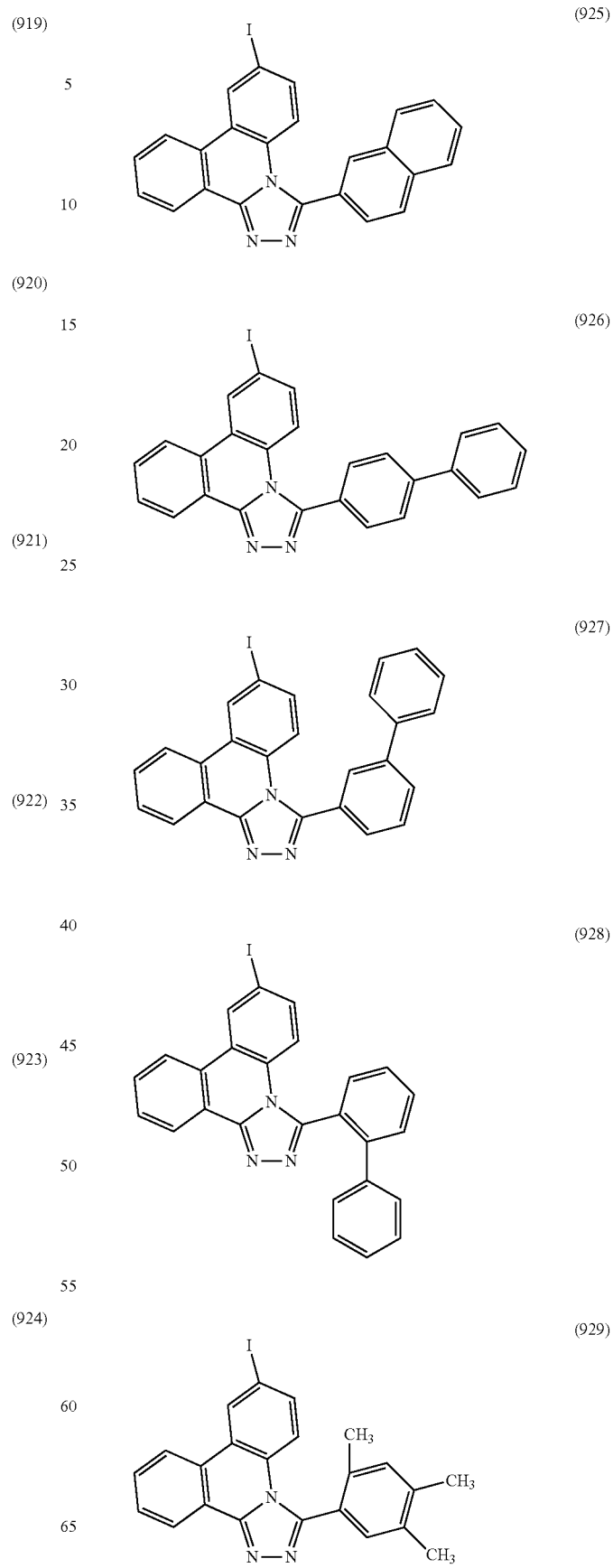

-continued (930) 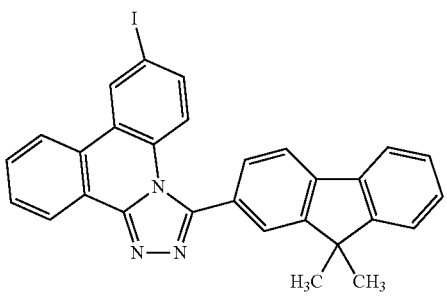

(931) 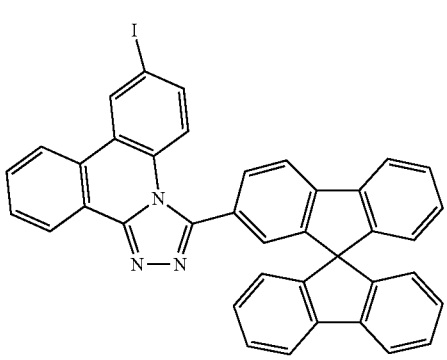

(932) 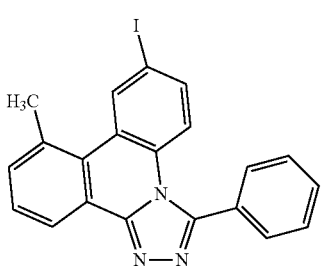

(933) 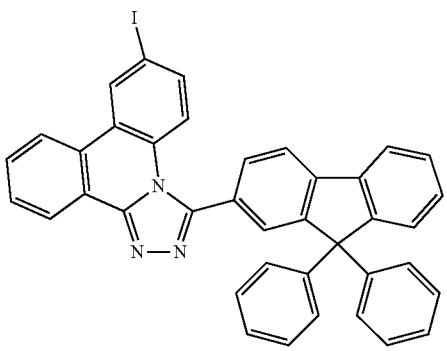

(934) 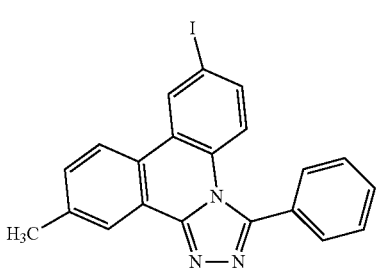

-continued (935) 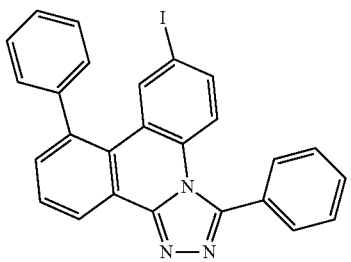

(936) 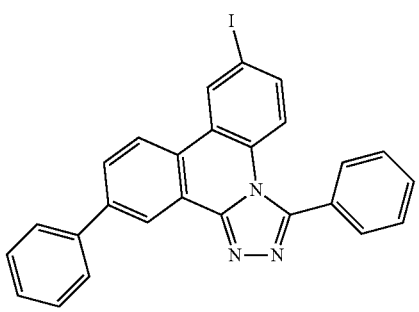

A variety of reactions can be applied to a method of synthesizing a triazole derivative of this embodiment and to a method of synthesizing a heterocyclic compound used in the synthesis of the triazole derivative. For example, the triazole derivative of one embodiment of the present invention can be synthesized by synthesis reactions described below. Description will be now given of methods of synthesizing a compound (G0) illustrated below, which is an example of a triazole derivative of one embodiment of the present invention. Note that a method of synthesizing a triazole derivative of one embodiment of the present invention is not limited to the synthesis methods described below.

[Method 1 of Synthesizing Triazole Derivative Represented by General Formula (G0)]

First, a synthesis scheme (A-1) is illustrated below.

(A-1)

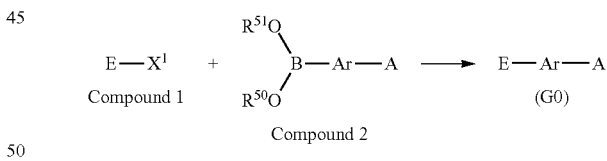

As illustrated in the synthesis scheme (A-1), a halide of a triazolo[4,3-f]phenanthridine derivative or of a triazolo[3,4-α]isoquinoline derivative or a triazolo[4,3-f]phenanthridine having a triflate group or a triazolo[3,4-α]isoquinoline derivative having a triflate group (Compound 1) is coupled with an organoboron compound or boronic acid of a carbazole derivative, of a dibenzofuran derivative or of a dibenzothiophene derivative (Compound 2) by a Suzuki-Miyaura reaction, so that the compound (G0) which is the object of the synthesis can be obtained.

In the synthesis scheme (A-1), A represents a carbazolyl group, a dibenzothiophenyl group, or a dibenzofuranyl group, E represents a triazolo[4,3-f]phenanthridine derivative or a triazolo[3,4-α]isoquinoline derivative, Ar represents a substituted or unsubstituted arylene group having 6 to 13 carbon atoms, and $R^{50}$ and $R^{51}$ separately represent hydrogen or an alkyl group having 1 to 6 carbon atoms. In the synthesis scheme (A-1), $R^{50}$ and $R^{51}$ may be bonded to each other to form a ring. Furthermore, X' represents a halogen or a triflate group, and iodine or bromine is preferred as the halogen.

Examples of a palladium catalyst that can be used in the synthesis scheme (A-1) are, but not limited to, palladium(II) acetate, tetrakis(triphenylphosphine)palladium(0), bis(triphenylphosphine)palladium(II) dichloride, and the like. Examples of a ligand of the palladium catalyst which can be used in the synthesis scheme (A-1) are, but not limited to, tri(ortho-tolyl)phosphine, triphenylphosphine, tricyclohexylphosphine, and the like.

Examples of a base that can be used in the synthesis scheme (A-1) are, but not limited to, organic bases, such as sodium tert-butoxide, inorganic bases, such as potassium carbonate and sodium carbonate, and the like.

Examples of a solvent that can be used in the synthesis scheme (A-1) are, but not limited to, the following solvents: a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of water and an ether such as ethylene glycol dimethyl ether; and the like. In particular, a mixed solvent of toluene and water, a mixed solvent of toluene, ethanol, and water, or a mixed solvent of water and an ether such as ethylene glycol dimethyl ether is preferred.

As a coupling reaction illustrated in the synthesis scheme (A-1), the Suzuki-Miyaura reaction using the organoboron compound or the boronic acid represented by Compound 2 may be replaced with a cross coupling reaction using an organoaluminum compound, an organozirconium compound, an organozinc compound, an organotin compound, or the like. However, the present invention is not limited thereto.

Further, in the synthesis scheme (A-1), an organoboron compound or boronic acid of a triazolo[4,3-f]phenanthridine derivative or of a triazolo[3,4-α]isoquinoline derivative may be coupled with a halide of a carbazole derivative, of a dibenzofuran derivative or of a dibenzothiophene derivative or a carbazole derivative having a triflate group, a dibenzofuran derivative having a triflate group or a dibenzothiophene derivative having a triflate group by a Suzuki-Miyaura reaction.

In the above manner, a triazole derivative of this embodiment can be synthesized.

[Method 2 of Synthesizing Triazole Derivative Represented by General Formula (G0)]

First, a synthesis scheme (B-1) is illustrated below.

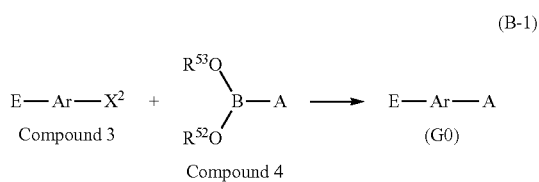

Compound 3    Compound 4    (G0)    (B-1)

As shown in the synthesis scheme (B-1), a halide of a triazolo[4,3-f]phenanthridine derivative or of a triazolo[3,4-α]isoquinoline derivative or a triazolo[4,3-f]phenanthridine derivative having a triflate group or a triazolo[3,4-α]isoquinoline derivative having a triflate group (Compound 3) is coupled with an organoboron compound or boronic acid of a carbazole derivative, of a dibenzofuran derivative or of a dibenzothiophene derivative (Compound 4) by a Suzuki-Miyaura reaction, so that the compound (G0) which is the object of the synthesis can be obtained.

In the synthesis scheme (B-1), A represents a carbazolyl group, a dibenzothiophenyl group, or a dibenzofuranyl group, E represents a triazolo[4,3-f]phenanthridine derivative or a triazolo[3,4-α]isoquinoline derivative, Ar represents a substituted or unsubstituted arylene group having 6 to 13 carbon atoms, and $R^{52}$ and $R^{53}$ separately represent hydrogen or an alkyl group having 1 to 6 carbon atoms. In the synthesis scheme (B-1), $R^{52}$ and $R^{53}$ may be bonded to each other to form a ring. Furthermore, $X^2$ represents a halogen or a triflate group, and iodine or bromine is preferred as the halogen.

Examples of a palladium catalyst that can be used in the synthesis scheme (B-1) are, but not limited to, palladium(II) acetate, tetrakis(triphenylphosphine)palladium(0), bis(triphenylphosphine)palladium(II) dichloride, and the like. Examples of a ligand of the palladium catalyst which can be used in the synthesis scheme (B-1) are, but not limited to, tri(ortho-tolyl)phosphine, triphenylphosphine, tricyclohexylphosphine, and the like.

Examples of a base that can be used in the synthesis scheme (B-1) are, but not limited to, organic bases, such as sodium tert-butoxide, inorganic bases, such as potassium carbonate and sodium carbonate, and the like.

Examples of a solvent that can be used in the synthesis scheme (B-1) are, but not limited to, the following solvents: a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of water and an ether such as ethylene glycol dimethyl ether; and the like. In particular, a mixed solvent of toluene and water, a mixed solvent of toluene, ethanol, and water, or a mixed solvent of water and an ether such as ethylene glycol dimethyl ether is preferred.

As a coupling reaction illustrated in the synthesis scheme (B-1), the Suzuki-Miyaura reaction using the organoboron compound or the boronic acid represented by Compound 2 may be replaced with a cross coupling reaction using an organoaluminum compound, an organozirconium compound, an organozinc compound, an organotin compound, or the like. However, the present invention is not limited thereto. Further, in this coupling, a triflate group or the like may be used other than the halogen; however, the present invention is not limited thereto.

Further, in the synthesis scheme (B-1), an organoboron compound or boronic acid of a triazolo[4,3-f]phenanthridine derivative or of a triazolo[3,4-α]isoquinoline derivative may be coupled with a halide of a carbazole derivative, of a dibenzofuran derivative or of a dibenzothiophene derivative, or a carbazole derivative having a triflate group, a dibenzofuran derivative having a triflate group or a dibenzothiophene derivative having a triflate group by a Suzuki-Miyaura reaction.

For the synthesis of a triazole derivative with A in the general formula (G0) as an N-carbazolyl group, application of a scheme (B-2) to the synthesis can give a triazole derivative represented by a general formula (G10).

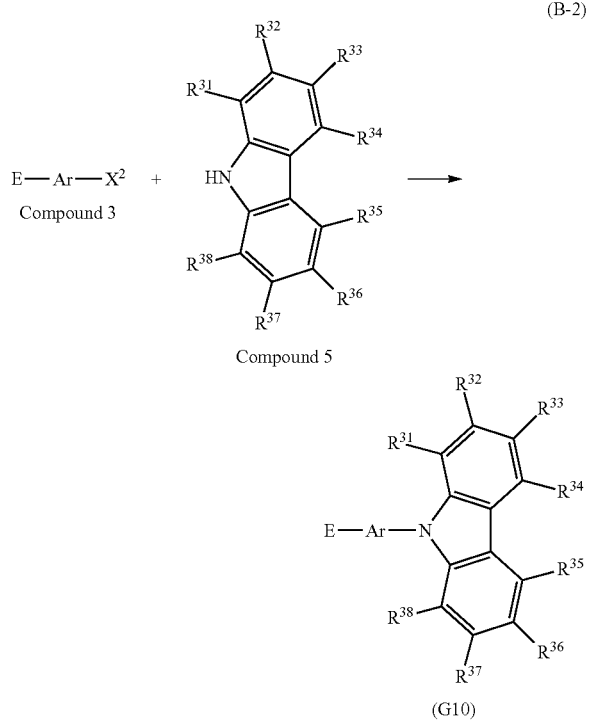

As shown in the synthesis scheme (B-2), a halide of a triazolo[4,3-f]phenanthridine derivative or of a triazolo[3,4-α]isoquinoline derivative or a triazolo[4,3-f]phenanthridine derivative having a triflate group or a triazolo[3,4-α]isoquinoline derivative having a triflate group (Compound 3) is coupled with a 9H-carbazole derivative (Compound 5) using a metal catalyst, metal, or a metal compound in the presence of a base, so that the compound (G10) which is the object of the synthesis can be obtained.

In the synthesis scheme (B-2), E represents a triazolo[4,3-f]phenanthridine derivative or a triazolo[3,4-α]isoquinoline derivative, $R^{31}$ to $R^{38}$ separately represent hydrogen, an alkyl group having 1 to 4 carbon atoms, or a substituted or unsubstituted aryl group having 6 to 13 carbon atoms, and Ar represents a substituted or unsubstituted arylene group having 6 to 13 carbon atoms. Further, $X^2$ represents a halogen or a triflate group, and iodine or bromine is preferred as the halogen.

For the synthesis scheme (B-2), in the case where the Hartwig-Buchwald reaction is performed, Examples of a palladium catalyst that can be used are bis(dibenzylideneacetone)palladium(0), palladium(II) acetate, and the like. Note that examples of a ligand of the palladium catalyst which can be used in the synthesis scheme (B-2) are tri(tert-butyl)phosphine, tri(n-hexyl)phosphine, tricyclohexylphosphine, and the like.

Examples of a base that can be used in the synthesis scheme (B-2) are organic bases, such as sodium tert-butoxide, inorganic bases, such as potassium carbonate, and the like.

Further, examples of a solvent that can be used in the synthesis scheme (B-2) are toluene, xylene, benzene, tetrahydrofuran, and the like.

Other than the Hartwig-Buchwald reaction, the Ullmann reaction or the like may be used, and the reaction is not limited to these.

In the above manner, a triazole derivative of this embodiment can be synthesized.

A triazole derivative of this embodiment has a triazolo[4,3-f]phenanthridine skeleton or a triazolo[3,4-α]isoquinoline skeleton. Since a triazole derivative of this embodiment is a substance which has a carrier-transport property in addition to high triplet excitation energy, the triazole derivative can be suitably used for a light-emitting element. Owing to the high triplet excitation energy, a triazole derivative of this embodiment can be used for a light-emitting layer in combination with a substance that emits phosphorescence. In particular, even when a triazole derivative of one embodiment of the present invention is used for a light-emitting layer in combination with a phosphorescent substance that emits short-wavelength light having an emission peak wavelength greater than or equal to 400 nm and less than or equal to 500 nm, the high emission efficiency can be realized. By using a triazole derivative of this embodiment for a light-emitting element, a light-emitting element having high emission efficiency can be provided. Alternatively, a light-emitting element driven with a low voltage can be provided. Alternatively, a light-emitting element having a long lifetime can be provided.

(Embodiment 2)

In Embodiment 2, a light-emitting element of one embodiment of the present invention will be described with reference to FIGS. 1A and 1B.

One embodiment of the present invention is a light-emitting element including a triazolo[4,3-f]phenanthridine derivative or a triazolo[3,4-α]isoquinoline derivative.

By using a triazolo[4,3-f]phenanthridine derivative or a triazolo[3,4-α]isoquinoline derivative for a light-emitting element, a light-emitting element having high emission efficiency can be realized. Alternatively, a light-emitting element driven with a low voltage can be realized. Alternatively, a light-emitting element having a long lifetime can be realized.

A triazole derivative of one embodiment of the present invention which is given in Embodiment 1 is a non-limiting example of the triazolo[4,3-f]phenanthridine derivative or triazolo[3,4-α]isoquinoline derivative that can be used for a light-emitting element of one embodiment of the present invention.

In Embodiment 2, a light-emitting element including 3-[4-(dibenzothiophen-4-yl)phenyl]-1,2,4-triazolo[4,3-f]phenanthridine (abbreviation: DBTTPt-II), which is represented by the structural formula (100) in Embodiment 1, will be described using FIGS. 1A and 1B.

In a light-emitting element of this embodiment, an EL layer having at least a light-emitting layer is interposed between a pair of electrodes. The EL layer may have a plurality of layers in addition to the light-emitting layer. The plurality of layers is a structure in which a layer containing a substance having a high carrier-injection property and a layer containing a substance having a high carrier-transport property are combined and stacked so that a light-emitting region is formed in a region away from the electrodes, that is, so that carriers recombine in a region away from the electrodes. In this specification, the layer containing a substance having a high carrier-injection property and the layer containing a substance having a high carrier-transport property are each also referred to as a functional layer which has a function of injection or transport of carriers, for example. As a functional layer, a hole-injection layer, a hole-transport layer, an electron-injection layer, an electron-transport layer, or the like can be used.

In the light-emitting element of this embodiment illustrated in FIG. 1A, an EL layer 102 having a light-emitting layer 113 is provided between a pair of electrodes, a first electrode 101 and a second electrode 103. The EL layer 102 includes a hole-injection layer 111, a hole-transport layer 112, the light-emitting layer 113, an electron-transport layer 114, and an electron-injection layer 115. The light-emitting element in FIG. 1A includes the first electrode 101 formed over a substrate 100, the hole-injection layer 111, the hole-transport layer 112, the light-emitting layer 113, the electron-transport layer 114, and the electron-injection layer 115 which are stacked over the first electrode 101 in this order, and the second electrode 103 provided thereover. Note that, in a light-emitting element described in this embodiment, the first electrode 101 functions as an anode and the second electrode 103 functions as a cathode.

The substrate 100 is used as a support of the light-emitting element. For the substrate 100, for example, glass, quartz, plastic, or the like can be used. A flexible substrate can also be used. The flexible substrate is a substrate that can be bent, such as a plastic substrate made of polycarbonate, polyarylate, or polyether sulfone, for example. A film (made of polypropylene, polyester, vinyl, polyvinyl fluoride, vinyl chloride, or the like), an inorganic film formed by evaporation, or the like can also be used. Note that materials other than these can be used as far as they can function as a support of the light-emitting element.

For the first electrode 101, any of metals, alloys, conductive compounds, mixtures thereof, and the like which has a high work function (specifically, a work function of 4.0 eV or more) is preferably used. Specific examples include indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), and the like. Films of these conductive metal oxides are usually formed by sputtering, but may be formed by application of a sol-gel method or the like. For example, an IZO film can be formed by a sputtering method using a target obtained by adding 1 wt % to 20 wt % of zinc oxide to indium oxide. Further, an IWZO film can be formed by a sputtering method using a target obtained by adding 0.5 wt % to 5 wt % of tungsten oxide and 0.1 wt % to 1 wt % of zinc oxide to indium oxide. Other examples are gold, platinum, nickel, tungsten, chromium, molybdenum, iron, cobalt, copper, palladium, nitrides of metal materials (e.g., titanium nitride), and the like.

Note that when a layer included in the EL layer 102 formed in contact with the first electrode 101 is formed using a later described composite material formed by combining an organic compound and an electron acceptor (acceptor), as a substance used for the first electrode 101, any of a variety of metals, alloys, and electrically-conductive compounds, a mixture thereof, and the like can be used regardless of the work function; for example, aluminum, silver, an alloy containing aluminum (e.g., Al—Si), or the like can also be used.

The EL layer 102 formed over the first electrode 101 has at least the light-emitting layer 113 and includes a triazole derivative which is one embodiment of the present invention. For part of the EL layer 102, a known substance can be used, and either a low molecular compound or a high molecular compound can be used. Note that substances forming the EL layer 102 may consist of organic compounds or may include an inorganic compound as a part.

Figure 1B:
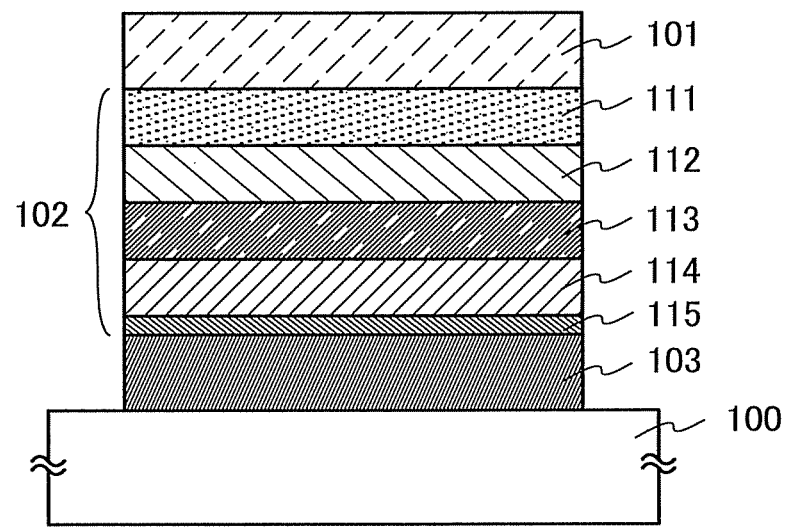

Further, as illustrated in FIGS. 1A and 1B, the EL layer 102 is formed by stacking as appropriate the hole-injection layer 111, the hole-transport layer 112, the electron-transport layer 114, the electron-injection layer 115, and the like in combination in addition to the light-emitting layer 113.

The hole-injection layer 111 is a layer containing a substance having a high hole-injection property. Examples of a substance having a high hole-injection property which can be used are metal oxides, such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide. Other examples of a substance that can be used are phthalocyanine-based compounds, such as phthalocyanine (abbreviation: $H_2Pc$) and copper(II) phthalocyanine (abbreviation: CuPc).

Other examples of a substance that can be used are aromatic amine compounds which are low molecular organic compounds, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Still other examples of a substance that can be used are high molecular compounds (e.g., oligomers, dendrimers, and polymers), such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD), and high molecular compounds to which acid is added, such as poly(3,4-ethylenedioxythiophene)/poly(styrenesulfonic acid) (PEDOT/PSS), or polyaniline/poly(styrenesulfonic acid) (PAni/PSS).

For the hole-injection layer 111, the composite material formed by combining an organic compound and an electron acceptor (acceptor) may be used. Such a composite material, in which holes are generated in the organic compound by the electron acceptor, has an excellent hole injection and transport properties. In this case, the organic compound is preferably a material excellent in transporting the generated holes (a substance having a high hole-transport property).

Examples of the organic compound used for the composite material are a variety of compounds, such as aromatic amine compounds, carbazole derivatives, aromatic hydrocarbons, and high molecular compounds (e.g., oligomers, dendrimers, and polymers). The organic compound used for the composite material is preferably organic compounds having a high hole-transport property, and specifically preferably a substance having a hole mobility of $10^{-6}$ $cm^2/Vs$ or more. Note that other than these substances, any substance that has a property of transporting more holes than electrons may be used. Organic compounds that can be used for the composite material will be specifically described below.

Examples of an organic compound that can be used for the composite material are aromatic amine compounds, such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4-phenyl-4'-(9-phenylfluoren-9-yl)triphenylamine (abbreviation: BPAFLP), and carbazole derivatives, such as 4,4'-di(N-carbazolyl)biphenyl (abbreviation: CBP), 1,3,5-tris[4-(N-carbazoly)phenyl]benzene (abbreviation: TCPB), 9-[4-(10-phenyl-9-anthryl)phenyl]-9H-carbazole (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl-2,3,5,6-tetraphenylbenzene.

Other examples of an organic compound that can be used are aromatic hydrocarbon compounds, such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, and 2,3,6,7-tetramethyl-9,10-di(1-naphthyl)anthracene.

Other examples of an organic compound that can be used are aromatic hydrocarbon compounds, such as 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl)phenyl]anthracene (abbreviation: DPVPA).

Further, examples of the electron acceptor are organic compounds, such as 7,7,8,8-tetracyano-2,3,5,6-tetrafluoro-quinodimethane (abbreviation: $F_4$-TCNQ) and chloranil, transition metal oxides, and oxides of metals that belong to Groups 4 to 8 in the periodic table. Specific preferred examples include vanadium oxide, niobium oxide, tantalum oxide, chromium oxide, molybdenum oxide, tungsten oxide, manganese oxide, and rhenium oxide because their electron-acceptor properties are high. Among these, molybdenum oxide is especially preferable since it is stable in the air and its hygroscopic property is low and is easily treated.

The composite material may be formed using the above-described electron acceptor and the above-described high molecular compound such as PVK, PVTPA, PTPDMA, or Poly-TPD and used for the hole-injection layer 111.

The hole-transport layer 112 is a layer that contains a substance having a high hole-transport property. Examples of a substance that can be used having a high hole-transport property are aromatic amine compounds, such as NPB, TPD, BPAFLP, 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB). The substances mentioned here are mainly substances that have a hole mobility of $10^{-6}$ cm$^2$/Vs or more. Note that other than the above substances, any substance that has a property of transporting more holes than electrons may be used. Further, the layer including a substance having a high hole-transport property is not limited to a single layer, and may be a stack of two or more layers containing any of the above substances.

For the hole-transport layer 112, a carbazole derivative, such as CBP, CzPA, or PCzPA, or an anthracene derivative, such as t-BuDNA, DNA, or DPAnth, may be used.

For the hole-transport layer 112, a high molecular compound, such as PVK, PVTPA, PTPDMA, or Poly-TPD, can be used.

The light-emitting layer 113 is a layer including a light-emitting substance. Note that in Embodiment 2, the case where DBTTPt-II described in Embodiment 1 is used for the light-emitting layer is described. Therefore, for the light-emitting layer in which a light-emitting substance (a guest material) is dispersed in another substance (a host material), DBTTPt-II is particularly preferably used as the host material. By dispersing the guest material which is a light-emitting substance in DBTTPt-II, light emission from the guest material can be obtained.

In addition, more than one kind of substances can be used as the substances (host materials) in which the light-emitting substance (guest material) is dispersed. The light-emitting layer may thus include a host material in addition to DBTTPt-II.

As the light-emitting substance, for example, a fluorescent compound, which emits fluorescence, or a phosphorescent compound, which emits phosphorescence, can be used. As a fluorescent compound that can be used for the light-emitting layer 113, the following light-emitting materials can be given, for example: materials that emit blue light, such as N,N'-bis[4-(9H-carbazol-9-yl)phenyl]-N,N'-diphenylstilbene-4,4'-diamine (abbreviation: YGA2S),4-(9H-carbazol-9-yl)-4'-(10-phenyl-9-anthryl)triphenylamine (abbreviation: YGAPA), and 4-(10-phenyl-9-anthryl)-4'-(9-phenyl-9H-carbazol-3-yl)triphenylamine (abbreviation: PCBAPA); materials that emit green light, such as N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), and N,N,9-triphenylanthracen-9-amine (abbreviation: DPhAPhA); materials that emit yellow light, such as rubrene and 5,12-bis(1,1'-biphenyl-4-yl)-6,11-diphenyltetracene (abbreviation: BPT); and materials that emit red light, such as N,N,N',N'-tetrakis(4-methylphenyl)tetracene-5,11-diamine (abbreviation: p-mPhTD) and 7,14-diphenyl-N,N,N',N'-tetrakis(4-methylphenyl)acenaphtho[1,2-α]fluoranthene-3,10-diamine (abbreviation: p-mPhAFD).

As a phosphorescent compound that can be used for the light-emitting layer 113, the following light-emitting materials can be given, for example: materials that emit blue light, such as bis[2-(4',6'-difluorophenyl)pyridinato-N, C$^{2'}$]iridium (III) tetrakis(1-pyrazolyl)borate (abbreviation: FIr6), bis[2-(4',6'-difluorophenyl)pyridinato-N,C']iridium(III) picolinate (abbreviation: FIrpic), bis{2-[3',5'-bis(trifluoromethyl)phenyl]pyridinato-N,C$^{2'}$}iridium(III) picolinate (abbreviation: Ir(CF$_3$ ppy)$_2$(pic)), and bis[2-(4',6'-difluorophenyppyridinato-N,C$^{2'}$]iridium(III) acetylacetonate (abbreviation: FIr(acac)); materials that emit green light, such as tris(2-phenylpyridinato-N,C$^{2'}$)iridium(III) (abbreviation: Ir(ppy)$_3$), bis(2-phenylpyridinato-N,C$^{2'}$)iridium(III) acetylacetonate (abbreviation: Ir(ppy)$_2$(acac)), bis(1,2-diphenyl-1H-benzimidazolato)iridium(III) acetylacetonate (abbreviation: Ir(pbi)$_2$(acac)), bis(benzo[h]quinolinato)iridium(III)acetylacetonate (abbreviation: Ir(bzq)$_2$(acac)), and tris(benzo[h]quinolinato)iridium(III) (abbreviation: Ir(bzq)$_3$); materials that emit yellow light, such as bis(2,4-diphenyl-1,3-oxazolato-N,C$^{2'}$)iridium(III) acetylacetonate (abbreviation: Ir(dpo)$_2$(acac)), bis[2-(4'-(perfluorophenylphenyl)pyridinato]iridium(III) acetylacetonate (abbreviation: Ir(p-PF-ph)$_2$ (acac)), bis(2-phenylbenzothiazolato-N,C$^{2'}$)iridium(III) acetylacetonate (abbreviation: Ir(bt)$_2$(acac)), (acetylacetonato)bis[2,3-bis(4-fluorophenyl)-5-methylpyrazinato]iridium(III) (abbreviation: Ir(Fdppr-Me)$_2$(acac)), and (acetylacetonato)bis{2-(4-methoxyphenyl)-3,5-dimethylpyrazinato}iridium(III) (abbreviation: Ir(dmmoppr)$_2$ (acac)); materials that emit orange light, such as tris(2-phenylquinolinato-N,C$^{2'}$)iridium(III) (abbreviation:

Ir(pq)$_3$), bis(2-phenylquinolinato-N,C$^{2'}$)iridium(III)acetylacetonate (abbreviation: Ir(pq)$_2$(acac)), (acetylacetonato)bis(3,5-dimethyl-2-phenylpyrazinato)iridium(III) (abbreviation: Ir(mppr-Me)$_2$(acac)), and (acetylacetonato)bis(5-isopropyl-3-methyl-2-phenylpyrazinato)iridium(III) (abbreviation: Ir(mppr-iPr)$_2$(acac)); and materials that emit red light, for example, organometallic complexes, such as bis[2-(2'-benzo[4,5-α]thienyl)pyridinato-N,C$^{3'}$)iridium(III) acetylacetonate (abbreviation: Ir(btp)$_2$(acac)), bis(1-phenylisoquinolinato-N,C$^{2'}$)iridium(III)acetylacetonate (abbreviation: Ir(piq)$_2$(acac), (acetylacetonato)bis[2,3-bis(4-fluorophenyl)quinoxalinato]iridium(III) (abbreviation: Ir(Fdpq)$_2$(acac)), acetylacetonato)bis(2,3,5-triphenylpyrazinato)iridium(III) (abbreviation: Ir(tppr)$_2$(acac)), (dipivaloylmethanato)bis(2,3,5-triphenylpyrazinato)iridium(III) (abbreviation: Ir(tppr)$_2$(dpm)), and (2,3,7,8,12,13,17,18-octaethyl-21H,23H-porphine)platinum(II) (abbreviation: PtOEP). Any of the following rare-earth metal complexes can be used as a phosphorescent compound: tris(acetylacetonato) (monophenanthroline)terbium(III) (abbreviation: [Tb(acac)$_3$ (Phen)); tris(1,3-diphenyl-1,3-propanedionato) (monophenanthroline)europium(III) (abbreviation: [Eu (DBM)$_3$(Phen)); and tris[1-(2-thenoyl)-3,3,3-trifluoroacetonato] (monophenanthroline)europium(III) (abbreviation: [Eu(TTA)$_3$(Phen)), because their light emission is from a rare-earth metal ion (electronic transition between different multiplicities) in such a rare-earth metal complex.

As the light-emitting substance, a high molecular compound can be used. Specifically, the following light-emitting materials can be given, for example: materials that emit blue light, such as poly(9,9-dioctylfluorene-2,7-diyl) (abbreviation: PFO), poly[(9,9-dioctylfluorene-2,7-diyl)-co-(2,5-dimethoxybenzene-1,4-diyl)] (abbreviation: PF-DMOP), and poly{(9,9-dioctylfluorene-2,7-diyl)-co-[N,N-di-(p-butylphenyl)-1,4-diaminobenzene]} (abbreviation: TAB-PFH); materials that emit green light, such as poly(p-phenylenevinylene) (abbreviation: PPV), poly[(9,9-dihexylfluorene-2,7-diyl)-alt-co-(benzo[2,1,3]thiadiazole-4,7-diyl)] (abbreviation: PFBT), and poly[(9,9-dioctyl-2,7-divinylenefluorenylene)-alt-co-(2-methoxy-5-(2-ethylhexyloxy)-1,4-phenylene)]; and materials that emit orange to red light, such as poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly{[9,9-dihexyl-2,7-bis(1-cyanovinylene)fluorenylene]-alt-co-[2,5-bis(N,N'-diphenyl amino)-1,4-phenylene]}, and poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN-PPV-DPD).

The electron-transport layer 114 is a layer including a substance having a high electron-transport property. A triazole derivative of one embodiment of the present invention can be used for the electron-transport layer 114, since the triazole derivative has a high electron-transport property. Other examples of the substance having a high electron-transport property are metal complexes having a quinoline skeleton or a benzoquinoline skeleton, such as tris(8-quinolinolato)aluminum (abbreviation: Alq), tris(4-methyl-8-quinolinolato) aluminum (abbreviation: Almq$_3$), bis(10-hydroxybenzo[h]-quinolinato)beryllium (abbreviation: BeBq$_2$), and bis(2-methyl-8-quinolinolato)(4-phenylphenolato)aluminum. (abbreviation: BAlq). A metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$), or the like can also be used. Other than metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can be used. The substances described here are mainly substances having an electron mobility of $10^{-6}$ cm$^2$/Vs or more. Further, the electron-transport layer is not limited to a single layer, and may be a stack of two or more layers containing any of the above substances are stacked.

The electron-injection layer 115 is a layer that contains a substance having a high electron-injection property. Examples of the substance that can be used for the electron-injection layer 115 are alkali metals, alkaline earth metals, and compounds thereof, such as lithium, cesium, calcium, lithium fluoride, cesium fluoride, calcium fluoride, and lithium oxide, rare earth-metal compounds, such as erbium fluoride, and the above-mentioned substances for forming the electron-transport layer 114.

Alternatively, a composite material formed by combining an organic compound and an electron donor (donor) may be used for the electron-injection layer 115. Such a composite material, in which electrons are generated in the organic compound by the electron donor, has excellent electron injection and transport properties. The organic compound here is preferably a material excellent in transporting the generated electrons, as which specifically any of the above substances (such as metal complexes and heteroaromatic compounds) for the electron-transport layer 114 can be used. The electron donor can be a substance exhibiting an electron-donating property for the organic compound. Specific examples of the electron donor are alkali metals, alkaline earth metals, and rare earth-metals, such as lithium, cesium, magnesium, calcium, erbium, and ytterbium. Any of alkali metal oxides and alkaline earth metal oxides is preferable, examples of which are lithium oxide, calcium oxide, barium oxide, and the like, and a Lewis base such as magnesium oxide or an organic compound such as tetrathiafulvalene (abbreviation: TTF) can be used.

Note that the hole-injection layer 111, the hole-transport layer 112, the light-emitting layer 113, the electron-transport layer 114, and the electron-injection layer 115 which are described above can each be formed by a method, such as an evaporation method (e.g., a vacuum evaporation method), an inkjet method, or a coating method.

When the second electrode 103 functions as a cathode, any of metals, alloys, conductive compounds, mixtures thereof, and the like which has a low work function (specifically, a work function of 3.8 eV or less) is preferably used for the second electrode 103. Specific examples of the substance that can be used are elements that belong to Groups 1 and 2 in the periodic table, that is, alkali metals such as lithium and cesium, alkaline earth metals such as magnesium, calcium, and strontium, alloys thereof (e.g., Mg—Ag and Al—Li), rare earth-metals such as europium and ytterbium, alloys thereof, aluminum, silver, and the like.

When a layer included in the EL layer 102 formed in contact with the second electrode 103 is formed using the composite material formed by combining the organic compound and the electron donor (donor), which are described above, a variety of conductive materials, such as aluminum, silver, ITO, and indium oxide-tin oxide containing silicon or silicon oxide, can be used regardless of the work function.

Note that when the second electrode 103 is formed, a vacuum evaporation method or a sputtering method can be used. In the case of using a silver paste or the like, a coating method, an inkjet method, or the like can be used.

In the above-described light-emitting element, a current flows due to a potential difference generated between the first electrode 101 and the second electrode 103 and holes and electrons recombine in the EL layer 102, so that light is emitted. Then, this light emission is extracted outside through one or both of the first electrode 101 and the second electrode 103. Therefore, one or both of the first electrode 101 and the second electrode 103 are electrodes having a property of transmitting visible light.

Further, the structure of the layers provided between the first electrode 101 and the second electrode 103 is not limited to the above-described structure. A structure other than the above may alternatively be employed as far as a light-emitting region in which holes and electrons recombine is provided in a portion away from the first electrode 101 and the second electrode 103 so as to prevent quenching due to proximity of the light-emitting region to metal.

In other words, there is no particular limitation on a stack structure of the layers. A layer including a substance having a high electron-transport property, a substance having a high hole-transport property, a substance having a high electron-injection property, a substance having a high hole-injection property, a bipolar substance (a substance having a high electron-transport property and a high hole-transport property), a hole-blocking material, or the like may freely be combined with a light-emitting layer including DBTTPt-II as a host material.

In the light-emitting element illustrated in FIG. 1B, the EL layer 102 is provided between the first electrode 101 and the second electrode 103 over the substrate 100. The EL layer 102 includes the hole-injection layer 111, the hole-transport layer 112, the light-emitting layer 113, the electron-transport layer 114, and the electron-injection layer 115. The light-emitting element in FIG. 1B includes the second electrode 103 serving as a cathode over the substrate 100, the electron-injection layer 115, the electron-transport layer 114, the light-emitting layer 113, the hole-transport layer 112, and the hole-injection layer 111 which are stacked over the second electrode 103 in this order, and the first electrode 101 provided thereover which serves as an anode.

A method of forming the light-emitting element will now be specifically described.

In a light-emitting element of this embodiment, the EL layer is interposed between the pair of electrodes. The EL layer has at least the light-emitting layer, and the light-emitting layer is formed using DBTTPt-II as a host material. Further, the EL layer may include a functional layer (e.g., the hole-injection layer, the hole-transport layer, the electron-transport layer, or the electron-injection layer) in addition to the light-emitting layer. The electrodes (the first electrode and the second electrode), the light-emitting layer, and the functional layer may be formed by any of the wet processes such as a droplet discharging method (an inkjet method), a spin coating method, and a printing method, or by a dry processes such as a vacuum evaporation method, a CVD method, and a sputtering method. A wet process allows formation at atmospheric pressure with a simple device and by a simple process, which gives the effects of simplifying the process and improving productivity. In contrast, a dry process does not need dissolution of a material and enables use of a material that has low solubility in a solution, which expands the range of material choices.

All the thin films included in a light-emitting element may be formed by a wet process. In this case, the light-emitting element can be manufactured with only facilities needed for a wet process. Alternatively, the following method may be employed: formation of the stacked layers up to formation of the light-emitting layer is performed by a wet process whereas the functional layer, the first electrode, and the like which are stacked over the light-emitting layer are formed by a dry process. Further alternatively, the following method may be employed: the second electrode and the functional layer are formed by a dry process before the foiniation of the light-emitting layer whereas the light-emitting layer, the functional layer stacked thereover, and the first electrode are formed by a wet process. Needless to say, this embodiment is not limited to these, and a light-emitting element can be formed by appropriate selection from a wet process and a dry process depending on a material to be used, necessary film thickness, and the interface state.

In this embodiment, a light-emitting element is fabricated over a substrate made of glass, plastic or the like. By forming a plurality of such light-emitting elements over one substrate, a passive matrix light-emitting device can be manufactured. Further, a light-emitting element may be fabricated in such a way that a thin film transistor (TFT), for example, is formed over a substrate made of glass, plastic, or the like and the light-emitting element is formed over an electrode electrically connected to the TFT. Thus, an active matrix light-emitting device in which the TFT controls the driving of the light-emitting element can be manufactured. Note that there is no particular limitation on the structure of the TFT: a staggered TFT or an inverted staggered TFT may be employed. In addition, there is no particular limitation on the crystallinity of a semiconductor used for the TFT, and an amorphous semiconductor or a crystalline semiconductor may be used. Furthermore, a driver circuit formed in a TFT substrate may be formed with both n-channel TFTs and p-channel TFTs or may be formed with either n-channel TFTs or p-channel TFTs.

Thus, a light-emitting element can be fabricated using DBTTPt-II described in Embodiment 1. According to one embodiment of the present invention, by including a triazolo[4,3-f]phenanthridine derivative or a triazolo[3,4-α]isoquinoline derivative, a light-emitting element driven with a low voltage can be realized. Alternatively, a light-emitting element having high current efficiency can be realized. Alternatively, a light-emitting element having a long lifetime can be realized.

Furthermore, a light-emitting device using a light-emitting element of one embodiment of the present invention which is obtained as above can realize low power consumption.

By use of a light-emitting element described in this embodiment, a passive matrix light-emitting device or an active matrix light-emitting device in which driving of the light-emitting element is controlled by a transistor can be manufactured.

This embodiment can be used in appropriate combination with any of the other embodiments.

(Embodiment 3)

In this embodiment, a mode of a light-emitting element having a structure in which a plurality of light-emitting units is stacked (hereinafter, referred to as a stacked-type element) will be described with reference to FIGS. 2A and 2B. This light-emitting element is a light-emitting element including a plurality of light-emitting units between a first electrode and a second electrode.

Figure 2A:
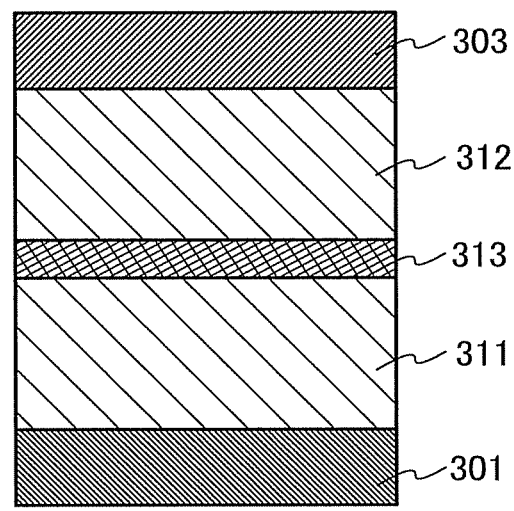
FIGS. 2A and 2B each illustrate a light-emitting element of one embodiment of the present invention.

In FIG. 2A, a first light-emitting unit 311 and a second light-emitting unit 312 are stacked between a first electrode 301 and a second electrode 303. In Embodiment 3, the first electrode 301 functions as an anode and the second electrode 303 functions as a cathode. Note that the first electrode 301 and the second electrode 303 can have the same structure as those in Embodiment 2. Further, the first light-emitting unit 311 and the second light-emitting unit 312 may have the same or different structures. The first light-emitting unit 311 and the second light-emitting unit 312 may have the same structure as in Embodiment 2, or either of the units may differ in structure from that in Embodiment 2.

Further, a charge generation layer 313 is provided between the first light-emitting unit 311 and the second light-emitting unit 312. The charge generation layer 313 has a function of injecting electrons into one of the light-emitting units and injecting holes into the other of the light-emitting units when a voltage is applied to the first electrode 301 and the second electrode 303. In the case of this embodiment, when a voltage is applied so that the potential of the first electrode 301 is higher than that of the second electrode 303, the charge generation layer 313 injects electrons into the first light-emitting unit 311 and injects holes into the second light-emitting unit 312.

Note that the charge generation layer 313 preferably has a property of transmitting visible light in terms of light extraction efficiency. Further, the charge generation layer 313 functions even if it has lower conductivity than the first electrode 301 or the second electrode 303.

The charge generation layer 313 may have a structure in which it includes the organic compound having a high hole-transport property and the electron acceptor (acceptor) or a structure in which it includes an organic compound having a high electron-transport property and the electron donor (donor), or may be a stack of both of these structures.

In the case of the structure in which the electron acceptor is added to the organic compound having a high hole-transport property, examples of the substance that can be used as the organic compound having a high hole-transport property are aromatic amine compounds, such as NPB, TPD, TDATA, MTDATA, and 4,4'-bis[N-(spiro-9,9'-bifluoren-2-yl)-N-phenylamino]biphenyl (abbreviation: BSPB), and the like. The substances mentioned here are mainly substances that have a hole mobility of $10^{-6}$ cm$^2$/Vs or more. Note that other than the above substances, any organic compound that has a property of transporting more holes than electrons may be used.

Examples of the electron acceptor are 7,7,8,8-tetracyano-2,3,5,6-tetrafluoroquinodimethane (abbreviation: F$_4$-TCNQ), chloranil, oxides of transition metals, and oxides of metals that belong to Groups 4 to 8 in the periodic table, and the like. Specific preferred examples include vanadium oxide, niobium oxide, tantalum oxide, chromium oxide, molybdenum oxide, tungsten oxide, manganese oxide, and rhenium oxide because their electron-acceptor properties are high. Among these, molybdenum oxide is especially preferable since it is stable in the air and its hygroscopic property is low and is easily treated.

In the case of the structure in which the electron donor is added to the organic compound having a high electron-transport property, any of the following substances can be used as the organic compound having a high electron-transport property, for example: metal complexes having a quinoline skeleton or a benzoquinoline skeleton such as Alq, Almq$_3$, BeBq$_2$, and BAlq; metal complexes having an oxazole-based ligand or a thiazole-based ligand, such as Zn(BOX)$_2$ and Zn(BTZ)$_2$; and the like. Examples other than the metal complexes are PBD, OXD-7, TAZ, BPhen, BCP, and the like. The substances described here are mainly substances having an electron mobility of $10^{-6}$ cm$^2$/Vs or more. Note that other than the above substances, any organic compound that has a property of transporting more electrons than holes may be used.

Examples of the electron donor that can be used are alkali metals, alkaline-earth metals, rare-earth metals, metals that belong to Group 13 in the periodic table and oxides or carbonates thereof, and preferably specifically lithium, cesium, magnesium, calcium, ytterbium, indium, lithium oxide, cesium carbonate, and the like. An organic compound, such as tetrathianaphthacene, may be used as the electron donor.

By forming the charge generation layer 313 with any of the above materials, it is possible to suppress an increase in driving voltage caused when the EL layers are stacked.

Figure 2B:
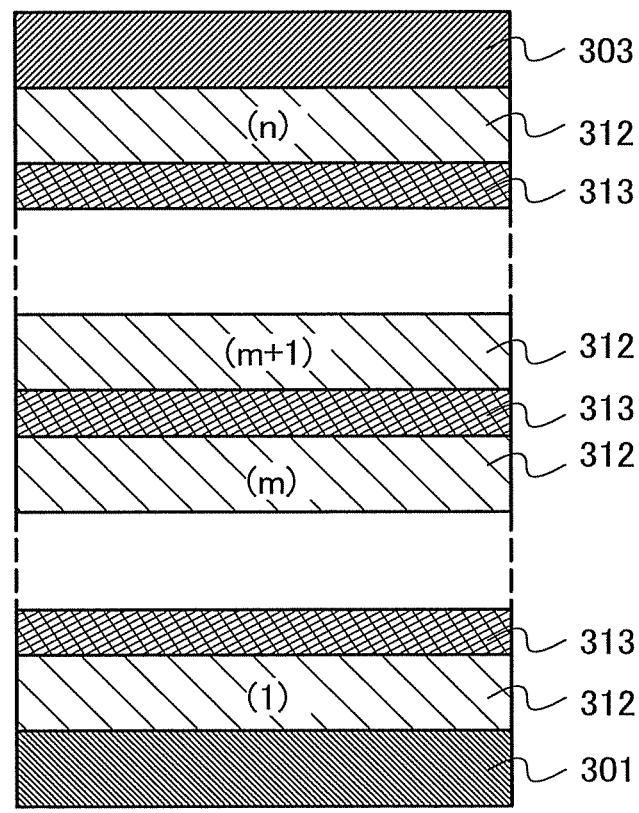

Although the light-emitting element having two light-emitting units is described in this embodiment, the embodiment can be applied to a light-emitting element in which three or more light-emitting units are stacked as illustrated in FIG. 2B. When a plurality of light-emitting units with a charge generation layer interposed therebetween is arranged between a pair of electrodes, as in the light-emitting element of this embodiment, it is possible to realize an element having a long lifetime which can emit light with a high luminance while current density is kept low.

Furthermore, by making emission colors of the light-emitting units different, light having a desired color can be obtained from the light-emitting element as a whole. For example, the emission colors of first and second light-emitting units are complementary in a light-emitting element having the two light-emitting units, so that the light-emitting element can be made to emit white light as a whole. Note that the term "complementary" means color relationship in which an achromatic color is obtained when colors are mixed. That is, emission of white light can be obtained by mixture of light emitted from substances whose emission colors are complementary colors. Further, the same can be applied to a light-emitting element having three light-emitting units. For example, the light-emitting element as a whole can emit white light when the emission color of the first light-emitting unit is red, the emission color of the second light-emitting unit is green, and the emission color of the third light-emitting unit is blue.

Note that this embodiment can be combined with any of the other embodiments as appropriate.

(Embodiment 4)

In Embodiment 4, a light-emitting device having a light-emitting element of one embodiment of the present invention will be described with reference to FIGS. 3A and 3B. Note that FIG. 3A is a top view illustrating the light-emitting device, and FIG. 3B is a cross-sectional view taken along lines A-B and C-D of FIG. 3A.

Figure 3A:
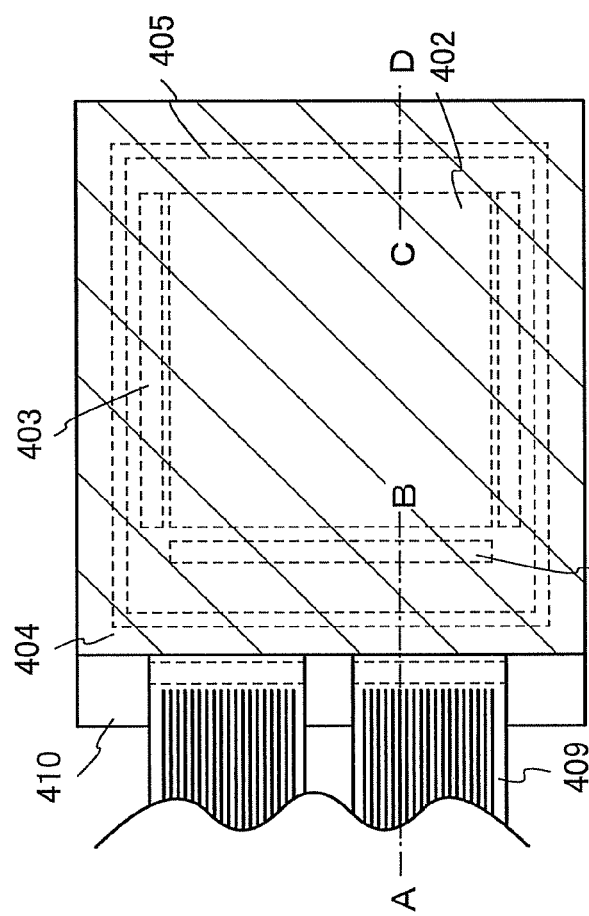
FIGS. 3A and 3B illustrate a light-emitting device of one embodiment of the present invention.
Figure 3B:
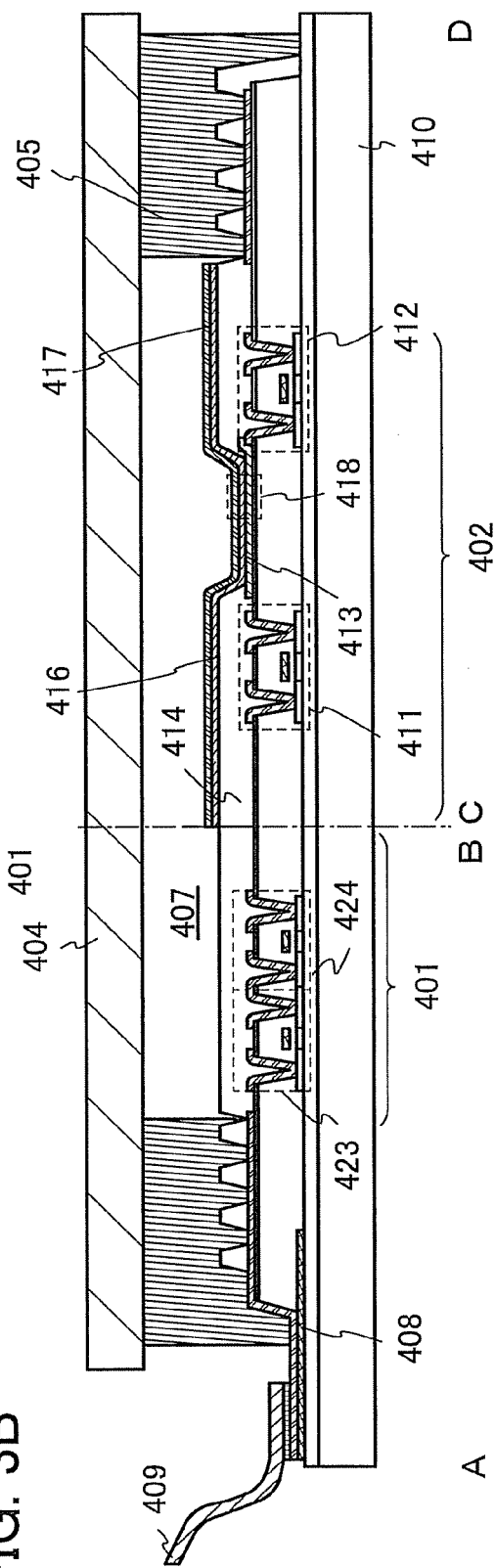

In FIG. 3A, reference numeral 401 denotes a driver circuit portion (a source driver circuit), reference numeral 402 denotes a pixel portion, and reference numeral 403 denotes a driver circuit portion (a gate driver circuit), which are each indicated by dotted lines. Reference numeral 404 denotes a sealing substrate, reference numeral 405 denotes a sealant, and a portion enclosed by the sealing material 405 is a space 407.

Note that a lead wiring 408 is a wiring for transmitting signals that are to be inputted to the source driver circuit 401 and the gate driver circuit 403, and receives a video signal, a clock signal, a start signal, a reset signal, and the like from an FPC (flexible printed circuit) 409 which serves as an external input terminal. Although only the FPC is illustrated here, a printed wiring board (PWB) may be attached to the FPC. The light-emitting device in this specification includes not only a light-emitting device itself but also a light-emitting device to which an FPC or a PWB is attached.

Next, a cross-sectional structure will be described with reference to FIG. 3B. The driver circuit portion and the pixel portion are formed over an element substrate 410. Here, the source driver circuit 401 which is the driver circuit portion and one pixel in the pixel portion 402 are illustrated.

Note that as the source driver circuit 401, a CMOS circuit which includes an n-channel TFT 423 and a p-channel TFT 424 is formed. The driver circuit may be any of a variety of circuits formed with TFTs, such as a CMOS circuit, a PMOS circuit, or an NMOS circuit. Although a driver-integrated type in which a driver circuit is formed over the substrate is described in this embodiment, the present invention is not limited to this type, and the driver circuit can be formed outside the substrate.

The pixel portion 402 includes a plurality of pixels having a switching TFT 411, a current control TFT 412, and a first electrode 413 electrically connected to a drain of the current control TFT 412. Note that an insulator 414 is formed to cover an end portion of the first electrode 413. Here, the insulator 414 is formed by using a positive type photosensitive acrylic resin film.

In order to improve coverage, the insulator 414 is provided such that either an upper end portion or a lower end portion of the insulator 414 has a curved surface with a curvature. For example, when positive photosensitive acrylic is used as a material for the insulator 414, it is preferable that only an upper end portion of the insulator 414 have a curved surface with a radius of curvature (0.2 μm to 3 μm). For the insulator 414, it is also possible to use either a negative type that becomes insoluble in an etchant by light irradiation or a positive type that becomes soluble in an etchant by light irradiation.

A light-emitting layer 416 and a second electrode 417 are formed over the first electrode 413. Here, as a material for forming the first electrode 413 functioning as the anode, a material having a high work function is preferably used. For example, it is possible to use a single layer of an ITO film, an indium tin oxide film that includes silicon, an indium oxide film that includes 2 wt % to 20 wt % of zinc oxide, a titanium nitride film, a chromium film, a tungsten film, a Zn film, a Pt film, or the like, a stacked layer of a titanium nitride film and a film that mainly includes aluminum, a three-layer structure of a titanium nitride film, a film that mainly includes aluminum and a titanium nitride film, or the like. Note that, when a stacked layer structure is employed, resistance of a wiring is low and a favorable ohmic contact is obtained.

In addition, the light-emitting layer 416 is formed by any of various methods such as an evaporation method using an evaporation mask, a droplet discharging method like an inkjet method, a printing method, and a spin coating method. The light-emitting layer 416 includes a triazole derivative described in Embodiment 1. Further, another material included in the light-emitting layer 416 may be a low molecular material, an oligomer, a dendrimer, a high molecular material, or the like.

As a material used for the second electrode 417 which is formed over the light-emitting layer 416 and serves as a cathode, it is preferable to use a material having a low work function (e.g., Al, Mg, Li, Ca, or an alloy or a compound thereof such as Mg—Ag, Mg—In, Al—Li, LiF, or $CaF_2$). In order that light generated in the light-emitting layer 416 be transmitted through the second electrode 417, a stack of a metal thin film having a reduced thickness and a transparent conductive film (e.g., ITO, indium oxide containing 2 wt % to 20 wt % of zinc oxide, indium oxide-tin oxide that includes silicon or silicon oxide, or zinc oxide) is preferably used for the second electrode 417.

Further, the sealing substrate 404 is attached to the element substrate 410 with the sealing material 405 so that, a light-emitting element 418 is provided in the space 407 enclosed by the element substrate 410, the sealing substrate 404, and the sealing material 405. The space 407 may be filled with an inert gas (such as nitrogen or argon), or the sealing material 405.

Note that an epoxy-based resin is preferably used as the sealing material 405. Such a material preferably allows as little moisture and oxygen as possible to penetrate. As a material used for the sealing substrate 404, a plastic substrate formed of FRP (fiberglass-reinforced plastics), PVF (polyvinyl fluoride), polyester, acrylic, or the like can be used other than a glass substrate or a quartz substrate.

As described above, the active matrix light-emitting device having the light-emitting element of one embodiment of the present invention can be obtained.

Figure 4A:
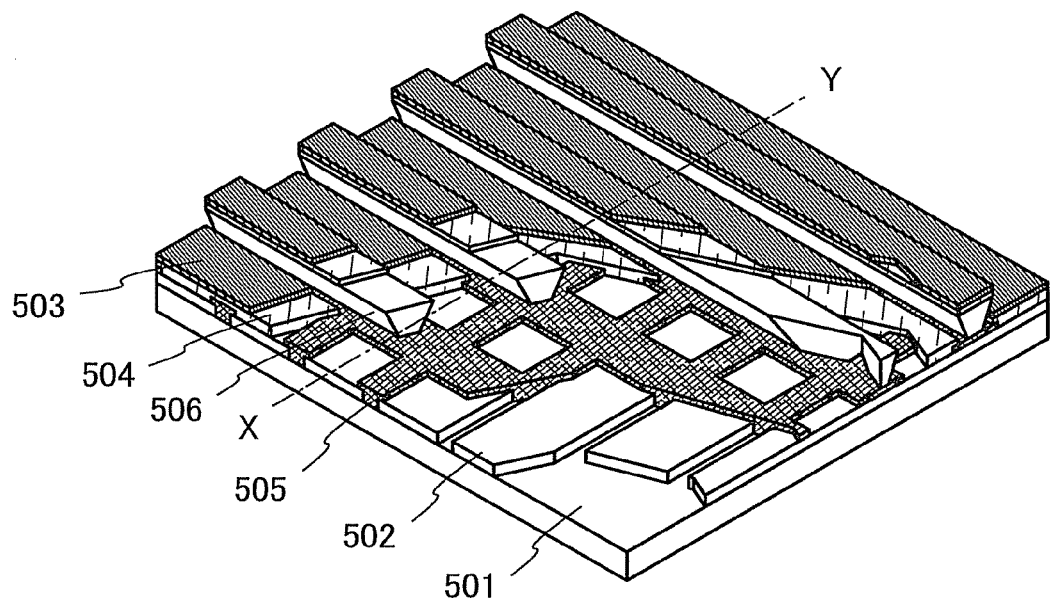
FIGS. 4A and 4B illustrate a light-emitting device of one embodiment of the present invention.
Figure 4B:
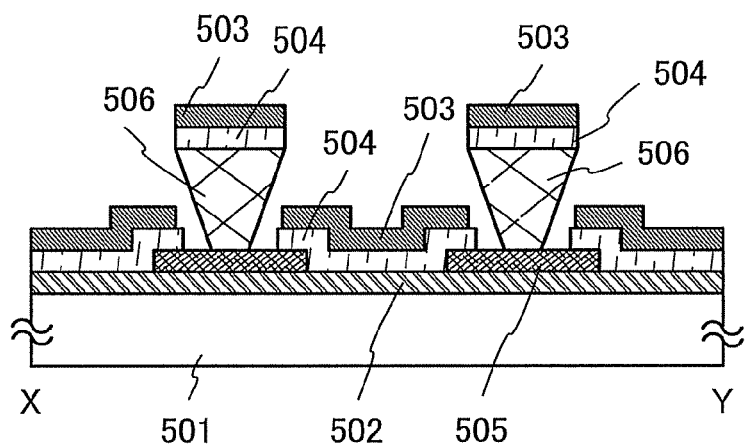

Further, a light-emitting element of the present invention can be used for a passive matrix light-emitting device as well as the above active matrix light-emitting device. FIGS. 4A and 4B illustrate a perspective view and a cross-sectional view of a passive matrix light-emitting device using a light-emitting element of the present invention. Note that FIG. 4A is a perspective view of the light-emitting device, and FIG. 4B is a cross-sectional view taken along line X-Y of FIG. 4A.

In FIGS. 4A and 4B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 are aslope so that a distance between both the sidewalls is gradually narrowed toward the surface of the substrate. In other words, a cross section taken along the direction of the short side of the partition layer 506 is trapezoidal, and the base (side in contact with the insulating layer 505) is shorter than the upper side (side not in contact with the insulating layer 505). By providing of the partition layer 506 in such a way, a defect of a light-emitting element due to crosstalk or the like can be prevented.

Thus, the passive matrix light-emitting device having a light-emitting element of one embodiment of the present invention can be obtained.

The light-emitting devices described in Embodiment 4 (the active matrix light-emitting device and the passive matrix light-emitting device) are both formed using a light-emitting element of one embodiment of the present invention, and accordingly, the light-emitting devices have low power consumption.

Note that this embodiment can be combined with any other embodiment as appropriate.

(Embodiment 5)

In Embodiment 5, with reference to FIGS. 5A to 5E and FIG. 6, description is given of examples of a variety of electronic devices and lighting devices that are completed by using a light-emitting device which is one embodiment of the present invention.

Examples of the electronic devices to which the light-emitting device is applied are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic devices and a lighting device are illustrated in FIGS. 5A to 5E.

Figure 5A:
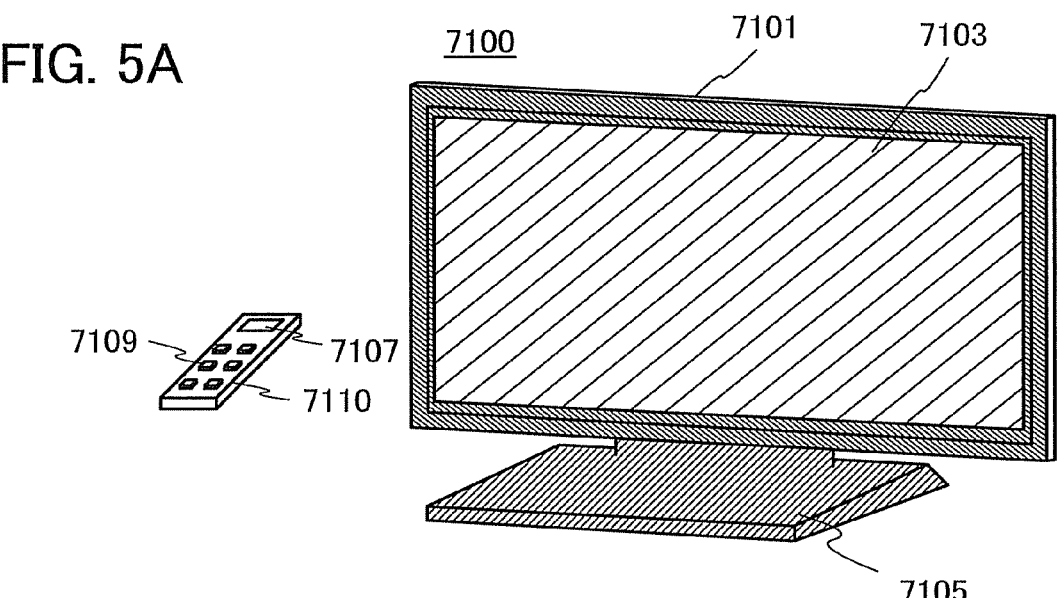
FIGS. 5A to 5E each illustrate an electronic device of one embodiment of the present invention.

FIG. 5A illustrates an example of a television device. In the television device 7100, a display portion 7103 is incorporated into a housing 7101. The display portion 7103 is capable of displaying images, and the light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, general television broadcasting can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 5B:
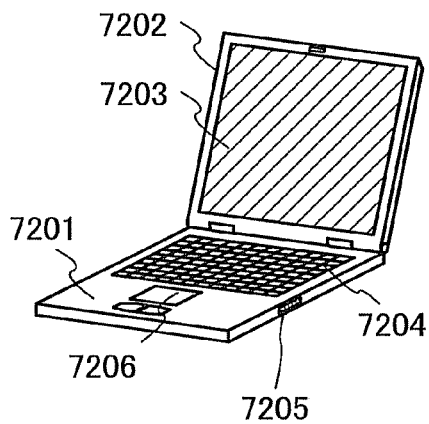

FIG. 5B illustrates a computer having a main body 7201, a housing 7202, a display portion 7203, a keyboard 7204, an external connecting port 7205, a pointing device 7206, and the like. This computer is manufactured by using a light-emitting device for the display portion 7203.

Figure 5C:
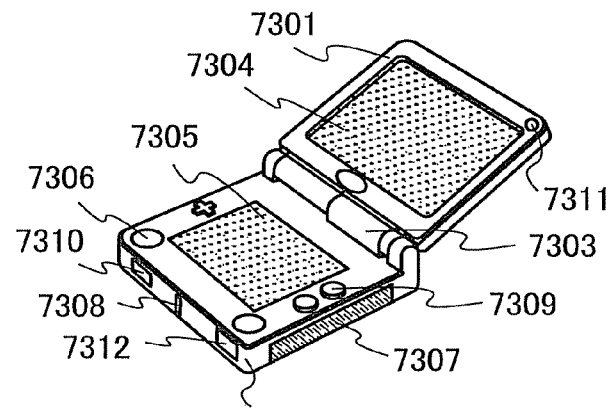

FIG. 5C illustrates a portable game machine having two housings, a housing 7301 and a housing 7302, which are connected with a joint portion 7303 so that the portable game machine can be opened or folded. A display portion 7304 is incorporated into the housing 7301 and a display portion 7305 is incorporated into the housing 7302. In addition, the portable game machine illustrated in FIG. 5C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable games machine is not limited to the above as far as a light-emitting device can be used for at least either the display portion 7304 or the display portion 7305, or both, and may include other accessories as appropriate. The portable game machine illustrated in FIG. 5C has a function of reading out a program or data stored in a storage medium to display it on the display portion, and a function of sharing information with another portable game machine by wireless communication. The portable game machine illustrated in FIG. 5C can have a variety of functions without limitation to the above.

Figure 5D:
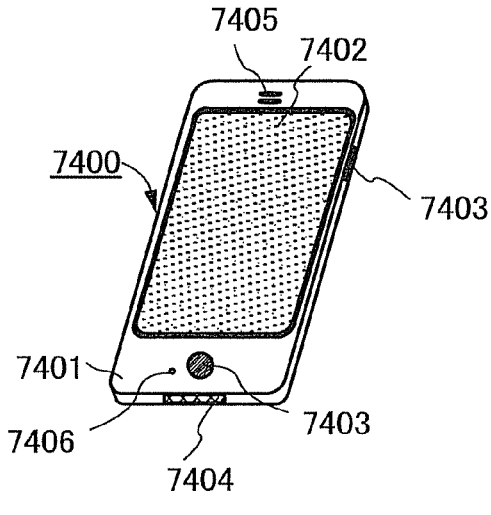

FIG. 5D illustrates an example of a cellular phone. The cellular phone 7400 is provided with operation buttons 7403, an external connection port 7404, a speaker 7405, a microphone 7406, and the like, in addition to a display portion 7402 incorporated into a housing 7401. Note that the cellular phone 7400 is manufactured using a light-emitting device for the display portion 7402.

When the display portion 7402 of the cellular phone 7400 illustrated in FIG. 5D is touched with a finger or the like, data can be input into the cellular phone 7400. Further, operations such as making a call and creating e-mail can be performed by touch on the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are mixed.

For example, in the case of making a call or creating e-mail, a text input mode mainly for inputting text is selected for the display portion 7402 so that text displayed on a screen can be inputted. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are switched by touch on the display portion 7402 or operation with the operation buttons 7403 of the housing 7401. Alternatively, the screen modes can be switched depending on kinds of images displayed on the display portion 7402. For example, when a signal for an image displayed on the display portion is data of moving images, the screen mode is switched to the display mode. When the signal is text data, the screen mode is switched to the input mode.

Moreover, in the input mode, if a signal detected by an optical sensor in the display portion 7402 is detected and the input by touch on the display portion 7402 is not performed during a certain period, the screen mode may be controlled so as to be switched from the input mode to the display mode.

The display portion 7402 can function as an image sensor. For example, an image of a palm print, a fingerprint, or the like is taken by touch on the display portion 7402 with the palm or the finger, so that personal authentication can be performed. Furthermore, by provision of a backlight or a sensing light source emitting a near-infrared light for the display portion, an image of a finger vein, a palm vein, or the like can also be taken.

Figure 5E:
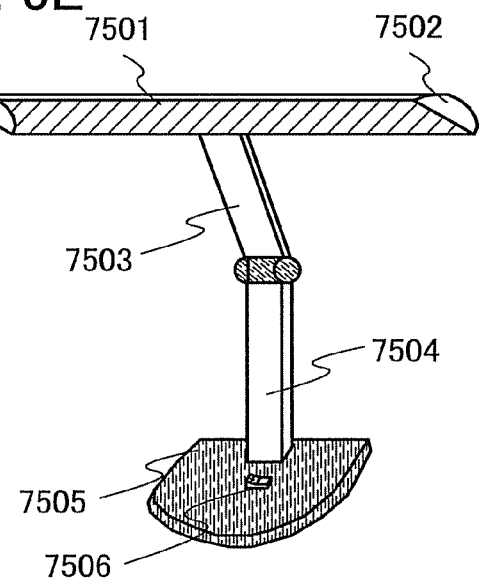

FIG. 5E illustrates a desk lamp including a lighting portion 7501, a shade 7502, an adjustable arm 7503, a support 7504, a base 7505, and a power supply 7506. The desk lamp is manufactured using a light-emitting device for the lighting portion 7501. Note that the "lighting device" also includes ceiling lights, wall lights, and the like.

Figure 6:
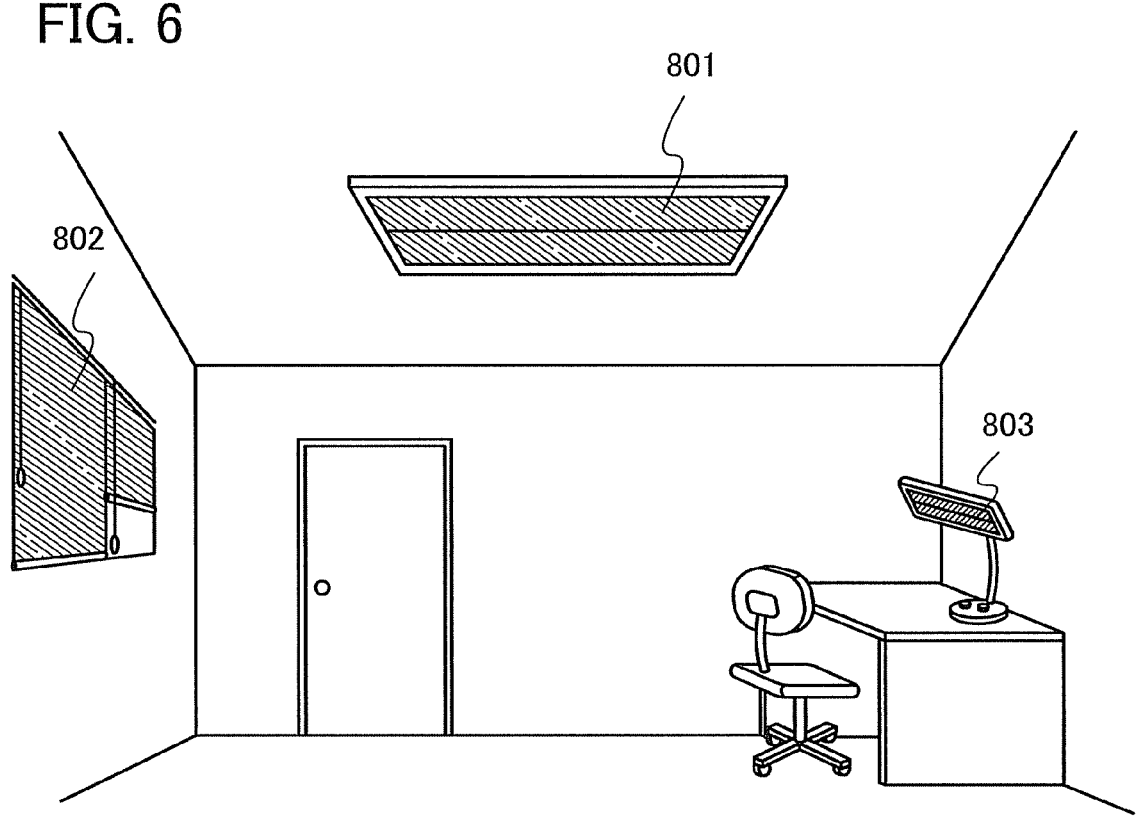
FIG. 6 illustrates lighting devices of one embodiment of the present invention.

FIG. 6 illustrates an example in which a light-emitting device is used for an interior lighting device 801. Since the light-emitting device can have a larger area, it can be used as a lighting device having a large area. Furthermore, the light-emitting device can be used as a roll-type lighting device 802. As illustrated in FIG. 6, a desk lamp 803 described with reference to FIG. 5E may be used together in a room provided with the interior lighting device 801.

In the above-described manner, electronic devices or lighting devices can be obtained by application of a light-emitting device of one embodiment of the present invention. Application range of the light-emitting device is so wide that the light-emitting device can be applied to electronic devices in a variety of fields.

Note that the structure described in this embodiment can be combined with any of the structures described in Embodiments 1 to 4 as appropriate.

EXAMPLE 1

Synthesis Example 1

This example gives descriptions of a method of synthesizing 3-[4-(dibenzothiophen-4-yl)phenyl]-1,2,4-triazolo[4,3- f]phenanthridine (abbreviation: DBTTPt-II), which is the triazole derivative of one embodiment of the present invention represented by the structural formula (100) in Embodiment 1, and a method of synthesizing 3-(4-bromophenyl)-1,2,4-triazolo[4,3-f]phenanthridine, which is the heterocyclic compound of one embodiment of the present invention represented by the structural formula (700) in Embodiment 1.

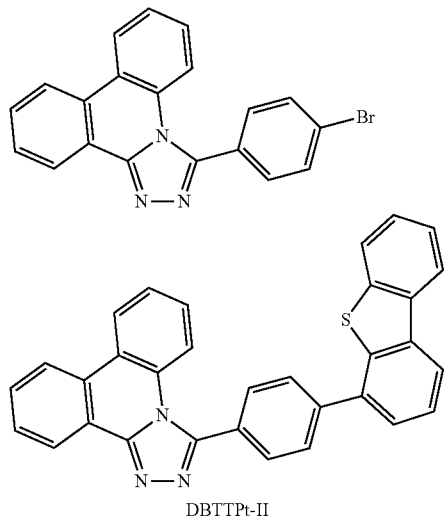

DBTTPt-II

Step 1: Synthesis of N-(4-Bromobenzoyl)-N-(phenanthridin-6-yl)hydrazine

The synthesis scheme of Step 1 is illustrated in (C-1).

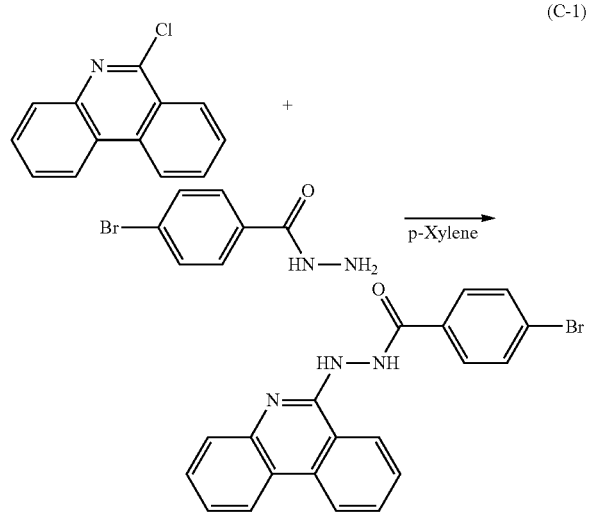

(C-1)

To a 200-mL three-neck flask were added 4.3 g (20 mmol) of 6-chlorophenanthridine, 4.7 g (22 mmol) of 4-bromobenzoylhydrazine, and 80 mL of para-xylene. This mixture was refluxed at 160° C. for 21 hours under a nitrogen stream. After a predetermined time elapsed, this mixture was cooled to room temperature, and the precipitated solid was collected by suction filtration. The obtained solid was washed with heated chloroform and then with water. This solid was dried, so that the substance which was the object of the synthesis was obtained as 6.0 g of a pale yellow powder in 75% yield.

Step 2: Synthesis of 3-(4-Bromophenyl)-1,2,4-triazolo[4,3-f]phenanthridine

The synthesis scheme of Step 2 is illustrated in (C-2).

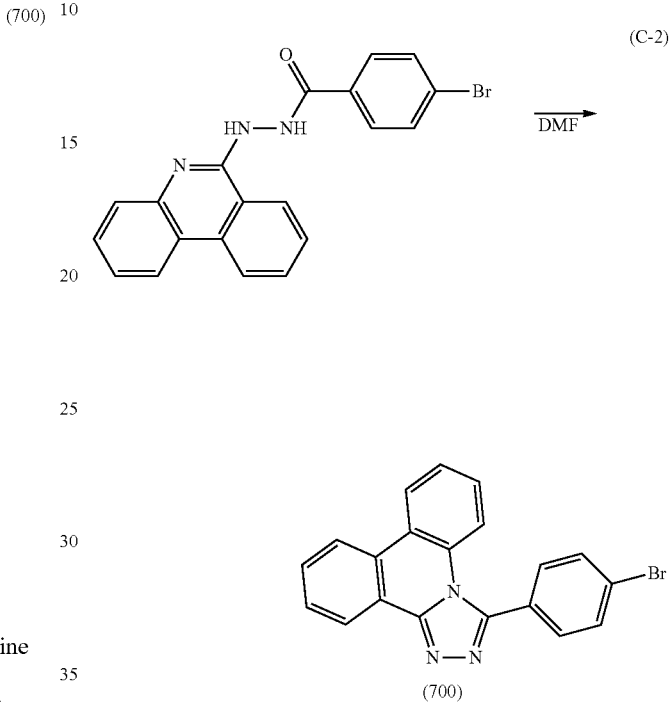

(C-2)

(700)

To a 300-mL three-neck flask were added 2.0 g (5.0 mmol) of N-(4-bromobenzoyl)-N-(phenanthridin-6-yl)hydrazine synthesized in Step 1 and 100 mL of N,N-dimethylformamide. This mixture was stirred at 120° C. for 3 hours under a nitrogen stream. After a predetermined time elapsed, this mixture was cooled to room temperature and added to 1N hydrochloric acid. Organic substances were extracted from the aqueous layer with chloroform. The obtained extract solution was washed with 1N hydrochloric acid, a saturated aqueous solution of sodium hydrogen carbonate and saturated brine, and the organic layer was dried over magnesium sulfate. The obtained mixture was gravity-filtered, and the filtrate was concentrated to give a solid. A methanol suspension of the obtained solid was irradiated with ultrasonic waves, and a solid was collected by suction filtration, so that the substance which was the object of the synthesis was obtained as 1.5 g of a white powder in 78% yield.

This compound was identified as 3-(4-bromophenyl)-1,2,4-triazolo[4,3-f]phenanthridine, which was the object of the synthesis, by nuclear magnetic resonance (NMR) spectroscopy.

$^1$H NMR data of the obtained compound are as follows: $^1$H NMR (CDCl$_3$, 300 MHz): δ=7.36 (t, J=8.4 Hz, 1H), 7.51-7.63 (m, 4H), 7.70-7.80 (m, 4H), 8.39 (d, J=8.4 Hz, 1H), 8.46 (d, J=8.4 Hz, 1H), 8.84 (dd, J=7.8 Hz, 1.5 Hz, 1H).

Figure 7A:
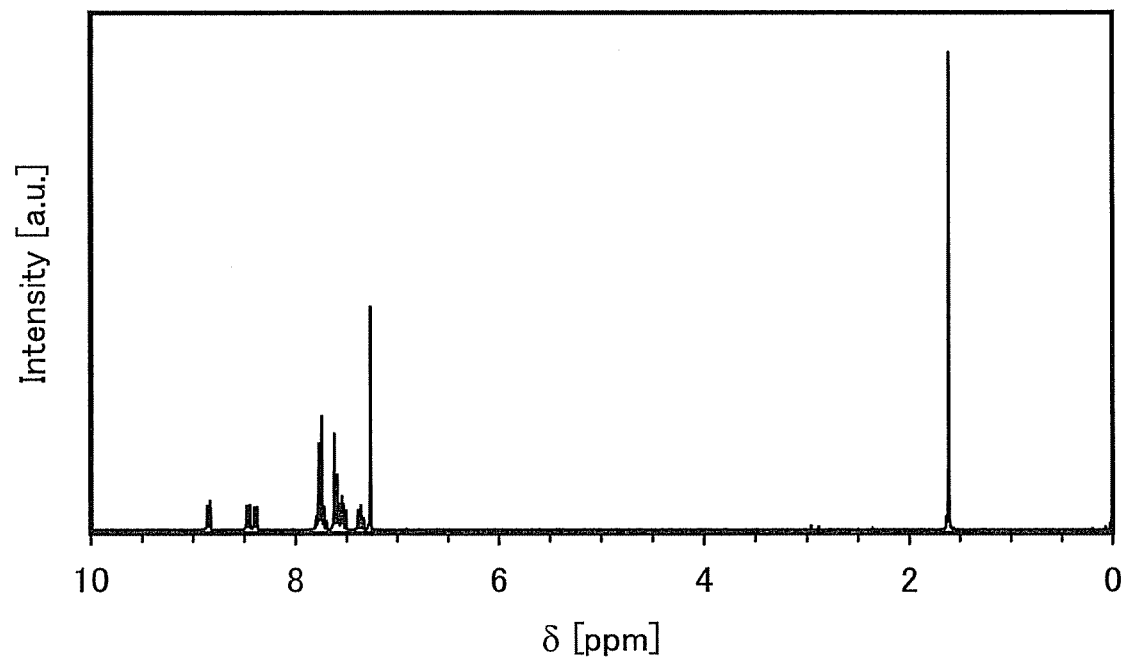
FIGS. 7A and 7B are $^1$H NMR charts of 3-(4-bromophenyl)-1,2,4-triazolo[4,3-f]phenanthridine.
Figure 7B:
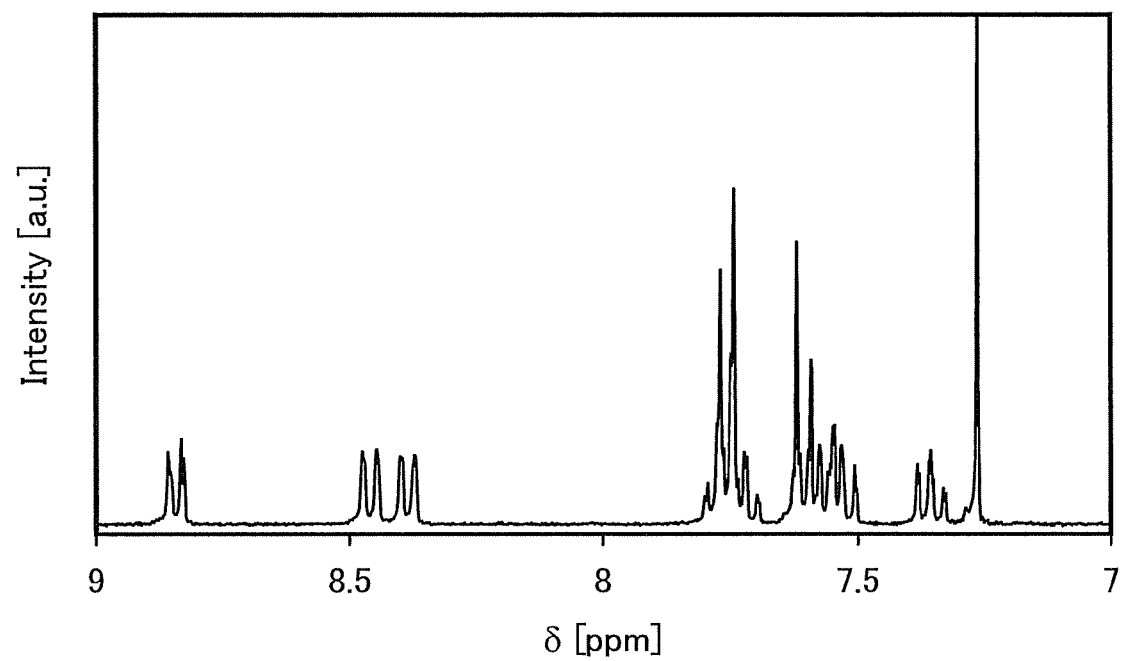

Further, the $^1$H NMR charts are shown in FIGS. 7A and 7B. Note that FIG. 7B is a chart where the range of from 7.0 ppm to 9.0 ppm in FIG. 7A is enlarged.

Step 3: Synthesis of 3-[4-(Dibenzothiophen-4-yl)phenyl]-1,2,4-triazolo[4,3-f]phenanthridine (abbreviation: DBTTPt-II)

The synthesis scheme of Step 3 is illustrated in (C-3).

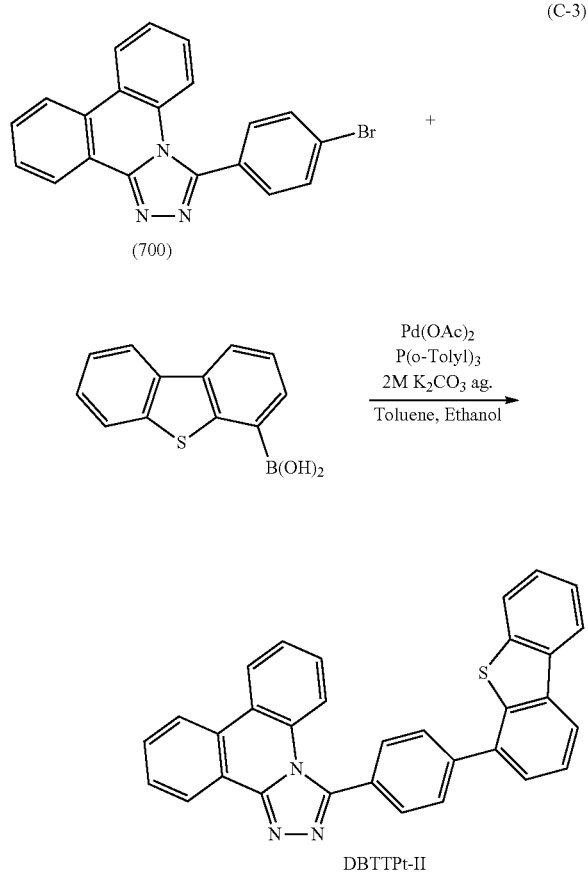

(C-3)

DBTTPt-II

To a 50-mL three-neck flask were added 1.0 g (2.7 mmol) of 3-(4-bromophenyl)-1,2,4-triazolo[4,3-f]phenanthridine synthesized in Step 2, 0.7 g (3.1 mmol) of dibenzothiophene-4-boronic acid, and 40 mg (0.1 mmol) of tri(ortho-tolyl)phosphine, and the air in the flask was replaced with nitrogen. To this flask were added 10 mL of toluene, 3.3 mL of ethanol, and 3 mL a 2M aqueous potassium carbonate solution. This mixture was degassed by being stirred under reduced pressure. To this mixture, 6 mg (27 μmol) of palladium(II) acetate was added. This mixture was refluxed at 90° C. for 6.5 hours under a nitrogen stream. After a predetermined time elapsed, water was added to the obtained mixture, and organic substances were extracted from the aqueous layer with chloroform. The obtained extract solution combined with the organic layer was washed with saturated brine, and the organic layer was dried over magnesium sulfate. The obtained mixture was gravity-filtered, and the filtrate was concentrated to give a solid. This solid was purified by silica gel column chromatography (toluene:ethyl acetate=4:1), and further recrystallized from toluene, so that the substance which was the object of the synthesis was obtained as 1.2 g of a white powder in 95% yield.

By a train sublimation method, 1.1 g of the obtained white powder of the substance which was the object of the synthesis was purified. The purification was conducted by heating of the white powder at 280° C. under a pressure of 2.3 Pa with a flow rate of argon gas of 5 mL/min. After the purification, the substance which was the object of the synthesis was obtained as 0.9 g of a white powder in 80% yield.

This compound was identified as DBTTPt-II, which was the object of the synthesis, by nuclear magnetic resonance (NMR) spectroscopy.

$^1$H NMR data of the obtained compound are as follows: NMR (CDCl$_3$, 300 MHz): δ=7.41 (t, J=7.2 Hz, 1H), 7.49-7.57 (m, 3H), 7.63-7.64 (m, 2H), 7.71-7.81 (m, 3H), 7.86-7.90 (m, 3H), 8.00 (d, J=8.1 Hz, 2H), 8.21-8.26 (m, 2H), 8.41 (d, J=7.5 Hz, 1H), 8.48 (d, J=7.8 Hz, 1H), 8.88 (dd, J=7.5 Hz, 1.8 Hz, 1H).

Figure 8A:
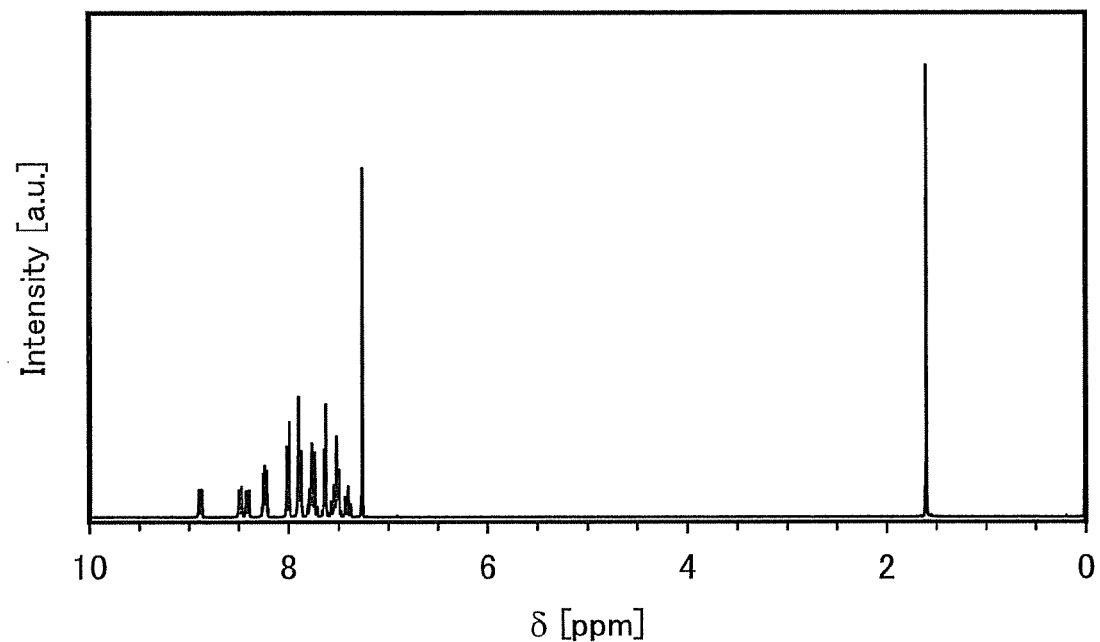
FIGS. 8A and 8B are $^1$H NMR charts of DBTTPt-II.
Figure 8B:
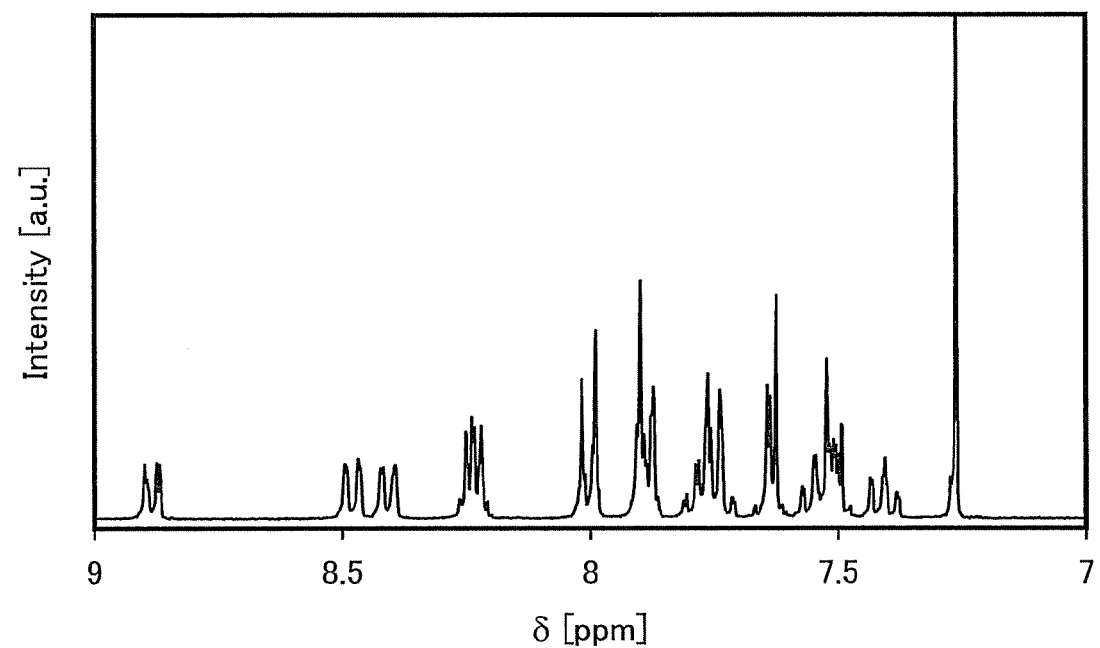

Further, the $^1$H NMR charts are shown in FIGS. 8A and 8B. Note that FIG. 8B is a chart where the range of from 7.0 ppm to 9.0 ppm in FIG. 8A is enlarged.

Figure 9A:
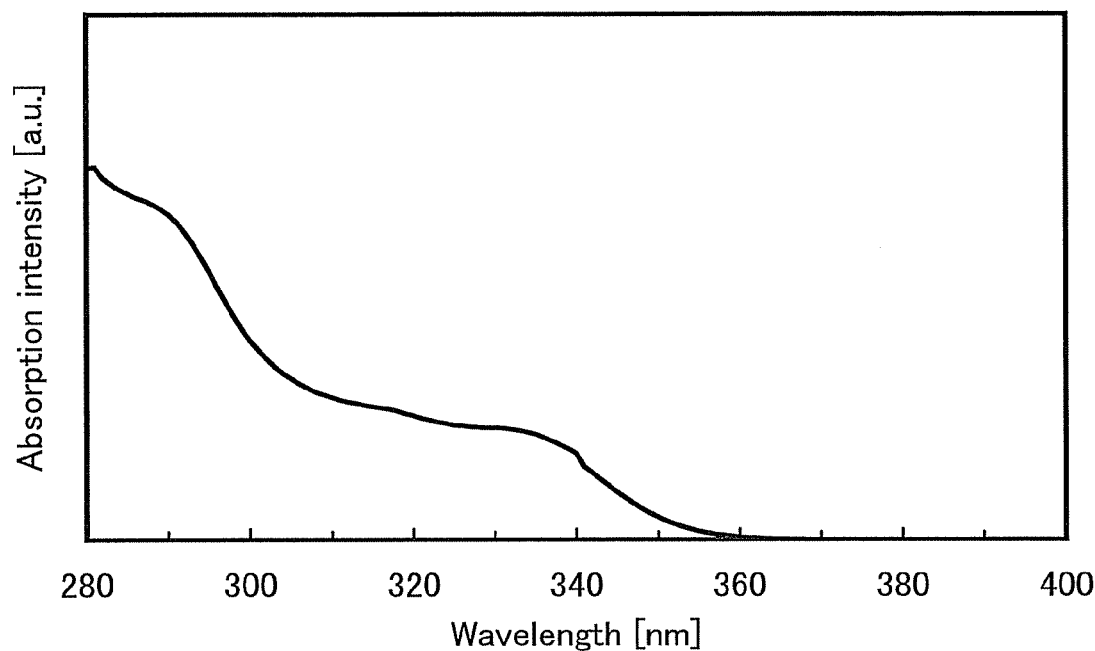
FIGS. 9A and 9B show an absorption and emission spectra of a toluene solution of DBTTPt-II.
Figure 9B:
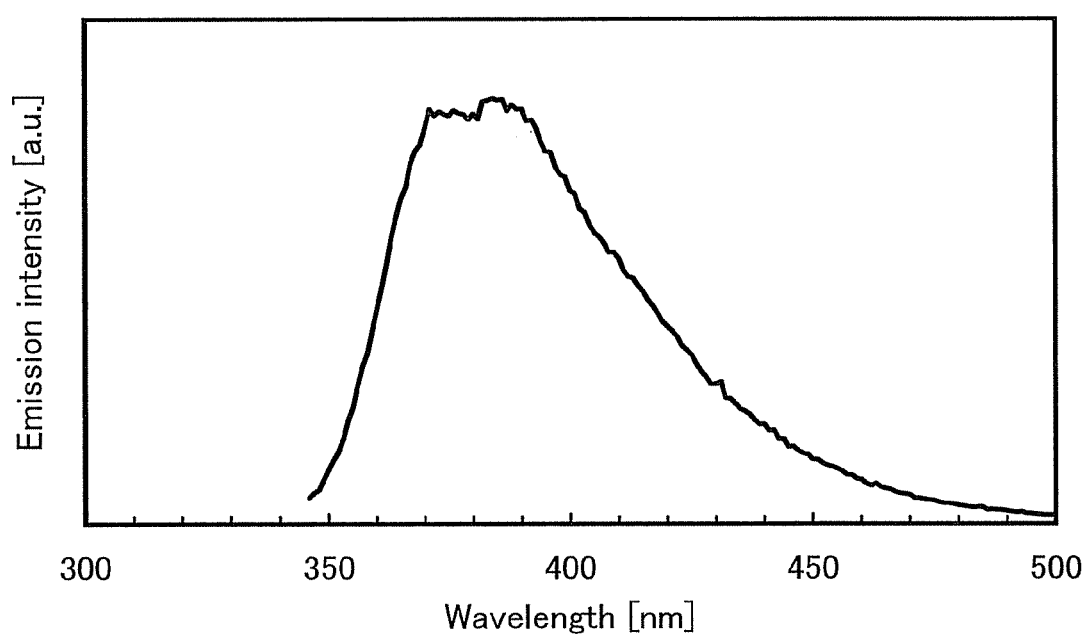
Figure 10A:
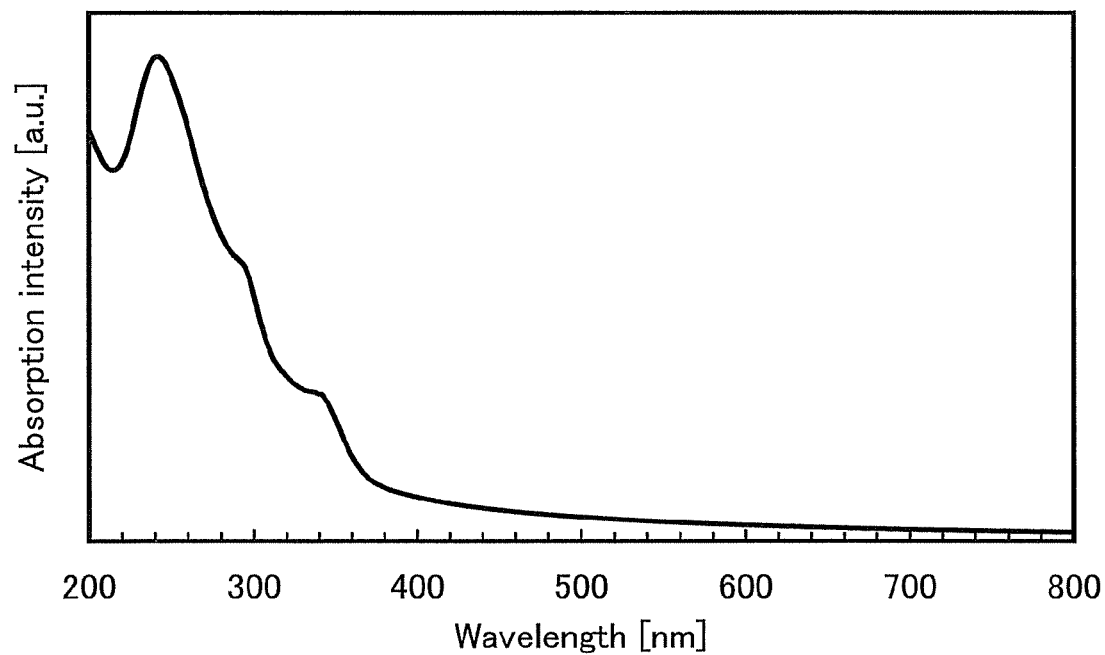
FIGS. 10A and 10B show an absorption and emission spectra of a thin film of DBTTPt-II.
Figure 10B:
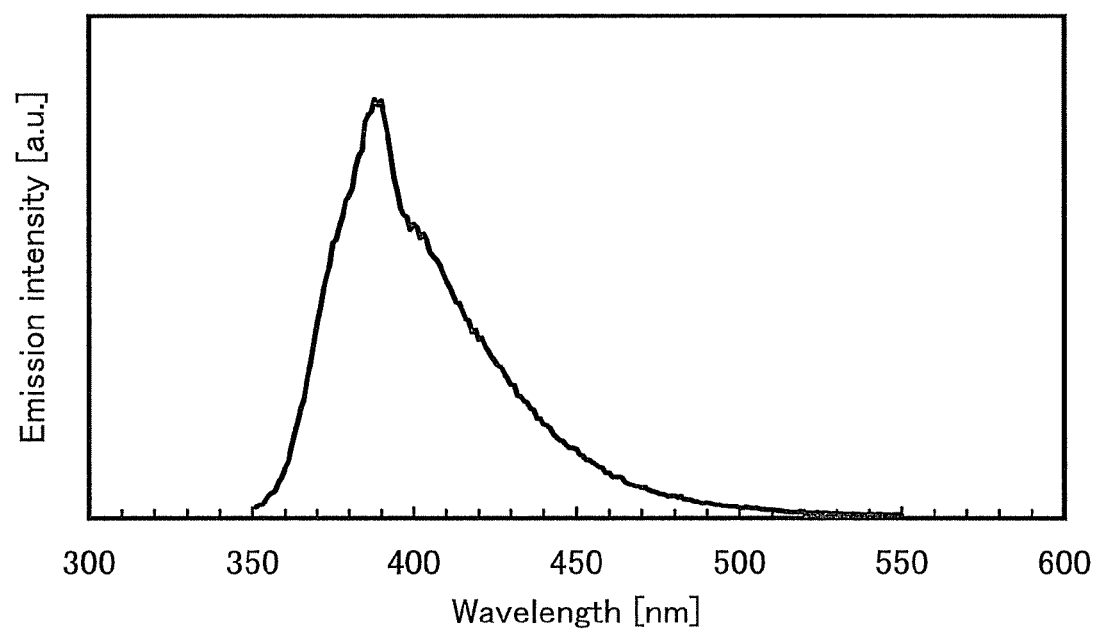

Further, FIG. 9A shows the absorption spectrum of a toluene solution of DBTTPt-II, and FIG. 9B shows the emission spectrum thereof. In addition, FIG. 10A shows the absorption spectrum of a thin film of DBTTPt-II, and FIG. 10B shows the emission spectrum thereof. An ultraviolet-visible spectrophotometer (V-550, manufactured by JASCO Corporation) was used for the measurements. Samples were prepared in such a way that the solution was put into a quartz cell and the thin film was formed on a quartz substrate by evaporation. Here are shown the absorption spectrum for the solution which was obtained by subtracting the absorption spectra of quartz and toluene from those of quartz and the solution, and the absorption spectrum for the thin film which was obtained by subtracting the absorption spectrum of a quartz substrate from those of the quartz substrate and the thin film. In FIG. 9A and FIG. 10A, the horizontal axis represents wavelength (nm) and the vertical axis represents absorption intensity (arbitrary unit). In FIG. 9B and FIG. 10B, the horizontal axis represents wavelength (nm) and the vertical axis represents emission intensity (arbitrary unit). In the case of the toluene solution, absorption peaks were found to be at around 281 nm, 314 nm, and 332 nm, and the peak of the emission wavelength was at 384 nm (at an excitation wavelength of 335 nm). In the case of the thin film, absorption peaks were found to be at around 242 nm, 291 nm, and 337 nm, and the peak of the emission wavelength was at 389 nm (at an excitation wavelength of 339 nm).

EXAMPLE 2

Synthesis Example 2

This example gives descriptions of a method of synthesizing 3-[4-(9H-carbazol-9-yl)phenyl]-1,2,4-triazolo[4,3-f]phenanthridine (abbreviation: CzTPt), which is the triazole derivative of one embodiment of the present invention represented by the structural formula (300) in Embodiment 1.

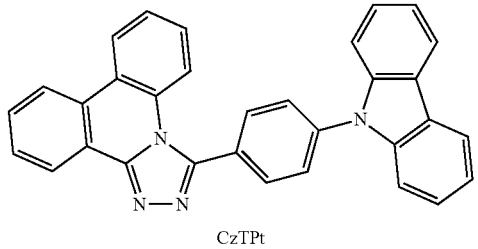 [SMILES: c1ccc2c(c1)c1ccccc1n1c(-c3ccc(-n4c5ccccc5c5ccccc54)cc3)nnc21]

CzTPt

193

A scheme of the synthesis of CzTPt is illustrated in (D-1).

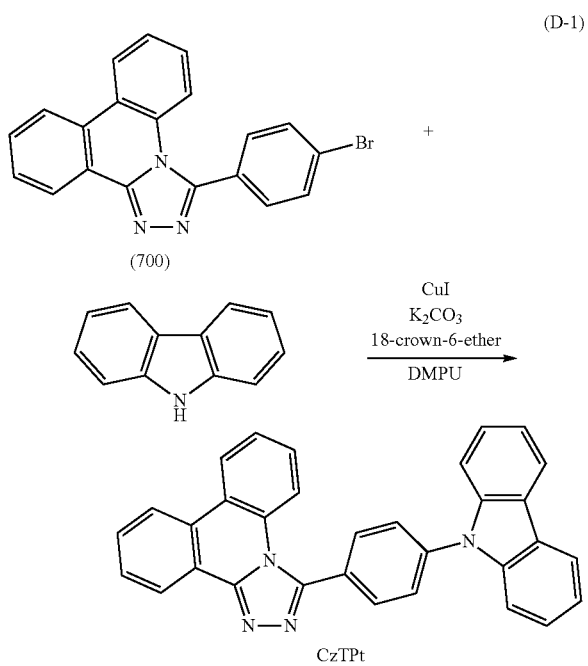

(D-1)

To a 50-mL recovery flask were added 1.0 g (2.7 mmol) of 3-(4-bromophenyl)-1,2,4-triazolo[4,3-f]phenanthridine, 0.7 g (4.2 mmol) of 9H-carbazole, 0.5 g (3.6 mmol) of potassium carbonate, and 2 mL of 1,3-dimethyl-3,4,5,6-tetrahydro-2(1H)-pyrimidinone (DMPU). To this mixture were added 21 mg (79 μmol) of 18-crown-6-ether and 15 mg (79 μmol) of copper(I) iodide, and the mixture was stirred at 180° C. for 6 hours under a nitrogen stream. After a predetermined time elapsed, toluene was added to the obtained mixture, the organic layer was washed with water and saturated brine. The obtained organic layer was dried over magnesium sulfate. The obtained mixture was gravity-filtered, and the filtrate was concentrated to give a solid. This solid was purified by silica gel column chromatography (toluene:ethyl acetate=4:1), and further recrystallized twice from toluene, so that the substance which was the object of the synthesis was obtained as 1.0 g of a white powder in 79% yield.

By a train sublimation method, 1.0 g of the obtained white powder of the substance which was the object of the synthesis was purified. The purification was conducted by heating of the white powder at 260° C. under a pressure of 3.0 Pa with a flow rate of argon gas of 5 mL/min. After the purification, the substance which was the object of the synthesis was obtained as 0.8 g of a white powder in 83% yield.

This compound was identified as CzTPt, which was the object of the synthesis, by nuclear magnetic resonance (NMR) spectroscopy.

$^1$H NMR data of the obtained compound are as follows: $^1$H NMR (CDCl$_3$, 300 MHz): δ=7.36 (t, J=7.2 Hz, 2H), 7.41-7.60 (m, 6H), 7.72-7.82 (m, 3H), 7.86 (d, J=8.7 Hz, 2H), 7.99 (d, J=8.4 Hz, 2H), 8.19 (d, J=7.8 Hz, 2H), 8.42 (dd, J=7.2 Hz, 1.5 Hz, 1H), 8.50 (dd, J=8.4 Hz, 1.5 Hz, 1H), 8.89 (dd, J=7.2 Hz, 1.8 Hz, 1H).

Figure 11A:
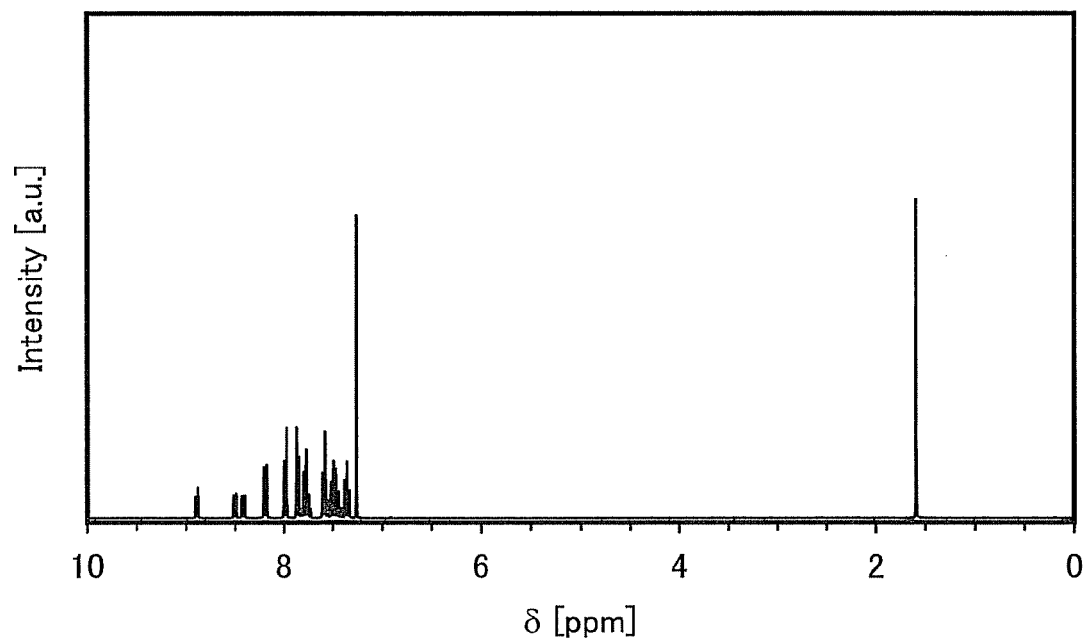
FIGS. 11A and 11B are $^1$H NMR charts of CzTPt.
Figure 11B:
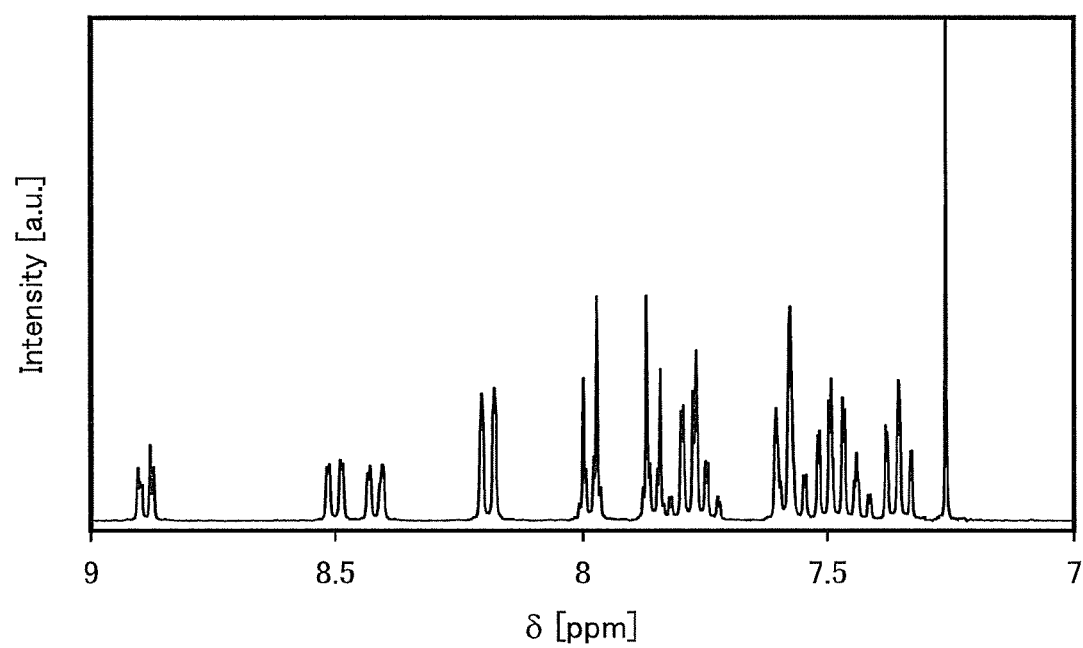

Further, the $^1$H NMR charts are shown in FIGS. 11A and 11B. Note that FIG. 11B is a chart where the range of from 7.0 ppm to 9.0 ppm in FIG. 11A is enlarged.

194

Figure 12A:
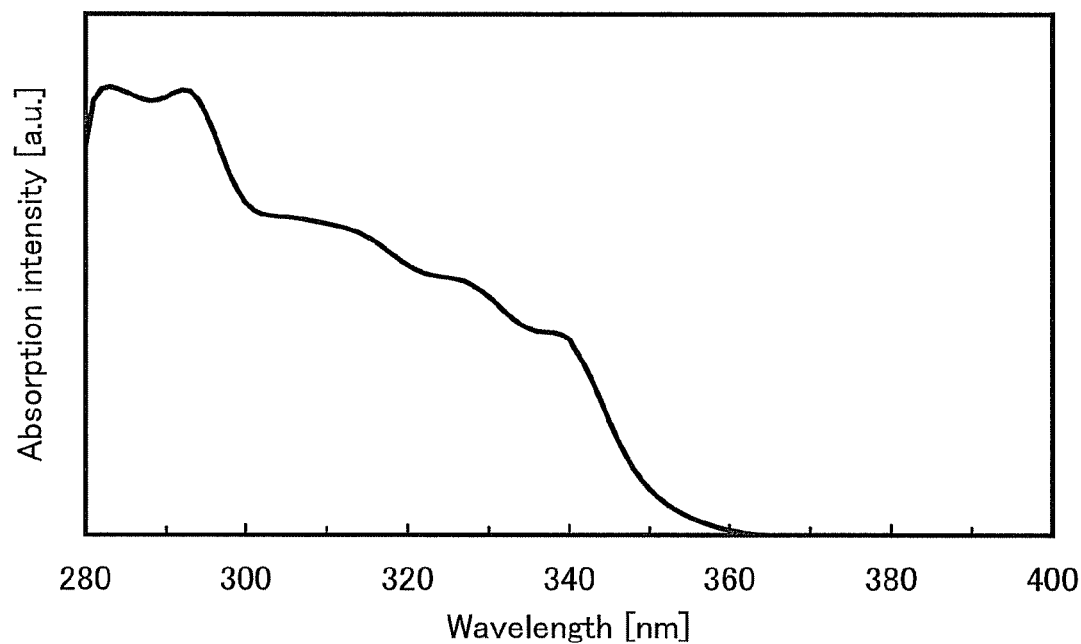
FIGS. 12A and 12B show an absorption and emission spectra of a toluene solution of CzTPt.
Figure 12B:
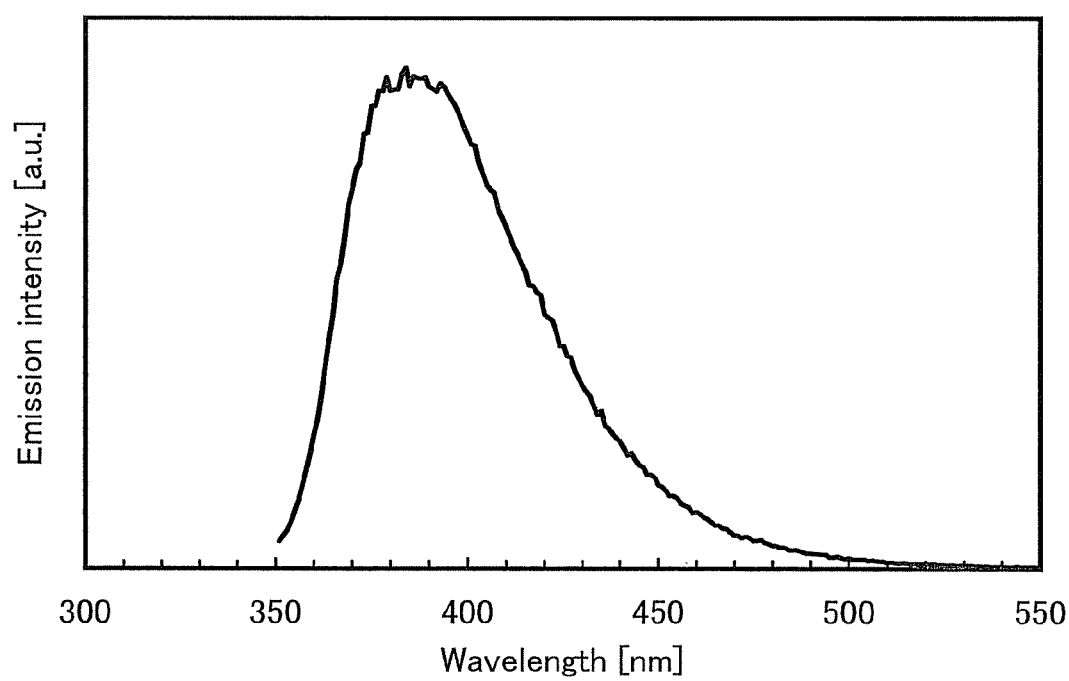
Figure 13A:
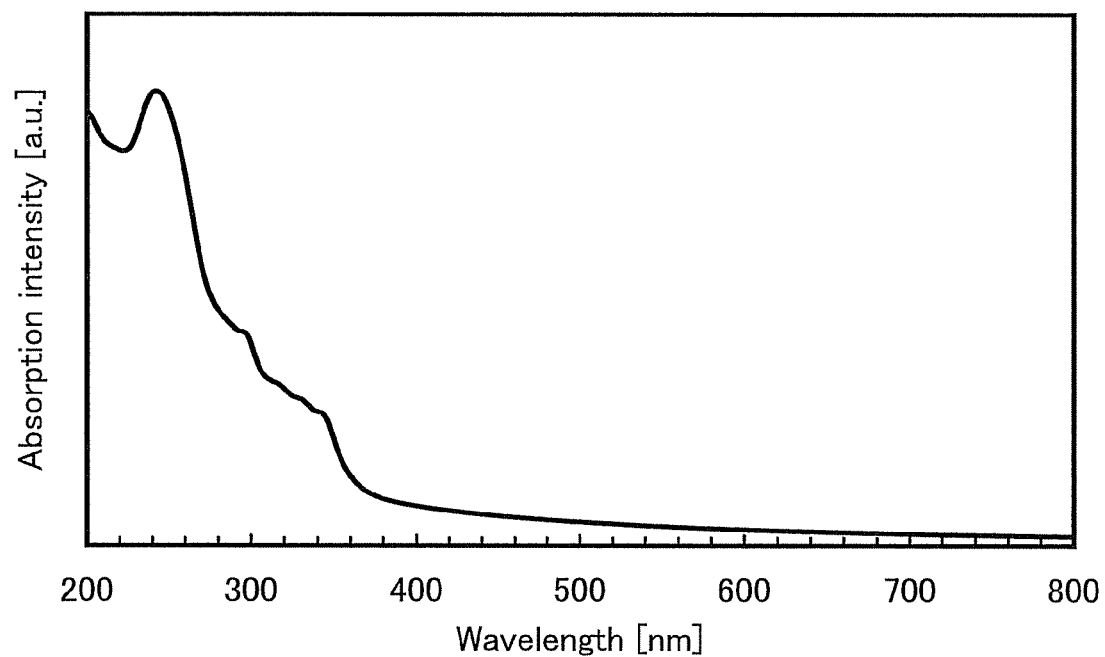
FIGS. 13A and 13B show an absorption and emission spectra of a thin film of CzTPt.
Figure 13B:
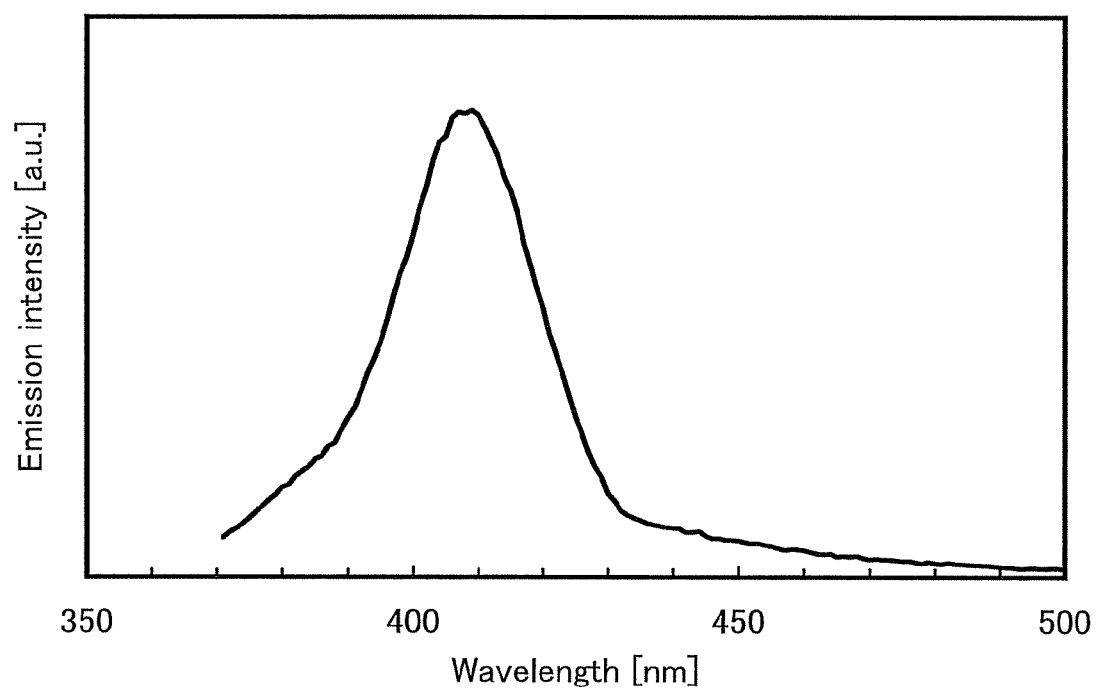

Further, FIG. 12A shows the absorption spectrum of a toluene solution of CzTPt, and FIG. 12B shows the emission spectrum thereof. In addition, FIG. 13A shows the absorption spectrum of a thin film of CzTPt, and FIG. 13B shows the emission spectrum thereof. An ultraviolet-visible spectrophotometer (V-550, manufactured by JASCO Corporation) was used for the measurements. Samples were prepared in such a way that the solution was put into a quartz cell and the thin film was formed on a quartz substrate by evaporation. Here are shown the absorption spectrum for the solution which was obtained by subtracting the absorption spectra of quartz and toluene from those of quartz and the solution, and the absorption spectrum for the thin film which was obtained by subtracting the absorption spectrum of a quartz substrate from those of the quartz substrate and the thin film. In FIG. 12A and FIG. 13A, the horizontal axis represents wavelength (nm) and the vertical axis represents absorption intensity (arbitrary unit). In FIG. 12B and FIG. 13B, the horizontal axis represents wavelength (nm) and the vertical axis represents emission intensity (arbitrary unit). In the case of the toluene solution, absorption peaks were found to be at around 282 nm, 292 nm, 307 nm, 326 nm, and 339 nm and the peak of the emission wavelength was at 384 nm (at an excitation wavelength of 340 nm). In the case of the thin film, absorption peaks were found to be at around 242 nm, 315 nm, 328 nm, and 342 nm, and the peak of the emission wavelength was at 408 nm (at an excitation wavelength of 342 nm).

EXAMPLE 3

Synthesis Example 3

This example gives descriptions of a method of synthesizing 3-[4-(dibenzothiophen-4-yl)phenyl]-1,2,4-triazolo[3,4-α]isoquinoline (abbreviation: DBTTIq-II), which is the triazole derivative of one embodiment of the present invention represented by the structural formula (400) in Embodiment 1, and a method of synthesizing 3-(4-bromophenyl)-1,2,4-triazolo[3,4-α]isoquinoline, which is the heterocyclic compound of one embodiment of the present invention represented by the structural formula (741) in Embodiment 1.

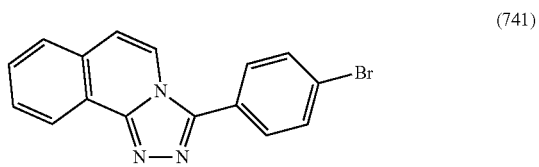

(741)

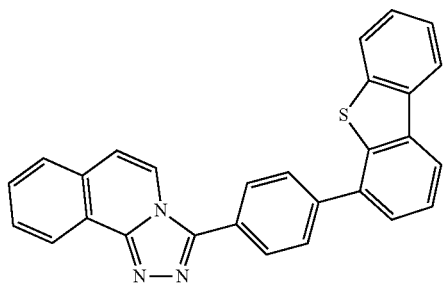

DBTTIq-II

Step 1: Synthesis of 3-(4-Bromophenyl)-1,2,4-triazolo[3,4-α]isoquinoline

The synthesis scheme of Step 1 is illustrated in (E-1).

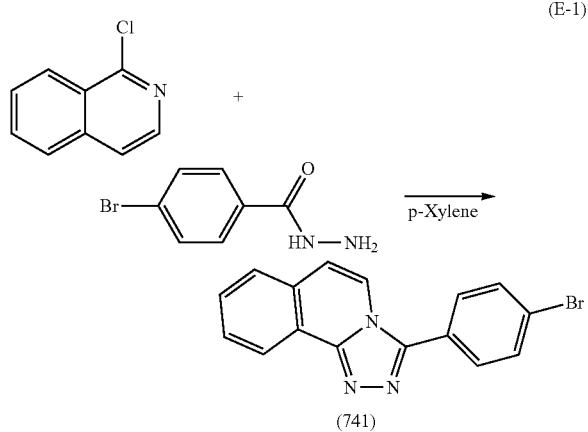

(E-1)

To a 50-mL three-neck flask were added 0.8 g (5.0 mmol) of 1-chloroisoquinoline, 1.1 g (5.0 mmol) of 4-bromobenzoylhydrazine, and 10 mL of para-xylene. This mixture was stirred at 100° C. for 4 hours under a nitrogen stream. After a predetermined time elapsed, this mixture was cooled to room temperature, and the precipitated solid was collected by suction filtration. The obtained solid was purified by silica gel column chromatography (chloroform:ethyl acetate=10:1), so that the substance which was the object of the synthesis was obtained as 0.5 g of a white powder in 29% yield.

This compound was identified as 3-(4-bromophenyl)-1,2,4-triazolo[3,4-α]isoquinoline by nuclear magnetic resonance (NMR) spectroscopy.

$^1$H NMR data of the obtained compound are as follows: $^1$H NMR (CDCl$_3$, 300 MHz): δ=7.13 (d, J=7.2 Hz, 1H), 7.68-7.78 (m, 7H), 7.95 (d, J=7.2 Hz, 1H), 8.80 (dd, J=6.9 Hz, 1.8 Hz, 1H).

Figure 14A:
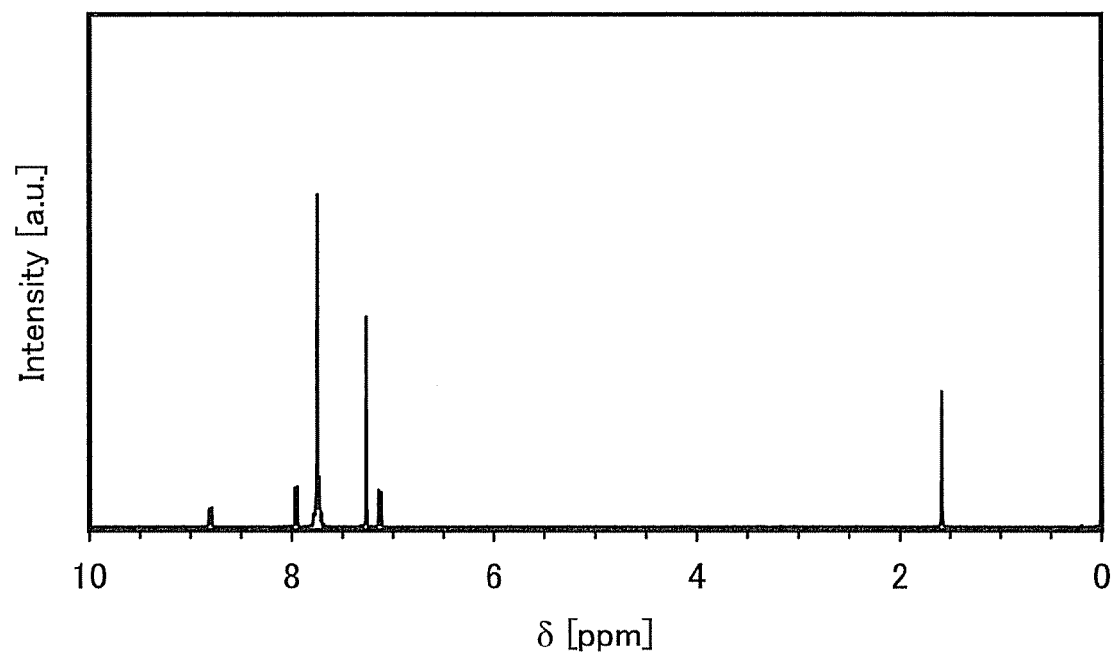
FIGS. 14A and 14B are NMR charts of 3-(4-bromophenyl)-1,2,4-triazolo[3,4-a]isoquinoline.
Figure 14B:
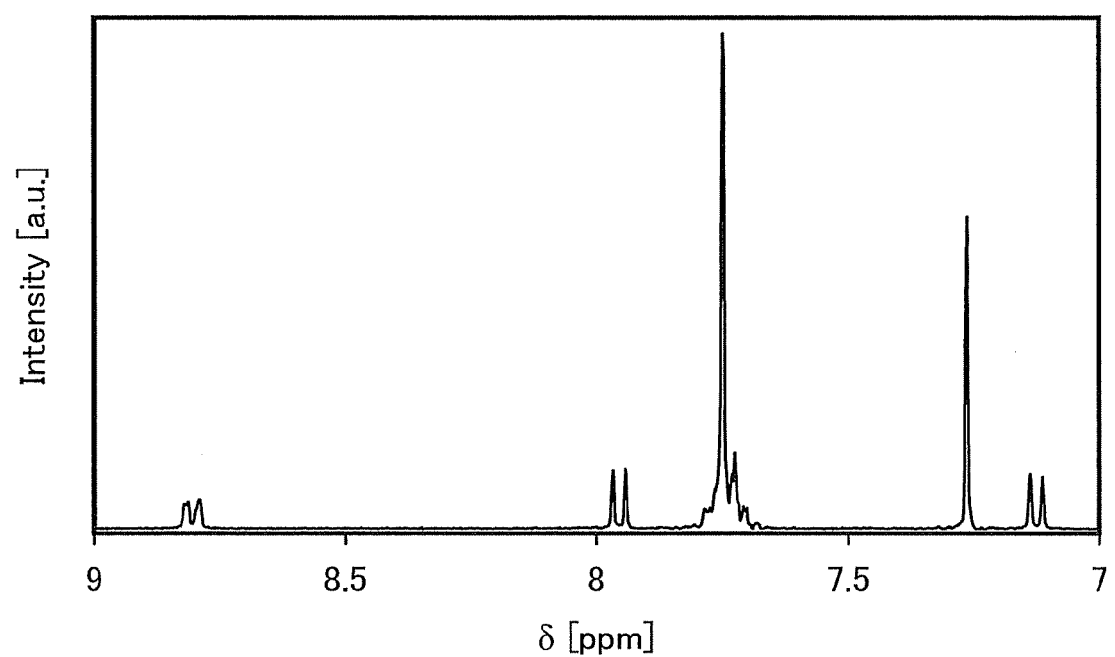

Further, the $^1$H NMR charts are shown in FIGS. 14A and 14B. Note that FIG. 14B is a chart where the range of from 7.0 ppm to 9.0 ppm in FIG. 14A is enlarged.

Step 2: Synthesis of 3-[4-(Dibenzothiophen-4-yl)phenyl]-1,2,4-triazolo[3,4-α]isoquinoline (abbreviation: DBTTIq-II)

The synthesis scheme of Step 2 is illustrated in (E-2).

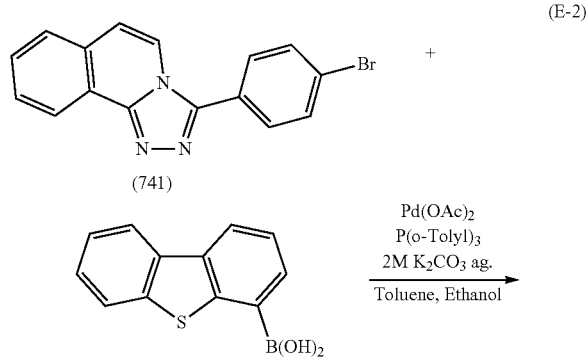

(E-2)

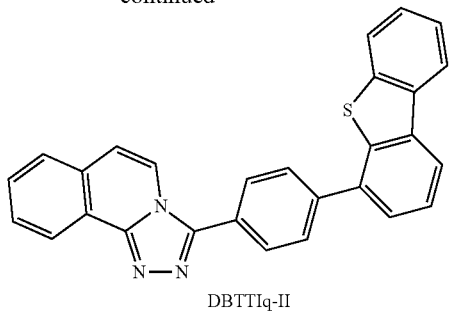

DBTTIq-II

To a 50-mL three-neck flask were added 1.1 g (3.4 mmol) of 3-(4-bromophenyl)triazolo[3,4-α]isoquinoline, 0.9 g (3.9 mmol) of dibenzothiophene-4-boronic acid, and 53 mg (0.2 mmol) of tri(ortho-tolyl)phosphine, and the air in the flask was replaced with nitrogen. To this mixture were added 3.9 mL of a 2.0M aqueous potassium carbonate solution, 13 mL of toluene, and 4.4 mL of ethanol, and the mixture was degassed by being stirred under reduced pressure. To this mixture was added 7.9 mg (35 μmol) of palladium(II) acetate, and the mixture was stirred at 90° C. for 7 hours under a nitrogen stream. After a predetermined time elapsed, water was added to the obtained mixture, and organic substances were extracted from the aqueous layer with chloroform. The obtained extract solution combined with the organic layer was washed with saturated brine, and then the obtained organic layer was dried over magnesium sulfate. This mixture was separated by gravity filtration, and the filtrate was concentrated to give an oily substance. This oily substance was purified by silica gel column chromatography to give a solid. The developing solvent for the chromatography was a mixed solvent of toluene and ethyl acetate (toluene:ethyl acetate=10:1). The obtained solid was washed with hot chloroform, so that the substance which was the object of the synthesis was obtained as 1.0 g of a white powder in 65% yield.

By a train sublimation method, 1.0 g of the white powder of the substance which was the object of the synthesis was purified. The purification was conducted by heating of the white powder at 255° C. under a pressure of 2.3 Pa with a flow rate of argon gas of 5 mL/min. After the purification, the substance which was the object of the synthesis was obtained as 0.8 g of a white powder in 84% yield.

This compound was identified as DBTTIq-II, which was the object of the synthesis, by nuclear magnetic resonance (NMR) spectroscopy.

$^1$H NMR data of the obtained compound are as follows: $^1$H NMR (DMSO-d$_6$, 300 MHz): δ=7.43 (t, J=7.8 Hz, 1H), 7.54-7.60 (m, 2H), 7.69-7.75 (m, 2H), 7.78-7.84 (m, 2H), 7.99-8.09 (m, 4H), 8.16 (d, J=8.4 Hz, 2H), 8.43-8.51 (m, 3H), 8.61-8.67 (m, 1H).

Figure 15A:
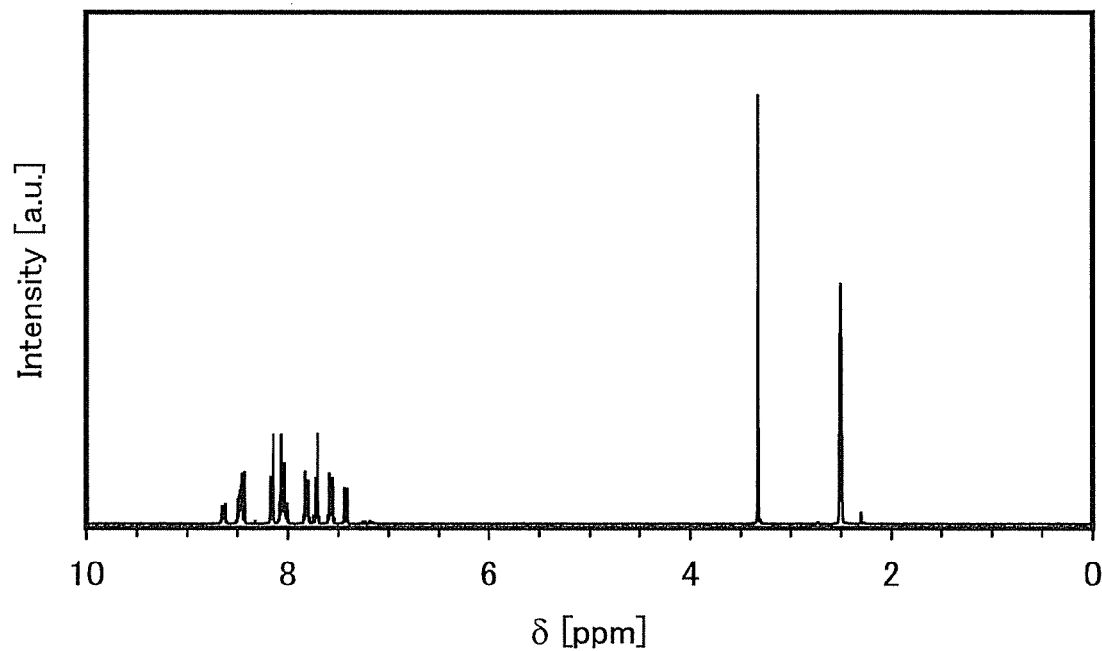
FIGS. 15A and 15B are $^1$H NMR charts of DBTTIq-II.
Figure 15B:
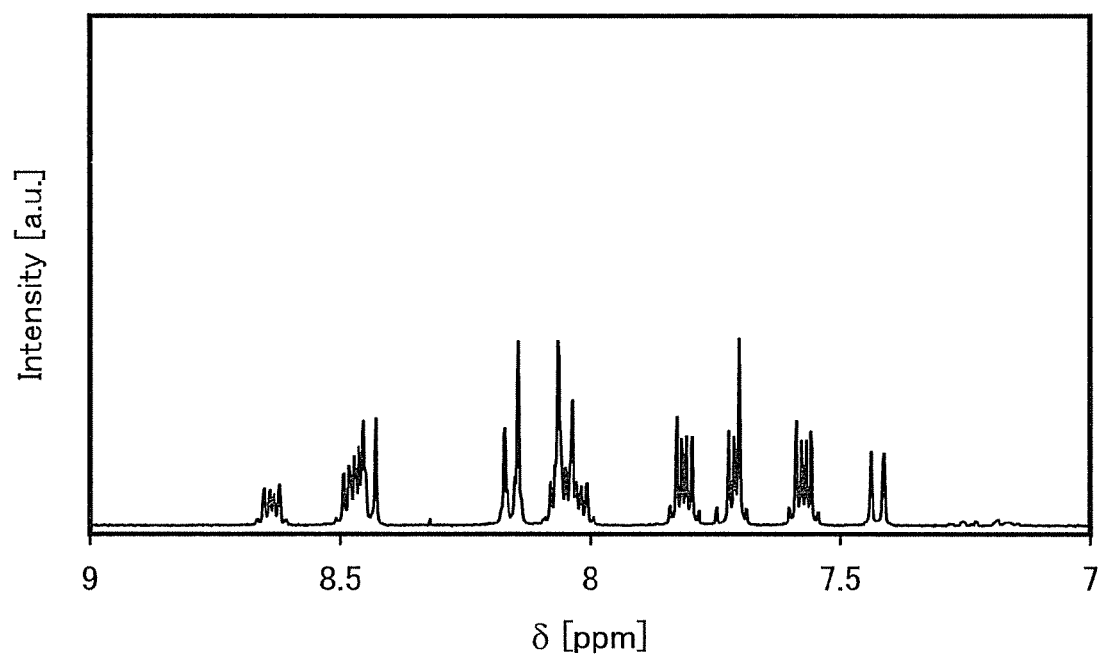

Further, the $^1$H NMR charts are shown in FIGS. 15A and 15B are NMR charts. Note that FIG. 15B is a chart where the range of from 7.0 ppm to 9.0 ppm in FIG. 15A is enlarged.

Figure 16A:
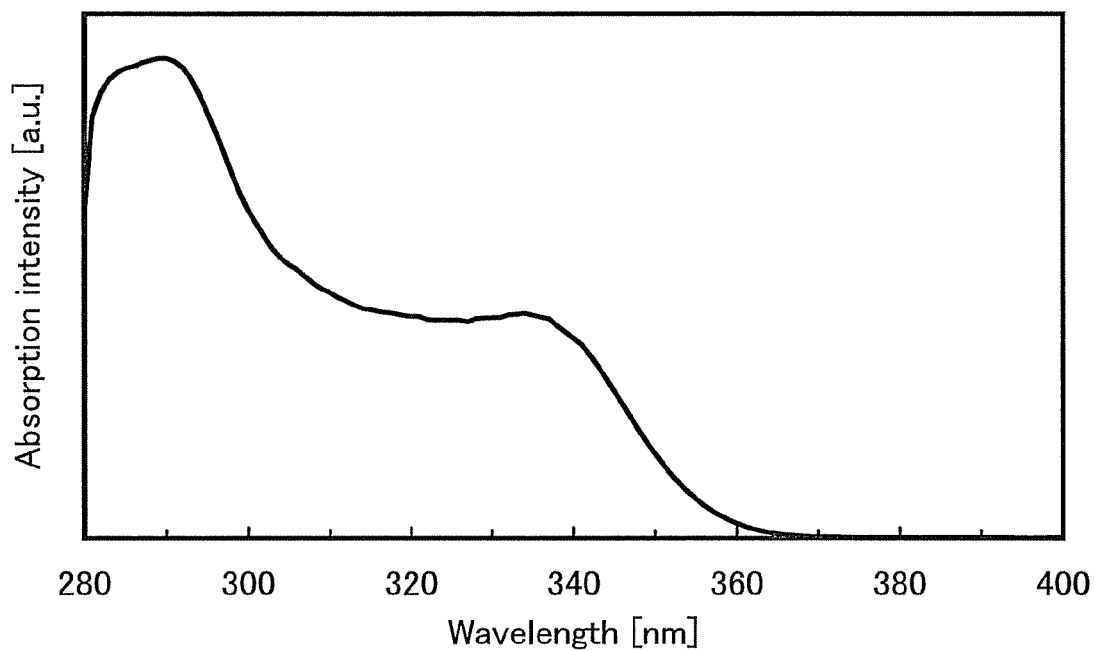
FIGS. 16A and 16B show an absorption and emission spectra of a toluene solution of DBTTIq-II.
Figure 16B:
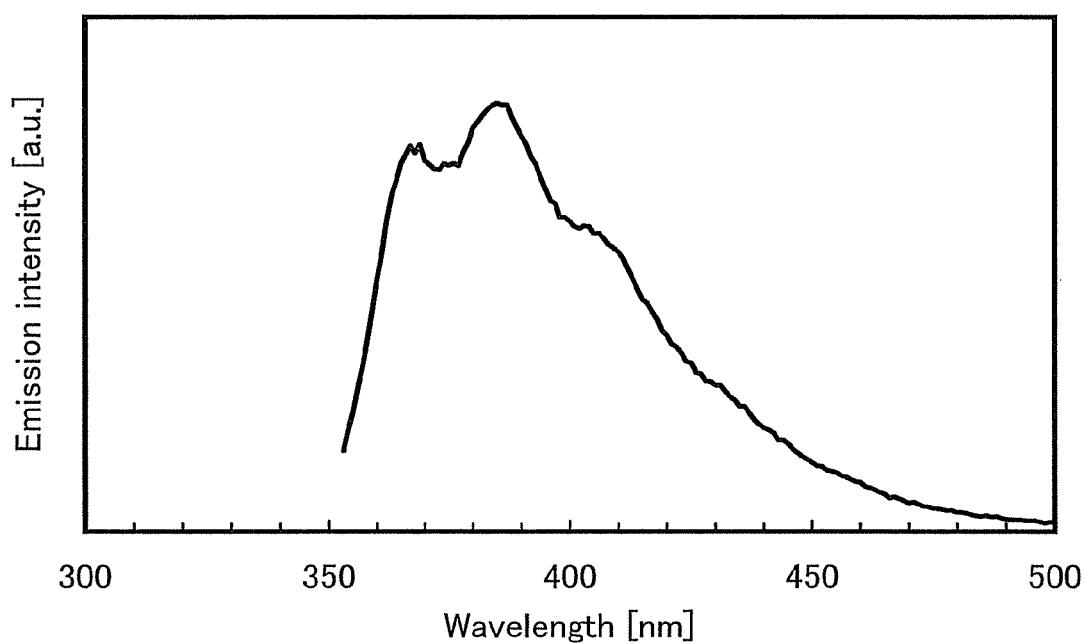
Figure 17A:
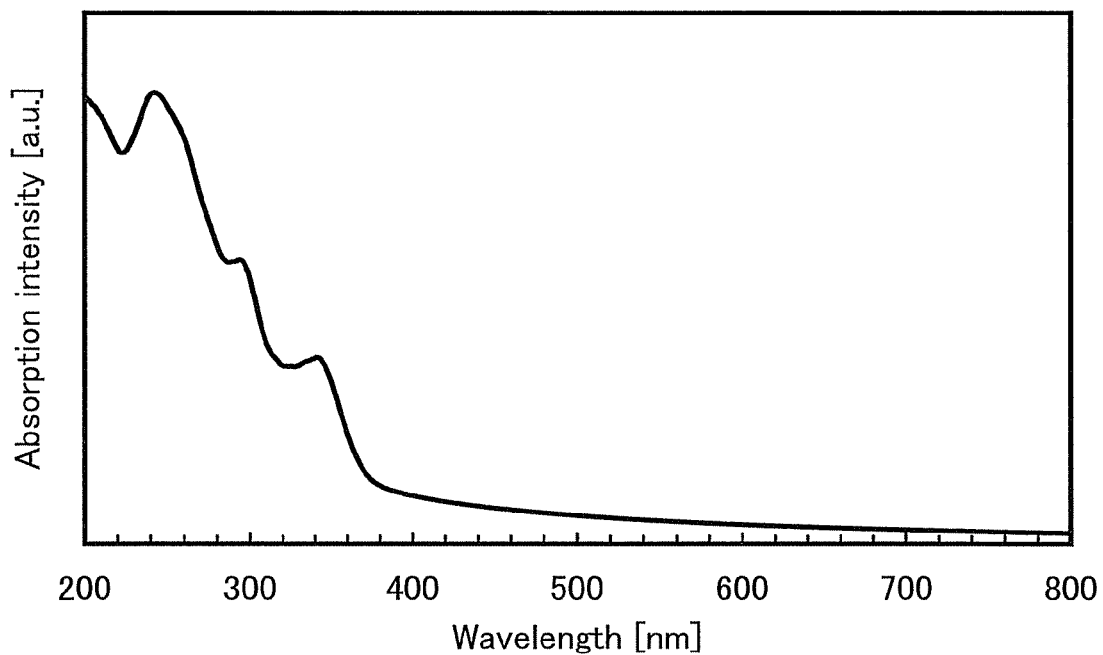
FIGS. 17A and 17B show an absorption and emission spectra of a thin film of DBTTIq-II.
Figure 17B:
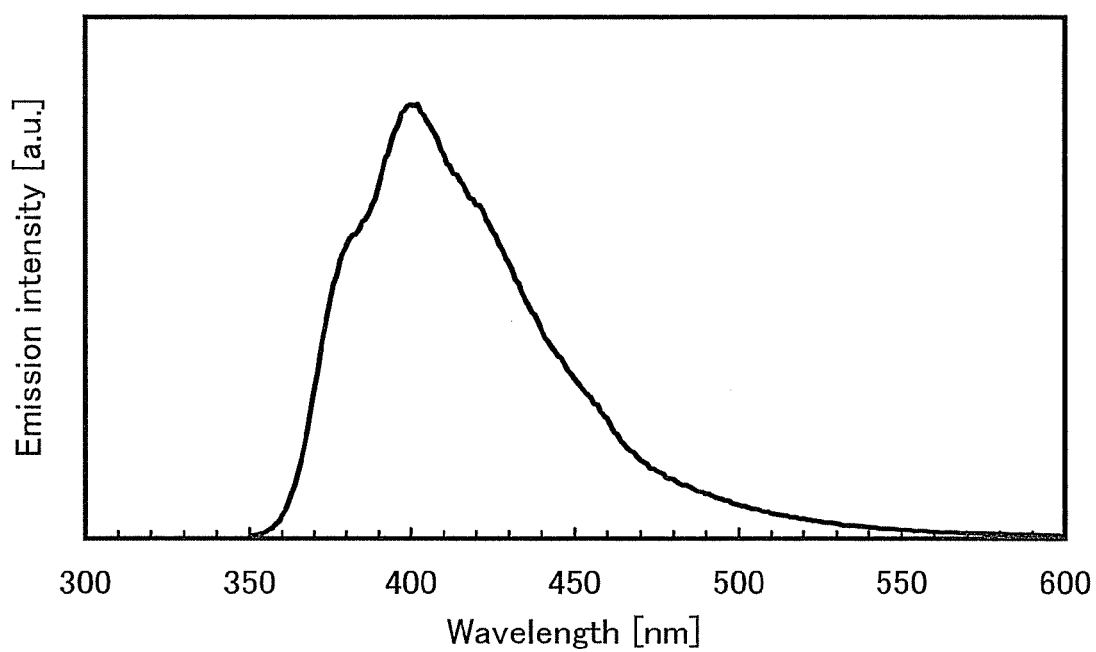

Further, FIG. 16A shows the absorption spectrum of a toluene solution of DBTTIq-II, and FIG. 16B shows the emission spectrum thereof. In addition, FIG. 17A shows the absorption spectrum of a thin film of DBTTIq-II, and FIG. 17B shows the emission spectrum thereof. An ultraviolet-visible spectrophotometer (V-550, manufactured by JASCO Corporation) was used for the measurements. Samples were prepared in such a way that the solution was put into a quartz cell and the thin film was formed on a quartz substrate by evaporation. Here are shown the absorption spectrum for the solution which was obtained by subtracting the absorption spectra of quartz and toluene from those of quartz and the solution, and the absorption spectrum for the thin film which was obtained by subtracting the absorption spectrum of a quartz substrate from those of the quartz substrate and the thin film. In FIG. 16A and FIG. 17A, the horizontal axis represents wavelength (nm) and the vertical axis represents absorption intensity (arbitrary unit). In FIG. 16B and FIG. 17B, the horizontal axis represents wavelength (nm) and the vertical axis represents emission intensity (arbitrary unit). In the case of the toluene solution, absorption peaks were found to be at around 288 nm and 333 nm, and peaks of the emission wavelength were at 365 nm, 385 nm, and 403 nm (at an excitation wavelength of 337 nm). In the case of the thin film, absorption peaks were found to be at around 243 nm, 294 nm, and 341 nm, and the peak of the emission wavelength was at 401 nm (at an excitation wavelength of 338 nm).

EXAMPLE 4

Synthesis Example 4

This example gives descriptions of a method of synthesizing 3-[3-(dibenzothiophen-4-yl)phenyl]-1,2,4-triazolo[4,3-f]phenanthridine (abbreviation: mDBTTPt-II), which is the triazole derivative of one embodiment of the present invention represented by the structural formula (101) in Embodiment 1, and a method of synthesizing 3-(3-bromophenyl)-1,2,4-triazolo[4,3-f]phenanthridine, which is the heterocyclic compound of one embodiment of the present invention represented by the structural formula (701) in Embodiment 1.

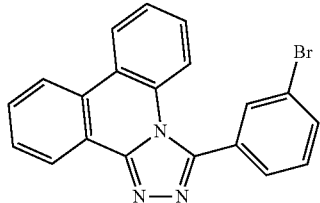

(701)

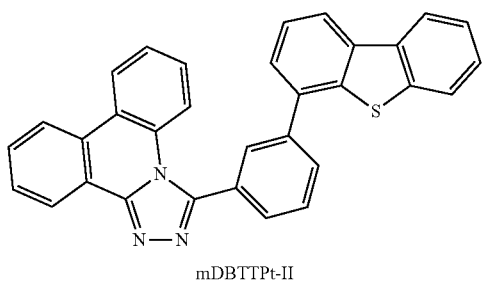

mDBTTPt-II

Step 1: Synthesis of 1-(3-Bromobenzoyl)-2-(phenanthridin-6-yl)hydrazine

The synthesis scheme of Step 1 is illustrated in (F-1).

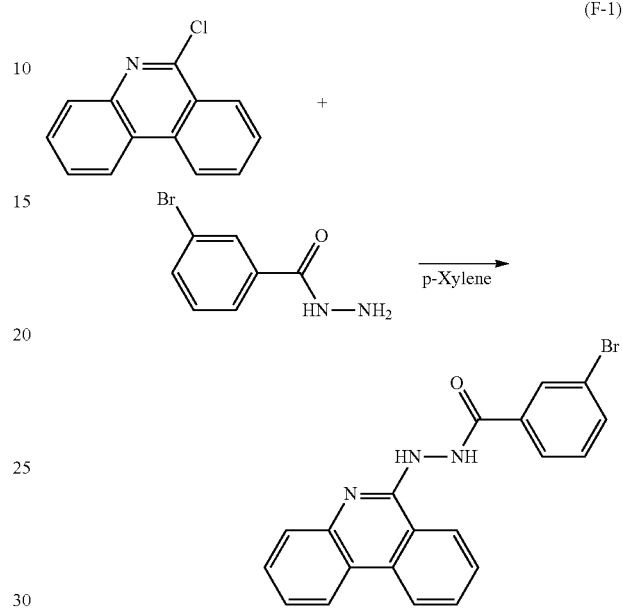

(F-1)

To a 100-mL three-neck flask were added 1.1 g (5.1 mmol) of 6-chlorophenanthridine, 1.2 g (5.5 mmol) of 3-bromobenzoylhydrazine, and 40 mL of para-xylene. This mixture was refluxed at 160° C. for 4 hours under a nitrogen stream. After a predetermined time elapsed, this mixture was cooled to room temperature, and the precipitated solid was collected by suction filtration and washed with toluene, water, and a saturated aqueous solution of sodium hydrogen carbonate. A methanol suspension of the obtained solid was irradiated with ultrasonic waves, and a solid was collected by suction filtration, so that the substance which was the object of the synthesis was obtained as 1.3 g of a pale yellow powder in 66% yield.

Step 2: Synthesis of 3-(3-Bromophenyl)-1,2,4-triazolo[4,3-f]phenanthridine

The synthesis scheme of Step 2 is illustrated in (F-2).

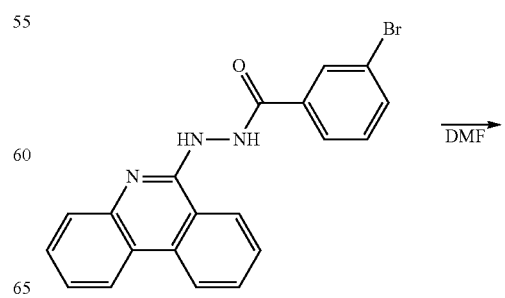

(F-2)

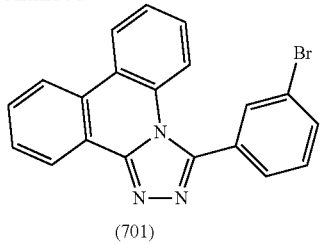

(701)

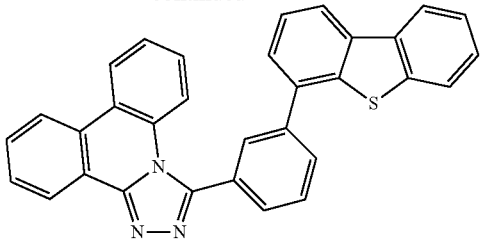

mDBTTPt-II

To a 200-mL three-neck flask were added 1.3 g (3.3 mmol) of 1-(3-bromobenzoyl)-2-(phenanthridin-6-yl)hydrazine synthesized in Step 1 and 70 mL of N,N-dimethylformamide. This solution was stirred at 120° C. for 5 hours under a nitrogen stream. After a predetermined time elapsed, this mixture was cooled to room temperature, and chloroform was added thereto. This solution was added to 1N hydrochloric acid, and organic substances were extracted from the aqueous layer with chloroform. The obtained extract solution was washed with water, a saturated aqueous solution of sodium hydrogen carbonate and saturated brine, and the organic layer was dried over magnesium sulfate. The obtained mixture was gravity-filtered, and the filtrate was concentrated to give a solid. A methanol suspension of the obtained solid was irradiated with ultrasonic waves, and a solid was collected by suction filtration, so that the substance which was the object of the synthesis was obtained as 0.9 g of a white powder in 69% yield.

This compound was identified as 3-(3-bromophenyl)-1,2,4-triazolo[4,3-f]phenanthridine, which was the object of the synthesis, by nuclear magnetic resonance (NMR) spectroscopy.

$^1$H NMR data of the obtained compound are as follows: $^1$H NMR (CDCl$_3$, 300 MHz): δ=7.31-7.37 (m, 1H), 7.44-7.54 (m, 3H), 7.63 (d, J=7.8 Hz, 1H), 7.68-7.79 (m, 3H), 7.88-7.89 (m, 1H), 8.37 (d, J=7.8 Hz, 1H), 8.44 (d, J=7.2 Hz, 1H), 8.83 (dd, J=7.2 Hz, 1.8 Hz, 1H).

Figure 18A:
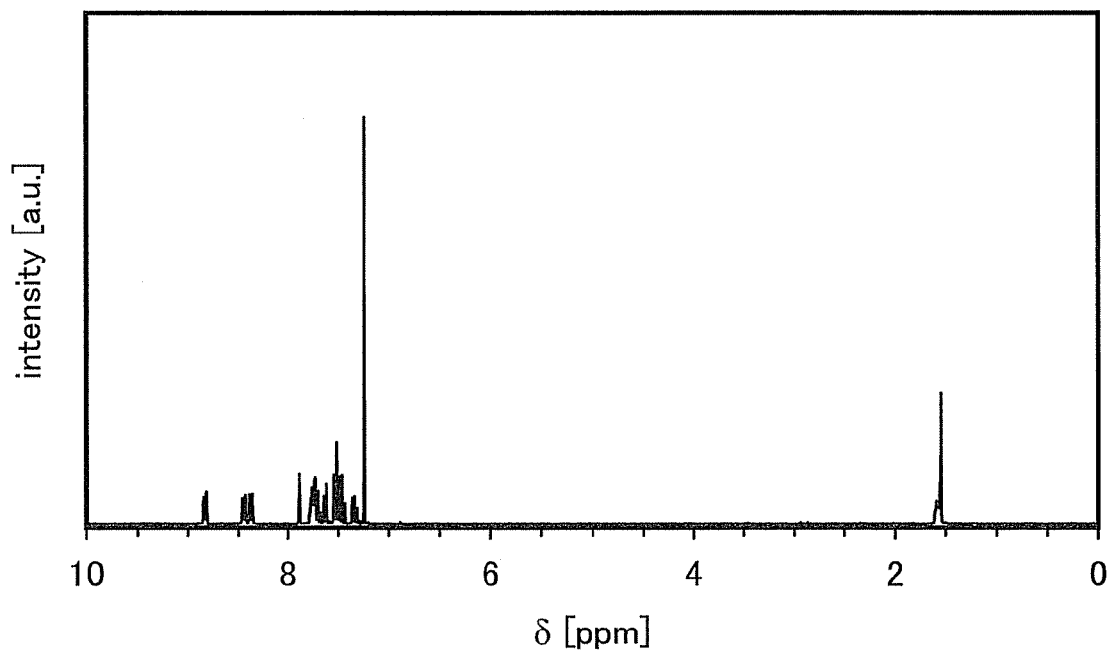
FIGS. 18A and 18B are $^1$H NMR charts of 3-(3-bromophenyl)-1,2,4-triazolo[4,3-f]phenanthridine.
Figure 18B:
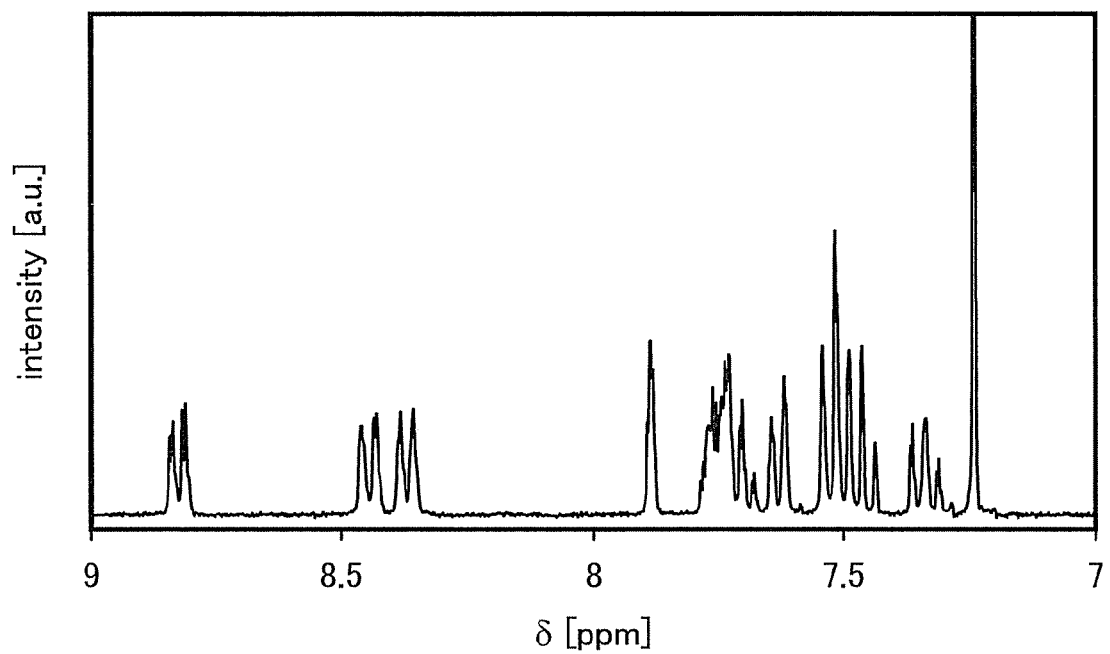

Further, the $^1$H NMR charts are shown in FIGS. 18A and 18B. Note that FIG. 18B is a chart where the range of from 7.0 ppm to 9.0 ppm in FIG. 18A is enlarged.

Step 3: Synthesis of 3-[3-(Dibenzothiophen-4-yl)phenyl]-1,2,4-triazolo[4,3-f]phenanthridine (abbreviation: mDBTTPt-II)

The synthesis scheme of Step 3 is illustrated in (F-3).

(F-3)

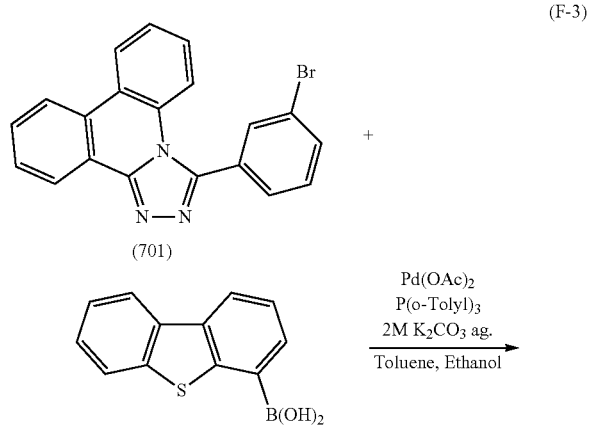

To a 100-mL three-neck flask were added 0.9 g (2.3 mmol) of 3-(3-bromophenyl)-1,2,4-triazolo[4,3-f]phenanthridine, 0.5 g (2.4 mmol) of dibenzothiophene-4-boronic acid, 0.1 g (0.4 mmol) of tri(ortho-tolyl)phosphine, 25 mL of toluene, 3 mL of ethanol, and 2.5 mL of a 2M aqueous potassium carbonate solution. This mixture was degassed by being stirred under reduced pressure, and the air in the flask was replaced with nitrogen. To this mixture, 18 mg (80 μmol) of palladium (II) acetate was added. This mixture was stirred at 80° C. for 6 hours under a nitrogen stream. After a predetermined time elapsed, water was added to the obtained mixture, and organic substances were extracted from the aqueous layer with chloroform. The obtained extract solution combined with the organic layer was washed with a saturated aqueous solution of sodium hydrogen carbonate and saturated brine, and the organic layer was dried over magnesium sulfate. This mixture was gravity-filtered, and the filtrate was concentrated to give a solid. The obtained solid was purified by silica gel column chromatography. The developing solvent for the chromatography was a mixed solvent of chloroform and ethyl acetate (chloroform:ethyl acetate=4:1). Furthermore, recrystallization from toluene was carried out, so that the substance which was the object of the synthesis was obtained as 0.8 g of a white powder in 74% yield.

By a train sublimation method, 0.82 g of the obtained white powder was purified. The purification was conducted by heating of the white powder at 270° C. under a pressure of 2.7 Pa with a flow rate of argon gas of 5 mL/min. After the purification, the substance which was the object of the synthesis was obtained as 0.67 g of a white powder in 81% yield.

This compound was identified as mDBTTPt-II, which was the object of the synthesis, by nuclear magnetic resonance (NMR) spectroscopy.

$^1$H NMR data of the obtained compound are as follows: $^1$H NMR (CDCl$_3$, 300 MHz): δ=7.38-7.61 (m, 6H), 7.69-7.83 (m, 6H), 8.01-8.06 (m, 2H), 8.16-8.21 (m, 2H), 8.39 (dd, J=7.8 Hz, 1.5 Hz, 1H), 8.46 (dd, J=8.1 Hz, 1.5 Hz, 1H), 8.86 (dd, J=7.2 Hz, 2.1 Hz, 1H).

Figure 19A:
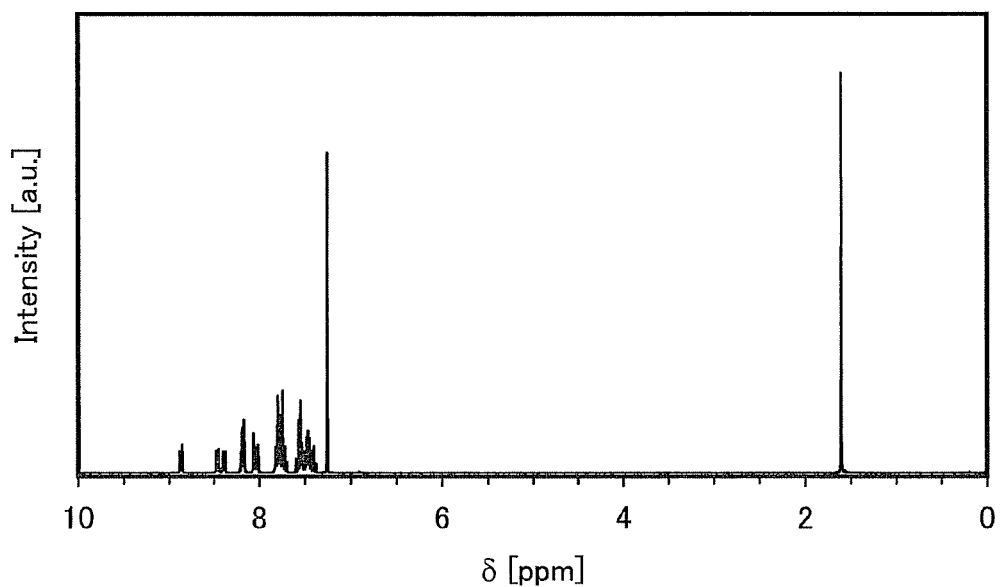
FIGS. 19A and 19B are $^1$H NMR charts of mDBTTPt-II.
Figure 19B:
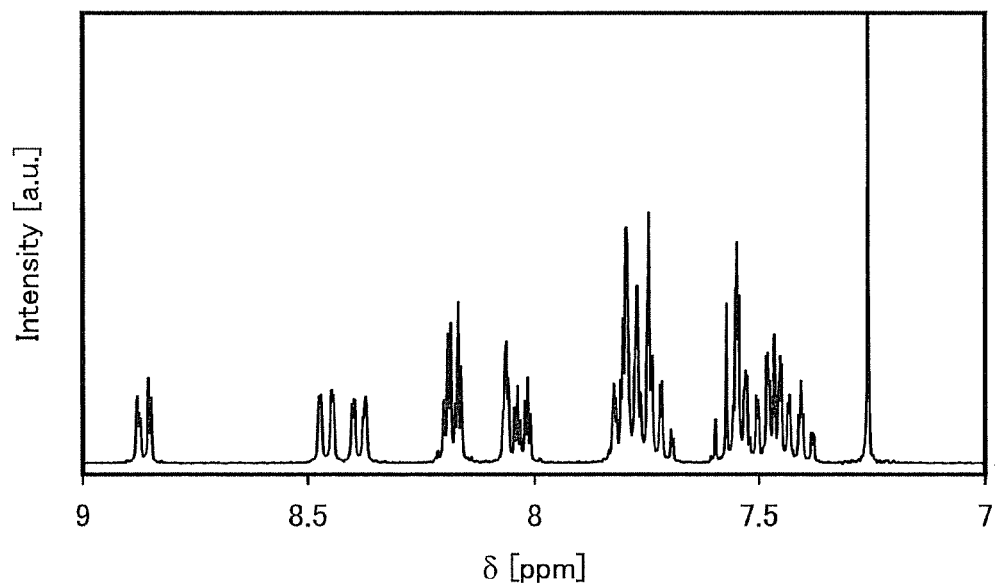

Further, the $^1$H NMR charts are shown in FIGS. 19A and 19B. Note that FIG. 19B is a chart where the range of from 7.0 ppm to 9.0 ppm in FIG. 19A is enlarged.

Figure 20A:
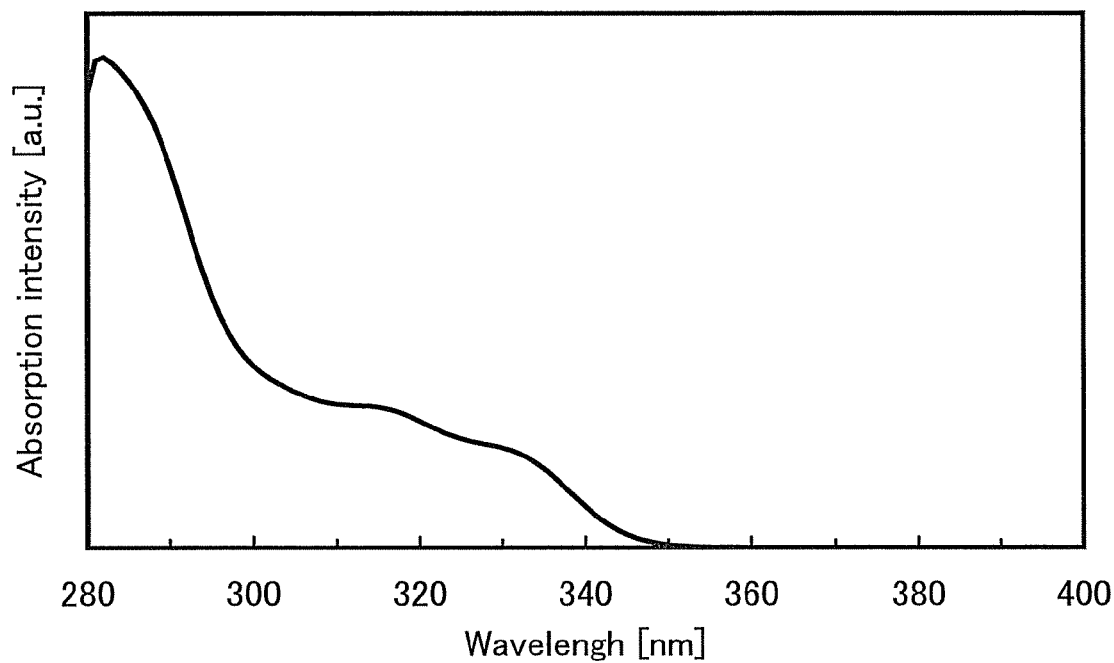
FIGS. 20A and 20B show an absorption and emission spectra of a toluene solution of mDBTTPt-II.
Figure 20B:
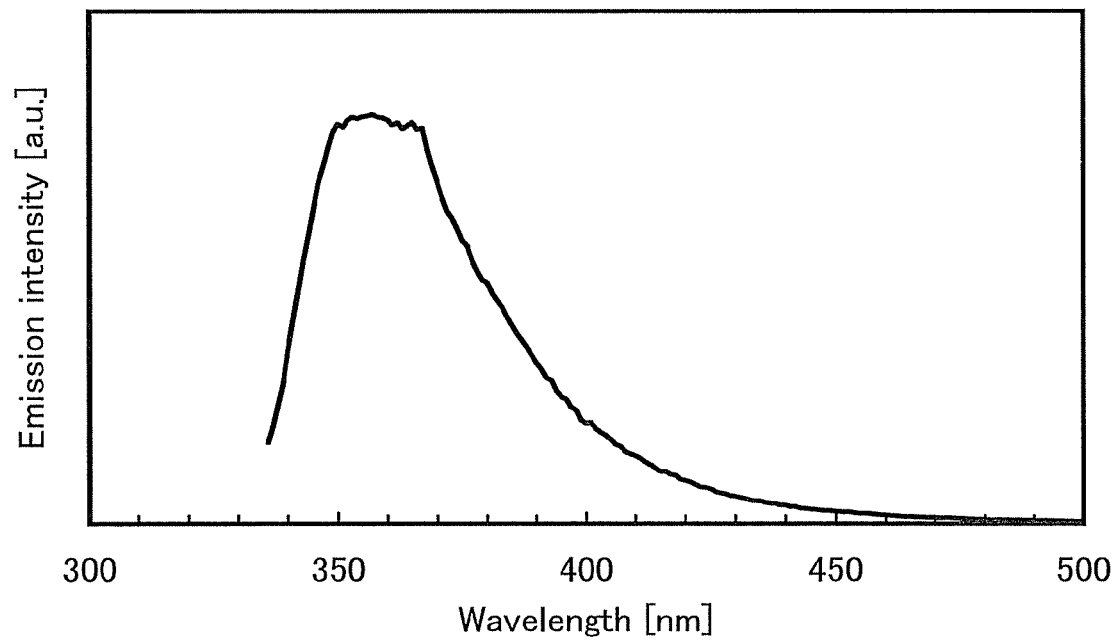
Figure 21A:
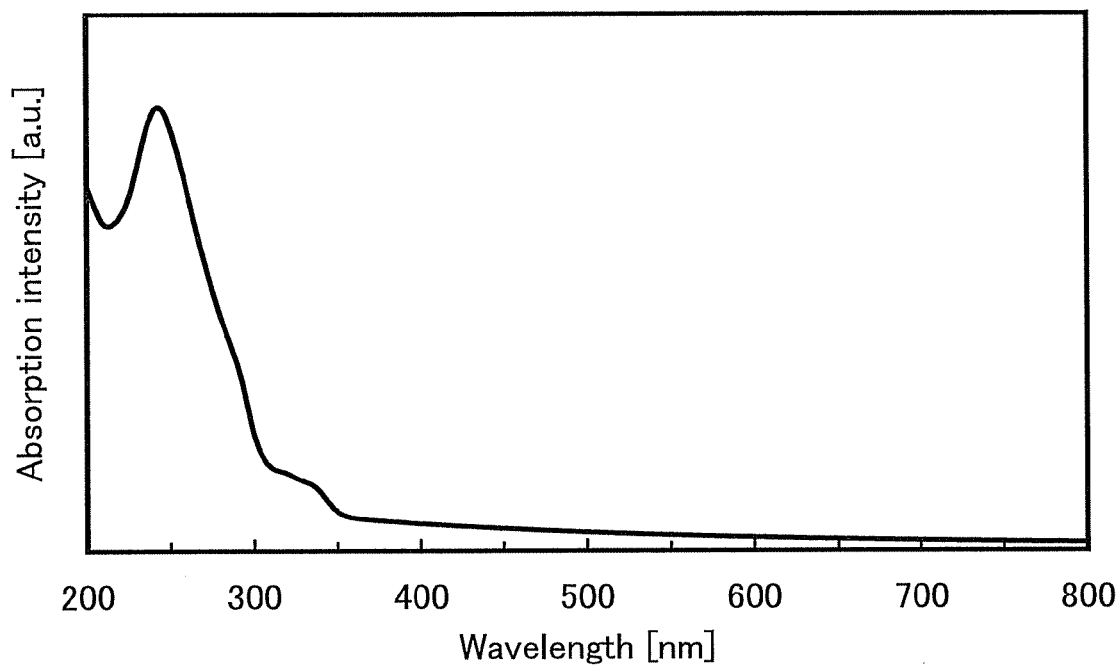
FIGS. 21A and 21B show an absorption and emission spectra of a thin film of mDBTTPt-II.
Figure 21B:
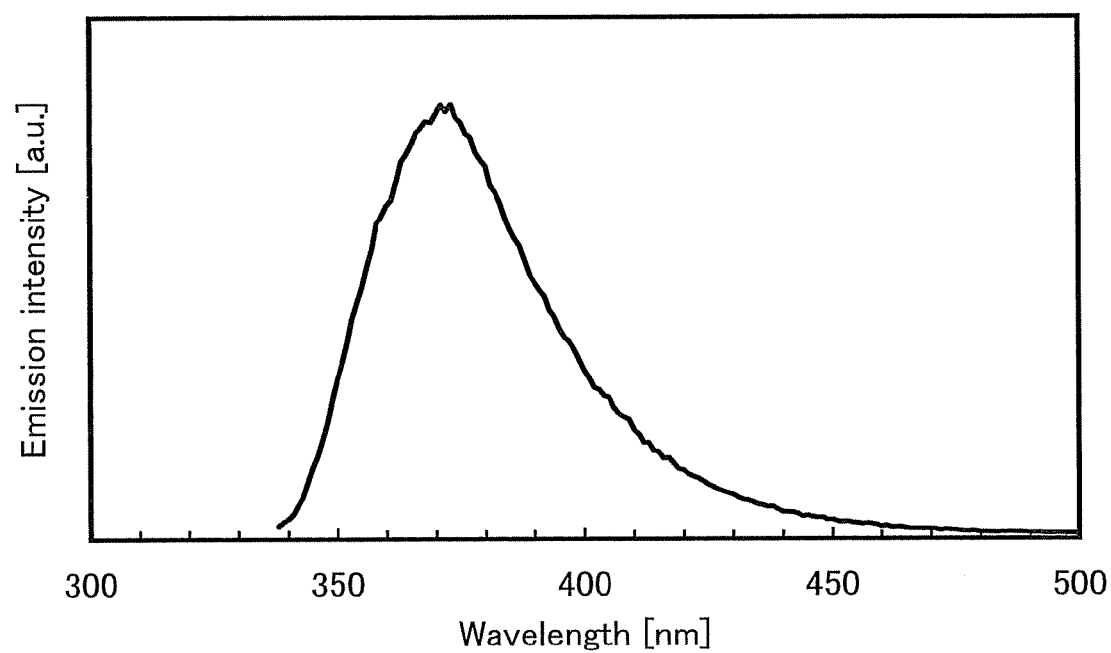

Further, FIG. 20A shows the absorption spectrum of a toluene solution of mDBTTPt-II, and FIG. 20B shows the emission spectrum thereof. In addition, FIG. 21A shows the absorption spectrum of a thin film of mDBTTPt-II, and FIG. 21B shows the emission spectrum thereof. An ultraviolet-visible spectrophotometer (V-550, manufactured by JASCO Corporation) was used for the measurements. Samples were prepared in such a way that the solution was put into a quartz cell and the thin film was fowled on a quartz substrate by evaporation. Here are shown the absorption spectrum for the solution which was obtained by subtracting the absorption spectra of quartz and toluene from those of quartz and the solution, and the absorption spectrum for the thin film which was obtained by subtracting the absorption spectrum of a quartz substrate from those of the quartz substrate and the thin film. In FIG. 20A and FIG. 21A, the horizontal axis represents wavelength (nm) and the vertical axis represents absorption intensity (arbitrary unit). In FIG. 20B and FIG. 21B, the horizontal axis represents wavelength (nm) and the vertical axis represents emission intensity (arbitrary unit). In the case of the toluene solution, absorption peaks were found to be at around 280 nm, 317 nm, and 332 nm, and the peak of the emission wavelength was at 357 nm (at an excitation wavelength of 330 nm). In the case of the thin film, absorption peaks were found to be at around 243 nm, 287 nm, 317 nm, and 332 nm, and the peak of the emission wavelength was at 372 nm (at an excitation wavelength of 332 nm).

EXAMPLE 5

Figure 22A:
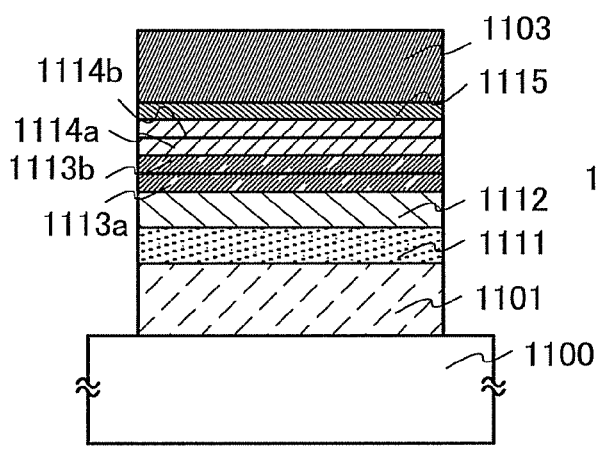
FIGS. 22A to 22D illustrate light-emitting elements of Examples.

In this example, a light-emitting element of one embodiment of the present invention will be described with reference to FIG. 22A. The chemical formulae of materials used in this example are illustrated below.

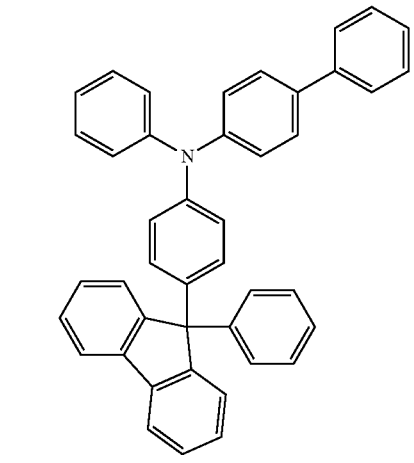

BPAFLP

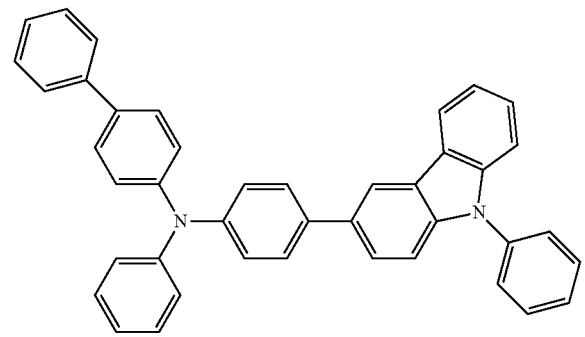

PCBA1BP

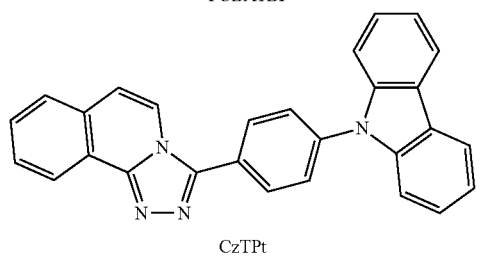

CzTPt

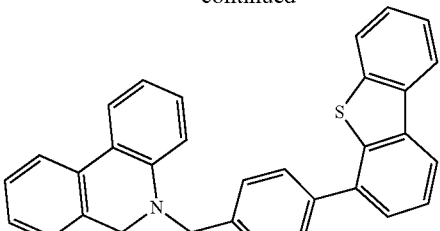

DBTTPt-II

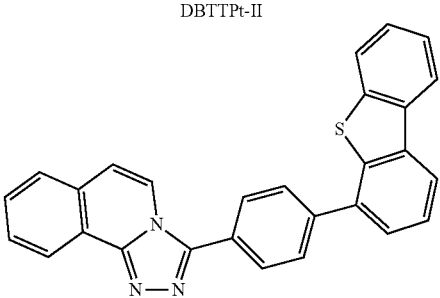

DBTTIq-II

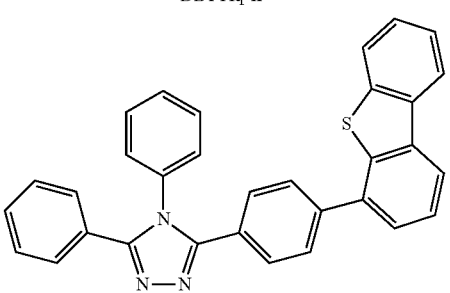

DBTTAZ-II

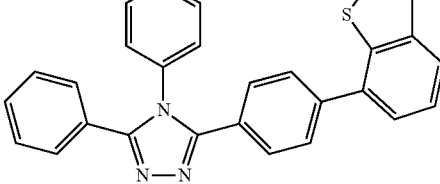

Ir(ppy)₃

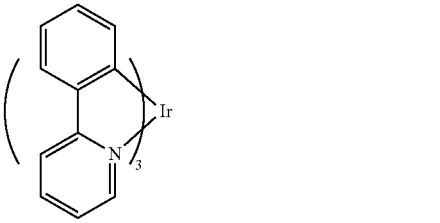

BPhen

The ways how Light-Emitting Elements 1 to 3 and Reference Light-Emitting Element 4 of this example were fabricated will now be described.

(Light-Emitting Element 1)

First, a film of indium tin oxide containing silicon oxide (ITSO) was formed on a glass substrate 1100 by a sputtering method, so that a first electrode 1101 was formed. Note that its thickness was set to 110 nm and the electrode area was set to 2 mm×2 mm.

In pretreatment for forming the light-emitting element on the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about $10^{-4}$ Pa. Then, 4-phenyl-4'-(9-phenylfluoren-9-yl)triphenylamine (abbreviation: BPAFLP) and molybdenum(VI) oxide were co-evaporated to form a hole-injection layer 1111 on the first electrode 1101. The thickness of the hole-injection layer 1111 was set to 50 nm, and the weight ratio of BPAFLP to molybdenum(VI) oxide was adjusted to 4:2 (=BPAFLP:molybdenum oxide). Note that the co-evaporation method refers to an evaporation method in which evaporation is carried out from a plurality of evaporation sources at the same time in one treatment chamber.

Next, on the hole-injection layer 1111, a BPAFLP film was formed to a thickness of 10 nm to form a hole-transport layer 1112.

Further, 3-[4-(9H-carbazol-9-yl)phenyl]-1,2,4-triazolo[4,3-f]phenanthridine (abbreviation: CzTPt) synthesized in Example 2, 4-phenyl-4'-(9-phenyl-9H-carbazol-3-yl)triphenylamine (abbreviation: PCBA1BP), and tris(2-phenylpyridinato-N,$C^{2'}$)iridium(III) (abbreviation: Ir(ppy)$_3$) were co-evaporated to form a first light-emitting layer 1113a on the hole-transport layer 1112. Here, the weight ratio of CzTPt to PCBA1BP and Ir(ppy)$_3$ was adjusted to 1:0.25:0.06 (=CzTPt:PCBA1BP:Ir(ppy)$_3$). In addition, the thickness of the first light-emitting layer 1113a was set to 20 nm.

Next, on the first light-emitting layer 1113a, CzTPt and Ir(ppy)$_3$ were co-evaporated to form a second light-emitting layer 1113b. Here, the weight ratio of CzTPt to Ir(ppy)$_3$ was adjusted to 1:0.06 (=CzTPt:Ir(ppy)$_3$). In addition, the thickness of the second light-emitting layer 1113b was set to 20 nm.

Further, on the second light-emitting layer 1113b, a CzTPt film was formed to a thickness of 15 nm to form a first electron-transport layer 1114a.

Then, on the first electron-transport layer 1114a, a bathophenanthroline (abbreviation: BPhen) film was formed to a thickness of 15 nm to form a second electron-transport layer 1114b.

Further, on the second electron-transport layer 1114b, a 1-nm-thick lithium fluoride (LiF) film was formed by evaporation to form an electron-injection layer 1115.

Lastly, a 200-nm-thick aluminum film was formed by evaporation as a second electrode 1103 functioning as a cathode. Thus, Light-Emitting Element 1 of this example was fabricated.

Note that, in the above evaporation steps, evaporation was all performed by a resistance heating method.

(Light-Emitting Element 2)

The first light-emitting layer 1113a of Light-Emitting Element 2 was formed by co-evaporation of 3-[4-(dibenzothiophen-4-yl)phenyl]-1,2,4-triazolo[4,3-f]phenanthridine (abbreviation: DBTTPt-II) synthesized in Example 1, PCBA1BP, and Ir(ppy)$_3$. Here, the weight ratio of DBTTPt-II to PCBA1BP and Ir(ppy)$_3$ was adjusted to 1:0.25:0.06 (=DBTTPt-II:PCBA1BP:Ir(ppy)$_3$). In addition, the thickness of the first light-emitting layer 1113a was set to 20 nm.

Furthermore, the second light-emitting layer 1113b of Light-Emitting Element 2 was formed by co-evaporation of DBTTPt-II and Ir(ppy)$_3$. Here, the weight ratio of DBTTPt-II to Ir(ppy)$_3$ was adjusted to 1:0.06 (=DBTTPt-II:Ir(ppy)$_3$). In addition, the thickness of the second light-emitting layer 1113b was set to 20 nm.

Then, a DBTTPt-II film was formed to a thickness of 15 nm to form the first electron-transport layer 1114a of Light-Emitting Element 2. The components other than the first light-emitting layer 1113a, the second light-emitting layer 1113b, and the first electron-transport layer 1114a were formed in the same way as those of Light-Emitting Element 1.

(Light-Emitting Element 3)

The first light-emitting layer 1113a of Light-Emitting Element 3 was formed by co-evaporation of 3-[4-(dibenzothiophen-4-yl)phenyl]-1,2,4-triazolo[3,4-α]isoquinoline (abbreviation: DBTTIq-II) synthesized in Example 3, PCBA1BP, and Ir(ppy)$_3$. Here, the weight ratio of DBTTIq-II to PCBA1BP and Ir(ppy)$_3$ was adjusted to 1:0.3:0.06 (=DBTTIq-II:PCBA1BP:Ir(ppy)$_3$). In addition, the thickness of the first light-emitting layer 1113a was set to 20 nm.

Furthermore, the second light-emitting layer 1113b of Light-Emitting Element 3 was formed by co-evaporation of DBTTIq-II and Ir(ppy)$_3$. Here, the weight ratio of DBTTIq-II to Ir(ppy)$_3$ was adjusted to 1:0.06 (=DBTTIq-II:Ir(ppy)$_3$). In addition, the thickness of the second light-emitting layer 1113b was set to 20 nm.

Then, a DBTTIq-II film was formed to a thickness of 15 nm to form the first electron-transport layer 1114a of Light-Emitting Element 3. The components other than the first light-emitting layer 1113a, the second light-emitting layer 1113b, and the first electron-transport layer 1114a were formed in the same way as those of Light-Emitting Element 1.

(Reference Light-Emitting Element 4)

The first light-emitting layer 1113a of Reference Light-Emitting Element 4 was formed by co-evaporation of 3-[4-(dibenzothiophen-4-yl)phenyl)]-4,5-diphenyl-4H-triazole (abbreviation: DBTTAZ-II), PCBA1BP, and Ir(ppy)$_3$. Here, the weight ratio of DBTTAZ-II to PCBA1BP and Ir(ppy)$_3$ was adjusted to 1:0.3:0.06 (=DBTTAZ-II:PCBA1BP:Ir(ppy)$_3$). In addition, the thickness of the first light-emitting layer 1113a was set to 20 nm.

Furthermore, the second light-emitting layer 1113b of Reference Light-Emitting Element 4 was formed by co-evaporation of DBTTAZ-II and Ir(ppy)$_3$. Here, the weight ratio of DBTTAZ-II to Ir(ppy)$_3$ was adjusted to 1:0.06 (=DBTTAZ-II:Ir(ppy)$_3$). In addition, the thickness of the second light-emitting layer 1113b was set to 20 nm.

Then, a DBTTAZ-II film was formed to a thickness of 15 nm to form the first electron-transport layer 1114a of Reference Light-Emitting Element 4. The components other than the first light-emitting layer 1113a, the second light-emitting layer 1113b, and the first electron-transport layer 1114a were formed in the same way as those of Light-Emitting Element 1.

Table 1 shows element structures of Light-Emitting Elements 1 to 3 and Reference Light-Emitting Element 4 obtained as described above.

TABLE 1

| | first electrode | hole-injection layer | hole-transport layer | first light-emitting layer |
|---|---|---|---|---|
| Light-Emitting Element 1 | ITSO 110 nm | BPAFLP:MoOx (=4:2) 50 nm | BPAFLP 10 nm | CzTPt:PCBA1BP:Ir(ppy)$_3$ (=1:0.25:0.06) 20 nm |
| Light-Emitting Element 2 | ITSO 110 nm | BPAFLP:MoOx (=4:2) 50 nm | BPAFLP 10 nm | DBTTPt-II:PCBA1BP:Ir(ppy)$_3$ (=1:0.25:0.06) 20 nm |
| Light-Emitting Element 3 | ITSO 110 nm | BPAFLP:MoOx (=4:2) 50 nm | BPAFLP 10 nm | DBTTIq-II:PCBA1BP:Ir(ppy)$_3$ (=1:0.3:0.06) 20 nm |
| Reference Light-Emitting Element 4 | ITSO 110 nm | BPAFLP:MoOx (=4:2) 50 nm | BPAFLP 10 nm | DBTTAZ-II:PCBA1BP:Ir(ppy)$_3$ (=1:0.3:0.06) 20 nm |

| | second light-emitting layer | first electron-transport layer | second electron-transport layer | electron-injection layer | second electrode |
|---|---|---|---|---|---|
| Light-Emitting Element 1 | CzTPt:Ir(ppy)$_3$ (=1:0.06) 20 nm | CzTPt 15 nm | BPhen 15 nm | LiF 1 nm | Al 200 nm |
| Light-Emitting Element 2 | DBTTPt-II:Ir(ppy)$_3$ (=1:0.06) 20 nm | DBTTPt-II 15 nm | BPhen 15 nm | LiF 1 nm | Al 200 nm |
| Light-Emitting Element 3 | DBTTIq-II:Ir(ppy)$_3$ (=1:0.06) 20 nm | DBTTIq-II 15 nm | BPhen 15 nm | LiF 1 nm | Al 200 nm |
| Reference Light-Emitting Element 4 | DBTTAZ-II:Ir(ppy)$_3$ (=1:0.06) 20 nm | DBTTAZ-II 15 nm | BPhen 15 nm | LiF 1 nm | Al 200 nm |

In a glove box containing a nitrogen atmosphere, Light-Emitting Elements 1 to 3 and Reference Light-Emitting Element 4 were sealed so as not to be exposed to air. Then, operation characteristics of these elements were measured. Note that the measurements were carried out at room temperature (in the atmosphere kept at 25° C.).

Figure 23:
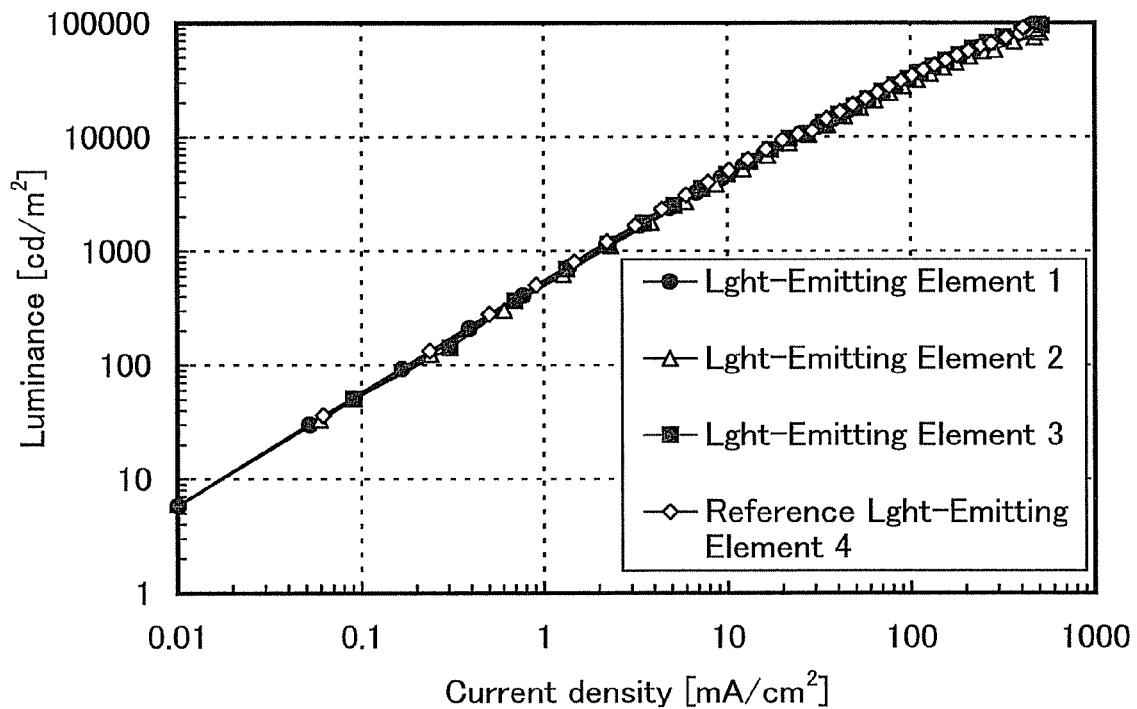
FIG. 23 shows luminance versus current density characteristics of light-emitting elements of Example 5.
Figure 24:
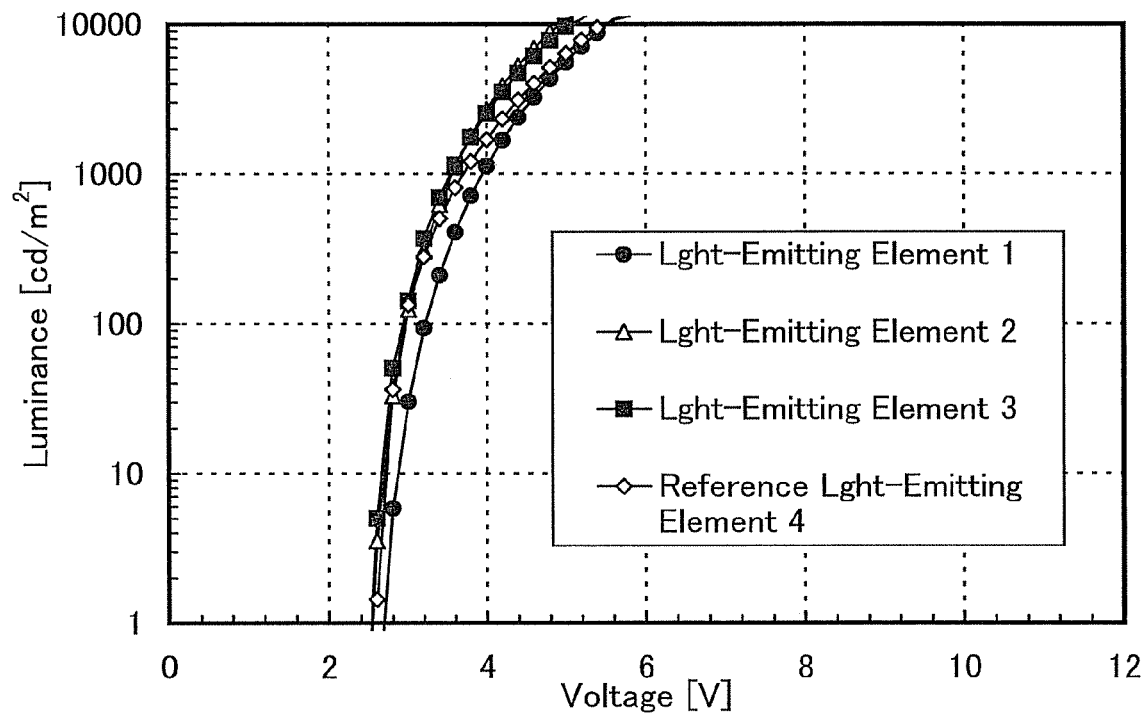
FIG. 24 shows luminance versus voltage characteristics of the light-emitting elements of Example 5.
Figure 25:
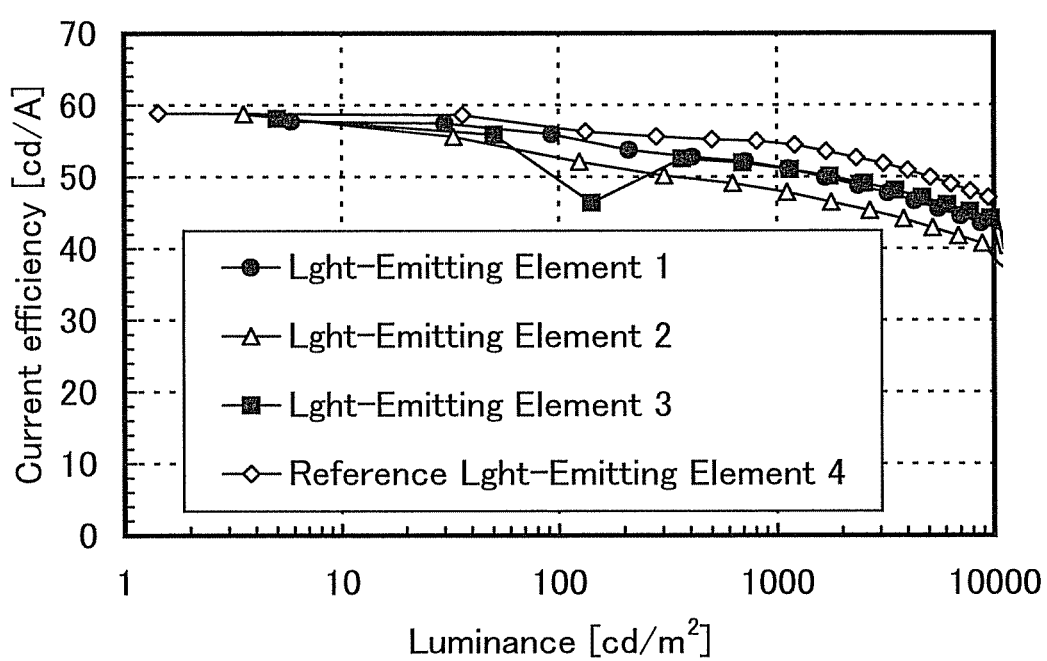
FIG. 25 shows current efficiency versus luminance characteristics of the light-emitting elements of Example 5.

FIG. 23 shows the luminance versus current density characteristics of Light-Emitting Elements 1 to 3 and Reference Light-Emitting Element 4. In FIG. 23, the horizontal axis represents current density (mA/cm$^2$) and the vertical axis represents luminance (cd/m$^2$). In addition, FIG. 24 shows the luminance versus voltage characteristics. In FIG. 24, the horizontal axis represents voltage (V) and the vertical axis represents luminance (cd/m$^2$). FIG. 25 shows the current efficiency versus luminance characteristics. In FIG. 25, the horizontal axis represents luminance (cd/m$^2$) and the vertical axis represents current efficiency (cd/A). Further, Table 2 shows the voltage (V), current density (mA/cm$^2$), CIE chromaticity coordinates (x, y), current efficiency (cd/A), and external quantum efficiency (%) for each light-emitting element at a luminance of around 1000 cd/m$^2$.

TABLE 2

| | Voltage (V) | Current density (mA/cm$^2$) | Chromaticity coordinates (x, y) | Luminance (cd/m$^2$) | Current efficiency (cd/A) | External quantum yield (%) |
|---|---|---|---|---|---|---|
| Light-Emitting Element 1 | 4.0 | 2.2 | 0.32, 0.62 | 1100 | 51 | 15 |
| Light-Emitting Element 2 | 3.6 | 2.3 | 0.32, 0.61 | 1100 | 48 | 14 |
| Light-Emitting Element 3 | 3.6 | 2.2 | 0.33, 0.61 | 1100 | 51 | 15 |
| Reference Light-Emitting Element 4 | 3.6 | 1.5 | 0.32, 0.61 | 810 | 55 | 16 |

As shown in Table 2, the CIE chromaticity coordinates of Light-Emitting Element 1 (x, y) were (0.32, 0.62) at a luminance of 1100 cd/m$^2$. The CIE chromaticity coordinates of Light-Emitting Element 2 (x, y) were (0.32, 0.61) at a luminance of 1100 cd/m$^2$. The CIE chromaticity coordinates of Light-Emitting Element 3 (x, y) were (0.33, 0.61) at a luminance of 1100 cd/m². The CIE chromaticity coordinates of Reference Light-Emitting Element 4 (x, y) were (0.32, 0.61) at a luminance of 810 cd/m². All these light-emitting elements were found to provide light emission from Ir(ppy)$_3$.

It can be confirmed from FIG. 23, FIG. 24, FIG. 25, and Table 2 that Light-Emitting Elements 1 to 3 and Reference Light-Emitting Element 4 are each a light-emitting element having high current efficiency. In addition, it can be confirmed the elements are each a light-emitting element capable of low-voltage driving.

Figure 26:
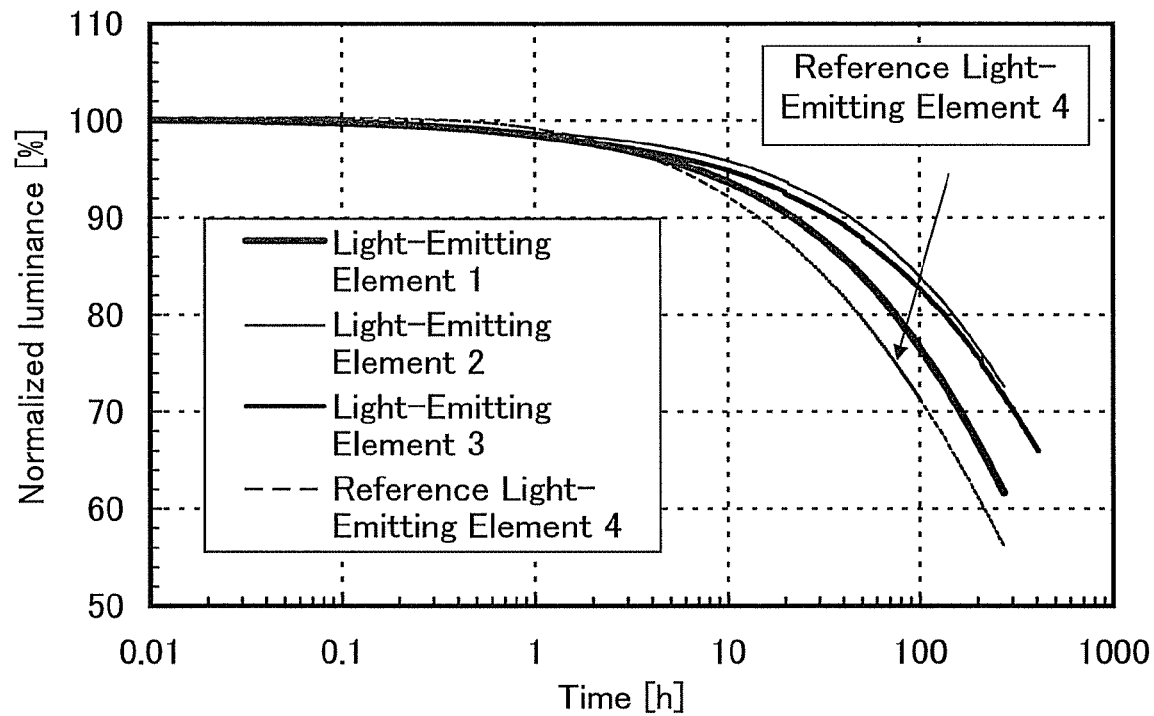
FIG. 26 shows results of reliability tests of the light-emitting elements of Example 5.
Figure 27:
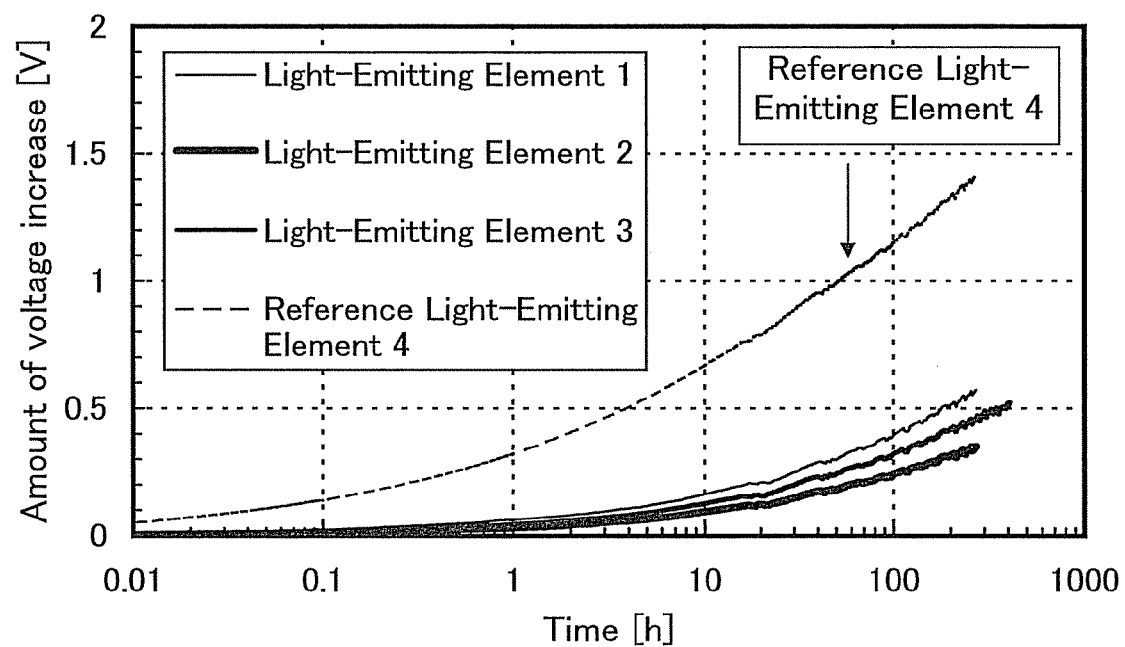
FIG. 27 shows results of the reliability tests of the light-emitting elements of Example 5.

Next, Light-Emitting Elements 1 to 3 and Reference Light-Emitting Element 4 were subjected to reliability tests. Results of the reliability tests are shown in FIG. 26 and FIG. 27. In FIG. 26, the vertical axis represents normalized luminance (%) with an initial luminance of 100%, and the horizontal axis represents driving time (h) of the elements. In FIG. 27, the vertical axis represents the amount of voltage increase (V), and the horizontal axis represents driving time (h) of the elements.

In the reliability tests, Light-Emitting Elements 1 to 3 and Reference Light-Emitting Element 4 of this example were driven under the conditions where the initial luminance was set to 1000 cd/m² and the current density was constant.

As can be seen from FIG. 26, Light-Emitting Element 1 kept 62% of the initial luminance after 270 hours elapsed. Light-Emitting Element 2 kept 73% of the initial luminance after 270 hours elapsed. Light-Emitting Element 3 kept 66% of the initial luminance after 410 hours elapsed. Reference Light-Emitting Element 4 kept 56% of the initial luminance after 270 hours elapsed. Furthermore, it is found from FIG. 27 that a voltage change over time is smaller in each of Light-Emitting Elements 1 to 3 than in Reference Light-Emitting Element 4.

It was made apparent that Light-Emitting Elements 1 to 3, to which embodiments of the present invention were applied, had a longer lifetime than Reference Light-Emitting Element 4, in which DBTTAZ-II, a substance having substantially as high triplet excitation energy as a triazole derivative of one embodiment of the present invention, was used as a host material of the light-emitting layers and as a material of the electron-transport layer.

As described above, the triazole derivatives according to embodiments of the present invention synthesized in Examples 1 to 3 were each used as a host material of the light-emitting layers and as a material of the electron-transport layer, so that the light-emitting elements having high current efficiency and capability of low-voltage driving were able to be fabricated. In addition, the light-emitting elements were able to be fabricated so as to have a longer lifetime.

EXAMPLE 6

In this example, a light-emitting element of one embodiment of the present invention will be described with reference to FIG. 22A. The chemical formula of a material used in this example is illustrated below. Note that the chemical formulae of materials which are already illustrated will be omitted.

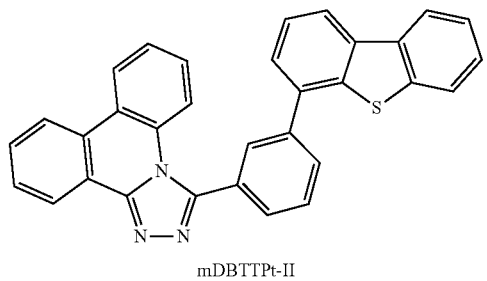

mDBTTPt-II

The ways how Light-Emitting Element 5 and Reference Light-Emitting Element 6 of this example were fabricated will now be described.
(Light-Emitting Element 5)

First, the first electrode 1101, the hole-injection layer 1111, and the hole-transport layer 1112 were formed on the glass substrate 1100 in the same way as those of Light-Emitting Element 1 described in Example 5.

Next, 3-[3-(dibenzothiophen-4-yl)phenyl]-1,2,4-triazolo[4,3-f]phenanthridine (abbreviation: mDBTTPt-II) synthesized in Example 4, PCBA1BP, and Ir(ppy)$_3$ were co-evaporated to form the first light-emitting layer 1113a on the hole-transport layer 1112. Here, the weight ratio of mDBTTPt-II to PCBA1BP and Ir(ppy)$_3$ was adjusted to 1:0.3:0.08 (=mDBTTPt-II:PCBA1BP:Ir(ppy)$_3$). In addition, the thickness of the first light-emitting layer 1113a was set to 20 nm.

Next, mDBTTPt-II and Ir(ppy)$_3$ were co-evaporated on the first light-emitting layer 1113a, so that the second light-emitting layer 1113b was formed on the first light-emitting layer 1113a. Here, the weight ratio of mDBTTPt-II to Ir(ppy)$_3$ was adjusted to 1:0.08 (=mDBTTPt-II:Ir(ppy)$_3$). In addition, the thickness of the second light-emitting layer 1113b was set to 20 nm.

Further, on the second light-emitting layer 1113b, a film of mDBTTPt-II was formed to a thickness of 15 nm to form the first electron-transport layer 1114a.

Then, on the first electron-transport layer 1114a, a BPhen film was formed to a thickness of 15 nm to form the second electron-transport layer 1114b.

Further, on the second electron-transport layer 1114b, a 1-nm-thick LiF film was formed by evaporation to form the electron-injection layer 1115.

Lastly, a 200-nm-thick aluminum film was formed by evaporation as the second electrode 1103 functioning as a cathode. Thus, Light-Emitting Element 5 of this example was fabricated.

Note that, in the above evaporation steps, evaporation was all performed by a resistance heating method.
(Reference Light-Emitting Element 6)

The first light-emitting layer 1113a of Reference Light-Emitting Element 6 was formed by co-evaporation of DBTTAZ-II, PCBA1BP and Ir(ppy)$_3$. Here, the weight ratio of DBTTAZ-II to PCBA1BP and Ir(ppy)$_3$ was adjusted to 1:0.3:0.08 (=DBTTAZ-II:PCBA1BP:Ir(ppy)$_3$). In addition, the thickness of the first light-emitting layer 1113a was set to 20 nm.

Furthermore, the second light-emitting layer 1113b of Reference Light-Emitting Element 6 was formed by co-evaporation of DBTTAZ-II and Ir(ppy)$_3$.

Here, the weight ratio of DBTTAZ-II to Ir(ppy)$_3$ was adjusted to 1:0.08 (=DBTTAZ-II:Ir(ppy)$_3$). In addition, the thickness of the second light-emitting layer 1113b was set to 20 nm.

Then, a DBTTAZ-II film was formed to a thickness of 15 nm to form the first electron-transport layer 1114a of Reference Light-Emitting Element 6. The components other than the first light-emitting layer 1113a, the second light-emitting layer 1113b, and the first electron-transport layer 1114a were formed in the same way as those of Light-Emitting Element 5.

Table 3 shows element structures of Light-Emitting Element 5 and Reference Light-Emitting Element 6 obtained as described above.

TABLE 3

| | first electrode | hole-injection layer | hole-transport layer | first light-emitting layer |
|---|---|---|---|---|
| Light-Emitting Element 5 | ITSO 110 nm | BPAFLP:MoOx (=4:2) 50 nm | BPAFLP 10 nm | mDBTTPt-II:PCBA1BP:Ir(ppy)$_3$ (=1:0.3:0.08) 20 nm |
| Reference Light-Emitting Element 6 | ITSO 110 nm | BPAFLP:MoOx (=4:2) 50 nm | BPAFLP 10 nm | DBTTAZ-II:PCBA1BP:Ir(ppy)$_3$ (=1:0.3:0.08) 20 nm |

| | second light-emitting layer | first electron-transport layer | second electron-transport layer | electron-injection layer | second electrode |
|---|---|---|---|---|---|
| Light-Emitting Element 5 | mDBTTPt-II:Ir(ppy)$_3$ (=1:0.08) 20 nm | mDBTTPt-II 15 nm | BPhen 15 nm | LiF 1 nm | Al 200 nm |
| Reference Light-Emitting Element 6 | DBTTAZ-II:Ir(ppy)$_3$ (=1:0.08) 20 nm | DBTTAZ-II 15 nm | BPhen 15 nm | LiF 1 nm | Al 200 nm |

Figure 28:
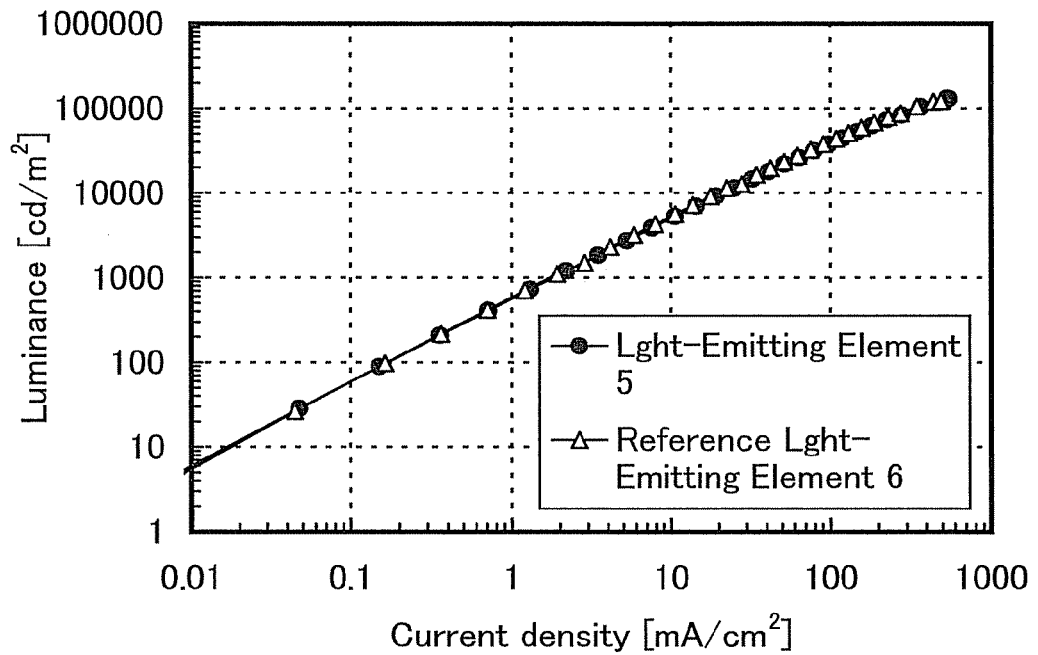
FIG. 28 shows luminance versus current density characteristics of light-emitting elements of Example 6.
Figure 29:
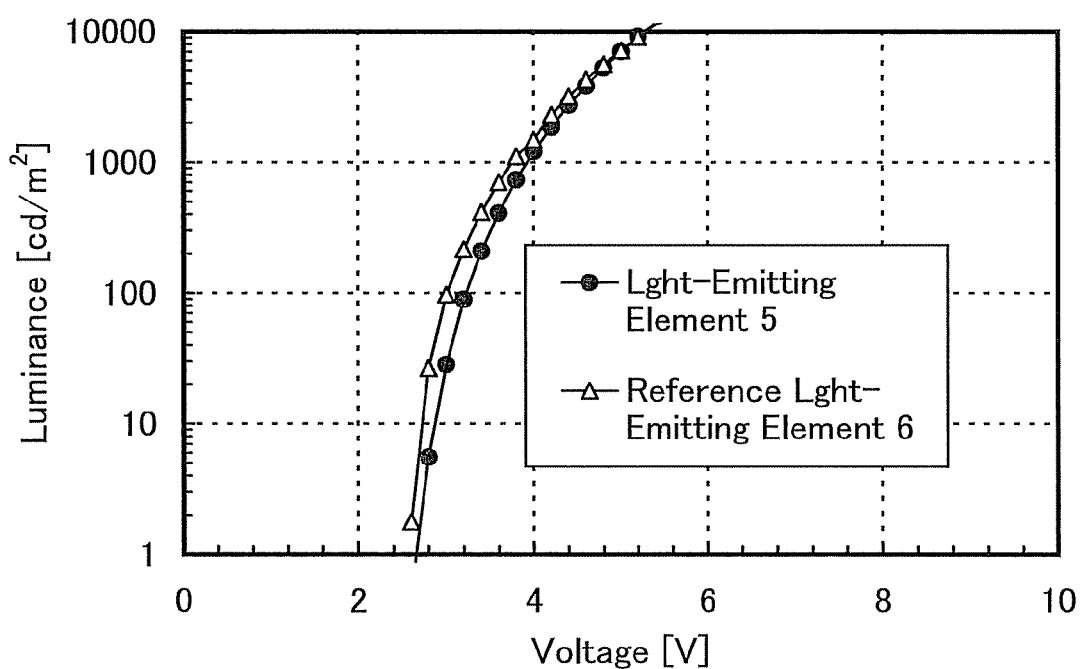
FIG. 29 shows luminance versus voltage characteristics of the light-emitting elements of Example 6.
Figure 30:
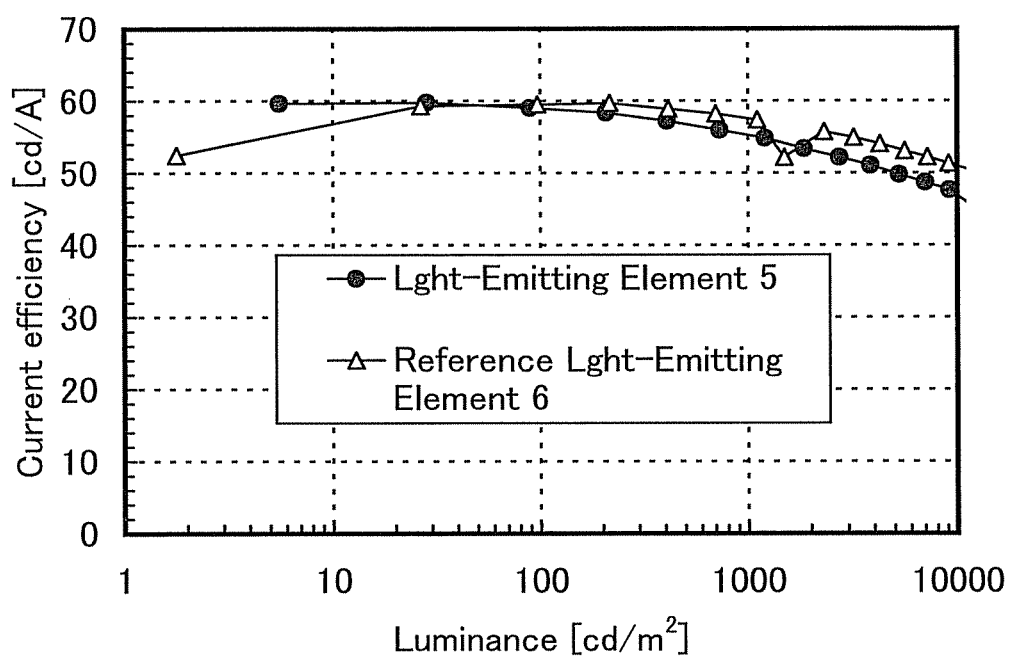
FIG. 30 shows current efficiency versus luminance characteristics of the light-emitting elements of Example 6.

In a glove box containing a nitrogen atmosphere, Light-Emitting Element 5 and Reference Light-Emitting Element 6 were sealed so as not to be exposed to air. Then, operation characteristics of these elements were measured. Note that FIG. 28 shows the luminance versus current density characteristics of Light-Emitting Element 5 and Reference Light-Emitting Element 6. In FIG. 28, the horizontal axis represents current density (mA/cm$^2$) and the vertical axis represents luminance (cd/m$^2$). In addition, FIG. 29 shows the luminance versus voltage characteristics. In FIG. 29, the horizontal axis represents voltage (V) and the vertical axis represents luminance (cd/m$^2$). FIG. 30 shows the current efficiency versus luminance characteristics. In FIG. 30, the horizontal axis represents luminance (cd/m$^2$) and the vertical axis represents current efficiency (cd/A). Further, Table 4 shows the voltage (V), current density (mA/cm$^2$), CIE chromaticity coordinates (x, y), current efficiency (cd/A), and external quantum efficiency (%) for each light-emitting element at a luminance of around 1100 cd/m$^2$.

TABLE 4

|  | Voltage (V) | Current density (mA/cm$^2$) | Chromaticity coordinates (x, y) | Luminance (cd/m$^2$) | Current efficiency (cd/A) | External quantum yield (%) |
|---|---|---|---|---|---|---|
| Light-Emitting Element 5 | 4.0 | 2.2 | 0.35, 0.60 | 1200 | 55 | 16 |
| Reference Light-Emitting Element 6 | 3.8 | 1.9 | 0.34, 0.60 | 1100 | 57 | 17 |

As shown in Table 4, the CIE chromaticity coordinates of Light-Emitting Element 5 (x, y) were (0.35, 0.60) at a luminance of 1200 cd/m$^2$. The CIE chromaticity coordinates of Reference Light-Emitting Element 6 (x, y) were (0.34, 0.60) at a luminance of 1100 cd/m$^2$. All these light-emitting elements were found to provide light emission from Ir(ppy)$_3$.

It can be confirmed from FIG. 28, FIG. 29, FIG. 30, and Table 4 that Light-Emitting Element 5 and Reference Light-Emitting Element 6 are each a light-emitting element having high current efficiency and capability of low-voltage driving.

Figure 31:
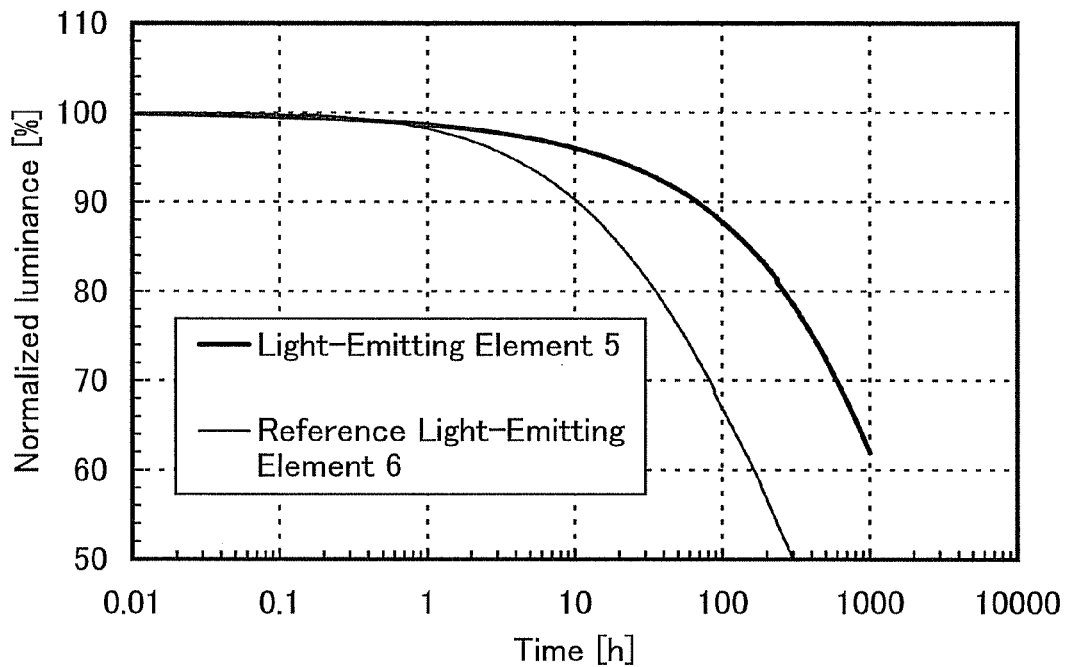
FIG. 31 shows results of reliability tests of the light-emitting elements of Example 6.
Figure 32:
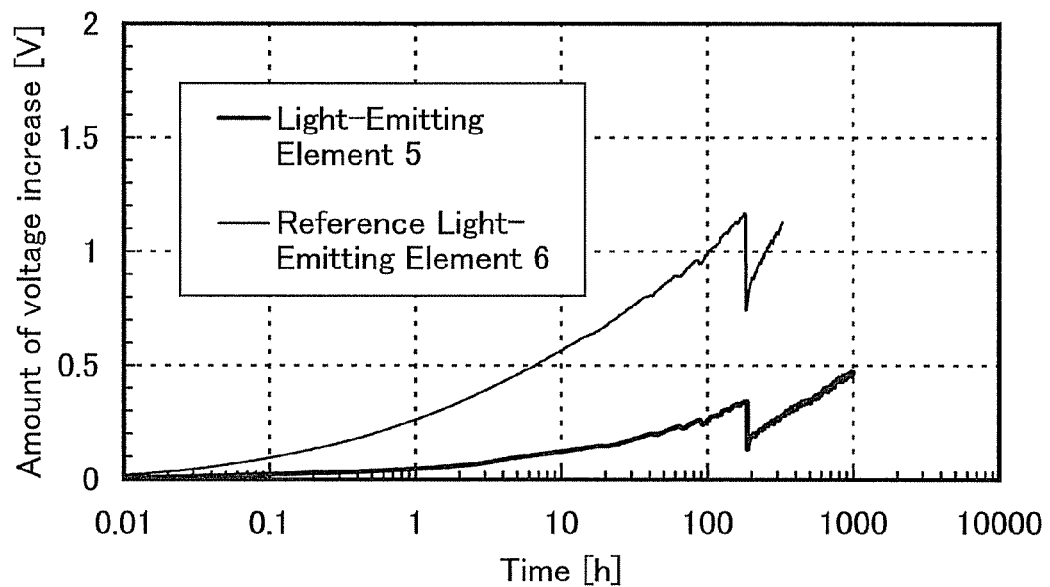
FIG. 32 shows results of the reliability tests of the light-emitting elements of Example 6.

Next, Light-Emitting Element 5 and Reference Light-Emitting Element 6 were subjected to reliability tests. Results of the reliability tests are shown in FIG. 31 and FIG. 32. In FIG. 31, the vertical axis represents normalized luminance (%) with an initial luminance of 100%, and the horizontal axis represents driving time (h) of the elements. In FIG. 32, the vertical axis represents the amount of voltage increase (V), and the horizontal axis represents driving time (h) of the elements.

In the reliability tests, Light-Emitting Element 5 of this example and Reference Light-Emitting Element 6 were driven under the conditions where the initial luminance was set to 1000 cd/m$^2$ and the current density was constant.

As can be seen from FIG. 31, Light-Emitting Element 5 kept 62% of the initial luminance after 1000 hours elapsed. Reference Light-Emitting Element 6 kept 50% of the initial luminance after 300 hours elapsed. Furthermore, it is found from FIG. 32 that a voltage change over time is smaller in Light-Emitting Element 5 than in Reference Light-Emitting Element 6.

It was made apparent that Light-Emitting Element 5, to which one embodiment of the present invention was applied, had a longer lifetime than Reference Light-Emitting Element 6, in which DBTTAZ-II, a substance having substantially as high triplet excitation energy as the triazole derivative of one embodiment of the present invention, was used as a host material of the light-emitting layers and as a material of the electron-transport layer.

As described above, the triazole derivative according to one embodiment of the present invention synthesized in Example 4 was used as a host material of the light-emitting layers and as a material of the electron-transport layer, so that the light-emitting element having high current efficiency and capability of low-voltage driving was able to be fabricated. In addition, the light-emitting element was able to be fabricated so as to have a longer lifetime.

EXAMPLE 7

Figure 22B:
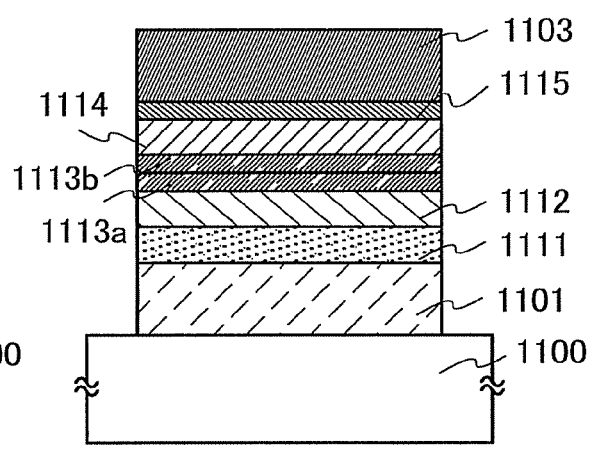

In this example, a light-emitting element of one embodiment of the present invention will be described with reference to FIG. 22B. The chemical formulae of materials used in this example are illustrated below. Note that the chemical formulae of materials which are already illustrated will be omitted.

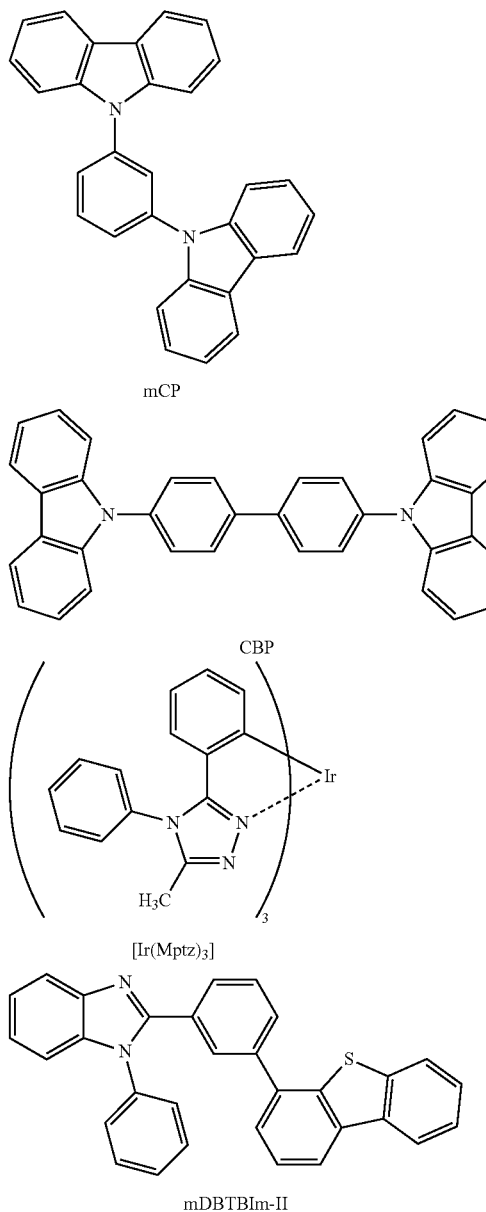

mCP

CBP

[Ir(Mptz)$_3$]

mDBTBIm-II

The way how Light-Emitting Element 7 was fabricated will now be described.

(Light-Emitting Element 7)

First, an ITSO film was formed on a glass substrate 1100 by a sputtering method, so that the first electrode 1101 was formed. Note that its thickness was set to 110 nm and the electrode area was set to 2 mm×2 mm.

In pretreatment for forming the light-emitting element on the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about $10^{-4}$ Pa. Then, 4,4'-di(N-carbazolyl)biphenyl (abbreviation: CBP) and molybdenum(VI) oxide were co-evaporated to form the hole-injection layer 1111 on the first electrode 1101. The thickness of the hole-injection layer 1111 was set to 50 nm, and the weight ratio of CBP to molybdenum(VI) oxide was adjusted to 4:2 (=CBP:molybdenum oxide).

Next, on the hole-injection layer 1111, a film of 1,3-bis(N-carbazolyl)benzene (abbreviation: mCP) was foamed to a thickness of 10 nm to form the hole-transport layer 1112.

Further, CzTPt synthesized in Example 2 and tris(5-methyl-3,4-diphenyl-4H-1,2,4-triazolato)iridium(III) (abbreviation: Ir(Mptz)$_3$) were co-evaporated to form the first light-emitting layer 1113a on the hole-transport layer 1112. The thickness of the first light-emitting layer 1113a was set to 30 nm, and the weight ratio of CzTPt to Ir(Mptz)$_3$ was adjusted to 1:0.08 (=CzTPt:Ir(Mptz)$_3$).

Then, 2-[3-(dibenzothiophen-4-yl)phenyl]-1-phenyl-1H-benzmidzole (abbreviation: mDBTBIm-II) and Ir(Mptz)$_3$ were co-evaporated, so that the second light-emitting layer 1113b was formed on the first light-emitting layer 1113a. The weight ratio of mDBTBIm-II to Ir(Mptz)$_3$ was adjusted to 1:0.08 (=mDBTBIm-II:Ir(Mptz)$_3$). The thickness of the second light-emitting layer 1113b was set to 10 nm.

Next, on the second light-emitting layer 1113b, a BPhen film was formed to a thickness of 15 nm to form an electron-transport layer 1114.

Further, on the electron-transport layer 1114, a 1-nm-thick LiF film was formed by evaporation to form the electron-injection layer 1115.

Lastly, a 200-nm-thick aluminum film was formed by evaporation as the second electrode 1103 functioning as a cathode. Thus, Light-Emitting Element 7 of this example was fabricated.

Note that, in the above evaporation steps, evaporation was all performed by a resistance heating method.

Table 5 shows an element structure of Light-Emitting Element 7 obtained as described above.

TABLE 5

|  | first electrode | hole-injection layer | hole-transport layer | first light-emitting layer | second light-emitting layer | electron-transport layer | electron-injection layer | second electrode |
|---|---|---|---|---|---|---|---|---|
| Light-Emitting Element 7 | ITSO 110 nm | CBP:MoOx (=4:2) 50 nm | mCP 10 nm | CzTPt:Ir(Mptz)$_3$ (=1:0.08) 30 nm | mDBTBIm-II:Ir(Mptz)$_3$ (=1:0.08) 10 nm | BPhen 15 nm | LiF 1 nm | Al 200 nm |

In a glove box containing a nitrogen atmosphere, Light-Emitting Element 7 was sealed so as not to be exposed to air. Then, operation characteristics of Light-Emitting Element 7 were measured. Note that the measurements were carried out at room temperature (in the atmosphere kept at 25° C.).

Figure 33:
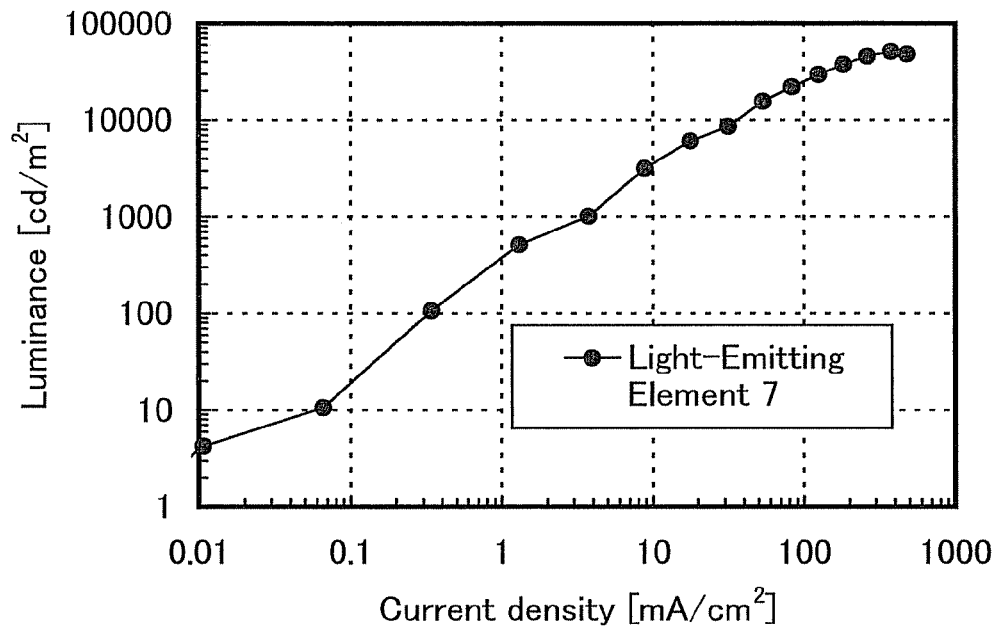
FIG. 33 shows luminance versus current density characteristics of a light-emitting element of Example 7.
Figure 34:
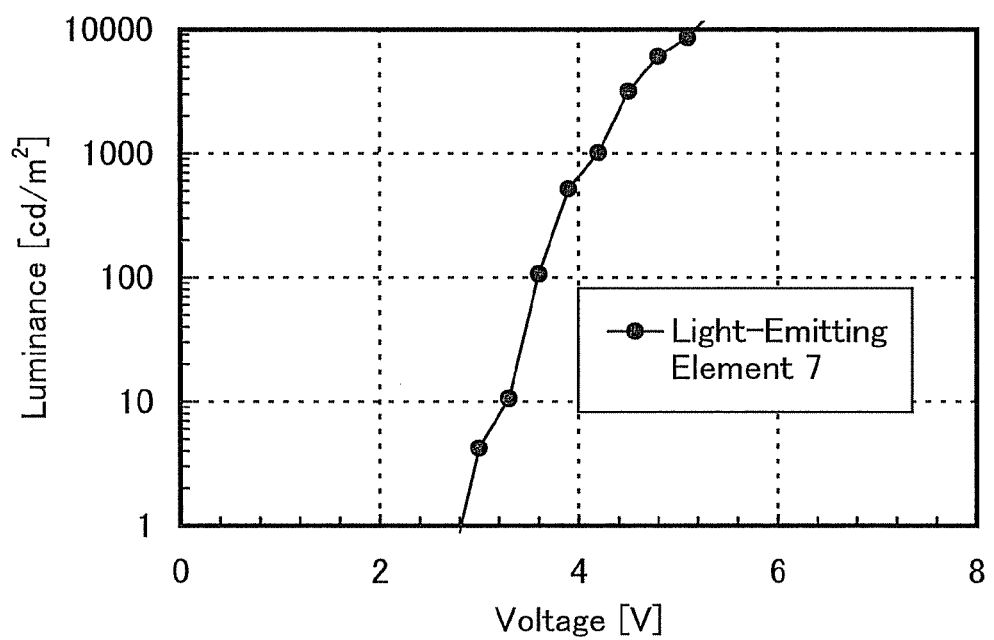
FIG. 34 shows luminance versus voltage characteristics of the light-emitting element of Example 7.
Figure 35:
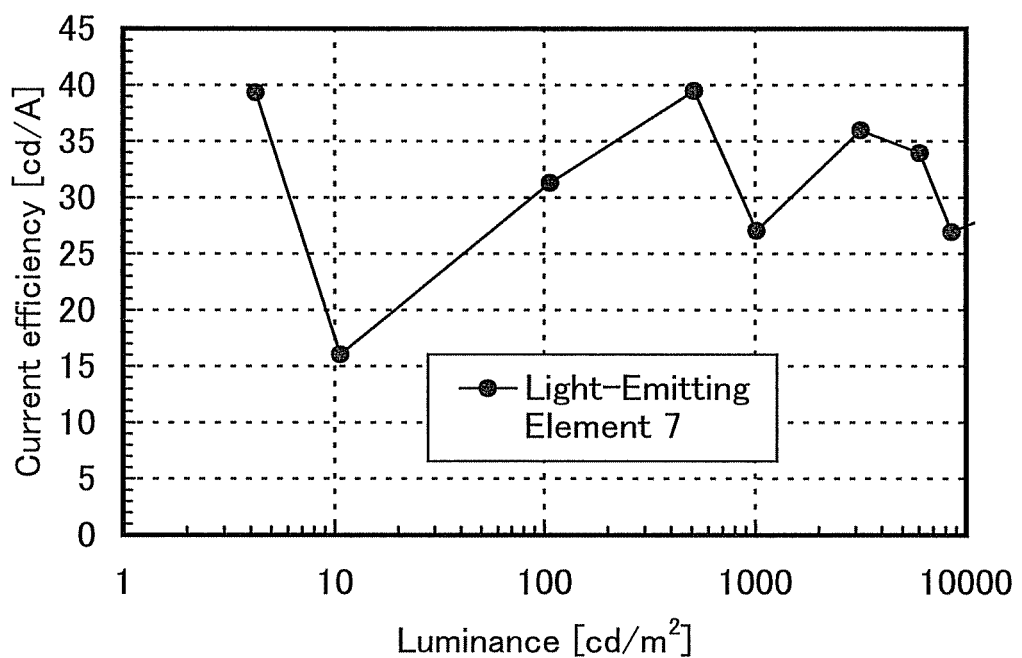
FIG. 35 shows current efficiency versus luminance characteristics of the light-emitting element of Example 7.

FIG. 33 shows the luminance versus current density characteristics of Light-Emitting Element 7. In FIG. 33, the horizontal axis represents current density (mA/cm$^2$) and the vertical axis represents luminance (cd/m$^2$). In addition, FIG. 34 shows the luminance versus voltage characteristics. In FIG. 34, the horizontal axis represents voltage (V) and the vertical axis represents luminance (cd/m$^2$). FIG. 35 shows the current efficiency versus luminance characteristics. In FIG. 35, the horizontal axis represents luminance (cd/m$^2$) and the vertical axis represents current efficiency (cd/A). Further, Table 6 shows the voltage (V), current density (mA/cm$^2$), CIE chromaticity coordinates (x, y), current efficiency (cd/A), and external quantum efficiency (%) of Light-Emitting Element 7 at a luminance of 520 cd/m$^2$.

TABLE 6

|  | Voltage (V) | Current density (mA/cm$^2$) | Chromaticity coordinates (x, y) | Luminance (cd/m$^2$) | Current efficiency (cd/A) | External quantum yield (%) |
|---|---|---|---|---|---|---|
| Light-Emitting Element 7 | 3.9 | 1.3 | 0.24, 0.49 | 520 | 39 | 14 |

As shown in Table 6, the CIE chromaticity coordinates of Light-Emitting Element 7 (x, y) were (0.24, 0.49) at a luminance of 520 cd/m². Light-Emitting Element 7 was found to provide light emission from Ir(Mptz)₃. Because the light-emitting element of this example includes the triazole derivative having high triplet excitation energy, Ir(Mptz)₃, which exhibits short-wavelength blue emission, can be made to emit light efficiently. It was shown that application of one embodiment of the present invention enabled efficient light emission from Ir(Mptz)₃, a phosphorescent compound that exhibits short-wavelength light emission.

EXAMPLE 8

Figure 22C:
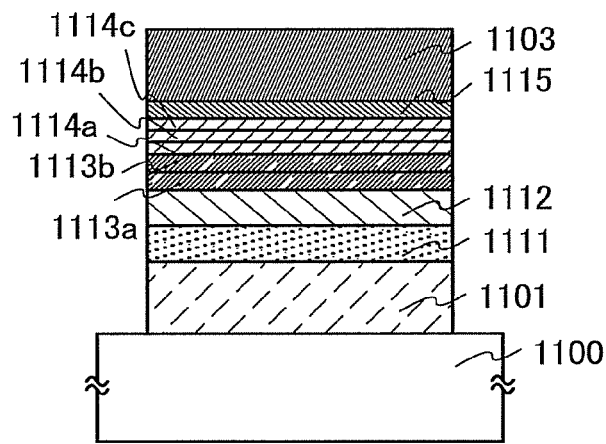

In this example, a light-emitting element of one embodiment of the present invention will be described with reference to FIG. 22C. The chemical formulae of materials used in this example are illustrated below. Note that the chemical formulae of materials which are already illustrated will be omitted.

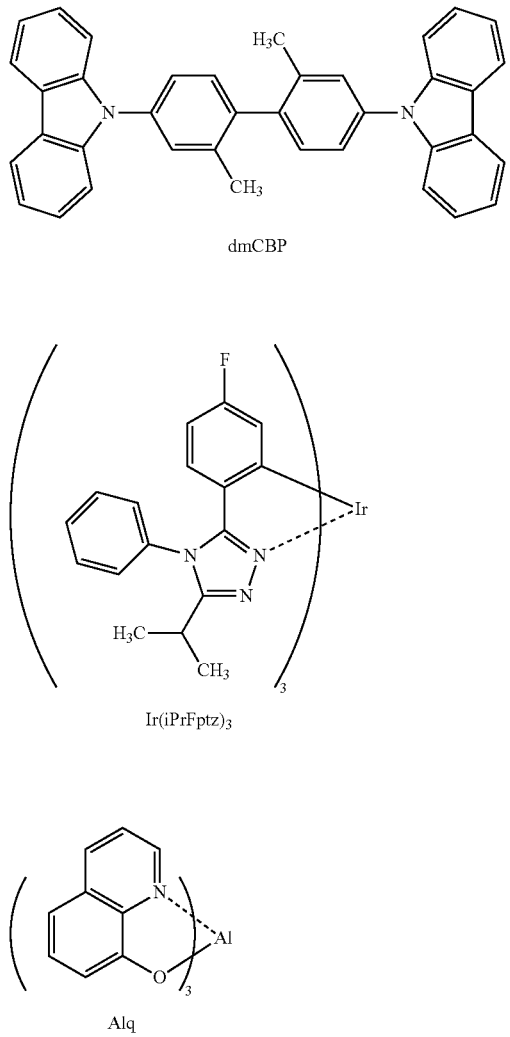

The way how Light-Emitting Element 8 was fabricated will now be described.
(Light-Emitting Element 8)
First, an ITSO film was formed on a glass substrate 1100 by a sputtering method, so that the first electrode 1101 was formed. Note that its thickness was set to 110 nm and the electrode area was set to 2 mm×2 mm.

In pretreatment for forming the light-emitting element on the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately 10⁻⁴ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about 10⁴ Pa. Then, 4,4'-bis(9-carbazole)-2,2'-dimethyl-biphenyl (abbreviation: dmCBP) and molybdenum(VI) oxide were co-evaporated to faun the hole-injection layer 1111 on the first electrode 1101. The thickness of the hole-injection layer 1111 was set to 50 nm, and the weight ratio of dmCBP to molybdenum(VI) oxide was adjusted to 4:2 (=dmCBP:molybdenum oxide).

Next, on the hole-injection layer 1111, a dmCBP film was formed to a thickness of 10 nm to form the hole-transport layer 1112.

Further, mCP and tris[3-(4-fluorophenyl)-5-isopropyl-4-phenyl-4H-1,2,4-triazolato]iridium(III) (abbreviation: Ir(iPrFptz)₃) were co-evaporated to form the first light-emitting layer 1113a on the hole-transport layer 1112. The thickness of the first light-emitting layer 1113a was set to 30 nm, and the weight ratio of mCP to Ir(iPrFptz)₃ was adjusted to 1:0.06 (=mCP:Ir(iPrFptz)₃).

Then, DBTTPt-II synthesized in Example 1 and Ir(iPrFptz)₃ were co-evaporated, so that the second light-emitting layer 1113b was formed on the first light-emitting layer 1113a. Here, the weight ratio of DBTTPt-II to Ir(iPrFptz)₃ was adjusted to 1:0.06 (=DBTTPt-II:Ir(iPrFptz)₃). In addition, the thickness of the second light-emitting layer 1113b was set to 10 nm.

Next, on the second light-emitting layer 1113b, a DBTTPt-II film was formed to a thickness of 10 nm to from the first electron-transport layer 1114a.

Then, on the first electron-transport layer 1114a, an Alq film was formed to a thickness of 10 nm to form the second electron-transport layer 1114b.

Then, on the second electron-transport layer 1114b, a BPhen film was formed to a thickness of 15 nm to form a third electron-transport layer 1114c.

Further, on the third electron-transport layer 1114c, a 1-nm-thick LiF film was formed by evaporation to form the electron-injection layer 1115.

Lastly, a 200-nm-thick aluminum film was formed by evaporation as the second electrode 1103 functioning as a cathode. Thus, Light-Emitting Element 8 of this example was fabricated.

Note that, in the above evaporation steps, evaporation was all performed by a resistance heating method.

Table 7 shows an element structure of Light-Emitting Element 8 obtained as described above.

TABLE 7

| | first electrode | hole-injection layer | hole-transport layer | first light-emitting layer | second light-emitting layer | first electron-transport layer | second electron-transport layer | third electron-transport layer | electron-injection layer | second electrode |
|---|---|---|---|---|---|---|---|---|---|---|
| Light-Emitting Element 8 | ITSO 110 nm | dmCBP:MoOx (=4:2) 50 nm | dmCBP 10 nm | mCP:Ir(iPrFptz)$_3$ (=1:0.06) 30 nm | DBTTPt-II:Ir(iPrFptz)$_3$ (=1:0.06) 10 nm | DBTTPt-II 10 nm | Alq 10 nm | BPhen 15 nm | LiF 1 nm | Al 200 nm |

In a glove box containing a nitrogen atmosphere, Light-Emitting Element 8 was sealed so as not to be exposed to air. Then, operation characteristics of Light-Emitting Element 8 were measured. Note that the measurements were carried out at room temperature (in the atmosphere kept at 25° C.).

Figure 36:
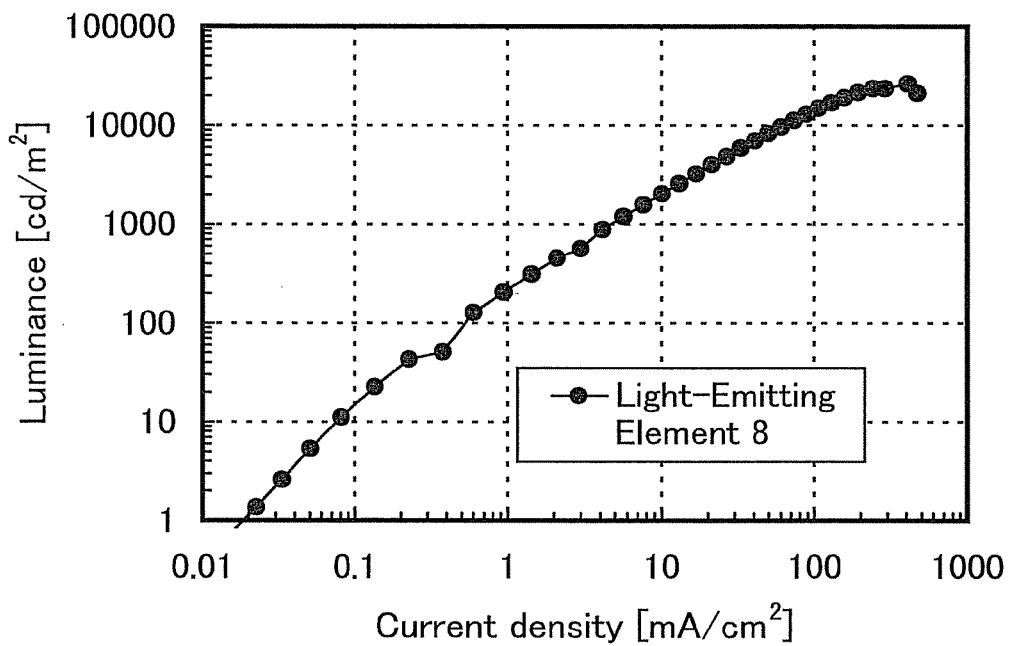
FIG. 36 shows luminance versus current density characteristics of a light-emitting element of Example 8.
Figure 37:
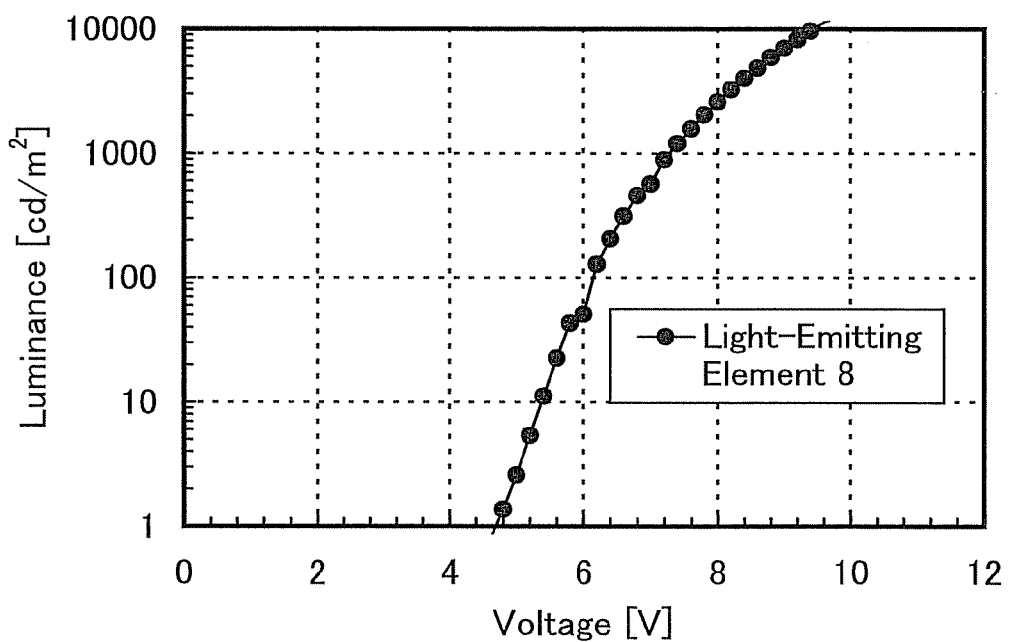
FIG. 37 shows luminance versus voltage characteristics of the light-emitting element of Example 8.
Figure 38:
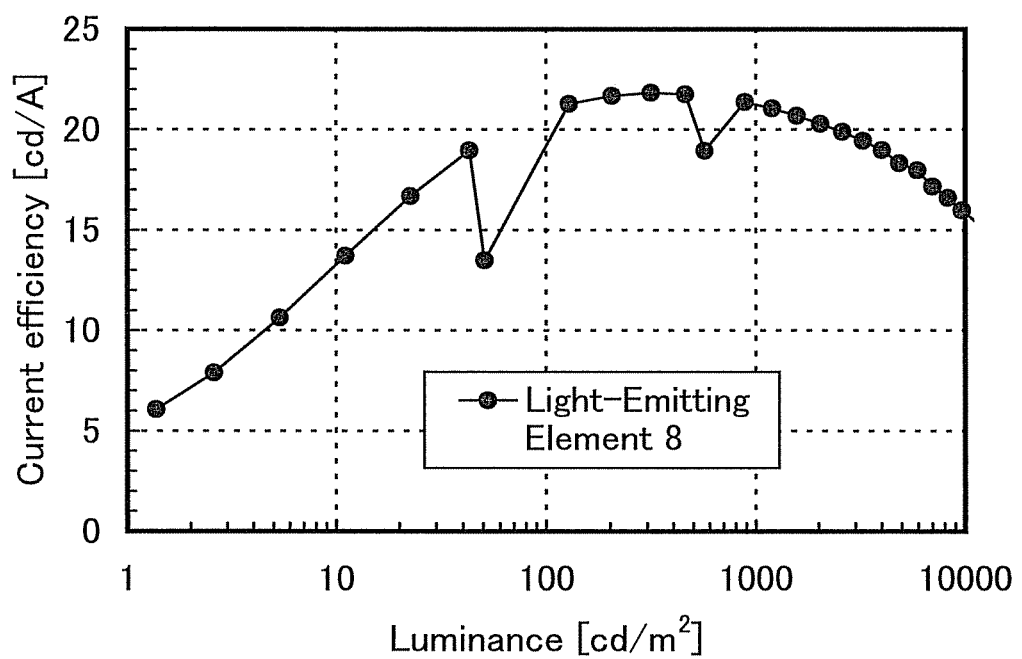
FIG. 38 shows current efficiency versus luminance characteristics of the light-emitting element of Example 8.

FIG. 36 shows the luminance versus current density characteristics of Light-Emitting Element 8. In FIG. 36, the horizontal axis represents current density (mA/cm$^2$) and the vertical axis represents luminance (cd/m$^2$). In addition, FIG. 37 shows the luminance versus voltage characteristics. In FIG. 37, the horizontal axis represents voltage (V) and the vertical axis represents luminance (cd/m$^2$). FIG. 38 shows the current efficiency versus luminance characteristics. In FIG. 38, the horizontal axis represents luminance (cd/m$^2$) and the vertical axis represents current efficiency (cd/A). Further, Table 8 shows the voltage (V), current density (mA/cm$^2$), CIE chromaticity coordinates (x, y), current efficiency (cd/A), and external quantum efficiency (%) of Light-Emitting Element 8 at a luminance of 890 cd/m$^2$.

TABLE 8

| | Voltage (V) | Current density (mA/cm$^2$) | Chromaticity coordinates (x, y) | Luminance (cd/m$^2$) | Current efficiency (cd/A) | External quantum yield (%) |
|---|---|---|---|---|---|---|
| Light-Emitting Element 8 | 7.2 | 4.2 | 0.18, 0.29 | 890 | 21 | 11 |

As shown in Table 8, the CIE chromaticity coordinates of Light-Emitting Element 8 (x, y) were (0.18, 0.29) at a luminance of 890 cd/m$^2$. Light-Emitting Element 8 was found to provide light emission from Ir(iPrFptz)$_3$. It is understood that because the light-emitting element of this example includes the triazole derivative having high triplet excitation energy, Ir(iPrFptz)$_3$, which exhibits short-wavelength blue emission, can be made to emit light efficiently. It was shown that application of one embodiment of the present invention enabled efficient light emission from Ir(iPrFptz)$_3$, a phosphorescent compound that exhibits short-wavelength light emission.

EXAMPLE 9

In this example, a light-emitting element of one embodiment of the present invention will be described with reference to FIG. 22C. The materials used in this example are illustrated in the above Examples, and therefore the chemical formulae thereof are omitted here.

The way how Light-Emitting Element 9 was fabricated will now be described.

(Light-Emitting Element 9)

First, the first electrode 1101, the hole-injection layer 1111, and the hole-transport layer 1112 were formed on the glass substrate 1100 in the same way as those of Light-Emitting Element 8 fabricated in Example 8.

Furthermore, dmCBP and Ir(iPrFptz)$_3$ were co-evaporated to form the first light-emitting layer 1113a on the hole-transport layer 1112. The thickness of the first light-emitting layer 1113a was set to 30 nm, and the weight ratio of dmCBP to Ir(iPrFptz)$_3$ was adjusted to 1:0.06 (=dmCBP:Ir(iPrFptz)$_3$).

Next, DBTTIq-II synthesized in Example 3 and Ir(iPrFptz)$_3$ were co-evaporated to form the second light-emitting layer 1113b on the first light-emitting layer 1113a. Here, the weight ratio of DBTTIq-II to Ir(iPrFptz)$_3$ was adjusted to 1:0.06 (=DBTTIq-II:Ir(iPrFptz)$_3$). In addition, the thickness of the second light-emitting layer 1113b was set to 10 nm.

Further, on the second light-emitting layer 1113b, a DBTTIq-II film was formed to a thickness of 10 nm to form the first electron-transport layer 1114a.

Next, on the first electron-transport layer 1114a, an Alq film was formed to a thickness of 10 nm to form the second electron-transport layer 1114b.

Then, on the second electron-transport layer 1114b, a BPhen film was formed to a thickness of 15 nm to form the third electron-transport layer 1114c.

Further, on the third electron-transport layer 1114c, a 1-nm-thick LiF film was formed by evaporation to form the electron-injection layer 1115.

Lastly, a 200-nm-thick aluminum film was formed by evaporation as the second electrode 1103 functioning as a cathode. Thus, Light-Emitting Element 9 of this example was fabricated.

Note that, in the above evaporation steps, evaporation was all performed by a resistance heating method.

Table 9 shows an element structure of Light-Emitting Element 9 obtained as described above.

TABLE 9

| | first electrode | hole-injection layer | hole-transport layer | first light-emitting layer | second light-emitting layer | first electron-transport layer | second electron-transport layer | third electron-transport layer | electron-injection layer | second electrode |
|---|---|---|---|---|---|---|---|---|---|---|
| Light-Emitting Element 9 | ITSO 110 nm | dmCBP:MoOx (=4:2) 50 nm | dmCBP 10 nm | dmCBP:Ir(iPrFptz)$_3$ (=1:0.06) 30 nm | DBTTIq-II:Ir(iPrFptz)$_3$ (=1:0.06) 10 nm | DBTTIq-II 10 nm | Alq 10 nm | BPhen 15 nm | LiF 1 nm | Al 200 nm |

In a glove box containing a nitrogen atmosphere, Light-Emitting Element 9 was sealed so as not to be exposed to air. Then, operation characteristics of Light-Emitting Element 9 were measured. Note that the measurements were carried out at room temperature (in the atmosphere kept at 25° C.).

Figure 39:
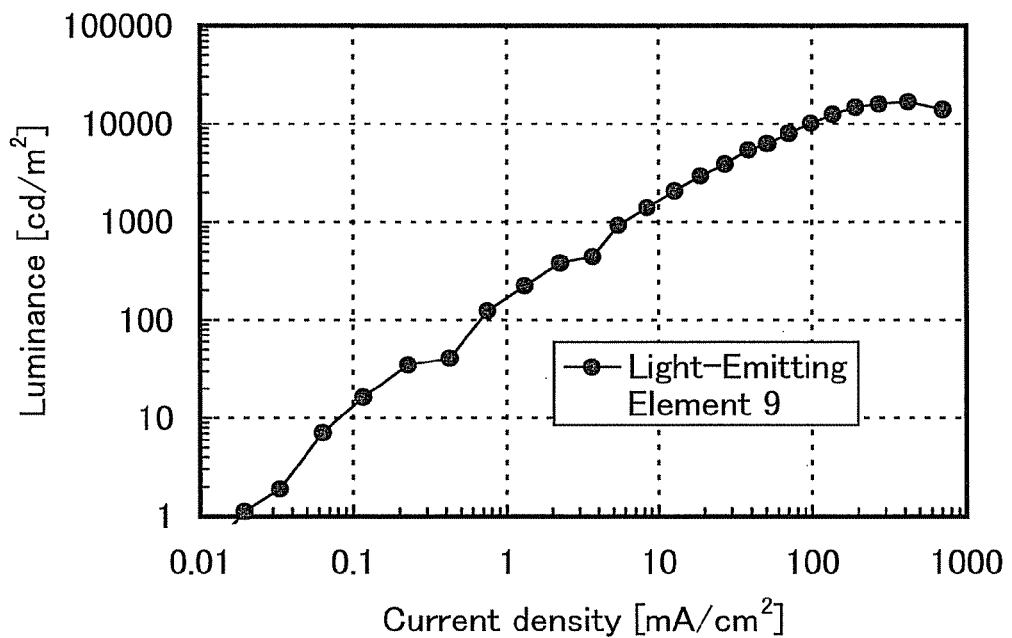
FIG. 39 shows luminance versus current density characteristics of a light-emitting element of Example 9.
Figure 40:
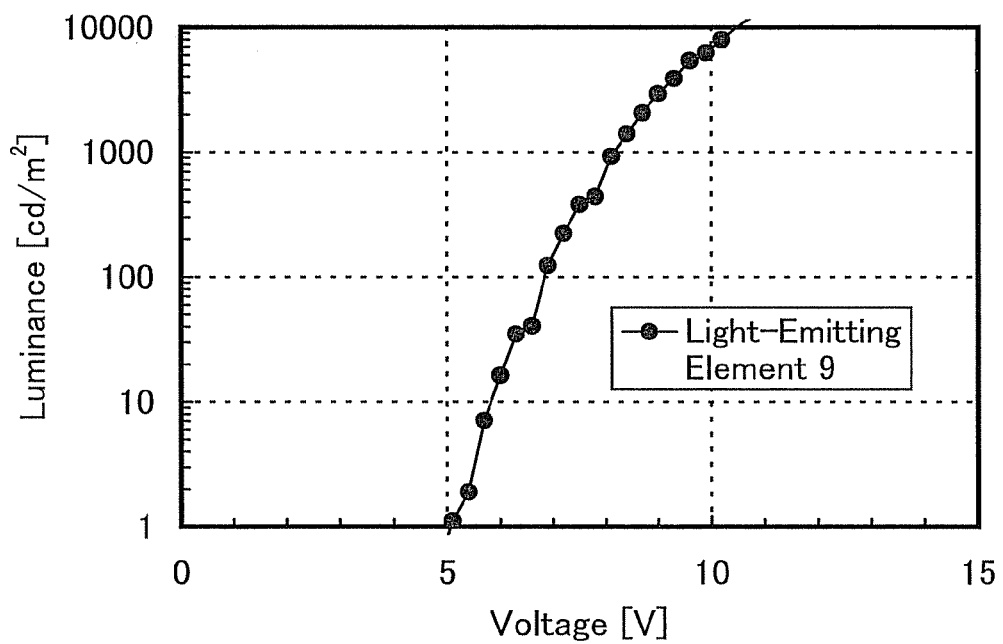
FIG. 40 shows luminance versus voltage characteristics of the light-emitting element of Example 9.
Figure 41:
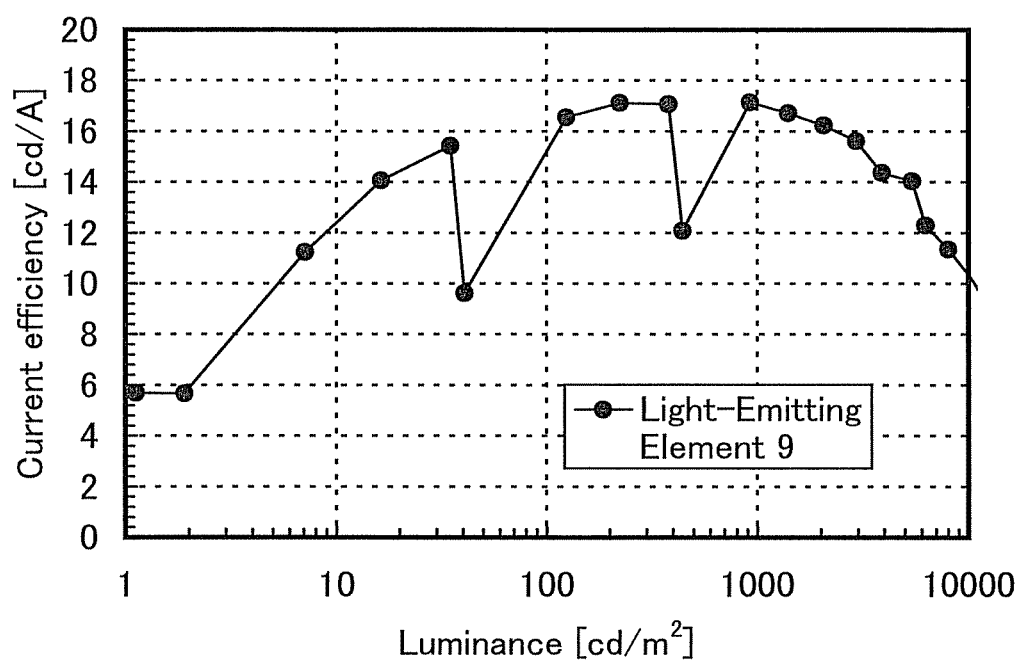
FIG. 41 shows current efficiency versus luminance characteristics of the light-emitting element of Example 9.

FIG. 39 shows the luminance versus current density characteristics of Light-Emitting Element 9. In FIG. 39, the horizontal axis represents current density (mA/cm$^2$) and the vertical axis represents luminance (cd/m$^2$). In addition, FIG. 40 shows the luminance versus voltage characteristics. In FIG. 40, the horizontal axis represents voltage (V) and the vertical axis represents luminance (cd/m$^2$). FIG. 41 shows the current efficiency versus luminance characteristics. In FIG. 41, the horizontal axis represents luminance (cd/m$^2$) and the vertical axis represents current efficiency (cd/A). Further, Table 10 shows the voltage (V), current density (mA/cm$^2$), CIE chromaticity coordinates (x, y), current efficiency (cd/A), and external quantum efficiency (%) of Light-Emitting Element 9 at a luminance of 930 cd/m$^2$.

TABLE 10

| | Voltage (V) | Current density (mA/cm$^2$) | Chromaticity coordinates (x, y) | Luminance (cd/m$^2$) | Current efficiency (cd/A) | External quantum yield (%) |
|---|---|---|---|---|---|---|
| Light-Emitting Element 9 | 8.1 | 5.4 | 0.20, 0.29 | 930 | 17 | 8.8 |

As shown in Table 10, the CIE chromaticity coordinates of Light-Emitting Element 9 (x, y) were (0.20, 0.29) at a luminance of 930 cd/m$^2$. Light-Emitting Element 9 was found to provide light emission from Ir(iPrFptz)$_3$. It is understood that, because the light-emitting element of this example includes the triazole derivative having high triplet excitation energy, Ir(iPrFptz)$_3$, which exhibits short-wavelength blue emission, can be made to emit light efficiently. It was shown that application of one embodiment of the present invention enabled efficient light emission from Ir(iPrFptz)$_3$, a phosphorescent compound that exhibits short-wavelength light emission.

EXAMPLE 10

In this example, a light-emitting element of one embodiment of the present invention will be described with reference to FIG. 22C. The materials used in this example are illustrated in the above Examples, and therefore chemical formulae thereof are omitted here.

The way how Light-Emitting Element 10 was fabricated will now be described.

(Light-Emitting Element 10)

First, an ITSO film was formed on a glass substrate 1100 by a sputtering method, so that the first electrode 1101 was formed. Note that its thickness was set to 110 nm and the electrode area was set to 2 mm×2 mm.

In pretreatment for forming the light-emitting element on the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately 10$^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about 10$^{-4}$ Pa. Then, CBP and molybdenum(VI) oxide were co-evaporated to form the hole-injection layer 1111 on the first electrode 1101. The thickness of the hole-injection layer 1111 was set to 50 nm, and the weight ratio of CBP to molybdenum(VI) oxide was adjusted to 4:2 (=CBP:molybdenum oxide).

Next, on the hole-injection layer 1111, a film of mCP was formed to a thickness of 10 nm to form the hole-transport layer 1112.

Further, mCP and Ir(iPrFptz)$_3$ were co-evaporated to form the first light-emitting layer 1113a on the hole-transport layer 1112. The thickness of the first light-emitting layer 1113a was set to 30 nm, and the weight ratio of mCP to Ir(iPrFptz)$_3$ was adjusted to 1:0.08 (=mCP:Ir(iPrFptz)$_3$).

Then, mDBTTPt-II synthesized in Example 4 and Ir(iPrFptz)$_3$ were co-evaporated, so that the second light-emitting layer 1113b was formed on the first light-emitting layer 1113a. Here, the weight ratio of mDBTTPt-II to Ir(iPrFptz)$_3$ was adjusted to 1:0.08 (=mDBTTPt-II:Ir(iPrFptz)$_3$). In addition, the thickness of the second light-emitting layer 1113b was set to 10 nm.

Next, a film of mDBTTPt-II was formed to a thickness of 10 nm on the second light-emitting layer 1113b, so that the first electron-transport layer 1114a was formed.

Then, on the first electron-transport layer 1114a, an Alq film was formed to a thickness of 10 nm to form the second electron-transport layer 1114b.

Then, on the second electron-transport layer 1114b, a BPhen film was formed to a thickness of 15 nm to form the third electron-transport layer 1114c.

221

Further, on the third electron-transport layer 1114c, a 1-nm-thick LiF film was formed by evaporation to foam the electron-injection layer 1115.

Lastly, a 200-nm-thick aluminum film was fowled by evaporation as the second electrode 1103 functioning as a cathode. Thus, Light-Emitting Element 10 of this example was fabricated.

Note that, in the above evaporation steps, evaporation was all performed by a resistance heating method.

Table 11 shows an element structure of Light-Emitting Element 10 obtained as described above.

TABLE 11

|  | first electrode | hole-injection layer | hole-transport layer | first light-emitting layer | second light-emitting layer | first electron-transport layer | second electron-transport layer | third electron-transport layer | electron-injection layer | second electrode |
|---|---|---|---|---|---|---|---|---|---|---|
| Light-Emitting Element 10 | ITSO 110 nm | CBP:MoOx (=4:2) 50 nm | mCP 10 nm | mCP:Ir(iPrFptz)3 (=1:0.08) 30 nm | mDBTTPt-II:Ir(iPrFptz)3 (=1:0.08) 10 nm | mDBTTPt-II 10 nm | Alq 10 nm | BPhen 15 nm | LiF 1 nm | Al 200 nm |

In a glove box containing a nitrogen atmosphere, Light-Emitting Element 10 was sealed so as not to be exposed to air. Then, operation characteristics of Light-Emitting Element 10 were measured. Note that the measurements were carried out at room temperature (in the atmosphere kept at 25° C.).

Figure 42:
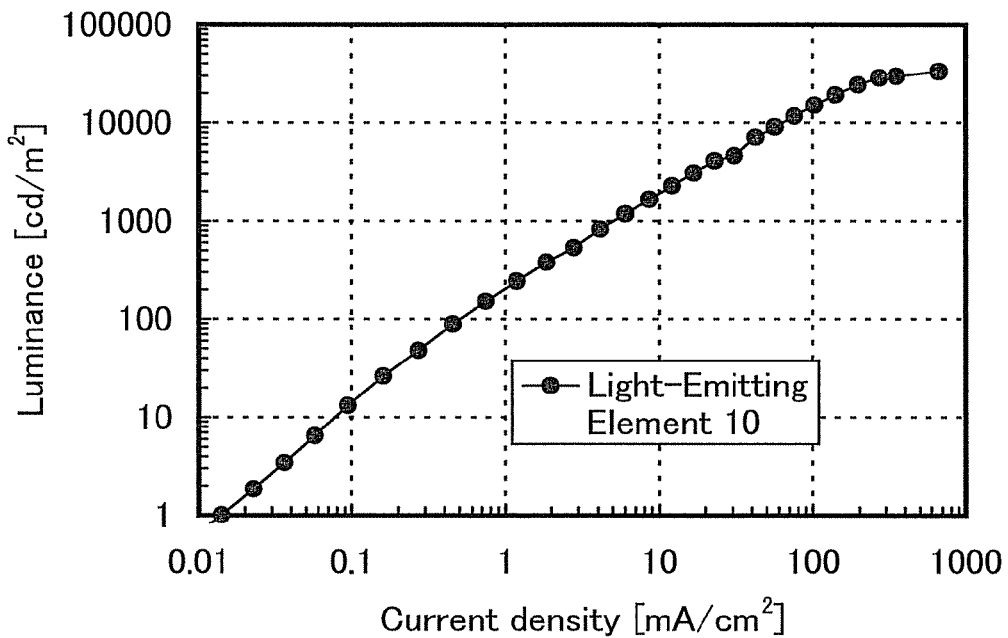
FIG. 42 shows luminance versus current density characteristics of a light-emitting element of Example 10.
Figure 43:
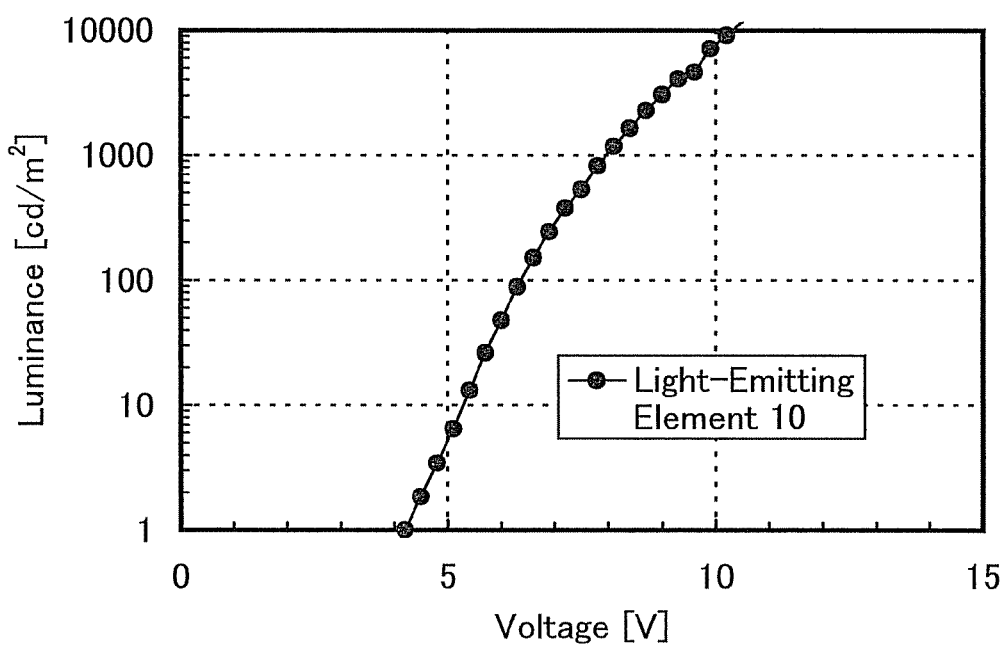
FIG. 43 shows luminance versus voltage characteristics of the light-emitting element of Example 10.
Figure 44:
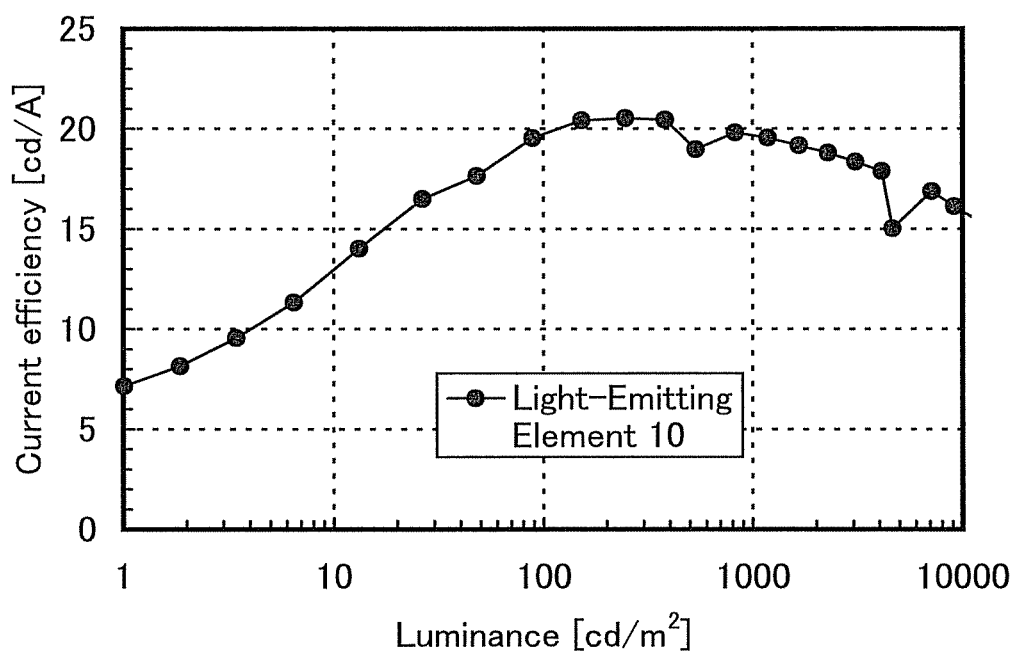
FIG. 44 shows current efficiency versus luminance characteristics of the light-emitting element of Example 10.

FIG. 42 shows the luminance versus current density characteristics of Light-Emitting Element 10. In FIG. 42, the horizontal axis represents current density (mA/cm$^2$) and the vertical axis represents luminance (cd/m$^2$). In addition, FIG. 43 shows the luminance versus voltage characteristics. In FIG. 43, the horizontal axis represents voltage (V) and the vertical axis represents luminance (cd/m$^2$). FIG. 44 shows the current efficiency versus luminance characteristics. In FIG. 44, the horizontal axis represents luminance (cd/m$^2$) and the vertical axis represents current efficiency (cd/A). Further, Table 12 shows the voltage (V), current density (mA/cm$^2$), CIE chromaticity coordinates (x, y), current efficiency (cd/A), and external quantum efficiency (%) of Light-Emitting Element 10 at a luminance of 830 cd/m$^2$.

TABLE 12

|  | Voltage (V) | Current density (mA/cm$^2$) | Chromaticity coordinates (x, y) | Luminance (cd/m$^2$) | Current efficiency (cd/A) | External quantum yield (%) |
|---|---|---|---|---|---|---|
| Light-Emitting Element 10 | 7.8 | 4.2 | 0.19, 0.29 | 830 | 20 | 10 |

As shown in Table 12, the CIE chromaticity coordinates of Light-Emitting Element 10 (x, y) were (0.10, 0.29) at a luminance of 830 cd/m$^2$. Light-Emitting Element 10 was found to provide light emission from Ir(iPrFptz)$_3$. It is understood that, because the light-emitting element of this example includes the triazole derivative having high triplet excitation energy, Ir(iPrFptz)$_3$, which exhibits short-wavelength blue emission, can be made to emit light efficiently. It was shown that application of one embodiment of the present invention enabled efficient light emission from Ir(iPrFptz)$_3$, a phosphorescent compound that exhibits short-wavelength light emission.

222

EXAMPLE 11

Synthesis Example 5

This example gives descriptions of a method of synthesizing 3-{3-[3-(dibenzofuran-4-yl)phenyl]phenyl}-1,2,4-triazolo[4,3-f]phenanthridine (abbreviation: mDBFPTPt-II), which is a triazole derivative of one embodiment of the present invention represented by the structural formula (209) in Embodiment 1.

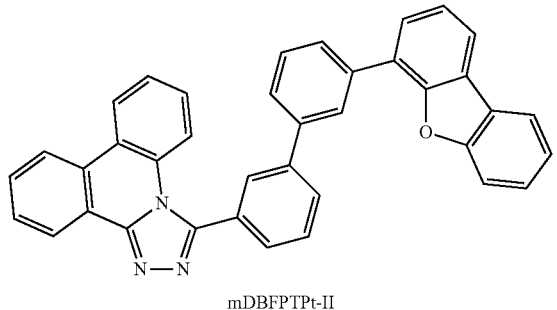 [SMILES: c1cc(-c2cccc(-c3nnc4c5ccccc5c5ccccc5n34)c2)cc(-c2cccc3c2oc2ccccc23)c1]

mDBFPTPt-II

A scheme of the synthesis of mDBFPTPt-II is illustrated in (G-1).

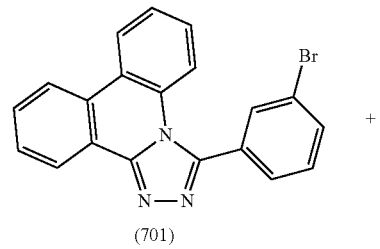

(G-1)

(701)

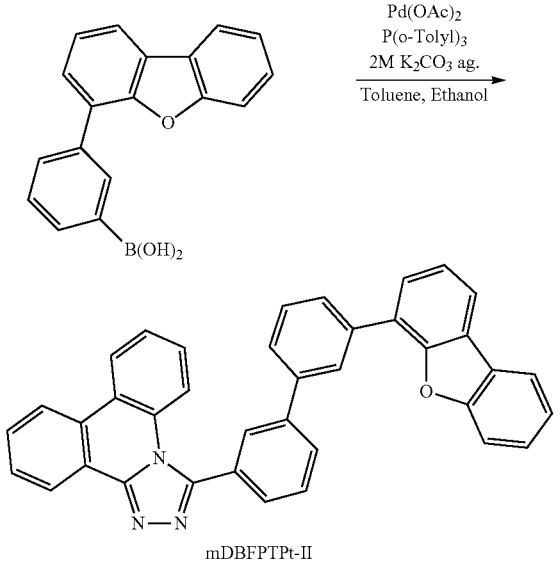

mDBFPTPt-II

To a 100-mL three-neck flask were added 1.1 g (3.0 mmol) of 3-(3-bromophenyl)-1,2,4-triazolo[4,3-f]phenanthridine, 0.87 g (3.0 mmol) of 3-(dibenzofuran-4-yl)phenylboronic acid, 0.13 g (0.43 mmol) of tri(ortho-tolyl)phosphine, 30 mL of toluene, 3 mL of ethanol, and 3 mL of a 2M aqueous potassium carbonate solution. This mixture was degassed by being stirred under reduced pressure, and the air in the flask was replaced with nitrogen. To this mixture, 15 mg (66 μmol) of palladium(II) acetate was added. This mixture was stirred at 80° C. for 6 hours under a nitrogen stream. After the stirring, water was added to the obtained mixture, and organic substances were extracted from the aqueous layer with chloroform. The obtained extract solution combined with the organic layer was washed with saturated brine, and the organic layer was dried over magnesium sulfate. The obtained mixture was gravity-filtered, and the filtrate was concentrated to give a solid. This solid was purified by silica gel column chromatography (toluene:ethyl acetate=4:1) to give an oily substance. Methanol was added to the obtained oily substance, and irradiation with ultrasonic waves was performed. The precipitated solid was collected by suction filtration, so that the substance which was the object of the synthesis was obtained as 1.3 g of a white powder in 82% yield.

By a train sublimation method, 1.3 g of the obtained white powder of the substance which was the object of the synthesis was purified. The purification was conducted by heating of the white powder at 300° C. under a pressure of 3.9 Pa with a flow rate of argon gas of 5 mL/min. After the purification, the substance which was the object of the synthesis was obtained as 0.95 g of a white powder in 72% yield.

This compound was identified as mDBFPTPt-II, which was the object of the synthesis, by nuclear magnetic resonance (NMR) spectroscopy.

$^1$H NMR data of the obtained compound are as follows: $^1$H NMR (CDCl$_3$, 300 MHz): δ=7.29-7.49 (m, 5H), 7.56 (d, J=7.8 Hz, 1H), 7.61-7.79 (m, 8H), 7.93-8.01 (m, 4H), 8.06 (s, 1H), 8.16-8.17 (m, 1H), 8.38 (dd, J=7.5 Hz, 1.5 Hz, 1H), 8.43 (dd, J=8.4 Hz, 1.2 Hz, 1H), 8.87 (dd, J=7.5 Hz, 1.8 Hz, 1H).

Figure 45A:
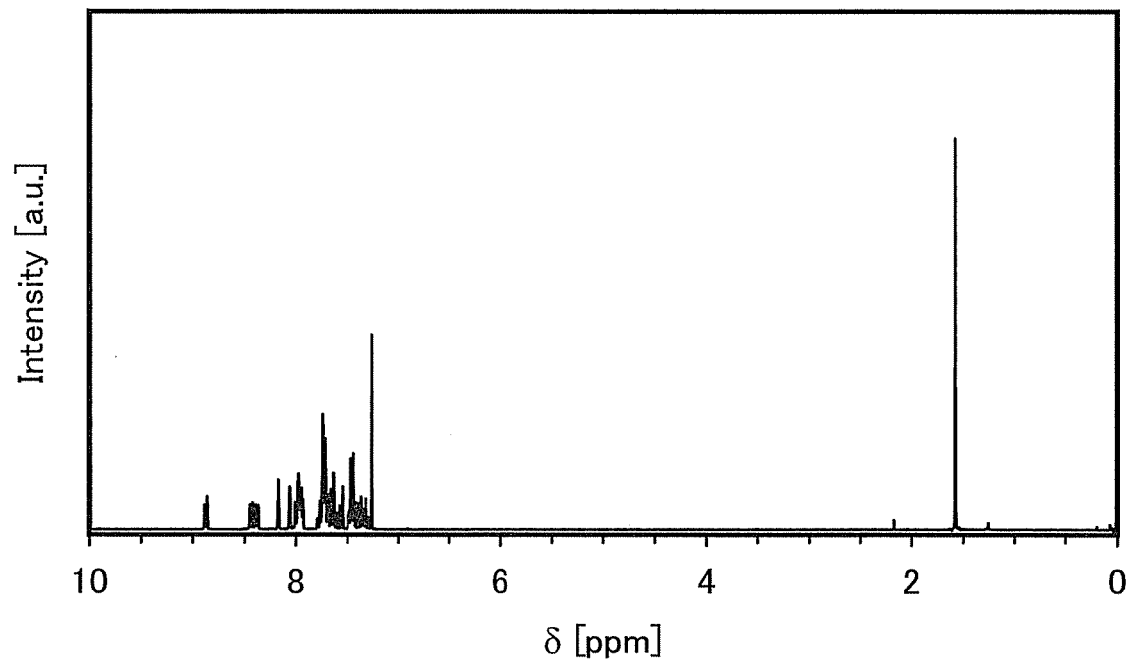
FIGS. 45A and 45B are $^1$H NMR charts of mDBFPTPt-II.
Figure 45B:
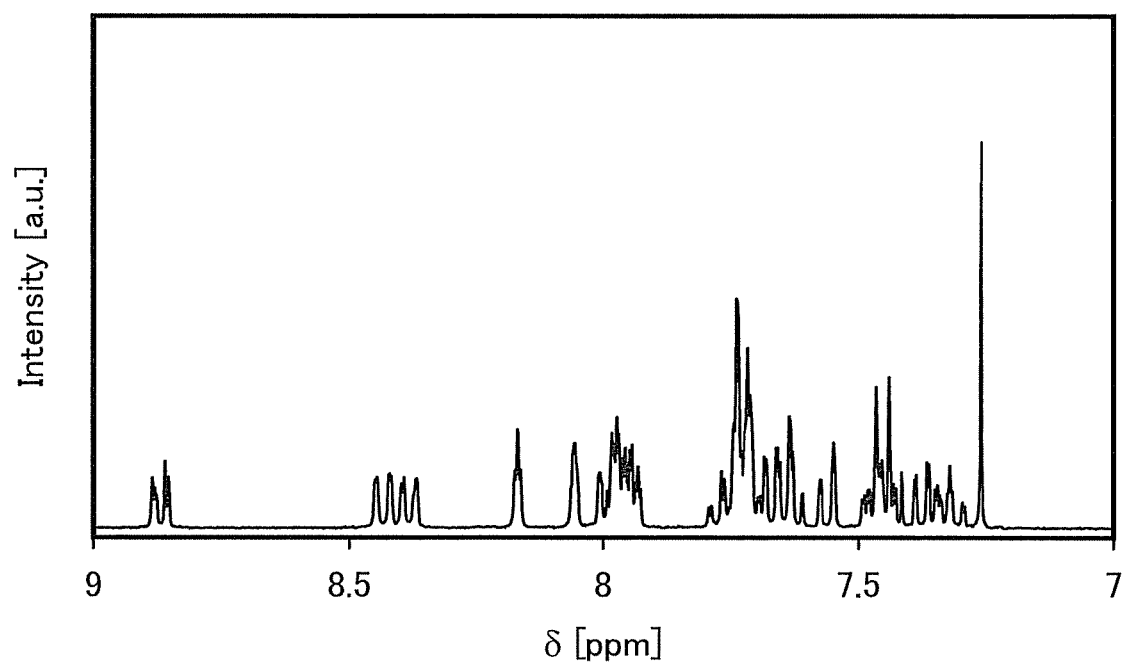

Further, the $^1$H NMR charts are shown in FIGS. 45A and 45B. Note that FIG. 45B is a chart where the range of from 7.0 ppm to 9.0 ppm in FIG. 45A is enlarged.

Figure 46A:
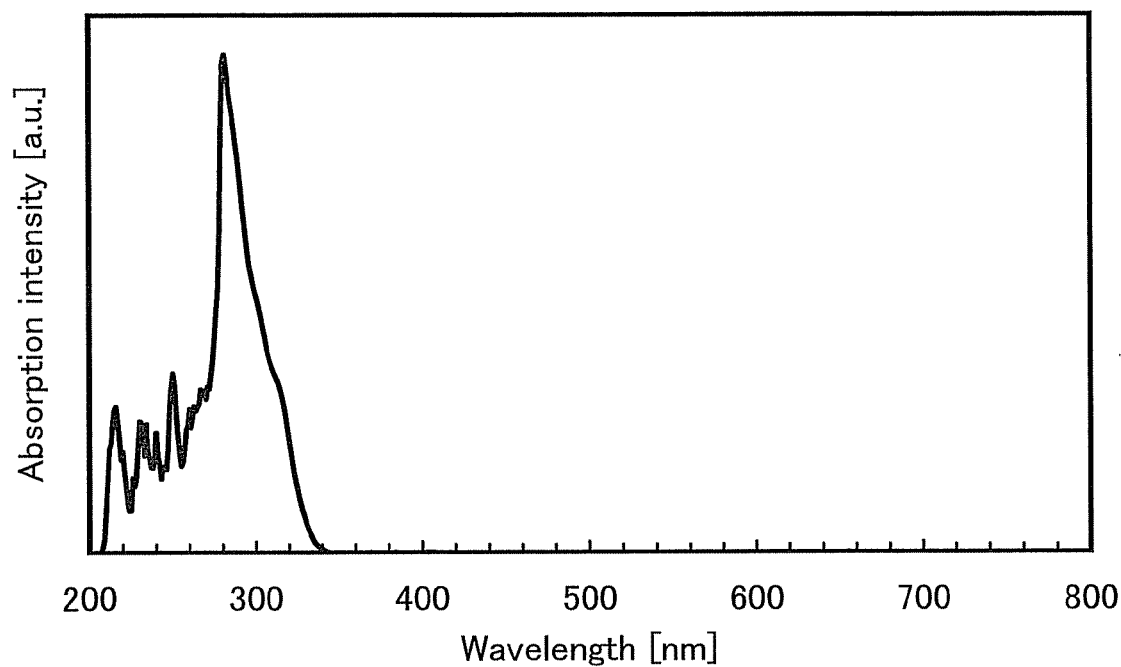
FIGS. 46A and 46B show an absorption and emission spectra of a toluene solution of mDBFPTPt-II.
Figure 46B:
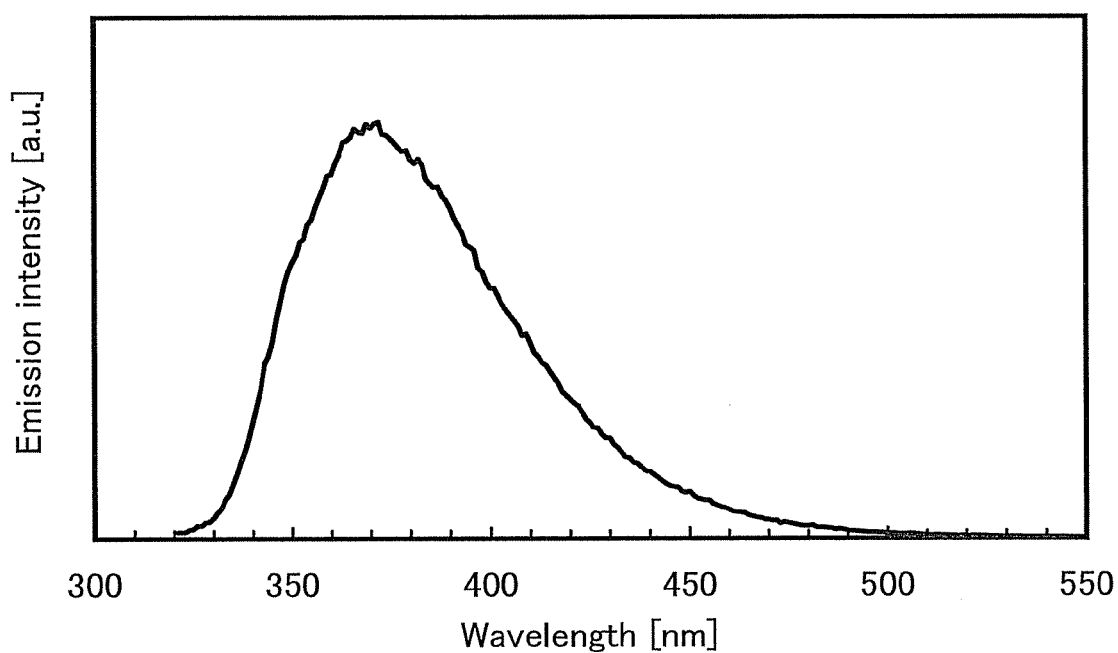
Figure 47A:
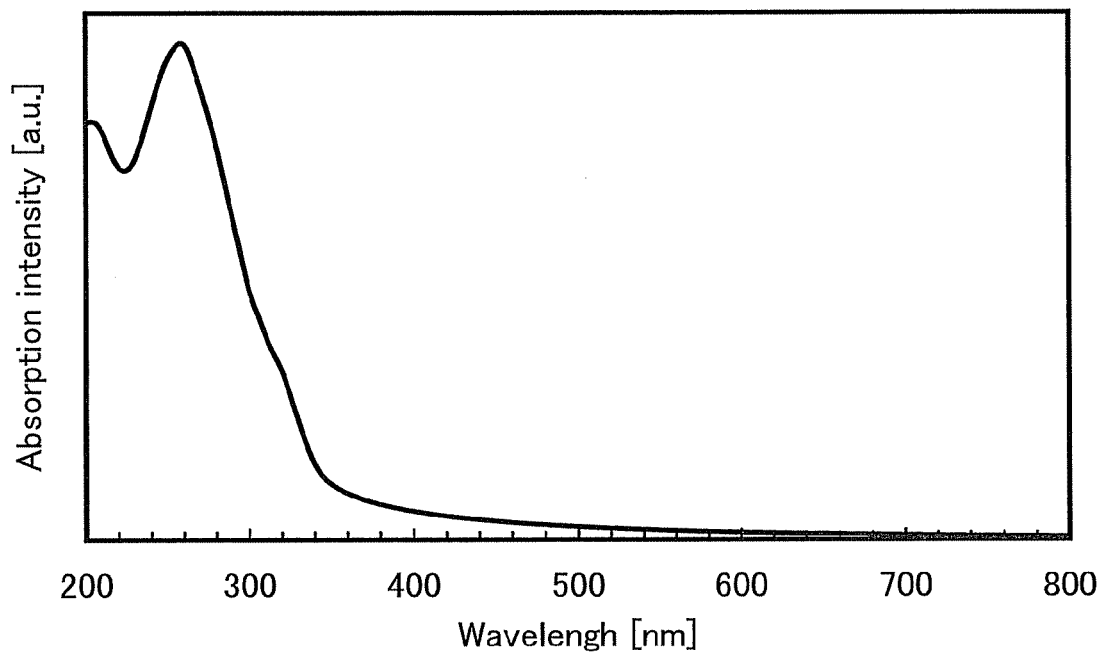
FIGS. 47A and 47B show an absorption and emission spectra of a thin film of mDBFPTPt-II.
Figure 47B:
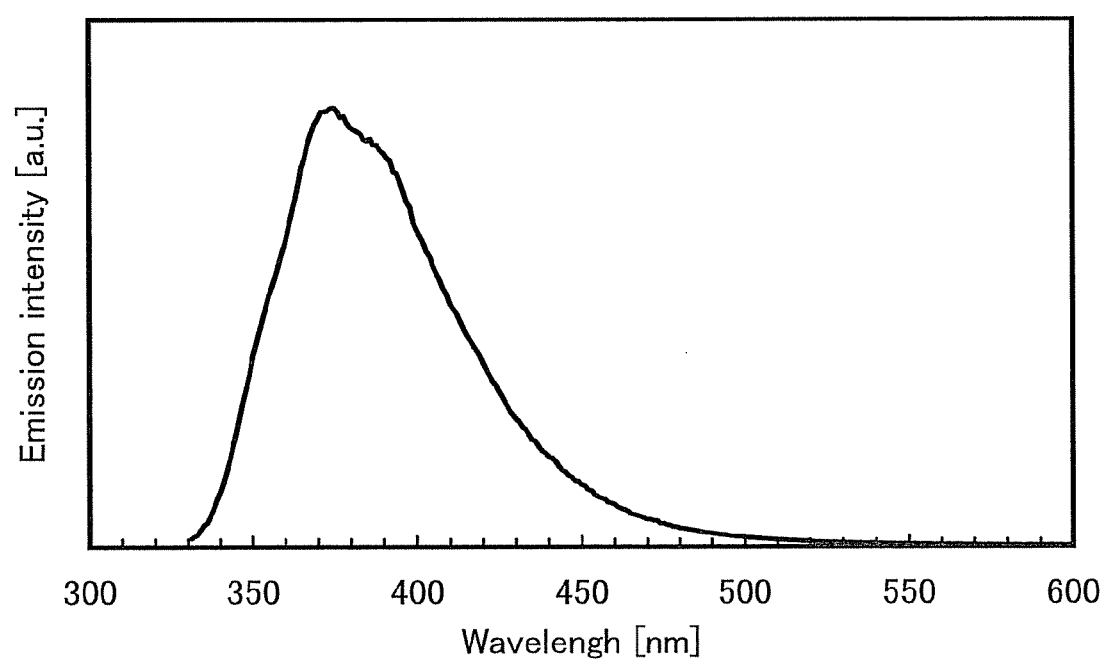

Further, FIG. 46A shows the absorption spectrum of a toluene solution of mDBFPTPt-II, and FIG. 46B shows the emission spectrum thereof. In addition, FIG. 47A shows the absorption spectrum of a thin film of mDBFPTPt-II, and FIG. 47B shows the emission spectrum thereof. An ultraviolet-visible spectrophotometer (V-550, manufactured by JASCO Corporation) was used for the measurements. Samples were prepared in such a way that the solution was put into a quartz cell and the thin film was formed on a quartz substrate by evaporation. Here are shown the absorption spectrum for the solution which was obtained by subtracting the absorption spectra of quartz and toluene from those of quartz and the solution, and the absorption spectrum for the thin film which was obtained by subtracting the absorption spectrum of a quartz substrate from those of the quartz substrate and the thin film. In FIG. 46A and FIG. 47A, the horizontal axis represents wavelength (nm) and the vertical axis represents absorption intensity (arbitrary unit). In FIG. 46B and FIG. 47B, the horizontal axis represents wavelength (nm) and the vertical axis represents emission intensity (arbitrary unit). In the case of the toluene solution, absorption peaks were found to be at around 282 nm and 314 nm, and the peak of the emission wavelength was at 371 nm (at an excitation wavelength of 315 nm). In the case of the thin film, absorption peaks were found to be at around 204 nm, 258 nm, 272 nm, 303 nm and 315 nm, and the peaks of the emission wavelength were at 374 nm and 386 nm (at an excitation wavelength of 316 nm).

EXAMPLE 12

Synthesis Example 6

This example gives descriptions of a method of synthesizing 3-[3-(9H-carbazol-9-yl)phenyl]-1,2,4-triazolo[4,3-f]phenanthridine (abbreviation: mCzTPt), which is a triazole derivative of one embodiment of the present invention represented by the structural formula (301) in Embodiment 1.

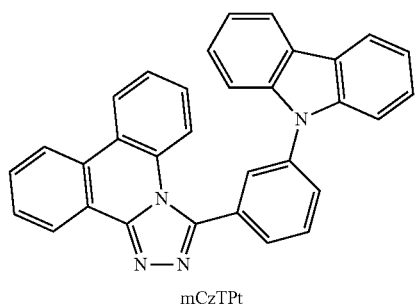 [SMILES: c1cc(-c2nnc3c4ccccc4c4ccccc4n23)cc(-n2c3ccccc3c3ccccc32)c1]

mCzTPt

A scheme of the synthesis of mCzTPt is illustrated in (H-1).

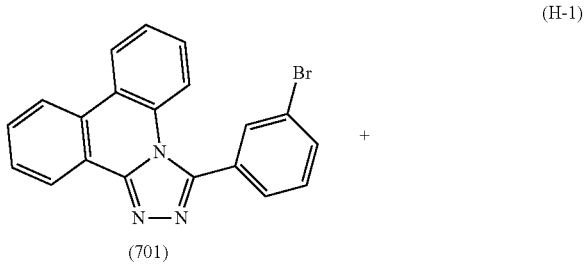

(H-1)

(701)

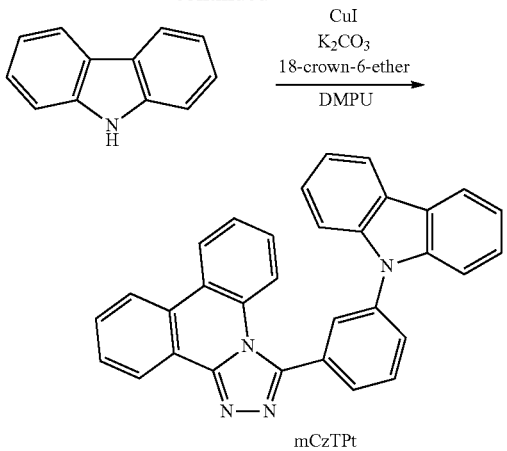

-continued mCzTPt

To a 200-mL three-neck flask were added 1.4 g (3.8 mmol) of 3-(3-bromophenyl)-1,2,4-triazolo[4,3-f]phenanthridine, 0.72 g (4.3 mmol) of 9H-carbazole, 0.17 g (0.64 mmol) of 18-crown-6-ether, 1.2 g (8.4 mmol) of potassium carbonate, and 3 mL of 1,3-dimethyl-3,4,5,6-tetrahydro-2(1H)-pyrimidinone (DMPU). To this mixture was added 93 mg (0.49 mmol) of copper(I) iodide, and the mixture was stirred at 180° C. for 19 hours under a nitrogen stream. After the stirring, this mixture was cooled to room temperature, and chloroform was added thereto. The organic layer of the resulting mixture was washed with water, a saturated aqueous solution of sodium hydrogen carbonate and saturated brine, and the organic layer was dried over magnesium sulfate. The obtained mixture was gravity-filtered, and the filtrate was concentrated to give a solid. This solid was purified by silica gel column chromatography (toluene:ethyl acetate=5:1), and further recrystallized from toluene, so that the substance which was the object of the synthesis was obtained as 1.2 g of a white powder in 69% yield.

By a train sublimation method, 1.2 g of the obtained white powder of the substance which was the object of the synthesis was purified. The purification was conducted by heating of the white powder at 290° C. under a pressure of 2.2 Pa with a flow rate of argon gas of 10 mL/min. After the purification, the substance which was the object of the synthesis was obtained as 0.56 g of a white powder in 46% yield.

This compound was identified as mCzTPt, which was the object of the synthesis, by nuclear magnetic resonance (NMR) spectroscopy.

$^1$H NMR data of the obtained compound are as follows: $^1$H NMR (CDCl$_3$, 300 MHz): δ=7.30 (td, J=7.8 Hz, 1.2 Hz, 2H), 7.38-7.59 (m, 6H), 7.70-7.93 (m, 7H), 8.14 (d, J=7.8 Hz, 2H), 8.39 (dd, J=7.8 Hz, 1.5 Hz, 1H), 8.48 (dd, J=7.8 Hz, 1.5 Hz, 1H), 8.86 (dd, J=7.2 Hz, 2.1 Hz, 1H).

Figure 48A:
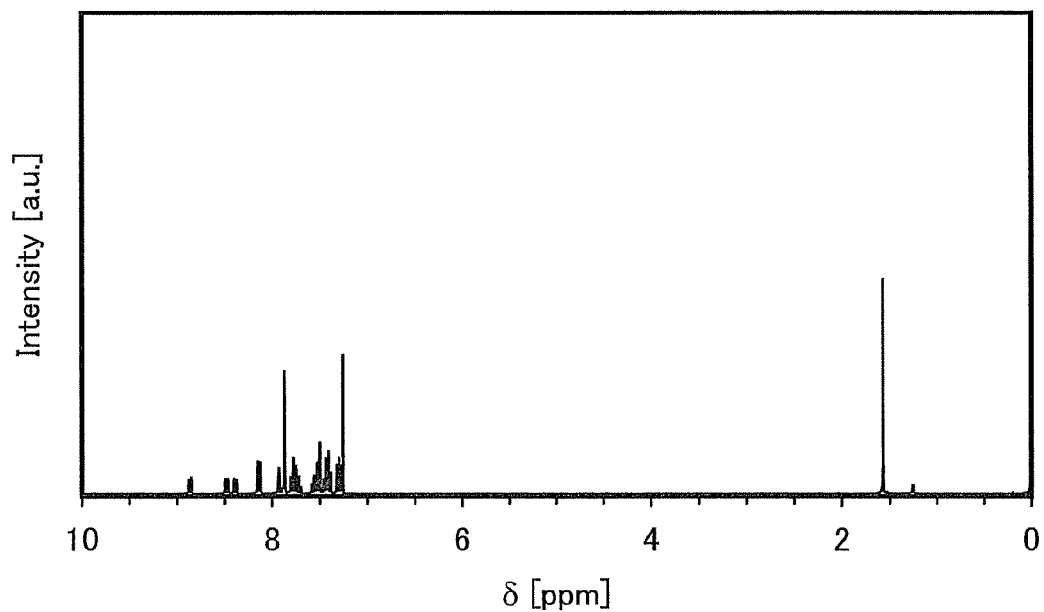
FIGS. 48A and 48B are $^1$H NMR charts of mCzTPt.
Figure 48B:
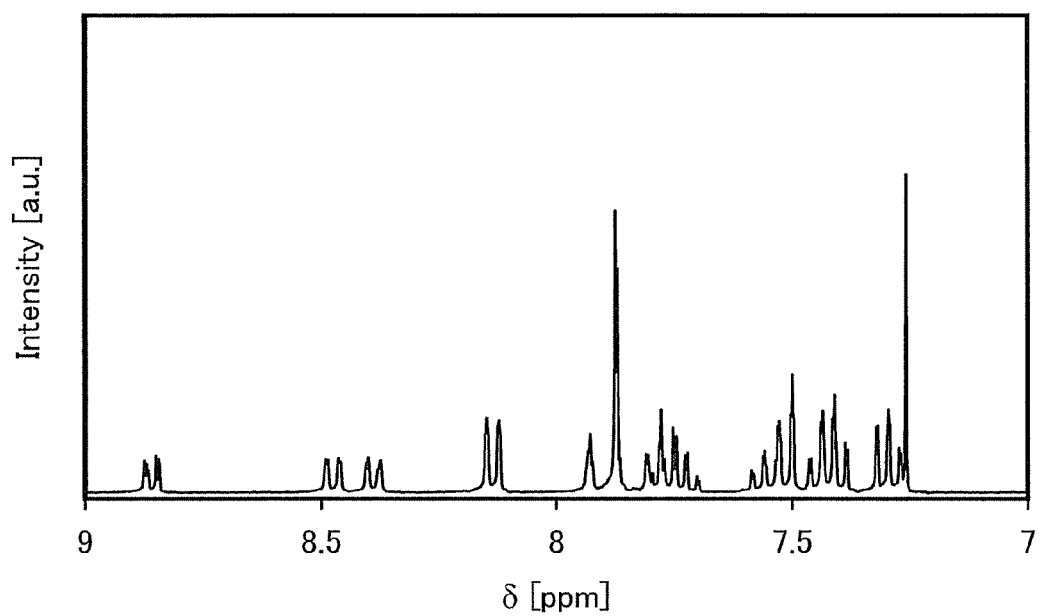

Further, the $^1$H NMR charts are shown in FIGS. 48A and 48B. Note that FIG. 48B is a chart where the range of from 7.0 ppm to 9.0 ppm in FIG. 48A is enlarged.

Figure 49A:
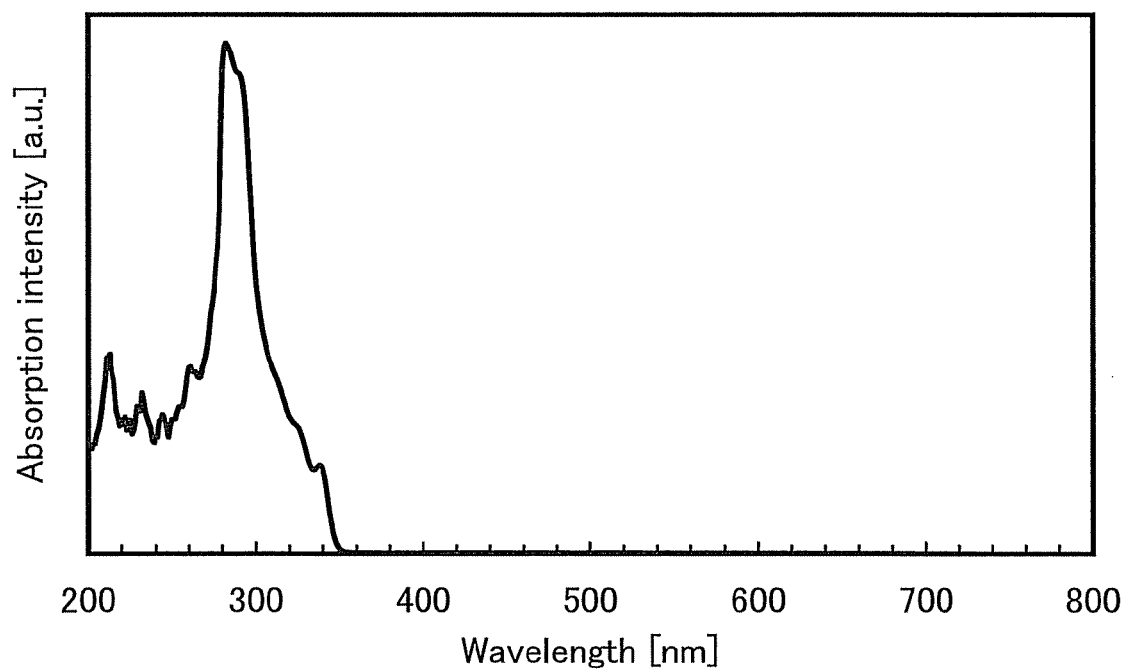
FIGS. 49A and 49B show an absorption and emission spectra of a toluene solution of mCzTPt.
Figure 49B:
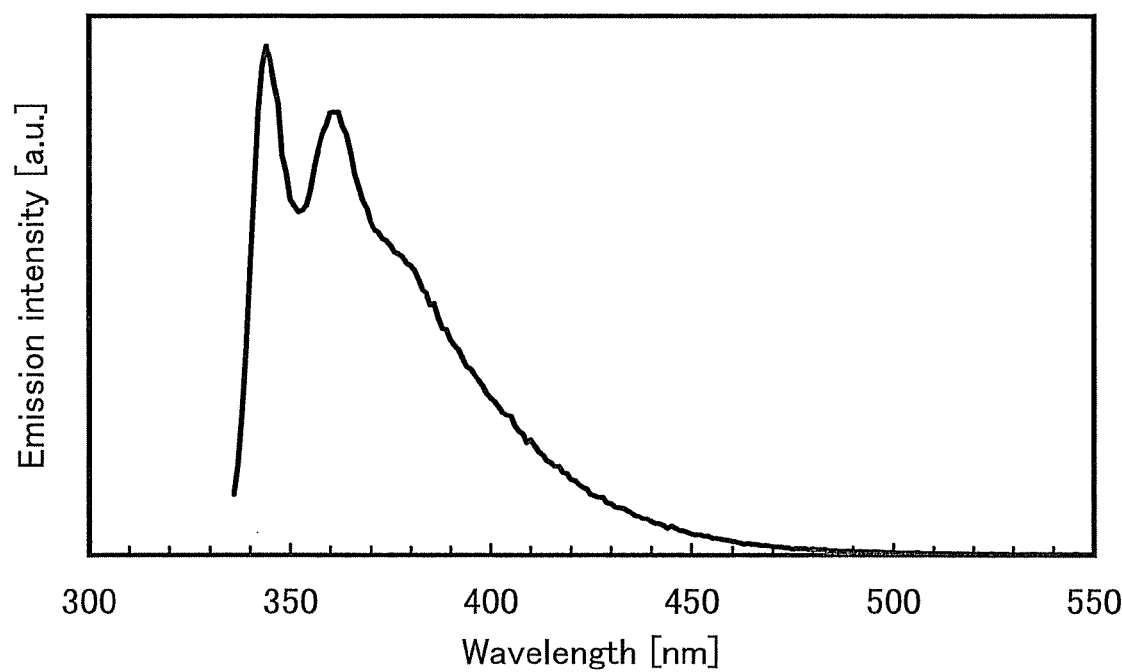
Figure 50A:
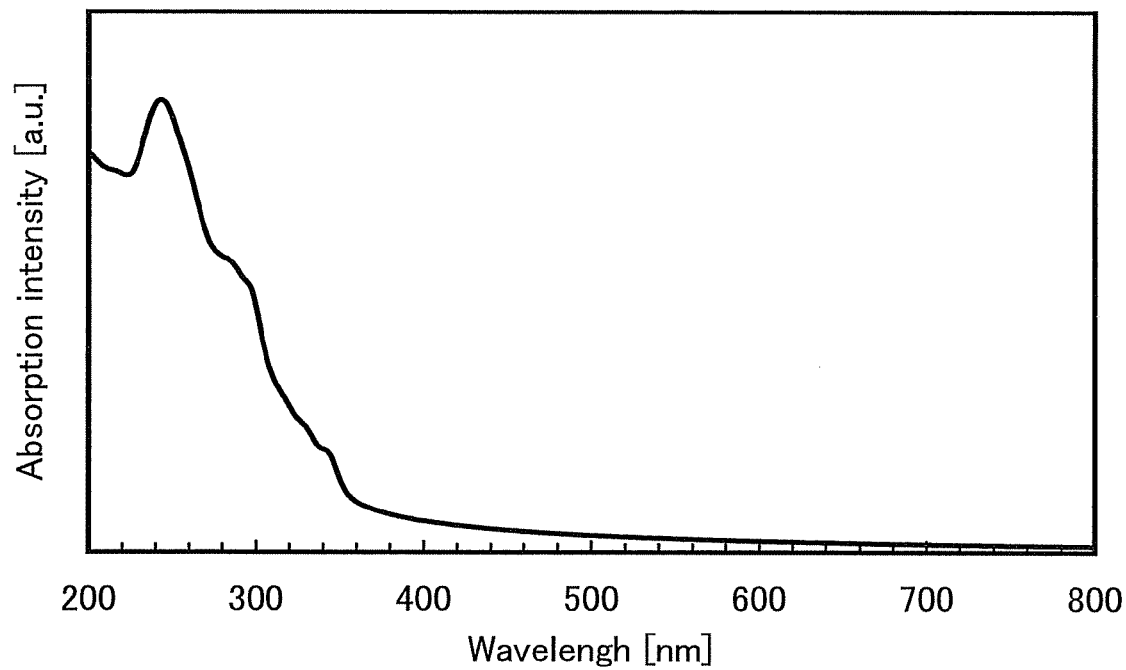
FIGS. 50A and 50B show an absorption and emission spectra of a thin film of mCzTPt.
Figure 50B:
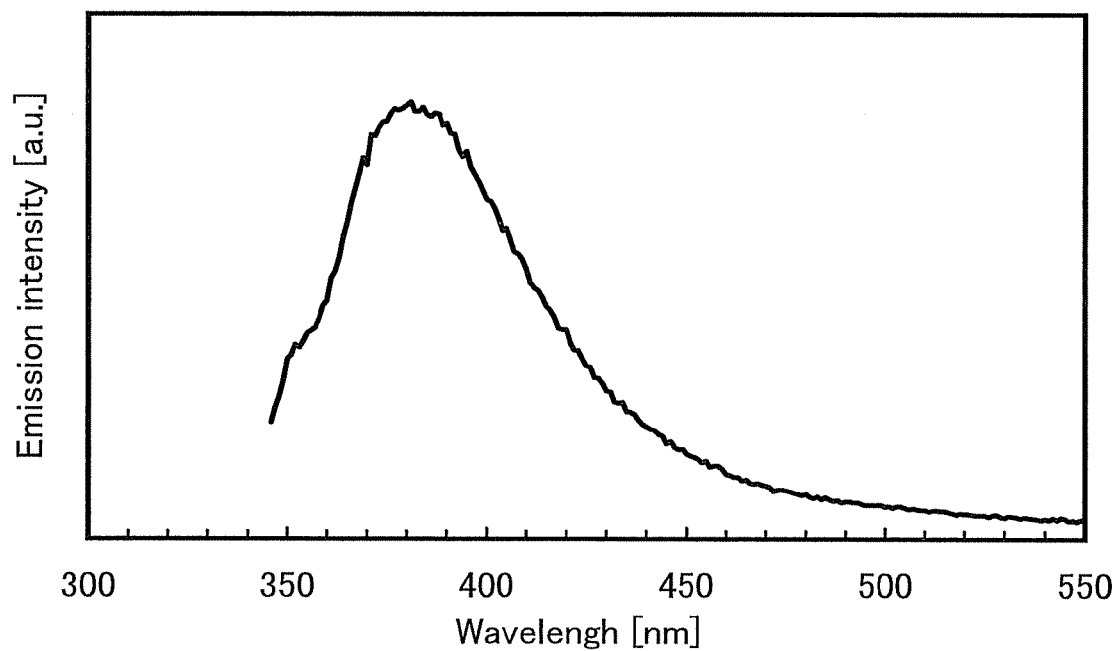

Further, FIG. 49A shows the absorption spectrum of a toluene solution of mCzTPt, and FIG. 49B shows the emission spectrum thereof. In addition, FIG. 50A shows the absorption spectrum of a thin film of mCzTPt, and FIG. 50B shows the emission spectrum thereof. An ultraviolet-visible spectrophotometer (V-550, manufactured by JASCO Corporation) was used for the measurements. Samples were prepared in such a way that the solution was put into a quartz cell and the thin film was formed on a quartz substrate by evaporation. Here are shown the absorption spectrum for the solution which was obtained by subtracting the absorption spectra of quartz and toluene from those of quartz and the solution, and the absorption spectrum for the thin film which was obtained by subtracting the absorption spectrum of a quartz substrate from those of the quartz substrate and the thin film. In FIG. 49A and FIG. 50A, the horizontal axis represents wavelength (nm) and the vertical axis represents absorption intensity (arbitrary unit). In FIG. 49B and FIG. 50B, the horizontal axis represents wavelength (nm) and the vertical axis represents emission intensity (arbitrary unit). In the case of the toluene solution, absorption peaks were found to be at around 282 nm and 338 nm, and peaks of the emission wavelength were at 346 nm and 360 nm (at an excitation wavelength of 325 nm). In the case of the thin film, absorption peaks were found to be at around 216 nm, 243 nm, 281 nm, 295 nm, 327 nm, and 341 nm, and the peak of the emission wavelength was at 380 nm (at an excitation wavelength of 342 nm).

EXAMPLE 13

Synthesis Example 7

This example gives descriptions of a method of synthesizing 3-[4-(9H-carbazol-9-yl)phenyl]-1,2,4-triazolo[3,4-α]isoquinoline (abbreviation: CzTIq), which is a triazole derivative of one embodiment of the present invention represented by the structural formula (600) in Embodiment 1.

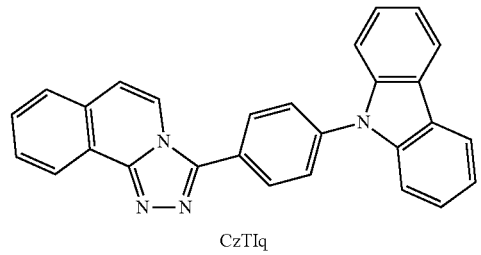 [SMILES: c1ccc2c(c1)ccn1c(-c3ccc(-n4c5ccccc5c5ccccc54)cc3)nnc21]

CzTIq

A scheme of the synthesis of CzTIq is illustrated in (1-1).

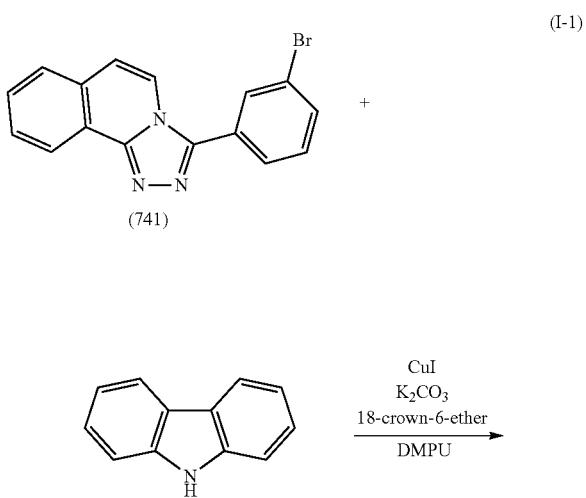

(I-1)

(741)

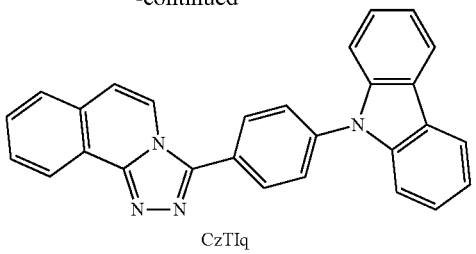
CzTIq

To a 200-mL three-neck flask were added 1.6 g (5.0 mmol) of 3-(4-bromophenyl)-1,2,4-triazolo[3,4-α]isoquinoline, 0.92 g (5.5 mmol) of 9H-carbazole, 0.19 g (0.72 mmol) of 18-crown-6-ether, 1.4 g (10 mmol) of potassium carbonate, and 3 mL of 1,3-dimethyl-3,4,5,6-tetrahydro-2(1H)-pyrimidinone (DMPU). To this mixture was added 58 mg (0.31 mmol) of copper(I) iodide, and the mixture was stirred at 180° C. for 6 hours under a nitrogen stream. After the stirring, this mixture was cooled to 100° C., and toluene was added thereto. This mixture was washed with water, a saturated aqueous solution of sodium hydrogen carbonate and saturated brine, and the organic layer was dried over magnesium sulfate. The obtained mixture was gravity-filtered, and the filtrate was concentrated to give a solid. This solid was purified by silica gel column chromatography (toluene:ethyl acetate=4:1) and further recrystallized from toluene, so that the substance which was the object of the synthesis was obtained as 1.5 g of a white powder in 70% yield.

By a train sublimation method, 1.4 g of the obtained white powder of the substance which was the object of the synthesis was purified. The purification was conducted by heating of the white powder at 260° C. under a pressure of 3.1 Pa with a flow rate of argon gas of 5 mL/min. After the purification, the substance which was the object of the synthesis was obtained as 1.2 g of a white powder in 84% yield.

This compound was identified as CzTIq, which was the object of the synthesis, by nuclear magnetic resonance (NMR) spectroscopy.

$^1$H NMR data of the obtained compound are as follows: $^1$H NMR (CDCl$_3$, 300 MHz): δ=7.18 (d, J=7.2 Hz, 1H), 7.34 (td, J=7.8 Hz, 1.2 Hz, 2H), 7.47 (td, J=6.9 Hz, 1.2 Hz, 2H), 7.54 (d, J=8.4 Hz, 2H), 7.73-7.87 (m, 5H), 8.10-8.19 (m, 5H), 8.85 (dd, J=6.3 Hz, 1.8 Hz, 1H).

Figure 51A:
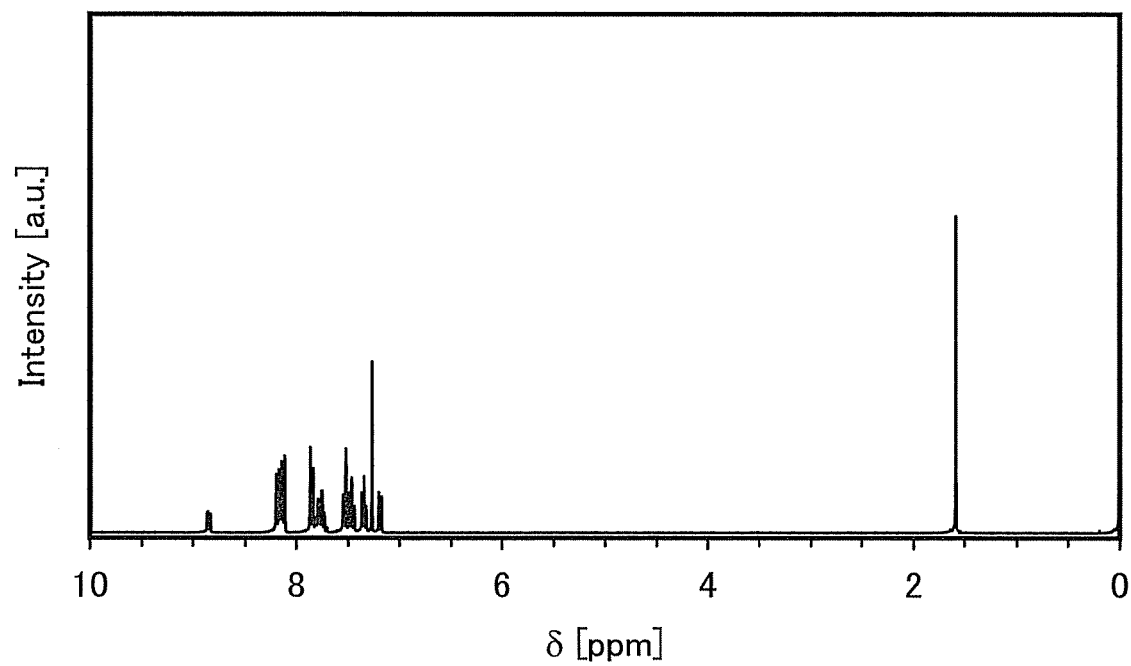
FIGS. 51A and 51B are $^1$H NMR charts of CzTIq.
Figure 51B:
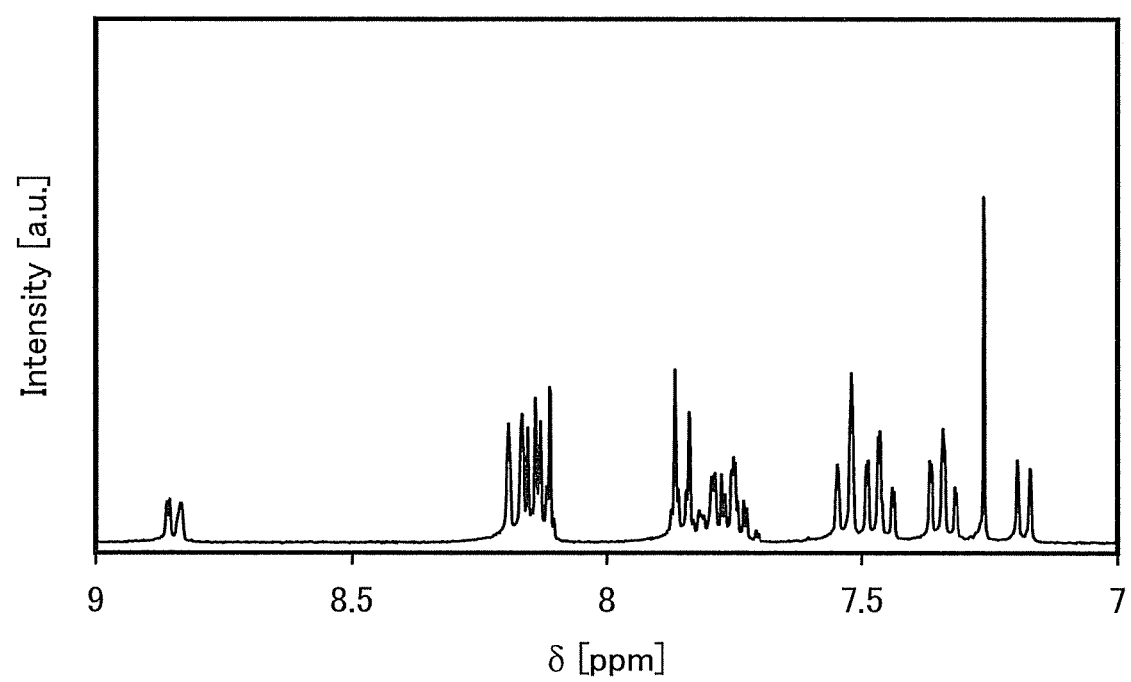

Further, the $^1$H NMR charts are shown in FIGS. 51A and 51B. Note that FIG. 51B is a chart where the range of from 7.0 ppm to 9.0 ppm in FIG. 51A is enlarged.

Figure 52A:
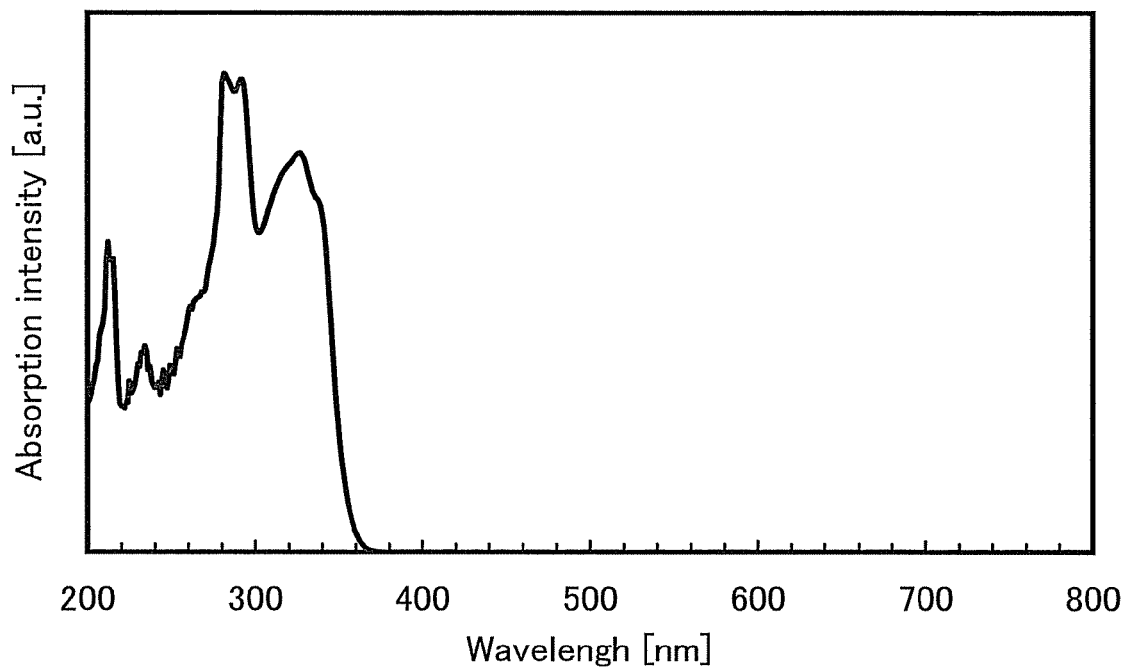
FIGS. 52A and 52B show an absorption and emission spectra of a toluene solution of CzTIq.
Figure 52B:
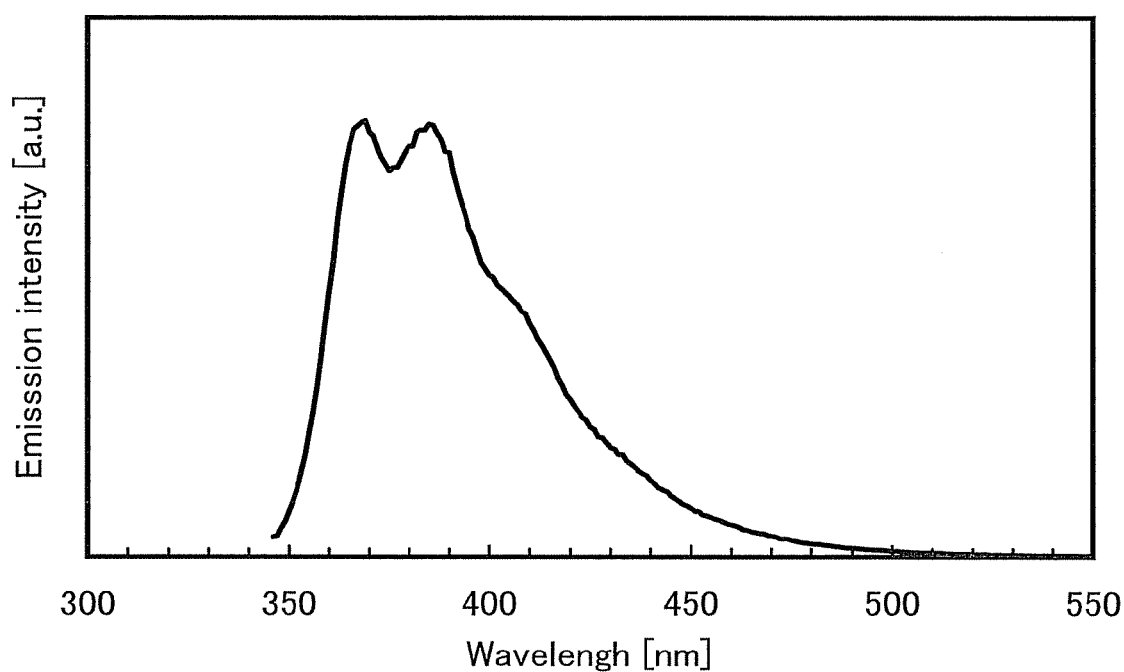
Figure 53A:
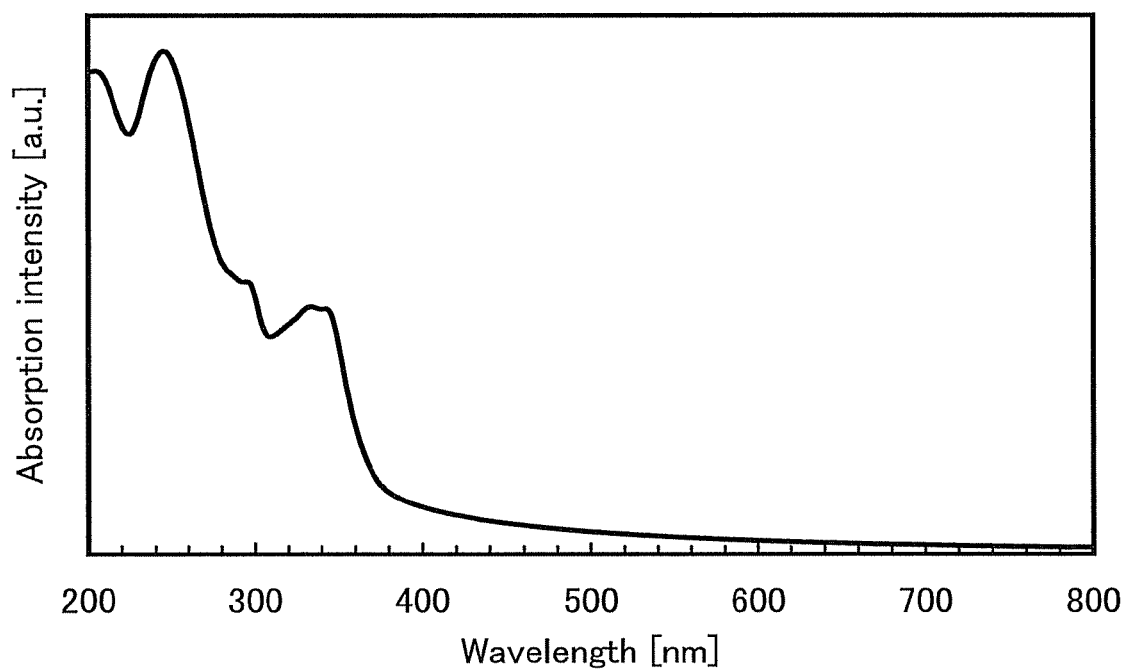
FIGS. 53A and 53B show an absorption and emission spectra of a thin film of CzTIq.
Figure 53B:
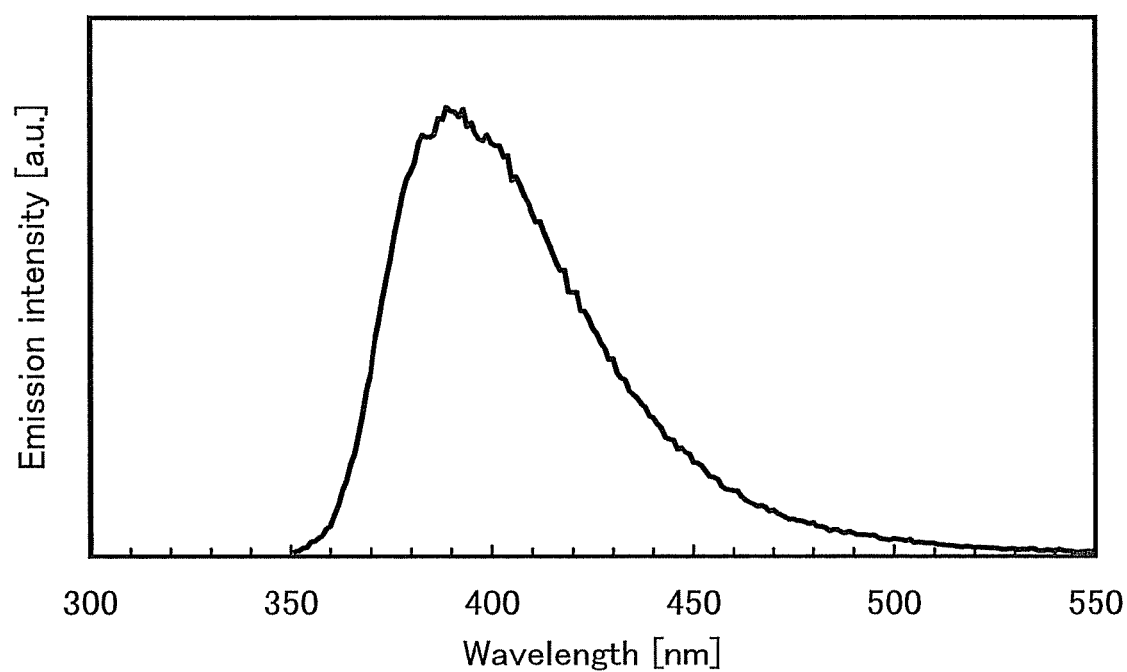

Further, FIG. 52A shows the absorption spectrum of a toluene solution of CzTIq, and FIG. 52B shows the emission spectrum thereof. In addition, FIG. 53A shows the absorption spectrum of a thin film of CzTIq, and FIG. 53B shows the emission spectrum thereof. An ultraviolet-visible spectrophotometer (V-550, manufactured by JASCO Corporation) was used for the measurements. Samples were prepared in such a way that the solution was put into a quartz cell and the thin film was formed on a quartz substrate by evaporation. Here are shown the absorption spectrum for the solution which was obtained by subtracting the absorption spectra of quartz and toluene from those of quartz and the solution, and the absorption spectrum for the thin film which was obtained by subtracting the absorption spectrum of a quartz substrate from those of the quartz substrate and the thin film. In FIG. 52A and FIG. 53A, the horizontal axis represents wavelength (nm) and the vertical axis represents absorption intensity (arbitrary unit). In FIG. 52B and FIG. 53B, the horizontal axis represents wavelength (nm) and the vertical axis represents emission intensity (arbitrary unit). In the case of the toluene solution, absorption peaks were found to be at around 281 nm, 292 nm, 326 nm, and 336 nm, and peaks of the emission wavelength were at 368 nm and 385 nm (at an excitation wavelength of 340 nm). In the case of the thin film, absorption peaks were found to be at around 204 nm, 245 nm, 285 nm, 333 nm, and 343 nm, and peaks of the emission wavelength were at 390 nm and 399 nm (at an excitation wavelength of 343 nm).

EXAMPLE 14

Synthesis Example 8

This example gives descriptions of a method of synthesizing 3-[3-(9H-carbazol-9-yl)phenyl]-1,2,4-triazolo[3,4-α] isoquinoline (abbreviation: mCzTIq), which is the triazole derivative of one embodiment of the present invention represented by the structural formula (601) in Embodiment 1, and a method of synthesizing 3-(3-bromophenyl)-1,2,4-triazolo [3,4-α]isoquinoline, which is the heterocyclic compound of one embodiment of the present invention represented by the structural formula (742) in Embodiment 1.

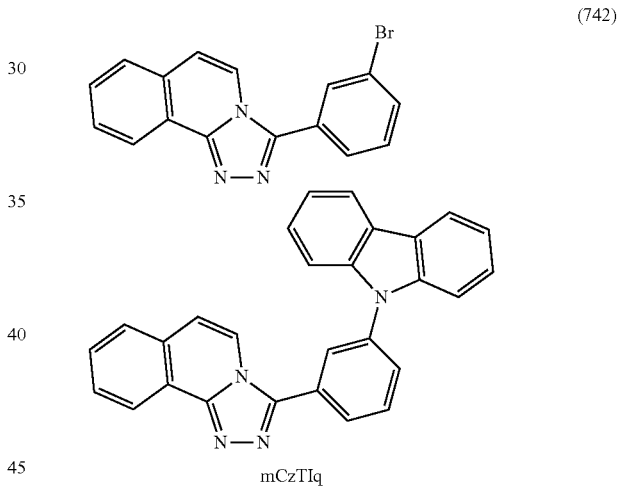
(742)

mCzTIq

Step 1: Synthesis of
N-(3-Bromobenzoyl)-N-(1-isoquinolyl)hydrazine

The synthesis scheme of Step 1 is illustrated in (J-1).

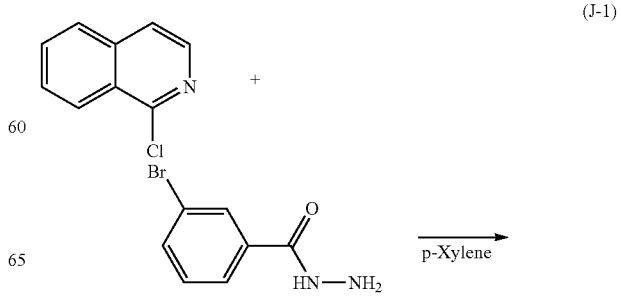
(J-1)

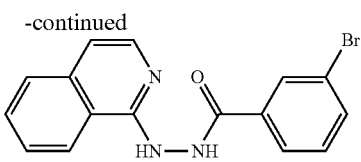

To a 200-mL three-neck flask were added 3.3 g (20 mmol) of 1-chloroisoquinoline, 4.3 g (20 mmol) of 3-bromobenzoylhydrazine, and 80 mL of para-xylene. This mixture was refluxed at 150° C. for 14 hours under a nitrogen stream. After a predetermined time elapsed, this mixture was cooled to room temperature, and the precipitated solid was collected by suction filtration. The obtained solid was washed with toluene, a saturated aqueous solution of sodium hydrogen carbonate, and water. This solid was dried, so that the substance which was the object of the synthesis was obtained as 6.2 g of a pale yellow powder in 90% yield.

Step 2: Synthesis of 3-(3-Bromophenyl)-1,2,4-triazolo[3,4-a]isoquinoline

The synthesis scheme of Step 2 is illustrated in (J-2).

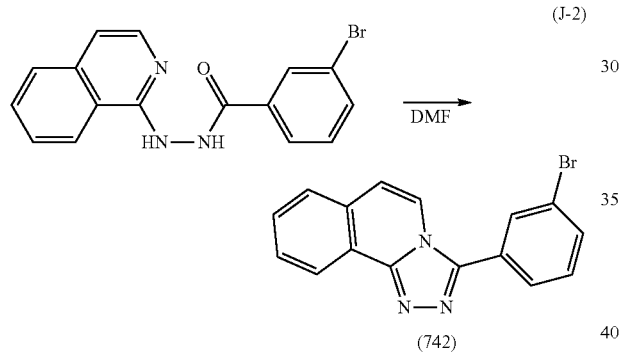

To a 500-mL three-neck flask were added 6.2 g (18 mmol) of N'-(3-bromobenzoyl)-N-(1-isoquinolyl)hydrazine and 200 mL of N,N-dimethylformamide (DMF). This mixture was stirred at 120° C. for 9 hours under a nitrogen stream. After a predetermined time elapsed, this mixture was cooled to room temperature, and chloroform and water were added thereto. Organic substances were extracted from the aqueous layer with chloroform. The obtained extract solution was washed with a saturated aqueous solution of sodium hydrogen carbonate and saturated brine, and the organic layer was dried over magnesium sulfate. The obtained mixture was gravity-filtered, and the filtrate was concentrated to give a solid. The obtained solid was purified by silica gel column chromatography (chloroform:ethyl acetate=10:1) to give a solid. A methanol suspension of this solid was irradiated with ultrasonic waves, and a solid was collected by suction filtration, so that the substance which was the object of the synthesis was obtained as 5.5 g of a white powder in 92% yield.

This compound was identified as 3-(3-bromophenyl)-1,2,4-triazolo[3,4-a]isoquinoline, which was the object of the synthesis, by nuclear magnetic resonance (NMR) spectroscopy.

$^1$H NMR data of the obtained compound are as follows: $^1$H NMR (DMSO-$d_6$, 300 MHz): δ=7.38 (d, J=7.5 Hz, 1H), 7.61 (t, J=7.8 Hz, 1H), 7.75-7.87 (m, 3H), 7.92-8.02 (m, 2H), 8.09-8.10 (m, 1H), 8.30 (d, J=7.2 Hz, 1H), 8.56-8.61 (m, 1H).

Figure 54A:
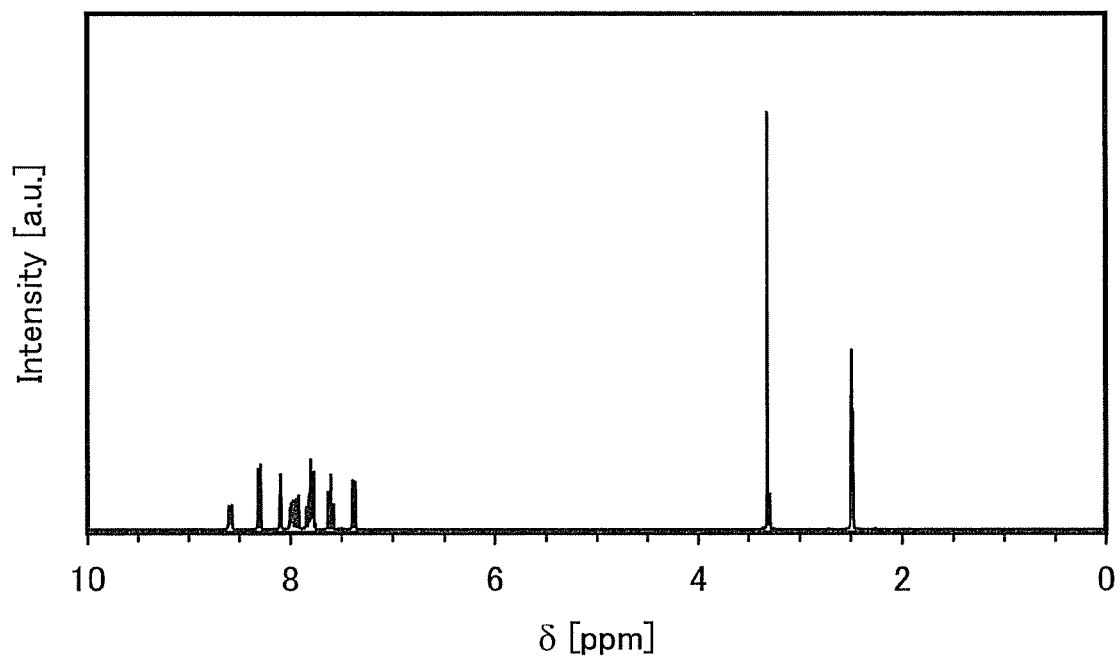
FIGS. 54A and 54B are $^1$H NMR charts of 3-(3-bromophenyl)-1,2,4-triazolo[3,4-c] isoquinoline.
Figure 54B:
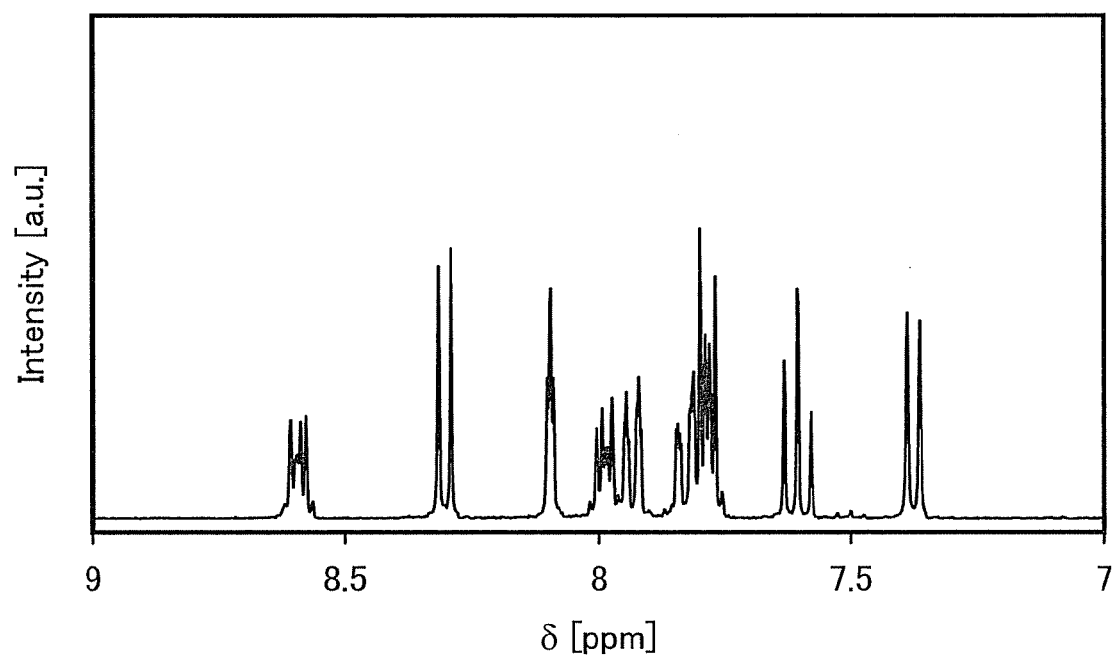

Further, the $^1$H NMR charts are shown in FIGS. 54A and 54B. Note that FIG. 54B is a chart where the range of from 7.0 ppm to 9.0 ppm in FIG. 54A is enlarged.

Step 3: Synthesis of 3-[3-(9H-Carbazol-9-yl)phenyl]-1,2,4-triazolo[3,4-a]isoquinoline (abbreviation: mCzTIq)

The synthesis scheme of Step 3 is illustrated in (J-3).

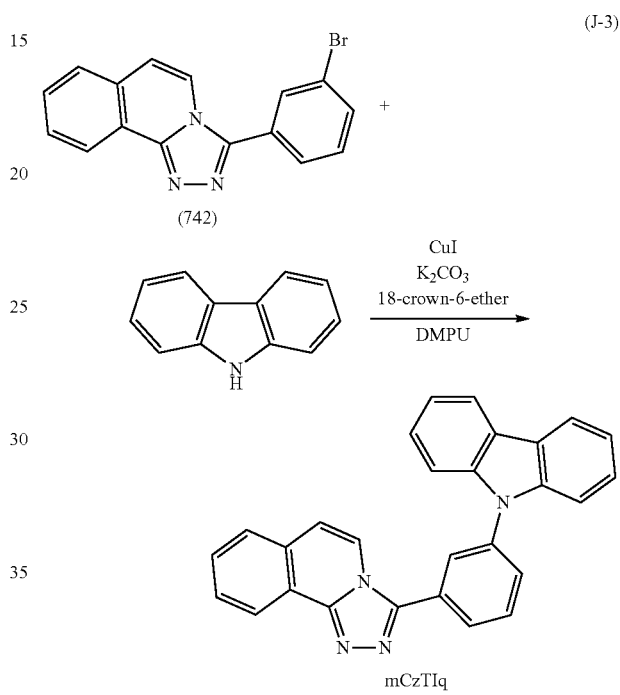

To a 200-mL three-neck flask were added 1.6 g (5.0 mmol) of 3-(3-bromophenyl)-1,2,4-triazolo[3,4-a]isoquinoline synthesized in Step 2, 0.92 g (5.5 mmol) of 9H-carbazole, 0.16 g (0.61 mmol) of 18-crown-6-ether, 1.4 g (10 mmol) of potassium carbonate, and 3 mL of 1,3-dimethyl-3,4,5,6-tetrahydro-2(1H)-pyrimidinone (DMPU). To this mixture was added 82 mg (0.43 mmol) of copper(I) iodide, and the mixture was stirred at 180° C. for 6 hours under a nitrogen stream. After the stirring, this mixture was cooled to room temperature, and chloroform was added thereto. The organic layer of the resulting mixture was washed with water, a saturated aqueous solution of sodium hydrogen carbonate and saturated brine, and the organic layer was dried over magnesium sulfate. The obtained mixture was gravity-filtered, and the filtrate was concentrated to give a solid. This solid was purified by silica gel column chromatography (toluene:ethyl acetate=5:1) to give a solid. A methanol suspension of the obtained solid was irradiated with ultrasonic waves, and the solid was collected by suction filtration. Further, this solid was recrystallized from toluene, so that the substance which was the object of the synthesis was obtained as 1.6 g of a white powder in 78% yield.

By a train sublimation method, 1.6 g of the obtained white powder of the substance which was the object of the synthesis was purified. The purification was conducted by heating of the white powder at 270° C. under a pressure of 2.6 Pa with a flow rate of argon gas of 5 mL/min. After the purification, the substance which was the object of the synthesis was obtained as 1.4 g of a white powder in 86% yield.

This compound was identified as mCzTIq, which was the object of the synthesis, by nuclear magnetic resonance (NMR) spectroscopy.

$^1$H NMR data of the obtained compound are as follows: $^1$H NMR (CDCl$_3$, 300 MHz): δ=7.12 (d, J=7.5 Hz, 1H), 7.32 (td, J=7.8 Hz, 0.9 Hz, 2H), 7.42-7.52 (m, 4H), 7.68-7.89 (m, 5H), 7.98-8.01 (m, 1H), 8.05 (d, J=7.5 Hz, 1H), 8.09-8.10 (m, 1H), 8.17 (d, J=7.8 Hz, 2H), 8.82 (d, J=8.4 Hz, 1H).

Figure 55A:
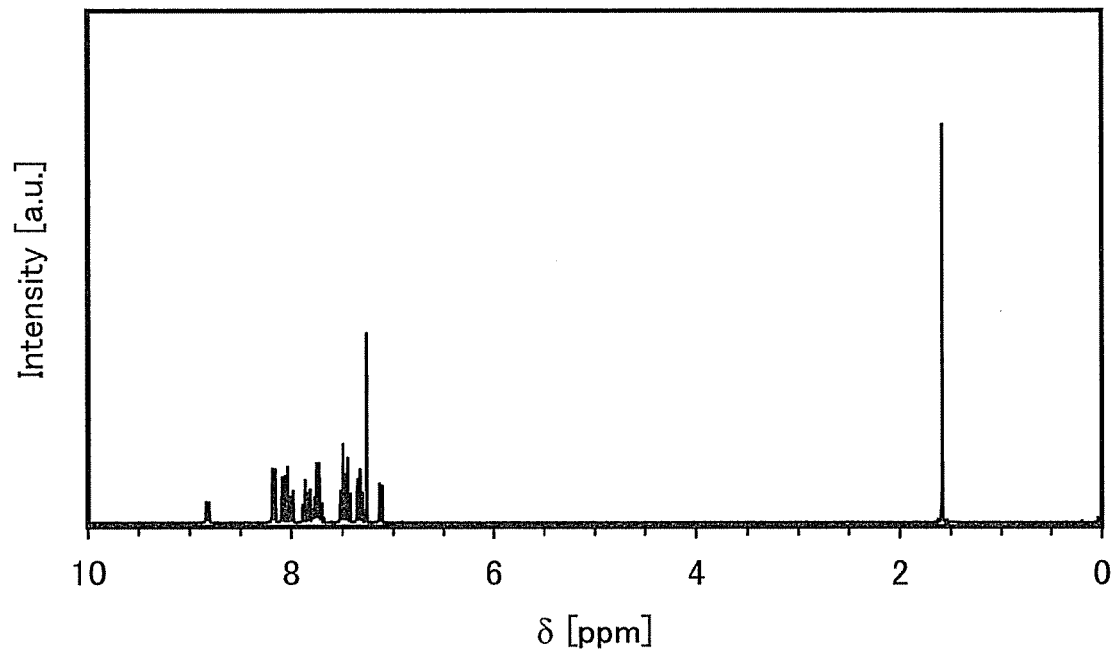
FIGS. 55A and 55B are $^1$H NMR charts of mCzTIq.
Figure 55B:
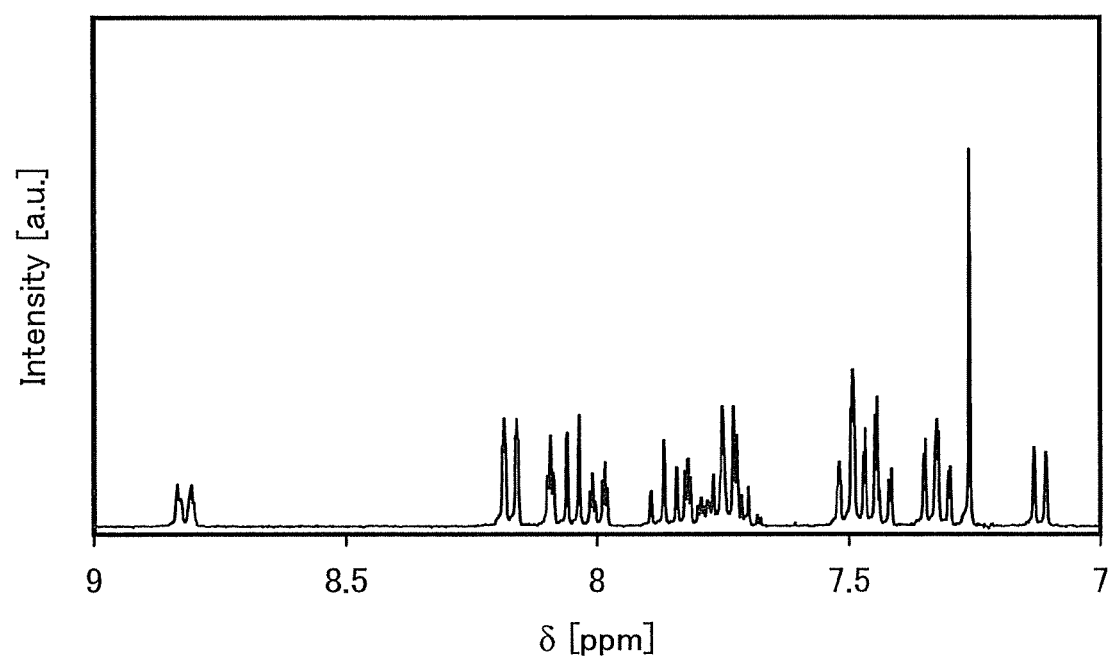

Further, the $^1$H NMR charts are shown in FIGS. 55A and 55B. Note that FIG. 55B is a chart where the range of from 7.0 ppm to 9.0 ppm in FIG. 55A is enlarged.

Figure 56A:
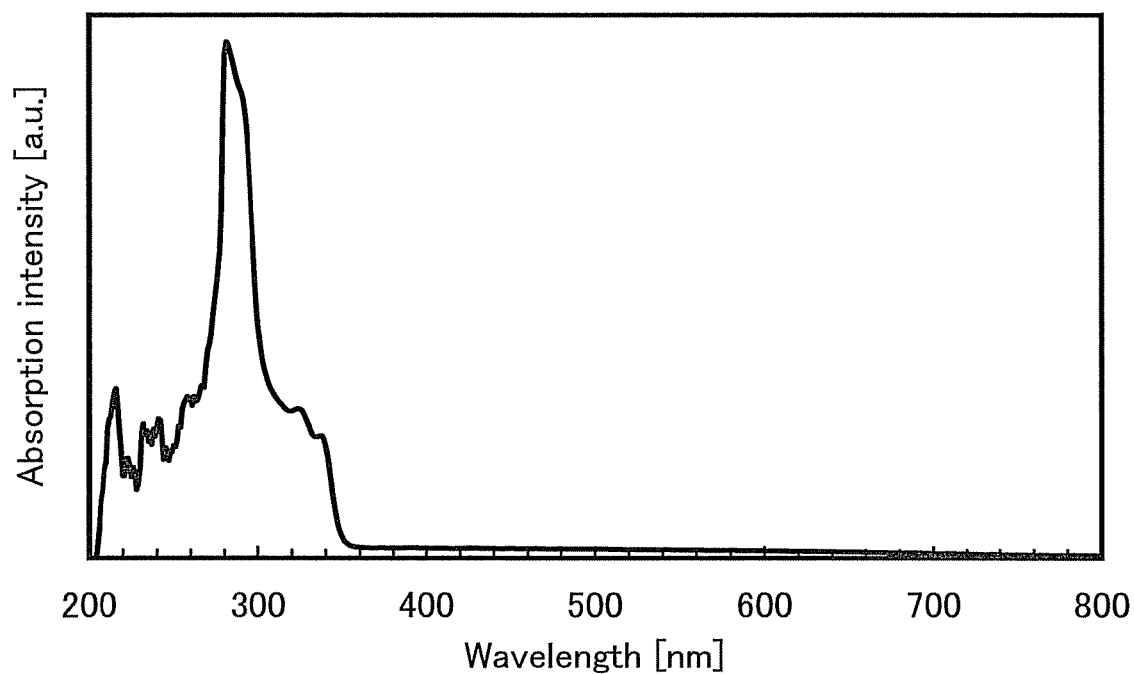
FIGS. 56A and 56B show an absorption and emission spectra of a toluene solution of mCzTIq.
Figure 56B:
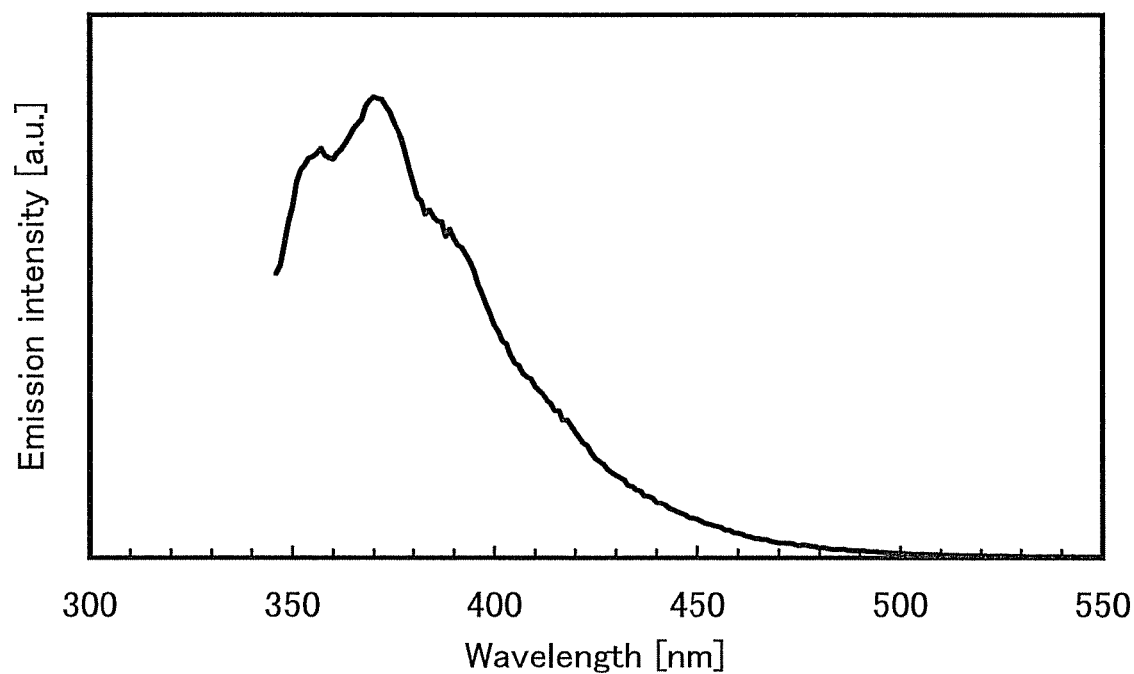
Figure 57A:
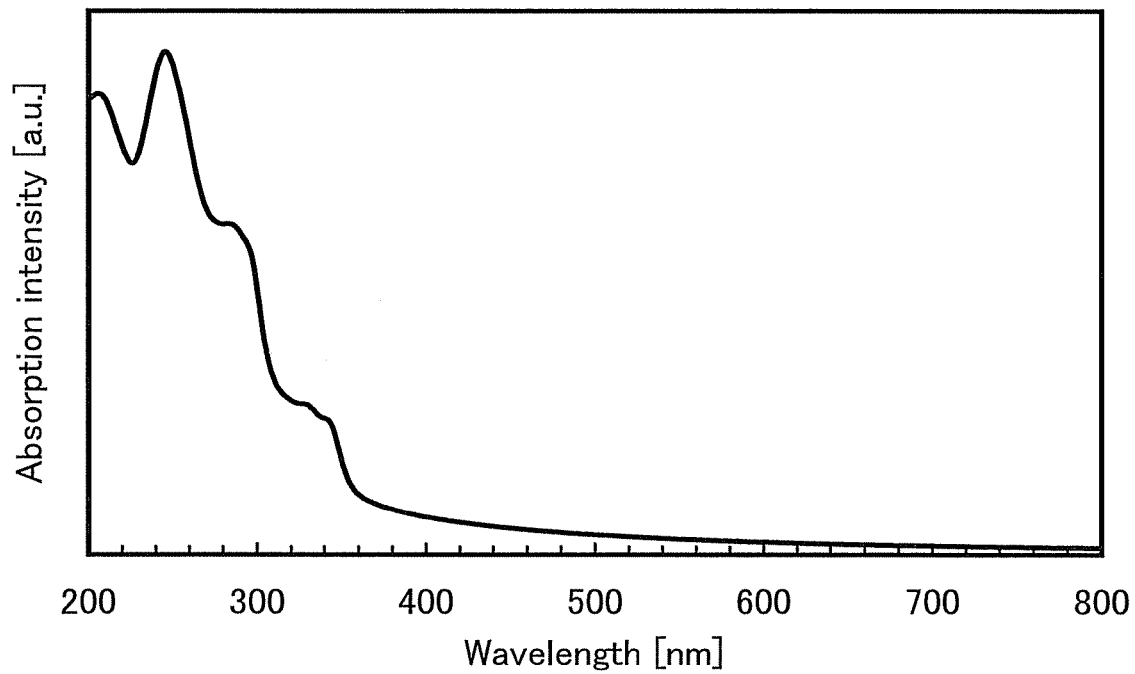
FIGS. 57A and 57B show an absorption and emission spectra of a thin film of mCzTIq.
Figure 57B:
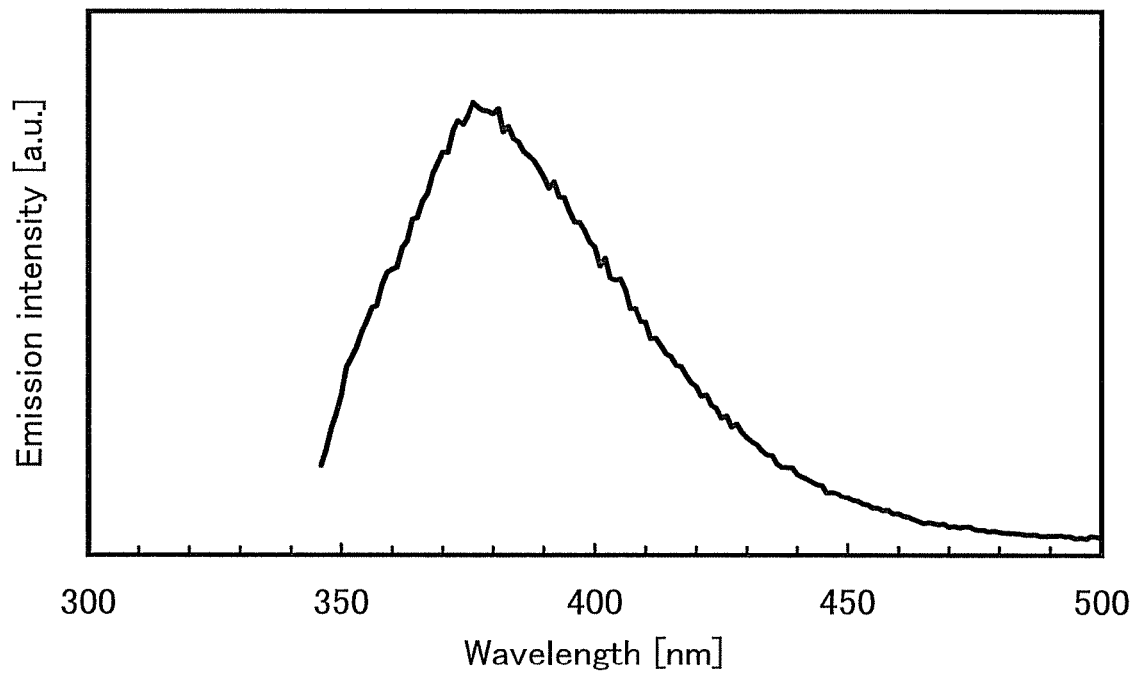

Further, FIG. 56A shows the absorption spectrum of a toluene solution of mCzTIq, and FIG. 56B shows the emission spectrum thereof. In addition, FIG. 57A shows the absorption spectrum of a thin film of mCzTIq, and FIG. 57B shows the emission spectrum thereof. An ultraviolet-visible spectrophotometer (V-550, manufactured by JASCO Corporation) was used for the measurements. Samples were prepared in such a way that the solution was put into a quartz cell and the thin film was formed on a quartz substrate by evaporation. Here are shown the absorption spectrum for the solution which was obtained by subtracting the absorption spectra of quartz and toluene from those of quartz and the solution, and the absorption spectrum for the thin film which was obtained by subtracting the absorption spectrum of a quartz substrate from those of the quartz substrate and the thin film. In FIG. 56A and FIG. 57A, the horizontal axis represents wavelength (nm) and the vertical axis represents absorption intensity (arbitrary unit). In FIG. 56B and FIG. 57B, the horizontal axis represents wavelength (nm) and the vertical axis represents emission intensity (arbitrary unit). In the case of the toluene solution, absorption peaks were found to be at around 281 nm, 324 nm, and 337 nm, and peaks of the emission wavelength were at 371 nm and 357 nm (at an excitation wavelength of 339 nm). In the case of the thin film, absorption peaks were found to be at around 206 nm, 246 nm, 284 nm, 329 nm, and 340 nm, and the peak of the emission wavelength was at 377 nm (at an excitation wavelength of 340 nm).

EXAMPLE 15

Synthesis Example 9

This example gives descriptions of a method of synthesizing 7-[4-(dibenzothiophen-4-yl)phenyl]-3-phenyl-1,2,4-triazolo[4,3-f]phenanthridine (abbreviation: 3Ph-7 DBTPTPt-II), which is the triazole derivative of one embodiment of the present invention represented by the structural formula (1005) in Embodiment 1, and a method of synthesizing 7-bromo-3-phenyl-1,2,4-triazolo[4,3-f]phenanthridine, which is the heterocyclic compound of one embodiment of the present invention represented by the structural formula (905) in Embodiment 1.

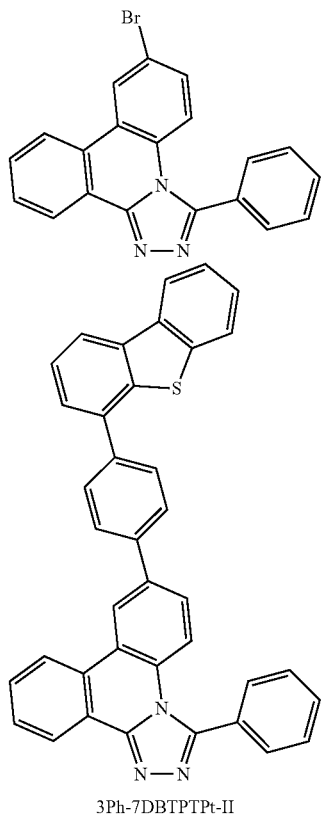

3Ph-7DBTPTPt-II

Step 1: Synthesis of N-Benzoyl-N-(2-bromophenanthridin-6-yl)hydrazine

The synthesis scheme of Step 1 is illustrated in (K-1).

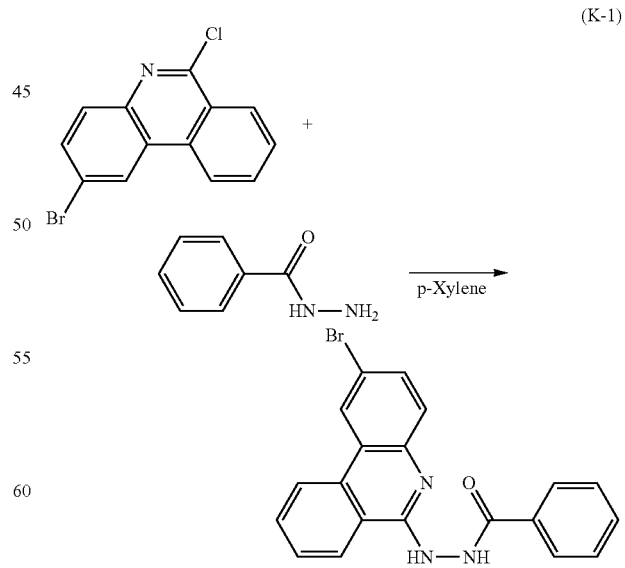

To a 200-mL three-neck flask were added 3.2 g (11 mmol) of 2-bromo-6-chlorophenanthridine, 1.8 g (13 mmol) of benzoylhydrazine, and 45 mL of para-xylene. This mixture was refluxed at 160° C. for 6 hours under a nitrogen stream. After a predetermined time elapsed, the temperature of this mixture was reduced to 100° C., and 100 mL of toluene was added thereto. This mixture was cooled to room temperature, and the precipitated solid was collected by suction filtration. The obtained solid was washed with toluene, water, a saturated aqueous solution of sodium hydrogen carbonate, and methanol. This solid was dried, so that a pale yellow powder of the substance that was the object of the synthesis was obtained. Further, the obtained organic solution was concentrated, and the resulting solid was washed with toluene and methanol, so that a pale yellow powder of the substance which was the object of the synthesis was obtained. Through these operations, the substance which was the object of the synthesis was obtained as 4.0 g of a pale yellow powder in 92% yield in total.

Step 2: Synthesis of 7-Bromo-3-phenyl-1,2,4-triazolo[4,3-f]phenanthridine

The synthesis scheme of Step 2 is illustrated in (K-2).

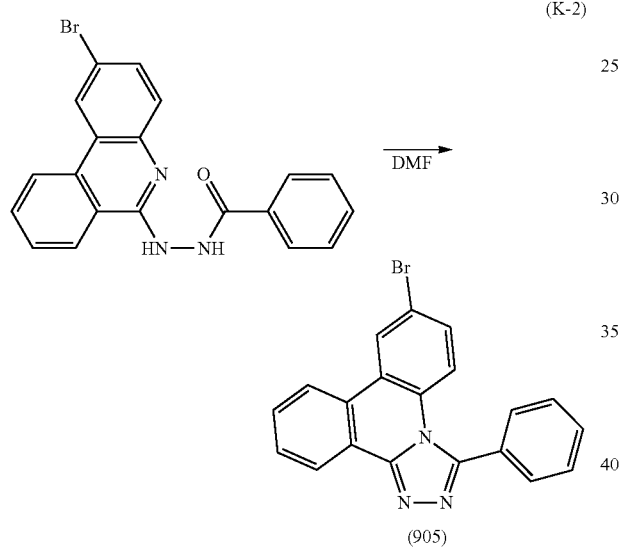

To a 500-mL three-neck flask were added 4.0 g (10 mmol) of N-benzoyl-N-(2-bromophenanthridin-6-yl)hydrazine and 200 mL of N,N-dimethylformamide. This mixture was stirred at 120° C. for 6 hours under a nitrogen stream. After a predetermined time elapsed, this mixture was cooled to room temperature, and chloroform and water were added thereto. Organic substances were extracted from the aqueous layer with chloroform. The obtained extract solution and the organic layer were washed with a saturated aqueous solution of sodium hydrogen carbonate and saturated brine, and the organic layer was dried over magnesium sulfate. The obtained mixture was gravity-filtered, and the filtrate was concentrated to give a solid. The obtained solid was purified by silica gel column chromatography (toluene:ethyl acetate=4:1) to give a solid. A methanol suspension of this solid was irradiated with ultrasonic waves, and a solid was collected by suction filtration, so that the substance which was the object of the synthesis was obtained as 2.9 g of a white powder in 75% yield.

This compound was identified as 7-bromo-3-phenyl-1,2,4-triazolo[4,3-f]phenanthridine, which was the object of the synthesis, by nuclear magnetic resonance (NMR) spectroscopy.

$^1$H NMR data of the obtained compound are as follows: $^1$H NMR (CDCl$_3$, 300 MHz): δ=7.40 (s, 2H), 7.58-7.80 (m, 7H), 8.29-8.32 (m, 1H), 8.54 (s, 1H), 8.83-8.86 (m, 1H).

Figure 58A:
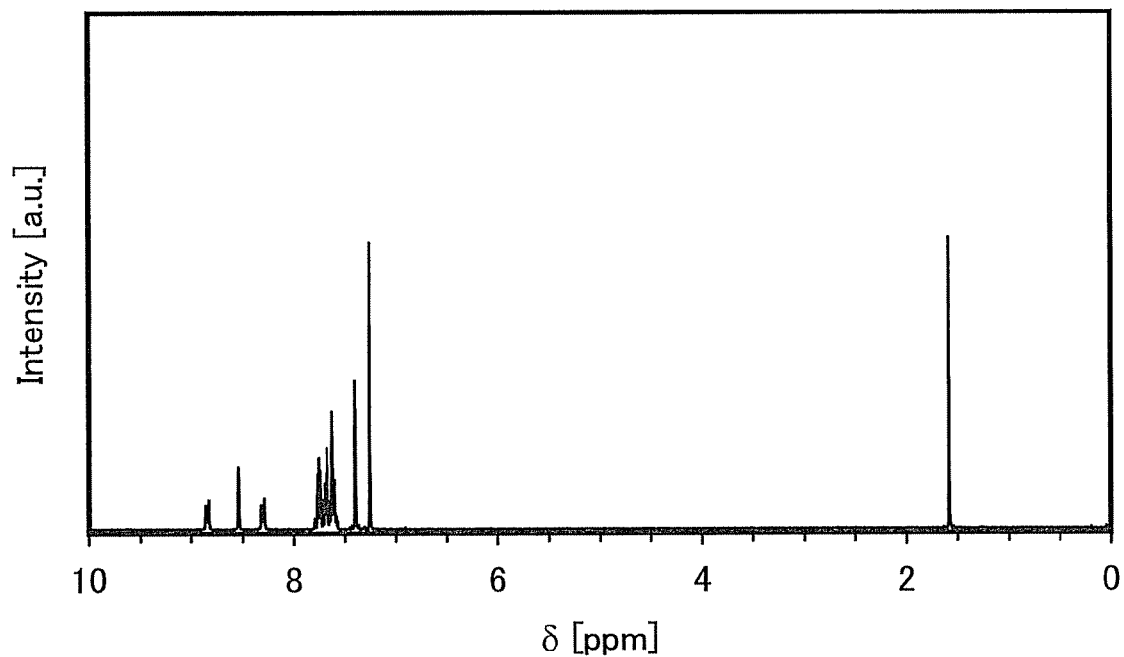
FIGS. 58A and 58B are $^1$H NMR charts of 7-bromo-3-phenyl-1,2,4-triazolo[4,3-f]phenanthridine.
Figure 58B:
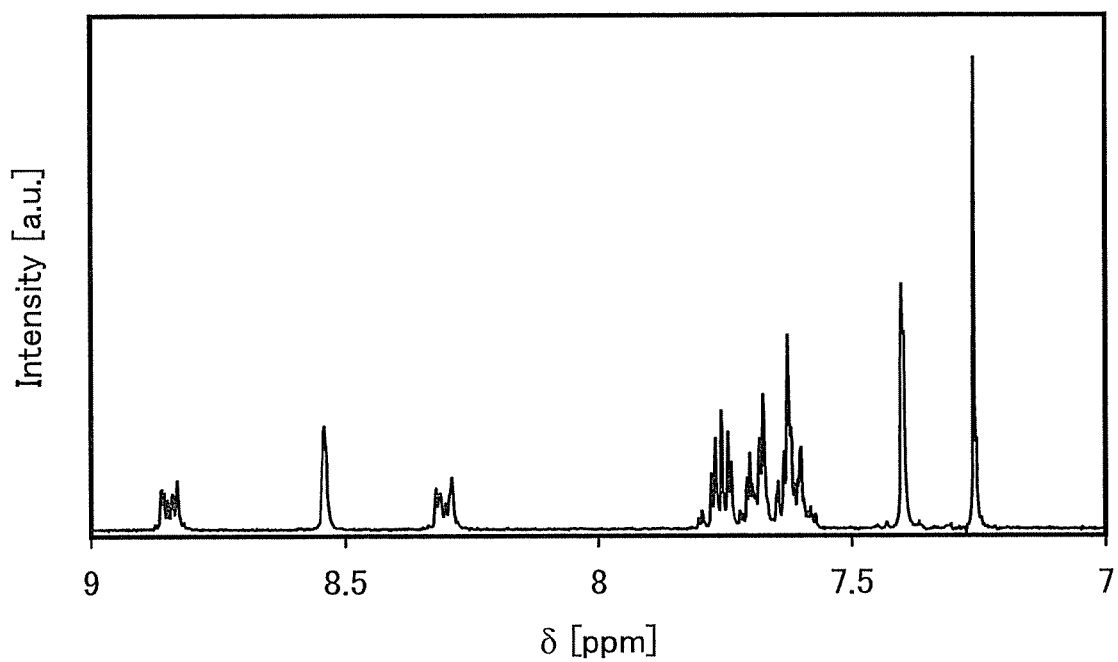

Further, the $^1$H NMR charts are shown in FIGS. 58A and 58B. Note that FIG. 58B is a chart where the range of from 7.0 ppm to 9.0 ppm in FIG. 58A is enlarged.

Step 3: Synthesis of 7-[4-(Dibenzothiophen-4-yl)phenyl]-3-phenyl-1,2,4-triazolo[4,3-f]phenanthridine (abbreviation: 3Ph-7 DBTPTPt-II)

The synthesis scheme of Step 3 is illustrated in (K-3).

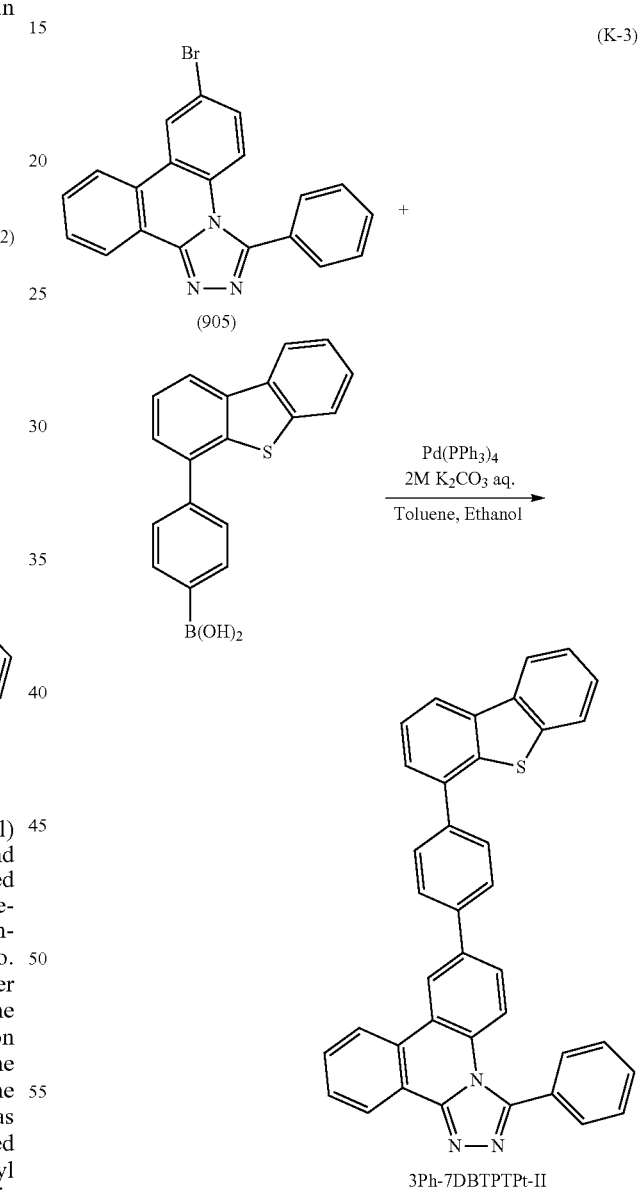

To a 100-mL three-neck flask were added 0.94 g (2.5 mmol) of 7-bromo-3-phenyl-1,2,4-triazolo[4,3-f]phenanthridine synthesized in Step 2, 0.84 g (2.8 mmol) of 4-(dibenzothiophen-4-yl)phenylboronic acid, 25 mL of toluene, 3 mL of ethanol, and 3 mL of a 2M aqueous potassium carbonate solution. This mixture was degassed by being stirred under reduced pressure, and the air in the flask was replaced with nitrogen. To this mixture were added 71 mg (62 μmol) of tetrakis(triphenylphosphine)palladium(0). This mixture was stirred at 80° C. for 8 hours under a nitrogen stream. After the stirring, water was added to the obtained mixture, and organic substances were extracted from the aqueous layer with chloroform. The obtained extract solution combined with the organic layer was washed with a saturated aqueous solution of sodium hydrogen carbonate and saturated brine, and the organic layer was dried over magnesium sulfate. The obtained mixture was gravity-filtered, and the filtrate was concentrated to give a solid. Methanol was added to the obtained solid, and irradiation with ultrasonic waves was performed. The precipitated solid was collected by suction filtration. This solid was purified by alumina column chromatography (toluene:ethyl acetate=10:1), and further recrystallized from toluene, so that the substance which was the object of the synthesis was obtained as 0.74 g of a white powder in 53% yield.

By a train sublimation method, 0.68 g of the obtained white powder of the substance which was the object of the synthesis was purified. The purification was conducted by heating of the white powder at 330° C. for 15 hours under a pressure of 2.6 Pa with a flow rate of argon gas of 5 mL/min. After the purification, the substance which was the object of the synthesis was obtained as 0.59 g of a white powder in 87% yield.

This compound was identified as 3Ph-7 DBTPTPt-II, which was the object of the synthesis, by nuclear magnetic resonance (NMR) spectroscopy.

$^1$H NMR data of the obtained compound are as follows: $^1$H NMR (CDCl$_3$, 300 MHz): δ=7.46-7.70 (m, 9H), 7.72-7.91 (m, 9H), 8.18-8.24 (m, 2H), 8.51 (d, J=7.2 Hz, 1H), 8.72 (d, J=1.5 Hz, 1H), 8.89 (dd, J=7.2 Hz, 1.5 Hz, 1H).

Figure 59A:
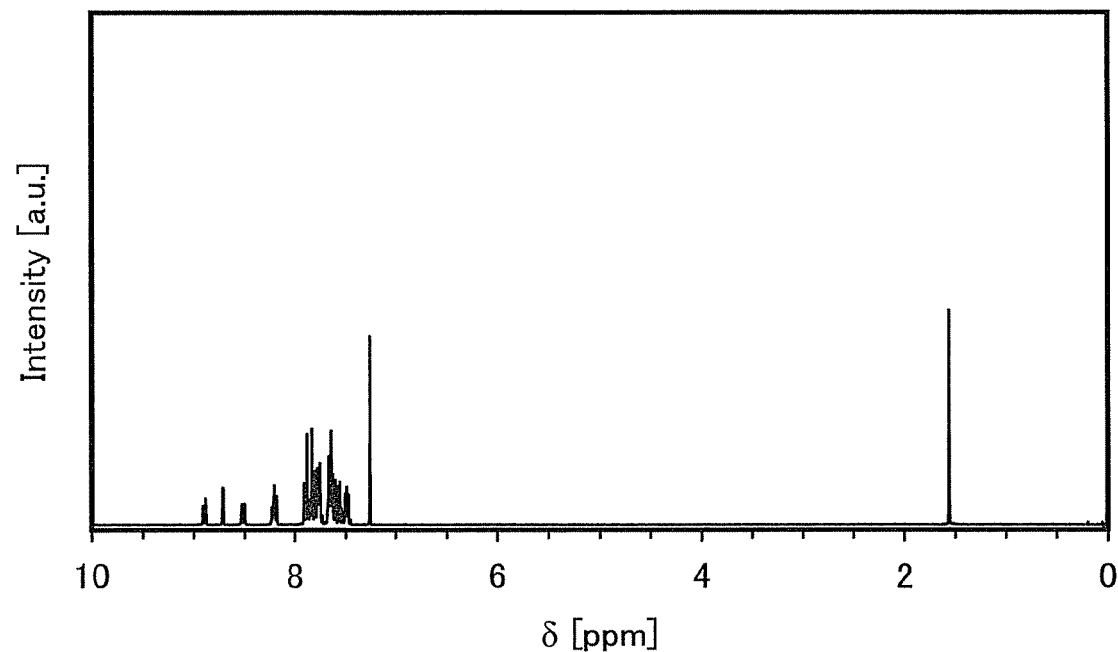
FIGS. 59A and 59B are $^1$H NMR charts of 3Ph-7 DBTPTPt-II.
Figure 59B:
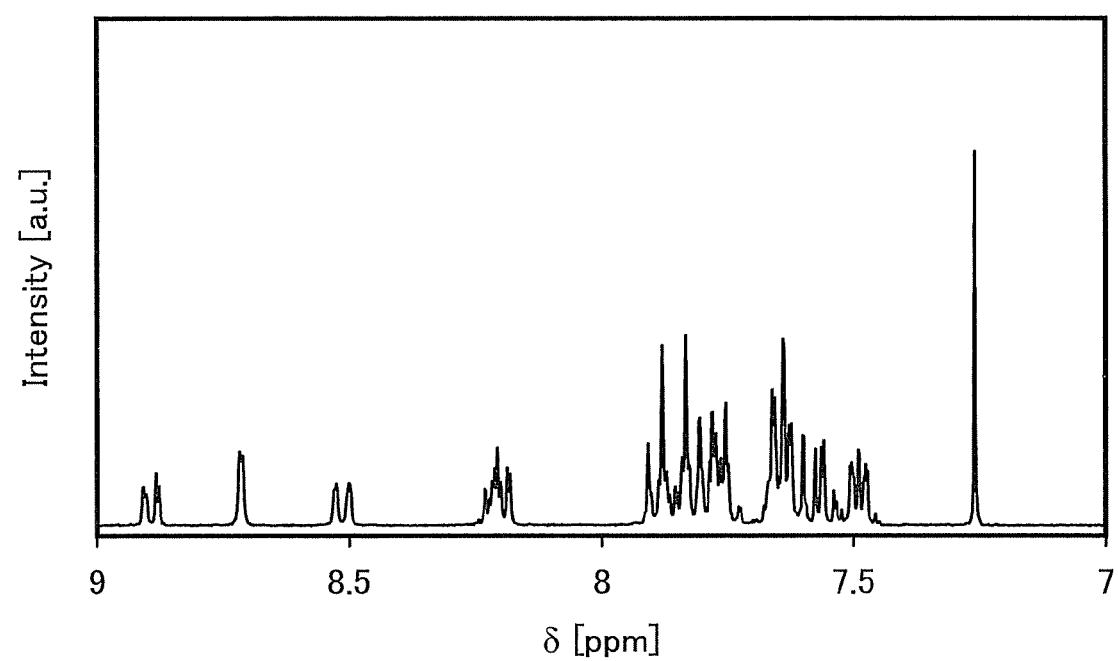

Further, the $^1$H NMR charts are shown in FIGS. 59A and 59B. Note that FIG. 59B is a chart where the range of from 7.0 ppm to 9.0 ppm in FIG. 59A is enlarged.

Figure 60A:
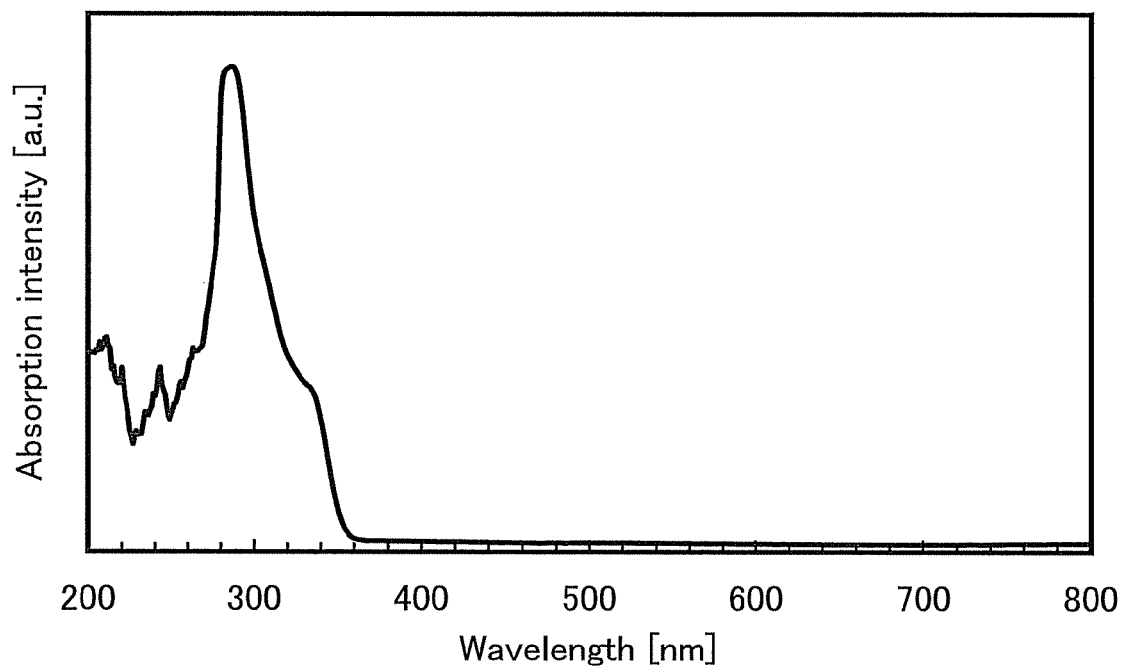
FIGS. 60A and 60B show an absorption and emission spectra of a toluene solution of 3Ph-7DBTPTPt-II.
Figure 60B:
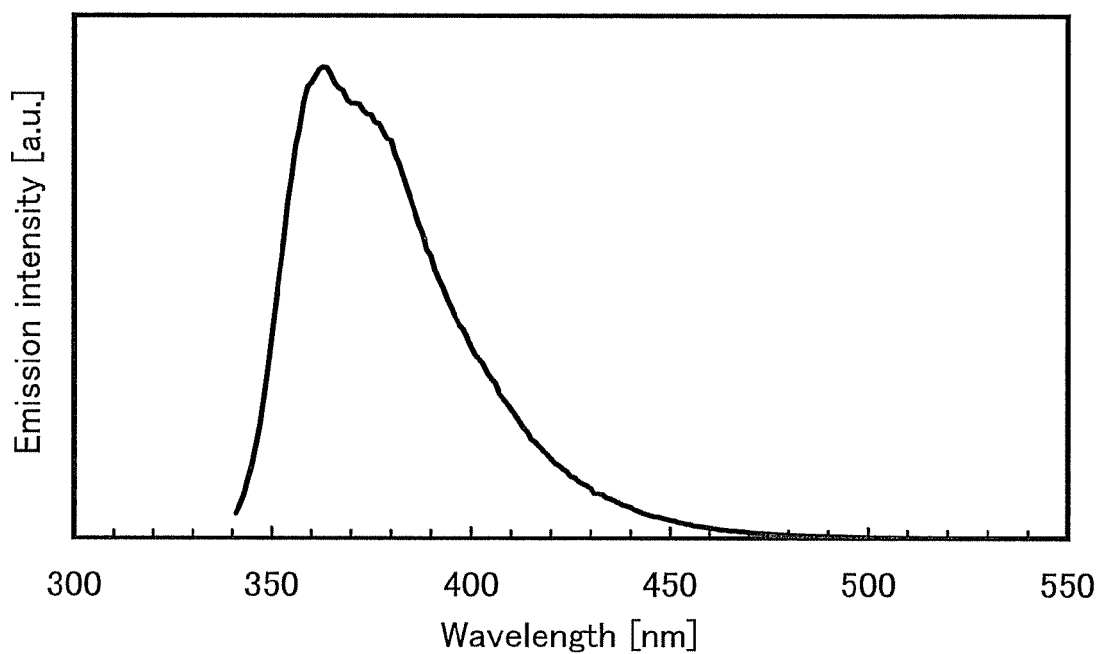
Figure 61A:
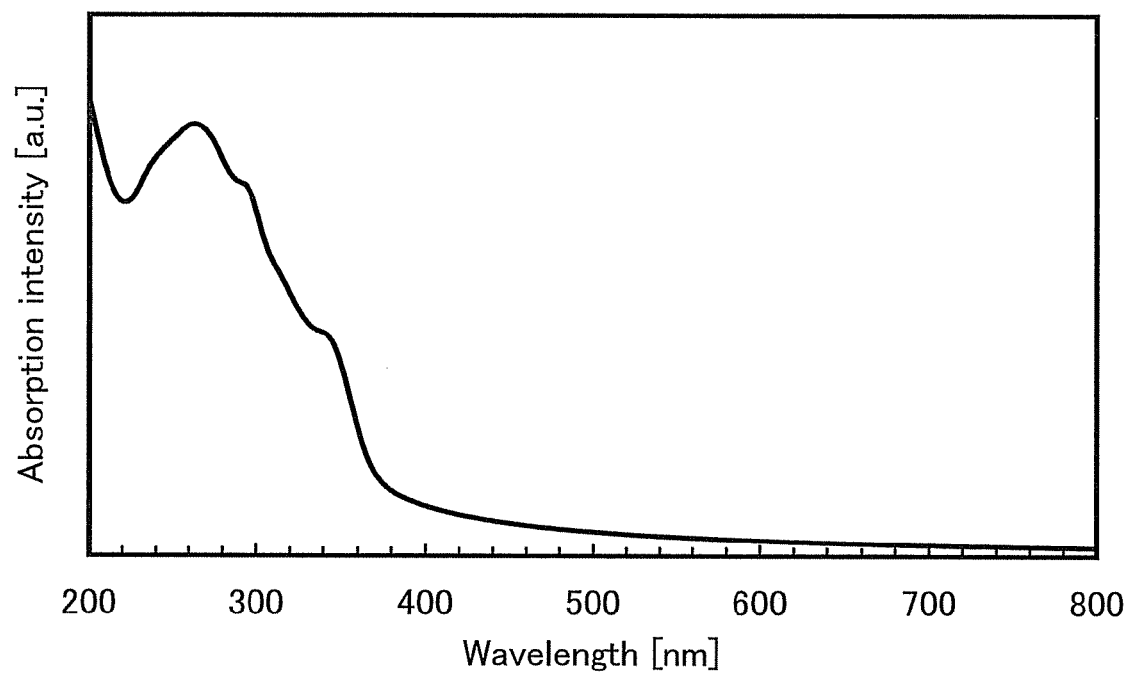
FIGS. 61A and 61B show an absorption and emission spectra of a thin film of 3Ph-7 DBTPTPt-II.
Figure 61B:
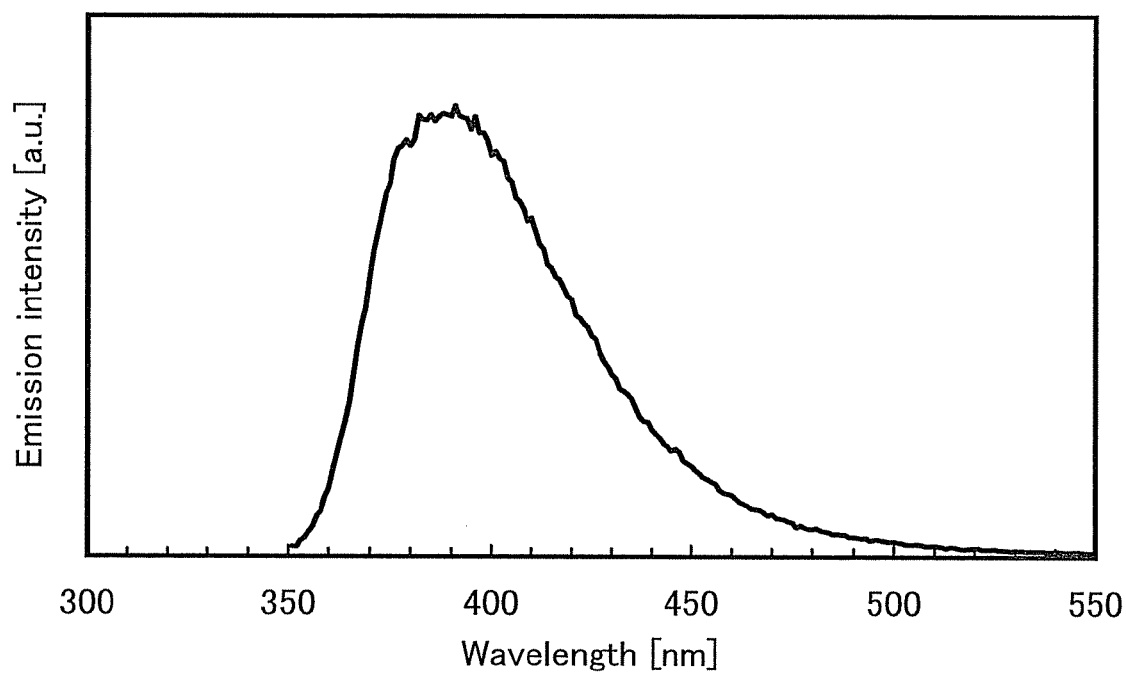

Further, FIG. 60A shows the absorption spectrum of a toluene solution of 3Ph-7 DBTPTPt-II, and FIG. 60B shows the emission spectrum thereof. In addition, FIG. 61A shows the absorption spectrum of a thin film of 3Ph-7 DBTPTPt-II, and FIG. 61B shows the emission spectrum thereof. An ultraviolet-visible spectrophotometer (V-550, manufactured by JASCO Corporation) was used for the measurements. Samples were prepared in such a way that the solution was put into a quartz cell and the thin film was formed on a quartz substrate by evaporation. Here are shown the absorption spectrum for the solution which was obtained by subtracting the absorption spectra of quartz and toluene from those of quartz and the solution, and the absorption spectrum for the thin film which was obtained by subtracting the absorption spectrum of a quartz substrate from those of the quartz substrate and the thin film. In FIG. 60A and FIG. 61A, the horizontal axis represents wavelength (nm) and the vertical axis represents absorption intensity (arbitrary unit). In FIG. 60B and FIG. 61B, the horizontal axis represents wavelength (nm) and the vertical axis represents emission intensity (arbitrary unit). In the case of the toluene solution, absorption peaks were found to be at around 286 nm and 334 nm, and the peak of the emission wavelength was at 363 nm (at an excitation wavelength of 336 nm). In the case of the thin film, absorption peaks were found to be at around 242 nm, 264 nm, 292 nm, and 340 nm, and the peak of the emission wavelength was at 390 nm (at an excitation wavelength of 346 nm).

EXAMPLE 16

Synthesis Example 10

This example gives descriptions of a method of synthesizing 7-[3-(dibenzothiophen-4-yl)phenyl]-3-phenyl-1,2,4-triazolo[4,3-f]phenanthridine (abbreviation: 3Ph-7mDBTPTPt-II), which is the triazole derivative of one embodiment of the present invention represented by the structural formula (1014) in Embodiment 1.

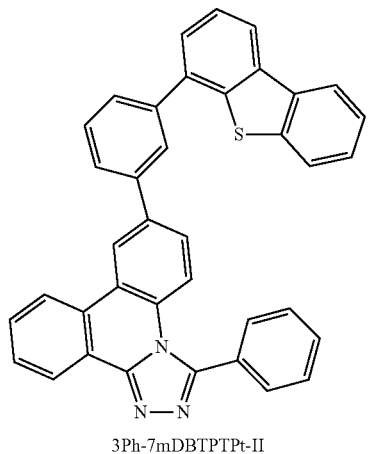 [SMILES: c1ccc(-c2nnc3c4ccccc4c4cc(-c5cccc(-c6cccc7c6sc6ccccc67)c5)ccc4n23)cc1]

3Ph-7mDBTPTPt-II

A scheme of the synthesis of 3Ph-7mDBTPTPt-II is illustrated in (L-1).

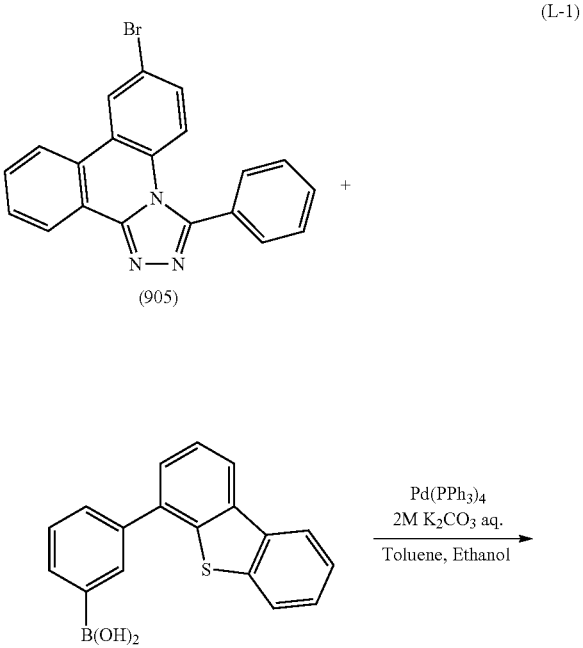

(L-1)

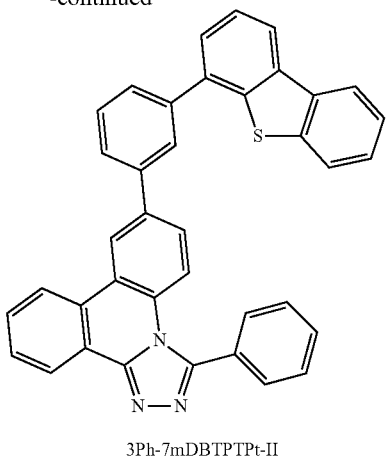

3Ph-7mDBTPTPt-II

To a 100-mL three-neck flask were added 0.94 g (2.5 mmol) of 7-bromo-3-phenyl-1,2,4-triazolo[4,3-f]phenanthridine, 0.87 g (2.9 mmol) of 3-(dibenzothiophen-4-yl)phenylboronic acid, 25 mL of toluene, 3 mL of ethanol, and 3 mL of a 2M aqueous potassium carbonate solution. This mixture was degassed by being stirred under reduced pressure, and the air in the flask was replaced with nitrogen. To this mixture were added 87 mg (75 μmol) of tetrakis(triphenylphosphine)palladium(0). This mixture was stirred at 100° C. for 7 hours under a nitrogen stream. After the stirring, water was added to the obtained mixture, and organic substances were extracted from the aqueous layer with toluene. The obtained extract solution combined with the organic layer was washed with a saturated aqueous solution of sodium hydrogen carbonate and saturated brine, and the organic layer was dried over magnesium sulfate. The obtained mixture was gravity-filtered, and the filtrate was concentrated to give an oily substance. The obtained oily substance was purified by alumina column chromatography (toluene:ethyl acetate=10:1) to give an oily substance. This oily substance was purified by high performance liquid column chromatography. The high performance liquid column chromatography was performed by using chloroform as a developing solvent. The obtained fraction was concentrated to give an oily substance. Methanol was added to this oily substance, and irradiation with ultrasonic waves was performed. The precipitated solid was collected by suction filtration, so that the substance which was the object of the synthesis was obtained as 0.92 g of a white powder in 66% yield.

By a train sublimation method, 0.89 g of the obtained white powder of the substance which was the object of the synthesis was purified. The purification was conducted by heating of the white powder at 310° C. under a pressure of 2.8 Pa with a flow rate of argon gas of 5 mL/min. After the purification, the substance which was the object of the synthesis was obtained as 0.76 g of a white powder in 85% yield.

This compound was identified as 3Ph-7mDBTPTPt-II, which was the object of the synthesis, by nuclear magnetic resonance (NMR) spectroscopy.

$^1$H NMR data of the obtained compound are as follows: $^1$H NMR (CDCl$_3$, 300 MHz): δ=7.47-7.86 (m, 17H), 8.05-8.06 (m, 1H), 8.18-8.22 (m, 2H), 8.47 (dd, J=7.2 Hz, 1.8 Hz, 1H), 8.70 (s, 1H), 8.87 (dd, J=7.5 Hz, 1.5 Hz, 1H).

Figure 62A:
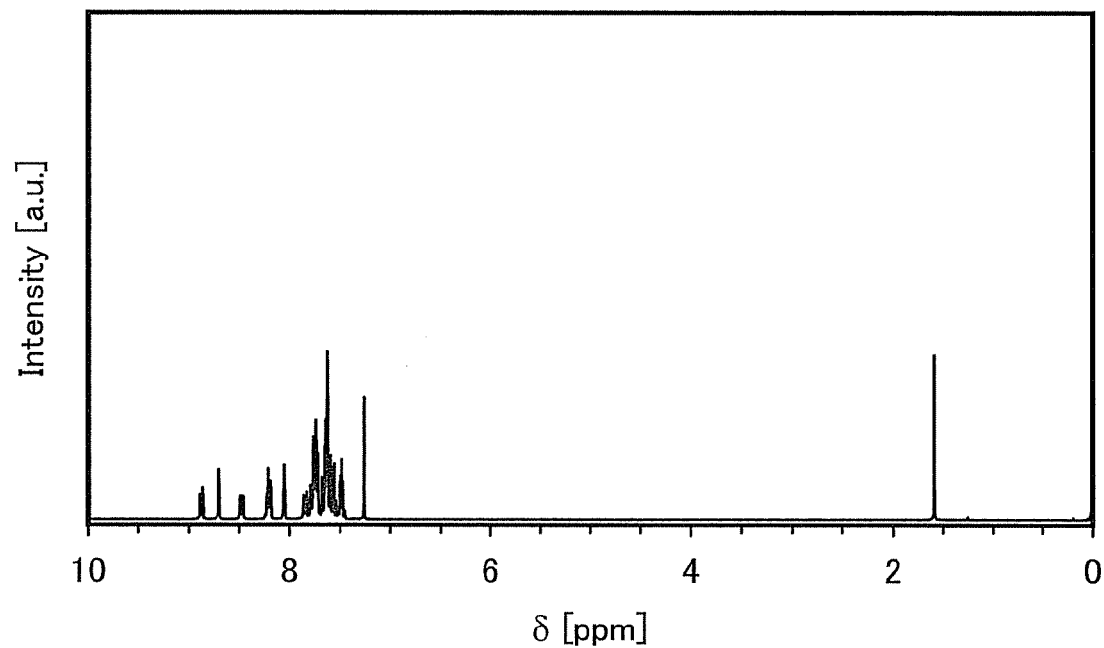
FIGS. 62A and 62B are $^1$H NMR charts of 3Ph-7mDBTPTPt-II.
Figure 62B:
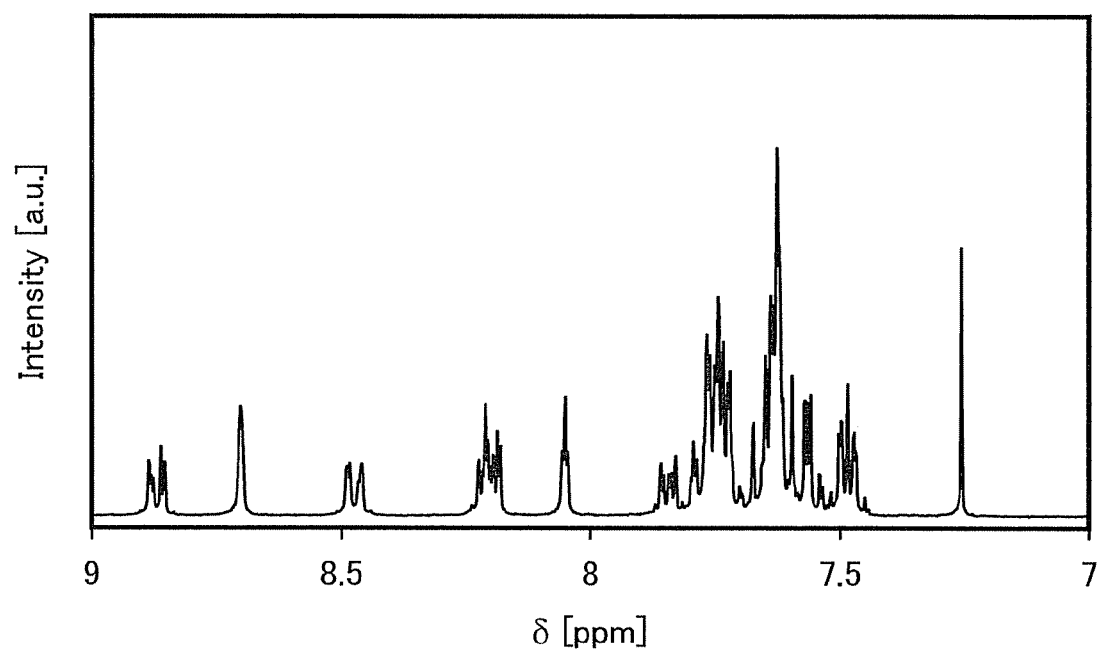

Further, the NMR charts are shown in FIGS. 62A and 62B. Note that FIG. 62B is a chart where the range of from 7.0 ppm to 9.0 ppm in FIG. 62A is enlarged.

Figure 63A:
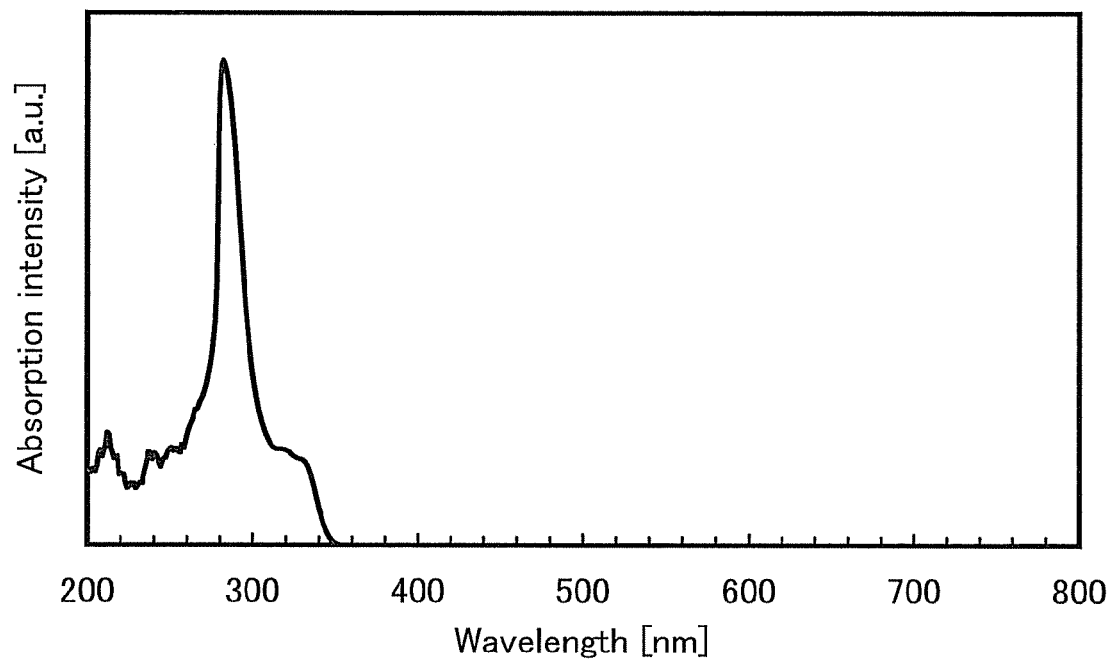
FIGS. 63A and 63B show an absorption and emission spectra of a toluene solution of 3Ph-7mDBTPTPt-II.
Figure 63B:
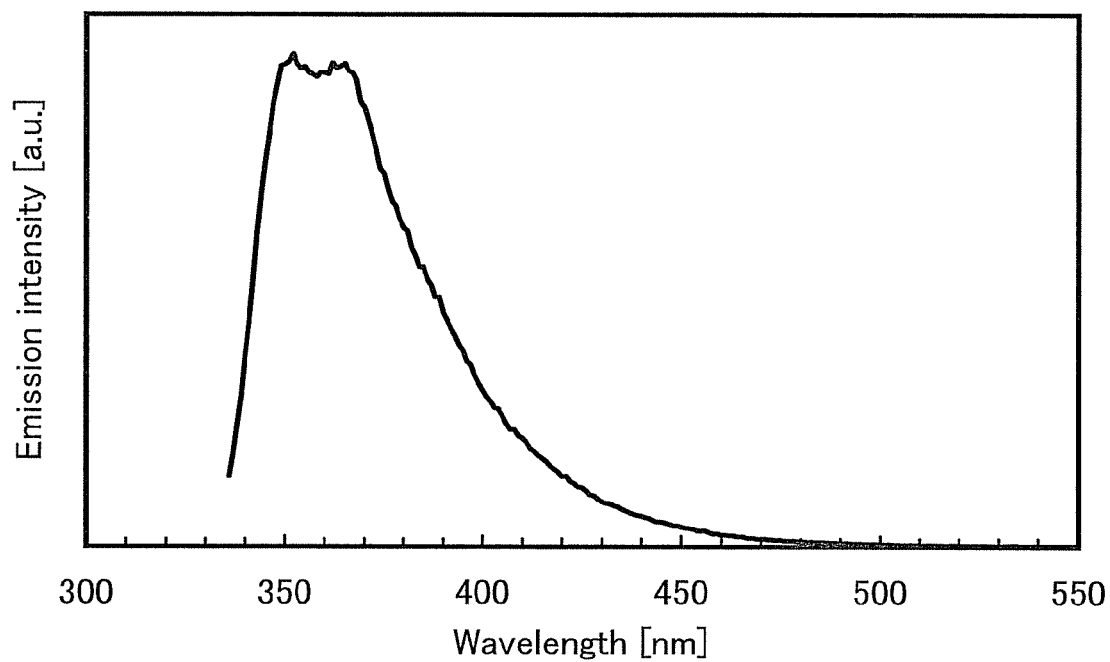
Figure 64A:
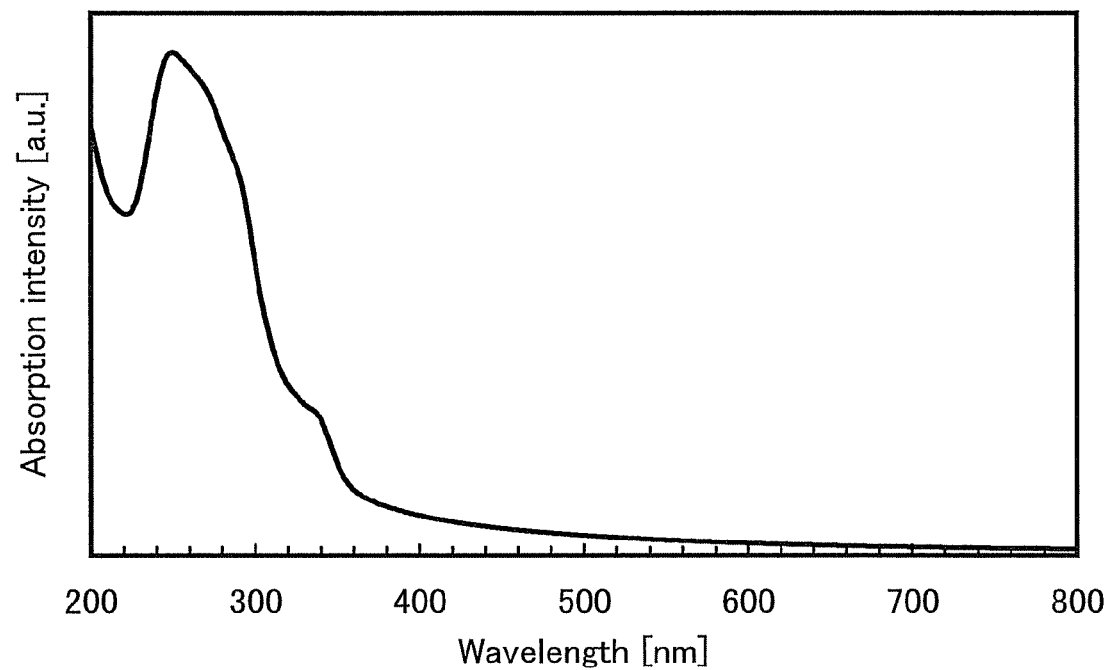
FIGS. 64A and 64B show an absorption and emission spectra of a thin film of 3Ph-7mDBTPTPt-II.
Figure 64B:
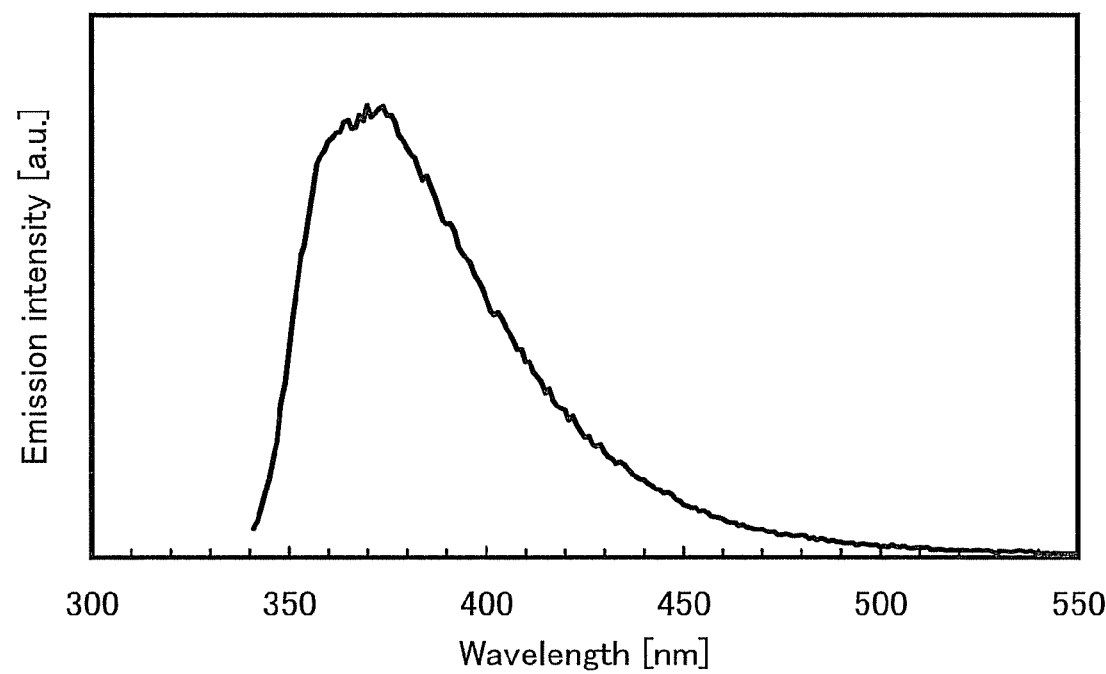

Further, FIG. 63A shows the absorption spectrum of a toluene solution of 3Ph-7mDBTPTPt-II, and FIG. 63B shows the emission spectrum thereof. In addition, FIG. 64A shows the absorption spectrum of a thin film of 3Ph-7mDBTPTPt-II, and FIG. 64B shows the emission spectrum thereof. An ultraviolet-visible spectrophotometer (V-550, manufactured by JASCO Corporation) was used for the measurements. Samples were prepared in such a way that the solution was put into a quartz cell and the thin film was formed on a quartz substrate by evaporation. Here are shown the absorption spectrum for the solution which was obtained by subtracting the absorption spectra of quartz and toluene from those of quartz and the solution, and the absorption spectrum for the thin film which was obtained by subtracting the absorption spectrum of a quartz substrate from those of the quartz substrate and the thin film. In FIG. 63A and FIG. 64A, the horizontal axis represents wavelength (nm) and the vertical axis represents absorption intensity (arbitrary unit). In FIG. 63B and FIG. 64B, the horizontal axis represents wavelength (nm) and the vertical axis represents emission intensity (arbitrary unit). In the case of the toluene solution, absorption peaks were found to be at around 282 nm and 329 nm, and emission wavelength peaks were 352 nm and 364 nm (at an excitation wavelength of 331 nm). In the case of the thin film, absorption peaks were found to be at around 250 nm, 266 nm, 287 nm, and 335 nm, and the peak of the emission wavelength was at 373 nm (at an excitation wavelength of 335 nm).

EXAMPLE 17

Synthesis Example 11

This example gives descriptions of a method of synthesizing 7-bromo-1,2,4-triazolo[4,3-f]phenanthridine, which is the heterocyclic compound of one embodiment of the present invention represented by the structural formula (900) in Embodiment 1.

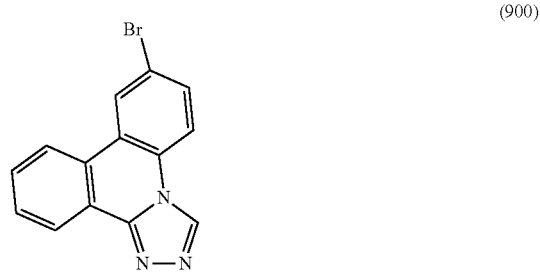 [SMILES: Brc1ccc2c(c1)c1ccccc1c1nncn21]

A scheme of the synthesis of 7-bromo-1,2,4-triazolo[4,3-f]phenanthridine is illustrated in (M-1).

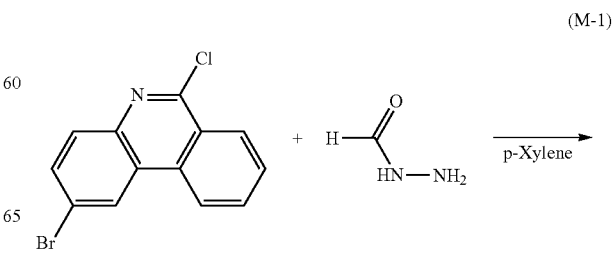

-continued

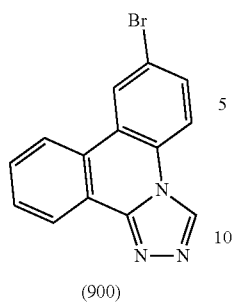

(900)

To a 500-mL three-neck flask were added 2.6 g (8.9 mmol) of 2-bromo-6-chlorophenanthridine, 0.65 g (11 mmol) of formylhydrazine, and 36 mL of para-xylene. Under a nitrogen stream, this mixture was stirred at 120° C. for 8 hours and refluxed at 160° C. for 12 hours. After the reflux, this mixture was cooled to room temperature, 100 mL of toluene and 50 mL of water were added thereto, and the solid in the mixture was subjected to suction filtration, followed by washing with methanol, so that a solid was obtained. The obtained filtrate was washed with a saturated aqueous solution of sodium hydrogen carbonate and saturated brine, and the organic layer was dried over magnesium sulfate. The obtained mixture was gravity-filtered, and the filtrate was concentrated to give a solid. These obtained solids were purified by silica gel column chromatography (chloroform:ethyl acetate=4:1), and further recrystallized from toluene, so that the substance which was the object of the synthesis was obtained as 1.1 g of a white powder in 40% yield.

This compound was identified as 7-bromo-1,2,4-triazolo[4,3-J]phenanthridine, which was the object of the synthesis, by nuclear magnetic resonance (NMR) spectroscopy.

$^1$H NMR data of the obtained compound are as follows: $^1$H NMR (CDCl$_3$, 300 MHz): δ=7.73-7.85 (m, 4H), 8.33 (dd, 7.2 Hz, 2.1 Hz, 1H), 8.59 (d, 2.1 Hz, 1H), 8.79 (dd, 7.2 Hz, 2.1 Hz, 1H), 9.18 (s, 1H).

Figure 65A:
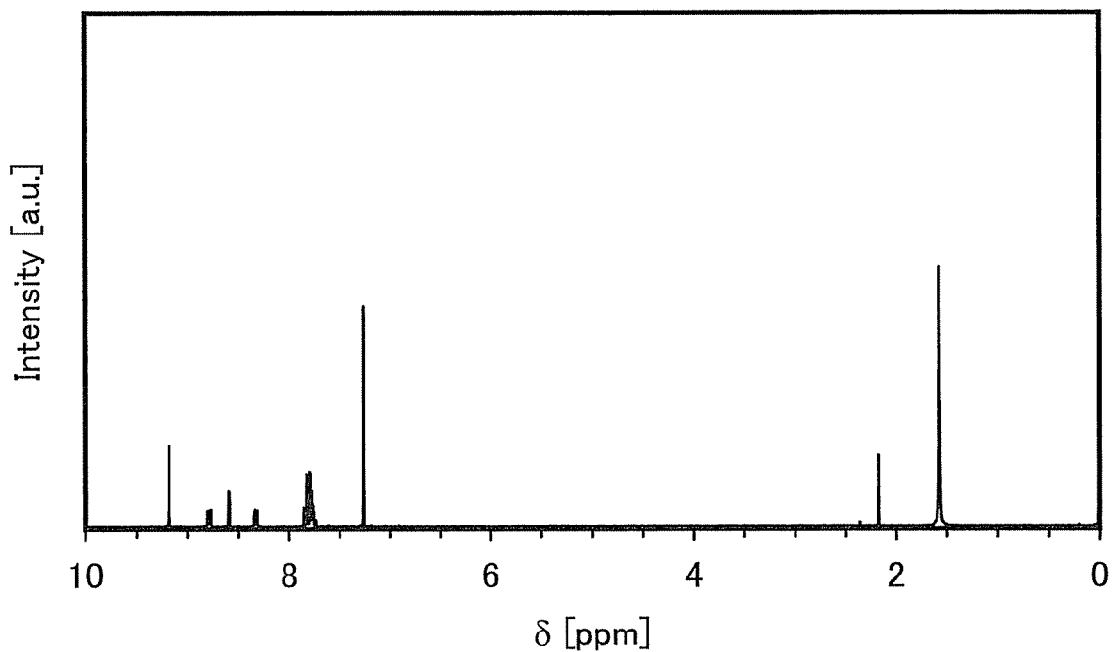
FIGS. 65A and 65B show NMR charts of 7-bromo-1,2,4-triazolo[4,3-f]phenanthridine.
Figure 65B:
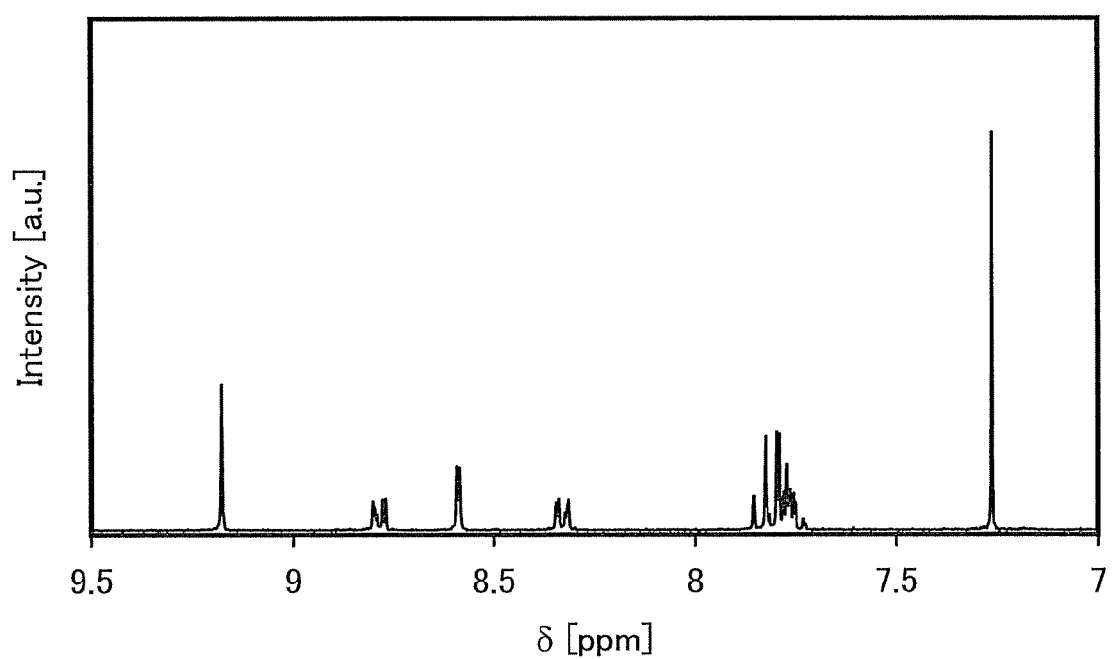

Further, the $^1$H NMR charts are shown in FIGS. 65A and 65B. Note that FIG. 65B is a chart where the range of from 7.0 ppm to 9.5 ppm in FIG. 65A is enlarged

EXAMPLE 18

Figure 22D:
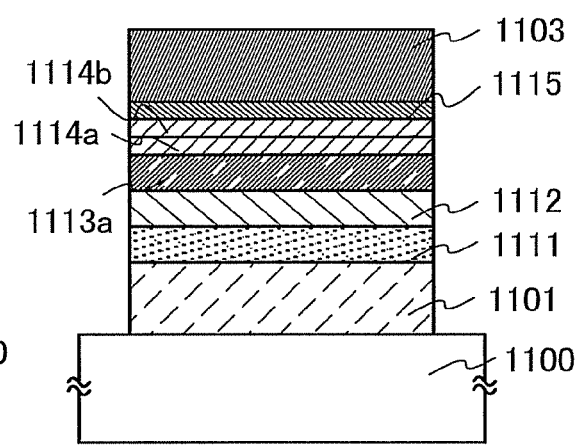

In this example, a light-emitting element of one embodiment of the present invention will be described with reference to FIG. 22D. The chemical formula of a material used in this example is illustrated below. Note that the chemical formulae of materials which are already illustrated will be omitted.

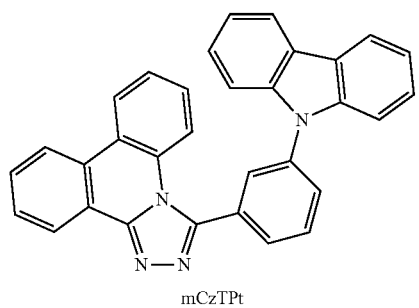 [SMILES: c1cc(-c2nnc3c4ccccc4c4ccccc4n23)cc(-n2c3ccccc3c3ccccc32)c1]

mCzTPt

The way how Light-Emitting Element 11 was fabricated will now be described.

(Light-Emitting Element 11)

First, an ITSO film was formed on a glass substrate 1100 by a sputtering method, so that the first electrode 1101 was formed. Note that its thickness was set to 110 nm and the electrode area was set to 2 mm×2 mm.

In pretreatment for forming the light-emitting element on the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about $10^{-4}$ Pa. Then, CBP and molybdenum(VI) oxide were co-evaporated to foam the hole-injection layer 1111 on the first electrode 1101. The thickness of the hole-injection layer 1111 was set to 60 nm, and the weight ratio of CBP to molybdenum(VI) oxide was adjusted to 4:2 (=CBP:molybdenum oxide).

Next, on the hole-injection layer 1111, a BPAFLP film was formed to a thickness of 30 nm to form the hole-transport layer 1112.

Further, 3-[3-(9H-carbazol-9-yl)phenyl]-1,2,4-triazolo[4,3-f]phenanthridine (abbreviation: mCzTPt) synthesized in Example 12 and Ir(ppy)$_3$ were co-evaporated to form a light-emitting layer 1113 on the hole-transport layer 1112. Here, the weight ratio of mCzTPt to Ir(ppy)$_3$ was adjusted to 1:0.08 (=mCzTPt:Ir(ppy)$_3$). In addition, the thickness of the light-emitting layer 1113 was set to 30 nm.

Further, on the light-emitting layer 1113, a film of DBT-TPt-II synthesized in Example 1 was formed to a thickness of 15 nm to form the first electron-transport layer 1114a.

Then, on the first electron-transport layer 1114a, a BPhen film was formed to a thickness of 15 nm to form the second electron-transport layer 1114b.

Further, on the second electron-transport layer 1114b, a 1-nm-thick LiF film was formed by evaporation to form the electron-injection layer 1115.

Lastly, a 200-nm-thick aluminum film was formed by evaporation as the second electrode 1103 functioning as a cathode. Thus, Light-Emitting Element 11 of this example was fabricated.

Note that, in the above evaporation steps, evaporation was all performed by a resistance heating method.

Table 13 shows an element structure of Light-Emitting Element 11 obtained as described above.

TABLE 13

|  | first electrode | hole-injection layer | hole-transport layer | light-emitting layer | first electron-transport layer | second electron-transport layer | electron-injection layer | second electrode |
|---|---|---|---|---|---|---|---|---|
| Light-Emitting Element 11 | ITSO 110 nm | CBP:MoOx (=4:2) 60 nm | BPAFLP 30 nm | mCzTPt:Ir(ppy)$_3$ (=1:0.08) 30 nm | DBTTPt-II 15 nm | BPhen 15 nm | LiF 1 nm | Al 200 nm |

In a glove box containing a nitrogen atmosphere, Light-Emitting Element 11 was sealed so as not to be exposed to air. Then, operation characteristics of Light-Emitting Element 11 were measured. Note that the measurements were carried out at room temperature (in the atmosphere kept at 25° C.).

Figure 66:
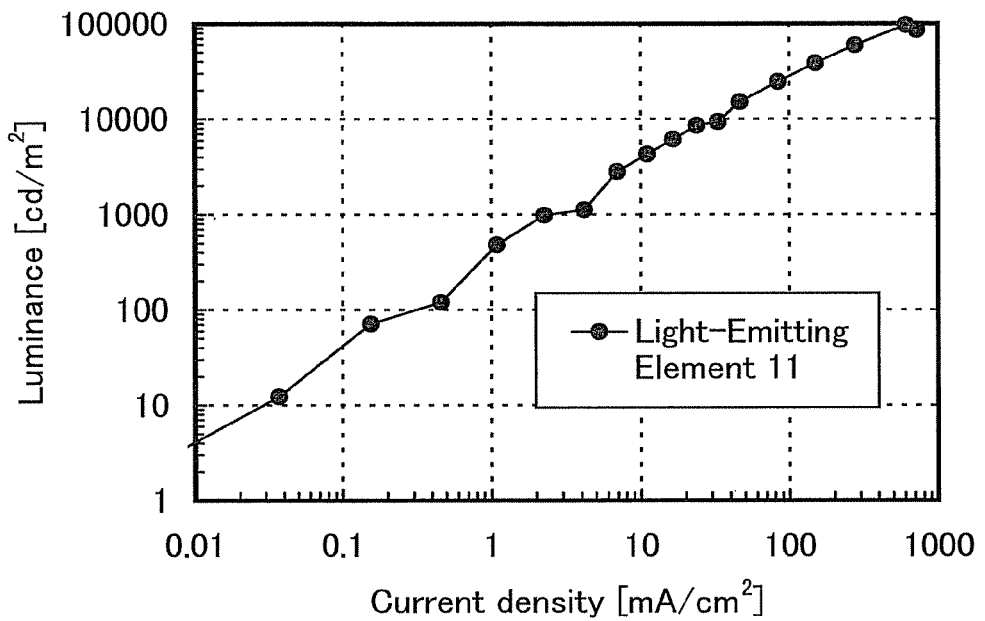
FIG. 66 shows luminance versus current density characteristics of a light-emitting element of Example 18.
Figure 67:
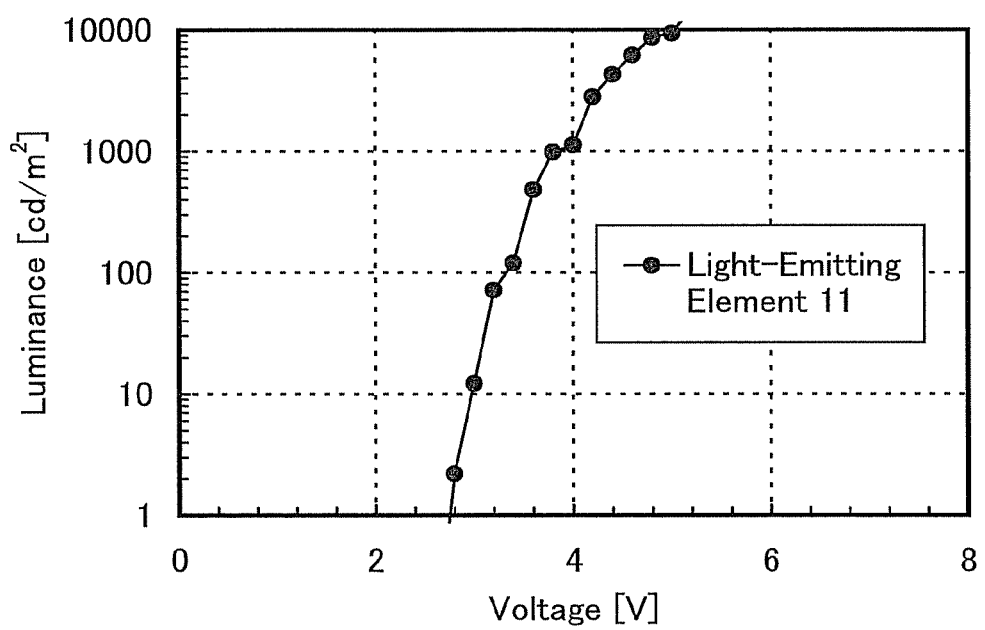
FIG. 67 shows luminance versus voltage characteristics of the light-emitting element of Example 18.
Figure 68:
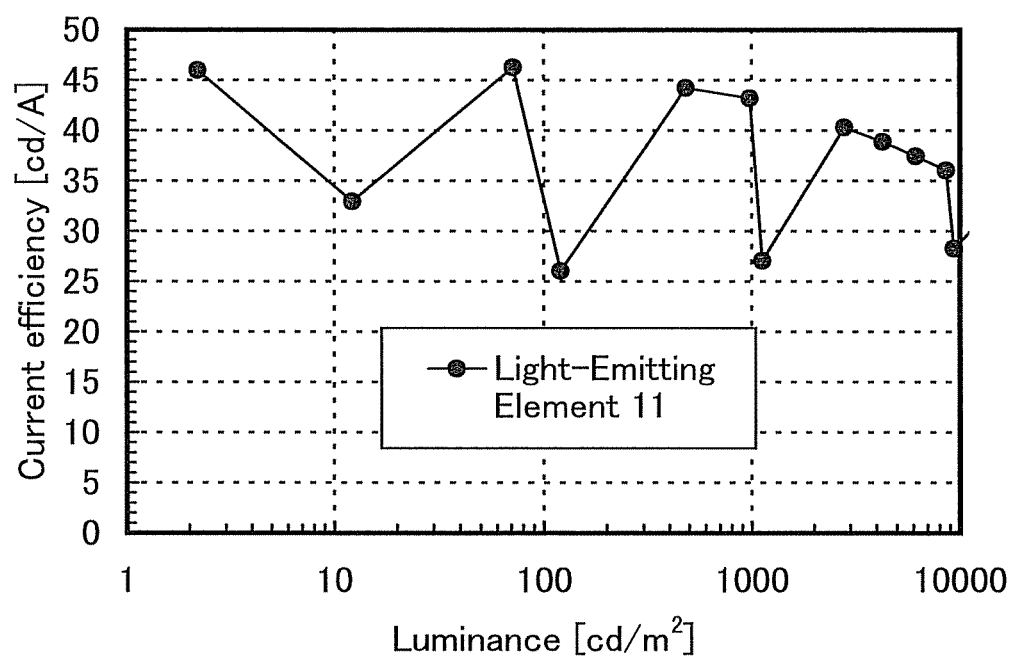
FIG. 68 shows current efficiency versus luminance characteristics of the light-emitting element of Example 18.

FIG. 66 shows the luminance versus current density characteristics of Light-Emitting Element 11. In FIG. 66, the horizontal axis represents current density (mA/cm$^2$) and the vertical axis represents luminance (cd/m$^2$). In addition, FIG. 67 shows the luminance versus voltage characteristics. In FIG. 67, the horizontal axis represents voltage (V) and the vertical axis represents luminance (cd/m$^2$). FIG. 68 shows the current efficiency versus luminance characteristics. In FIG. 68, the horizontal axis represents luminance (cd/m$^2$) and the vertical axis represents current efficiency (cd/A). Further, Table 14 shows the voltage (V), current density (mA/cm$^2$), CIE chromaticity coordinates (x, y), current efficiency (cd/A), and external quantum efficiency (%) of Light-Emitting Element 11 at a luminance of 980 cd/m$^2$.

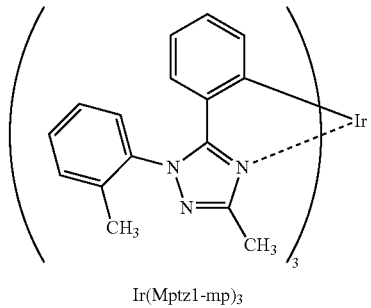

Ir(Mptz1-mp)$_3$

The way how Light-Emitting Element 12 was fabricated will now be described.

(Light-Emitting Element 12)

First, the first electrode 1101 and the hole-injection layer 1111 were formed on the glass substrate 1100 in the same way

TABLE 14

|  | Voltage (V) | Current density (mA/cm$^2$) | Chromaticity coordinates (x, y) | Luminance (cd/m$^2$) | Current efficiency (cd/A) | External quantum yield (%) |
|---|---|---|---|---|---|---|
| Light-Emitting Element 11 | 3.8 | 2.3 | 0.33, 0.62 | 980 | 43 | 13 |

As shown in Table 14, the CIE chromaticity coordinates of Light-Emitting Element 11 (x, y) were (0.33, 0.62) at a luminance of 980 cd/m$^2$. Light-Emitting Element 11 was found to provide light emission from Ir(ppy)$_3$.

It can be confirmed from FIG. 66, FIG. 67, FIG. 68, and Table 14 that Light-Emitting Element 11 is a light-emitting element having high current efficiency. In addition, it can be confirmed the element is a light-emitting element capable of low-voltage driving.

As described above, the triazole derivatives according to embodiments of the present invention synthesized in Examples 1 and 12 were respectively used as a material of the electron-transport layer and as a host material of the light-emitting layer, so that the light-emitting element having high current efficiency and capability of low-voltage driving was able to be fabricated.

EXAMPLE 19

In this example, a light-emitting element of one embodiment of the present invention will be described with reference to FIG. 22B. The chemical formula of a material used in this example is illustrated below. Note that the chemical formulae of materials which are already illustrated will be omitted.

as those of Light-Emitting Element 11 fabricated in Example 18.

Next, on the hole-injection layer 1111, a film of mCP was formed to a thickness of 20 nm to form the hole-transport layer 1112.

Further, mCzTPt synthesized in Example 12 and tris[3-methyl-1-(2-methylphenyl)-5-phenyl-11'-1,2,4-triazolato] iridium(III) (abbreviation: Ir(Mptz1-mp)$_3$) were co-evaporated to form the first light-emitting layer 1113a on the hole-transport layer 1112. The thickness of the first light-emitting layer 1113a was set to 30 um, and the weight ratio of mCzTPt to Ir(Mptz1-mp)$_3$ was adjusted to 1:0.08 (=mCzTPt:Ir(Mptz1-mp)$_3$).

Next, DBTTPt-II synthesized in Example 1 and Ir(Mptz1-mp)$_3$ were co-evaporated to form the second light-emitting layer 1113b on the first light-emitting layer 1113a. Here, the weight ratio of DBTTPt-II to Ir(Mptz1-mp)$_3$ was adjusted to 1:0.08 (=DBTTPt-II:Ir(Mptz1-mp)$_3$). In addition, the thickness of the second light-emitting layer 1113b was set to 10 nm.

Next, on the second light-emitting layer 1113b, a BPhen film was formed to a thickness of 15 nm to Rhin the electron-transport layer 1114.

After that, on the electron-transport layer 1114, a 1-nm-thick LiF film was formed by evaporation to form the electron-injection layer 1115.

Lastly, a 200-nm-thick aluminum film was formed by evaporation as the second electrode 1103 functioning as a cathode. Thus, Light-Emitting Element 12 of this example was fabricated.

Note that, in the above evaporation steps, evaporation was all performed by a resistance heating method.

Table 15 shows an element structure of Light-Emitting Element 12 obtained as described above.

TABLE 15

| | first electrode | hole-injection layer | hole-transport layer | first light-emitting layer | second light-emitting layer | electron-transport layer | electron-injection layer | second electrode |
|---|---|---|---|---|---|---|---|---|
| Light-Emitting Element 12 | ITSO 110 nm | CBP:MoOx (=4:2) 60 nm | mCP 20 nm | mCzTPt:Ir(Mptz1-mp)$_3$ (=1:0.08) 30 nm | DBTTPt-II:Ir(Mptz1-mp)$_3$ (=1:0.08) 10 nm | BPhen 15 nm | LiF 1 nm | Al 200 nm |

In a glove box containing a nitrogen atmosphere, Light-Emitting Element 12 was sealed so as not to be exposed to air. Then, operation characteristics of Light-Emitting Element 12 were measured. Note that the measurements were carried out at room temperature (in the atmosphere kept at 25° C.).

Figure 69:
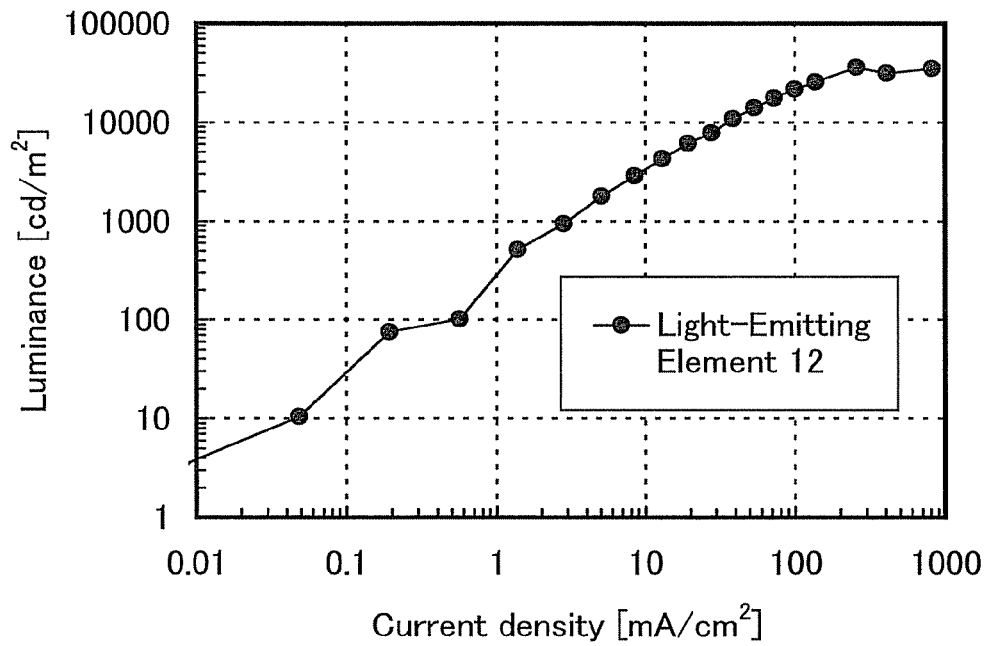
FIG. 69 shows luminance versus current density characteristics of a light-emitting element of Example 19.
Figure 70:
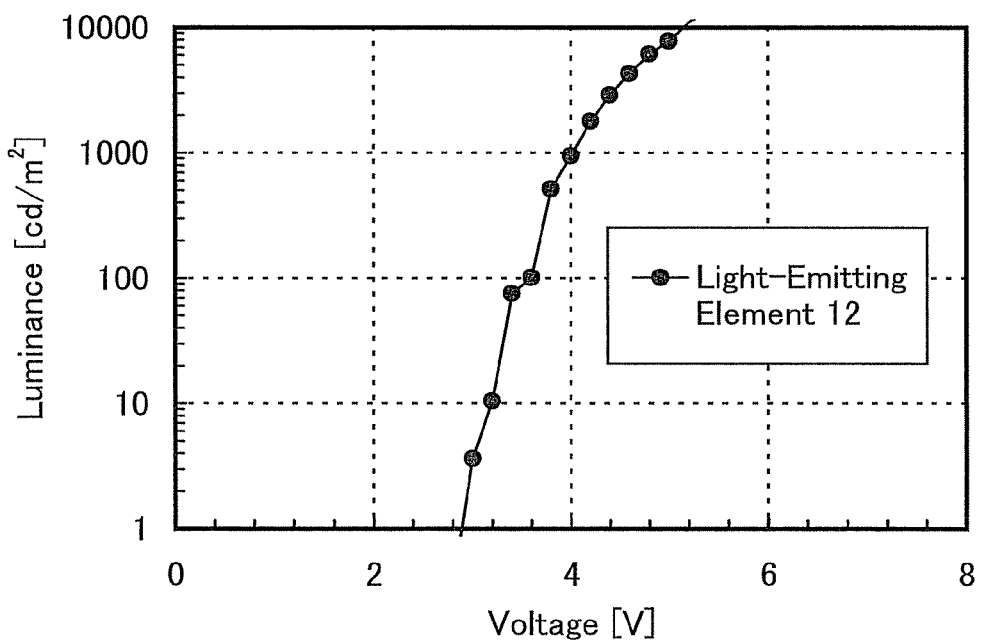
FIG. 70 shows luminance versus voltage characteristics of the light-emitting element of Example 19.
Figure 71:
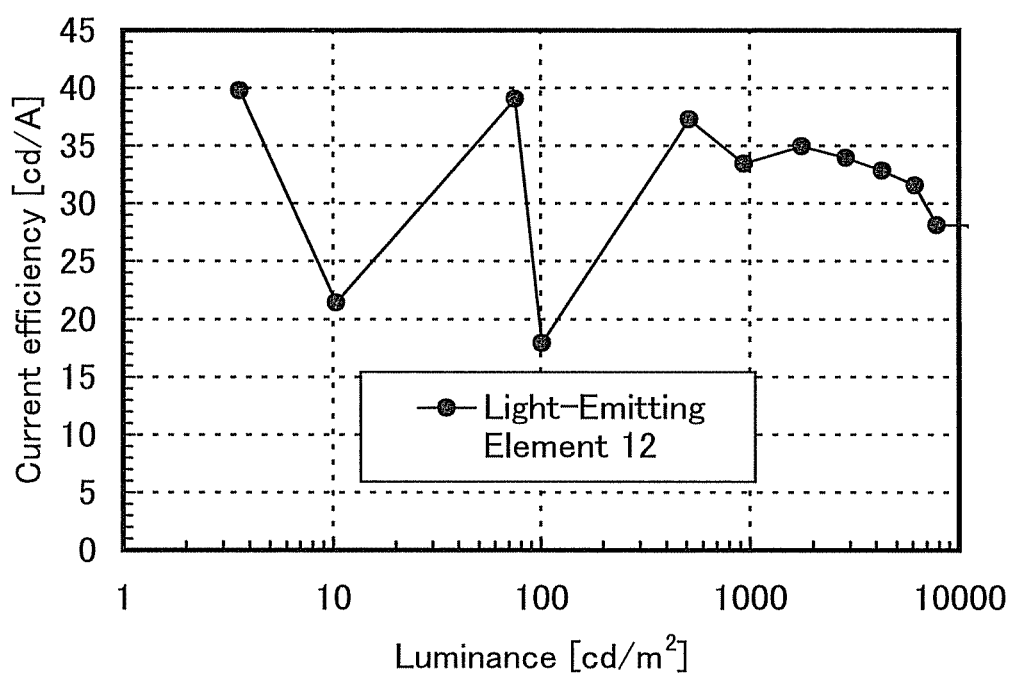
FIG. 71 shows current efficiency versus luminance characteristics of the light-emitting element of Example 19.

FIG. 69 shows the luminance versus current density characteristics of Light-Emitting Element 12. In FIG. 69, the horizontal axis represents current density (mA/cm$^2$) and the vertical axis represents luminance (cd/m$^2$). In addition, FIG. 70 shows the luminance versus voltage characteristics. In FIG. 70, the horizontal axis represents voltage (V) and the vertical axis represents luminance (cd/m$^2$). FIG. 71 shows the current efficiency versus luminance characteristics. In FIG. 71, the horizontal axis represents luminance (cd/m$^2$) and the vertical axis represents current efficiency (cd/A). Further, Table 16 shows the voltage (V), current density (mA/cm$^2$), CIE chromaticity coordinates (x, y), current efficiency (cd/A), and external quantum efficiency (%) of Light-Emitting Element 12 at a luminance of 520 cd/m$^2$.

TABLE 16

| | Voltage (V) | Current density (mA/cm$^2$) | Chromaticity coordinates (x, y) | Luminance (cd/m$^2$) | Current efficiency (cd/A) | External quantum yield (%) |
|---|---|---|---|---|---|---|
| Light-Emitting Element 12 | 3.8 | 1.4 | 0.19, 0.33 | 520 | 37 | 18 |

As shown in Table 16, the CIE chromaticity coordinates of Light-Emitting Element 12 (x, y) were (0.19, 0.33) at a luminance of 520 cd/m$^2$. Light-Emitting Element 12 was found to provide light emission from Ir(Mptz1-mp)$_3$. It is understood that, because the light-emitting element of this example includes the triazole derivative having high triplet excitation energy, Ir(Mptz1-mp)$_3$, which exhibits short-wavelength blue emission, can be made to emit light efficiently. It was shown that application of one embodiment of the present invention enabled efficient light emission from Ir(Mptz1-mp)$_3$, a phosphorescent compound that exhibits short-wavelength light emission.

EXAMPLE 20

In this example, a light-emitting element of one embodiment of the present invention will be described with reference to FIG. 22D. The chemical formulae of materials used in this example are illustrated below. Note that the chemical formulae of materials which are already illustrated will be omitted.

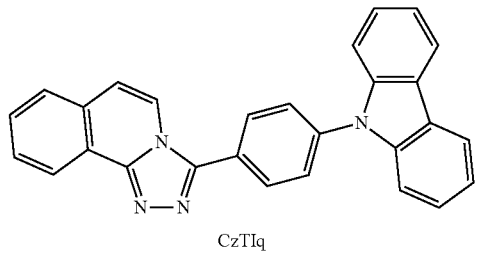

CzTIq

-continued

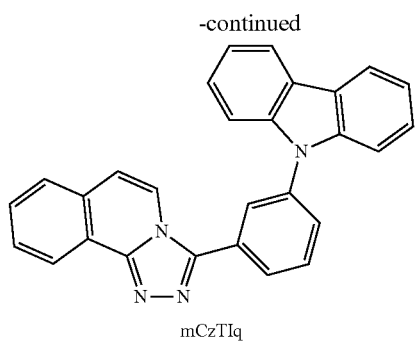

mCzTIq

The ways how Light-Emitting Elements 13 and 14 of this example were fabricated will now be described.

(Light-Emitting Element 13)

First, the first electrode 1101, the hole-injection layer 1111, and the hole-transport layer 1112 were formed on the glass substrate 1100 in the same way as those of Light-Emitting Element 11 described in Example 18. The thickness of the hole-transport layer 1112 was set to 20 nm.

Next, 3-[4-(9H-carbazol-9-yl)phenyl]-1,2,4-triazolo[3,4-a]isoquinoline (abbreviation: CzTIq) synthesized in Example 13 and Ir(ppy)$_3$ were co-evaporated to form the light-emitting layer 1113 on the hole-transport layer 1112. The thickness of the light-emitting layer 1113 was set to 30 nm, and the weight ratio of CzTIq to Ir(ppy)$_3$ was adjusted to 1:0.08 (=CzTIq:Ir(ppy)$_3$).

Further, on the light-emitting layer 1113, a film of mDBTBIm-II was formed to a thickness of 15 nm to form the first electron-transport layer 1114a.

Then, on the first electron-transport layer 1114a, a BPhen film was formed to a thickness of 15 nm to form the second electron-transport layer 1114b.

Further, on the second electron-transport layer 1114b, a 1-nm-thick LiF film was formed by evaporation to form the electron-injection layer 1115.

Lastly, a 200-nm-thick aluminum film was formed by evaporation as the second electrode 1103 functioning as a cathode. Thus, Light-Emitting Element 13 of this example was fabricated.

Note that, in the above evaporation steps, evaporation was all performed by a resistance heating method.

(Light-Emitting Element 14)

The light-emitting layer 1113 of Light-Emitting Element 14 was formed by co-evaporation of 3-[3-(9H-carbazol-9-yl)phenyl]-1,2,4-triazolo[3,4-a]isoquinoline (abbreviation: mCzTIq) synthesized in Example 14 and Ir(ppy)$_3$. Here, the weight ratio of mCzTIq to Ir(ppy)$_3$ was adjusted to 1:0.08 (=mCzTIq:Ir(ppy)$_3$). In addition, the thickness of the light-emitting layer 1113 was set to 30 nm. The layers other than the light-emitting layer 1113 were formed in the same manner as Light-Emitting Element 13.

Table 17 shows element structures of Light-Emitting Elements 13 and Element 14 obtained as described above.

TABLE 17

| | first electrode | hole-injection layer | hole-transport layer | light-emitting layer | first electron-transport layer | second electron-transport layer | electron-injection layer | second electrode |
|---|---|---|---|---|---|---|---|---|
| Light-Emitting Element 13 | ITSO 110 nm | CBP:MoOx (=4:2) 60 nm | BPAFLP 20 nm | CzTIq:Ir(ppy)$_3$ (=1:0.08) 30 nm | mDBTBIm-II 15 nm | BPhen 15 nm | LiF 1 nm | Al 200 nm |
| Light-Emitting Element 14 | ITSO 110 nm | CBP:MoOx (=4:2) 60 nm | BPAFLP 20 nm | mCzTIq:Ir(ppy)$_3$ (=1:0.08) 30 nm | mDBTBIm-II 15 nm | BPhen 15 nm | LiF 1 nm | Al 200 nm |

In a glove box containing a nitrogen atmosphere, Light-Emitting Elements 13 and 14 were sealed so as not to be exposed to air. Then, operation characteristics of these elements were measured. Note that the measurements were carried out at room temperature (in the atmosphere kept at 25° C.).

Figure 72:
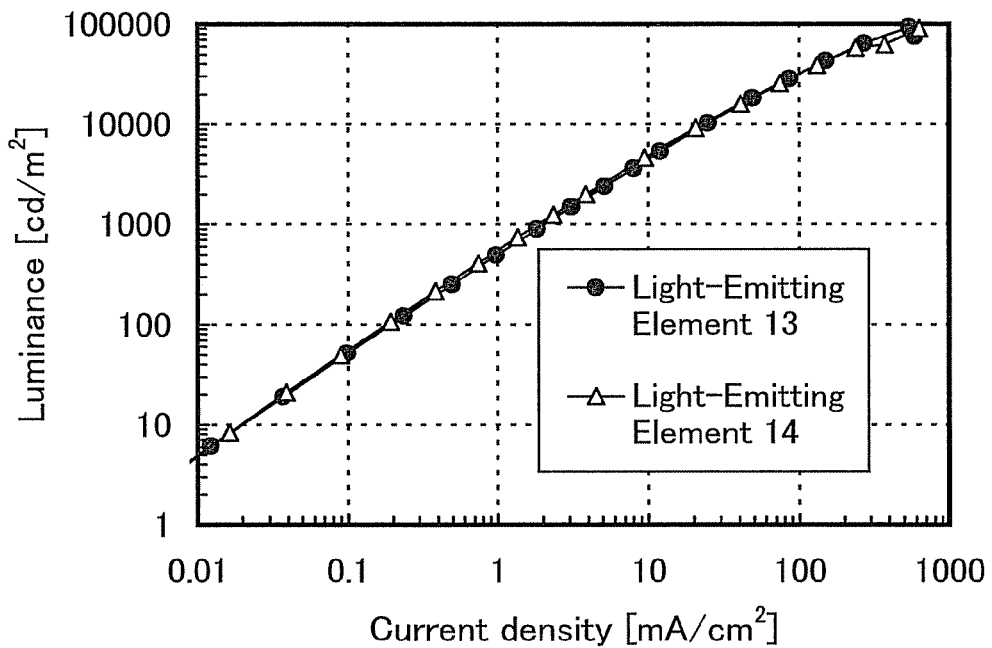
FIG. 72 shows luminance versus current density characteristics of a light-emitting element of Example 20.
Figure 73:
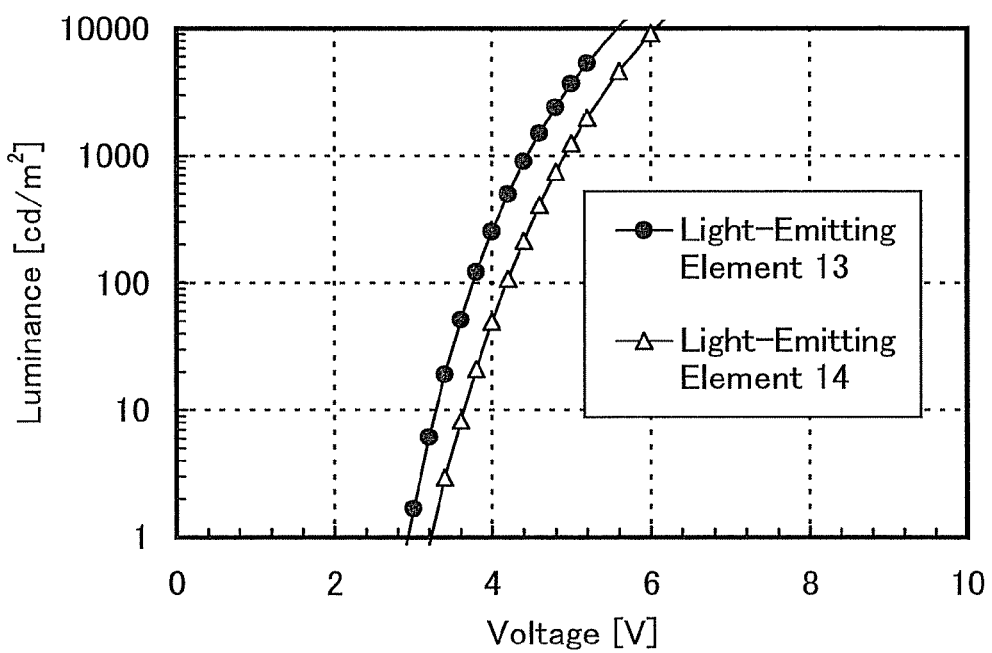
FIG. 73 shows luminance versus voltage characteristics of the light-emitting element of Example 20.
Figure 74:
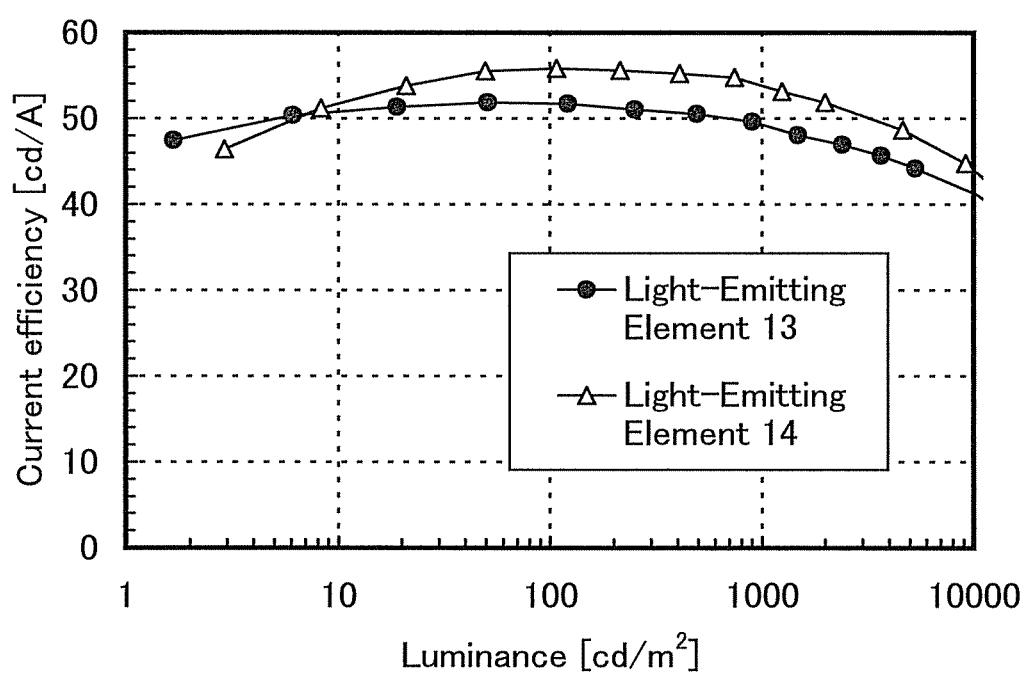
FIG. 74 shows current efficiency versus luminance characteristics of the light-emitting element of Example 20.

FIG. 72 shows the luminance versus current density characteristics of Light-Emitting Elements 13 and 14. In FIG. 72, the horizontal axis represents current density (mA/cm$^2$) and the vertical axis represents luminance (cd/m$^2$). In addition, FIG. 73 shows the luminance versus voltage characteristics. In FIG. 73, the horizontal axis represents voltage (V) and the vertical axis represents luminance (cd/m$^2$). FIG. 74 shows the current efficiency versus luminance characteristics. In FIG. 74, the horizontal axis represents luminance (cd/m$^2$) and the vertical axis represents current efficiency (cd/A). Further, Table 18 shows the voltage (V), current density (mA/cm$^2$), CIE chromaticity coordinates (x, y), current efficiency (cd/A), and external quantum efficiency (%) for each light-emitting element at a luminance of around 1000 cd/m$^2$.

TABLE 18

| | Voltage (V) | Current density (mA/cm$^2$) | Chromaticity coordinates (x, y) | Luminance (cd/m$^2$) | Current efficiency (cd/A) | External quantum yield (%) |
|---|---|---|---|---|---|---|
| Light-Emitting Element 13 | 4.4 | 1.8 | 0.34, 0.62 | 900 | 50 | 15 |
| Light-Emitting Element 14 | 5.0 | 2.3 | 0.33, 0.62 | 1200 | 53 | 16 |

As shown in Table 18, the CIE chromaticity coordinates of Light-Emitting Element 13 (x, y) were (0.34, 0.62) at a luminance of 900 cd/m$^2$. The CIE chromaticity coordinates of Light-Emitting Element 14 (x, y) were (0.33, 0.62) at a luminance of 1200 cd/m$^2$. All these light-emitting elements were found to provide light emission from Ir(ppy)$_3$.

It can be confirmed from FIG. 72, FIG. 73, FIG. 74, and Table 18 that Light-Emitting Elements 13 and 14 are each a light-emitting element having high current efficiency and capability of low-voltage driving.

As described above, the triazole derivatives according to embodiments of the present invention synthesized in Examples 13 and 14 were each used as the host material of the light-emitting layer, so that the light-emitting elements having high current efficiency and capability of low-voltage driving were able to be fabricated

EXAMPLE 21

In this example, a light-emitting element of one embodiment of the present invention will be described with reference to FIG. 22A. The chemical formulae of materials used in this example are illustrated below. Note that the chemical formulae of materials which are already illustrated will be omitted.

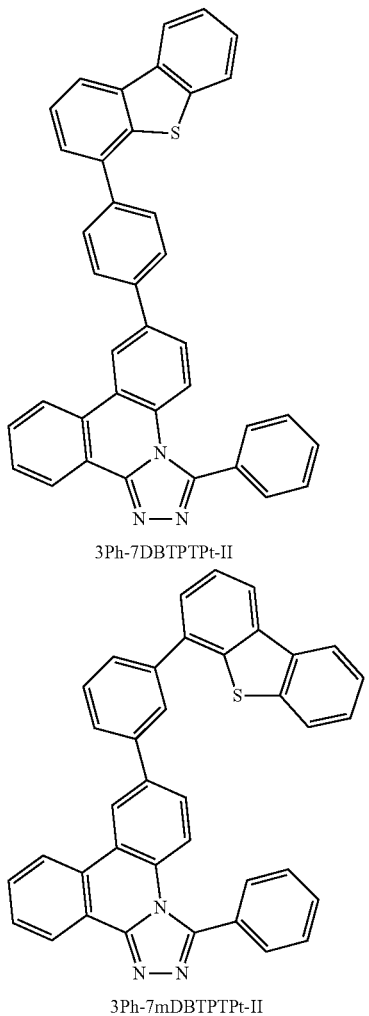

3Ph-7DBTPTPt-II

3Ph-7mDBTPTPt-II

The ways how Light-Emitting Elements 15 and 16 of this example were fabricated will now be described.
(Light-Emitting Element 15)

First, an ITSO film was formed on a glass substrate 1100 by a sputtering method, so that the first electrode 1101 was formed. Note that its thickness was set to 110 nm and the electrode area was set to 2 mm×2 mm.

In pretreatment for Banning the light-emitting element on the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about $10^{-4}$ Pa. Then, BPAFLP and molybdenum(VI) oxide were co-evaporated to form the hole-injection layer 1111 on the first electrode 1101. The thickness of the hole-injection layer 1111 was set to 50 nm, and the weight ratio of BPAFLP to molybdenum(VI) oxide was adjusted to 4:2 (=BPAFLP:molybdenum oxide).

Next, on the hole-injection layer 1111, a BPAFLP film was formed to a thickness of 20 nm to form the hole-transport layer 1112.

Further, 7-[4-(dibenzothiophen-4-yl)phenyl]-3-phenyl-1, 2,4-triazolo[4,3-f]phenanthridine (abbreviation: 3Ph-7 DBTPTPt-II) synthesized in Example 15, PCBA1BP, and Ir(ppy)$_3$ were co-evaporated to form the first light-emitting layer 1113a on the hole-transport layer 1112. Here, the weight ratio of 3Ph-7 DBTPTPt-II to PCBA1BP and Ir(ppy)$_3$ was adjusted to 1:0.3:0.06 (=3Ph-7 DBTPTPt-II:PCBA1BP:Ir(ppy)$_3$). In addition, the thickness of the first light-emitting layer 1113a was set to 20 nm.

Next, on the first light-emitting layer 1113a, 3Ph-7 DBTPTPt-II and Ir(ppy)$_3$ were co-evaporated to form the second light-emitting layer 1113b. Here, the weight ratio of 3Ph-7 DBTPTPt-II to Ir(ppy)$_3$ was adjusted to 1:0.06 (=3Ph-7 DBTPTPt-II:Ir(ppy)$_3$). In addition, the thickness of the second light-emitting layer 1113b was set to 20 nm.

Further, on the second light-emitting layer 1113b, a film of 3Ph-7 DBTPTPt-II was formed to a thickness of 15 nm to form the first electron-transport layer 1114a.

Then, on the first electron-transport layer 1114a, a BPhen film was formed to a thickness of 15 nm to form the second electron-transport layer 1114b.

Further, on the second electron-transport layer 1114b, a 1-nm-thick LW film was formed by evaporation to form the electron-injection layer 1115.

Lastly, a 200-nm-thick aluminum film was formed by evaporation as the second electrode 1103 functioning as a cathode. Thus, Light-Emitting Element 15 of this example was fabricated.

Note that, in the above evaporation steps, evaporation was all performed by a resistance heating method.
(Light-Emitting Element 16)

The first light-emitting layer 1113a of Light-Emitting Element 16 was formed 7-[3-(dibenzothiophen-4-yl)phenyl]-3-phenyl-1,2,4-triazolo[4,3-f]phenanthridine (abbreviation: 3Ph-7mDBTPTPt-II) synthesized in Example 16, PCBA1BP, and Ir(ppy)$_3$. Here, the weight ratio of 3Ph-7mDBTPTPt-II to PCBA1BP and Ir(ppy)$_3$ was adjusted to 1:0.3:0.06 (=3Ph-7mDBTPTPt-II:PCBA1BP:Ir(ppy)$_3$). In addition, the thickness of the first light-emitting layer 1113a was set to 20 nm.

Furthermore, the second light-emitting layer 1113b of Light-Emitting Element 16 was formed by co-evaporation of 3Ph-7mDBTPTPt-II and Ir(ppy)$_3$. Here, the weight ratio of 3Ph-7mDBTPTPt-II to Ir(ppy)$_3$ was adjusted to 1:0.06 (=3Ph-7mDBTPTPt-II:Ir(ppy)$_3$). In addition, the thickness of the second light-emitting layer 1113b was set to 20 nm.

Then, a 3Ph-7mDBTPTPt-II film was formed to a thickness of 15 nm to form the first electron-transport layer 1114a of Light-Emitting Element 16. The components other than the first light-emitting layer 1113a, the second light-emitting layer 1113b, and the first electron-transport layer 1114a were formed in the same way as those of Light-Emitting Element 15.

Table 19 shows element structures of Light-Emitting Elements 15 and 16 obtained as described above.

As shown in Table 20, the CIE chromaticity coordinates of Light-Emitting Element 15 and 16 (x, y) were each (0.34, 0.61) at a luminance of 1200 cd/m$^2$. All these light-emitting elements were found to provide light emission from Ir(ppy)$_3$.

Figure 75:
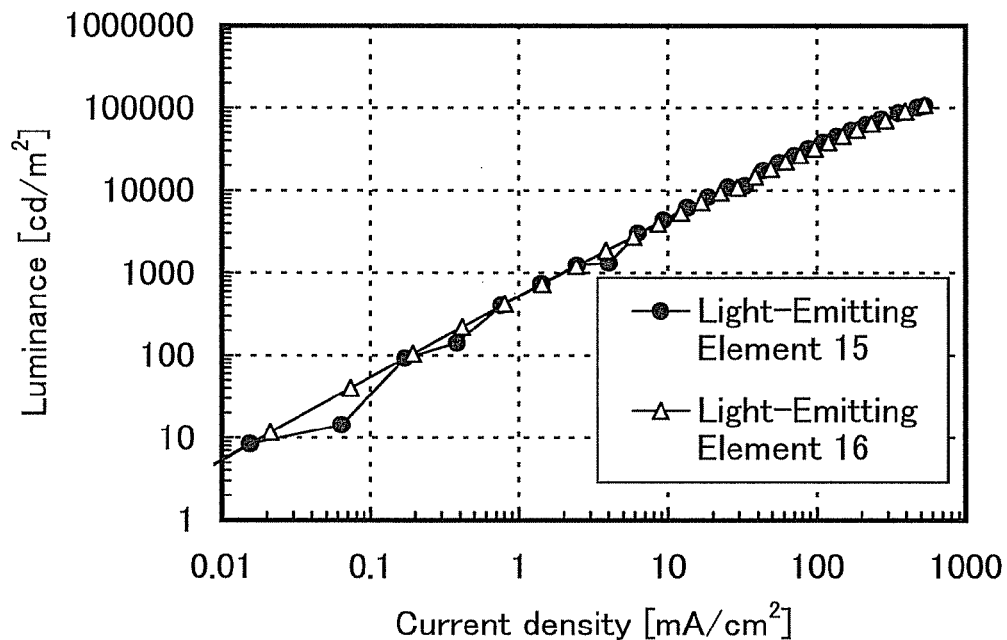
FIG. 75 shows luminance versus current density characteristics of light-emitting elements of Example 21.
Figure 76:
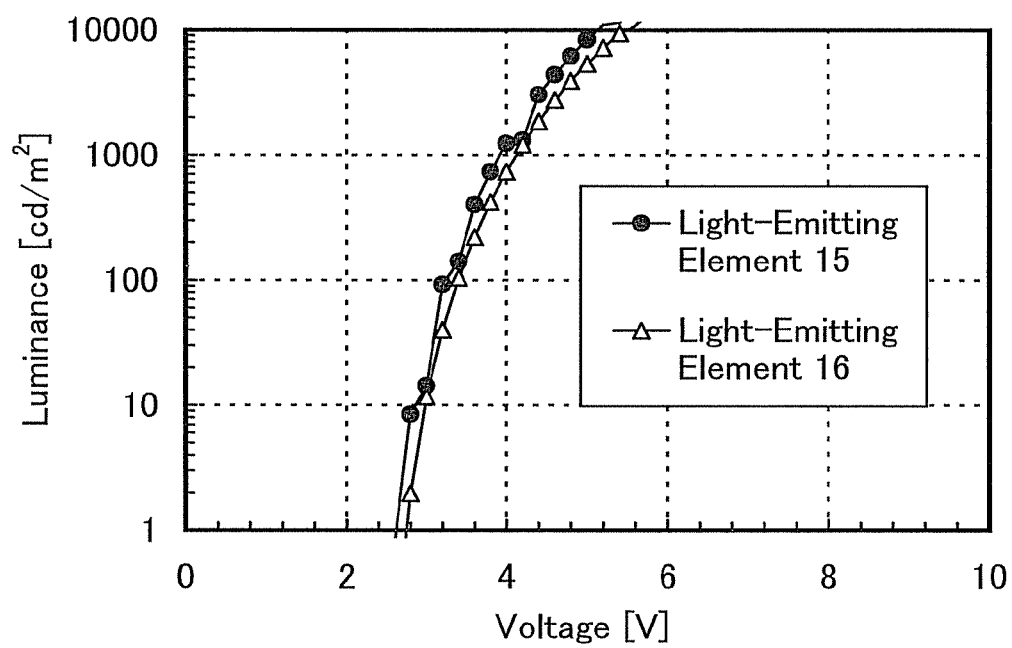
FIG. 76 shows luminance versus voltage characteristics of the light-emitting elements of Example 21.
Figure 77:
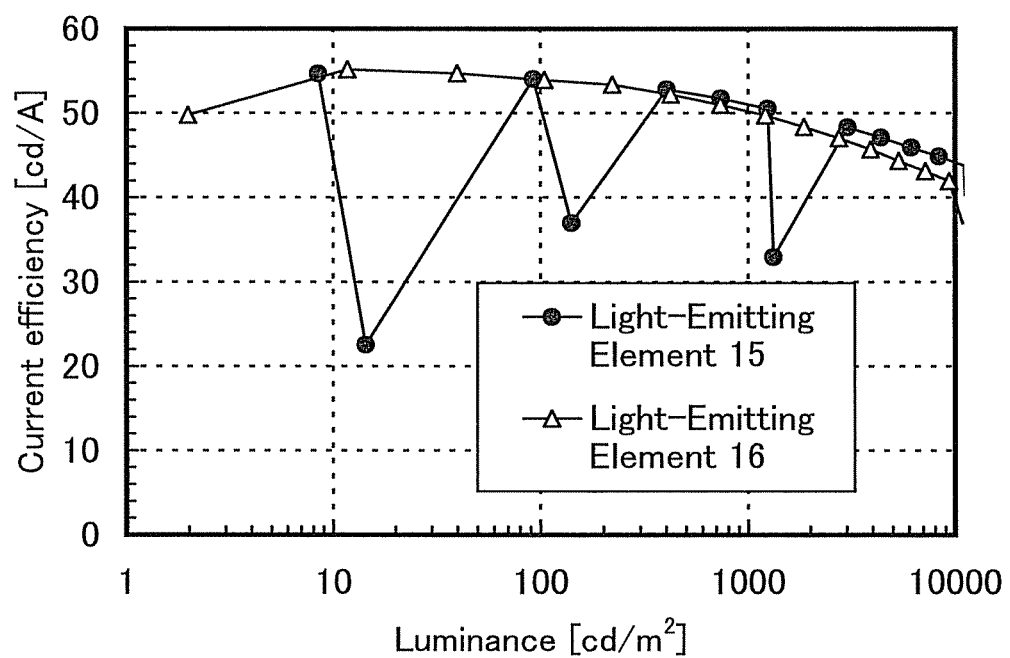
FIG. 77 shows current efficiency versus luminance characteristics of the light-emitting elements of Example 21.

It can be confirmed from FIG. 75, FIG. 76, FIG. 77, and Table 20 that Light-Emitting Elements 15 and 16 are each a

TABLE 19

| | first electrode | hole-injection layer | hole-transport layer | first light-emitting layer | second light-emitting layer |
|---|---|---|---|---|---|
| Light-Emitting Element 15 | ITSO 110 nm | BPAFLP: MoOx (=4:2) 50 nm | BPAFLP 20 nm | 3Ph-7DBTPTPt-II: PCBA1BP:Ir(ppy)$_3$ (=1:0.3:0.06) 20 nm | 3Ph-7DBTPTPt-II: Ir(ppy)$_3$ (=1:0.06) 20 nm |
| Light-Emitting Element 16 | ITSO 110 nm | BPAFLP: MoOx (=4:2) 50 nm | BPAFLP 20 nm | 3Ph-7mDBTPTPt-II: PCBA1BP:Ir(ppy)$_3$ (=1:0.3:0.06) 20 nm | 3Ph-7mDBTPTPt-II: Ir(ppy)$_3$ (=1:0.06) 20 nm |

| | first electron-transport layer | second electron-transport layer | electron-injection layer | second electrode |
|---|---|---|---|---|
| Light-Emitting Element 15 | 3Ph-7DBTPTPt-II 15 nm | BPhen 15 nm | LiF 1 nm | Al 200 nm |
| Light-Emitting Element 16 | 3Ph-7mDBTPTPt-II 15 nm | BPhen 15 nm | LiF 1 nm | Al 200 nm |

In a glove box containing a nitrogen atmosphere, Light-Emitting Elements 15 and 16 were sealed so as not to be exposed to air. Then, operation characteristics of these elements were measured. Note that the measurements were carried out at room temperature (in the atmosphere kept at 25° C.).

FIG. 75 shows the luminance versus current density characteristics of Light-Emitting Elements 15 and 16. In FIG. 75, the horizontal axis represents current density (mA/cm$^2$) and the vertical axis represents luminance (cd/m$^2$). In addition, FIG. 76 shows the luminance versus voltage characteristics. In FIG. 76, the horizontal axis represents voltage (V) and the vertical axis represents luminance (cd/m$^2$). FIG. 77 shows the current efficiency versus luminance characteristics. In FIG. 77, the horizontal axis represents luminance (cd/m$^2$) and the vertical axis represents current efficiency (cd/A). Further, Table 20 shows the voltage (V), current density (mA/cm$^2$), CIE chromaticity coordinates (x, y), current efficiency (cd/A), and external quantum efficiency (%) for each light-emitting element at a luminance of around 1200 cd/m$^2$.

light-emitting element having high current efficiency. In addition, it can be confirmed the elements are each a light-emitting element capable of low-voltage driving.

As described above, the triazole derivatives according to embodiments of the present invention synthesized in Examples 15 and 16 were each used as a host material of the light-emitting layers and as a material of the electron-transport layer, so that the light-emitting elements having high current efficiency and capability of low-voltage driving were able to be fabricated.

REFERENCE EXAMPLE 1

A method of synthesizing 3-[4-(dibenzothiophen-4-yl) phenyl]-4,5-diphenyl-4H-1,2,4-triazole (abbreviation: DBT-TAZ-II) used in the above Examples will be described. A structure of DBTTAZ-II is shown below.

TABLE 20

| | Voltage (V) | Current density (mA/cm$^2$) | Chromaticity coordinates (x, y) | Luminance (cd/m$^2$) | Current efficiency (cd/A) | External quantum yield (%) |
|---|---|---|---|---|---|---|
| Light-Emitting Element 15 | 4.0 | 2.5 | 0.34, 0.61 | 1200 | 50 | 15 |
| Light-Emitting Element 16 | 4.2 | 2.4 | 0.34, 0.61 | 1200 | 50 | 15 |

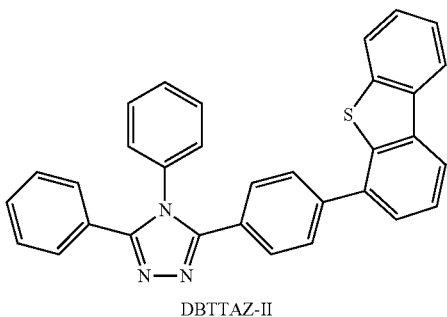 [SMILES: c1ccc(-c2nnc(-c3ccc(-c4cccc5c4sc4ccccc45)cc3)n2-c2ccccc2)cc1]

DBTTAZ-II

A scheme of the synthesis of DBTTAZ-II is illustrated in (a-1).

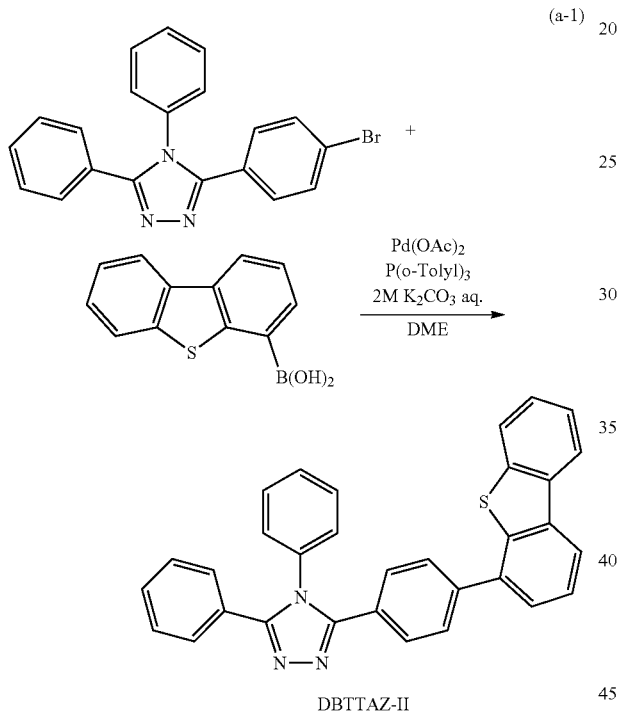

(a-1)

DBTTAZ-II

To a 300-mL three-neck flask were added 1.9 g (5.3 mmol) of 3-(4-bromophenyl)-4,5-diphenyl-4H-1,2,4-triazole, 1.3 g (5.8 mmol) of dibenzothiophene-4-boronic acid, 0.17 g (0.56 mmol) of tri(ortho-tolyl)phosphine, 50 mL of ethylene glycol dimethyl ether, and 5 mL of a 2M aqueous solution of potassium carbonate. This mixture was degassed by being stirred under reduced pressure, and the air in the flask was replaced with nitrogen. To this mixture was added 29 mg (0.13 mmol) of palladium(II) acetate. This mixture was stirred at 80° C. for 4 hours under a nitrogen stream. After a predetermined time elapsed, water was added to this mixture, and organic substances were extracted from the aqueous layer with toluene. The obtained extract solution combined with the organic layer was washed with saturated brine and the organic layer was dried over magnesium sulfate. The obtained mixture was gravity-filtered, and the filtrate was concentrated to give a solid. The obtained solid was purified by silica gel column chromatography. At this time, a mixed solvent (chloroform and ethyl acetate in a 6:1 ratio) was used as a developing solvent. Furthermore, recrystallization from toluene was carried out, so that the substance that was the object of the synthesis was obtained as 2.3 g of a white powder in 89% yield.

By a train sublimation method, 2.3 g of the obtained white powder of the substance that was the object of the synthesis was purified. In the purification, the white powder was heated at 250° C. under a pressure of 10 Pa with a flow rate of argon gas of 5 mL/min. After the purification, 1.5 g of a white powder was obtained in 65% yield.

This compound was identified as 3-[4-(dibenzothiophen-4-yl)phenyl]-4,5-diphenyl-4H-triazole (abbreviation: DBT-TAZ-II), which was the object of the synthesis, by nuclear magnetic resonance (NMR) spectroscopy.

$^1$H NMR data of the obtained compound are as follows: $^1$H NMR (DMSO-$d_6$, 300 MHz): δ (ppm)=7.34-7.45 (m, 5H), 7.52-7.66 (m, 11H), 7.76 (d, J=8.4 Hz, 2H), 8.02-8.04 (m, 1H), 8.41-8.43 (m, 2H).

REFERENCE EXAMPLE 2

A method of synthesizing 4-phenyl-4'-(9-phenylfluoren-9-yl)triphenylamine (abbreviation: BPAFLP) used in the above Examples will be specifically described. A structure of BPAFLP is illustrated below.

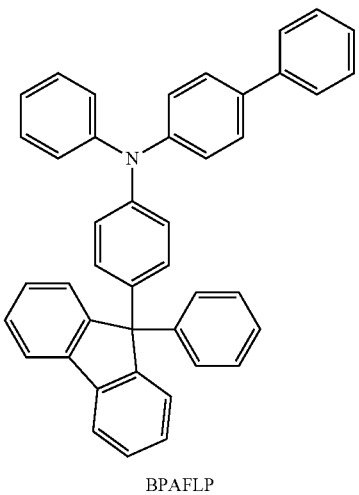 [SMILES: c1ccc(-c2ccc(N(c3ccccc3)c3ccc(C4(c5ccccc5)c5ccccc5-c5ccccc54)cc3)cc2)cc1]

BPAFLP

Step 1: Method of Synthesizing
9-(4-Bromophenyl)-9-phenylfluorene

In a 100-mL three-neck flask, 1.2 g (50 mmol) of magnesium was heated and stirred for 30 minutes under reduced pressure to be activated. The activated magnesium was cooled to room temperature, and the flask was made to contain a nitrogen atmosphere. Then, several drops of dibromoethane were added, so that foam formation and heat generation were confirmed. After 12 g (50 mmol) of 2-bromobiphenyl dissolved in 10 mL of diethyl ether was slowly added dropwise to this mixture, the mixture was heated and stirred under reflux for 2.5 hours, so that a Grignard reagent was prepared.

Into a 500-mL three-neck flask were placed 10 g (40 mmol) of 4-bromobenzophenone and 100 mL of diethyl ether. After the Grignard reagent which was synthesized in advance was slowly added dropwise to this mixture, the mixture was heated and stirred under reflux for 9 hours After reaction, this mixture solution was filtered to give a residue. The obtained residue was dissolved in 150 mL of ethyl acetate, and 1N-hydrochloric acid was added to the mixture until it was made acid, which was then stirred for 2 hours. The organic layer of this liquid was washed with water, and magnesium sulfate was added thereto to remove moisture. This suspension was filtered, and the obtained filtrate was concentrated to give a highly viscous substance.

Into a 500-mL recovery flask were placed this highly viscous substance, 50 mL of glacial acetic acid, and 1.0 mL of hydrochloric acid. The mixture was stirred and heated at 130° C. for 1.5 hours under a nitrogen atmosphere to be reacted.

After the reaction, this reaction mixture solution was filtered to give a residue. The obtained residue was washed with water, an aqueous sodium hydroxide solution, water, and methanol in this order. Then, the mixture was dried, so that the substance which was the object of the synthesis was obtained as 11 g of a white powder in 69% yield. A reaction scheme of the above synthesis method is illustrated in the following (b-1).

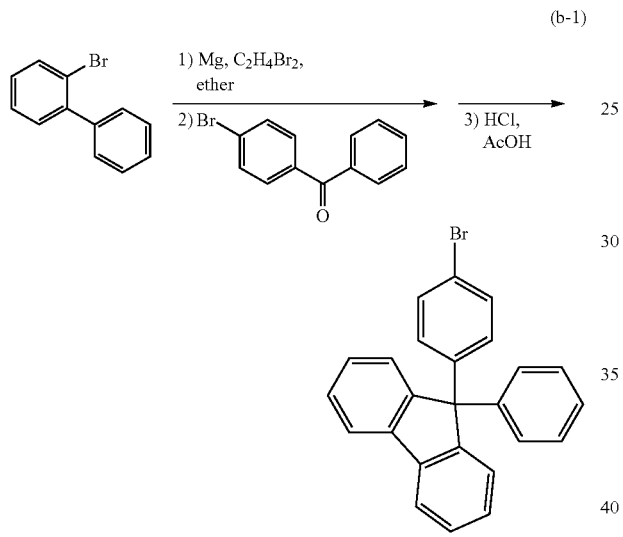

Step 2: Method of Synthesizing 4-Phenyl-4'-(9-phenylfluoren-9-yl)triphenylamine (abbreviation: BPAFLP)

Into a 100-mL three-neck flask were placed 3.2 g (8.0 mmol) of 9-(4-bromophenyl)-9-phenylfluorene, 2.0 g (8.0 mmol) of 4-phenyl-diphenylamine, 1.0 g (10 mmol) of sodium tert-butoxide, and 23 mg (0.04 mmol) of bis(dibenzylideneacetone)palladium(0), and the air in the flask was replaced with nitrogen. Then, 20 mL of dehydrated xylene was added to this mixture. After the mixture was degassed by being stirred under reduced pressure, 0.2 mL (0.1 mmol) of tri(tert-butyl)phosphine (a 10 wt % hexane solution) was added to the mixture. This mixture was stirred and heated at 110° C. for 2 hours under a nitrogen atmosphere to be reacted.

After the reaction, 200 mL of toluene was added to this reaction mixture solution, and this suspension was filtered through Florisil (produced by Wako Pure Chemical Industries, Ltd., Catalog No. 540-00135) and Celite (produced by Wako Pure Chemical Industries, Ltd., Catalog No. 531-16855). The obtained filtrate was concentrated, and the resulting substance was purified by silica gel column chromatography (with a developing solvent of toluene and hexane in a 1:4 ratio). The obtained fraction was concentrated, and acetone and methanol were added to the mixture. The mixture was irradiated with ultrasonic waves and then recrystallized, so that the substance which was the object of the synthesis was obtained as 4.1 g of a white powder in 92% yield. A reaction scheme of the above synthesis method is illustrated in the following (b-2).

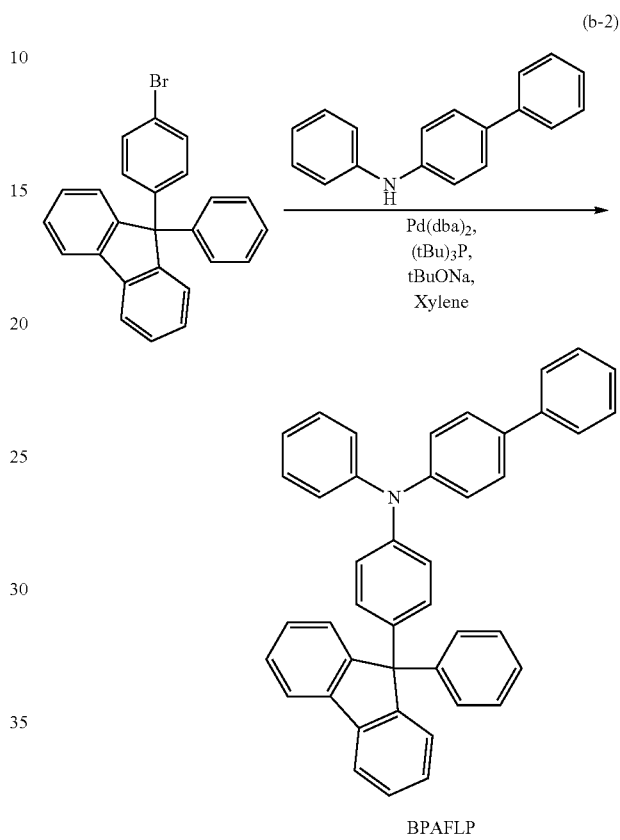

The Rf values of the substance that was the object of the synthesis, 9-(4-bromophenyl)-9-phenylfluorene, and 4-phenyl-diphenylamine were respectively 0.41, 0.51, and 0.27, which were found by silica gel thin layer chromatography (TLC) (with a developing solvent of ethyl acetate and hexane in a 1:10 ratio).

The compound obtained in the above Step 2 was subjected to nuclear magnetic resonance (NMR) spectroscopy. The measurement data are shown below. The measurement results indicate that the obtained compound was BPAFLP, which is a fluorene derivative.

$^1$H NMR (CDCl$_3$, 300 MHz): δ (ppm)=6.63-7.02 (m, 3H), 7.06-7.11 (m, 6H), 7.19-7.45 (m, 18H), 7.53-7.55 (m, 2H), 7.75 (d, J=6.9, 2H).

REFERENCE EXAMPLE 3

A method of synthesizing tris(5-methyl-3,4-diphenyl-4H-1,2,4-triazolato)iridium(III) (abbreviation: Ir(Mptz)$_3$) used in the above Example will be described.

Step 1: Synthesis of 3-Methyl-4,5-diphenyl-4H-1,2,4-triazole (abbreviation: HMptz)

First, 5.04 g of thioacetanilide, 5.44 g of benzoylhydrazine, and 50 mL of 1-butanol were put into a round-bottom flask provided with a reflux pipe, and the air in the flask was replaced with argon. This reaction container was irradiated with microwaves (2.45 GHz, 100W) for 2 hours and 45 minutes to be heated. Then, water was added to this solution and the organic layer was extracted with dichloromethane. The obtained organic layer was washed with water and dried over magnesium sulfate. The solution which had been dried was filtered. The solvent of this solution was distilled off, and the resulting residue was purified by silica gel column chromatography using ethyl acetate as a developing solvent, so that 3-methyl-4,5-diphenyl-4H-1,2,4-triazole (abbreviation: HMptz) was obtained (a pale yellow powder, 18% yield). A scheme of the synthesis of Step 1 is shown in the following (c-1).

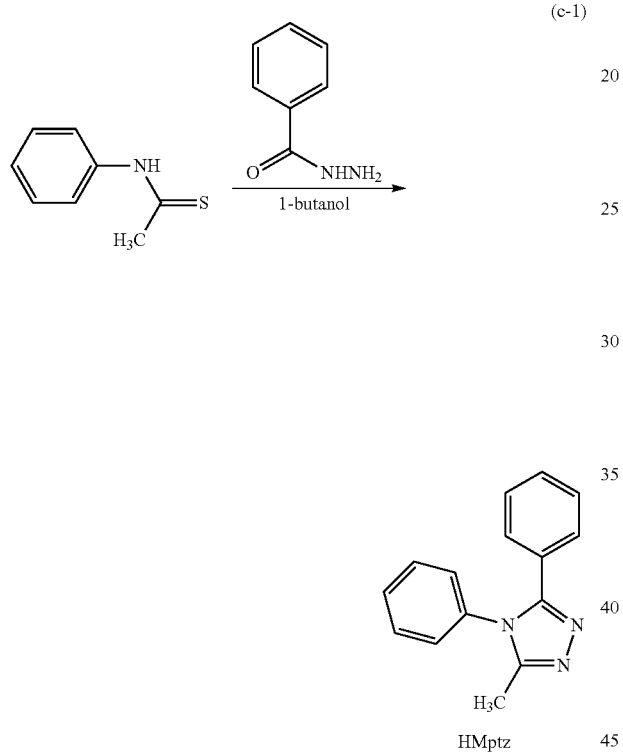

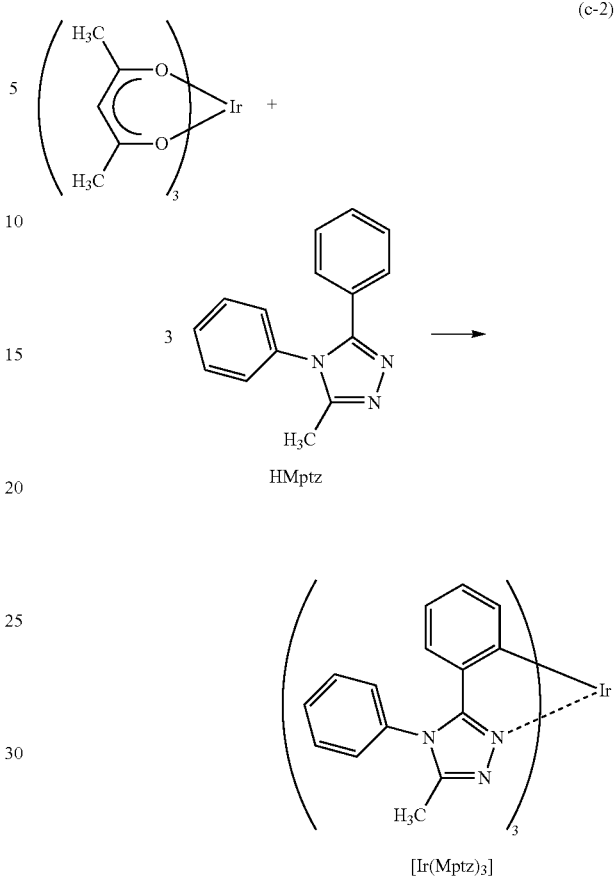

Step 2: Synthesis of Tris(5-methyl-3,4-diphenyl-4H-1,2,4-triazolato)iridium(III) (abbreviation: Ir(Mptz)₃)

Next, 1.40 g of the ligand HMptz obtained in the above Step 1 and 0.58 g of tris(acetylacetonato)iridium(III) were put into a reaction container provided with a three-way cock, and the air in the reaction container was replaced with argon. Then, the mixture was heated at 250° C. for 17 hours and 30 minutes to be reacted. The reactant was dissolved in dichloromethane, and this solution was filtered. The solvent of the obtained filtrate was distilled off and purification was conducted by silica gel column chromatography using ethyl acetate as a developing solvent. Further, recrystallization from a mixed solvent of dichloromethane and hexane was carried out, so that the organometallic complex Ir(Mptz)₃, which was the object of the synthesis, was obtained (a yellow powder, 22% yield). A scheme of the synthesis of Step 2 is shown in the following (c-2).

Analysis results by nuclear magnetic resonance ($^1$H NMR) spectroscopy of the yellow powder obtained in the above Step 2 are shown below. These results revealed that the organometallic complex Ir(Mptz)₃ was obtained.

$^1$H NMR. δ (CDCl₃): 2.17 (s, 9H), 6.38 (d, 3H), 6.54 (t, 3H), 6.72 (dt, 3H), 6.87 (dd, 3H), 7.34 (m, 3H), 7.51 (brm, 3H), 7.57 (m, 9H).

REFERENCE EXAMPLE 4

A method of synthesizing 2-[3-(dibenzothiophen-4-yl)phenyl]-1-phenyl-1H-benzimidazole (abbreviation: mDBTBIm-II) used in the above Examples will be described. A structure of mDBTBIm-II is shown below.

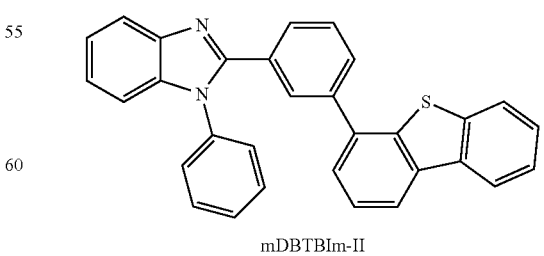

A scheme of the synthesis of mDBTBIm-II is illustrated in (d-1).

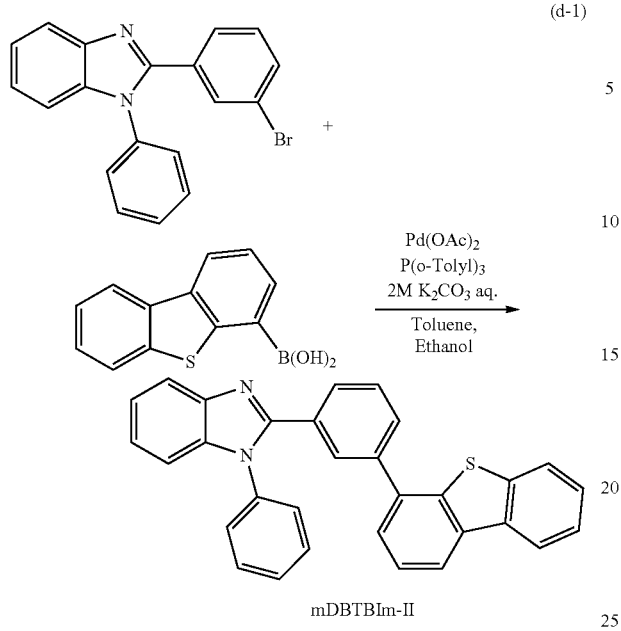

mDBTBIm-II

Into a 50-mL three-neck flask were put 1.2 g (3.3 mmol) of 2-(3-bromophenyl)-1-phenyl-1H-benzimidazole, 0.8 g (3.3 mmol) of dibenzothiophen-4-boronic acid, and 50 mg (0.2 mmol) of tri(ortho-tolyl)phosphine. The air in the flask was replaced with nitrogen. To this mixture were added 3.3 mL of a 2.0 mmol/L aqueous solution of potassium carbonate, 12 mL of toluene, and 4 mL of ethanol. Under reduced pressure, this mixture was stirred to be degassed. Then, 7.4 mg (33 μmol) of palladium(II) acetate was added to this mixture, and the mixture was stirred at 80° C. for 6 hours under a nitrogen stream.

After a predetermined time, organic substances were extracted from the aqueous layer of the obtained mixture with toluene. The obtained extract solution combined with the organic layer was washed with saturated brine, and then the organic layer was dried over magnesium sulfate. This mixture was separated by gravity filtration, and the filtrate was concentrated to give an oily substance. This oily substance was purified by silica gel column chromatography. The silica gel column chromatography was carried out using toluene as a developing solvent. The obtained fraction was concentrated to give an oily substance. This oily substance was purified by high performance liquid chromatography. The high performance liquid column chromatography was performed using chloroform as a developing solvent. The obtained fraction was concentrated to give an oily substance. This oily substance was recrystallized from a mixed solvent of toluene and hexane, so that the substance which was the object of the synthesis was obtained as 0.8 g of a pale yellow powder in 51% yield.

By a train sublimation method, 0.8 g of the obtained pale yellow powder was purified. In the purification, the pale yellow powder was heated at 215° C. under a pressure of 3.0 Pa with a flow rate of argon gas of 5 mL/min. After the purification, 0.6 g of a white powder of the substance which was the object of the synthesis was obtained in a yield of 82%.

This compound was identified as mDBTBIm-II, which was the object of the synthesis, by nuclear magnetic resonance (NMR) spectroscopy.

$^1$H NMR data of the obtained compound are as follows: $^1$H NMR (CDCl$_3$, 300 MHz): δ (ppm)=7.23-7.60 (m, 13H), 7.71-7.82 (m, 3H), 7.90-7.92 (m, 2H), 8.10-8.17 (m, 2H).

REFERENCE EXAMPLE 5

A method of synthesizing tris[3-methyl-1-(2-methylphenyl)-5-phenyl-1H-1,2,4-triazolato]iridium(III) (abbreviation: Ir(Mptz1-mp)$_3$) used in the above Example will be described. A structure of Ir(Mptz1-mp)$_3$ is shown below.

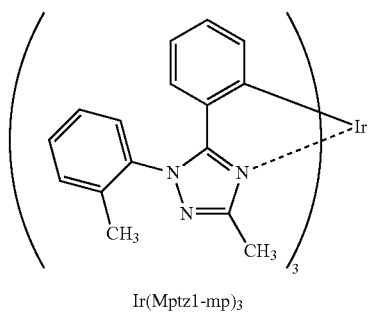

Ir(Mptz1-mp)$_3$

Step 1: Synthesis of
N-(1-Ethoxyethylidene)benzamide

First, 15.5 g of ethyl acetimidate hydrochloride, 150 mL of toluene, and 31.9 g of triethylamine (Et$_3$N) were put into a 500-mL three-neck flask and stirred at room temperature for 10 minutes. With a 50-mL dropping funnel, a mixed solution of 17.7 g of benzoyl chloride and 30 mL of toluene were added dropwise to this mixture, and the mixture was stirred at room temperature for 24 hours. After a predetermined time elapsed, the reaction mixture was suction-filtered, and the solid was washed with toluene. The obtained filtrate was concentrated to give N-(1-ethoxyethylidene)benzamide (a red oily substance, 82% yield). A scheme of the synthesis of Step 1 is shown in the following (e-1).

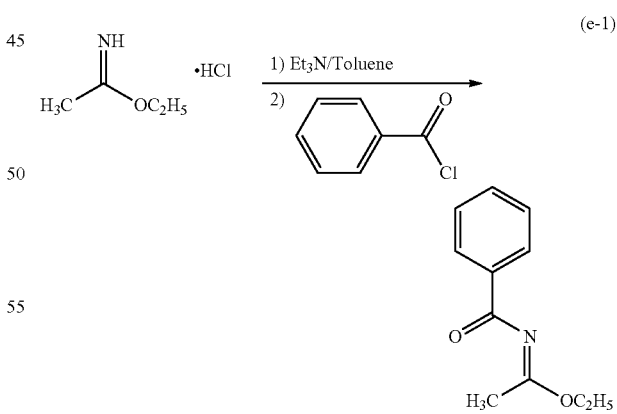

Step 2: Synthesis of 3-Methyl-1-(2-methylphenyl)-5-phenyl-1H-1,2,4-triazole (abbreviation: HMptz1-mp)

Next, into a 300-mL recovery flask were put 8.68 g of ortho-tolyl hydrazine hydrochloride, 100 mL of carbon tetrachloride, and 35 mL of Et$_3$N, and the mixture was stirred at room temperature for 1 hour. After a predetermined time elapsed, 8.72 g of N-(1-ethoxyethylidene)benzamide obtained in the above Step 1 was added to this mixture, and the mixture was stirred at room temperature for 24 hours. After a predetermined time elapsed, water was added to the reaction mixture, and organic substances were extracted from the aqueous layer with chloroform. The organic layer of the resulting mixture was washed with saturated brine, and dried with anhydrous magnesium sulfate added thereto. The obtained mixture was gravity-filtered, and the filtrate was concentrated to give an oily substance. The obtained oily substance was purified by silica gel column chromatography. Dichloromethane was used as a developing solvent. The obtained fraction was concentrated to give 3-methyl-1-(2-methylphenyl)-5-phenyl-1H-1,2,4-triazole (abbreviation: HMptz1-mp) (an orange oily substance, 84% yield). A synthesis scheme of Step 2 is shown in the following (e-2).

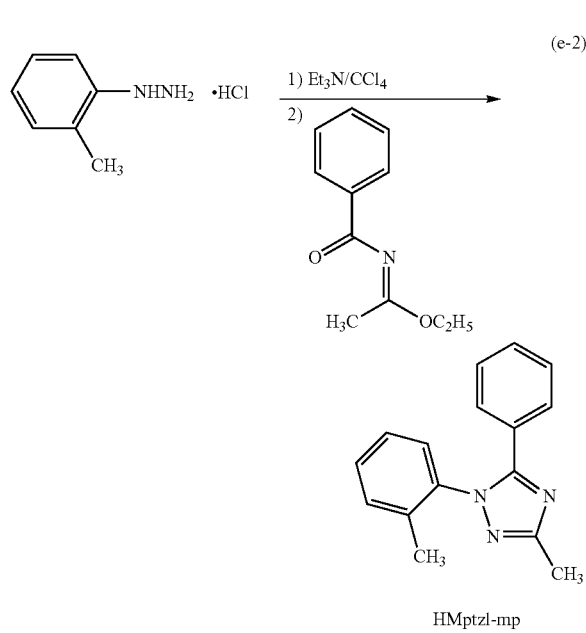

Step 3: Synthesis of Tris[3-methyl-1-(2-methylphenyl)-5-phenyl-1H-1,2,4-triazolato]iridium(III) (abbreviation: Ir(Mptz1-mp)$_3$)

Next, 2.71 g of the ligand HMptz1-mp obtained in the above Step 2 and 1.06 g of tris(acetylacetonato)iridium(III) were put into a reaction container provided with a three-way cock. The air in this flask was replaced with argon, and heated at 250° C. for 48 hours to be reacted. This reaction mixture was dissolved in dichloromethane and purified by silica gel column chromatography. As the developing solvent, dichloromethane was first used, and a mixed solvent of dichloromethane and ethyl acetate in a volume ratio of 10:1 was then used. The obtained fraction was concentrated to give a solid. This solid was washed with ethyl acetate, and recrystallized from a mixed solvent of dichloromethane and ethyl acetate to give the organometallic complex Ir(Mptz1-mp)$_3$ (a yellow powder, 35% yield). A scheme of the synthesis of Step 3 is shown in the following (e-3).

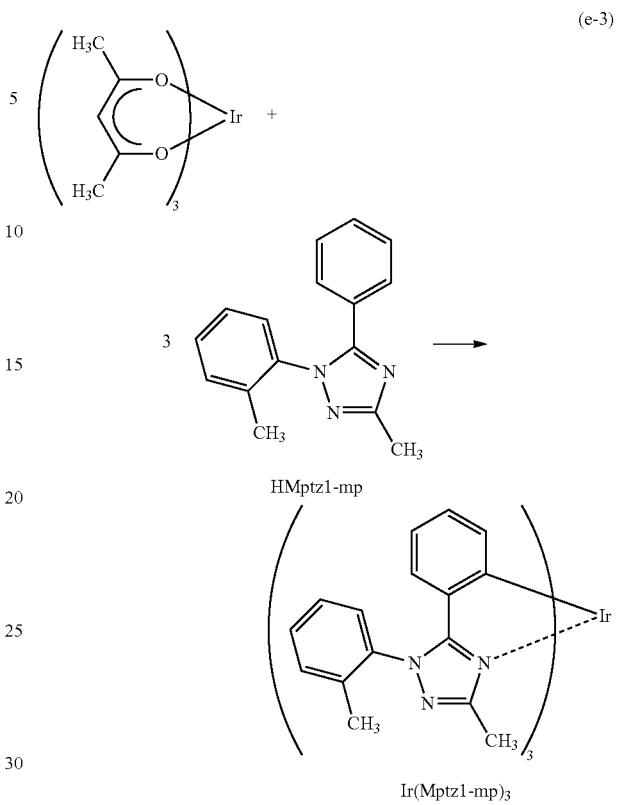

This compound was identified as Ir(Mptz1-mp)$_3$, which was the object of the synthesis, by nuclear magnetic resonance (NMR) spectroscopy.

$^1$H NMR data of the obtained compound are as follows: $^1$H NMR (CDCl$_3$): 1.94-2.21 (m, 18H), 6.47-6.76 (m, 12H), 7.29-7.52 (m, 12H).

REFERENCE NUMERALS

100: substrate, 101: first electrode, 102: EL layer, 103: second electrode, 111: hole-injection layer, 112: hole-transport layer, 113: light-emitting layer, 114: electron-transport layer, 115: electron-injection layer, 301: first electrode, 303: second electrode, 311: light-emitting unit, 312: light-emitting unit, 313: charge generation layer, 401: source driver circuit, 402: pixel portion, 403: gate driver circuit, 404: sealing substrate, 405: sealant, 407: space, 408: wiring, 409: FPC (flexible printed circuit), 410: element substrate, 411: switching TFT, 412: current control TFT, 413: first electrode, 414: insulator, 416: light-emitting layer, 417: second electrode, 418: light-emitting element, 423: n-channel TFT, 424: p-channel TFT, 501: substrate, 502: first electrode, 503: second electrode, 504: EL layer, 505: insulating layer, 506: partition layer, 801: lighting device, 802: lighting device, 803: desk lamp, 1100: substrate, 1101: first electrode, 1103: second electrode, 1111: hole-injection layer, 1112: hole-transport layer, 1113: light-emitting layer, 1113*a*: first light-emitting layer, 1113*b*: second light-emitting layer, 1114: electron-transport layer, 1114*a*: first electron-transport layer, 1114*b*: second electron-transport layer, 1114*c*: third electron-transport layer, 1115: electron-injection layer, 7100: television device, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7301: housing, 7302: housing, 7303: joint portion, 7304: display portion, 7305: display portion, 7306: speaker portion, 7307: storage medium insertion portion, 7308: LED lamp, 7309: operation key, 7310: connection terminal, 7311: sensor, 7312 microphone, 7400: cellular phone, 7401: housing, 7402: display portion, 7403: operation button, 7404: external connection port, 7405: speaker, 7406 microphone, 7501: lighting portion, 7502: shade, 7503: adjustable arm, 7504: support, 7505: base, 7506: power supply.

This application is based on Japanese Patent Application serial No. 2010-173707 filed with the Japan Patent Office on Aug. 2, 2010, the entire contents of which are hereby incorporated by reference.

The invention claimed is:

1. A triazole derivative represented by a general formula (G0),

E-Ar-A                                              (G0)

wherein:

A represents a substituted or unsubstituted carbazolyl group, a substituted or unsubstituted dibenzothiophenyl group, or a substituted or unsubstituted dibenzofuranyl group;

E represents a substituted or unsubstituted triazolo[4,3-f]phenanthridine; and

Ar represents a substituted or unsubstituted arylene group having 6 to 13 carbon atoms.

2. The triazole derivative according to claim 1, wherein the triazole derivative is represented by a general formula (G1-2),

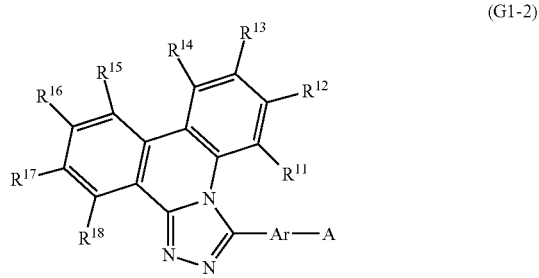

(G1-2)

wherein $R^{11}$ to $R^{18}$ separately represent hydrogen, an alkyl group having 1 to 4 carbon atoms, or a substituted or unsubstituted aryl group having 6 to 13 carbon atoms.

3. The triazole derivative according to claim 1, wherein the triazole derivative is represented by a general formula (G2-2),

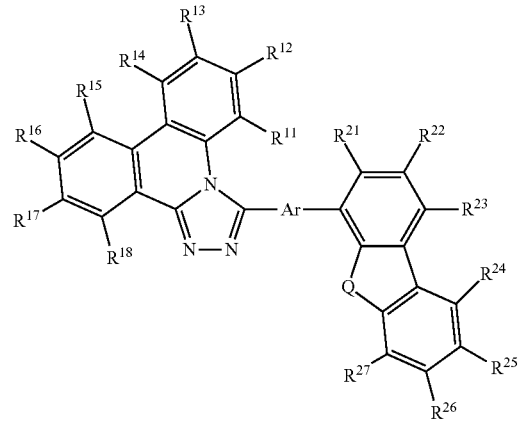

(G2-2)

wherein:

Q represents oxygen or sulfur; and $R^{11}$ to $R^{18}$ and $R^{21}$ to $R^{27}$ separately represent hydrogen, an alkyl group having 1 to 4 carbon atoms, or a substituted or unsubstituted aryl group having 6 to 13 carbon atoms.

4. The triazole derivative according to claim 1, wherein the triazole derivative is represented by a general formula (G3-2),

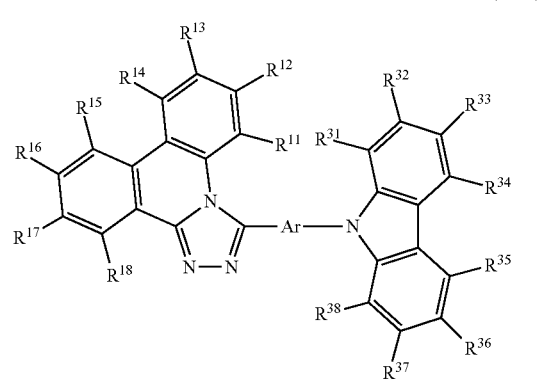

(G3-2)

wherein $R^{11}$ to $R^{18}$ and $R^{31}$ to $R^{38}$ separately represent hydrogen, an alkyl group having 1 to 4 carbon atoms, or a substituted or unsubstituted aryl group having 6 to 13 carbon atoms.

5. The triazole derivative according to claim 1, wherein substituents of the arylene group are bonded to form a ring.

6. The triazole derivative according to claim 1, wherein Ar is a substituted or unsubstituted biphenyldiyl group.

7. The triazole derivative according to claim 1, wherein Ar is a substituted or unsubstituted phenylene group.

8. A light-emitting device comprising the triazole derivative according to claim 1.

9. An electronic device comprising the light-emitting device according to claim 8.

10. A lighting device comprising the light-emitting device according to claim 8.

11. A triazole derivative represented by a general formula (G0),

E-Ar-A                                              (G0)

wherein:

A represents a substituted or unsubstituted carbazolyl group, a substituted or unsubstituted dibenzothiophenyl group, or a substituted or unsubstituted dibenzofuranyl group;

E represents a substituted or unsubstituted triazolo[3,4-α]isoquinoline; and

Ar represents a substituted or unsubstituted arylene group having 6 to 13 carbon atoms.

12. The triazole derivative according to claim 11, wherein the triazole derivative is represented by a general formula (G1-1),

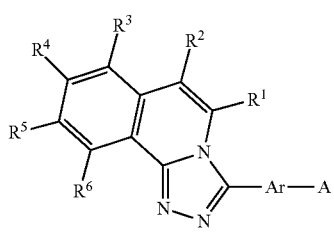

(G1-1)

wherein $R^1$ to $R^6$ separately represent hydrogen, an alkyl group having 1 to 4 carbon atoms, or a substituted or unsubstituted aryl group having 6 to 13 carbon atoms.

13. The triazole derivative according to claim 11, wherein the triazole derivative is represented by a general formula (G2-1),

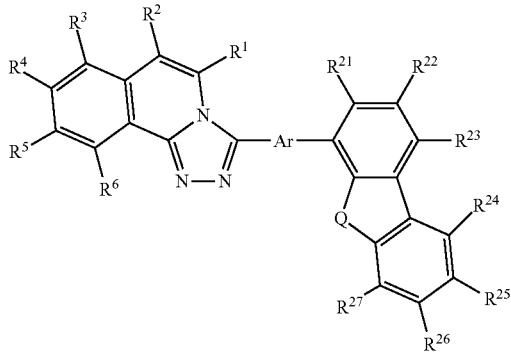

(G2-1)

wherein:

Q represents oxygen or sulfur; and $R^1$ to $R^6$ and $R^{21}$ to $R^{27}$ separately represent hydrogen, an alkyl group having 1 to 4 carbon atoms, or a substituted or unsubstituted aryl group having 6 to 13 carbon atoms.

14. The triazole derivative according to claim 11, wherein the triazole derivative is represented by a general formula (G3-1),

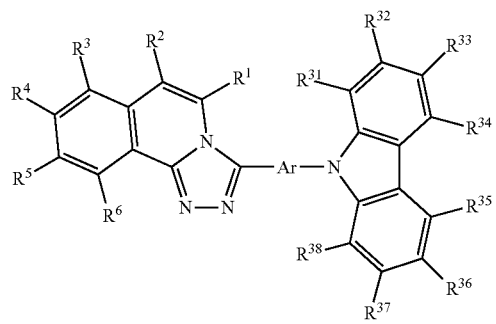

(G3-1)

wherein $R^1$ to $R^6$ and $R^{31}$ to $R^{38}$ separately represent hydrogen, an alkyl group having 1 to 4 carbon atoms, or a substituted or unsubstituted aryl group having 6 to 13 carbon atoms.

15. The triazole derivative according to claim 11, wherein substituents of the arylene group are bonded to form a ring.

16. The triazole derivative according to claim 11, wherein Ar is a substituted or unsubstituted biphenyldiyl group.

17. The triazole derivative according to claim 11, wherein Ar is a substituted or unsubstituted phenylene group.

18. A light-emitting device 0comprising the triazole derivative according to claim 11.

19. An electronic device comprising the light-emitting device according to claim 18.

20. A lighting device comprising the light-emitting device according to claim 18.

21. A heterocyclic compound represented by a general formula (G4),

E-Ar—X    (G4)

wherein:

E represents a substituted or unsubstituted triazolo[4,3-f]phenanthridine;

X represents iodine or bromine; and

Ar represents a substituted or unsubstituted biphenyldiyl group.

22. A heterocyclic compound represented by a general formula (G5-2),

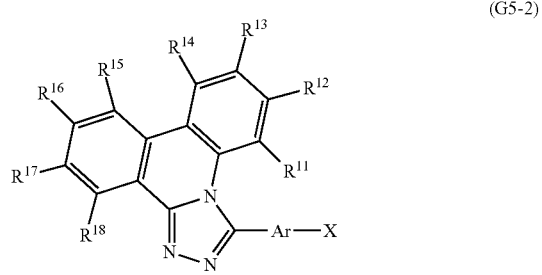

(G5-2)

wherein:

$R^{11}$ to $R^{18}$ separately represent hydrogen or an alkyl group having 1 to 4 carbon atoms;

X represents iodine or bromine; and

Ar represents a substituted or unsubstituted arylene group having 6 to 13 carbon atoms.

23. The heterocyclic compound according to claim 22, wherein substituents of the arylene group are bonded to form a ring.

24. The heterocyclic compound according to claim 22, wherein Ar is a substituted or unsubstituted biphenyldiyl group.

25. The heterocyclic compound according to claim 22, wherein Ar is a substituted or unsubstituted phenylene group.

26. A heterocyclic compound represented by a general formula (G4),

E-Ar—X                                         (G4)

wherein:
E represents a substituted or unsubstituted triazolo[3,4-a]isoquinoline;
X represents iodine or bromine; and
Ar represents a substituted or unsubstituted arylene group having 6 to 13 carbon atoms.

27. The heterocyclic compound according to claim 26, wherein the heterocyclic compound is represented by a general formula (G5-1),

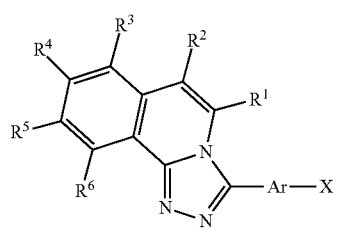

(G5-1)

wherein $R^1$ to $R^6$ separately represent hydrogen, an alkyl group having 1 to 4 carbon atoms, or a substituted or unsubstituted aryl group having 6 to 13 carbon atoms.

28. The heterocyclic compound according to claim 26, wherein substituents of the arylene group are bonded to form a ring.

29. The heterocyclic compound according to claim 26, wherein Ar is a substituted or unsubstituted biphenyldiyl group.

30. The heterocyclic compound according to claim 26, wherein Ar is a substituted or unsubstituted phenylene group.

31. A light-emitting element comprising:
a pair of electrodes; and
a light-emitting layer between the pair of electrodes, the light-emitting layer comprising:
a phosphorescent material; and
a triazolo[4,3-f]phenanthridine derivative,
wherein the phosphorescent material is a guest material,
wherein the triazolo[4,3-f]phenanthridine derivative is a host material, and
wherein the guest material is dispersed in the host material.

32. A light-emitting device comprising the light-emitting element according to claim 31.

33. An electronic device comprising the light-emitting device according to claim 32.

34. A lighting device comprising the light-emitting device according to claim 32.

35. A light-emitting element comprising:
a pair of electrodes., and
a light-emitting layer between the pair of electrodes, the light-emitting layer comprising:
a phosphorescent material; and
a triazolo[3,4-a]isoquinoline derivative,
wherein the phosphorescent material is a guest material,
wherein the triazolo[3,4-a]isoquinoline derivative is a host material, and
wherein the guest material is dispersed in the host material.

36. A light-emitting device comprising the light-emitting element according to claim 35.

37. An electronic device comprising the light-emitting device according to claim 36.

38. A lighting device comprising the light-emitting device according to claim 36.

39. The heterocyclic compound according to claim 21, wherein substituents of the biphenyldiyl group are bonded to form a ring.

* * * * *

UNITED STATES PATENT AND TRADEMARK OFFICE
CERTIFICATE OF CORRECTION

| | | |
|---|---|---|
| PATENT NO. | : 9,034,486 B2 | Page 1 of 3 |
| APPLICATION NO. | : 13/194196 | |
| DATED | : May 19, 2015 | |
| INVENTOR(S) | : Hiroshi Kadoma et al. | |

It is certified that error appears in the above-identified patent and that said Letters Patent is hereby corrected as shown below:

On the Title Page, item 57:

Abstract, line 6; Change "[4,3 f]" to --[4, 3-f]--.

In the Specification:

Column 8, Line 32; Change "NMR" to --$^1$H NMR--.

Column 9, Line 42; Change "[3,4-c]" to --[3,4-α]--.

Column 9, Line 55; Change "3Ph-7 DBTPTPt-II." to --3Ph-7DBTPTPt-II.--.

Column 9, Line 62; Change "NMR" to --$^1$H NMR--.

Column 10, Line 44; Change "[4,3-j]" to --[4, 3-f]--.

Column 10, Line 45; Change "[3,4-a]" to --[3, 4-α]--.

Column 14, Line 24; Change "faun" to --form--.

Column 15, Line 27; Change "faun" to --form--.

Column 171, Line 3; Change "X' represents" to --$X^1$ represents--.

Column 176, Line 63; Change "(N-carbazoly)" to --(N-carbazolyl)--.

Column 176, Lines 63 to 64; Change "(abbrevation:" to --(abbreviation:--.

Column 178, Line 43; Change "-N,C']" to -- -N,$C^{2'}$]--.

Column 178, Line 44; Change "Flrpic)," to --FIrpic),--.

Column 178, Lines 46 to 47; Change "6'-difluorophenyppyridinato-" to --6'-difluorophenyl)pyridinato- --.

Column 179, Line 35; Change "[N,N-di-(" to --[N,N'-di-(--.

Signed and Sealed this
Third Day of November, 2015

Michelle K. Lee
*Director of the United States Patent and Trademark Office*

CERTIFICATE OF CORRECTION (continued)
U.S. Pat. No. 9,034,486 B2

In the Specification:

Column 179, Line 62; Change "aluminum." to --aluminum--.

Column 182, Line 8; Change "foiniation" to --formation--.

Column 192, Line 9; Change "NMR" to --$^1$H NMR--.

Column 196, Line 57; Change "NMR" to --$^1$H NMR--.

Column 199, Line 35; Change "$^1$ H NMR" to --$^1$H NMR--.

Column 200, Line 44; Change "mDBTTPt-H," to --mDBTTPt-II,--.

Column 200, Line 63; Change "fowled" to --formed--.

Column 213, Line 27; Change "foamed" to --formed--.

Column 216, Line 22; Change "faun" to --form--.

Column 221, Line 2; Change "foam" to --form--.

Column 221, Line 4; Change "fowled" to --formed--.

Column 224, Line 4; Change "mDBFPTPt-H," to --mDBFPTPt-II,--.

Column 226, Line 45; Change "(1-1)." to --(I-1).--.

Column 231, Lines 59 to 60; Change "3Ph-7 DBTPTPt-II)," to --3Ph-7DBTPTPt-II),--.

Column 233, Line 46; Change "N-benzoyl-" to --N'-benzoyl- --.

Column 234, Line 10; Change "3Ph-7 DBTPTPt-II)" to --3Ph-7DBTPTPt-II)--.

Column 235, Line 28; Change "3Ph-7 DBTPTPt-II," to --3Ph-7DBTPTPt-II,--.

Column 235, Line 41; Change "3Ph-7 DBTPTPt-II," to --3Ph-7DBTPTPt-II,--.

Column 235, Line 43; Change "3Ph-7 DBTPTPt-II," to --3Ph-7DBTPTPt-II,--.

Column 237, Line 65; Change "NMR" to --$^1$H NMR--.

Column 239, Line 34; Change "[4,3-J]" to --[4,3-f]--.

Column 240, Line 29; Change "foam" to --form--.

Column 242, Line 49; Change "-5-phenyl-11'-" to -- -5-phenyl-1H- --.

Column 242, Line 53; Change "30 um," to --30 nm,--.

Column 242, Line 63; Change "Rhin" to --form--.

Column 247, Line 64; Change "Banning" to --forming--.

Column 248, Line 25; Change "3Ph-7 DBTPTPt-II" to --3Ph-7DBTPTPt-II--.

Column 248, Line 26; Change "3Ph-7 DBTPTPt-II" to --3Ph-7DBTPTPt-II--.

Column 248, Line 32; Change "3Ph-7 DBTPTPt-II" to --3Ph-7DBTPTPt-II--.

Column 248, Line 33; Change "3Ph-7 DBTPTPt-II" to --3Ph-7DBTPTPt-II--.

Column 248, Line 36; Change "3Ph-7 DBTPTPt-II" to --3Ph-7DBTPTPt-II--.

Column 248, Line 42; Change "LW film" to --LiF film--.

Column 248, Line 52; Change "was formed 7-[" to --was formed by co-evaporation of 7-[--.

CERTIFICATE OF CORRECTION (continued)
U.S. Pat. No. 9,034,486 B2

In the Claims:

Column 262, Line 48, Claim 4; Change "1to 4" to --1 to 4--.

Column 264, Line 19, Claim 14; Change "6to 13" to --6 to 13--.

Column 264, Line 27, Claim 18; Change "device θcomprising" to --device comprising--.

Column 266, Line 20, Claim 35; Change "electrodes.," to --electrodes;--.

Column 266, Line 24, Claim 35; Change "[3,4-a]" to --[3, 4-α]--.

Column 266, Line 26, Claim 35; Change "[3,4-a]" to --[3, 4-α]--.